United States Patent
Bonito et al.

(10) Patent No.: US 10,858,687 B2
(45) Date of Patent: Dec. 8, 2020

(54) LIPID BIOSYNTHESIS AND ABIOTIC STRESS RESILIENCE IN PHOTOSYNTHETIC ORGANISMS

(71) Applicant: Board of Trustees of Michigan State University, East Lansing, MI (US)

(72) Inventors: Gregory Bonito, East Lansing, MI (US); Zhi-Yan Du, East Lansing, MI (US); Christoph Benning, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 93 days.

(21) Appl. No.: 16/058,632

(22) Filed: Aug. 8, 2018

(65) Prior Publication Data
US 2018/0346954 A1 Dec. 6, 2018

Related U.S. Application Data

(63) Continuation-in-part of application No. 15/894,457, filed on Feb. 12, 2018.

(60) Provisional application No. 62/458,236, filed on Feb. 13, 2017.

(51) Int. Cl.
| | |
|---|---|
| *C12P 39/00* | (2006.01) |
| *C12N 1/12* | (2006.01) |
| *C12P 7/64* | (2006.01) |
| *C12N 9/02* | (2006.01) |
| *C12N 1/14* | (2006.01) |
| *A01H 15/00* | (2006.01) |
| *C12N 9/00* | (2006.01) |
| *C12N 15/82* | (2006.01) |
| *C12R 1/85* | (2006.01) |
| *C12R 1/885* | (2006.01) |
| *C12R 1/89* | (2006.01) |
| *C12R 1/77* | (2006.01) |
| *C12R 1/80* | (2006.01) |
| *C12R 1/66* | (2006.01) |
| *C12R 1/72* | (2006.01) |
| *C12R 1/84* | (2006.01) |

(52) U.S. Cl.
CPC .............. *C12P 39/00* (2013.01); *A01H 15/00* (2013.01); *C12N 1/12* (2013.01); *C12N 1/14* (2013.01); *C12N 9/00* (2013.01); *C12N 9/0004* (2013.01); *C12N 15/8245* (2013.01); *C12P 7/6463* (2013.01); *C12N 15/8205* (2013.01); *C12P 7/649* (2013.01); *C12R 1/66* (2013.01); *C12R 1/72* (2013.01); *C12R 1/77* (2013.01); *C12R 1/80* (2013.01); *C12R 1/84* (2013.01); *C12R 1/85* (2013.01); *C12R 1/885* (2013.01); *C12R 1/89* (2013.01)

(58) Field of Classification Search
CPC ..................................................... C12N 1/14
See application file for complete search history.

(56) References Cited

U.S. PATENT DOCUMENTS

| | | |
|---|---|---|
| 5,258,300 A | 11/1993 | Glassman et al. |
| 2008/0264858 A1 | 10/2008 | Stamets |
| 2010/0255550 A1 | 10/2010 | Benning et al. |
| 2018/0230420 A1 | 8/2018 | Bonito et al. |

OTHER PUBLICATIONS

Gorbushina et al., Mycol. Res., 2005, 109(11):1288-1296.*
"U.S. Appl. No. 15/894,457, Advisory Action dated May 1, 2020", 3 pgs.
"U.S. Appl. No. 15/894,457, Final Office Action dated Feb. 24, 2020", 10 pgs.
"U.S. Appl. No. 15/894,457, Non-Final Office Action dated Aug. 19, 2019", 10 pgs.
"U.S. Appl. No. 15/894,457, Notice of Allowance dated Jun. 17, 2020", 9 pgs.
"U.S. Appl. No. 15/894,457, Response filed Apr. 24, 2020 to Final Office Action dated Feb. 24, 2020", 9 pgs.
"U.S. Appl. No. 15/894,457, Response Filed Jul. 3, 2019 to Restriction Requirement dated May 10, 2019", 6 pgs.
"U.S. Appl. No. 15/894,457, Response filed Dec. 19, 2019 to Non-Final Office Action dated Aug. 19, 2019", 11 pgs.
"U.S. Appl. No. 15/894,457, Restriction Requirement dated May 10, 2019", 6 pgs.
"International Application Serial No. PCT/US2020/020412, International Search Report dated Jun. 15, 2020", 3 pgs.
"International Application Serial No. PCT/US2020/020412, Written Opinion dated Jun. 15, 2020", 7 pgs.
Ahmadjian, V., "Artificial Reestablishment of the Lichen Cladonia cristatella", Science 151(3707), (1966), 199-201.
An, G., "[17] Binary ti vectors for plant transformation and promoter analysis", Methods in Enzymology, vol. 153, (1987), 292-305.
Atsatt, P. R., "Are vascular plants "inside-out" lichens?", Ecology. 69(1), (1988), 17-23.
Behera, et al., Food Technol. Biotechnol, (2009), 47(1):7-12.
Bevan, M., "Binary Agrobacterium vectors for plant transformation.", Nucleic Acids Research, 12(22), (1984), 8711-8721.
Bonfante, P., et al., "Mechanisms underlying beneficial plant-fungus interactions in mycorrhizal symbiosis", Nat. Commun. 1:48, (2010), 1-11.

(Continued)

*Primary Examiner* — Bin Shen
(74) *Attorney, Agent, or Firm* — Schwegman Lundberg & Woessner, P.A.

(57) ABSTRACT

This application describes consortium between fungi and algae, where the algae are incorporated within hyphae of the fungi. The fungi, the algae, or both can be modified to express heterologous lipid synthesizing enzymes. Incorporation of algae into fungi facilitates harvesting of the algae and products produced by the consortia. Such consortia are robust. For example, the fungi and algae can symbiotically provide nutrients to each other and are tolerant of environmental stresses.

24 Claims, 35 Drawing Sheets
(28 of 35 Drawing Sheet(s) Filed in Color)
Specification includes a Sequence Listing.

(56) References Cited

OTHER PUBLICATIONS

Bonito, G., et al., "Isolating a functionally relevant guild of fungi from the root microbiome of Populus", Fungal Ecol. 22, (Aug. 2016), 35-42.
Brenner, K., et al., "Engineering microbial consortia: a new frontier in synthetic biology", Trends Biotechnol. 26(9), (2008), 483-489.
Chen, H. L., et al., "Conditional production of a functional fish growth hormone in the transgenic line of Nannochloropsis oculata (Eustigmatophyceae)", J. Phycol., 44(3), (2008), 768-776.
Delaux, P.-M., et al., "Algal ancestor of land plants was preadapted for symbiosis", Proc. Natl. Acad. Sci. USA. 112(43), (2015), 13390-13395.
Field, K. J., et al., "Functional analysis of liverworts in dual symbiosis with Glomeromycota and Mucoromycotina fungi under a simulated Palaeozoic CO2 decline", ISME J. 10, (2015), 1514-1526.
Field, K. J., et al., "Symbiotic options for the conquest of land", Trends Ecol. Evol. 30(8), Pressel, (2015), 477-486.
Georgianna, D. R., et al., "Exploiting diversity and synthetic biology for the production of algal biofuels", Nature 2012, 488(7411), (2012), 329-335.
Hom, E. F. Y., et al., "Niche engineering demonstrates a latent capacity for fungal-algal mutualism", Science, 345(6192), (2014), 94-98.
Jefferson, R. A., "Assaying Chimeric Genes in Plants: The GUS Gene Fusion System", Plant Mol. Biol. Rep., 5(4), (1987), 387-405.
Jia, Jing, et al., "Molecular mechanisms for photosynthetic carbon partitioning into storage neutral lipids in Nannochloropsis oceanica under nitrogen-depletion conditions", (Abstract Only), Algal Research, vol. 7, (2015), 66-77, (Jan. 2015), 1 page.
Little, A. F., et al., "Flexibility in Algal Endosymbioses Shapes Growth in Reef Corals", Science. 304(5676), (2004), 1492-1494.
Mollenhauer, D., "Studies on initiation and development of the partner association in Geosiphon pyriforme (Kütz.) v. Wettstein, a unique endocytobiotic system of a fungus (Glomales) and the cyanobacterium Nostoc punctiforme (Kütz.) Hariot", Protoplasma. 193(1-4), (1996), 3-9.
Murakami, T., et al., "The Bialaphos Biosynthetic Genes of Streptomyces hygroscopicus: Molecular Cloning and Characterization of the Gene Cluster", Mol. Gen. Genet., 205, (1986), 42-50.
Okamoto, N., et al., "A secondary symbiosis in progress?", Science, 310(5746), (2005), p. 287.
Partida-Martinez, I. P., et al., "A Gene Cluster Encoding Rhizoxin Biosynthesis in "Burkholderia Rhizoxina", the Bacterial Endosymbiont of the Fungus Rhizopus microsporus", Chembiochem., 8(1), (2007), 41-45.
Poliner, E., et al., "Transcriptional coordination of physiological responses in Nannochloropsis oceanicaCCMP1779 under light/dark cycles", The Plant Journal, 83(6), (2015), 1097-1113.
Redecker, D., et al., "Glomalean fungi from the Ordovician", Science. 289(5486), (2000), 1920-1921.
Scholz, M. J., et al., "Ultrastructure and Composition of the Nannochloropsis gaditana Cell Wall", Eukaryot. Cell. 13, (2014), 1450-1464.
Service, R. F., et al., "Algae's Second Try", Science, 333(6047), (2011), 1238-1239.
Simon, J., et al., "Self-supporting artificial system of the green alga Chlamydomonas reinhardtii and the ascomycetous fungus Alternaria infectoria", Symbiosis, 71(3), (Mar. 2017), 199-209.
Spatafora, J. W., et al., "A phylum-level phylogenetic classification of zygomycete fungi based on genome-scale data", Mycologia, 108(5), (2016), 1028-1046.
Thillet, J., et al., "Site-directed Mutagenesis of Mouse Dihydrofolate Reductase. Mutants with increased resistance to methotrexate and trimethoprim", The Journal of Biological Chemistry, 263(25), (Sep. 5, 1988), 12500-12508.
Tisserant, E., et al., "Genome of an arbuscular mycorrhizal fungus provides insight into the oldest plant symbiosis", Proc. Natl. Acad. Sci. USA. 110(50), (2013), 20117-20122 (8 pgs.).
Tsai, C.-H., et al., "The protein Compromised Hydrolysis of Triacylglycerols 7 (CHT7) acts as a repressor of cellular quiescence in Chlamydomonas", Proc. Natl. Acad. Sci. USA, 111, (2014), 15833-15838.
Velichkov, A. D., et al., "A simple procedure for dissolving fungal cell wall preparations for the analysis of neutral sugars", World J. Microbiol. Biotechnol., 8(5), (1992), 527-528.
Vieler, A., et al., "Genome, Functional Gene Annotation, and Nuclear Transformation of the Heterokont Oleaginous Alga Nannochloropsis oceanica CCMP1779", PLoS Genet. 8(11): e1003064, (2012), 1-25.
Wodniok, S., et al., "Origin of land plants: do conjugating green algae hold the key?", BMC Evol. Biol. 11:104, (2011), 10 pgs.
Zienkiewicz, K., et al., "Nannochloropsis, a rich source of diacylglycerol acyltransferases for engineering of triacylglycerol content in different hosts", Biotechnol Biofuels, 10:8, (2017), 20 pgs.
"U.S. Appl. No. 15/894,457, Corrected Notice of Allowability dated Jul. 13, 2020", 2 pgs.

* cited by examiner

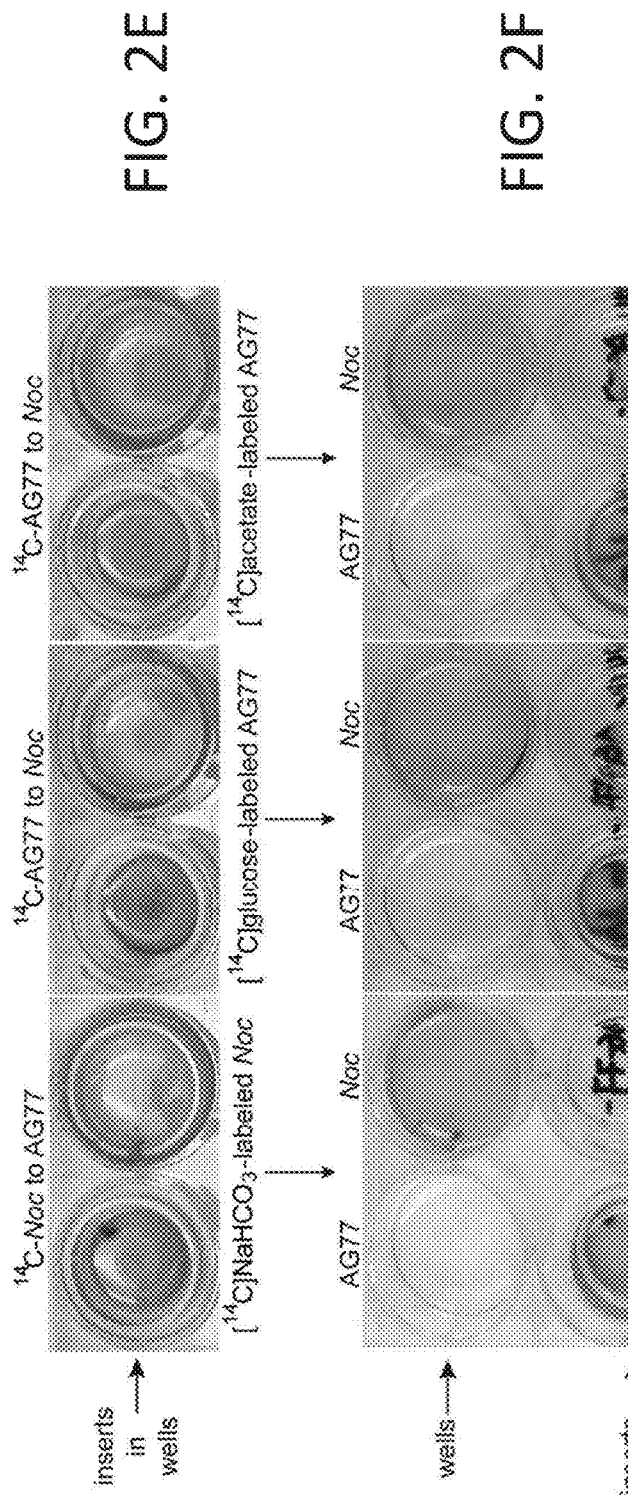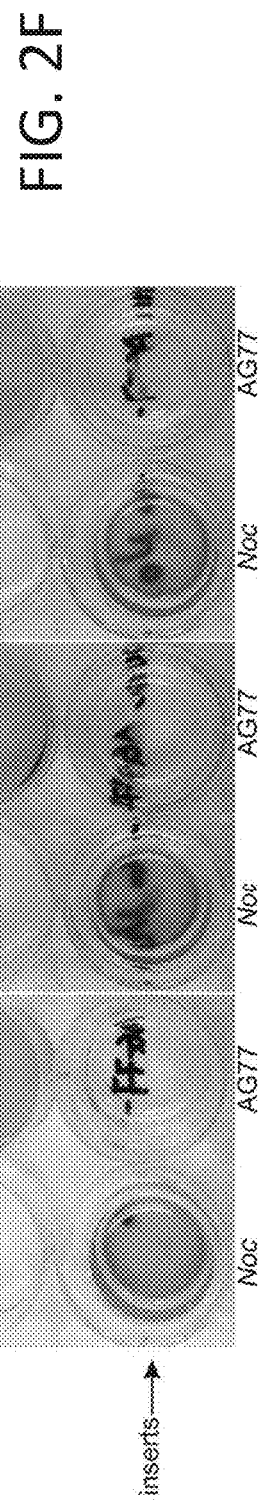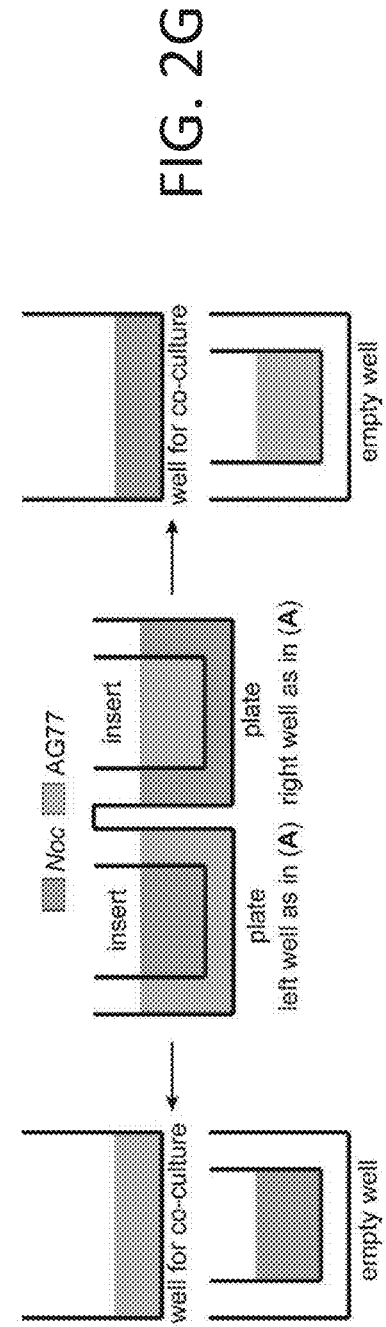

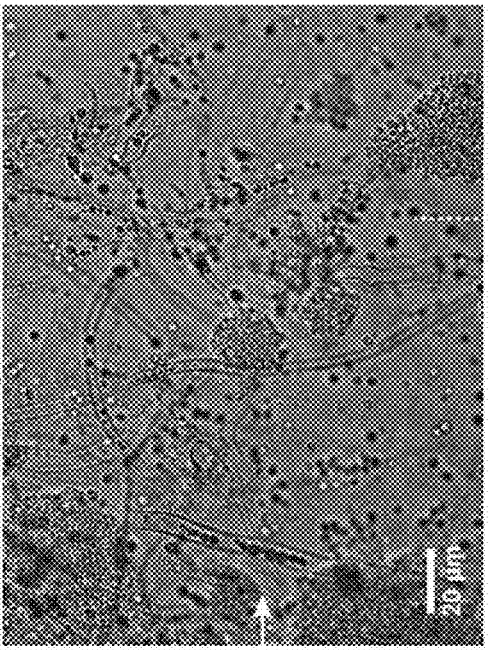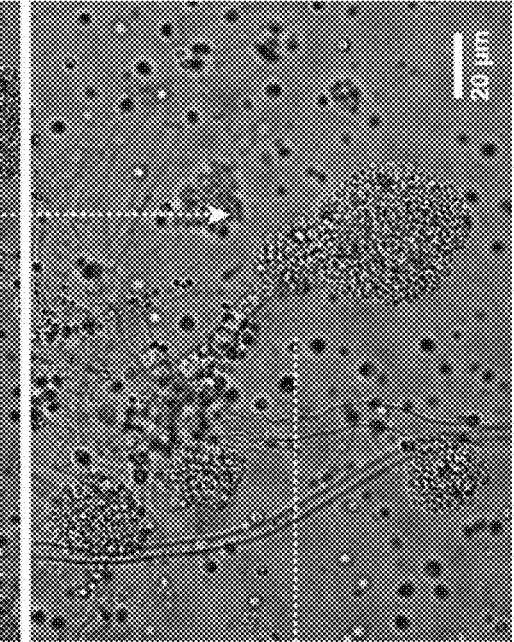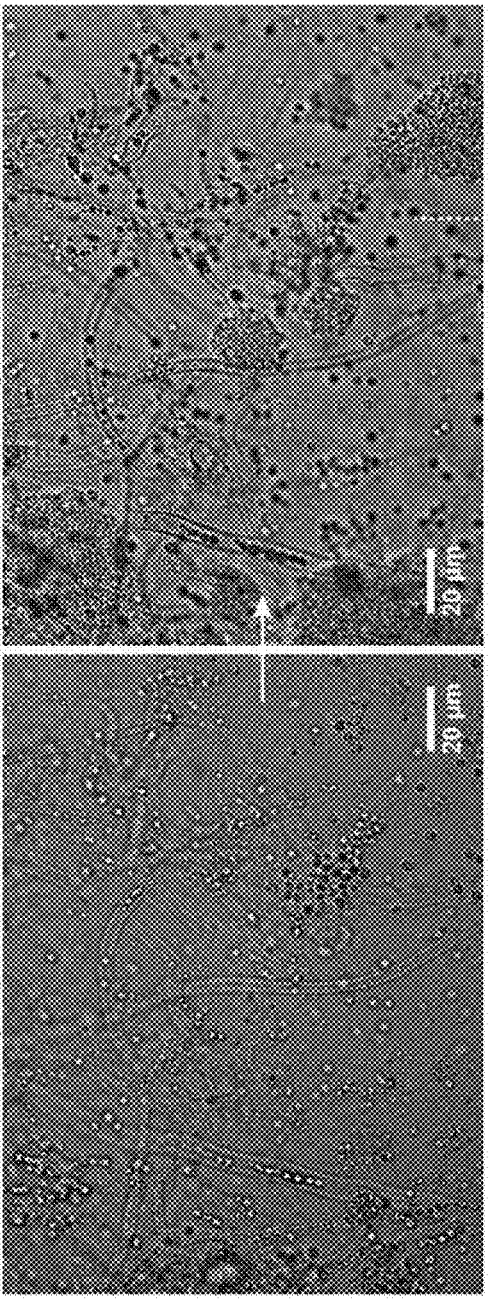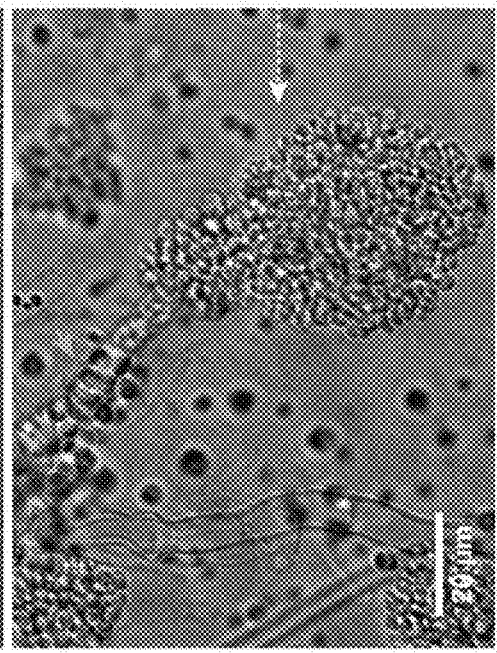
FIG. 4I-1  FIG. 4I-2  FIG. 4I-3  FIG. 4I-4

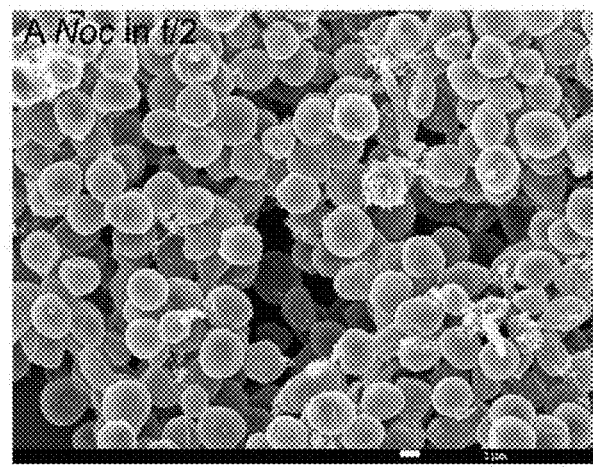
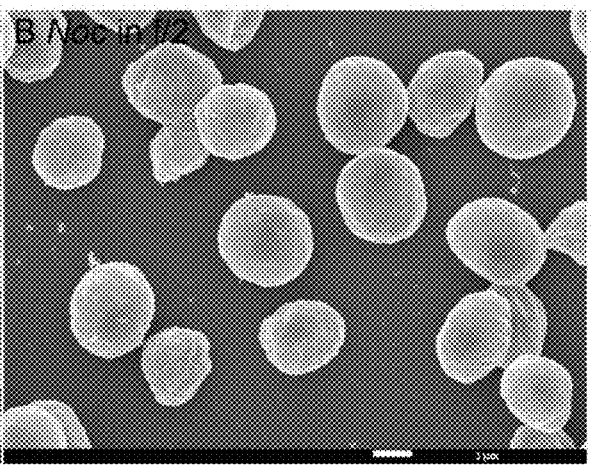
FIG. 5A        FIG. 5B
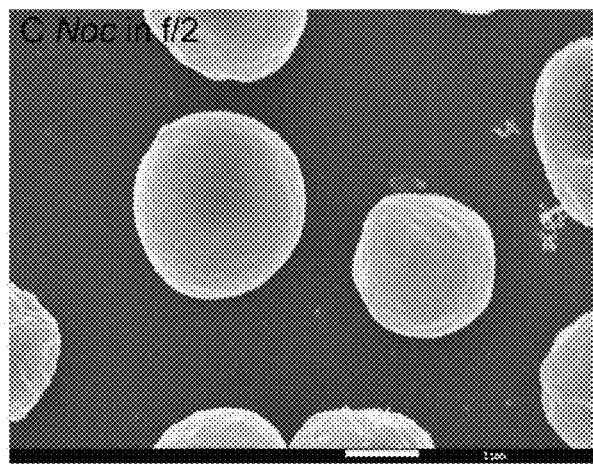
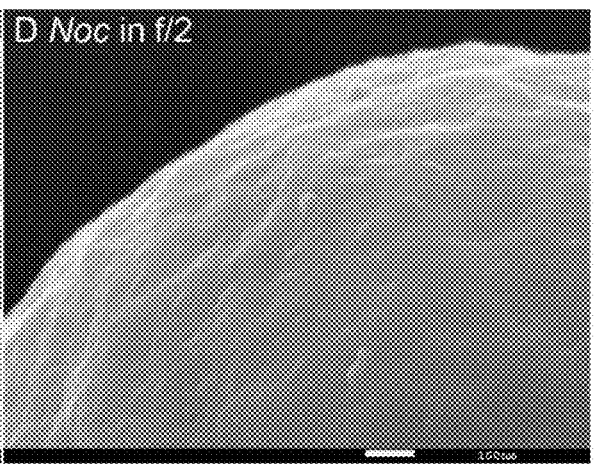
FIG. 5C        FIG. 5D

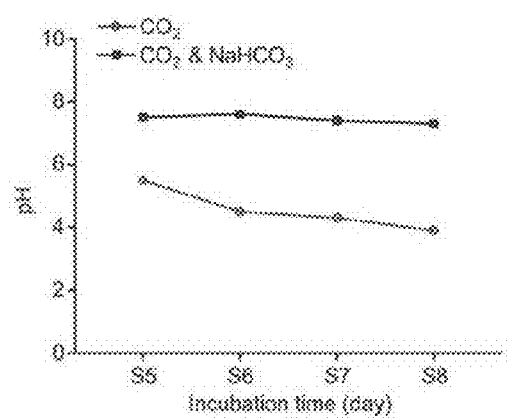 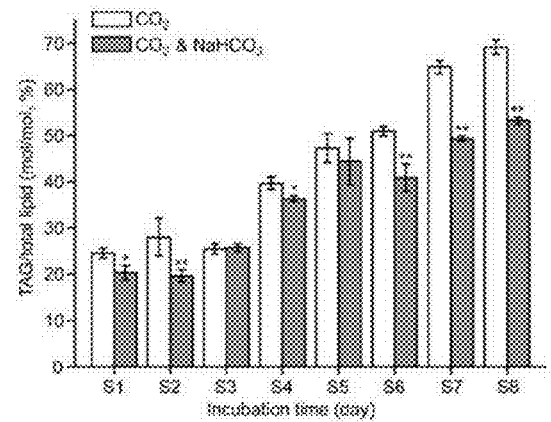
FIG. 14A          FIG. 14B
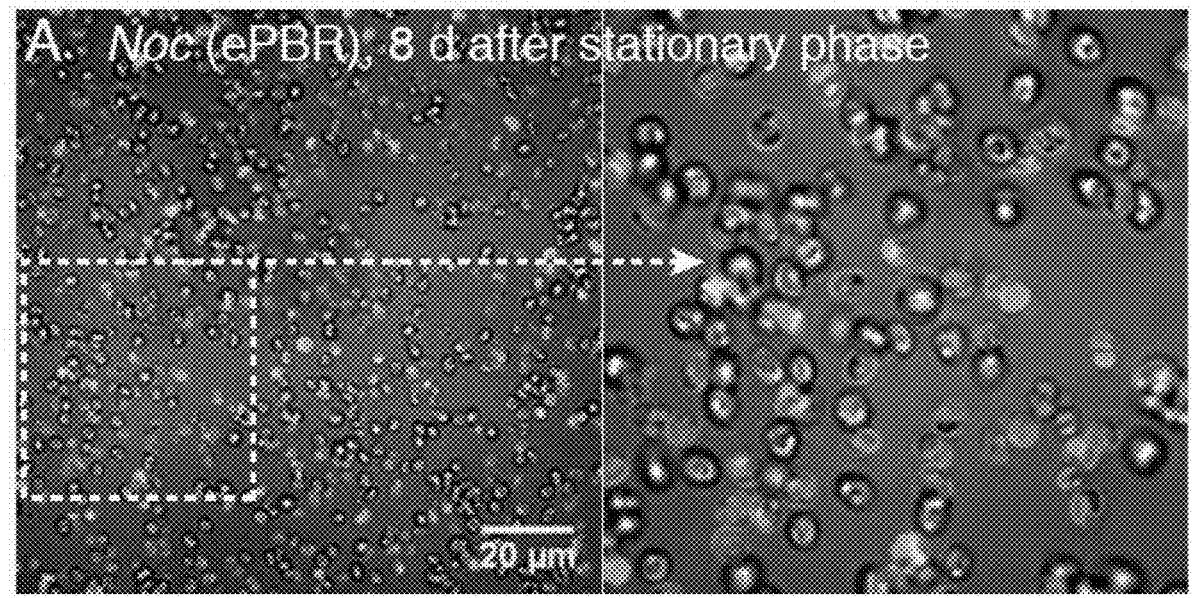
FIG. 15A

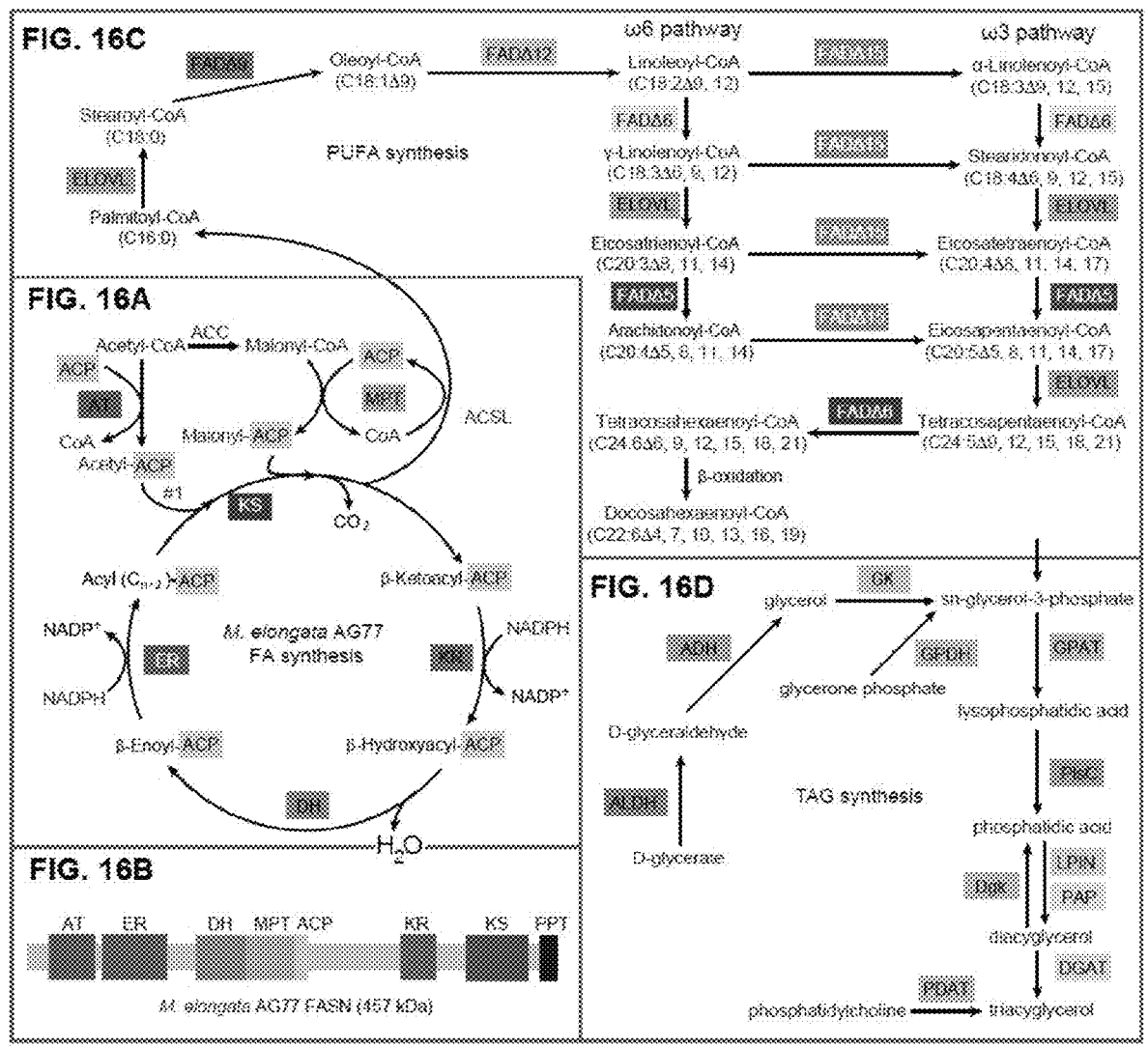

SEQUENCE LISTING

<160> NUMBER OF SEQ ID NOS: 112

<210> SEQ ID NO 1
<211> LENGTH: 19
<212> TYPE: DNA
<213> ORGANISM: N. oceanica

<400> SEQUENCE: 1
agaggagcca tggtaggac                                                    19

<210> SEQ ID NO 2
<211> LENGTH: 17
<212> TYPE: DNA
<213> ORGANISM: N. oceanica

<400> SEQUENCE: 2
tcgttccacg cgctggg                                                      17

<210> SEQ ID NO 3
<211> LENGTH: 19
<212> TYPE: DNA
<213> ORGANISM: M. elongata

<400> SEQUENCE: 3
cttgccaccc ttgccatcg                                                    19

<210> SEQ ID NO 4
<211> LENGTH: 21
<212> TYPE: DNA
<213> ORGANISM: M. elongata

<400> SEQUENCE: 4
aacgtcgtcg ttatcggaca c                                                 21

<210> SEQ ID NO 5
<211> LENGTH: 19
<212> TYPE: DNA
<213> ORGANISM: M. elongata

<400> SEQUENCE: 5
tcacgwcctc ccatggcgt                                                    19

<210> SEQ ID NO 6
<211> LENGTH: 20
<212> TYPE: DNA
<213> ORGANISM: M. elongata

<400> SEQUENCE: 6
aaggagggtc gtcttcgtgg                                                   20

<210> SEQ ID NO 7
<211> LENGTH: 2226
<212> TYPE: PRT
<213> ORGANISM: Mortierella elongata

<400> SEQUENCE: 7

Met Thr Ser Asn Val Gln Ser Phe Ile Gly Gly Asn Ala Leu Asp Lys
1               5                   10                  15

Ala Pro Ala Gly Ala Val His Asp Phe Val Ser Gln His Gly Gly His
                20                  25                  30

Ser Val Ile Thr Lys Ile Leu Ile Ala Asn Asn Gly Ile Ala Ala Val
        35                  40                  45

```
Lys Glu Ile Arg Ser Val Arg Lys Trp Ala Tyr Glu Thr Phe Gly Asp
    50                  55                  60
Glu Arg Ala Ile Gln Phe Thr Val Met Ala Thr Pro Glu Asp Leu Lys
 65                  70                  75                  80
Val Asn Ala Glu Tyr Ile Arg Met Ala Asp Gln Tyr Val Glu Val Pro
                 85                  90                  95
Gly Gly Ser Asn Asn Asn Tyr Ala Asn Val Asp Leu Ile Val Asp
                100                 105                 110
Ile Ala Glu Arg Thr Gly Val His Ala Val Trp Ala Gly Trp Gly His
                115                 120                 125
Ala Ser Glu Asn Pro Lys Leu Pro Glu Ser Leu Arg Asp Ser Pro Gln
130                 135                 140
Lys Ile Ile Phe Ile Gly Pro Pro Gly Ser Ala Met Arg Ser Leu Gly
145                 150                 155                 160
Asp Lys Ile Ser Ser Thr Ile Val Ala Gln Ser Ala Asp Val Pro Thr
                165                 170                 175
Met Gly Trp Ser Gly Thr Gly Ile Thr Glu Thr Glu Met Asp Pro Asn
                180                 185                 190
Gly Phe Val Thr Val Pro Glu Asp Ala Tyr Gln Ala Ala Cys Val Thr
                195                 200                 205
Asp Ala Glu Asp Gly Leu Lys Lys Ala His Ala Ile Gly Phe Pro Ile
210                 215                 220
Met Ile Lys Ala Ser Glu Gly Gly Gly Gly Lys Gly Ile Arg Lys Val
225                 230                 235                 240
Glu Asp Pro Glu Lys Phe Ala Gln Ala Phe His Gln Val Leu Gly Glu
                245                 250                 255
Val Pro Gly Ser Pro Val Phe Ile Met Lys Leu Ala Gly Asn Ala Arg
                260                 265                 270
His Leu Glu Val Gln Leu Leu Ala Asp Gln Tyr Gly His Ala Ile Ser
                275                 280                 285
Leu Phe Gly Arg Asp Cys Ser Val Gln Arg Arg His Gln Lys Ile Ile
                290                 295                 300
Glu Glu Ala Pro Val Thr Ile Ala Lys Pro Asp Thr Phe Glu Ala Met
305                 310                 315                 320
Glu Lys Ala Ala Val Arg Leu Ala Lys Leu Val Gly Tyr Val Ser Ala
                325                 330                 335
Gly Thr Val Glu Tyr Leu Tyr Ser His Ala Thr Asp Thr Tyr Phe Phe
                340                 345                 350
Leu Glu Leu Asn Pro Arg Leu Gln Val Glu His Pro Thr Thr Glu Ile
                355                 360                 365
Val Ser Gly Val Asn Leu Pro Ala Ala Gln Leu Gln Ile Ala Met Gly
370                 375                 380
Leu Pro Leu Asn Arg Ile Lys Asp Ile Arg Val Leu Tyr Gly Leu Gln
385                 390                 395                 400
Pro Ser Gly Thr Ser Glu Ile Asp Phe Glu Phe Ala Gln Gln Val Ser
                405                 410                 415
Phe Glu Thr Gln Arg Lys Pro Ala Pro Lys Gly His Val Ile Ala Val
                420                 425                 430
Arg Ile Thr Ala Glu Asn Pro Asp Ala Gly Phe Lys Pro Ser Ser Gly
                435                 440                 445
Met Met His Asp Leu Asn Phe Arg Ser Thr Asn Val Trp Gly Tyr
450                 455                 460
Phe Ser Val Ser Ser Ala Gly Gly Leu His Glu Phe Ala Asp Ser Gln
```

```
465                 470                 475                 480

Phe Gly His Ile Phe Ala Tyr Gly Gln Asp Arg Gly Gln Ser Arg Lys
                485                 490                 495

Asn Met Val Val Ala Leu Lys Glu Leu Ser Ile Arg Gly Asp Phe Arg
                500                 505                 510

Thr Thr Val Glu Tyr Leu Ile Arg Leu Leu Glu Thr Gln Glu Phe Glu
                515                 520                 525

Glu Asn Thr Ile Asn Thr Gly Trp Leu Asp Ser Leu Ile Ser Asn Asn
            530                 535                 540

Leu Thr Ala Glu Arg Pro Glu Thr Met Leu Ala Val Met Cys Gly Ala
545                 550                 555                 560

Val Asn Arg Ala His Thr Ile Ser Glu Asn Cys Leu Lys Glu Tyr Lys
                565                 570                 575

Lys Ser Leu Glu Lys Gly Gln Ile Pro Ser Lys Asp Val Leu Arg Ser
                580                 585                 590

Val Asn Gln Leu Asp Phe Ile Tyr Asp Gly Val Arg Tyr Asn Phe Thr
            595                 600                 605

Ala Thr Arg Ser Gly Pro Asn Ser Tyr Thr Met Tyr Leu Asn Gly Ser
            610                 615                 620

Met Ile Ser Ile Ser Val Arg Pro Leu Thr Asp Gly Gly Leu Leu Val
625                 630                 635                 640

Leu Leu Asp Gly Lys Ala His Thr Thr Tyr Ser Leu Glu Glu Val Gln
                645                 650                 655

Ala Thr Arg Leu Met Val Asp Gly Lys Thr Cys Leu Leu Glu Lys Glu
                660                 665                 670

Asn Asp Pro Thr Gln Leu Arg Ser Pro Ser Pro Gly Lys Leu Val Arg
                675                 680                 685

Phe Leu Val Glu Ser Gly Asp His Val Lys Ala Ser Gln Ala Tyr Ala
                690                 695                 700

Glu Ile Glu Val Met Lys Met Tyr Met Pro Leu Ile Ala Thr Glu Asp
705                 710                 715                 720

Gly Ile Val Gln Phe Ile Lys Gln Pro Gly Thr Thr Leu Asp Ala Gly
                725                 730                 735

Asp Ile Ile Gly Ile Leu Ser Leu Asp Asp Pro Ser Arg Val Lys His
                740                 745                 750

Ala Lys Pro Phe Glu Gly Gln Leu Pro Pro Met Gly Gln Pro Thr Ile
                755                 760                 765

His Gly Ala Lys Pro His Gln Arg Tyr Arg Glu Leu Arg Leu Ile Leu
                770                 775                 780

Asp Asn Ala Met Asp Gly Tyr Asp Asn Gln Ala Leu Val Gln Pro Thr
785                 790                 795                 800

Leu Lys Glu Ile Phe Glu Val Leu Gln Thr Pro Glu Leu Pro Tyr Leu
                805                 810                 815

Glu Phe Asn Glu Val Phe Ala Ala Leu Ser Gly Arg Ile Pro Pro Lys
                820                 825                 830

Leu Glu Ile Ser Leu His Gln Glu Val Asp Gln Ser Met Lys Asn His
                835                 840                 845

Glu His Phe Pro Ala Arg Thr Leu Gln Ala Leu Ile Asp Ala His Cys
                850                 855                 860

Arg Ala Asn Phe Ser Lys Pro Ala Asp Val Ser Ser Phe Leu Ala Ser
865                 870                 875                 880

Val Ala Pro Leu Thr Thr Ile Ile Gln Glu Tyr Gln Thr Gly Leu Lys
                885                 890                 895
```

```
Thr His Ser Trp Thr Phe Ile Ala His Tyr Leu Thr Lys Tyr His Glu
            900                 905                 910
Val Glu Ser Leu Phe Asp Asp Ser Ala Arg Glu Glu Glu Thr Ile Leu
            915                 920                 925
Ala Ile Arg Asp Gln Tyr Lys Asp Asp Val Lys Val Ile Asn Ile
            930                 935                 940
Ala Leu Ser His Ser Arg Val Thr Ala Lys Asn Asn Leu Val Leu Ser
945                 950                 955                 960
Leu Leu Asp Gln Ile Lys Pro Thr Ser Gly Gly Ala Leu Asp Lys
            965                 970                 975
Phe Phe Ser Pro Ile Leu Lys Lys Leu Ala Glu Leu Asn Gly Arg Leu
            980                 985                 990
Thr Ser Lys Val Ser Leu Lys Ala Arg Glu Leu Leu Ile His Val Gln
            995                 1000                1005
Leu Pro Ser Phe Glu Glu Arg Gln Ala Gln Met Glu Lys Ile Leu Arg
            1010                1015                1020
Ser Ser Val Thr Glu Glu Ile Tyr Gly Gly Asp His Glu Ala Arg Met
1025                1030                1035                1040
Pro Asn Tyr Asp Asn Leu Lys Glu Leu Val Asp Thr Thr Tyr Thr Val
            1045                1050                1055
Phe Asp Val Leu Pro Asn Phe Phe Tyr His Glu Ser Ala His Val Arg
            1060                1065                1070
Leu Ala Ala Phe Glu Val Tyr Cys Arg Arg Ala Tyr His Ala Tyr Glu
            1075                1080                1085
Ile Leu Asp Ile Asn Tyr His Met Glu His Asn Pro Leu Leu Ile Thr
            1090                1095                1100
Trp Lys Phe Leu Leu Asn Thr Pro Asn Lys Ser Ser Glu Gly Gly Pro
1105                1110                1115                1120
Asn Arg Val Ala Ser Val Ser Asp Met Ser Tyr Leu Ile Asn Lys Ala
            1125                1130                1135
Asp Pro Glu Pro Val Arg Thr Gly Gly Ile Leu Ala Val Arg Asp Ile
            1140                1145                1150
Lys Glu Leu Glu Gly Arg Phe Gln Ser Val Leu Asp Phe Phe Pro Thr
            1155                1160                1165
Val Lys Ser Asn Lys His Leu Ala His Val Gln Ala Thr Ser Val His
            1170                1175                1180
Asn Asn Val Leu Asn Val Val Leu Lys Ser Glu Ser Ile His Pro Asn
1185                1190                1195                1200
Asp Asp Asp Tyr Trp Leu Asn Leu Leu Ser Pro Ile Val Lys Gly Gln
            1205                1210                1215
Ser Glu His Leu Arg Ser His Gly Ile Arg Arg Met Thr Phe Leu Ile
            1220                1225                1230
Phe Arg Gln Gly Asn Tyr Pro Ser Tyr Phe Thr Phe Arg Glu Arg Asn
            1235                1240                1245
Asn Tyr Ala Glu Asp Gln Thr Ile Arg His Ile Glu Pro Ala Met Ala
            1250                1255                1260
Tyr Arg Leu Glu Leu Ser Arg Leu Ser Asn Phe Asp Ile Lys Pro Cys
1265                1270                1275                1280
Phe Ile Asp Asn Arg Gln Val His Val Tyr Tyr Ala Val Gly Lys Glu
            1285                1290                1295
Asn Val Ser Asp Cys Arg Phe Phe Val Cys Ala Leu Val Arg Pro Gly
            1300                1305                1310
```

```
Arg Leu Arg Ser Ser Val Arg Thr Ala Asp Tyr Leu Ile Ser Glu Thr
        1315                1320                1325

Asp Arg Leu Leu Asn Asp Ile Leu Asp Ala Leu Glu Ile Val Gly Ala
        1330                1335                1340

Thr Tyr Lys Gln Ser Asp Cys Asn His Leu Phe Ile Asn Phe Ile Pro
1345                1350                1355                1360

Thr Phe Gln Leu Asp Ala Thr Glu Val Glu Ser Ala Leu Lys Gly Phe
            1365                1370                1375

Ile Asp Arg His Gly Lys Arg Leu Trp Arg Leu Arg Val Thr Gly Ala
        1380                1385                1390

Glu Ile Arg Phe Asn Val Gln Ser Lys Asn Asp Ala Ala Asp Pro Ile
        1395                1400                1405

Pro Leu Arg Phe Ile Ile Ser Asn Val Ser Gly Tyr Val Leu Asn Val
        1410                1415                1420

Asp Thr Tyr Arg Glu Ile Gln Thr Asp Lys Gly Ala Ile Phe Lys Ser
1425                1430                1435                1440

Val Gly Pro Ser Gly Pro Phe His Leu Leu Pro Val Asn Gln Pro Tyr
            1445                1450                1455

Pro Thr Lys Glu Trp Leu Gln Pro Arg Arg Tyr Lys Ala His Leu Met
            1460                1465                1470

Gly Thr Thr Tyr Val Tyr Asp Phe Gly Glu Leu Phe Arg Gln Ala Val
            1475                1480                1485

Arg Ala Gln Trp Asn His Ala Val Lys Val Asn Pro Ser Leu Lys Ala
            1490                1495                1500

Pro Asn Gln Val Leu Glu Met Arg Glu Leu Val Leu Asp Glu Lys Gln
1505                1510                1515                1520

Gln Leu Gln Gln Val Val Arg Glu Ala Gly Ser Asn Asn Cys Gly Met
            1525                1530                1535

Val Ala Trp Ile Phe Thr Leu Arg Thr Pro Glu Tyr Pro Glu Gly Arg
            1540                1545                1550

Gln Ile Ile Val Ile Ala Asn Asp Ile Thr Tyr Asn Ile Gly Ser Phe
            1555                1560                1565

Gly Pro Glu Glu Asp Leu Val Phe Tyr Lys Ala Ser Glu Leu Ala Arg
            1570                1575                1580

Lys Leu Gly Ile Pro Arg Val Tyr Leu Ser Ala Asn Ser Gly Ala Arg
1585                1590                1595                1600

Ile Gly Leu Ala Ser Glu Val Ile Gly Leu Phe Asn Ser Cys Trp Asn
            1605                1610                1615

Asp Ala Ser Asn Pro Ser Lys Gly Phe Lys Tyr Ile Tyr Leu Thr Asp
            1620                1625                1630

Ala Gly Leu Lys Gln Leu Glu Ala Gln Glu Glu Arg Ser Gly Lys Lys
            1635                1640                1645

Ser Val Leu Thr Glu Thr Val Val Glu Asp Gly Glu Thr Arg His Lys
1650                1655                1660

Ile Thr Asp Val Ile Gly Ala Val Asp Gly Leu Gly Val Glu Asn Leu
1665                1670                1675                1680

Arg Gly Ser Gly Leu Ile Ala Gly Glu Thr Ser Arg Ala Tyr Asp Asp
            1685                1690                1695

Ile Phe Thr Ile Thr Leu Val Thr Cys Arg Ser Val Gly Ile Gly Ala
            1700                1705                1710

Tyr Leu Val Arg Leu Gly Gln Arg Thr Ile Gln Asn Glu Gly Gln Pro
            1715                1720                1725

Ile Ile Leu Thr Gly Ala Pro Ala Leu Asn Lys Leu Leu Gly Arg Asp
```

1730                1735               1740
Val Tyr Thr Ser Asn Leu Gln Leu Gly Gly Thr Gln Ile Met Tyr Lys
1745                1750                1755               1760

Asn Gly Val Ser His Leu Thr Ala Gln Asn Asp Tyr Glu Gly Ile Gly
                    1765                1770               1775

Lys Ile Val Asn Trp Leu Ser Tyr Ile Pro Glu Arg Lys Asn Ala Pro
                    1780                1785               1790

Val Pro Ile Thr Val Ser Asn Asp Thr Trp Asp Arg Asp Ile Asp Tyr
                    1795                1800               1805

Leu Pro Pro Lys Gly Ala Val Tyr Asp Pro Arg Trp Leu Ile Gly Gly
                    1810                1815               1820

Lys Asp Ala Glu Glu Gly Ala Ala Phe Gln Thr Gly Phe Phe Asp
1825                1830                1835               1840

Lys Gly Ser Phe Thr Glu Thr Leu Thr Gly Trp Ala Arg Thr Val Val
                    1845                1850               1855

Val Gly Arg Ala Arg Leu Gly Gly Val Pro Met Gly Val Ile Ala Val
                    1860                1865               1870

Glu Thr Arg Ser Val Glu His Ile Ile Pro Ala Asp Pro Ala Asn Gly
                    1875                1880               1885

Asp Ser Val Glu Gln Val Leu Met Glu Ala Gly Asn Val Trp Tyr Pro
     1890                1895                1900

Asn Ser Ala Tyr Lys Thr Ala Gln Ala Ile Asn Asp Phe Asn Lys Gly
1905                1910                1915               1920

Glu Gln Leu Pro Leu Met Ile Phe Ala Asn Trp Arg Gly Phe Ser Gly
                    1925                1930               1935

Gly Gln Arg Asp Met Tyr Asn Glu Ile Leu Lys Tyr Gly Ser Phe Ile
                    1940                1945               1950

Val Asp Ala Leu Ser Ser Tyr Lys Gln Pro Val Phe Val Tyr Val Val
                    1955                1960               1965

Pro Asn Gly Glu Leu Arg Gly Gly Ala Trp Val Val Asp Pro Thr
     1970                1975                1980

Ile Asn Glu Asn Met Met Glu Met Tyr Ala Asp Lys Arg Ser Arg Ala
1985                1990                1995               2000

Gly Val Leu Glu Pro Glu Gly Ile Val Glu Ile Lys Phe Arg Lys Ala
                    2005                2010               2015

Gln Leu Leu Ala Thr Met Glu Arg Leu Asp Asp Lys Tyr Arg Asp Leu
                    2020                2025               2030

Lys Ala Gln Tyr Glu Lys Pro Asp Leu Ala Gly Ala Asp Arg Glu Ala
                    2035                2040               2045

Ile Lys Thr Lys Leu Thr Glu Arg Glu Gln Glu Leu Leu Pro Val Tyr
2050                2055                2060

Gln Gln Leu Ala Ile Gln Phe Ala Asp Leu His Asp Thr Ala Gly Arg
2065                2070                2075               2080

Met Lys Ala Lys Gly Thr Ile Arg Glu Ser Leu Asp Trp Thr Asn Ala
                    2085                2090               2095

Arg Arg Tyr Phe Tyr Trp Arg Val Arg Arg Arg Leu Ala Glu Glu Tyr
                    2100                2105               2110

Ile Arg Arg Arg Met Thr Ile Ala Ser Lys Thr Gln Thr Arg Asp Asp
                    2115                2120               2125

Gln Thr Ala Thr Leu Lys Ala Trp Phe Gly Arg Asp Thr Val His Ala
                    2130                2135               2140

Ser Glu Ala Glu Leu Thr Gln Ile Trp Glu His Glu Asp Arg Val Val
2145                2150                2155               2160

Leu Glu Trp Phe Glu Gly Gln Ser Arg Lys Val Asp Ala Leu Ile Gln
            2165                2170                2175

Glu Leu Thr Ala Ala Gly Thr Ala Glu Val Val Arg Met Tyr Thr
    2180                2185                2190

Ser Asp Arg Ala Gly Val Val Glu Gly Phe Arg Ile Leu Gln Ser
    2195                2200                2205

Leu Ser Asp Gln Glu Lys Gln Asp Ile Leu Ala Lys Phe Ala Thr Met
    2210                2215                2220

Thr Val
2225

<210> SEQ ID NO 8
<211> LENGTH: 2137
<212> TYPE: PRT
<213> ORGANISM: Nannochloropsis oculate

<400> SEQUENCE: 8

Met Ala Thr Thr Ile Pro Ser Ser Asn Arg Arg Ala Met Arg Ala Gly
1               5                   10                  15

Ala Ala Leu Val Ala Val Ser Ser Ile Leu Val Leu Leu Met Gly Pro
            20                  25                  30

Val Ala Glu Ala Trp Arg Val Pro Gly Phe Gly Gln Gly Arg Ser Ser
        35                  40                  45

Gly Val Thr Lys Pro Val His Ala Pro Gly Phe Leu Gly Arg Phe Ser
    50                  55                  60

Thr Pro Ser Ser Leu Gly Pro Ser Ser Ala Ser Cys Pro Thr Ile Ser
65              70                  75                  80

Ala Val Gly Pro Leu Ser Ala Ala Thr Met Ala Pro Pro Ala Leu Ser
                85                  90                  95

Pro Glu Ala Gln Lys Lys Lys Asp Ala Val Ala Ala Tyr Val Lys Ser
            100                 105                 110

Arg Gly Gly Asn Leu Ala Ile Arg Lys Val Leu Ile Ala Asn Asn Gly
        115                 120                 125

Met Ala Ala Thr Lys Ser Ile Leu Ser Met Arg Gln Trp Ala Tyr Met
130                 135                 140

Glu Leu Gly Asp Asp Arg Ala Ile Glu Phe Val Val Met Ala Thr Pro
145                 150                 155                 160

Glu Asp Leu Asn Ala Asn Ala Glu Phe Ile Arg Leu Ala Asp Arg Phe
                165                 170                 175

Val Glu Val Pro Gly Gly Ser Asn Lys Asn Asn Tyr Ala Asn Val Asp
            180                 185                 190

Leu Ile Val Gln Met Ala Gln Arg Glu Gly Val Asp Ala Val Trp Pro
        195                 200                 205

Gly Trp Gly His Ala Ser Glu Asn Pro Arg Leu Pro Asn Thr Leu Lys
    210                 215                 220

Gln Leu Gly Ile Lys Phe Ile Gly Pro Thr Gly Pro Val Met Ser Val
225                 230                 235                 240

Leu Gly Asp Lys Ile Ala Ala Asn Ile Leu Ala Gln Thr Ala Lys Val
                245                 250                 255

Pro Ser Ile Pro Trp Ser Gly Asp Gly Leu Thr Ala Glu Leu Thr Ala
            260                 265                 270

Glu Gly Thr Ile Pro Asp Glu Thr Phe Gln Lys Ala Met Val Arg Thr
        275                 280                 285

Ser Glu Glu Ala Leu Ala Ala Ala Asn Arg Ile Gly Tyr Pro Val Met

-continued

```
                290                 295                 300
Leu Lys Ala Ser Glu Gly Gly Gly Lys Gly Ile Arg Met Ser Asn
305                 310                 315                 320
Asn Asp Lys Glu Leu Glu Thr Asn Phe Ile Gln Val Gln Asn Glu Val
                325                 330                 335
Pro Gly Ser Pro Met Phe Met Met Gln Leu Cys Thr Gln Ala Arg His
                340                 345                 350
Ile Glu Val Gln Ile Val Gly Asp Glu His Gly Asn Ala Ala Ala Leu
                355                 360                 365
Asn Gly Arg Asp Cys Ser Thr Gln Arg Arg Phe Gln Lys Ile Phe Glu
370                 375                 380
Glu Gly Pro Pro Thr Ile Val Pro Pro Glu Val Phe Lys Gln Met Glu
385                 390                 395                 400
Leu Ala Ala Gln Arg Leu Thr Gln Ser Ile Gly Tyr Ile Gly Ala Gly
                405                 410                 415
Thr Val Glu Tyr Leu Phe Asn Ala Ala Thr Gly Lys Tyr Phe Phe Leu
                420                 425                 430
Glu Leu Asn Pro Arg Leu Gln Val Glu His Pro Val Thr Glu Gly Leu
435                 440                 445
Ser Leu Val Asn Leu Pro Ala Thr Gln Leu Gln Ile Ala Met Gly Ile
450                 455                 460
Pro Leu Asn Arg Ile Pro Asp Ile Arg Arg Phe Tyr Gly Lys Asp Asp
465                 470                 475                 480
Pro Tyr Gly Asp Ser Pro Ile Asp Phe Phe Asn Asp Asp Tyr Ala Glu
                485                 490                 495
Leu Pro Ser His Val Ile Ala Ala Arg Ile Thr Ala Glu Asn Pro Asp
                500                 505                 510
Glu Gly Phe Lys Pro Thr Ser Gly Arg Ile Glu Arg Val Lys Phe Gln
                515                 520                 525
Ser Thr Ala Asn Val Trp Gly Tyr Phe Ser Val Gly Ala Asn Gly Gly
530                 535                 540
Ile His Glu Tyr Ala Asp Ser Gln Phe Gly His Leu Phe Ala Lys Gly
545                 550                 555                 560
Lys Ser Arg Glu Asp Ala Arg Lys Ser Leu Val Leu Ala Leu Lys Glu
                565                 570                 575
Ile Glu Val Arg Gly Asp Ile Arg Thr Thr Val Glu Tyr Leu Val Gln
                580                 585                 590
Leu Leu Glu Thr Glu Ala Phe Lys Glu Asn Thr Ile Asp Thr Ser Trp
                595                 600                 605
Leu Asp Gly Leu Ile Arg Glu Lys Ser Val Arg Val Glu Leu Asn Pro
                610                 615                 620
His Asp Val Ala Leu Ser Ala Ala Ile Ala Arg Ala Phe Ala Arg Ser
625                 630                 635                 640
Val Asp Glu Glu Arg Lys Phe Val Glu Asn Leu Ser Lys Gly Gln Val
                645                 650                 655
Ser Ile Gln Gly Ile Arg Ser Ile Asn Ser Phe Pro Met Glu Ile Thr
                660                 665                 670
Tyr Lys Asp Tyr Lys Tyr Ser Phe His Cys Thr Arg Val Gly Pro Asp
                675                 680                 685
Lys Leu Arg Leu Ala Ile Asn Asp Gln Ile Leu Glu Thr Lys Val Arg
                690                 695                 700
Gln Gln Pro Asp Gly Ser Leu Ile Ala Glu Phe Gly Gly Thr Thr His
705                 710                 715                 720
```

```
Thr Ile Tyr Ala Leu Glu Glu Pro Leu Gly Leu Arg Met Val Leu Asp
                725                 730                 735

Gly Val Thr Val Leu Leu Pro Thr Val Tyr Asp Pro Ser Glu Leu Arg
            740                 745                 750

Thr Asp Val Thr Gly Lys Ile Val Arg Tyr Leu Gln Glu Asp Gly Thr
        755                 760                 765

Glu Ile Gln Ala Gly Gln Pro Tyr Val Glu Val Glu Ala Met Lys Met
    770                 775                 780

Ile Met Pro Leu Lys Ala Thr Glu Ser Gly Thr Val Ala His Arg Leu
785                 790                 795                 800

Ser Pro Gly Ser Ile Ile Thr Ala Gly Asp Leu Leu Ala Asn Val Gln
                805                 810                 815

Leu Lys Asp Pro Ser Lys Val Lys Lys Ile Thr Pro Phe Lys Gly Ala
            820                 825                 830

Leu Glu Leu Val Gly Ser Asp Asp Glu Pro Gly Val Thr Gly Phe Gln
        835                 840                 845

Ala Val Leu Lys Thr Met Asn Met Val Leu Asp Gly Tyr Asp Tyr Glu
    850                 855                 860

Val Glu Phe Leu Ala Gln Asn Leu Val Thr Ser Ala Gln Asp Gly Lys
865                 870                 875                 880

Glu Leu Leu Asp Ala Ala Thr Ala Leu Val Thr Lys Tyr Leu Ala Val
                885                 890                 895

Glu Glu Gln Phe Ala Gly Lys Val Leu Asp Glu Ala Met Val Gly Leu
            900                 905                 910

Val Lys Ala Asn Lys Asp Ser Leu Pro Thr Val Leu Ala Leu Ala Thr
        915                 920                 925

Ala His Arg Glu Leu Pro Arg Arg Asn Lys Met Val Ser Ala Leu Ile
    930                 935                 940

Arg Gln Leu Gln Ala Leu Val Glu Arg Ser Ser Asn Asp Leu Ser Leu
945                 950                 955                 960

Asp Thr Leu Ile Ala Leu Leu Asp Arg Ala Ser Arg Leu Pro Gly Lys
                965                 970                 975

Glu Tyr Gly Glu Val Ala Ile Ser Ser Ala Gln Ala Leu Leu Ala Leu
            980                 985                 990

Arg Ala Pro Pro Phe Ser Thr Arg Gln Asp Glu Leu Arg Thr Thr Leu
        995                 1000                1005

Leu Asn Thr Lys Asp Asn Asp Ala Leu Ala Arg Ser Ala Thr Leu Thr
    1010                1015                1020

Ala Gly Val Asp Leu Leu Thr Ala Met Phe Thr Asp Pro Asp Ala Asn
1025                1030                1035                1040

Val Arg Lys Asn Ala Ile Glu Val Tyr Ile Arg Arg Ile Tyr Arg Ala
                1045                1050                1055

His Arg Ile Leu Ser Leu Thr Val Glu Glu Val Asp Gly Val Met Ile
            1060                1065                1070

Ala Asn Trp Ser Phe Lys Phe Ala Asp Thr Pro Asp Glu Glu Ser Pro
        1075                1080                1085

Leu Arg Arg Gly Phe Phe Thr Val Phe Pro Ser Leu Glu Ala Tyr Thr
    1090                1095                1100

Ala Gly Ser Glu Lys Phe Ser Lys Val Leu Lys Thr Ala Leu Ala Gly
1105                1110                1115                1120

Gln Glu Ala Tyr Ser Gln Pro Thr Asn Val Phe His Val Ala Val Ala
                1125                1130                1135
```

-continued

```
Gln Leu Pro Glu Ser Gln Gln Pro Glu Val Ile Ala Asn Ile Glu Gly
                1140                1145                1150

Ile Leu Ala Glu Asn Lys Asp Leu Leu Thr Glu Cys Arg Val Arg Met
        1155                1160                1165

Val Asn Val Leu Phe Val Gln Gly Ala Lys Asn Pro Arg Tyr Phe Thr
    1170                1175                1180

Phe Thr Ala Val Lys Asp Phe Lys Glu Asp Pro Leu Arg Arg Asp Met
1185                1190                1195                1200

Arg Pro Thr Phe Pro Gln Leu Leu Glu Leu Ser Arg Leu Ala Ala Asn
                1205                1210                1215

Tyr Glu Leu Gln Arg Leu Pro Ser Ile Gly Arg Asn Thr Gln Val Tyr
        1220                1225                1230

Leu Gly Ser Glu Arg Ala Pro Val Gly Thr Lys Lys Arg Gly Pro Gly
            1235                1240                1245

Asn Gln Val Leu Phe Val Arg Gly Ile Ser His Ser Glu Gln Thr Gln
    1250                1255                1260

Thr Pro Met Gly Ala Glu Arg Val Leu Leu Met Ala Met Asp Glu Leu
1265                1270                1275                1280

Asp Tyr Ala Leu Leu Asp Glu Arg Val Gly Gly Ser Ala Ser Ser Arg
                1285                1290                1295

Leu Phe Leu Asn Leu Leu Val Pro Ile Asp Ser Asp Pro Lys Thr Leu
        1300                1305                1310

Ala Gly Glu Trp Ser Lys Ile Met Asp Arg Leu Leu Ala Lys Tyr Ala
            1315                1320                1325

Thr Arg Leu Leu Lys Leu Gly Val Asp Glu Ile Glu Ile Lys Val Arg
    1330                1335                1340

Val Ala Ala Gly Ser Gly Ser Ala Ile Thr Pro Val Arg Leu Met Ala
1345                1350                1355                1360

Ser Ser Met Thr Gly Glu Phe Leu Arg Thr Asp Ala Phe Leu Glu Tyr
                1365                1370                1375

Pro Asp Pro Val Thr Gly Ile Thr Lys Gln Phe Cys Ser Val Thr Ser
        1380                1385                1390

Glu Asp Gln Val Cys Leu Leu Asn Pro Tyr Pro Ala Ser Asn Ser Ile
            1395                1400                1405

Gln Thr Arg Arg Ala Ser Ala Arg Arg Ile Gly Ser Thr Tyr Ala Tyr
    1410                1415                1420

Asp Phe Leu Gly Val Met Glu Val Ser Leu Ile Gln Lys Trp Asp Lys
1425                1430                1435                1440

His Leu Lys Glu Leu Thr Ser Val Tyr Thr Ser Arg Val Asp Asp Lys
                1445                1450                1455

Met Pro Glu Gln Leu Phe Gln Ala Asp Glu Leu Val Leu Glu Asp Gly
        1460                1465                1470

Val Leu Lys Pro Thr Gln Arg Leu Val Gly Leu Asn Asp Val Gly Met
            1475                1480                1485

Val Ala Trp His Ala Thr Met Lys Thr Pro Glu Tyr Pro Glu Gly Arg
    1490                1495                1500

Glu Leu Val Ile Ile Ala Asn Asp Val Thr Phe Gln Ser Gly Ser Phe
1505                1510                1515                1520

Gly Val Lys Glu Asp Asp Phe Phe Arg Ala Ala Ser Glu Tyr Ala Arg
                1525                1530                1535

Val Arg Gly Leu Pro Arg Ile Tyr Leu Ser Ser Asn Ser Gly Ala Arg
        1540                1545                1550

Ile Gly Leu Val Asp Asp Leu Lys Gly Lys Phe Arg Ile Ala Trp Asn
```

-continued

```
                1555                1560                1565

Asp Pro Ala Asn Pro Ser Leu Gly Phe Lys Tyr Leu Tyr Leu Thr Pro
    1570                1575                1580

Glu Glu Tyr Glu Gly Leu Lys Pro Gly Thr Val Asn Ala Asn Leu Val
1585                1590                1595                1600

Leu Ser Glu Glu Gly Glu Lys Arg Trp Ala Leu Gln Asp Ile Ile Gly
                1605                1610                1615

Gln Val His Gly Ile Gly Val Glu Asn Leu Arg Gly Ser Gly Met Ile
                1620                1625                1630

Ala Gly Glu Thr Ser Arg Ala Tyr Asp Glu Thr Phe Thr Leu Ser Tyr
                1635                1640                1645

Val Thr Gly Arg Ser Val Gly Ile Gly Ala Tyr Leu Val Arg Leu Gly
                1650                1655                1660

Gln Arg Thr Ile Gln Met Val Asn Gly Pro Leu Ile Leu Thr Gly Tyr
1665                1670                1675                1680

Ser Ala Leu Asn Lys Leu Leu Gly Arg Glu Val Tyr Thr Ser Gln Asp
                1685                1690                1695

Gln Leu Gly Gly Pro Gln Ile Met Ala Pro Asn Gly Val Ser His Leu
                1700                1705                1710

Val Val Asp Asn Asp Lys Glu Gly Ile Ser Ser Ile Asp Trp Leu
                1715                1720                1725

Ser Phe Val Pro Lys Asp Lys Phe Ser Ser Val Pro Ile Ile Asp Leu
                1730                1735                1740

Pro Thr Asp Ser Pro Glu Arg Asp Val Glu Phe Gln Pro Thr Lys Thr
1745                1750                1755                1760

Pro Tyr Asp Pro Arg His Met Leu Ala Gly Thr Val Gly Pro Asp Gly
                1765                1770                1775

Ala Phe Val Pro Gly Phe Phe Asp Arg Gly Ser Phe Ile Glu Thr Leu
                1780                1785                1790

Gly Gly Trp Gly Lys Ser Val Val Thr Gly Arg Ala Lys Leu Gly Gly
                1795                1800                1805

Ile Pro Met Gly Ile Ile Ser Val Glu Thr Arg Thr Leu Val Glu Gln Arg
                1810                1815                1820

Ile Pro Ala Asp Pro Ala Asn Pro Glu Ser Arg Glu Ser Leu Leu Pro
1825                1830                1835                1840

Gln Ala Gly Gln Val Trp Tyr Pro Asp Ser Ala Phe Lys Thr Ala Gln
                1845                1850                1855

Ala Ile Glu Asp Phe Asn Arg Gly Glu Asn Leu Pro Leu Met Ile Phe
                1860                1865                1870

Ala Asn Trp Arg Gly Phe Ser Gly Gly Thr Arg Asp Met Tyr Gly Glu
                1875                1880                1885

Ile Leu Lys Phe Gly Ala Lys Ile Val Asp Ala Leu Arg Thr Tyr Arg
                1890                1895                1900

His Pro Val Phe Val Tyr Ile Pro Pro Asn Gly Glu Leu Arg Gly Gly
1905                1910                1915                1920

Ala Trp Val Val Ile Asp Pro Thr Ile Asn Glu Glu Met Met Glu Met
                1925                1930                1935

Tyr Ala Asp Lys Asp Ser Arg Gly Gly Ile Leu Glu Pro Pro Gly Ile
                1940                1945                1950

Cys Glu Val Lys Phe Arg Ala Ala Asp Gln Ile Ser Ala Met His Arg
                1955                1960                1965

Leu Asp Pro Val Ile Gln Ala Leu Asp Gly Glu Leu Gln Asn Ala Lys
                1970                1975                1980
```

```
Thr Glu Ala Asp Ala Ile Lys Leu Lys Gln Gln Leu Lys Glu Arg Glu
1985                1990                1995                2000

Glu Ala Leu Leu Pro Leu Tyr Met Gln Val Ala His Glu Phe Ala Asp
                2005                2010                2015

Leu His Asp Arg Ala Gly Arg Met Lys Ala Lys Gly Val Ile Arg Asp
                2020                2025                2030

Val Val Thr Trp Lys Arg Ser Arg Ser Tyr Phe Tyr Trp Arg Ala Arg
                2035                2040                2045

Arg Arg Val Ala Glu Asp Gly Leu Val Arg Ala Met Gln Lys Ala Asp
                2050                2055                2060

Ala Ser Leu Ser Val Gln Asp Gly Arg Glu Lys Leu Glu Ala Leu Ala
2065                2070                2075                2080

Thr Ser Gly Val Tyr Gly Asp Asp Lys Ala Phe Val Ala Trp Val Thr
                2085                2090                2095

Glu Ser Gly Ser Lys Ile Glu Glu Gln Leu Val Ser Val Lys His Ala
                2100                2105                2110

Ala Val Lys Ala Ser Leu Ala Ser Leu Leu Glu Glu Leu Ser Pro Glu
                2115                2120                2125

Glu Arg Lys Lys Val Leu Ser Gly Leu
        2130                2135

<210> SEQ ID NO 9
<211> LENGTH: 2139
<212> TYPE: PRT
<213> ORGANISM: Nannochloropsis gaditana

<400> SEQUENCE: 9

Met Ala Ser Phe Pro Pro Ser Asn Arg Arg Ala Thr Pro Ala Arg Val
1               5                   10                  15

Met Val Val Ile Phe Ser Ser Val Leu Ile Leu Leu Ala Gly Pro Val
                20                  25                  30

Gly Asp Ala Trp Arg Met Pro Ser Ile Ala Pro Gly Gln Ser Thr Gly
            35                  40                  45

Val Ala Lys Thr Ser Arg Trp Ala Gly Phe Leu Gly Asn Phe Ala Arg
        50                  55                  60

Arg Ser Pro Ser Ile Ser Thr Ser Pro Ser Leu Pro Pro Ser Leu Pro
65                  70                  75                  80

Ala Ser Ser Leu Gly Pro Leu Ser Ala Ala Thr Met Ala Pro Pro Ser
                85                  90                  95

Thr Leu Ser Pro Ala Ala Gln Lys Lys Lys Asp Ala Val Ala Ala Tyr
                100                 105                 110

Val Lys Ser Arg Gly Gly Asn Leu Gly Ile Arg Lys Val Leu Ile Ala
            115                 120                 125

Asn Asn Gly Met Ala Ala Thr Lys Ser Ile Leu Ser Ile Arg Gln Trp
        130                 135                 140

Ala Tyr Met Glu Leu Gly Asp Asp Lys Ala Ile Glu Phe Val Val Met
145                 150                 155                 160

Ala Thr Pro Glu Asp Leu Asn Ala Asn Ala Glu Phe Ile Arg Leu Ala
                165                 170                 175

Asp Arg Phe Val Glu Val Pro Gly Gly Ser Asn Lys Asn Asn Tyr Ala
                180                 185                 190

Asn Val Asp Leu Ile Val Gln Val Ala Glu Arg Glu Gly Val Asp Ala
            195                 200                 205

Val Trp Pro Gly Trp Gly His Ala Ser Glu Asn Pro Arg Leu Pro Asn
```

```
             210                 215                 220
Thr Leu Lys Glu Met Gly Ile Lys Phe Ile Gly Pro Thr Gly Pro Val
225                 230                 235                 240

Met Ser Val Leu Gly Asp Lys Ile Ala Ala Asn Ile Leu Ala Gln Thr
                245                 250                 255

Ala Lys Val Pro Ser Ile Pro Trp Ser Gly Asp Gly Leu Thr Ala Glu
                260                 265                 270

Leu Thr Ala Glu Gly Thr Ile Pro Asp Glu Thr Phe Gln Lys Ala Met
            275                 280                 285

Val Arg Thr Ala Glu Glu Ala Leu Ala Ala Ala Asn Arg Ile Gly Tyr
        290                 295                 300

Pro Val Met Leu Lys Ala Ser Glu Gly Gly Gly Lys Gly Ile Arg
305                 310                 315                 320

Met Ser Asn Asn Asp Glu Glu Leu Lys Asn Asn Phe Val Gln Val Ser
                325                 330                 335

Asn Glu Val Pro Gly Ser Pro Met Phe Met Met Gln Leu Cys Thr Gln
                340                 345                 350

Ala Arg His Ile Glu Val Gln Ile Val Gly Asp Glu His Gly Asn Ala
            355                 360                 365

Ala Ala Leu Asn Gly Arg Asp Cys Ser Thr Gln Arg Arg Phe Gln Lys
        370                 375                 380

Ile Phe Glu Glu Gly Pro Pro Thr Ile Val Pro Pro Glu Val Phe Lys
385                 390                 395                 400

Gln Met Glu Leu Ala Ala Gln Arg Leu Thr Gln Ser Ile Gly Tyr Ile
                405                 410                 415

Gly Ala Gly Thr Val Glu Tyr Leu Phe Asn Ala Ala Thr Gly Lys Tyr
                420                 425                 430

Phe Phe Leu Glu Leu Asn Pro Arg Leu Gln Val Glu His Pro Val Thr
            435                 440                 445

Glu Gly Leu Ser Leu Val Asn Leu Pro Ala Thr Gln Leu Gln Ile Ala
        450                 455                 460

Met Gly Ile Pro Leu Asn Arg Ile Pro Asp Ile Arg Arg Phe Tyr Gly
465                 470                 475                 480

Lys Glu Asp Pro Tyr Gly Asp Ser Pro Ile Glu Phe Phe Glu Asp Asp
                485                 490                 495

Tyr Ala Asp Leu Ala Ser His Val Ile Ala Ala Arg Ile Thr Ala Glu
                500                 505                 510

Asn Pro Asp Glu Gly Phe Lys Pro Thr Ser Gly Arg Ile Glu Arg Val
            515                 520                 525

Lys Phe Gln Ser Thr Ala Asn Val Trp Gly Tyr Phe Ser Val Gly Ala
        530                 535                 540

Asn Gly Gly Ile His Glu Phe Ala Asp Ser Gln Phe Gly His Leu Phe
545                 550                 555                 560

Ala Lys Gly Lys Thr Arg Glu Asp Ala Arg Lys Ser Leu Val Leu Ala
                565                 570                 575

Leu Lys Glu Ile Glu Val Arg Gly Asp Ile Arg Thr Thr Val Glu Tyr
                580                 585                 590

Leu Val Gln Leu Leu Glu Thr Asp Ala Phe Lys Glu Asn Thr Ile Asp
            595                 600                 605

Thr Ser Trp Leu Asp Gly Leu Ile Arg Glu Lys Ser Val Arg Val Glu
        610                 615                 620

Leu Ala Pro His Glu Val Ala Leu Ser Ala Ala Ile Ala Arg Ala Phe
625                 630                 635                 640
```

-continued

Ala Arg Ser Gln Glu Glu Lys Lys Phe Val Asn Leu Gly Lys
               645                 650                 655

Gly Gln Val Ser Ile Gln Ser Ile Arg Ser Ile Asn Ser Phe Pro Met
                660                 665                 670

Glu Ile Thr Tyr Lys Asp Ser Lys Tyr Ser Phe Leu Cys Ser Arg Ile
                675                 680                 685

Gly Pro Asp Lys Leu Arg Leu Thr Ile Asn Gly Gln Val Leu Glu Thr
                690                 695                 700

Lys Val Arg Gln Gln Pro Asp Gly Ser Leu Ile Ala Glu Phe Gly Gly
705                 710                 715                 720

Thr Thr His Thr Ile Tyr Ala Leu Glu Glu Pro Leu Gly Leu Arg Met
                725                 730                 735

Val Leu Asp Gly Val Thr Val Leu Leu Pro Thr Val Tyr Asp Pro Ser
                740                 745                 750

Glu Leu Arg Thr Asp Val Thr Gly Lys Val Val Arg Tyr Leu Gln Asp
                755                 760                 765

Asp Gly Ala Glu Ile Gln Ala Gly Gln Pro Tyr Val Glu Val Glu Ala
                770                 775                 780

Met Lys Met Ile Met Pro Leu Lys Ala Ser Glu Ser Gly Thr Val Thr
785                 790                 795                 800

His Arg Leu Ser Pro Gly Ser Ile Ile Thr Ala Gly Asp Leu Leu Ala
                805                 810                 815

Asn Ile Gln Leu Lys Asp Pro Ser Lys Val Lys Lys Ile Ile Pro Phe
                820                 825                 830

Lys Asp Thr Leu Glu Leu Ala Gly Ser Gly Glu Pro Gly Thr Thr
                835                 840                 845

Glu Ile Glu Ser Val Leu Lys Thr Met Asn Leu Val Leu Asp Gly Phe
                850                 855                 860

Asp Tyr Glu Val Glu Phe Leu Ala Gln Asn Leu Val Thr Ser Val Arg
865                 870                 875                 880

Asp Gly Lys Glu Leu Leu Asp Ala Ala Val Ala Leu Val Ser Lys Tyr
                885                 890                 895

Leu Ala Val Glu Glu Gln Phe Ala Gly Lys Ala Leu Asp Glu Ala Met
                900                 905                 910

Val Ala Leu Val Lys Ala Asn Lys Glu Ser Leu Gly Thr Val Leu Gln
                915                 920                 925

Leu Ala Thr Ala His Arg Glu Leu Pro Arg Arg Asn Lys Met Val Ser
                930                 935                 940

Ala Leu Ile Arg Gln Leu Gln Ala Leu Val Glu Arg Pro Gly Thr Ser
945                 950                 955                 960

Glu Leu Ala Leu Gly Pro Leu Ile Asp Leu Leu Glu Arg Thr Ser His
                965                 970                 975

Leu Pro Gly Lys Glu Tyr Gly Glu Val Ala Ile Ser Ser Ala Gln Ala
                980                 985                 990

Leu Leu Ala Leu Lys Ala Pro Pro Phe Asn Ile Arg Lys Asp Glu Leu
                995                 1000                1005

Arg Ala Thr Leu Met Gln Thr Gln Asp Asn Asp Ala Leu Ala Arg Ser
                1010                1015                1020

Ala Thr Leu Thr Ala Gly Val Asp Leu Leu Thr Ala Met Phe Thr Asp
1025                1030                1035                1040

Pro Asp Val Thr Val Arg Lys Asn Ala Ile Glu Val Tyr Ile Arg Arg
                1045                1050                1055

```
Ile Tyr Arg Ala His Arg Ile Leu Ser Leu Ser Val Glu Glu Val Asp
            1060                1065                1070

Gly Val Met Val Ala Arg Trp Ser Phe Lys Phe Ala Asp Thr Pro Asp
        1075                1080                1085

Glu Glu Ser Pro Leu Arg Tyr Gly Phe Phe Thr Val Phe Pro Ser Leu
    1090                1095                1100

Glu Ala Tyr Thr Glu Gly Thr Glu Lys Phe Ser Lys Val Leu Lys Ser
1105                1110                1115                1120

Ser Leu Gly Gly Lys Glu Val Tyr Ser Glu Pro Thr Asn Val Phe His
            1125                1130                1135

Val Ala Val Ala Gln Leu Pro Glu Ser Asp Gln Pro Glu Val Ile Ala
        1140                1145                1150

Asn Ile Glu Ala Ile Leu Ala Glu Lys Lys Glu Leu Leu Thr Glu Cys
    1155                1160                1165

Gln Val Arg Met Val Asn Val Leu Phe Val Lys Gly Ala Ser Asn Pro
1170                1175                1180

Arg Tyr Tyr Thr Phe Thr Ala Ala Glu Asn Phe Lys Glu Asp Pro Leu
            1185                1190                1195                1200

Arg Arg Asp Met Arg Pro Thr Phe Pro Gln Leu Leu Glu Leu Ser Arg
        1205                1210                1215

Leu Ala Ala Asn Tyr Glu Leu Gln Arg Leu Pro Ser Ile Gly Arg Asn
    1220                1225                1230

Thr Gln Val Tyr Leu Gly Thr Glu Arg Ala Ala Ala Gly Val Lys Lys
        1235                1240                1245

Arg Gly Gly Ser Gln Val Leu Phe Val Arg Gly Ile Ser His Ser Glu
    1250                1255                1260

Gln Thr Gln Thr Pro Leu Gly Ala Glu Arg Val Leu Leu Met Ala Met
1265                1270                1275                1280

Asp Glu Leu Asp Tyr Ala Leu Leu Asp Pro Arg Val Gly Gly Ser Ala
            1285                1290                1295

Ser Ser Arg Leu Phe Leu Asn Leu Leu Val Pro Ile Thr Thr Asp Pro
        1300                1305                1310

Glu Ala Leu Ala Gly Glu Trp Asn Gln Val Met Asp Arg Leu Leu Ala
    1315                1320                1325

Lys Tyr Ala Thr Arg Leu Leu Lys Leu Gly Val Asp Glu Ile Glu Ile
        1330                1335                1340

Lys Val Arg Val Thr Ala Asp Gly Asn Thr Ile Thr Pro Val Arg Leu
1345                1350                1355                1360

Met Ala Thr Ser Met Thr Gly Glu Phe Leu Arg Thr Asp Ala Phe Leu
            1365                1370                1375

Glu Tyr Pro Asp Pro Val Asn Gly Ile Thr Lys Gln Phe Cys Ser Ile
        1380                1385                1390

Thr Arg Glu Asp Gln Ile Cys Leu Leu Asn Pro Tyr Pro Ala Ser Asn
    1395                1400                1405

Ser Ile Gln Thr Arg Arg Ala Ser Ala Arg Ile Gly Ser Thr Tyr
        1410                1415                1420

Ala Tyr Asp Phe Leu Gly Val Met Glu Val Ser Leu Ile Gln Lys Trp
1425                1430                1435                1440

Asp Lys His Leu Lys Glu Leu Ser Ser Val Tyr Pro Ser Arg Val Asp
            1445                1450                1455

Asp Lys Met Pro Glu Gln Leu Phe Thr Ala His Glu Leu Val Leu Glu
        1460                1465                1470

Asp Asp Glu Leu Gln Pro Thr Gln Arg Leu Val Gly Leu Asn Asp Ile
```

-continued

```
            1475                1480                1485
Gly Met Ile Ala Trp His Ala Thr Met Lys Thr Pro Glu Tyr Pro Glu
            1490                1495                1500
Gly Arg Glu Leu Val Ile Ile Ala Asn Asp Val Thr Phe Gln Ser Gly
1505                1510                1515                1520
Ser Phe Gly Val Lys Glu Asp Glu Phe Phe Arg Ala Ala Ser Glu Tyr
            1525                1530                1535
Ala Arg Val Arg Gly Leu Pro Arg Ile Tyr Leu Ser Ser Asn Ser Gly
            1540                1545                1550
Ala Arg Ile Gly Leu Val Asp Asp Leu Lys Gly Lys Phe Arg Ile Ala
            1555                1560                1565
Trp Asn Asp Pro Ala Asn Pro Ser Leu Gly Phe Lys Tyr Leu Tyr Leu
            1570                1575                1580
Pro Pro Glu Glu Tyr Glu Ala Leu Lys Pro Gly Thr Val Asn Ala Asn
1585                1590                1595                1600
Leu Val Glu Thr Glu Glu Gly Glu Lys Arg Trp Ala Leu Gln Asp Ile
            1605                1610                1615
Val Gly Gln Val His Gly Ile Gly Val Glu Asn Leu Arg Gly Ser Gly
            1620                1625                1630
Met Ile Ala Gly Glu Thr Ser Arg Ala Tyr Asp Glu Thr Phe Thr Leu
            1635                1640                1645
Ser Tyr Val Thr Gly Arg Ser Val Gly Ile Gly Ala Tyr Leu Val Arg
            1650                1655                1660
Leu Gly Gln Arg Thr Ile Gln Met Val Asn Gly Pro Leu Ile Leu Thr
1665                1670                1675                1680
Gly Tyr Ser Ala Leu Asn Lys Leu Leu Gly Arg Glu Val Tyr Thr Ser
            1685                1690                1695
Gln Asp Gln Leu Gly Gly Pro Gln Ile Met Ala Pro Asn Gly Val Ser
            1700                1705                1710
His Leu Val Val Gly Asn Asp Lys Glu Gly Val Ser Ser Ile Ile Asp
            1715                1720                1725
Trp Leu Ser Phe Val Pro Lys Asp Lys Phe Ser Ala Pro Pro Ile Leu
            1730                1735                1740
Asp Leu Pro Thr Asp Ser Pro Glu Arg Asp Val Glu Phe Leu Pro Thr
1745                1750                1755                1760
Lys Thr Pro Tyr Asp Pro Arg His Met Leu Ala Gly Thr Val Gly Pro
            1765                1770                1775
Asp Gly Ala Phe Val Pro Gly Phe Phe Asp Arg Gly Ser Phe Ile Glu
            1780                1785                1790
Thr Leu Gly Gly Trp Gly Lys Ser Val Val Thr Gly Arg Ala Lys Leu
            1795                1800                1805
Gly Gly Ile Pro Met Gly Val Ile Ser Val Glu Thr Arg Leu Val Glu
            1810                1815                1820
Gln Arg Val Pro Ala Asp Pro Ala Asn Pro Asp Ser Arg Glu Ser Ile
1825                1830                1835                1840
Leu Pro Gln Ala Gly Gln Val Trp Tyr Pro Asp Ser Ala Phe Lys Thr
            1845                1850                1855
Ala Gln Ala Met Glu Asp Phe Asn Arg Gly Glu Asn Leu Pro Leu Ile
            1860                1865                1870
Ile Phe Ala Asn Trp Arg Gly Phe Ser Gly Gly Thr Arg Asp Met Phe
            1875                1880                1885
Gly Glu Ile Leu Lys Phe Gly Ala Lys Ile Val Asp Ala Leu Arg Thr
            1890                1895                1900
```

Tyr Arg His Pro Val Phe Val Tyr Ile Pro Pro Asn Gly Glu Leu Arg
1905                1910                1915                1920

Gly Gly Ala Trp Val Val Ile Asp Pro Thr Ile Asn Glu Glu Met Met
            1925                1930                1935

Glu Met Tyr Ala Asp Lys Asp Ser Arg Gly Gly Ile Leu Glu Pro Pro
        1940                1945                1950

Gly Ile Cys Glu Val Lys Phe Arg Asn Ala Asp Gln Val Ser Ala Met
    1955                1960                1965

His Arg Leu Asp Pro Val Ile Gln Ala Leu Asp Gly Glu Leu Gln Asn
1970                1975                1980

Ala Lys Thr Glu Gln Asp Ala Ala Lys Leu Thr Gln Gln Leu Lys Glu
1985                1990                1995                2000

Arg Glu Glu Ala Leu Leu Pro Leu Tyr Thr Gln Val Ala His Glu Phe
                2005                2010                2015

Ala Asp Leu His Asp Arg Ala Gly Arg Met Lys Ala Lys Gly Val Ile
            2020                2025                2030

Arg Asp Val Val Thr Trp Lys Arg Ser Arg Ser Tyr Phe Phe Trp Arg
        2035                2040                2045

Ala Arg Arg Arg Ile Ala Glu Asp Gly Leu Ile Arg Glu Met Gln Arg
    2050                2055                2060

Val Asp Pro Thr Leu Ser Val Gln Gln Gly Arg Glu Lys Val Ser Ala
2065                2070                2075                2080

Leu Ala Ser Pro Ala Val Tyr Glu Asp Asp Lys Ala Phe Val Ala Trp
                2085                2090                2095

Val Glu Glu Gly Gly Glu Ala Ile Ala Lys Glu Leu Lys Ile Lys
            2100                2105                2110

Gln Ala Ala Val Lys Ala Ser Leu Ala Ser Leu Leu Glu Gly Leu Ser
        2115                2120                2125

Ala Glu Glu Arg Lys Gln Val Leu Ala Gly Leu
    2130                2135

<210> SEQ ID NO 10
<211> LENGTH: 288
<212> TYPE: PRT
<213> ORGANISM: Streptococcus salivarius

<400> SEQUENCE: 10

Met Gly Leu Phe Asp Arg Lys Glu Lys Tyr Ile Arg Ile Asn Pro Asn
1                5                  10                 15

Arg Ser Val Arg Asn Gly Val Asp His Gln Val Pro Glu Val Pro Asp
            20                  25                  30

Glu Leu Phe Ala Lys Cys Pro Gly Cys Lys Gln Ala Ile Tyr Gln Lys
        35                  40                  45

Asp Leu Gly Gln Ala Lys Ile Cys Pro Asn Cys Ser Tyr Thr Phe Arg
    50                  55                  60

Ile Ser Ala Lys Glu Arg Leu Asp Leu Thr Val Asp Glu Gly Ser Phe
65                  70                  75                  80

Gln Glu Leu Phe Thr Gly Ile Lys Thr Glu Asn Pro Leu Asn Phe Pro
                85                  90                  95

Gly Tyr Met Glu Lys Leu Ala Ala Thr Lys Glu Lys Thr Gly Leu Asp
            100                 105                 110

Glu Ala Val Val Thr Gly Phe Ala Ser Ile Lys Gly Gln Lys Thr Ala
        115                 120                 125

Leu Ala Ile Met Asp Ser Asn Phe Ile Met Ala Ser Met Gly Thr Val

```
            130                 135                 140
Val Gly Glu Lys Ile Thr Lys Leu Phe Glu His Ala Ile Glu Glu Lys
145                 150                 155                 160

Leu Pro Val Val Ile Phe Thr Ala Ser Gly Ala Arg Met Gln Glu
                165                 170                 175

Gly Ile Met Ser Leu Met Gln Met Ala Lys Ile Ser Ala Ala Val Lys
                180                 185                 190

Arg His Ser Asn Ala Gly Leu Leu Tyr Leu Thr Val Leu Thr Asp Pro
                195                 200                 205

Thr Thr Gly Gly Val Thr Ala Ser Phe Ala Met Glu Gly Asp Ile Ile
                210                 215                 220

Leu Ala Glu Pro Gln Thr Leu Ile Gly Phe Ala Gly Arg Arg Val Ile
225                 230                 235                 240

Glu Asn Thr Val Arg Glu Thr Leu Pro Asp Asp Phe Gln Lys Ala Glu
                245                 250                 255

Phe Leu Gln Glu His Gly Phe Val Asp Ala Ile Val Lys Arg Thr Glu
                260                 265                 270

Leu Ala Asp Thr Ile Ala Thr Leu Leu Ser Phe His Gly Gly Val Gln
                275                 280                 285

<210> SEQ ID NO 11
<211> LENGTH: 253
<212> TYPE: PRT
<213> ORGANISM: Collimonas fungivorans

<400> SEQUENCE: 11

Met Tyr Arg Thr Asp Leu Glu Ser Asn Ile His Val Cys Pro Lys Cys
1                   5                   10                  15

Asp His His Met Arg Ile Arg Ala Arg Glu Arg Leu Asp Ala Leu Leu
                20                  25                  30

Asp Ala Gly Gly Arg Tyr Glu Ile Gly Gln Glu Thr Leu Pro Ile Asp
                35                  40                  45

Thr Leu Lys Phe Lys Asp Ser Lys Lys Tyr Pro Asp Arg Leu Lys Ala
    50                  55                  60

Ala Met Asp Ala Thr Gly Glu Thr Asp Ala Leu Ile Val Leu Gly Gly
65                  70                  75                  80

Ser Ile Met Thr Leu Pro Val Val Ala Ala Phe Glu Phe Glu Phe
                85                  90                  95

Met Gly Gly Ser Met Gly Ser Val Val Gly Glu Arg Phe Val Arg Gly
                100                 105                 110

Ala Gln Val Ala Leu Glu Gln Lys Val Pro Phe Ile Cys Ile Thr Ala
                115                 120                 125

Thr Gly Gly Ala Arg Met Gln Glu Gly Leu Leu Ser Leu Met Gln Met
                130                 135                 140

Ala Lys Thr Thr Ser Met Leu Thr Lys Leu Ser Glu Lys Lys Leu Pro
145                 150                 155                 160

Phe Ile Ser Val Leu Thr Asp Pro Thr Met Gly Gly Val Ser Ala Ser
                165                 170                 175

Phe Ala Phe Met Gly Asp Val Val Ile Ala Glu Pro Lys Ala Leu Ile
                180                 185                 190

Gly Phe Ala Gly Pro Arg Val Ile Glu Asn Thr Val Arg Glu Lys Leu
                195                 200                 205

Pro Glu Gly Phe Gln Arg Ala Glu Phe Leu Val Thr Lys Gly Ala Val
                210                 215                 220
```

```
Asp Met Ile Val Asp Arg Arg Lys Met Arg Glu Glu Ile Ala Arg Leu
225                 230                 235                 240

Leu Ala Leu Leu Gln Asp Gln Pro Val Glu Ser Ile Ala
            245                 250
```

<210> SEQ ID NO 12
<211> LENGTH: 308
<212> TYPE: PRT
<213> ORGANISM: Marinobacter sp.

<400> SEQUENCE: 12

```
Met Ser Asn Trp Leu Asp Lys Ile Met Pro Ser Lys Ile Arg Ser Glu
1               5                   10                  15

Ser Lys Gln Arg Thr Gly Val Pro Glu Gly Leu Trp Lys Lys Cys Pro
            20                  25                  30

Lys Cys Gly Ala Phe Leu Tyr Lys Pro Glu Leu Asp Lys Asn Leu Asp
        35                  40                  45

Val Cys Pro Lys Cys Gln His His Leu Arg Ile Thr Ala Arg Arg Arg
50                  55                  60

Leu Asp Val Phe Leu Asp Ala Asp Gly Arg Gln Glu Ile Ala Ala Asp
65                  70                  75                  80

Leu Glu Pro Trp Asp Arg Leu Lys Phe Lys Asp Ser Lys Arg Tyr Lys
                85                  90                  95

Asp Arg Leu Ser Gln Asn Gln Lys Thr Thr Gly Glu Lys Asp Ala Leu
            100                 105                 110

Val Ala Met Arg Gly Ala Cys Leu Asp Ile Pro Leu Val Ala Val Ala
        115                 120                 125

Phe Glu Phe Asn Phe Leu Gly Gly Ser Met Gly Gln Val Val Gly Glu
130                 135                 140

Lys Phe Val Gln Ala Ala Asn Val Cys Leu Glu Glu Arg Ile Pro Leu
145                 150                 155                 160

Val Cys Phe Ser Ala Ser Gly Gly Ala Arg Met Gln Glu Ala Ile Leu
                165                 170                 175

Ser Leu Met Gln Met Ser Lys Thr Ala Ala Val Leu Glu Arg Met Lys
            180                 185                 190

Gln Glu Gly Ile Pro Tyr Ile Ser Val Met Thr Asp Pro Val Phe Gly
        195                 200                 205

Gly Val Ser Ala Ser Leu Ala Met Leu Gly Asp Leu Asn Ile Ala Glu
210                 215                 220

Pro Tyr Ala Leu Ile Gly Phe Ala Gly Pro Arg Val Ile Glu Gln Thr
225                 230                 235                 240

Val Arg Glu Lys Leu Pro Glu Gly Phe Gln Arg Ser Glu Phe Leu Leu
                245                 250                 255

Glu His Gly Ala Ile Asp Met Ile Leu His Arg His Gln Met Arg Glu
            260                 265                 270

Arg Ile Ala Ala Val Leu Ala Lys Phe Thr Asp Leu Asp Gln Pro Ala
        275                 280                 285

Thr Glu Ala Pro Ile Glu Phe Glu Val Ser Glu Arg Pro Glu Thr Asp
290                 295                 300

Val Pro Ala Glu
305
```

<210> SEQ ID NO 13
<211> LENGTH: 471
<212> TYPE: PRT
<213> ORGANISM: Helicosporidium ex Simulium jonesi

<400> SEQUENCE: 13

```
Met Thr Ile Leu Ala Trp Ile Lys Asp Lys Lys Asn Lys Ala Ile Leu
1               5                   10                  15

Asn Thr Pro Glu Tyr Ser Ser Gln Ser Ser Leu Ser Trp Cys Phe Thr
            20                  25                  30

His Lys Glu Ala Ala Ser Asn Lys Ala Val Ser Phe Ile Asn Leu Ser
        35                  40                  45

Lys Arg Arg Ala Leu Trp Thr Arg Cys Glu Lys Cys Gly Met Ile Gln
    50                  55                  60

Phe Met Arg Phe Phe Lys Glu Asn Ala Asn Leu Cys Leu Ser Cys Ser
65                  70                  75                  80

Tyr His His Ile Met Thr Ser Asp Glu Arg Ile Ala Leu Leu Val Glu
                85                  90                  95

Lys Gly Thr Trp Tyr Pro Leu Asn Glu Thr Ile Ser Pro Lys Asp Pro
            100                 105                 110

Ile Lys Phe Thr Asp Thr Gln Ser Tyr Ala Gln Arg Ile Gln Ser Thr
        115                 120                 125

Gln Glu Lys Leu Gly Met Gln Asp Ala Val Gln Thr Gly Thr Gly Leu
    130                 135                 140

Ile Asn Gly Ile Pro Phe Ala Ile Gly Ile Met Asp Phe Arg Phe Met
145                 150                 155                 160

Gly Gly Ser Met Gly Ser Val Val Gly Glu Lys Leu Thr Arg Leu Ile
                165                 170                 175

Glu Tyr Ala Thr Lys Gln Gly Leu Phe Leu Leu Ile Val Ser Ala Ser
            180                 185                 190

Gly Gly Ala Arg Met Gln Glu Gly Ile Tyr Ser Leu Met Gln Met Ala
        195                 200                 205

Lys Ile Ser Ala Ala Leu Asn Val Tyr Gln Asn Glu Ala Asn Leu Leu
    210                 215                 220

Tyr Ile Ser Leu Cys Thr Ser Pro Thr Thr Gly Gly Val Thr Ala Ser
225                 230                 235                 240

Phe Ala Met Leu Gly Asp Ile Ile Phe Ser Glu Pro Glu Ala Ile Ile
                245                 250                 255

Gly Phe Ala Gly Arg Arg Val Ile Gln Gln Thr Leu Gln Gln Glu Leu
            260                 265                 270

Pro Glu Asp Phe Gln Thr Ser Glu Ser Leu Leu His His Gly Leu Ile
        275                 280                 285

Asp Ala Ile Val Pro Arg Cys Phe Leu Val Asn Ala Ile Ser Glu Val
    290                 295                 300

Ala Ser Ile Phe Ala Tyr Ala Pro Ser Lys Tyr Lys Lys Leu Gly Asn
305                 310                 315                 320

Ile Ser His Tyr His Glu Asn Thr Leu Ser Trp Ala Thr Glu Glu Ile
                325                 330                 335

Leu Arg Arg Asn Cys Ile Asn Asn Lys Lys Val Glu Tyr Arg Thr Ile
            340                 345                 350

Glu Lys Ile Tyr Gln Thr Thr Leu Tyr Lys Glu Ser Phe Phe Arg Leu
        355                 360                 365

Asn Lys Leu Leu Ser Lys Lys Ser Glu Ile Asn Phe Thr Asn Lys
    370                 375                 380

Met Lys Lys Gln Asn Asn Ala Phe Asn Thr Ser Ser Val Tyr Ala Asn
385                 390                 395                 400

Tyr Tyr Asp Val Met Leu Cys Asn Tyr Asn Ile Gly Thr His Ser Leu
```

```
                    405                 410                 415
Asn Leu Leu Phe Asn Glu Glu Ser Glu Phe Cys Lys Tyr Phe Pro Phe
                420                 425                 430

Asn Met Asp His Met Lys Lys Glu Asn Arg Ile Lys Tyr Asn Phe Ile
            435                 440                 445

Thr Glu Asn Ser Asn Asp Phe Ile Arg Lys Lys Thr Ile Asn Asp Phe
        450                 455                 460

Ser Ile Met Leu Ile Gly Asp
465                 470

<210> SEQ ID NO 14
<211> LENGTH: 608
<212> TYPE: PRT
<213> ORGANISM: Mortierella elongata

<400> SEQUENCE: 14

Met Ser Arg Arg Leu Ile Ile Ser His Leu Ser Lys Pro Ser Ser Arg
1               5                   10                  15

Val Trp Ser Ser Ser Ser Ser Ser Ser Phe Tyr Ser Pro Ala Phe
            20                  25                  30

Ser Thr Ser Thr Thr Val Arg Ser Pro Phe His Ile Ala Thr Leu Gln
        35                  40                  45

Arg His Arg Thr Met Ala Ser Ile Ser Asn Gly Gly Ser Asn Asn Asn
    50                  55                  60

Asn Asn Asn Ser Ala Ser Ser Ser Asn Ala Ala Gly Ser Gly Thr
65                  70                  75                  80

Leu Gln Ala Leu Arg Ala Asn Val Val Glu Gln Tyr Trp Asn Asp Ile
                85                  90                  95

Ala Ala His Phe Arg Glu Pro Gly Phe Ser Thr Phe Asp Lys Glu Arg
            100                 105                 110

Thr Arg Arg Ala Ala Asp Arg Asp Pro Glu Phe Met Arg Lys Leu Leu
        115                 120                 125

Leu Ala Val Ile Thr Asp Arg Pro Gly Gln Gly Asp Ile Leu Pro Ser
    130                 135                 140

Val Ile Ala Lys Ser Ser Cys Asp Phe Phe Ser Ser Leu Asp Arg Asn
145                 150                 155                 160

Gly Lys Thr Glu Phe Leu Arg Leu Leu Ala Arg Asp Phe Gly Val Leu
                165                 170                 175

Gln Glu Asp Val Val Lys Ala Ala Glu Gln Tyr Gln Asp Tyr Ala His
            180                 185                 190

Lys Glu Pro Glu Ser Lys Ala Leu Leu Arg Ala Glu Gln Leu Leu Arg
        195                 200                 205

His Ala Ile Val Pro Gly His Ser Lys Phe Phe Asp Arg Val Ser Arg
    210                 215                 220

Leu Pro Gly Gly Leu Lys Phe Leu Ile Asp Met Arg Gln Asp Leu Leu
225                 230                 235                 240

Ser Ile Ile Gln Ala Asn Lys Gly Asp Val Tyr Leu Ser Ser Leu Asn
                245                 250                 255

Glu Ser Leu Lys Glu Lys Leu Gln Ala Trp Phe Val Gly Phe Leu Asp
            260                 265                 270

Leu Glu Arg Leu Thr Trp Gln Ser Pro Ala Val Leu Leu Glu Lys Ile
        275                 280                 285

Thr Gln Tyr Glu Ala Val His Lys Phe Lys Asp Val Gln Asp Leu Lys
    290                 295                 300
```

```
Arg Arg Val Gly Pro Gly Arg Arg Val Phe Ala Leu Met Asn Lys Ser
305                 310                 315                 320

Leu Pro Ala Glu Pro Leu Val Phe Val Gln Val Ala Leu Val Glu Arg
            325                 330                 335

Leu Ser Asp Asn Val Gln Asp Ile Leu Asn Asp Pro Ser Pro Gly His
        340                 345                 350

Ala Asn Pro Ala Glu Thr Val Lys Cys Ala Ile Phe Tyr Ser Ile Thr
    355                 360                 365

Thr Gln Gln Pro Tyr Leu Gln Trp Leu Ser Gly Ile Glu Leu Gly Asn
370                 375                 380

Phe Leu Ile Lys Arg Val Val Arg Ser Leu Lys Val Glu Phe Pro Gln
385                 390                 395                 400

Ile Glu Thr Phe Ser Thr Leu Ser Pro Ile Pro Gly Phe Arg Lys Trp
            405                 410                 415

Ile Gly Gln Cys Gln Asn Leu Gly Gln Lys Leu Leu Pro Gln Glu
        420                 425                 430

Glu Ser Ile Val Ser Gln Leu Gly Gln Glu Thr Gly Ala Ala Ser Gly
    435                 440                 445

Asp Val Glu Asp Gln Phe Ser Ala Ile Leu Lys His Pro Ser Thr Phe
450                 455                 460

Ser Asp Ser Glu Thr Met Ser Lys Leu Arg Pro Ile Leu Ser Arg Leu
465                 470                 475                 480

Cys Ala Arg Tyr Ile Leu Leu Glu Lys Arg His Leu Ala Leu Asp
            485                 490                 495

Pro Val Ala Asn Phe His Leu Arg Asn Gly Ala Cys Ala His Arg Leu
        500                 505                 510

Asn Trp Leu Gly Asp Thr Ser Thr Lys Gly Met Glu Glu Ser Phe Gly
    515                 520                 525

Leu Met Ile Asn Tyr Leu Tyr Ser Leu Asp His Ile Glu Met Asn Asn
530                 535                 540

Gln Gln Tyr Leu Leu Asp Gly Thr Ile Ser Val Ser Lys Asp Ala
545                 550                 555                 560

Gly Phe Gln Lys Val Leu Met Asp Ser Ala Val Gly Asn Ser Gln Ala
            565                 570                 575

Ala Gly Arg Gly Val Gly Glu Glu Gln Gly Glu Gly Gln Val
        580                 585                 590

Val Gln Val Asn Gly Ser Ser Phe Arg Leu Leu Glu Ile Val Thr Ala
    595                 600                 605

<210> SEQ ID NO 15
<211> LENGTH: 57
<212> TYPE: PRT
<213> ORGANISM: Mortierella elongata

<400> SEQUENCE: 15

Arg Tyr Ile Leu Glu Lys Lys Cys Arg His Leu Ala Met Asp Ser Val
1               5                   10                  15

Ala Asn Phe His Leu Arg Asn Gly Ala Cys Ala His Arg Leu Asn Trp
            20                  25                  30

Leu Asp Asp Thr Ser Pro Lys Gly Met Glu Glu Phe Phe Gly Ile Val
        35                  40                  45

Thr Glu Ser Arg Arg Ser Leu Ala Asp
    50                  55

<210> SEQ ID NO 16
```

```
<211> LENGTH: 124
<212> TYPE: PRT
<213> ORGANISM: Mortierella elongata

<400> SEQUENCE: 16

Met Phe Arg Ala Leu Val Arg Pro Ala Ser Thr Ile Tyr Arg Gln Ala
1               5                   10                  15

Ala Ile Lys Ala Thr Pro Ala Thr Val Ala Arg Met Pro Met Gly Leu
            20                  25                  30

Thr Phe Ala Arg Thr Tyr Ala Ser Ala Gly Leu Ala Arg Ser Asp Val
        35                  40                  45

Glu Lys Arg Val Leu Asp Ile Leu Ala Gly Phe Asn Lys Val Asp Ser
50                  55                  60

Asn Lys Ile Ser Leu Asn Ala Asn Phe Asn Asn Asp Leu Gly Leu Asp
65                  70                  75                  80

Ser Leu Asp Thr Val Glu Val Val Met Ala Ile Glu Glu Phe Ser
                85                  90                  95

Ile Glu Ile Pro Asp Lys Asp Ala Asp Glu Ile Lys Ser Ala Ala Gln
                100                 105                 110

Ala Val Glu Tyr Ile Thr Lys Arg Asp Asp Ala His
        115                 120

<210> SEQ ID NO 17
<211> LENGTH: 123
<212> TYPE: PRT
<213> ORGANISM: Mortierella elongata

<400> SEQUENCE: 17

Met Phe Arg Ala Ile Arg Pro Ala Ala Leu Tyr Arg Ser Ala Ala Leu
1               5                   10                  15

Tyr Lys Thr Ala Pro Ala Val Val Ala Arg Asn Ala Met Ala Leu Asn
            20                  25                  30

Phe Ala Arg Thr Tyr Ala Ser Ala Gly Leu Ala Arg Ser Asp Val Glu
        35                  40                  45

Lys Arg Val Leu Asp Ile Leu Ala Gly Phe Asn Lys Ile Asp Ala Asn
50                  55                  60

Lys Ile Ala Leu Lys Ala Asn Phe Asn Ala Asp Leu Gly Leu Asp Ser
65                  70                  75                  80

Leu Asp Thr Val Glu Val Val Met Ala Ile Glu Glu Phe Ser Ile
                85                  90                  95

Glu Ile Pro Asp Lys Asp Ala Asp Glu Ile Lys Ser Ala Glu Gln Ala
                100                 105                 110

Val Glu Tyr Ile Ser Lys Arg Glu Asp Ala His
        115                 120

<210> SEQ ID NO 18
<211> LENGTH: 120
<212> TYPE: PRT
<213> ORGANISM: Nannochloropsis gaditana

<400> SEQUENCE: 18

Met Arg Val Leu Ala Phe Leu Ala Leu Leu Ala Ala Pro Ala Phe Ala
1               5                   10                  15

Phe Val Pro Arg Met Pro Ala Pro Val Arg Ala Arg Ala Gly Leu Thr
            20                  25                  30

Leu Arg Phe Ser Gly Glu Tyr Ser Glu Lys Val Arg Ala Ile Val Leu
        35                  40                  45
```

```
Glu Asn Met Gly Asp Asp Ala Lys Val Gln Asp Tyr Leu Lys Ala Asn
            50                  55                  60

Gly Asp Asp Thr Ala Glu Phe Ala Ala Met Gly Phe Asp Ser Leu Asp
 65                  70                  75                  80

Leu Val Glu Phe Ser Met Ala Val Gln Lys Glu Phe Asp Leu Pro Asp
                    85                  90                  95

Leu Asn Glu Glu Asp Phe Ala Asn Leu Lys Thr Ile Lys Asp Val Val
                100                 105                 110

Thr Met Val Glu Ala Asn Lys Lys
                115                 120

<210> SEQ ID NO 19
<211> LENGTH: 352
<212> TYPE: PRT
<213> ORGANISM: Nannochloropsis gaditana

<400> SEQUENCE: 19

Met Met Ser Lys Ser Leu Ile Met Leu Gly Leu Leu Ser Pro Thr Ala
 1               5                  10                  15

Phe Ala Phe Val Pro Lys Leu Ser Thr Asn Val Leu Ser Arg Ala Ile
                20                  25                  30

Ser Ser His Ala Arg Lys Asn Leu Val Lys Ala Ser Ala Val Asp Tyr
            35                  40                  45

Lys Thr Ala Phe Met Phe Pro Gly Gln Gly Ala Gln Tyr Val Gly Met
 50                  55                  60

Gly Ala Gln Val Ser Glu Glu Val Pro Ala Ala Lys Ala Leu Phe Glu
 65                  70                  75                  80

Lys Ala Ser Glu Ile Leu Gly Tyr Asp Leu Leu Asp Arg Ala Met Asn
                    85                  90                  95

Gly Pro Lys Asp Leu Leu Asp Ser Thr Ala Val Ser Gln Pro Ala Ile
                100                 105                 110

Phe Val Ala Ser Ala Ala Val Glu Lys Leu Arg Ala Thr Glu Gly
                115                 120                 125

Glu Asp Ala Ala Asn Ala Ala Thr Val Ala Met Gly Leu Ser Leu Gly
130                 135                 140

Glu Tyr Ser Ala Leu Cys Tyr Ala Gly Ala Phe Ser Phe Glu Asp Gly
145                 150                 155                 160

Val Arg Leu Thr Lys Ala Arg Gly Glu Ala Met Gln Ala Ala Asp
                165                 170                 175

Leu Val Asp Thr Thr Met Val Ser Val Ile Gly Leu Glu Ala Asp Lys
                180                 185                 190

Val Asn Glu Leu Cys Ala Ala Ser Ser Lys Ser Gly Glu Lys Ile
                195                 200                 205

Gln Ile Ala Asn Tyr Leu Cys Pro Gly Asn Tyr Ala Val Ser Gly Ser
                210                 215                 220

Leu Lys Ala Ala Gln Val Leu Glu Glu Ile Ala Lys Pro Glu Phe Gly
225                 230                 235                 240

Ala Arg Met Thr Val Arg Leu Ala Val Ala Gly Ala Phe His Thr Glu
                245                 250                 255

Tyr Met Ala Pro Ala Leu Glu Lys Leu Lys Glu Val Leu Ala Lys Thr
                260                 265                 270

Glu Phe Lys Thr Pro Arg Ile Pro Val Ile Ser Asn Val Asp Gly Lys
                275                 280                 285

Pro His Ser Asp Pro Glu Glu Ile Lys Ala Ile Leu Ala Lys Gln Val
                290                 295                 300
```

Thr Ser Pro Val Gln Trp Glu Thr Thr Met Asn Asp Leu Val Lys Gly
305                 310                 315                 320

Gly Leu Glu Thr Gly Tyr Glu Leu Gly Pro Gly Lys Val Cys Ala Gly
                325                 330                 335

Ile Leu Lys Arg Ile Asp Arg Lys Ala Lys Met Val Asn Ile Glu Ala
                340                 345                 350

<210> SEQ ID NO 20
<211> LENGTH: 318
<212> TYPE: PRT
<213> ORGANISM: Mortierella elongata

<400> SEQUENCE: 20

Met Glu Ser Ile Ser Gln Phe Ile Pro Asn Lys Leu Pro Gln Asp Leu
1               5                   10                  15

Phe Ile Asp Phe Ala Thr Ala Phe Gly Val Arg Ala Ala Pro Tyr Val
                20                  25                  30

Asp Pro Leu Glu Asp Ala Leu Thr Ala Gln Met Glu Lys Phe Phe Pro
            35                  40                  45

Ala Leu Val His His Tyr Arg Ala Phe Leu Thr Ala Val Glu Ser Pro
        50                  55                  60

Leu Ala Ala Gln Leu Pro Leu Met Asn Pro Phe His Val Val Leu Ile
65                  70                  75                  80

Val Ile Ala Tyr Leu Val Thr Val Phe Val Gly Met Gln Ile Met Lys
                85                  90                  95

Asn Phe Asn Arg Phe Glu Val Lys Thr Phe Ser Leu Phe His Asn Phe
            100                 105                 110

Cys Leu Val Ser Ile Ser Ala Tyr Met Cys Gly Gly Ile Leu Tyr Glu
        115                 120                 125

Ala Tyr Gln Ser Lys Tyr Gly Leu Phe Glu Asn Leu Ala Asp His Thr
130                 135                 140

Ser Thr Gly Phe Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Ala Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Phe Ala Met Lys Val Met Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
290                 295                 300

Ala Lys Ala Asp Ala Ala Lys Glu Lys Ser Lys Lys Leu Gln
305                 310                 315

-continued

```
<210> SEQ ID NO 21
<211> LENGTH: 312
<212> TYPE: PRT
<213> ORGANISM: Mortierella elongata

<400> SEQUENCE: 21
```

Met Ala Ala Ala Phe Leu Asp Gln Val Asn Phe Ser Leu Asp Gln Pro
1               5                   10                  15

Phe Gly Ile Lys Leu Asp Asn Tyr Phe Ala Lys Gly Tyr Glu Leu Val
            20                  25                  30

Thr Gly Lys Ser Ile Asp Ser Phe Val Phe Gln Glu Gly Val Thr Pro
        35                  40                  45

Leu Ser Thr Gln Tyr Glu Val Ala Met Trp Thr Val Thr Tyr Phe Ile
50                  55                  60

Val Ile Phe Gly Gly Arg Gln Ile Met Lys Ser Gln Glu Ala Phe Lys
65                  70                  75                  80

Leu Lys Pro Leu Phe Ile Leu His Asn Phe Leu Thr Ile Ala Ser
                85                  90                  95

Gly Ala Leu Leu Leu Phe Ile Glu Asn Leu Val Pro Ile Leu Ala
                100                 105                 110

Arg Asn Gly Leu Phe Tyr Ala Ile Cys Asp Gln Gly Ala Trp Thr Gln
            115                 120                 125

Arg Leu Glu Leu Tyr Tyr Leu Asn Tyr Leu Val Lys Tyr Trp Glu
130                 135                 140

Leu Ala Asp Thr Val Phe Leu Val Leu Lys Lys Pro Leu Glu Phe
145                 150                 155                 160

Leu His Tyr Phe His His Ser Met Thr Met Ile Leu Cys Phe Val Gln
                165                 170                 175

Leu Gly Gly Tyr Thr Ser Val Ser Trp Val Pro Ile Thr Leu Asn Leu
            180                 185                 190

Thr Val His Val Leu Met Tyr Tyr Tyr Met Arg Ser Ala Ala Gly
                195                 200                 205

Val Arg Ile Trp Trp Lys Gln Tyr Leu Thr Thr Leu Gln Ile Val Gln
210                 215                 220

Phe Val Leu Asp Leu Gly Phe Ile Tyr Phe Cys Ser Tyr Thr Tyr Phe
225                 230                 235                 240

Ala Phe Thr Tyr Trp Pro His Leu Pro Asn Val Gly Lys Cys Ala Gly
                245                 250                 255

Thr Glu Gly Ala Ala Leu Phe Gly Cys Gly Leu Leu Ser Ser Tyr Leu
            260                 265                 270

Leu Leu Phe Ile Asn Phe Tyr Arg Leu Thr Tyr Asn Ala Lys Ala Lys
        275                 280                 285

Ala Ala Lys Glu Arg Gly Ser Asn Val Thr Pro Lys Thr Pro Lys Ala
290                 295                 300

Asp Lys Lys Lys Ser Lys His Ile
305                 310

```
<210> SEQ ID NO 22
<211> LENGTH: 274
<212> TYPE: PRT
<213> ORGANISM: Mortierella elongata

<400> SEQUENCE: 22
```

Met Glu Ser Ala Pro Met Pro Ala Gly Val Pro Phe Pro Glu Tyr Tyr
1               5                   10                  15

Asp Phe Phe Met Asn Trp Lys Thr Pro Leu Ala Ile Ala Ala Thr Tyr

```
            20                  25                  30
Thr Val Ala Val Thr Leu Phe Asn Pro Lys Val Gly Lys Val Ser Arg
        35                  40                  45
Val Val Ala Lys Ser Ala Asn Ala Lys Pro Ala Glu Lys Thr Gln Ser
    50                  55                  60
Gly Ala Ala Met Thr Ala Phe Val Phe Val His Asn Leu Ile Leu Cys
 65                 70                  75                  80
Val Tyr Ser Gly Ile Thr Phe Tyr Asn Met Phe Pro Ala Met Ile Lys
                85                  90                  95
Asn Phe Ala Thr His Ser Ile Phe Asp Ala Tyr Cys Asp Thr Asp Gln
            100                 105                 110
Ser Leu Trp Asn Gly Ser Leu Gly Tyr Trp Gly Tyr Ile Phe Tyr Leu
        115                 120                 125
Ser Lys Phe Tyr Glu Val Ile Asp Thr Ile Ile Ile Leu Lys Gly
    130                 135                 140
Arg Arg Ser Ser Leu Leu Gln Thr Tyr His His Ala Gly Ala Met Ile
145                 150                 155                 160
Thr Met Trp Ser Gly Ile Asn Tyr Gln Ala Thr Pro Ile Trp Ile Phe
                165                 170                 175
Val Val Phe Asn Ser Phe Ile His Thr Ile Met Tyr Ala Tyr Tyr Ala
            180                 185                 190
Ala Thr Ser Val Gly Leu His Pro Pro Gly Lys Lys Tyr Leu Thr Ser
        195                 200                 205
Met Gln Ile Thr Gln Phe Leu Val Gly Met Ser Ile Ala Val Ser Tyr
    210                 215                 220
Leu Phe Ile Pro Gly Cys Ile Arg Thr Pro Gly Ala Gln Met Ala Val
225                 230                 235                 240
Trp Ile Asn Val Gly Tyr Leu Phe Pro Leu Thr Tyr Leu Phe Val Asp
                245                 250                 255
Phe Ala Lys Arg Thr Tyr Ser Lys Arg Ser Ala Ala Pro Ala Lys Lys
            260                 265                 270
Thr Glu

<210> SEQ ID NO 23
<211> LENGTH: 805
<212> TYPE: PRT
<213> ORGANISM: Nannochloropsis gaditana

<400> SEQUENCE: 23

Met Gly Asn Gln Asn Ser Val Tyr Phe Gly Ala Pro Pro Val Arg Lys
 1               5                  10                  15
Lys Ala Pro Gln His Ala Asp Ile Gln Glu Ala Trp Arg Gln Ile Ala
            20                  25                  30
Ser Lys Val Ala Arg Asp Lys Gly Phe Glu His Gly Arg Lys Arg Lys
        35                  40                  45
Val Ala Ile Ile Gly Ser Val Ala Gly Leu Gly Ala Ala Tyr His
    50                  55                  60
Leu Leu Thr Cys Ala Ala Pro Gly Glu Glu Val Glu Leu Val Val Tyr
 65                 70                  75                  80
Glu Ala Ser Gly Thr Pro Gly Gly His Ala His Thr Glu Leu Val Arg
                85                  90                  95
Glu Glu Asp Gly Lys Ile Ile Ala Cys Asp Thr Gly Phe Met Val Phe
            100                 105                 110
Asn His Gln Asn Tyr Pro Asn Leu Val Glu Leu Phe Ala Glu Leu Gly
```

-continued

```
            115                 120                 125
Val Asp Asp Glu Asn Thr Asn Met Ser Phe Ala Val Ser Met Asp Glu
130                 135                 140

Gly Lys Val Glu Trp Cys Ser Glu Ser Val Lys Thr Leu Ala Gly Pro
145                 150                 155                 160

Val Tyr Arg Ala Met Leu Lys Asp Met Leu Arg Phe Asn Arg Thr Ala
                    165                 170                 175

Ser Asn Leu Leu Leu Ala Glu Pro Glu Asp Pro Arg Arg Ala Trp Thr
                180                 185                 190

Leu Ala Glu Phe Leu Glu Lys Glu Lys Tyr Gly Pro Glu Phe Thr Asn
            195                 200                 205

Tyr Tyr Ile Val Pro Met Cys Ala Ala Leu Trp Ser Ser Ala Ala
210                 215                 220

Asp Val Leu Ala Ala Ser Ala Tyr Ala Leu Leu Thr Phe Met Asp Asn
225                 230                 235                 240

His Cys Met Leu Gln Leu Phe Asn Arg Pro Gln Trp Lys Thr Val Ala
                    245                 250                 255

Gln Arg Ser Gln Thr Tyr Val Gln Lys Ile Val Ala Leu Leu Gly Glu
                260                 265                 270

Arg Leu Arg Leu Asn Ala Pro Val Lys Lys Val Val His Gly Lys
                275                 280                 285

Gly Lys Val Glu Val Thr Asp Ala Ser Tyr His Ala Glu Thr Phe Asp
290                 295                 300

Glu Ala Ile Phe Ala Cys His Pro Asp Gln Ser Leu Ala Leu Leu Glu
305                 310                 315                 320

Gly Glu Ala Arg Val Arg Leu Ala Pro Tyr Leu Glu Ala Phe Lys Tyr
                    325                 330                 335

Ala Pro Asn Ala Cys Tyr Leu His Ser Asp Pro Arg Leu Met Pro Arg
                340                 345                 350

Lys Lys Glu Ala Trp Gly Ser Trp Asn Tyr Ile Gly Thr Ser Ala Gly
                355                 360                 365

Met Leu Gly Pro Gly Arg Glu Lys Pro Val Phe Val Thr Tyr Trp Leu
370                 375                 380

Asn Gln Leu Gln Asn Leu Glu Thr Glu Thr Pro Tyr Phe Val Ser Leu
385                 390                 395                 400

Asn Pro Leu Phe Pro Pro Asp Arg Ala Leu Thr His Lys Ile Leu Arg
                    405                 410                 415

Glu Ser His Pro Gln Phe Thr Pro Ala Thr Glu Ala Ala Gln Arg Arg
                420                 425                 430

Met Thr Glu Val Gln Gly Gln Asp Gly Leu Trp Phe Cys Gly Ala Trp
                435                 440                 445

Met Gly His Gly Phe His Glu Asp Gly Leu Arg Ser Gly Leu Glu Val
                450                 455                 460

Ala Thr Ala Leu Ser Gly Gln Lys Ala Ala Trp Met Pro Pro Glu Ala
465                 470                 475                 480

Glu Ala Pro Val Tyr Pro Met Val Lys Ala His Met Asn Ala Arg Ser
                    485                 490                 495

Thr Trp Glu Arg Cys Gln Asp Leu Leu Gly Gln Leu Ala Cys Val Pro
                500                 505                 510

Ile Arg Asn Phe Leu Ala Ser Ser Ile Gln Glu Gly Cys Leu Val Leu
                515                 520                 525

Arg Leu Pro Gly Thr Gly Asp Lys Leu Trp Phe Gly Asp Arg Thr Ala
530                 535                 540
```

```
Gly Arg Lys Glu Thr Val Val Leu Arg Val Gln Ser Trp Phe Phe
545                 550                 555                 560

Val Arg Val Ala Leu Glu Tyr Asp Leu Gly Leu Ala Arg Ala Tyr Met
                565                 570                 575

Ala Gly Glu Phe Glu Val Glu Gly Thr Gly Trp Asn Ser Asp Gly Leu
            580                 585                 590

Thr Arg Leu Phe Leu Leu Phe Ile Arg Asn Arg Asp Ala Pro Ser Gly
        595                 600                 605

Gly Lys Arg Phe Ala Val Ser Ala Leu Leu Thr Ser Trp Ile Gly Tyr
    610                 615                 620

Gly Leu Asn Phe Leu Arg Tyr Arg Leu Ser Met Asp Asn Ser Leu Ala
625                 630                 635                 640

Gly Ser Arg Gln Asn Ile Ser Ala His Tyr Asp Ile Gly Asn Asp Leu
                645                 650                 655

Tyr Thr Leu Met Leu Asp Lys Ser Leu Met Met Tyr Ser Ser Ala Ile
            660                 665                 670

Tyr His Leu Glu Leu Thr Pro Ser Ser Leu Thr Ala Ser Ala Glu Ala
        675                 680                 685

Thr Ser Ser Asp Leu Val Pro Ala Gly Asn Gly Asn Gly Val Val Val
    690                 695                 700

Lys Ser Ser Phe Pro Pro Ser Ser Tyr Ser Met Ala Phe Lys Gly Ser
705                 710                 715                 720

Leu Glu Asp Ala Gln Leu Arg Lys Val Asp Thr Leu Ile Arg Thr Cys
                725                 730                 735

Arg Val Glu Arg Lys His Thr Leu Leu Asp Ile Gly Phe Gly Trp Gly
            740                 745                 750

Gly Ile Ala Ile Arg Ala Ala Glu Thr Ile Gly Cys Lys Val Val Gly
        755                 760                 765

Ile Thr Leu Ser Lys Glu Gln Lys Ala Leu Ala Glu Glu Lys Val Arg
    770                 775                 780

Ala Lys Gly Leu Glu His Leu Ile His Phe Glu Leu Val Asp Tyr Arg
785                 790                 795                 800

Val Phe Ala Arg Arg
                805

<210> SEQ ID NO 24
<211> LENGTH: 323
<212> TYPE: PRT
<213> ORGANISM: Mortierella elongata

<400> SEQUENCE: 24

Met Gly Arg Asp Leu Tyr Glu Ser Tyr Pro Ile Val Arg Gln Thr Ile
1               5                   10                  15

Asp Glu Ala Asp Ala Ile Leu Ser Ser Met Pro Ser Ser Ser Ser Ser
            20                  25                  30

Ser Ser Pro Gln Glu Gly Tyr Leu Lys Arg Val Met Phe Glu Gly
        35                  40                  45

Pro Gln Glu Glu Leu Thr Arg Thr Glu Asn Ala Gln Pro Ala Ile Leu
    50                  55                  60

Thr Thr Ser Ile Ala Leu Leu Arg Val Leu Glu Thr His Gly Leu
65                  70                  75                  80

Asp Leu Lys Glu Ser Cys Arg Phe Ala Leu Gly His Ser Leu Gly Glu
                85                  90                  95

Tyr Ser Ala Leu Val Ala Thr Arg Ala Leu Ser Leu Pro Asp Ala Val
```

```
                100                 105                 110
Arg Leu Val Arg Ile Arg Gly Asp Ala Met Ala Met Ala Val Thr Asp
            115                 120                 125

Lys Lys Gly Met Thr Ala Met Ser Ala Leu Val Val Arg Ala Ser Lys
130                 135                 140

Leu Asp Glu Leu Val Lys Ala Met His Glu Ile Gln Thr Glu Leu Ser
145                 150                 155                 160

Ser Thr Val Glu Ile Ala Glu Ile Ala Asn Ile Asn Ser Ser Phe Gln
                165                 170                 175

Val Val Ile Ser Gly Thr Val Lys Gly Val Asp His Ala Ser Lys Thr
            180                 185                 190

Leu Gln Phe Arg Lys Ile Ala Ala Lys Ala Val Asp Leu Pro Val Ser
        195                 200                 205

Ala Pro Phe His Cys Ser Leu Met Glu Pro Ala Ala Arg Val Met Lys
    210                 215                 220

Asp Ala Leu Ala Asp Ile Ser Phe Lys Gln Pro Ile Ile Pro Ile Val
225                 230                 235                 240

Ser Asn Val Gln Ala Gln Pro Ile Glu Ser Ser Asn Asp Ile Pro Ser
                245                 250                 255

Leu Leu Val Gln Gln Val Thr Asp Thr Val Gln Trp Arg Gln Ser Leu
            260                 265                 270

Val Asn Leu His Ser Gln Gln Gln Tyr Asp Ile Ser Glu Tyr Ile
        275                 280                 285

Cys Ile Gly Pro Gly Lys Val Ile Cys Asn Leu Leu Arg Lys Glu Tyr
    290                 295                 300

Pro Leu Asp Thr Ile Arg Ser Val Ser Thr Val Glu Asp Ile Gln Gln
305                 310                 315                 320

Trp Lys Leu

<210> SEQ ID NO 25
<211> LENGTH: 360
<212> TYPE: PRT
<213> ORGANISM: Saccharomyces cerevisiae

<400> SEQUENCE: 25

Met Lys Leu Leu Thr Phe Pro Gly Gln Gly Thr Ser Ile Ser Ile Ser
1               5                   10                  15

Ile Leu Lys Ala Ile Ile Arg Asn Lys Ser Arg Glu Phe Gln Thr Ile
            20                  25                  30

Leu Ser Gln Asn Gly Lys Glu Ser Asn Asp Leu Leu Gln Tyr Ile Phe
        35                  40                  45

Gln Asn Pro Ser Ser Pro Gly Ser Ile Ala Val Cys Ser Asn Leu Phe
    50                  55                  60

Tyr Gln Leu Tyr Gln Ile Leu Ser Asn Pro Ser Asp Pro Gln Asp Gln
65                  70                  75                  80

Ala Pro Lys Asn Met Thr Lys Ile Asp Ser Pro Asp Lys Lys Asp Asn
                85                  90                  95

Glu Gln Cys Tyr Leu Leu Gly His Ser Leu Gly Glu Leu Thr Cys Leu
            100                 105                 110

Ser Val Asn Ser Leu Phe Ser Leu Lys Asp Leu Phe Asp Ile Ala Asn
        115                 120                 125

Phe Arg Asn Lys Leu Met Val Thr Ser Thr Glu Lys Tyr Leu Val Ala
    130                 135                 140

His Asn Ile Asn Arg Ser Asn Lys Phe Glu Met Trp Ala Leu Ser Ser
```

```
            145                 150                 155                 160
Pro Arg Ala Thr Asp Leu Pro Gln Glu Val Gln Lys Leu Leu Asn Ser
                165                 170                 175

Pro Asn Leu Leu Ser Ser Gln Asn Thr Ile Ser Val Ala Asn Ala
            180                 185                 190

Asn Ser Val Lys Gln Cys Val Thr Gly Leu Val Asp Asp Leu Glu
            195                 200                 205

Ser Leu Arg Thr Glu Leu Asn Leu Arg Phe Pro Arg Leu Arg Ile Thr
    210                 215                 220

Glu Leu Thr Asn Pro Tyr Asn Ile Pro Phe His Asn Ser Thr Val Leu
225                 230                 235                 240

Arg Pro Val Gln Glu Pro Leu Tyr Asp Tyr Ile Trp Asp Ile Leu Lys
                245                 250                 255

Lys Asn Gly Thr His Thr Leu Met Glu Leu Asn His Pro Ile Ile Ala
                260                 265                 270

Asn Leu Asp Gly Asn Ile Ser Tyr Tyr Ile His His Ala Leu Asp Arg
            275                 280                 285

Phe Val Lys Cys Ser Ser Arg Thr Val Gln Phe Thr Met Cys Tyr Asp
    290                 295                 300

Thr Ile Asn Ser Gly Thr Pro Val Glu Ile Asp Lys Ser Ile Cys Phe
305                 310                 315                 320

Gly Pro Gly Asn Val Ile Tyr Asn Leu Ile Arg Arg Asn Cys Pro Gln
                325                 330                 335

Val Asp Thr Ile Glu Tyr Thr Ser Leu Ala Thr Ile Asp Ala Tyr His
            340                 345                 350

Lys Ala Ala Glu Glu Asn Lys Asp
            355                 360

<210> SEQ ID NO 26
<211> LENGTH: 437
<212> TYPE: PRT
<213> ORGANISM: Mortierella elongata

<400> SEQUENCE: 26

Met Ser Leu Asn Ala Arg Arg Val Val Val Thr Gly Leu Gly Leu Val
1               5                   10                  15

Thr Pro Leu Gly Ile Gly Val Gln Gln Ser Trp Ser Lys Leu Ile Ala
                20                  25                  30

Gly Glu Cys Gly Val Val Ser Leu Lys Asp Leu Pro Ser Pro Thr Pro
            35                  40                  45

Gly Leu Pro Gly Phe Asp Thr Leu Pro Ser Gln Val Gly Ala Ile Val
    50                  55                  60

Lys Arg Thr Gly Gly Lys Glu Leu Gly Gly Phe Asp Ser Thr Glu Trp
65                  70                  75                  80

Leu Asp Arg Gly Asp Glu Lys Arg Met Ala Val Phe Thr Gln Tyr Ala
                85                  90                  95

Ile Ala Ala Ala Arg Met Ala Ile Lys Asp Ala Asn Trp Glu Thr Thr
            100                 105                 110

Thr Glu Glu Glu Lys Glu Arg Thr Gly Val Cys Leu Gly Ser Gly Ile
        115                 120                 125

Gly Ser Leu Asp Asp Met Ala Thr Thr Ala Leu Ser Phe Ala Glu Ser
    130                 135                 140

Gly Tyr Arg Lys Met Ser Pro Met Phe Val Pro Lys Ile Leu Ile Asn
145                 150                 155                 160
```

```
Met Ala Ala Gly His Leu Thr Met Lys Tyr Gly Phe Lys Gly Pro Asn
                165                 170                 175

His Ala Val Ser Thr Ala Cys Thr Thr Gly Ala His Ser Leu Gly Asp
            180                 185                 190

Ala Met Arg Phe Ile Gln Tyr Gly Asp Ala Asp Val Met Val Ala Gly
        195                 200                 205

Gly Ser Glu Ala Cys Ile His Pro Leu Ala Val Ala Gly Phe Ala Lys
    210                 215                 220

Ala Lys Ser Leu Ala Thr Lys Tyr Asn Asp Ser Pro Ser Glu Ala Ser
225                 230                 235                 240

Arg Pro Phe Asp Lys Asn Arg Asp Gly Phe Val Ile Gly Glu Gly Ala
                245                 250                 255

Gly Val Val Leu Glu Glu Tyr Glu His Ala Lys Lys Arg Gly Ala
            260                 265                 270

His Ile Tyr Ala Glu Leu Arg Gly Tyr Gly Leu Ser Gly Asp Ala His
        275                 280                 285

His Met Thr Ala Pro Pro Glu Asn Gly Thr Gly Ala Ala Met Ala Met
    290                 295                 300

Arg Arg Ala Leu Lys Ala Ala Arg Leu Thr Pro Ala Asp Ile Gly Tyr
305                 310                 315                 320

Val Asn Ala His Ala Thr Ser Thr His Gln Gly Asp Ile Ala Glu Asn
                325                 330                 335

Arg Ala Ile Lys Ser Val Phe Asp Gly His His Asp Thr Ile Ala Val
            340                 345                 350

Ser Ser Thr Lys Gly Ala Val Gly His Leu Leu Gly Ala Ala Gly Ala
        355                 360                 365

Val Glu Ala Ile Phe Ala Ile Leu Ala Val Lys Asn Asn Ile Leu Pro
    370                 375                 380

Pro Thr Leu Asn Leu His Glu His Asp Asp Ser Gly Glu Phe Thr Leu
385                 390                 395                 400

Asn Tyr Val Pro Leu Lys Ala Gln Glu Lys Val Leu Lys Ala Ala Ile
                405                 410                 415

Thr Asn Ser Phe Gly Phe Gly Thr Asn Ala Ser Leu Cys Phe Ala
            420                 425                 430

Lys Val Asp Thr Lys
        435

<210> SEQ ID NO 27
<211> LENGTH: 458
<212> TYPE: PRT
<213> ORGANISM: Nannochloropsis gaditana

<400> SEQUENCE: 27

Met Arg Leu Ser Thr Leu Ser Val Leu Gly Pro Ala Leu Gly Cys Ala
1               5                   10                  15

Phe Leu Leu Phe Asp Ser Ser Leu Ala Tyr Leu Pro Ser Tyr Met Arg
            20                  25                  30

Gly Ser Lys Gly Gln Ile Tyr Met Lys Glu Lys Ser Gln Arg Val Val
        35                  40                  45

Val Thr Gly Leu Gly Pro Ile Ser Ala Val Gly Ile Gly Lys Asp Ala
    50                  55                  60

Phe Trp Lys Ala Leu Leu Glu Gly Lys Ser Gly Ile Asp Arg Ile Ser
65                  70                  75                  80

Gly Phe Asp Pro Ser Gly Leu Thr Cys Gln Ile Gly Ala Glu Val Lys
                85                  90                  95
```

Asp Phe Asp Ala Lys Pro Tyr Phe Lys Asp Arg Lys Ser Ala Val Arg
                100                 105                 110

Asn Asp Arg Val Thr Leu Met Gly Val Ala Ala Ser Arg Ile Ala Val
            115                 120                 125

Asp Asp Ala Lys Leu Asp Leu Ser Ser Val Glu Gly Glu Arg Phe Gly
        130                 135                 140

Val Val Val Gly Ser Ala Phe Gly Gly Leu Gln Thr Leu Glu Thr Gln
145                 150                 155                 160

Ile Gln Thr Met Asn Glu Lys Gly Pro Gly Ser Val Ser Pro Phe Ala
                165                 170                 175

Val Pro Ser Leu Leu Ser Asn Leu Ile Ser Gly Val Ile Ala Leu Glu
            180                 185                 190

Asn Gly Ala Lys Gly Pro Asn Tyr Val Val Asn Ser Ala Cys Ala Ala
        195                 200                 205

Ser Thr His Ala Leu Gly Leu Ala Tyr Ala His Ile Ala His Gly Glu
210                 215                 220

Ala Asp Val Cys Leu Ala Gly Gly Ser Glu Ala Ala Val Thr Pro Phe
225                 230                 235                 240

Gly Phe Ala Gly Phe Cys Ser Met Lys Ala Met Ala Thr Lys Tyr Asn
                245                 250                 255

Asp Asn Pro Ser Gln Gly Ser Arg Pro Phe Asp Lys Asp Arg Cys Gly
            260                 265                 270

Phe Val Met Gly Glu Gly Ala Gly Met Val Val Leu Glu Ser Leu Glu
        275                 280                 285

His Ala Gln Lys Arg Gly Ala His Ile Tyr Ala Glu Val Ala Gly Phe
290                 295                 300

Gly Gln Ala Cys Asp Ala His His Ile Thr Thr Pro His Pro Glu Gly
305                 310                 315                 320

Ala Gly Leu Ala Gln Ala Ile Thr Leu Ala Leu Glu Asp Ala Gly Met
                325                 330                 335

Ala Lys Glu Asp Leu Thr Tyr Ile Asn Ala His Gly Thr Ser Thr Ala
            340                 345                 350

Tyr Asn Asp Lys Phe Glu Thr Leu Ala Val Lys Ala Leu Gly Glu
        355                 360                 365

Glu Val Ala Lys Lys Met Tyr Leu Ser Ser Thr Lys Gly Ser Thr Gly
370                 375                 380

His Thr Leu Gly Ala Ala Gly Gly Leu Glu Ala Ile Ala Thr Val Leu
385                 390                 395                 400

Ala Ile Glu Thr Lys Thr Leu Pro Pro Thr Ile Asn Tyr Glu Thr Pro
                405                 410                 415

Asp Pro Asp Cys Asp Leu Asn Val Val Pro Asn Lys Pro Ile Thr Leu
            420                 425                 430

Asn Glu Ile Thr Gly Ala Ala Ser Gln Ser Ala Gly Phe Gly Gly His
        435                 440                 445

Asp Ser Val Val Val Phe Lys Pro Phe Lys
450                 455

<210> SEQ ID NO 28
<211> LENGTH: 429
<212> TYPE: PRT
<213> ORGANISM: Nannochloropsis gaditana

<400> SEQUENCE: 28

Met Ser Lys Arg Ser Arg Ala Ser Ser Arg Gly Leu Ala Tyr Ile Gln

-continued

```
1               5                   10                  15
Arg Leu His Leu Leu Ser Leu Ser Leu Cys Leu Leu Ser Leu Gln
            20                  25                  30
Cys Ser Ile Arg Ala Ala Ala Phe Leu Val Pro Ser Ser Pro Leu Pro
            35                  40                  45
Ser Leu Pro Ser Ser His Gly Pro Ser Leu Pro Ser Ser Arg Pro Pro
        50                  55                  60
Ser Ser Val Pro Lys Ser Gln Ala Leu Arg Met Ala Thr Ser Leu Thr
65                  70                  75                  80
Glu Gly Ser Ser Val Asp Ala Pro Ala Val Pro Gly Arg Ser Phe
                85                  90                  95
Leu Arg Ala Lys Pro Ile Gly Val Gly Ser Ala Ala Pro Glu Asp Val
                100                 105                 110
Ile Thr Asn Thr Asp Leu Glu Ser Ile Val Glu Thr Ser Asp Glu Trp
            115                 120                 125
Ile Phe Thr Arg Thr Gly Ile Ser Gln Arg Arg Ile Leu Thr Ser Gly
        130                 135                 140
Gly Gln Ile Arg Ala Leu Ala Ala Thr Ala Ala Ala Arg Ala Leu Ala
145                 150                 155                 160
Ser Ala Gly Leu Glu Gly Lys Asp Ile Asp Leu Val Val Leu Ala Thr
                165                 170                 175
Ser Ser Pro Asp Asp Leu Phe Gly Asp Ala Thr Ser Val Ala Ala Ala
                180                 185                 190
Val Gly Ala Thr Gln Ala Val Ala Phe Asp Leu Thr Ala Ala Cys Ser
            195                 200                 205
Gly Phe Leu Phe Gly Val Val Ser Ala Ser Gln Phe Leu His Ser Gly
        210                 215                 220
Cys Tyr Arg Arg Ala Leu Val Val Gly Ala Asp Ala Leu Ser Arg Trp
225                 230                 235                 240
Val Asp Trp Glu Asp Arg Asn Ser Cys Ile Leu Phe Gly Asp Gly Ala
                245                 250                 255
Gly Ala Val Val Leu Glu Ala Ala Glu Gly Glu Glu Asp Ser Gly Val
            260                 265                 270
Leu Gly Phe Ala Met His Ser Asp Gly Thr Gly Gln Gly Asp Leu Asn
        275                 280                 285
Leu Gln Phe Ser Arg Asp Asp Ser Gln Ser Pro Pro Ser Ile Arg Glu
        290                 295                 300
Val Thr Pro Tyr Lys Gly Lys Tyr Asn Asn Ile Ala Met Asn Gly Lys
305                 310                 315                 320
Glu Val Tyr Lys Phe Ala Thr Arg Lys Val Pro Thr Val Ile Glu Glu
                325                 330                 335
Ala Leu Ala Asn Ala Gly Leu Gly Val Glu Asn Val Asp Trp Leu Leu
            340                 345                 350
Leu His Gln Ala Asn Ile Arg Ile Met Asp Val Val Ala Asp Arg Leu
        355                 360                 365
Gly Leu Ser Lys Asp Lys Ile Leu Thr Asn Leu Ser Glu Tyr Gly Asn
        370                 375                 380
Thr Ser Ala Gly Ser Ile Pro Leu Ala Leu Asp Glu Ala Val Lys Ala
385                 390                 395                 400
Ala Lys Val Lys Lys Gly Asp Ile Ile Ala Cys Ala Gly Phe Gly Ala
                405                 410                 415
Gly Leu Ser Trp Gly Ser Ala Ile Ile Arg Trp Gln Gly
        420                 425
```

<210> SEQ ID NO 29
<211> LENGTH: 547
<212> TYPE: PRT
<213> ORGANISM: Mortierella elongata

<400> SEQUENCE: 29

Met Leu Asp Trp Arg Phe Phe Thr Glu Arg Thr Cys Ala Ala Val Arg
1               5                   10                  15

Ala Leu Gly Ser Glu Arg His Arg His Ser Thr Arg Trp Ala Leu Cys
            20                  25                  30

Leu Ser Asp Pro Phe Glu Phe Ala Cys Gly Leu Phe Ala Leu Leu Ala
        35                  40                  45

Ala Gly Lys Gln Ile Val Leu Pro Ser Asn His Lys Pro Ala Ala Leu
50                  55                  60

Leu Pro Leu Ala Gly Leu Tyr Asp Ser Val Leu Asp Asp Leu Asp Gly
65                  70                  75                  80

Leu Leu Ala Asn Gly Ala Gly Pro Cys Ala Lys Leu Arg Ile Asp
                85                  90                  95

Pro Arg Ala Pro Leu Ser Leu Val Thr Ser Gly Ser Ser Gly Val Pro
            100                 105                 110

Lys Val Ile Gln Lys Thr Leu Ala Gln Phe Glu Ala Glu Ile His Thr
        115                 120                 125

Leu Ala Thr Leu Trp Gly Thr Val Met Arg Gly Val Thr Val Val Ala
    130                 135                 140

Ser Val Pro His His Ile Tyr Gly Leu Leu Phe Arg Leu Leu Trp
145                 150                 155                 160

Pro Leu Ala Ala Gly Gln Pro Phe Asp Arg Met Thr Cys Val Glu Pro
                165                 170                 175

Ala Asp Val Arg Ala Arg Leu Ala Ala Leu Gln Asn Thr Val Leu Val
            180                 185                 190

Ser Ser Pro Ala Gln Leu Thr Arg Trp Pro Ser Leu Ile Asn Leu Thr
        195                 200                 205

Gln Leu Thr Pro Pro Pro Gly Leu Ile Phe Ser Ser Gly Gly Pro Leu
    210                 215                 220

Pro Ala Glu Thr Ala Ala Ile Tyr Thr Gln Ala Phe Gly Ala Ala Pro
225                 230                 235                 240

Ile Glu Val Tyr Gly Ser Thr Glu Thr Gly Gly Ile Ala Trp Arg Cys
                245                 250                 255

Gln Pro Gln Ala Thr His Gln Asn Glu Val Ser Asp Ala Trp Thr Pro
            260                 265                 270

Met Pro Ala Ile Asp Val Arg Cys Asp Thr Glu Gly Ala Leu Gln Leu
        275                 280                 285

Arg Ser Pro His Leu Pro Asp Asp Gln Trp Trp Arg Met Glu Asp Ala
    290                 295                 300

Val Gln Ile Glu Ala Asp Gly Arg Phe Arg Leu Arg Gly Arg Leu Asp
305                 310                 315                 320

Arg Ile Ile Lys Leu Glu Glu Lys Arg Val Ser Leu Pro Glu Leu Glu
                325                 330                 335

His Val Leu Met Arg His Pro Trp Val Lys Gln Ala Ala Val Ala Pro
            340                 345                 350

Leu Asn Gly Ala Arg Met Thr Leu Gly Ala Leu Leu Thr Leu Thr Glu
        355                 360                 365

Glu Gly Ile Gln Ala Trp Arg Ser Ala Ala Ser Arg Arg Phe Ile Thr

```
            370                 375                 380
Gln Ala Leu Arg Arg Tyr Leu Ala Glu Tyr Phe Asp Gly Val Val Leu
385                 390                 395                 400

Pro Arg His Trp Arg Phe Cys Met Gln Leu Pro Phe Asp Glu Arg Gly
                405                 410                 415

Lys Leu Ser Val Thr Gln Leu Ala Thr Arg Phe Ala Thr His Pro Leu
                420                 425                 430

Gln Pro Glu Val Leu Ala Glu Trp Cys Asp Asp Asn Thr Ala Leu Leu
            435                 440                 445

Glu Leu His Val Pro Ala Thr Leu Ile His Phe Ser Gly His Phe Pro
        450                 455                 460

Gly Leu Pro Ile Leu Pro Gly Val Val Gln Ile Asp Trp Val Val Arg
465                 470                 475                 480

Tyr Ala Ala His Tyr Phe Ala Arg Cys Asn Gly Phe Gln Thr Leu Glu
                485                 490                 495

Gln Ile Lys Phe Leu Ser Met Val Arg Pro Gly Thr Thr Leu Arg Leu
                500                 505                 510

Ala Leu Ala His Asp Pro Glu Arg Ala Arg Ile Thr Phe Arg Tyr Tyr
            515                 520                 525

Val Gly Glu Arg Asp Tyr Ala Thr Gly Arg Ile Val Tyr Ser Lys Ser
        530                 535                 540

Ala Val Val
545

<210> SEQ ID NO 30
<211> LENGTH: 202
<212> TYPE: PRT
<213> ORGANISM: Nannochloropsis gaditana

<400> SEQUENCE: 30

Met His Leu Leu Ala Ala Leu Val Ala Leu Pro Ala Met Cys Thr Ala
1               5                   10                  15

Phe Val Val Pro Leu Pro Ser Ala Pro Lys His Ala Val Arg Met Met
                20                  25                  30

Ala Asp Gly Asp Ala Ala Gly Ala Glu Trp Arg Gly Gly Gln Ala Ala
            35                  40                  45

Ser Ala Val Ser Lys Asp Leu Lys Thr Leu Leu Thr Asn Glu Asn Val
50                  55                  60

Ala Ser Ile Leu Pro His Arg Tyr Pro Phe Leu Leu Val Asp Lys Val
65                  70                  75                  80

Ile Glu Met Glu Pro Gly Lys Lys Ala Val Gly Ile Lys Gln Ile Thr
                85                  90                  95

Ala Asn Glu Pro Gln Phe Thr Gly His Phe Pro Glu Arg Pro Ile Met
                100                 105                 110

Pro Gly Val Leu Met Val Glu Ala Met Ala Gln Leu Ser Gly Val Leu
            115                 120                 125

Cys Leu Gln Pro Pro Val Ser Asp Gly Lys Gly Leu Phe Phe Ala
130                 135                 140

Gly Ile Asp Gly Val Lys Phe Arg Lys Pro Val Val Pro Gly Asp Thr
145                 150                 155                 160

Leu Val Met Glu Val Glu Leu Val Lys Phe Met Glu Ser Phe Gly Ile
                165                 170                 175

Ala Lys Leu Lys Gly Lys Ala Tyr Val Asp Gly Asp Val Ala Val Glu
                180                 185                 190
```

Ile Lys Glu Met Thr Phe Ala Leu Ser Lys
        195                 200

<210> SEQ ID NO 31
<211> LENGTH: 171
<212> TYPE: PRT
<213> ORGANISM: Nannochloropsis gaditana

<400> SEQUENCE: 31

Met Ala Asp Gly Asp Ala Ala Gly Ala Glu Trp Arg Gly Gly Gln Ala
1               5                   10                  15

Ala Ser Ala Val Ser Lys Asp Leu Lys Thr Leu Leu Thr Asn Glu Asn
            20                  25                  30

Val Ala Ser Ile Leu Pro His Arg Tyr Pro Phe Leu Leu Val Asp Lys
        35                  40                  45

Val Ile Glu Met Glu Pro Gly Lys Lys Ala Val Gly Ile Lys Gln Ile
    50                  55                  60

Thr Ala Asn Glu Pro Gln Phe Thr Gly His Phe Pro Glu Arg Pro Ile
65                  70                  75                  80

Met Pro Gly Val Leu Met Val Glu Ala Met Ala Gln Leu Ser Gly Val
                85                  90                  95

Leu Cys Leu Gln Pro Pro Val Ser Asp Gly Lys Gly Leu Phe Phe
            100                 105                 110

Ala Gly Ile Asp Gly Val Lys Phe Arg Lys Pro Val Val Pro Gly Asp
        115                 120                 125

Thr Leu Val Met Glu Val Glu Leu Val Lys Phe Met Glu Ser Phe Gly
    130                 135                 140

Ile Ala Lys Leu Lys Gly Lys Ala Tyr Val Asp Gly Asp Val Ala Val
145                 150                 155                 160

Glu Ile Lys Glu Met Thr Phe Ala Leu Ser Lys
                165                 170

<210> SEQ ID NO 32
<211> LENGTH: 258
<212> TYPE: PRT
<213> ORGANISM: Nannochloropsis gaditana

<400> SEQUENCE: 32

Met Ala Ser His His Leu Thr Thr Gln Glu His Ala Arg Arg Lys Val
1               5                   10                  15

Ala Val Val Thr Gly Ala Ala Gly Thr Leu Gly Glu Ser Ile Thr Gly
            20                  25                  30

Met Leu Leu Ser Glu Gly Tyr Val Ala Ala Leu Asp Ile Arg Ala
        35                  40                  45

Glu Gly Leu Ser Ala Phe Lys Ala Thr Leu Asp Lys Lys Ser Asp Gln
    50                  55                  60

Tyr His Ala Phe Ala Val Asp Ile Ser Ser Ala Ser Ala Val Glu Glu
65                  70                  75                  80

Val Cys Arg Thr Ile Leu Thr Arg Leu Gly Ala Val Ser Val Leu Ile
                85                  90                  95

Asn Asn Ala Gly Leu Leu Ser Asn His Lys Cys Val Gln Thr Ser Leu
            100                 105                 110

Thr Glu Trp His Arg Val Met His Val Asn Val Asp Gly Ala Phe Leu
        115                 120                 125

Leu Ser Gln Gln Leu Leu Pro Cys Met Arg Ser Met His Phe Gly Arg
    130                 135                 140

```
Ile Val Asn Ile Thr Ser Met Ala Ala Lys Thr Gly Gly Val Thr Ala
145                 150                 155                 160

Gly Thr Ala Tyr Ala Val Ser Lys Gly Ala Leu Ala Ser Leu Thr Phe
            165                 170                 175

Ser Leu Ala Arg Glu Thr Ala Gly Asp Gly Ile Thr Val Asn Gly Val
        180                 185                 190

Ala Pro Ala Tyr Val Lys Thr Pro Met Val Met Gln Gln Leu Arg Glu
    195                 200                 205

Glu Gln Arg Val Gln Val Leu Asn Ser Ile Pro Val Gly Arg Phe Cys
210                 215                 220

Glu Pro Glu Glu Val Ala His Thr Val Arg Phe Leu Ile Ser Pro Leu
225                 230                 235                 240

Ala Gly Phe Ile Thr Gly Glu Ile Ile Asp Gln Asn Gly Gly Tyr His
                245                 250                 255

Met Asp

<210> SEQ ID NO 33
<211> LENGTH: 241
<212> TYPE: PRT
<213> ORGANISM: Mortierella elongata

<400> SEQUENCE: 33

Met Arg Arg Arg Val Leu Val Thr Gly Ala Ser Arg Gly Ile Gly Arg
1               5                   10                  15

Ala Ile Ala Glu Gln Leu Ala Ser Asp Gly Phe Ala Leu Thr Ile His
                20                  25                  30

Ala His Ser Gly Trp Thr Glu Ala Gln Ala Val Val Ala Gly Ile Val
            35                  40                  45

Ala Gln Gly Gly Gln Ala Gln Ala Leu Arg Phe Asp Val Arg Glu Arg
        50                  55                  60

Ala Leu Cys Ser Lys Ile Leu Thr Glu Asp Val Ala Ala His Gly Ala
65                  70                  75                  80

Tyr Tyr Gly Ile Val Cys Asn Ala Gly Val Val Arg Asp Ala Val Phe
                85                  90                  95

Pro Ala Leu Ser Gly Glu Asp Trp Asp Thr Val Ile Asp Thr Ser Leu
            100                 105                 110

Asp Gly Phe Tyr Asn Val Val His Pro Leu Thr Met Pro Met Val Arg
        115                 120                 125

Ala Lys Ala Gly Gly Arg Ile Ile Thr Ile Ser Ser Val Ser Gly Met
130                 135                 140

Ile Gly Asn Arg Gly Gln Val Asn Tyr Ser Ala Ala Lys Ala Gly Leu
145                 150                 155                 160

Ile Gly Ala Ser Lys Ala Leu Ala Leu Glu Leu Ala Ser Arg Ala Ile
                165                 170                 175

Thr Val Asn Cys Val Ala Pro Gly Ile Ile Ala Thr Glu Met Ile Asn
            180                 185                 190

Thr Glu Leu Arg Glu Gln Ala Ser Lys Glu Val Pro Met Lys Arg Val
        195                 200                 205

Gly Thr Pro Ser Glu Val Ala Ala Leu Val Ser Phe Leu Met Ser Asp
210                 215                 220

Ala Ala Ala Tyr Ile Thr Arg Gln Val Ile Gly Val Asn Gly Gly Ile
225                 230                 235                 240

Val
```

```
<210> SEQ ID NO 34
<211> LENGTH: 318
<212> TYPE: PRT
<213> ORGANISM: Mortierella elongata

<400> SEQUENCE: 34

Met Glu Ser Ile Ser Gln Phe Ile Pro Asn Lys Leu Pro Gln Asp Leu
1               5                   10                  15

Phe Ile Asp Phe Ala Thr Ala Phe Gly Val Arg Ala Ala Pro Tyr Val
            20                  25                  30

Asp Pro Leu Glu Asp Ala Leu Thr Ala Gln Met Glu Lys Phe Phe Pro
        35                  40                  45

Ala Leu Val His His Tyr Arg Ala Phe Leu Thr Ala Val Glu Ser Pro
    50                  55                  60

Leu Ala Ala Gln Leu Pro Leu Met Asn Pro Phe His Val Val Leu Ile
65                  70                  75                  80

Val Ile Ala Tyr Leu Val Thr Val Phe Val Gly Met Gln Ile Met Lys
                85                  90                  95

Asn Phe Asn Arg Phe Glu Val Lys Thr Phe Ser Leu Phe His Asn Phe
            100                 105                 110

Cys Leu Val Ser Ile Ser Ala Tyr Met Cys Gly Gly Ile Leu Tyr Glu
        115                 120                 125

Ala Tyr Gln Ser Lys Tyr Gly Leu Phe Glu Asn Leu Ala Asp His Thr
    130                 135                 140

Ser Thr Gly Phe Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Ala Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Phe Ala Met Lys Val Met Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ser Lys Lys Leu Gln
305                 310                 315

<210> SEQ ID NO 35
<211> LENGTH: 312
<212> TYPE: PRT
<213> ORGANISM: Mortierella elongata

<400> SEQUENCE: 35

Met Ala Ala Ala Phe Leu Asp Gln Val Asn Phe Ser Leu Asp Gln Pro
1               5                   10                  15

Phe Gly Ile Lys Leu Asp Asn Tyr Phe Ala Lys Gly Tyr Glu Leu Val
```

```
                20                  25                  30
Thr Gly Lys Ser Ile Asp Ser Phe Val Phe Gln Glu Gly Val Thr Pro
             35                  40                  45
Leu Ser Thr Gln Tyr Glu Val Ala Met Trp Thr Val Thr Tyr Phe Ile
 50                  55                  60
Val Ile Phe Gly Gly Arg Gln Ile Met Lys Ser Gln Glu Ala Phe Lys
 65                  70                  75                  80
Leu Lys Pro Leu Phe Ile Leu His Asn Phe Leu Leu Thr Ile Ala Ser
                 85                  90                  95
Gly Ala Leu Leu Leu Leu Phe Ile Glu Asn Leu Val Pro Ile Leu Ala
                100                 105                 110
Arg Asn Gly Leu Phe Tyr Ala Ile Cys Asp Gln Gly Ala Trp Thr Gln
                115                 120                 125
Arg Leu Glu Leu Leu Tyr Tyr Leu Asn Tyr Leu Val Lys Tyr Trp Glu
                130                 135                 140
Leu Ala Asp Thr Val Phe Leu Val Leu Lys Lys Pro Leu Glu Phe
145                 150                 155                 160
Leu His Tyr Phe His His Ser Met Thr Met Ile Leu Cys Phe Val Gln
                165                 170                 175
Leu Gly Gly Tyr Thr Ser Val Ser Trp Val Pro Ile Thr Leu Asn Leu
                180                 185                 190
Thr Val His Val Leu Met Tyr Tyr Tyr Met Arg Ser Ala Ala Gly
                195                 200                 205
Val Arg Ile Trp Trp Lys Gln Tyr Leu Thr Thr Leu Gln Ile Val Gln
                210                 215                 220
Phe Val Leu Asp Leu Gly Phe Ile Tyr Phe Cys Ser Tyr Thr Tyr Phe
225                 230                 235                 240
Ala Phe Thr Tyr Trp Pro His Leu Pro Asn Val Gly Lys Cys Ala Gly
                245                 250                 255
Thr Glu Gly Ala Ala Leu Phe Gly Cys Gly Leu Leu Ser Ser Tyr Leu
                260                 265                 270
Leu Leu Phe Ile Asn Phe Tyr Arg Leu Thr Tyr Asn Ala Lys Ala Lys
                275                 280                 285
Ala Ala Lys Glu Arg Gly Ser Asn Val Thr Pro Lys Thr Pro Lys Ala
                290                 295                 300
Asp Lys Lys Lys Ser Lys His Ile
305                 310

<210> SEQ ID NO 36
<211> LENGTH: 274
<212> TYPE: PRT
<213> ORGANISM: Mortierella elongata

<400> SEQUENCE: 36

Met Glu Ser Ala Pro Met Pro Ala Gly Val Pro Phe Pro Glu Tyr Tyr
1               5                  10                  15
Asp Phe Phe Met Asn Trp Lys Thr Pro Leu Ala Ile Ala Ala Thr Tyr
                 20                  25                  30
Thr Val Ala Val Thr Leu Phe Asn Pro Lys Val Gly Lys Val Ser Arg
             35                  40                  45
Val Val Ala Lys Ser Ala Asn Ala Lys Pro Ala Glu Lys Thr Gln Ser
 50                  55                  60
Gly Ala Ala Met Thr Ala Phe Val Phe Val His Asn Leu Ile Leu Cys
 65                  70                  75                  80
```

```
Val Tyr Ser Gly Ile Thr Phe Tyr Asn Met Phe Pro Ala Met Ile Lys
                85                  90                  95

Asn Phe Ala Thr His Ser Ile Phe Asp Ala Tyr Cys Asp Thr Asp Gln
            100                 105                 110

Ser Leu Trp Asn Gly Ser Leu Gly Tyr Trp Gly Tyr Ile Phe Tyr Leu
            115                 120                 125

Ser Lys Phe Tyr Glu Val Ile Asp Thr Ile Ile Ile Leu Lys Gly
            130                 135                 140

Arg Arg Ser Ser Leu Leu Gln Thr Tyr His His Ala Gly Ala Met Ile
145                 150                 155                 160

Thr Met Trp Ser Gly Ile Asn Tyr Gln Ala Thr Pro Ile Trp Ile Phe
                165                 170                 175

Val Val Phe Asn Ser Phe Ile His Thr Ile Met Tyr Ala Tyr Tyr Ala
            180                 185                 190

Ala Thr Ser Val Gly Leu His Pro Pro Gly Lys Lys Tyr Leu Thr Ser
            195                 200                 205

Met Gln Ile Thr Gln Phe Leu Val Gly Met Ser Ile Ala Val Ser Tyr
            210                 215                 220

Leu Phe Ile Pro Gly Cys Ile Arg Thr Pro Gly Ala Gln Met Ala Val
225                 230                 235                 240

Trp Ile Asn Val Gly Tyr Leu Phe Pro Leu Thr Tyr Leu Phe Val Asp
                245                 250                 255

Phe Ala Lys Arg Thr Tyr Ser Lys Arg Ser Ala Ala Pro Ala Lys Lys
            260                 265                 270

Thr Glu

<210> SEQ ID NO 37
<211> LENGTH: 311
<212> TYPE: PRT
<213> ORGANISM: Mortierella elongata

<400> SEQUENCE: 37

Met Gly Leu Ser Lys Thr Val Gly Gln Ala Ser Asp Lys Asn Ile Cys
1               5                   10                  15

Met Ile Phe Cys Lys Gly Gln Pro Ile Gly Gln Val Gln Pro Glu Gly
                20                  25                  30

Ile Leu Tyr Pro Glu Tyr Phe Asp Val Leu Val Asn Trp Arg Thr Pro
            35                  40                  45

Val Ser Val Ala Ala Leu Tyr Val Leu Met Val Val Leu Leu Asn Pro
50                  55                  60

Lys Gln Gly Lys Val Ser Arg Val Val Ala Ala Asp Ser Ala Ala Lys
65                  70                  75                  80

Gly Asp Asn Lys Lys Gln Gln Glu Leu Ser Ser Ser Pro Ala Met
                85                  90                  95

Thr Ala Leu Val Phe Val His Asn Ala Ile Leu Cys Val Tyr Ser Ala
            100                 105                 110

Trp Thr Phe Tyr Gly Met Phe Phe Ala Trp Lys Lys Ala Phe Ala Thr
            115                 120                 125

His Thr Phe Met Glu Ala Val Cys Asp Ser Asp Asn Thr Phe Trp Asp
            130                 135                 140

Ser Leu Gly Tyr Tyr Ser Tyr Phe Tyr Leu Ser Lys Tyr Tyr Glu
145                 150                 155                 160

Ile Val Asp Thr Ile Ile Leu Leu Lys Gly Arg Arg Ser Ser Leu
                165                 170                 175
```

```
Leu Gln Thr Tyr His His Ala Gly Ala Ile Phe Thr Met Tyr Met Gly
            180                 185                 190

Phe Asn Tyr Arg Ala His Pro Ile Trp Ile Phe Thr Thr Phe Asn Ser
            195                 200                 205

Phe Ile His Thr Ile Met Tyr Ala Tyr Ala Ala Thr Ser Val Gly
            210                 215                 220

Leu Lys Pro Pro Gly Lys Lys Tyr Leu Thr Ser Met Gln Ile Thr Gln
225                 230                 235                 240

Phe Trp Thr Gly Thr Ala Leu Ala Phe Trp Tyr Glu Ile Gly Ser Pro
                245                 250                 255

Lys Gly Cys Phe Thr Asn Pro Gly Ser Arg Phe Ala Ile Trp Thr Val
            260                 265                 270

Leu Ala Tyr Val Phe Pro Leu Ile Tyr Leu Phe Thr Ser Phe Ala Ser
            275                 280                 285

Lys Met Tyr Gly Asn Arg Val Lys Ala Ala Ala Ala Lys Ala Thr
            290                 295                 300

Ser Gln Gln Lys Lys Val Leu
305                 310

<210> SEQ ID NO 38
<211> LENGTH: 321
<212> TYPE: PRT
<213> ORGANISM: Nannochloropsis oculata

<400> SEQUENCE: 38

Met Pro Lys Leu Pro Lys Ile Ser Asn Ile Phe Lys Phe Leu Lys Ala
1               5                   10                  15

Asp Pro Ser Lys Ile Val Pro Tyr Lys Ser Ile Pro Asp Lys Val Pro
                20                  25                  30

Phe Thr Gln Leu Phe Gln His Tyr Pro Val Leu Asp Pro Leu Tyr Thr
            35                  40                  45

Gln Tyr Glu Lys Asn Phe Tyr Ala Ser Thr Tyr Val Lys Phe Ala Gln
        50                  55                  60

Asp Thr Trp Pro Val Leu Pro Leu Ala Leu Cys Gly Met Tyr Ala Leu
65                  70                  75                  80

Met Ile Ile Val Gly Thr Lys Val Met Val Ser Arg Pro Lys His Glu
                85                  90                  95

Trp Lys Thr Ala Leu Ala Cys Trp Asn Leu Met Leu Ser Ile Phe Ser
            100                 105                 110

Phe Cys Gly Met Ile Arg Thr Val Pro His Leu Leu His Asn Val Ala
        115                 120                 125

Thr Leu Pro Phe Lys Asp Thr Ile Cys Arg His Pro Ala Glu Thr Tyr
130                 135                 140

Gly Glu Gly Ala Cys Gly Met Trp Val Met Leu Phe Ile Phe Ser Lys
145                 150                 155                 160

Val Pro Glu Leu Val Asp Thr Val Phe Ile Val Phe Arg Lys Ser Lys
                165                 170                 175

Leu Gln Phe Leu His Trp Tyr His His Ile Thr Val Leu Leu Phe Cys
            180                 185                 190

Trp His Ser Tyr Ala Val Thr Ser Ser Thr Gly Leu Tyr Phe Val Ala
        195                 200                 205

Met Asn Tyr Ser Val His Ala Ile Met Tyr Ala Tyr Tyr Tyr Leu Thr
            210                 215                 220

Ala Ile Asn Ala Trp Pro Lys Trp Ile Pro Pro Ser Ile Ile Thr Val
225                 230                 235                 240
```

```
Ala Gln Ile Ser Gln Met Ile Val Gly Val Gly Ile Cys Ala Ser Ser
            245                 250                 255

Phe Tyr Phe Leu Tyr Thr Asp Pro Glu His Cys Gln Val Lys Arg Gln
            260                 265                 270

Asn Val Tyr Ala Gly Ala Leu Met Tyr Gly Ser Tyr Leu Tyr Leu Phe
            275                 280                 285

Cys Asp Phe Phe Val Arg Arg Phe Leu Arg Gly Gly Lys Pro Arg Leu
            290                 295                 300

Gly Glu Glu Lys Ser Ala Val Leu Thr Met Ala Lys Lys Ile Lys Ala
305                 310                 315                 320

Met

<210> SEQ ID NO 39
<211> LENGTH: 173
<212> TYPE: PRT
<213> ORGANISM: Nannochloropsis oculata

<400> SEQUENCE: 39

Met Ser Phe Leu Ile Arg Thr Pro Ala Asp Gln Ile Lys Pro Tyr Phe
1               5                   10                  15

Ser Glu Ala Ala Gln Thr His Tyr Thr Gln Leu Phe Gln His Phe Pro
            20                  25                  30

Ile Leu Glu Arg Ala Tyr Phe Pro Phe Glu Lys Asn Phe Arg Ala Glu
            35                  40                  45

Pro Phe Val Asp Phe Ala Lys Ala Thr Trp Pro Leu Leu Pro Leu Ala
            50                  55                  60

Leu Cys Thr Ala Tyr Ala Leu Met Ile Val Ile Gly Thr Arg Val Met
65                  70                  75                  80

Lys Asn Arg Glu Lys Phe Asp Trp Arg Gly Pro Leu Ala Tyr Trp Asn
            85                  90                  95

Leu Thr Leu Ser Leu Phe Ser Phe Cys Gly Met Leu Arg Thr Val Pro
            100                 105                 110

His Leu Leu Asn Asn Ile Thr Thr Leu Ser Phe Arg Asp Thr Val Cys
            115                 120                 125

Thr Ser Ala Ala Lys Ser Tyr Gly Glu Gly Val Ser Gly Leu Trp Val
            130                 135                 140

Met Leu Phe Ile Phe Ser Lys Ile Pro Glu Leu Val Asp Thr Val Phe
145                 150                 155                 160

Ile Val Phe Arg Lys Ser Lys Leu Gln Phe Leu His Trp
            165                 170

<210> SEQ ID NO 40
<211> LENGTH: 359
<212> TYPE: PRT
<213> ORGANISM: Nannochloropsis oceanica

<400> SEQUENCE: 40

Met Val Phe Gln Leu Ala Arg Asp Ser Val Ser Ala Leu Val Tyr His
1               5                   10                  15

Phe Lys Glu Gly Asn Leu Asn Trp Pro Met Ile Ile Tyr Leu Val Leu
            20                  25                  30

Val His Leu Ala Gly Tyr Ile Gly Leu Thr Thr Ile Leu Ala Cys Lys
            35                  40                  45

Trp Gln Thr Leu Leu Glu Ala Phe Ile Leu Trp Pro Ile Thr Gly Leu
            50                  55                  60
```

Gly Ile Thr Ala Gly Val His Arg Leu Trp Ala His Arg Ser Tyr Asn
 65                  70                  75                  80

Ala Thr Leu Pro Tyr Arg Ile Leu Leu Met Leu Phe Asn Ser Ile Ala
                 85                  90                  95

Asn Gln Gly Ser Ile Tyr His Trp Ser Arg Asp His Arg Val His His
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
130                 135                 140

Val Glu Gly Gly Lys Gln Leu Asp Phe Ser Asp Leu Ala Ala Asp Pro
145                 150                 155                 160

Val Val Arg Phe Gln Arg Asp Trp Asp Pro Trp Phe Ala Gln Phe Met
                165                 170                 175

Cys Phe Val Met Pro Ala Leu Val Ala Ser Arg Phe Trp Gly Glu Ala
            180                 185                 190

Phe Trp Asn Ala Phe Trp Val Ala Gly Ala Leu Arg Tyr Met Leu Val
        195                 200                 205

Leu His Phe Thr Trp Met Val Asn Ser Ala Ala His Leu Tyr Gly Asp
210                 215                 220

His Pro Tyr Asp Pro Thr Met Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Gln Gln Phe Asn Pro
            260                 265                 270

Thr Lys Ala Phe Ile Asp Phe Phe Ala Ala Ile Gly Met Val Thr Asn
        275                 280                 285

Arg Lys Arg Ala Thr Gly Ala Trp Ala Lys Leu Lys Glu Ser Arg Ala
290                 295                 300

Arg Asp Ala Ala Asn Gly Lys Ser Met Lys Asp Phe Lys Gly Arg Gly
305                 310                 315                 320

Ser Gly Ser Asp Tyr Gly Thr Thr Asn Thr Asn Tyr Ala Val Ser Asn
                325                 330                 335

Lys Thr Val Val Thr Asp Lys Gly Ala Gln Gln Pro Gly Trp Glu Glu
            340                 345                 350

Ser Asn His Pro Lys Tyr Asn
        355

<210> SEQ ID NO 41
<211> LENGTH: 354
<212> TYPE: PRT
<213> ORGANISM: Nannochloropsis gaditana

<400> SEQUENCE: 41

Met Ala Ala Tyr Phe Gln Val Phe Arg Asn Ser Lys Ile Gly Ile Val
1               5                   10                  15

Leu Thr Leu Ser Leu Ile Phe Thr Thr Ala Met Ala Ser Pro Ser Ala
            20                  25                  30

Tyr Phe Pro Glu Lys Leu Ser Leu Leu Lys Thr Leu Ser Gly Ser
        35                  40                  45

Asp Arg Leu Val Asn Pro His Cys Ile Asp Asn Pro Phe Cys Ala Phe
    50                  55                  60

Asn Asp Trp Val Asn Ala Phe Leu Phe Arg Asp Ala Val Lys Ala Asp
65                  70                  75                  80

```
Val Met Ala Arg Leu Gly Pro Ala Gly Ala His Tyr Phe Leu Thr Tyr
            85                  90                  95

Val Arg Asp Leu Val Ala Gly Ser Val Leu Tyr Tyr Leu Thr Ala Gly
                100                 105                 110

Leu Trp His Thr Tyr Ile Tyr Gln Trp His Gly Asp Tyr Phe Phe Thr
            115                 120                 125

Gln Gln Gly Phe Glu Lys Pro Ser Ala Ala Thr Ile Lys Asp Gln Ile
    130                 135                 140

Gln Leu Ala Gln Ala Ser Met Phe Leu Tyr Ala Ala Leu Pro Val Leu
145                 150                 155                 160

Ala Glu Trp Leu Val Glu Ser Gly Trp Thr Gln Cys Tyr Tyr Tyr Val
                165                 170                 175

Glu Glu Ile Gly Gly Trp Pro Tyr Tyr Leu Ala Phe Thr Leu Leu Tyr
                180                 185                 190

Leu Ala Met Val Glu Val Gly Val Tyr Trp Met His Arg Thr Leu His
                195                 200                 205

Glu Asn Lys Val Leu Tyr Lys Tyr Ile His Gly Leu His His Lys Tyr
    210                 215                 220

Asn Lys Pro Ser Thr Leu Ser Pro Trp Ala Ser Val Ala Phe Asn Pro
225                 230                 235                 240

Ile Asp Gly Ile Leu Gln Ala Ser Pro Tyr Val Ile Cys Leu Phe Leu
                245                 250                 255

Val Pro Cys His Tyr Leu Thr His Val Ala Met Val Phe Phe Thr Ala
                260                 265                 270

Val Trp Ala Thr Asn Ile His Asp Ala Met Asp Gly Asn Thr Glu Pro
                275                 280                 285

Val Met Gly Ser Lys Tyr His Thr Val His His Thr His Tyr His Tyr
    290                 295                 300

Asn Phe Gly Gln Phe Phe Ile Phe Ala Asp Trp Met Phe Gly Thr Leu
305                 310                 315                 320

Arg Ile Pro Glu Pro Arg Ala Ala Lys Ala Val Leu Ser Pro Gly Val
                325                 330                 335

Val Pro Ser Ser Gly Val Arg Thr Thr Gly Lys Ser Gly Arg Gly Lys
                340                 345                 350

Met Asp

<210> SEQ ID NO 42
<211> LENGTH: 452
<212> TYPE: PRT
<213> ORGANISM: Nannochloropsis gaditana

<400> SEQUENCE: 42

Met Gly Arg Gly Gly Glu Lys Thr Val Thr Pro Pro Ser Lys Thr Phe
1               5                   10                  15

His Ala His Gly His Ser Leu Thr Ala Ser Asp Leu Ser Arg Ala Asp
            20                  25                  30

Ala Ala Ser Thr Ile Ser Ser Ser Val Arg Pro Ser Lys Ser Leu Glu
        35                  40                  45

Ala Met Pro Thr Glu Glu Leu Arg Lys Lys Ala Leu Gln Tyr Gly His
    50                  55                  60

Asp Ala Ser Ala Asp Arg Ala Ser Leu Leu Gln Ile Leu Ala Pro Tyr
65                  70                  75                  80

Gly Asp Ile Leu Leu Arg Thr Asp Ala Pro Pro Ser Leu Pro Leu Thr
                85                  90                  95
```

```
Pro Pro Pro Phe Thr Leu Ala Asp Ile Lys Ala Ala Val Pro Arg His
            100                 105                 110

Cys Phe Glu Arg Ser Leu Thr Thr Ser Phe Phe His Leu Ala Cys Asp
            115                 120                 125

Leu Val Leu Val Ala Leu Leu Gly Tyr Leu Ala Thr Leu Ile Gly His
    130                 135                 140

Pro Asp Val Pro Thr Met Ser Arg Tyr Leu Leu Trp Pro Leu Tyr Trp
145                 150                 155                 160

Tyr Ala Gln Gly Ser Val Leu Thr Gly Val Trp Val Ile Ala His Glu
                165                 170                 175

Cys Gly His Gln Ser Phe Ser Pro Tyr Glu Arg Val Asn Asn Leu Val
            180                 185                 190

Gly Trp Val Leu His Ser Ala Leu Leu Val Pro Tyr His Ser Trp Arg
        195                 200                 205

Ile Ser His Gly Lys His His Asn Asn Thr Gly Ser Cys Glu Asn Asp
    210                 215                 220

Glu Val Phe Ala Pro Pro Ile Lys Glu Asp Leu Met Asp Glu Ile Leu
225                 230                 235                 240

Leu His Ser Pro Leu Ala Asn Leu Ala Gln Ile Ile Met Leu Thr
                245                 250                 255

Val Gly Trp Met Pro Gly Tyr Leu Leu Met Asn Ala Thr Gly Pro Arg
            260                 265                 270

Lys Tyr Lys Gly Lys Asn Asn Ser His Phe Asp Pro Asn Ser Ala Leu
            275                 280                 285

Phe Ser Pro Lys Asp Arg Leu Asp Ile Ile Trp Ser Asp Ile Gly Phe
    290                 295                 300

Phe Leu Ala Leu Ala Gly Val Val Trp Ala Cys Thr Gln Tyr Gly Phe
305                 310                 315                 320

Ser Thr Val Gly Lys Tyr Tyr Leu Leu Pro Tyr Met Val Val Asn Tyr
                325                 330                 335

His Leu Val Leu Ile Thr Tyr Leu Gln His Thr Asp Val Phe Ile Pro
            340                 345                 350

His Phe Arg Gly Ala Glu Trp Ser Trp Phe Arg Gly Ala Leu Cys Thr
        355                 360                 365

Val Asp Arg Ser Phe Gly Trp Leu Leu Asp His Thr Phe His His Ile
    370                 375                 380

Ser Asp Thr His Val Cys His His Ile Phe Ser Lys Met Pro Phe Tyr
385                 390                 395                 400

His Ala Gln Glu Ala Ser Glu His Ile Lys Lys Ala Leu Gly Pro Tyr
                405                 410                 415

Tyr Leu Lys Asp Asp Thr Pro Ile Trp Lys Ala Leu Trp Arg Ser Tyr
            420                 425                 430

Thr Leu Cys Lys Tyr Val Asp Thr Asp Lys Asn Ala Val Phe Tyr Lys
        435                 440                 445

His Arg Ala Ser
    450

<210> SEQ ID NO 43
<211> LENGTH: 337
<212> TYPE: PRT
<213> ORGANISM: Nannochloropsis gaditana

<400> SEQUENCE: 43

Met Ser Arg Tyr Leu Leu Trp Pro Leu Tyr Trp Tyr Ala Gln Gly Ser
```

```
            1               5                  10                 15
            Val Leu Thr Gly Val Trp Val Ile Ala His Glu Cys Gly His Gln Ser
                       20                  25                  30

Phe Ser Pro Tyr Glu Arg Val Asn Asn Leu Val Gly Trp Val Leu His
                       35                  40                  45

Ser Ala Leu Leu Val Pro Tyr His Ser Trp Arg Ile Ser His Gly Lys
                50                  55                  60

His His Asn Asn Thr Gly Ser Cys Glu Asn Asp Glu Val Phe Ala Pro
            65                  70                  75                  80

Pro Ile Lys Glu Asp Leu Met Asp Glu Ile Leu Leu His Ser Pro Leu
                            85                  90                  95

Ala Asn Leu Ala Gln Ile Ile Ile Met Leu Thr Val Gly Trp Met Pro
                       100                 105                 110

Gly Tyr Leu Leu Met Asn Ala Thr Gly Pro Arg Lys Tyr Lys Gly Lys
                       115                 120                 125

Asn Asn Ser His Phe Asp Pro Asn Ser Ala Leu Phe Ser Pro Lys Asp
                130                 135                 140

Arg Leu Asp Ile Ile Trp Ser Asp Ile Gly Phe Phe Leu Ala Leu Ala
            145                 150                 155                 160

Gly Val Val Trp Ala Cys Thr Gln Tyr Gly Phe Ser Thr Val Gly Lys
                            165                 170                 175

Tyr Tyr Leu Leu Pro Tyr Met Val Val Asn Tyr His Leu Val Leu Ile
                       180                 185                 190

Thr Tyr Leu Gln His Thr Asp Val Phe Ile Pro His Phe Arg Gly Ala
                       195                 200                 205

Glu Trp Ser Trp Phe Arg Gly Ala Leu Cys Thr Val Asp Arg Ser Phe
                       210                 215                 220

Gly Trp Leu Leu Asp His Thr Phe His His Ile Ser Asp Thr His Val
            225                 230                 235                 240

Cys His His Ile Phe Ser Lys Met Pro Phe Tyr His Ala Gln Glu Ala
                            245                 250                 255

Ser Glu His Ile Lys Lys Ala Leu Gly Pro Tyr Tyr Leu Lys Asp Asp
                       260                 265                 270

Thr Pro Ile Trp Lys Ala Leu Trp Arg Ser Tyr Thr Leu Cys Lys Thr
                       275                 280                 285

Ala Glu Glu Glu Asp Asp Glu Trp Gly Val Val Pro Lys Pro Thr
                       290                 295                 300

Glu Gln Leu Tyr Leu Gly Asn Arg Lys Ala Arg Glu Leu Ile Gly Gly
            305                 310                 315                 320

Ala Tyr Ala Asp Val Asn Leu Ala Val Lys Val Ala His Asp Asp Thr
                            325                 330                 335

Lys

<210> SEQ ID NO 44
            <211> LENGTH: 482
            <212> TYPE: PRT
            <213> ORGANISM: Nannochloropsis gaditana

<400> SEQUENCE: 44

Met Gly Ser Thr Glu Pro Val Leu Ser Thr Ala Ala Val Pro Ala Thr
            1               5                  10                  15

Glu Pro Ala Gly Lys Ser Tyr Thr Trp Gln Glu Val Ala Glu His Asn
                       20                  25                  30

Thr Glu Lys Ser Leu Trp Val Thr Val Arg Gly Lys Val Tyr Asp Ile
```

```
                35                  40                  45
Ser Ser Trp Val Asp Asn His Pro Gly Gly Lys Glu Ile Leu Leu Leu
     50                  55                  60

Ala Ala Gly Arg Asp Ile Thr Tyr Ala Phe Asp Ser Tyr His Pro Phe
65                  70                  75                  80

Thr Glu Lys Pro Thr Gln Val Leu Asn Lys Phe Glu Ile Gly Arg Val
                 85                  90                  95

Thr Ser Tyr Glu Phe Pro Gln Tyr Lys Ala Asp Thr Arg Gly Phe Tyr
                100                 105                 110

Lys Ala Leu Cys Thr Arg Val Asn Asp Tyr Phe Val Ala His Lys Leu
             115                 120                 125

Asn Pro Lys Asp Pro Ile Pro Gly Ile Trp Arg Met Cys Leu Val Ala
             130                 135                 140

Leu Val Ala Leu Ala Ser Phe Val Val Cys Asn Gly Tyr Val Gly Val
145                 150                 155                 160

Glu Gly Thr Trp Ala Gly Thr Thr Trp Ala Arg Leu Val Ala Ala Val
                165                 170                 175

Val Phe Gly Ile Cys Gln Ala Leu Pro Leu Leu His Val Met His Asp
            180                 185                 190

Ser Ser His Leu Ala Phe Gly Asn Thr Glu Arg Trp Trp Gln Val Gly
         195                 200                 205

Gly Arg Leu Ala Met Asp Phe Phe Ala Gly Ala Asn Met Thr Ser Trp
210                 215                 220

His Asn Gln His Val Ile Gly His His Ile Tyr Thr Asn Val Phe Leu
225                 230                 235                 240

Ala Asp Pro Asp Leu Pro Asp Lys Ala Ala Gly Asp Pro Arg Arg Leu
                245                 250                 255

Val Gln Lys Gln Ala Trp Gln Ala Met Tyr Lys Trp Gln His Leu Tyr
             260                 265                 270

Leu Pro Pro Leu Tyr Gly Ile Leu Gly Ile Lys Phe Arg Val Gln Asp
         275                 280                 285

Ile Met Glu Thr Phe Gly Ser Gly Thr Asn Gly Pro Val Arg Val Asn
290                 295                 300

Pro Leu Ser Phe Phe Gln Trp Ala Glu Met Ile Phe Thr Lys Met Phe
305                 310                 315                 320

Trp Ala Gly Trp Arg Ile Ala Phe Pro Leu Leu Ser Pro Ser Phe His
                325                 330                 335

Thr Gly Trp Ala Ala Phe Ser Ala Leu Phe Leu Val Ser Glu Phe Met
             340                 345                 350

Thr Gly Tyr Phe Leu Ala Phe Asn Phe Gln Val Ser His Val Ser Ser
         355                 360                 365

Glu Cys Asp Tyr Pro Leu Gly Glu Ala Pro Arg Glu Gly Glu Asp Gly
     370                 375                 380

Asn Ile Val Asp Glu Trp Ala Val Ser Gln Ile Lys Ser Ser Val Asp
385                 390                 395                 400

Tyr Ala His Asn Asn Pro Val Thr Thr Phe Leu Cys Gly Ala Leu Asn
                405                 410                 415

Tyr Gln Val Thr His His Leu Phe Pro Thr Val Ser Gln Tyr His Tyr
             420                 425                 430

Pro Ala Ile Ala Pro Ile Ile Gln Asp Val Cys Arg Glu Phe Asn Val
         435                 440                 445

Asp Tyr Lys Val Leu Pro Asp Phe Val Thr Ala Phe His Ala His Ile
     450                 455                 460
```

Ala His Leu Lys Thr Leu Gly Glu Arg Gly Glu Ala Ala Glu Val His
465                 470                 475                 480

Met Gly

<210> SEQ ID NO 45
<211> LENGTH: 163
<212> TYPE: PRT
<213> ORGANISM: Nannochloropsis gaditana

<400> SEQUENCE: 45

Met Ser Gly Ser Gln Gly Arg Pro Glu Arg Val Gly Glu Gly His Pro
1               5                   10                  15

Arg Asp Ala Arg Arg Glu Glu Lys Cys Gly Ser Ala Asp Asn Gly Leu
            20                  25                  30

Arg Asp Gly Arg Ala Glu Arg Ala Lys Glu Glu Gly Arg Gly Ala Tyr
        35                  40                  45

Pro Asp Ala Met Asn Glu Val Ala Cys Val Phe Leu Tyr Pro Thr Leu
50                  55                  60

Pro Arg Ile Thr Ser Ser Pro Val Thr Val Pro Pro Gly Leu Gln
65                  70                  75                  80

Val Met Ala Ala Val Leu Arg His Ala Pro Phe Pro Leu Leu Leu
                85                  90                  95

Phe Leu Thr Tyr Thr Leu Ser Gly Ser Cys Asn His Phe Leu Thr Leu
            100                 105                 110

Ile Met His Glu Val Ala His Asn Leu Ala Phe Lys Arg Leu Phe Ala
        115                 120                 125

Asn Arg Val Phe Ser Ile Ile Val Asn Leu Pro Leu Gly Ile Pro Ala
130                 135                 140

Ala Met Trp Val Trp Glu Gly Pro Glu Gly Gly Val Gln Ala Pro
145                 150                 155                 160

Thr Ser Gly

<210> SEQ ID NO 46
<211> LENGTH: 445
<212> TYPE: PRT
<213> ORGANISM: Mortierella elongata

<400> SEQUENCE: 46

Met Ala Thr Pro Leu Pro Pro Thr Phe Val Val Pro Ala Thr Leu Thr
1               5                   10                  15

Glu Thr Arg Arg Asp Pro Leu Lys His Gln Glu Leu Pro Pro Leu Phe
            20                  25                  30

Pro Glu Lys Val Asn Ile Leu Asn Ile Trp Lys Tyr Leu Asp Tyr Lys
        35                  40                  45

His Val Val Gly Leu Gly Val Thr Pro Leu Ile Ala Leu Tyr Gly Leu
50                  55                  60

Leu Thr Thr Glu Ile Gln Arg Lys Thr Leu Ile Trp Ser Ile Ile Tyr
65                  70                  75                  80

Tyr Tyr Ala Thr Gly Leu Gly Ile Thr Ala Gly Tyr His Arg Leu Trp
                85                  90                  95

Ala His Arg Ser Tyr Asn Ala Gly Pro Ala Met Ser Phe Val Leu Ala
            100                 105                 110

Leu Leu Gly Ala Gly Ala Val Glu Gly Ser Ile Lys Trp Trp Ser Arg
        115                 120                 125

Gly His Arg Ala His His Arg Trp Thr Asp Thr Glu Lys Asp Pro Tyr

-continued

```
              130                 135                 140
Ser Ala His Arg Gly Leu Phe Phe Ser His Leu Gly Trp Met Leu Ile
145                 150                 155                 160

Lys Arg Pro Gly Trp Lys Ile Gly His Ala Asp Val Asp Asp Leu Asn
                165                 170                 175

Lys Asn Lys Leu Val Gln Trp Gln His Lys Asn Tyr Leu Ala Leu Ile
            180                 185                 190

Phe Leu Met Gly Val Val Phe Pro Thr Val Ala Gly Leu Gly Trp
                195                 200                 205

Gly Asp Trp Arg Gly Gly Tyr Phe Tyr Ala Ala Ile Leu Arg Leu Val
        210                 215                 220

Phe Val His His Ala Thr Phe Cys Val Asn Ser Leu Ala His Trp Leu
225                 230                 235                 240

Gly Glu Gly Pro Phe Asp Asp Arg His Ser Pro Arg Asp His Phe Ile
                245                 250                 255

Thr Ala Phe Met Thr Leu Gly Glu Gly Tyr His Asn Phe His His Gln
                260                 265                 270

Phe Pro Gln Asp Tyr Arg Asn Ala Ile Arg Phe Tyr Gln Tyr Asp Pro
            275                 280                 285

Thr Lys Trp Val Ile Ala Thr Cys Ala Phe Leu Gly Leu Ala Ser His
        290                 295                 300

Leu Lys Thr Phe Pro Glu Asn Glu Val Arg Lys Gly Gln Leu Gln Met
305                 310                 315                 320

Ile Glu Lys Arg Val Leu Glu Lys Lys Thr Lys Leu Gln Trp Gly Thr
                325                 330                 335

Pro Ile Ala Asp Leu Pro Val Met Ser Phe Glu Asp Tyr Arg His Ala
                340                 345                 350

Cys Lys Asn Asp Asn Lys Lys Trp Ile Leu Leu Glu Gly Val Val Tyr
            355                 360                 365

Asp Val Ala Asp Phe Met Ser Glu His Pro Gly Gly Glu Lys Tyr Ile
        370                 375                 380

Lys Met Gly Ile Gly Lys Asp Met Thr Ala Ala Phe Asn Gly Gly Leu
385                 390                 395                 400

Tyr Asp His Ser Asn Ala Ala Arg Asn Leu Leu Ser Leu Met Arg Val
                405                 410                 415

Ala Val Val Glu Phe Gly Gly Val Glu Ala Gln Lys Lys Asn Pro
                420                 425                 430

Ser Ala Pro Ile Tyr Gly Asp Asp His Ala Lys Ala Ala
            435                 440                 445
```

<210> SEQ ID NO 47
<211> LENGTH: 445
<212> TYPE: PRT
<213> ORGANISM: Mortierella alpina

<400> SEQUENCE: 47

```
Met Ala Thr Pro Leu Pro Pro Ser Phe Val Val Pro Ala Thr Gln Thr
1               5                   10                  15

Glu Thr Arg Arg Asp Pro Leu Gln His Glu Glu Leu Pro Pro Leu Phe
                20                  25                  30

Pro Glu Lys Ile Thr Ile Tyr Asn Ile Trp Arg Tyr Leu Asp Tyr Lys
            35                  40                  45

His Val Val Gly Leu Gly Leu Thr Pro Leu Ile Ala Leu Tyr Gly Leu
        50                  55                  60
```

Leu Thr Thr Glu Ile Gln Thr Lys Thr Leu Ile Trp Ser Ile Ile Tyr
 65                  70                  75                  80

Tyr Tyr Ala Thr Gly Leu Gly Ile Thr Ala Gly Tyr His Arg Leu Trp
                 85                  90                  95

Ala His Arg Ala Tyr Asn Ala Gly Pro Ala Met Ser Phe Val Leu Ala
            100                 105                 110

Leu Leu Gly Ala Gly Ala Val Glu Gly Ser Ile Lys Trp Trp Ser Arg
        115                 120                 125

Gly His Arg Ala His His Arg Trp Thr Asp Thr Glu Lys Asp Pro Tyr
    130                 135                 140

Ser Ala His Arg Gly Leu Phe Phe Ser His Ile Gly Trp Met Leu Ile
145                 150                 155                 160

Lys Arg Pro Gly Trp Lys Ile Gly His Ala Asp Val Asp Leu Asn
                165                 170                 175

Lys Ser Lys Leu Val Gln Trp Gln His Lys Asn Tyr Leu Pro Leu Val
            180                 185                 190

Leu Ile Met Gly Val Val Phe Pro Thr Leu Val Ala Gly Leu Gly Trp
        195                 200                 205

Gly Asp Trp Arg Gly Gly Tyr Phe Tyr Ala Ala Ile Leu Arg Leu Val
    210                 215                 220

Phe Val His His Ala Thr Phe Cys Val Asn Ser Leu Ala His Trp Leu
225                 230                 235                 240

Gly Asp Gly Pro Phe Asp Asp Arg His Ser Pro Arg Asp His Phe Ile
                245                 250                 255

Thr Ala Phe Val Thr Leu Gly Glu Gly Tyr His Asn Phe His His Gln
            260                 265                 270

Phe Pro Gln Asp Tyr Arg Asn Ala Ile Arg Phe Tyr Gln Tyr Asp Pro
        275                 280                 285

Thr Lys Trp Val Ile Ala Leu Cys Ala Phe Phe Gly Leu Ala Ser His
    290                 295                 300

Leu Lys Thr Phe Pro Glu Asn Glu Val Arg Lys Gly Gln Leu Gln Met
305                 310                 315                 320

Ile Glu Lys Arg Val Leu Glu Lys Lys Thr Lys Leu Gln Trp Gly Thr
                325                 330                 335

Pro Ile Ala Asp Leu Pro Ile Leu Ser Phe Glu Asp Tyr Gln His Ala
            340                 345                 350

Cys Lys Asn Asp Asn Lys Lys Trp Ile Leu Leu Glu Gly Val Val Tyr
        355                 360                 365

Asp Val Ala Asp Phe Met Ser Glu His Pro Gly Gly Glu Lys Tyr Ile
    370                 375                 380

Lys Met Gly Val Gly Lys Asp Met Thr Ala Ala Phe Asn Gly Gly Met
385                 390                 395                 400

Tyr Asp His Ser Asn Ala Ala Arg Asn Leu Leu Ser Leu Met Arg Val
                405                 410                 415

Ala Val Val Glu Tyr Gly Gly Glu Val Glu Ala Gln Lys Lys Asn Pro
            420                 425                 430

Ser Met Pro Ile Tyr Gly Thr Asp His Ala Lys Ala Glu
        435                 440                 445

<210> SEQ ID NO 48
<211> LENGTH: 446
<212> TYPE: PRT
<213> ORGANISM: Mortierella elongata

<400> SEQUENCE: 48

```
Met Ala Thr Pro Leu Pro Pro Thr Phe Val Pro Ala Thr Gln Thr
1               5                   10                  15

Glu Thr Arg Arg Leu Pro Leu Glu His Asp Glu Leu Pro Pro Leu Phe
                20                  25                  30

Pro Glu Lys Leu Thr Ile Thr Asn Ile Trp Lys Tyr Leu Asp Tyr Lys
            35                  40                  45

His Val Leu Gly Leu Gly Leu Thr Pro Leu Ile Ala Leu Tyr Gly Leu
    50                  55                  60

Leu Thr Thr Glu Ile Gln Thr Lys Thr Leu Ile Trp Ser Ile Val Tyr
65                  70                  75                  80

Tyr Tyr Ala Thr Gly Leu Gly Ile Thr Ala Gly Tyr His Arg Leu Trp
                85                  90                  95

Ala His Arg Ala Tyr Ser Ala Gly Pro Ala Met Ser Phe Ala Leu Ala
                100                 105                 110

Leu Leu Gly Ala Gly Ala Val Glu Gly Ser Ile Lys Trp Trp Ser Arg
            115                 120                 125

Gly His Arg Ala His His Arg Trp Thr Asp Thr Glu Lys Asp Pro Tyr
    130                 135                 140

Ser Ala His Arg Gly Leu Phe Phe Ser His Ile Gly Trp Met Leu Ile
145                 150                 155                 160

Lys Arg Pro Gly Trp Lys Ile Gly His Ala Asp Val Asp Asp Leu Asn
                165                 170                 175

Lys Asn Lys Leu Val Gln Trp Gln His Lys His Tyr Leu Pro Leu Val
            180                 185                 190

Leu Phe Met Gly Val Ile Phe Pro Thr Ile Val Ala Gly Leu Gly Trp
    195                 200                 205

Gly Asp Trp Arg Gly Gly Tyr Phe Tyr Ala Ala Ile Leu Arg Leu Val
    210                 215                 220

Phe Val His His Ala Thr Phe Cys Val Asn Ser Leu Ala His Trp Leu
225                 230                 235                 240

Gly Glu Gly Pro Phe Asp Asp Arg His Ser Pro Arg Asp His Phe Ile
                245                 250                 255

Thr Ala Phe Met Thr Leu Gly Glu Gly Tyr His Asn Phe His His Gln
                260                 265                 270

Phe Pro Gln Asp Tyr Arg Asn Ala Ile Arg Phe Tyr Gln Tyr Asp Pro
            275                 280                 285

Thr Lys Trp Val Ile Ala Ile Cys Ala Phe Phe Gly Leu Ala Ser His
    290                 295                 300

Leu Lys Thr Phe Pro Glu Asn Glu Val Arg Lys Gly Gln Leu Gln Met
305                 310                 315                 320

Ile Glu Lys Lys Val Leu Glu Lys Lys Thr Lys Leu Gln Trp Gly Thr
                325                 330                 335

Pro Ile Ala Asp Leu Pro Val Leu Ser Phe Glu Asp Tyr Gln His Ala
            340                 345                 350

Cys Lys Asn Asp Gly Lys Lys Trp Ile Leu Leu Glu Gly Val Val Tyr
                355                 360                 365

Asp Val Ala Glu Phe Met Asn Glu His Pro Gly Gly Glu Lys Tyr Ile
    370                 375                 380

Lys Met Gly Val Gly Lys Asp Met Thr Ala Ala Phe Asn Gly Gly Met
385                 390                 395                 400

Tyr Asp His Ser Asn Ala Ala Arg Asn Leu Leu Ser Leu Met Arg Val
                405                 410                 415
```

Ala Ile Val Glu Phe Gly Gly Glu Val Ala Gln Lys Lys Asn Pro
                420                 425                 430

Ser Val Pro Ile Tyr Gly Asp Asp His His Ser Lys Ser Glu
            435                 440                 445

<210> SEQ ID NO 49
<211> LENGTH: 457
<212> TYPE: PRT
<213> ORGANISM: Mortierella elongata

<400> SEQUENCE: 49

Met Ala Ala Thr Pro Ser Val Arg Thr Phe Thr Arg Ser Glu Ile Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Glu His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Ala Glu His Asp Arg Ala Ile Lys
                85                  90                  95

Gly Asp Asp Phe Ala Ala Glu Val Arg Lys Leu Arg Ser Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Leu Trp Ala Leu Ser Thr Phe Ile Val Ala Lys
130                 135                 140

Trp Gly Gln Thr Ser Thr Leu Ala Thr Ile Ala Ser Ala Ser Ile Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
290                 295                 300

Gln Leu Ser Leu Ala Met His Trp Thr Trp Tyr Phe Ala Thr Met Phe
305                 310                 315                 320

Leu Phe Ile Lys Asp Pro Val Asn Met Ile Val Tyr Phe Leu Val Ser
                325                 330                 335

Gln Ala Val Cys Gly Asn Leu Leu Ala Leu Val Phe Ser Leu Asn His
            340                 345                 350

```
Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Ser Leu Cys Lys Lys Tyr Gly Val Arg Tyr His Thr Thr Gly Met
                420                 425                 430

Val Asp Gly Thr Ala Glu Val Phe Ala Arg Leu Asn Glu Val Ser Arg
                435                 440                 445

Ala Ala Ser Lys Met Gly Lys Ser Thr
                450                 455

<210> SEQ ID NO 50
<211> LENGTH: 444
<212> TYPE: PRT
<213> ORGANISM: Mortierella elongata

<400> SEQUENCE: 50

Met Gly Ala Glu Lys Glu Phe Thr Trp Glu Glu Leu Ala Lys His Asn
1               5                   10                  15

Ile Ala Gly Asp Leu Tyr Val Ala Val Arg Gly Asn Val Tyr Asp Val
                20                  25                  30

Thr Lys Phe Leu Ser Arg His Pro Gly Gly Val Asp Thr Leu Leu Leu
            35                  40                  45

Gly Ala Gly Arg Asp Val Thr Pro Val Phe Asp Met Tyr His Ala Phe
        50                  55                  60

Gly Thr Gly Asp Ala Ile Met Lys Lys Tyr Tyr Val Gly Lys Leu Val
65                  70                  75                  80

Ser Asn Glu Leu Pro Ile Phe Pro Glu Pro Ser Gly Phe His Lys Val
                85                  90                  95

Val Lys Ser Arg Val Glu Gly Tyr Phe Lys Asp Ser Gly Lys Asp Pro
                100                 105                 110

Lys Asn Arg Pro Glu Ile Trp Gly Arg Tyr Phe Leu Ile Phe Ala Ala
            115                 120                 125

Leu Phe Leu Ser Tyr Tyr Ala Gln Phe Phe Val Pro Phe Val Val Glu
        130                 135                 140

Arg Thr Trp Leu Gln Val Ile Phe Ala Val Ile Met Gly Phe Ala Cys
145                 150                 155                 160

Ala Gln Ile Gly Leu Asn Pro Leu His Asp Ala Ser His Phe Ser Thr
                165                 170                 175

Thr His Asn Pro Thr Val Trp Lys Ile Leu Gly Ala Thr His Asp Phe
                180                 185                 190

Phe Asn Gly Ala Ser Tyr Leu Val Trp Met Tyr Gln His Met Leu Gly
            195                 200                 205

His His Pro Tyr Thr Asn Ile Ala Gly Ala Asp Pro Asp Val Ser Thr
        210                 215                 220

Ala Glu Arg Asp Val Arg Arg Ile Lys Pro Ser Gln Lys Trp Phe Trp
225                 230                 235                 240

Asn His Ile Asn Gln His Met Phe Val Pro Phe Leu Tyr Gly Leu Leu
                245                 250                 255

Ala Phe Lys Val Arg Ile Gln Asp Val Asn Ile Leu Tyr Phe Val Gly
```

```
                260                 265                 270
Thr Asn Asp Ala Ile Arg Val Asn Pro Ile Ser Leu Trp His Thr Val
        275                 280                 285
Met Phe Trp Gly Gly Lys Ile Phe Phe Phe Trp Tyr Arg Ile Tyr Val
        290                 295                 300
Pro Leu Gln Val Leu Pro Leu Lys Lys Val Leu Ile Leu Phe Thr Ile
305                 310                 315                 320
Ala Asp Met Ile Ser Ser Tyr Trp Leu Ala Leu Thr Phe Gln Ala Asn
                325                 330                 335
His Val Val Glu Glu Val Glu Trp Pro Leu Pro Asp Glu Asn Gly Ile
                340                 345                 350
Ile Gln Lys Asp Trp Ala Ala Met Gln Val Glu Thr Gln Asp Tyr
                355                 360                 365
Ala His Glu Ser Tyr Ile Trp Thr Ser Ile Thr Gly Ser Leu Asn Tyr
        370                 375                 380
Gln Ala Val His His Leu Phe Pro Asn Val Ser Gln His Tyr Tyr Pro
385                 390                 395                 400
Glu Ile Leu Ser Ile Ile Arg Asp Ala Cys Thr Glu Tyr Lys Val Pro
                405                 410                 415
Tyr Leu Val Lys Asp Thr Phe Trp Gln Ala Phe Ser Ser His Leu Glu
                420                 425                 430
His Met Arg Val Leu Gly Leu Arg Pro Lys Glu Glu
                435                 440

<210> SEQ ID NO 51
<211> LENGTH: 396
<212> TYPE: PRT
<213> ORGANISM: Mortierella elongata

<400> SEQUENCE: 51

Met Ala Pro Pro Asn Thr Ile Asp Ala Gly Leu Thr His Arg His Val
1               5                   10                  15
Val Asn Pro Thr Ala Ala Pro Val Lys Ala Ala Tyr Glu Arg Asn Tyr
                20                  25                  30
Glu Leu Pro Glu Phe Thr Ile Lys Glu Ile Arg Glu Cys Ile Pro Ala
        35                  40                  45
His Cys Phe Glu Arg Ser Gly Phe Arg Gly Leu Cys His Val Ala Ile
        50                  55                  60
Asp Leu Thr Trp Ala Ser Leu Leu Phe Leu Ala Ala Thr Gln Ile Asp
65                  70                  75                  80
Lys Phe Glu Asn Pro Leu Ile Arg Tyr Leu Ala Trp Pro Val Tyr Trp
                85                  90                  95
Val Met Gln Gly Ile Val Cys Thr Gly Ile Trp Val Leu Ala His Glu
                100                 105                 110
Cys Gly His Gln Ser Phe Ser Thr Ser Lys Thr Leu Asn Asn Thr Val
        115                 120                 125
Gly Trp Ile Leu His Ser Phe Leu Leu Val Pro Tyr His Ser Trp Arg
        130                 135                 140
Ile Ser His Ser Lys His His Lys Ala Thr Gly His Met Thr Lys Asp
145                 150                 155                 160
Gln Val Phe Val Pro Lys Thr Arg Thr Gln Val Gly Leu Pro Ala Lys
                165                 170                 175
Lys Glu Asn Val Val Glu Glu Asp Glu Ala Val His Leu Asp Glu Glu
                180                 185                 190
```

```
Ala Pro Ile Val Thr Leu Phe Trp Met Leu Val Gln Phe Thr Phe Gly
            195                 200                 205

Trp Pro Ala Tyr Leu Ala Val Asn Ala Ser Gly Gln Asp Tyr Gly Gln
210                 215                 220

Trp Thr Ser His Phe His Thr Trp Ser Pro Ile Phe Glu Ala Arg Asn
225                 230                 235                 240

Phe Thr Asp Val Ile Leu Ser Asp Leu Gly Val Leu Val Thr Leu Gly
                245                 250                 255

Ala Leu Ile Tyr Ala Ser Leu Gln Thr Ser Leu Leu Ala Val Thr Lys
            260                 265                 270

Tyr Tyr Ile Val Pro Tyr Leu Phe Val Asn Phe Trp Leu Val Leu Ile
        275                 280                 285

Thr Phe Leu Gln His Thr Asp Pro Lys Leu Pro His Tyr Arg Glu Asn
290                 295                 300

Val Trp Asn Phe Gln Arg Gly Ala Leu Cys Thr Val Asp Arg Ser Phe
305                 310                 315                 320

Gly Lys Phe Leu Asp His Met Phe His Gly Ile Val His Thr His Val
                325                 330                 335

Ala His His Leu Phe Ser Gln Met Pro Phe Tyr His Ala Glu Glu Ala
            340                 345                 350

Thr Ala Cys Leu Lys Lys Leu Leu Gly Lys His Tyr Ile Tyr Asp Asp
        355                 360                 365

Thr Pro Ile Val Leu Ala Thr Trp Arg Ser Phe Arg Glu Cys Arg Phe
370                 375                 380

Val Glu Asp Glu Gly Asp Val Val Phe Phe Lys Lys
385                 390                 395

<210> SEQ ID NO 52
<211> LENGTH: 457
<212> TYPE: PRT
<213> ORGANISM: Mortierella alpina

<400> SEQUENCE: 52

Met Ala Ala Ala Pro Ser Val Arg Thr Phe Thr Arg Ala Glu Ile Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Ala Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Phe Ile Val Ala Lys
130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175
```

His Gln Val Phe Gln Asp Arg Phe Trp Gly Asp Leu Phe Gly Ala Phe
            180                 185                 190

Leu Gly Gly Val Cys Gln Gly Phe Ser Ser Trp Trp Lys Asp Lys
        195                 200                 205

His Asn Thr His His Ala Ala Pro Asn Val His Gly Glu Asp Pro Asp
210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Met Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Ile Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Gly Val Arg Tyr His Thr Thr Gly Met
            420                 425                 430

Ile Glu Gly Thr Ala Glu Val Phe Ser Arg Leu Asn Gly Val Ser Lys
        435                 440                 445

Ala Ala Ser Lys Met Gly Lys Ala Gln
    450                 455

<210> SEQ ID NO 53
<211> LENGTH: 457
<212> TYPE: PRT
<213> ORGANISM: Mortierella alpina

<400> SEQUENCE: 53

Met Ala Ala Ala Pro Ser Val Arg Thr Phe Thr Arg Ala Glu Ile Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Ala Ile Lys 85                  90                  95

Asn Asp Asp Phe Ala Ala Glu Val Arg Lys Leu Arg Thr Leu Phe Gln
                100                 105                 110

Ser Leu Gly Tyr Tyr Asp Ser Ser Lys Ala Tyr Tyr Ala Phe Lys Val
                115                 120                 125

Ser Phe Asn Leu Cys Ile Trp Gly Leu Ser Thr Phe Ile Val Ala Lys
            130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
                180                 185                 190

Leu Gly Gly Val Cys Gln Gly Phe Ser Ser Trp Trp Lys Asp Lys
                195                 200                 205

His Asn Thr His His Ala Ala Pro Asn Val His Gly Glu Asp Pro Asp
            210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
                260                 265                 270

Arg Leu Ser Trp Cys Leu Gln Ser Ile Met Phe Val Leu Pro Asn Gly
                275                 280                 285

Gln Ala His Lys Pro Ser Gly Ala Arg Val Pro Ile Ser Leu Val Glu
            290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Ile Val Tyr Phe Leu Val Ser
                325                 330                 335

Gln Ala Val Cys Gly Asn Leu Leu Ala Ile Val Phe Ser Leu Asn His
                340                 345                 350

Asn Gly Met Pro Val Ile Ser Lys Glu Glu Ala Val Asp Met Asp Phe
            355                 360                 365

Phe Thr Lys Gln Ile Ile Thr Gly Arg Asp Val His Pro Gly Leu Phe
                370                 375                 380

Ala Asp Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Gly Val Arg Tyr His Thr Thr Gly Met
                420                 425                 430

Ile Glu Gly Thr Ala Glu Val Phe Ser Arg Leu Asn Glu Val Ser Lys
            435                 440                 445

Ala Ala Ser Lys Met Gly Lys Ala Gln
450                 455

<210> SEQ ID NO 54
<211> LENGTH: 454
<212> TYPE: PRT
<213> ORGANISM: Mortierella verticillata

<400> SEQUENCE: 54

-continued

```
Met Val Ala Thr Arg Thr Phe Thr Arg Ser Glu Ile Leu Asn Ala Glu
  1               5                  10                 15
Ala Leu Asn Glu Gly Lys Lys Asn Ala Asp Ala Pro Phe Leu Met Ile
             20                  25                  30
Ile Asp Asn Lys Val Tyr Asp Val Arg Glu Phe Val Pro Asp His Pro
             35                  40                  45
Gly Gly Ser Val Ile Leu Thr His Val Gly Lys Asp Gly Thr Asp Val
         50                  55                  60
Phe Asp Thr Phe His Pro Glu Ala Ala Trp Glu Thr Leu Ala Asn Phe
 65                  70                  75                  80
Tyr Val Gly Asp Ile Ala Glu Asn Asp Arg Ala Ile Lys Asn Asp Asp
                 85                  90                  95
Phe Ala Ala Glu Val Arg Lys Leu Arg Thr Leu Phe Gln Ser Leu Gly
                100                 105                 110
Tyr Tyr Asp Ser Ser Lys Ala Tyr Ala Phe Lys Val Ser Phe Asn
                115                 120                 125
Leu Cys Leu Trp Ala Leu Ser Thr Phe Ile Val Ala Lys Trp Gly Gln
    130                 135                 140
Thr Ser Thr Leu Ala Asn Val Leu Ser Ala Ser Ile Leu Gly Leu Phe
145                 150                 155                 160
Trp Gln Gln Cys Gly Trp Leu Ala His Asp Phe Leu His His Gln Val
                165                 170                 175
Phe Gln Asp Arg Phe Trp Gly Asp Leu Phe Gly Ala Phe Leu Gly Gly
                180                 185                 190
Val Cys Gln Gly Phe Ser Ser Ser Trp Trp Lys Asp Lys His Asn Thr
                195                 200                 205
His His Ala Ala Pro Asn Val His Gly Glu Asp Pro Asp Ile Asp Thr
    210                 215                 220
His Pro Leu Leu Thr Trp Ser Glu His Ala Leu Glu Met Phe Ser Asp
225                 230                 235                 240
Val Pro Asp Glu Glu Leu Thr Lys Met Trp Ser Arg Phe Met Val Leu
                245                 250                 255
Asn Gln Thr Trp Phe Tyr Phe Pro Ile Leu Ser Phe Ala Arg Leu Ser
                260                 265                 270
Trp Cys Leu Gln Ser Ile Met Phe Val Met Pro Asn Gly Gln Ala His
    275                 280                 285
Lys Pro Ser Gly Ala Arg Val Pro Ile Ser Leu Val Glu Gln Leu Ser
    290                 295                 300
Leu Ala Met His Trp Thr Trp Tyr Phe Ala Thr Met Phe Leu Phe Ile
305                 310                 315                 320
Lys Asp Pro Val Asn Ile Met Val Tyr Phe Leu Val Ser Gln Ala Val
                325                 330                 335
Cys Gly Asn Leu Leu Ala Leu Val Phe Ser Leu Asn His Asn Gly Met
                340                 345                 350
Pro Val Ile Ser Lys Glu Glu Ala Val Asp Met Asp Phe Phe Thr Lys
                355                 360                 365
Gln Ile Ile Thr Gly Arg Asp Val His Pro Gly Leu Phe Ala Asn Trp
    370                 375                 380
Phe Thr Gly Gly Leu Asn Tyr Gln Ile Glu His His Leu Phe Pro Ser
385                 390                 395                 400
Met Pro Arg His Asn Phe Ser Lys Ile Gln Pro Ala Val Ala Ser Leu
                405                 410                 415
Cys Lys Lys Tyr Asn Val Arg Tyr His Thr Thr Gly Met Val Asp Gly
```

```
            420                 425                 430
Thr Ala Glu Val Phe Ala Arg Leu Asn Glu Val Ser Arg Ala Ala Ser
            435                 440                 445
Lys Met Gly Lys Ser Ala
    450

<210> SEQ ID NO 55
<211> LENGTH: 457
<212> TYPE: PRT
<213> ORGANISM: Mortierella alpina

<400> SEQUENCE: 55

Met Ala Ala Ala Pro Ser Val Arg Thr Phe Thr Arg Ala Glu Ile Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile His Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Phe Val Val Ala Lys
130                 135                 140

Trp Gly Gln Thr Ser Thr Leu Ala Asn Val Val Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Met Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Val Lys Asp Pro Ile Asn Met Phe Val Tyr Phe Leu Val Ser
                325                 330                 335
```

```
Gln Ala Val Cys Gly Asn Leu Leu Ala Leu Val Phe Ser Leu Asn His
            340                 345                 350

Asn Gly Met Pro Val Ile Ser Lys Glu Glu Ala Val Asp Met Asp Phe
            355                 360                 365

Phe Thr Lys Gln Ile Ile Thr Gly Arg Asp Val His Pro Gly Leu Phe
            370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
            405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Arg
            435                 440                 445

Ala Ala Ser Lys Met Gly Lys Ala Gln
            450                 455

<210> SEQ ID NO 56
<211> LENGTH: 338
<212> TYPE: PRT
<213> ORGANISM: Mortierella elongata

<400> SEQUENCE: 56

Met Ser Asp Ser His Leu Thr Val Asp Pro Thr Ser Thr Thr Pro His
1               5                   10                  15

Pro Asp Ala Asp Gly Thr Thr Asn Asn Thr Ile Ile Glu Thr Met Leu
            20                  25                  30

Asp Leu Glu Glu Ile Asp Lys Asp Leu Tyr Arg Ser Lys Lys Leu Trp
        35                  40                  45

Val Pro Met Gly Ala Arg Gly Val Phe Gly Gly Asn Val Val Gly Gln
    50                  55                  60

Ala Leu Val Ala Ala Thr Asn Thr Val Ser Thr Asp Tyr Ser Val His
65                  70                  75                  80

Ser Leu His Ser Tyr Phe Leu Leu Pro Gly Asp His Thr Thr Pro Ile
                85                  90                  95

Leu Tyr His Val Glu Arg Val Arg Asp Gly Lys Ser Tyr Cys Thr Arg
            100                 105                 110

Thr Val Thr Ala Lys Gln Arg Gly Lys Asn Ile Phe Val Cys Thr Ala
            115                 120                 125

Ser Tyr Gln Val Pro Arg Pro Gly Ala Pro Ser His Gln Tyr Pro Met
        130                 135                 140

Pro Asn Val Pro His His Ser Thr Leu Pro Ser Gln Glu Glu Leu Ile
145                 150                 155                 160

His Ala Met Ile Asp Asn Pro Lys Leu Pro Glu Asn Leu Lys Asp Phe
                165                 170                 175

Leu Arg Leu Arg Leu Asp Glu Pro Val Ala Leu Glu Phe Lys Asp Thr
            180                 185                 190

Lys Arg His Thr Phe Lys Glu Leu Met Asn Pro Glu Val Arg Thr Asp
        195                 200                 205

Gln Ser Phe Trp Ile Arg Cys Lys Gly Gln Leu Gly Asp Ala Leu Ala
    210                 215                 220

Leu His Gln Cys Val Val Ala Tyr Gly Ser Asp His Asn Leu Leu Asn
225                 230                 235                 240

Thr Val Pro Leu Ala His Gly Ser Ser Trp Phe Ser Arg Arg Ser Gly
                245                 250                 255
```

Leu Ser Pro Lys Ile Thr Met Met Ala Ser Leu Asp His Ser Met Trp
                260                 265                 270

Phe His Cys Pro Phe Arg Ala Asp Glu Trp Leu Leu Tyr Val Cys Glu
            275                 280                 285

Thr Pro Arg Ser Gly Cys Asp Arg Gly Leu Thr Phe Gly Arg Ile Tyr
        290                 295                 300

Lys Glu Asp Gly Thr Leu Ala Ile Ser Val Ala Gln Glu Gly Val Val
305                 310                 315                 320

Arg Leu Gln Pro Lys Thr Pro Thr Pro Ala Ala Thr Val Glu Thr Pro
                325                 330                 335

Lys Leu

<210> SEQ ID NO 57
<211> LENGTH: 334
<212> TYPE: PRT
<213> ORGANISM: Lobosporangium transversale

<400> SEQUENCE: 57

Met Ser Ser Val Ser Glu Pro Gly Ser Thr Leu Asn Leu Ala Pro Thr
1               5                   10                  15

Pro Asp Gly Ser Ser Asn Asn Thr Ile Ile Glu Thr Met Leu Asp Leu
                20                  25                  30

Glu Glu Ile Asp Lys Asp Leu Tyr Arg Ser Lys Lys Leu Trp Leu Pro
            35                  40                  45

Leu Gly Ala Arg Gly Val Phe Gly Gly Asn Val Val Gly Gln Ala Leu
        50                  55                  60

Val Ala Ala Thr Asn Thr Val Ser Asp Leu Tyr Ser Val His Ser Leu
65                  70                  75                  80

His Ser Tyr Phe Leu Leu Pro Gly Asp Pro Thr Ile Pro Ile Leu Tyr
                85                  90                  95

His Val Asp Arg Leu Arg Asp Gly His Ser Tyr Cys Thr Arg Thr Val
                100                 105                 110

Thr Ala Thr Gln Arg Gly Lys Asn Ile Phe Val Cys Thr Ala Ser Phe
            115                 120                 125

Gln Val Pro Arg Pro Asn Ala Pro Ser His Gln Tyr Pro Met Pro Asn
        130                 135                 140

Val Pro His His Ser Thr Leu Pro Ser Gln Glu Asp Leu Ile Arg Ala
145                 150                 155                 160

Met Ile Asp Ser Pro Lys Ile Pro Glu Asn Leu Val Glu Phe Leu Lys
                165                 170                 175

Gln Arg Leu Asp Glu Pro Val Ala Leu Asp Phe Lys Asp Thr Arg Arg
            180                 185                 190

His Thr Leu Lys Asp Leu Met Asn Pro Pro Val Arg Thr Glu Gln Thr
        195                 200                 205

Phe Trp Ile Lys Cys Lys Gly Gly Leu Gly Asp Ala Leu Ala Leu His
    210                 215                 220

Gln Cys Val Val Ala Tyr Gly Ser Asp His Asn Leu Leu Asn Thr Val
225                 230                 235                 240

Pro Leu Ala His Gly Ser Thr Trp Leu Ser Arg Arg Ser Ser Ser Pro
                245                 250                 255

Ser Ile Val Met Met Ala Ser Leu Asp His Ser Met Trp Phe His Cys
            260                 265                 270

Pro Phe Arg Ala Asp Glu Trp Met Leu Tyr Val Cys Glu Thr Pro Arg
        275                 280                 285

Ser Gly Cys Asp Arg Gly Leu Thr Phe Gly Arg Ile Tyr Lys Glu Asp
            290                 295                 300

Gly Thr Leu Ala Val Ser Val Ala Gln Glu Gly Val Val Arg Leu Arg
305                 310                 315                 320

Ser Lys Ala Pro Ser Ser Ala Thr Val Asp Gln Pro Lys Leu
                325                 330

<210> SEQ ID NO 58
<211> LENGTH: 146
<212> TYPE: PRT
<213> ORGANISM: Mortierella elongata

<400> SEQUENCE: 58

Met Met Ala Lys Gln Ile Thr Gln Thr Val Leu Thr Ala Thr Val Gly
1               5                   10                  15

Ile Glu Val Pro Phe His Asp Ile Asp Ser Met Asn Ile Cys Trp His
                20                  25                  30

Gly His Tyr Val Lys Tyr Phe Glu Ile Ala Arg Ser Ala Leu Leu Arg
            35                  40                  45

Ser Phe Glu Tyr Asp Ala Met Arg Leu Ser Asn Tyr Leu Trp Pro Val
50                  55                  60

Val Glu Cys Arg Leu Lys Tyr Leu Arg Pro Ala Arg Tyr Gly Gln Leu
65                  70                  75                  80

Leu Asp Val Ser Ala Lys Leu Val Glu Tyr Glu Ser Arg Leu Lys Ile
                85                  90                  95

Gly Tyr Leu Ile Thr Asp Arg Glu Ser Gly Ala Gln Leu Thr Lys Gly
            100                 105                 110

Tyr Thr Ile Gln Val Ala Val Asp Ala Gln Thr Gln Ala Leu Gln Phe
        115                 120                 125

Val Leu Pro Arg Glu Leu Leu Asp Lys Leu Glu Pro Met Leu Ser Ala
    130                 135                 140

Val Cys
145

<210> SEQ ID NO 59
<211> LENGTH: 132
<212> TYPE: PRT
<213> ORGANISM: Mortierella elongata

<400> SEQUENCE: 59

Met His Ser Leu Ser His Leu Pro His Asp Lys Thr Leu Ala Leu Arg
1               5                   10                  15

Ala Val Pro Gln Pro Ser Asn Ala Asn Met His Gly Asp Val Phe Gly
                20                  25                  30

Gly Trp Ile Met Ala Gln Val Asp Ile Ala Gly Ser Ile Pro Ala Thr
            35                  40                  45

Arg Arg Ala His Gly Arg Val Val Thr Val Ala Val Asn Ser Leu Val
50                  55                  60

Phe Lys Gln Pro Val Phe Val Gly Asp Leu Leu Ser Phe Tyr Ala Asp
65                  70                  75                  80

Ile Ala Lys Val Gly Asn Thr Ser Val Ala Val Ser Val Glu Val Tyr
                85                  90                  95

Ala Gln Arg Leu Asn Phe Ala Glu Gln Ile Phe Lys Val Ala Glu Ala
            100                 105                 110

Thr Leu Thr Tyr Val Ala Thr Asp Asn Asp Arg Arg Pro Arg Ala Leu
        115                 120                 125

Pro Ala Glu Gly
    130

<210> SEQ ID NO 60
<211> LENGTH: 422
<212> TYPE: PRT
<213> ORGANISM: Nannochloropsis gaditana

<400> SEQUENCE: 60

Met Ser Leu Lys Thr Ile Ser Pro His Asp Tyr Arg Ser Lys Met Thr
1               5                   10                  15

Arg Gln Glu Arg Thr Ser Arg Gln Val Leu Glu Leu Leu His Ala Val
            20                  25                  30

Ser Lys Ser Ala Phe Ser Gly Val Leu Leu Arg Arg Asp Ile Glu Pro
        35                  40                  45

Asn Ala Thr Glu Leu Gln Asn Val Lys Ala Leu Lys Ile Gly Pro Gly
    50                  55                  60

Pro Gln Val Arg Leu Arg Leu Arg Val Pro Ser His Leu Cys Asp Asn
65                  70                  75                  80

Tyr Asn Asn His Arg Leu Leu Asp Ala Gly Ala Val Thr Ala Trp
                85                  90                  95

Phe Asp Glu Val Ser Ser Trp Ala Phe Val Ser Ala Asp Gly Arg His
            100                 105                 110

Arg Pro Gly Val Ser Val Ser Leu Asn Thr Thr Val Leu Ser Trp Val
        115                 120                 125

Pro Val Gly Thr Glu Val Glu Ile Gln Ser His Cys Lys Lys Ile Gly
    130                 135                 140

Glu Thr Leu Gly Phe Ala Asp Met Met Leu Leu Asp Val Ala Thr Gly
145                 150                 155                 160

Lys Glu Leu Ala His Gly Arg His Val Lys Phe Leu Lys Met Gly Thr
                165                 170                 175

Ala Trp Thr Val Ala Met His Ala Trp Ala Phe Pro Leu Thr Tyr Leu
            180                 185                 190

Met Ala Ser Ala Val Leu Leu Pro Ser Val Arg Gln Arg Thr Gln Lys
        195                 200                 205

Ser Ser Ser Phe Pro Pro Glu Met Ala Pro Ser Pro Asp Leu Pro Arg
    210                 215                 220

Thr Glu Pro Gly Ser Ala Val Asn Ile Asn Arg Leu Leu Ala Leu Asp
225                 230                 235                 240

Asn Phe His Val Tyr Glu Pro Ala Gly Ala Ser Pro Pro Leu Ala
                245                 250                 255

Phe Pro Ala Ser Val Pro Leu Thr Met Glu Ala Ser Ala Ser Phe Arg
            260                 265                 270

Val Ile Pro Gln Val Cys Asn Ser Phe Gly Ser Leu His Gly Gly Ala
        275                 280                 285

Ala Ala Ile Leu Ala Glu Arg Ala Leu Ala Leu Tyr His Gln Ala
    290                 295                 300

Ala Arg Trp Ala Gly Glu Arg Ser Gln His Ala Leu Pro Arg Val Arg
305                 310                 315                 320

Ser Leu Ser Ile Asp Tyr Met Ser Pro Cys Lys Lys Asn Thr Glu Leu
                325                 330                 335

Leu Leu Leu Val Arg Gly Met Arg Val Glu Arg Gly Ala Gly Glu Gly
            340                 345                 350

Asp Lys His Ser Pro Ser Arg Ser Leu Phe Pro Pro Leu Asp Val Ala

```
                355                 360                 365
Pro His Pro Gln Gly Asn Leu Ile Pro Met Ser Tyr Gln Val Leu Phe
370                     375                 380

Thr Arg Lys Lys Asp Gly Arg Tyr Leu Thr Gln Cys His Val Leu Leu
385                 390                 395                 400

Asp Ser Gln Gly Asp Ala Trp His His Gln Arg Gln Ser Arg Gly Glu
                405                 410                 415

Gly Asn Arg Ala Arg Leu
            420

<210> SEQ ID NO 61
<211> LENGTH: 272
<212> TYPE: PRT
<213> ORGANISM: Nannochloropsis gaditana

<400> SEQUENCE: 61

Met Ser Leu Lys Thr Ile Ser Pro His Gly Tyr Arg Ser Lys Met Thr
1               5                   10                  15

Arg Gln Glu Gln Thr Ser Arg Gln Val Leu Glu Leu His Ala Val
            20                  25                  30

Ser Lys Ser Ala Phe Ser Gly Val Leu Leu Arg Arg Asp Ile Glu Pro
            35                  40                  45

Asn Ala Thr Glu Leu Gln Asn Val Lys Ala Leu Lys Ile Gly Pro Gly
        50                  55                  60

Pro Arg Val Arg Leu Arg Leu Arg Val Pro Ser His Leu Cys Asp Asn
65                  70                  75                  80

Tyr Asp Asn Asn His Cys Leu Leu Asp Ala Gly Ala Val Thr Ala Trp
                85                  90                  95

Phe Asp Glu Val Ser Ser Trp Ala Phe Val Ser Ala Asp Gly Arg His
            100                 105                 110

Arg Pro Gly Val Ser Val Ser Leu Asn Thr Thr Val Leu Ser Trp Val
        115                 120                 125

Pro Val Gly Thr Glu Val Glu Ile Gln Ser His Cys Lys Lys Ile Gly
130                 135                 140

Glu Thr Leu Gly Phe Ala Asp Met Met Leu Leu Asp Val Ala Thr Gly
145                 150                 155                 160

Lys Glu Leu Ala His Gly Arg His Val Lys Phe Leu Lys Met Gly Thr
                165                 170                 175

Ala Trp Thr Val Ala Met His Ala Trp Ala Phe Pro Leu Thr Tyr Leu
            180                 185                 190

Met Ala Ser Ala Val Leu Leu Pro Ser Val Arg Gln Arg Thr Gln Lys
        195                 200                 205

Ser Ser Ser Phe Pro Pro Glu Met Ala Pro Ser Asp Leu Pro Arg
    210                 215                 220

Thr Glu Pro Gly Ser Ala Ala Ser Val Leu Ser Met Val Gly Pro Pro
225                 230                 235                 240

Gln Phe Trp Leu Ser Ala Leu Leu Leu Pro Cys Ile Thr Lys Pro Leu
                245                 250                 255

Gly Gly Pro Glu Arg Gly Ala Ser Thr Leu Cys Arg Val Phe Val Leu
            260                 265                 270

<210> SEQ ID NO 62
<211> LENGTH: 547
<212> TYPE: PRT
<213> ORGANISM: Mortierella elongata
```

<400> SEQUENCE: 62

```
Met Leu Asp Trp Arg Phe Phe Thr Glu Arg Thr Cys Ala Ala Val Arg
1               5                   10                  15
Ala Leu Gly Ser Glu Arg His Arg His Ser Thr Arg Trp Ala Leu Cys
            20                  25                  30
Leu Ser Asp Pro Phe Glu Phe Ala Cys Gly Leu Phe Ala Leu Leu Ala
        35                  40                  45
Ala Gly Lys Gln Ile Val Leu Pro Ser Asn His Lys Pro Ala Ala Leu
    50                  55                  60
Leu Pro Leu Ala Gly Leu Tyr Asp Ser Val Leu Asp Asp Leu Asp Gly
65                  70                  75                  80
Leu Leu Ala Asn Gly Ala Gly Gly Pro Cys Ala Lys Leu Arg Ile Asp
                85                  90                  95
Pro Arg Ala Pro Leu Ser Leu Val Thr Ser Gly Ser Ser Gly Val Pro
            100                 105                 110
Lys Val Ile Gln Lys Thr Leu Ala Gln Phe Glu Ala Glu Ile His Thr
        115                 120                 125
Leu Ala Thr Leu Trp Gly Thr Val Met Arg Gly Val Thr Val Val Ala
    130                 135                 140
Ser Val Pro His His His Ile Tyr Gly Leu Leu Phe Arg Leu Leu Trp
145                 150                 155                 160
Pro Leu Ala Ala Gly Gln Pro Phe Asp Arg Met Thr Cys Val Glu Pro
                165                 170                 175
Ala Asp Val Arg Ala Arg Leu Ala Ala Leu Gln Asn Thr Val Leu Val
            180                 185                 190
Ser Ser Pro Ala Gln Leu Thr Arg Trp Pro Ser Leu Ile Asn Leu Thr
        195                 200                 205
Gln Leu Thr Pro Pro Gly Leu Ile Phe Ser Ser Gly Gly Pro Leu
    210                 215                 220
Pro Ala Glu Thr Ala Ala Ile Tyr Thr Gln Ala Phe Gly Ala Ala Pro
225                 230                 235                 240
Ile Glu Val Tyr Gly Ser Thr Glu Thr Gly Gly Ile Ala Trp Arg Cys
                245                 250                 255
Gln Pro Gln Ala Thr His Gln Asn Glu Val Ser Asp Ala Trp Thr Pro
            260                 265                 270
Met Pro Ala Ile Asp Val Arg Cys Asp Thr Glu Gly Ala Leu Gln Leu
        275                 280                 285
Arg Ser Pro His Leu Pro Asp Asp Gln Trp Trp Arg Met Glu Asp Ala
    290                 295                 300
Val Gln Ile Glu Ala Asp Gly Arg Phe Arg Leu Arg Gly Arg Leu Asp
305                 310                 315                 320
Arg Ile Ile Lys Leu Glu Glu Lys Arg Val Ser Leu Pro Glu Leu Glu
                325                 330                 335
His Val Leu Met Arg His Pro Trp Val Lys Gln Ala Val Ala Pro
            340                 345                 350
Leu Asn Gly Ala Arg Met Thr Leu Gly Ala Leu Leu Thr Leu Thr Glu
        355                 360                 365
Glu Gly Ile Gln Ala Trp Arg Ser Ala Ala Ser Arg Arg Phe Ile Thr
    370                 375                 380
Gln Ala Leu Arg Arg Tyr Leu Ala Glu Tyr Phe Asp Gly Val Val Leu
385                 390                 395                 400
Pro Arg His Trp Arg Phe Cys Met Gln Leu Pro Phe Asp Glu Arg Gly
                405                 410                 415
```

```
Lys Leu Ser Val Thr Gln Leu Ala Thr Arg Phe Ala Thr His Pro Leu
            420                 425                 430

Gln Pro Glu Val Leu Ala Glu Trp Cys Asp Asp Asn Thr Ala Leu Leu
            435                 440                 445

Glu Leu His Val Pro Ala Thr Leu Ile His Phe Ser Gly His Phe Pro
            450                 455                 460

Gly Leu Pro Ile Leu Pro Gly Val Val Gln Ile Asp Trp Val Val Arg
465                 470                 475                 480

Tyr Ala Ala His Tyr Phe Ala Arg Cys Asn Gly Phe Gln Thr Leu Glu
                485                 490                 495

Gln Ile Lys Phe Leu Ser Met Val Arg Pro Gly Thr Thr Leu Arg Leu
            500                 505                 510

Ala Leu Ala His Asp Pro Glu Arg Ala Arg Ile Thr Phe Arg Tyr Tyr
            515                 520                 525

Val Gly Glu Arg Asp Tyr Ala Thr Gly Arg Ile Val Tyr Ser Lys Ser
            530                 535                 540

Ala Val Val
545

<210> SEQ ID NO 63
<211> LENGTH: 819
<212> TYPE: PRT
<213> ORGANISM: Mortierella elongata

<400> SEQUENCE: 63

Met Pro Asp Leu Ala Trp Ser Leu Pro Val Ala Arg Trp Ser Ala Trp
1               5                   10                  15

Asn Ala Glu Thr Ser Ala Ala Leu Asp Met Gly Leu Lys Val Ala Asn
            20                  25                  30

Asp Cys Ala Pro Val Gly Gln Pro Val Arg Val Ile Phe Ala Ser Arg
            35                  40                  45

His Gly Glu Ser Arg Arg Thr Thr Glu Leu Leu Lys Ala Gln Ala Gln
        50                  55                  60

Asp Pro Met Gln Pro Leu Ser Pro Asn Ala Phe Ser Leu Ser Val Leu
65              70                  75                  80

Asn Ala Ala Ala Gly Val Phe Ser Met Met Arg Gly Asp His Ser Asn
                85                  90                  95

Ala Thr Ala Leu Ala Ala Gly Ser Glu Thr Leu Gly Tyr Ala Leu Leu
            100                 105                 110

Glu Ala Phe Ala Gln Tyr Ala Ser Asp Pro Gln Ala Pro Val Leu Val
            115                 120                 125

Ile Tyr Ala Asp Glu Pro Pro Asp Pro Ile Tyr Ala Ser Val Asp Asp
            130                 135                 140

Thr Asp Ala Pro Ser Gly Ala Leu Ala Leu Trp Ile Ala Asp Asp Ala
145                 150                 155                 160

Pro Gly Val Leu Glu Cys Arg Leu Leu Ile Asp Ala Leu Asn Leu Glu
                165                 170                 175

Asp Leu Thr Leu Ala Asp Ile Gly Asp Asp Thr Pro Leu Phe Asp Thr
            180                 185                 190

Asp Gly Ile Gly Leu Asp Ser Ile Asp Ala Leu Glu Ile Gly Ile Ala
            195                 200                 205

Leu Arg Lys Lys Tyr Gln Leu Gln Ile Glu Thr Thr Asp Ser Arg Met
            210                 215                 220

Arg Glu His Phe Arg Ser Leu Leu Leu Asp Ala Leu Ala Gly Val Ser
```

```
                225                 230                 235                 240
Gln Arg Pro Thr Leu Phe Arg Met Thr Thr Pro Leu His Leu Leu Phe
                    245                 250                 255

Ser Asn Asp Cys Val Ala Thr Arg Pro Val Cys Ile Asp Gly Asp His
                260                 265                 270

Ile Leu Asp Trp Arg Phe Phe Thr Glu Arg Thr Cys Ala Ala Val Arg
            275                 280                 285

Ala Leu Gly Ser Glu Arg His Arg Arg Ser Ala Arg Trp Ala Leu Cys
        290                 295                 300

Leu Ser Asp Pro Phe Glu Phe Ala Cys Gly Leu Phe Ala Leu Leu Ala
305                 310                 315                 320

Ala Gly Lys Gln Ile Val Leu Pro Ser Asn His Lys Pro Ala Ala Leu
                325                 330                 335

Leu Pro Leu Ala Gly Leu Tyr Asp Ser Val Leu Asp Asp Leu Asp Ser
                340                 345                 350

Leu Phe Ala Asn Gly Ala Gly Gly Pro Cys Ala Lys Leu Arg Ile Asp
            355                 360                 365

Pro Arg Ala Pro Leu Ser Leu Val Thr Ser Gly Ser Ser Gly Val Pro
    370                 375                 380

Lys Val Ile His Lys Thr Leu Ala Gln Phe Glu Ala Glu Ile His Thr
385                 390                 395                 400

Leu Ala Thr Leu Trp Gly Thr Val Met Arg Asp Val Thr Val Val Ala
                405                 410                 415

Ser Val Pro His His His Ile Tyr Gly Leu Leu Phe Arg Leu Leu Trp
                420                 425                 430

Pro Leu Ala Ala Gly Gln Pro Phe Asp Arg Met Thr Cys Val Glu Pro
            435                 440                 445

Ala Asp Val Arg Ala Arg Leu Ala Leu Gln Asn Thr Val Leu Val
    450                 455                 460

Ser Ser Pro Ala Gln Leu Thr Arg Trp Pro Ser Leu Ile Asn Leu Ala
465                 470                 475                 480

Gln Leu Thr Pro Pro Gly Leu Ile Phe Ser Ser Gly Gly Pro Leu
                485                 490                 495

Pro Thr Glu Thr Ala Ala Ile Tyr Ala Gln Ala Phe Gly Ala Ala Pro
            500                 505                 510

Ile Glu Val Tyr Gly Ser Thr Glu Thr Gly Gly Ile Ala Trp Arg Cys
        515                 520                 525

Gln Pro Gln Ala Met His Gln Asn Glu Val Ser Asp Ala Trp Thr Pro
    530                 535                 540

Met Pro Ala Ile Asp Val Arg Cys Asp Thr Asp Gly Ala Leu Gln Leu
545                 550                 555                 560

Arg Ser Pro His Leu Pro Asp Asp Gln Trp Trp Arg Met Glu Asp Ala
                565                 570                 575

Val Gln Ile Lys Val Asp Gly Arg Phe Arg Leu Arg Gly Arg Leu Asp
            580                 585                 590

Arg Ile Ile Lys Leu Glu Glu Lys Arg Val Ser Leu Pro Glu Leu Glu
        595                 600                 605

His Val Leu Met Arg His Pro Trp Val Lys Gln Ala Ala Val Ala Pro
    610                 615                 620

Leu Asn Gly Ala Arg Met Thr Leu Gly Ala Leu Leu Thr Leu Thr Glu
625                 630                 635                 640

Glu Gly Ile Gln Ala Trp Arg Ser Ala Ala Ser Arg Arg Phe Ile Thr
                645                 650                 655
```

```
Gln Ala Leu Arg Arg Tyr Leu Ala Glu Tyr Phe Asp Gly Val Val Leu
            660                 665                 670

Pro Arg His Trp Arg Phe Cys Met Gln Leu Pro Phe Asp Glu Arg Gly
            675                 680                 685

Lys Leu Ser Val Thr Gln Leu Ala Ala Arg Phe Ala Thr His Pro Leu
            690                 695                 700

Gln Pro Glu Val Leu Ala Glu Trp Cys Asp Gly Asn Thr Ala Leu Leu
705                 710                 715                 720

Glu Leu His Val Pro Ala Thr Leu Ser His Phe Ser Gly His Phe Pro
                725                 730                 735

Gly Leu Pro Ile Leu Pro Gly Val Val Gln Ile Asp Trp Val Val Arg
            740                 745                 750

Tyr Ala Ala His Tyr Phe Ala Arg Cys Asn Gly Phe Gln Thr Leu Glu
            755                 760                 765

Gln Ile Lys Phe Leu Ser Met Val Arg Pro Gly Thr Thr Leu Arg Leu
            770                 775                 780

Ala Leu Ala His Asp Pro Glu Arg Ala Arg Ile Thr Phe Arg Tyr Tyr
785                 790                 795                 800

Val Gly Glu Arg Asp Tyr Ala Thr Gly Arg Ile Val Tyr Ser Lys Ser
                805                 810                 815

Ala Val Val

<210> SEQ ID NO 64
<211> LENGTH: 572
<212> TYPE: PRT
<213> ORGANISM: Mortierella elongata

<400> SEQUENCE: 64

Met Thr Thr Pro Leu His Leu Leu Phe Ser His Asp Cys Val Ala Thr
1               5                   10                  15

Arg Pro Val Cys Ile Asp Gly Asp His Met Leu Asp Trp Arg Phe Phe
            20                  25                  30

Thr Glu Arg Thr Cys Ala Ala Val Arg Ala Leu Gly Ser Glu Arg His
        35                  40                  45

Arg His Ser Thr Arg Trp Ala Leu Cys Leu Ser Asp Pro Phe Glu Phe
    50                  55                  60

Ala Cys Gly Leu Phe Ala Leu Leu Ala Ala Gly Lys Gln Ile Val Leu
65                  70                  75                  80

Pro Ser Asn His Lys Pro Ala Ala Leu Leu Pro Leu Ala Gly Leu Tyr
                85                  90                  95

Asp Ser Val Leu Asp Asp Leu Asp Gly Leu Leu Ala Asn Gly Ala Gly
            100                 105                 110

Gly Pro Cys Ala Lys Leu Arg Ile Asp Pro Arg Ala Pro Leu Ser Leu
        115                 120                 125

Val Thr Ser Gly Ser Ser Gly Val Pro Lys Val Ile Gln Lys Thr Leu
    130                 135                 140

Ala Gln Phe Glu Ala Glu Ile His Thr Leu Ala Thr Leu Trp Gly Thr
145                 150                 155                 160

Val Met Arg Gly Val Thr Val Val Ala Ser Val Pro His His Ile
                165                 170                 175

Tyr Gly Leu Leu Phe Arg Leu Leu Trp Pro Leu Ala Ala Gly Gln Pro
            180                 185                 190

Phe Asp Arg Met Thr Cys Val Glu Pro Ala Asp Val Arg Ala Arg Leu
        195                 200                 205
```

Ala Ala Leu Gln Asn Thr Val Leu Val Ser Ser Pro Ala Gln Leu Thr
210                 215                 220

Arg Trp Pro Ser Leu Ile Asn Leu Thr Gln Leu Thr Pro Pro Pro Gly
225                 230                 235                 240

Leu Ile Phe Ser Ser Gly Gly Pro Leu Pro Ala Glu Thr Ala Ala Ile
                245                 250                 255

Tyr Thr Gln Ala Phe Gly Ala Ala Pro Ile Glu Val Tyr Gly Ser Thr
            260                 265                 270

Glu Thr Gly Gly Ile Ala Trp Arg Cys Gln Pro Gln Ala Thr His Gln
        275                 280                 285

Asn Glu Val Ser Asp Ala Trp Thr Pro Met Pro Ala Ile Asp Val Arg
290                 295                 300

Cys Asp Thr Glu Gly Ala Leu Gln Leu Arg Ser Pro His Leu Pro Asp
305                 310                 315                 320

Asp Gln Trp Trp Arg Met Glu Asp Ala Val Gln Ile Glu Ala Asp Gly
                325                 330                 335

Arg Phe Arg Leu Arg Gly Arg Leu Asp Arg Ile Ile Lys Leu Glu Glu
            340                 345                 350

Lys Arg Val Ser Leu Pro Glu Leu Glu His Val Leu Met Arg His Pro
        355                 360                 365

Trp Val Lys Gln Ala Ala Val Ala Pro Leu Asn Gly Ala Arg Met Thr
370                 375                 380

Leu Gly Ala Leu Leu Thr Leu Thr Glu Glu Gly Ile Gln Ala Trp Arg
385                 390                 395                 400

Ser Ala Ala Ser Arg Arg Phe Ile Thr Gln Ala Leu Arg Arg Tyr Leu
                405                 410                 415

Ala Glu Tyr Phe Asp Gly Val Val Leu Pro Arg His Trp Arg Phe Cys
            420                 425                 430

Met Gln Leu Pro Phe Asp Glu Arg Gly Lys Leu Ser Val Thr Gln Leu
        435                 440                 445

Ala Thr Arg Phe Ala Thr His Pro Leu Gln Pro Glu Val Leu Ala Glu
450                 455                 460

Trp Cys Asp Asp Asn Thr Ala Leu Leu Glu Leu His Val Pro Ala Thr
465                 470                 475                 480

Leu Ile His Phe Ser Gly His Phe Pro Gly Leu Pro Ile Leu Pro Gly
                485                 490                 495

Val Val Gln Ile Asp Trp Val Val Arg Tyr Ala Ala His Tyr Phe Ala
            500                 505                 510

Arg Cys Asn Gly Phe Gln Thr Leu Glu Gln Ile Lys Phe Leu Ser Met
        515                 520                 525

Val Arg Pro Gly Thr Thr Leu Arg Leu Ala Leu Ala His Asp Pro Glu
530                 535                 540

Arg Ala Arg Ile Thr Phe Arg Tyr Tyr Val Gly Glu Arg Asp Tyr Ala
545                 550                 555                 560

Thr Gly Arg Ile Val Tyr Ser Lys Ser Ala Val Val
                565                 570

<210> SEQ ID NO 65
<211> LENGTH: 697
<212> TYPE: PRT
<213> ORGANISM: Neurospora crassa

<400> SEQUENCE: 65

Met Ala Asn Thr Gly Pro Gly Asn Val Pro Leu His Phe Ile Gln Lys

-continued

```
1               5                   10                  15
Pro Pro Phe Thr Val Glu Asp Pro Asn Ala Gln Pro Ile Pro Gly Glu
                20                  25                  30

Thr Ile Pro Arg Arg His Pro Lys Ala Lys Asn Gly Leu Ala Thr Arg
                35                  40                  45

Pro Ala Pro Gly Val Asn Thr Thr Leu Asp Leu Leu Thr Arg Thr Val
 50                  55                  60

Glu Leu Tyr Gly Asp Glu Arg Ala Ile Gly Ser Arg Lys Leu Ile Lys
 65                  70                  75                  80

Leu His Lys Asp Ile Lys Lys Val Pro Lys Val Val Asp Gly Glu Thr
                85                  90                  95

Val Met Val Asp Lys Glu Trp Gln Cys Phe Glu Leu Thr Pro Tyr Ser
                100                 105                 110

Tyr Ile Thr Tyr Gly Glu Tyr Phe Thr Ile Val Lys Gln Ile Gly Ala
                115                 120                 125

Gly Leu Arg Lys Leu Gly Leu Glu Pro Lys Asp Lys Leu His Ile Phe
                130                 135                 140

Ala Thr Thr Ser Pro Gln Trp Leu Gly Met Ser His Ala Ala Ser Ser
145                 150                 155                 160

Gln Ser Leu Thr Ile Val Thr Ala Tyr Asp Thr Leu Gly Glu Ser Gly
                165                 170                 175

Val Gln His Ser Leu Val Gln Ser Lys Ala Ser Ala Met Phe Thr Asp
                180                 185                 190

Pro His Leu Leu Lys Thr Ala Thr Asn Pro Leu Lys Glu Ala Thr Ser
                195                 200                 205

Val Lys Val Ile Tyr Asn Asn His Thr Thr Gln Pro Val Ser Gln
210                 215                 220

Asp Lys Ile Asp Ala Phe Lys Ala Glu His Pro Asp Leu Thr Val Leu
225                 230                 235                 240

Ser Phe Glu Glu Leu Arg Ala Leu Gly Glu Glu Asn Pro Val Pro Leu
                245                 250                 255

Thr Pro Pro Asn Pro Asp Asp Thr Tyr Cys Ile Met Tyr Thr Ser Gly
                260                 265                 270

Ser Thr Gly Pro Pro Lys Gly Val Pro Val Ser His Ala Gly Phe Val
                275                 280                 285

Ala Ala Val Ala Gly Leu Tyr Ala Val Met Glu Glu Ser Val Thr His
                290                 295                 300

Arg Asp Arg Val Leu Ala Tyr Leu Pro Leu Ala His Ile Phe Glu Leu
305                 310                 315                 320

Val Leu Glu Asn Leu Gly Val Phe Val Gly Gly Thr Leu Gly Tyr Ser
                325                 330                 335

Asn Ala Arg Thr Leu Ser Asp Thr Ser Met Arg Asn Cys Pro Gly Asp
                340                 345                 350

Met Arg Ala Phe Lys Pro Thr Ile Met Val Gly Val Pro Gln Val Trp
                355                 360                 365

Glu Thr Val Lys Lys Gly Ile Glu Gly Lys Val Asn Ser Ala Gly Ala
                370                 375                 380

Leu Thr Lys Ala Leu Phe Trp Gly Ala Tyr Asn Ile Lys Ser Phe Leu
385                 390                 395                 400

Val Ser Asn Asn Leu Pro Gly Lys Thr Ile Phe Asp Asp Leu Val Phe
                405                 410                 415

Gly Gln Val Arg Thr Met Thr Gly Gly Glu Leu Arg Phe Ile Val Asn
                420                 425                 430
```

Gly Ala Ser Gly Ile Ala Ala Ser Thr Gln His Phe Met Ser Met Val
                435                 440                 445

Val Ala Pro Met Leu Asn Gly Tyr Gly Leu Thr Glu Thr Cys Gly Asn
    450                 455                 460

Gly Ala Leu Gly Ser Pro Met Gln Trp Thr Ser Asn Ala Ile Gly Ala
465                 470                 475                 480

Met Pro Ala Ala Val Glu Met Lys Leu Val Ser Leu Pro Gly Leu Asn
                485                 490                 495

Tyr His Thr Asp Thr Val Pro Pro Gln Gly Glu Ile Leu Phe Arg Gly
                500                 505                 510

Ala Cys Val Ile Lys Glu Tyr Tyr Glu Asn Pro Glu Gly Thr Ala Lys
                515                 520                 525

Ala Ile Thr Pro Asp Gly Trp Phe Lys Ser Gly Asp Ile Gly Glu Ile
                530                 535                 540

Asp Ala Asn Gly His Leu Arg Val Ile Asp Arg Val Lys Asn Leu Val
545                 550                 555                 560

Lys Leu Gln Gly Gly Glu Tyr Ile Ala Leu Glu Lys Leu Glu Ala Val
                565                 570                 575

Tyr Arg Gly Ala Val Phe Val His Asn Ile Met Val His Gly Asp Asn
                580                 585                 590

Ser Ala Pro Arg Pro Ile Ala Val Val Pro Asn Glu Lys Ala Leu
                595                 600                 605

Ala Glu Lys Ala Glu Glu Leu Gly Leu Gly Ala Glu Ala Pro Gly Glu
                610                 615                 620

Met His Arg Asn Arg Lys Leu Arg Asp Ala Val Leu Lys Glu Leu Gln
625                 630                 635                 640

Ser Val Gly Arg Arg Ala Gly Leu Ser Gly Met Glu Thr Val Ala Gly
                645                 650                 655

Val Val Leu Val Asp Asp Glu Trp Thr Pro Ala Asn Gly Phe Val Thr
                660                 665                 670

Ala Thr Gln Lys Ile Asn Arg Arg Ala Val Lys Glu Arg Tyr Ser Lys
                675                 680                 685

Glu Ile Ser Asp Cys Leu Asp Gly Lys
                690                 695

<210> SEQ ID NO 66
<211> LENGTH: 671
<212> TYPE: PRT
<213> ORGANISM: Nannochloropsis gaditana

<400> SEQUENCE: 66

Met Asp Arg Tyr Lys Trp Arg Thr Leu Pro Asp Val Phe Glu Thr Val
1               5                   10                  15

Ala Ser Leu Ala Pro Glu Ala Val Ala Val Glu Asp Met Val His Thr
                20                  25                  30

Pro Thr Ala Lys Met Thr Tyr Gly Glu Leu Asn Arg Gln Ile Gly Ala
                35                  40                  45

Leu Ala Ala Phe Phe Gln His Glu Gly Leu Lys Pro Gly Gln Cys Val
        50                  55                  60

Ser Val Phe Ala Glu Asn Ser His Arg Trp Leu Ile Ala Asp Gln Ala
65              70                  75                  80

Ile Leu Lys Ala Gly Ala Cys Asn Ala Val Arg Gly Val Lys Ala Pro
                85                  90                  95

Val Asp Glu Leu Gln Tyr Ile Tyr Gln Asn Ser Glu Ser Val Ala Ser

```
                100             105             110
    Val Val Glu Ser Val Glu Gln Ile Glu Ala Leu Met Arg Thr Asn Gly
            115             120             125
    Gly Leu Thr Gly Arg Tyr Gly Pro Arg Phe Ile Leu Val Leu Phe
            130             135             140
    Pro Gly Glu Arg Ser Gly Gln Glu Ile Arg Glu Leu Ala Asn Leu Pro
145             150             155             160
    Pro Pro Thr Gln Val Leu Thr Phe Asp Glu Ala Leu Ser Ala Ser Leu
                165             170             175
    Ala Arg Pro Leu Thr Phe Arg Pro Val Pro Lys Asp Val Arg Ser Val
                180             185             190
    Ala Thr Leu Val Tyr Thr Ser Gly Thr Thr Asn Lys Pro Lys Gly Val
                195             200             205
    Val Leu Arg His Ser Asn Leu Leu His Gln Val Asn Tyr Asn Ser Phe
                210             215             220
    Thr Asp Ser Pro Ser Lys Glu Pro Ala Tyr Asn Pro Val Leu Gly Asp
225             230             235             240
    Val Leu Val Ser Val Leu Pro Cys Trp His Ile Phe Glu Arg Thr Ala
                    245             250             255
    Glu Tyr Trp Met Phe Ser Lys Gly Ile His Val Val Tyr Ser Asn Val
                    260             265             270
    Lys Asn Phe Lys Ala Asp Leu Ala Lys His Gln Pro Gln Phe Ile Val
                275             280             285
    Ala Val Pro Arg Leu Leu Glu Thr Ile Tyr Arg Gly Val Leu Gln Lys
                290             295             300
    Phe Ala Thr Glu Lys Gly Ala Lys Lys Ile Ile Glu Phe Phe Thr
305             310             315             320
    Arg Val Gly Ser Ala Trp Val Lys Ala Trp Arg Val Ala Arg Gly Leu
                    325             330             335
    Val Leu Arg Ser Arg Ala Pro Asn Pro Ile Glu Arg Leu Leu Ala Leu
                    340             345             350
    Val Leu Ala Leu Val Leu Ser Pro Leu Ala Ala Val Gly Asp Lys Leu
                    355             360             365
    Val Trp Ser Lys Val Arg Ala Gly Leu Gly Gly Arg Ile Lys Val Leu
                    370             375             380
    Val Ala Gly Gly Ser Ser Met Pro Leu Val Leu Glu Asp Phe Phe Glu
385             390             395             400
    Leu Leu Arg Thr Pro Val Ile Val Gly Tyr Gly Met Thr Glu Thr Ser
                    405             410             415
    Pro Val Ile Thr Asn Arg Val Ala Glu Lys Asn Leu Ala Gly Ser Val
                    420             425             430
    Gly Arg Thr Ala Arg Asp Thr Glu Val Lys Ile Val Asp Pro Glu Ser
                    435             440             445
    Gly Ala Arg Leu Pro Glu Gly Gln Pro Gly Leu Val Leu Met Arg Gly
                    450             455             460
    Pro Gln Met Met Ala Gly Tyr Lys Ser Asn Ala Glu Ala Ser Lys Ala
465             470             475             480
    Val Leu Asp Gln Glu Gly Phe Leu Asp Thr Gly Asp Leu Gly Arg Ile
                    485             490             495
    His Pro Leu Thr Lys His Leu Ile Ile Thr Gly Arg Ala Lys Asp Thr
                    500             505             510
    Ile Val Leu Ser Asn Gly Glu Asn Val Glu Pro Gln Pro Ile Glu Asp
                    515             520             525
```

```
Val Val Cys Ala Asn Ser Ala Leu Val Asp Gln Val Met Cys Val Gly
            530                 535                 540

Gln Asp Glu Lys Val Leu Gly Met Leu Val Val Pro Asn Val Arg Ala
545                 550                 555                 560

Leu Ala Arg Ala Gly Leu Val Asp Arg Gly Leu Ala Glu Arg Val Ala
            565                 570                 575

Glu Leu Gly Gly Gln Val Leu Thr Asn Gly Ile Ala Gly Ser Arg
            580                 585                 590

Ala Glu Leu Glu Glu Val Glu Ala Ser Leu Arg Glu Lys Lys Glu Val
            595                 600                 605

Lys Lys Ala Leu Leu Ala Asp Ile Ala Arg Ala Met Gly Lys Ser Phe
610                 615                 620

Arg Glu Thr Glu Arg Val Gly Ala Val Glu Val Leu Glu Pro Phe
625                 630                 635                 640

Asn Met Ala Asn Gly Phe Leu Thr Gln Thr Leu Lys Val Lys Arg Asn
            645                 650                 655

Val Val Ser Gly His Tyr Ala Gln Glu Ile Glu Gln Met Tyr Arg
            660                 665                 670

<210> SEQ ID NO 67
<211> LENGTH: 497
<212> TYPE: PRT
<213> ORGANISM: Nannochloropsis gaditana

<400> SEQUENCE: 67

Met His Gly Arg Ser Lys Lys Leu Gly Asn Ile Leu Glu Glu Leu Gly
1               5                   10                  15

Val Lys Lys Gly Asp Arg Val Ala Thr Leu Ala Met Asn Thr Tyr Arg
            20                  25                  30

His Met Glu Leu Tyr Phe Ala Val Ser Gly Ala Gly Ala Val Leu His
        35                  40                  45

Thr Leu Asn Pro Arg Leu Phe Ala Glu Thr Leu Thr Trp Ile Val His
    50                  55                  60

His Ala Gln Asp Ser Val Leu Phe Phe Asp Pro Cys Phe Ala Ser Leu
65                  70                  75                  80

Val Glu Arg Leu Leu Pro His Cys Pro Ser Val Lys His Trp Ile Cys
                85                  90                  95

Leu Val Asp Glu Glu Arg Met Pro Val Leu Pro Ser Leu Ser Pro Ser
            100                 105                 110

Ser Pro Phe Leu Ser Leu His Asn Tyr Glu Ala Leu Leu Arg Glu Gly
        115                 120                 125

Lys Glu Asp Tyr Val Trp Pro Ile Leu Glu Glu Thr Ala Ala Ser Ser
130                 135                 140

Leu Cys Tyr Thr Ser Gly Thr Thr Gly Ile Pro Tyr Thr Ala Ala Met
145                 150                 155                 160

Val Gly Cys Lys Leu Val Leu Pro Gly Ser Ala Leu Asp Gly Ala Ser
                165                 170                 175

Leu Tyr Glu Leu Met Lys Glu Glu Gly Val Thr Leu Ala Ala Gly Val
            180                 185                 190

Pro Thr Val Trp Leu Pro Val His His Leu Asp Gln Asp Pro Gly
        195                 200                 205

Gln Gly Leu Pro Lys Leu Arg Arg Leu Val Ile Gly Gly Ala Ala Cys
210                 215                 220

Pro Pro Ser Met Leu Arg Ala Phe Lys Glu Arg His Gly Ile Glu Gly
```

```
                225                 230                 235                 240
Lys His Leu Ala Leu Pro Thr Glu Asp Gln His Asn Val Leu Ser Thr
                    245                 250                 255

Gln Gly Arg Thr Ile Tyr Gly Val Asp Leu Arg Ile Val Ala Pro Ser
                260                 265                 270

Pro Pro Pro Tyr Leu Pro Ser Ser Ser Tyr Ser Pro Pro Tyr
            275                 280                 285

Pro Pro Arg Trp Ser Glu Val Pro Trp Asp Gly Val Ser Pro Gly Glu
        290                 295                 300

Leu Cys Ala Arg Gly His Trp Val Ala Thr Asp Tyr Phe Ser Pro Thr
305                 310                 315                 320

Gln Ala Pro Glu Glu Gly Glu Arg Asp Gly Val Arg Ala Gly His
                325                 330                 335

Gln Glu Ser Phe Tyr Thr Asp Asp Gly Glu Arg Trp Phe Leu Thr
                340                 345                 350

Gly Asp Val Ala Thr Ile Cys Pro Asp Gly Tyr Ile Lys Ile Thr Asp
                355                 360                 365

Arg Ser Lys Asp Val Ile Lys Ser Gly Gly Glu Trp Ile Ser Ser Ile
370                 375                 380

Glu Leu Glu Asn Ile Ala Thr Asn His Pro Glu Val Ala Leu Ala Ala
385                 390                 395                 400

Val Ile Ala Met Pro His Arg Lys Trp Asp Glu Arg Pro Leu Leu Ile
                405                 410                 415

Val Val Leu Lys Asp Ser Ala Ala Leu Ser Leu His Tyr Ser Thr Thr
                420                 425                 430

Ser Ser Ser Pro Ser Thr Ser Ser Asp Thr Asp Arg Ala Ile Arg Leu
                435                 440                 445

Thr Lys Glu Ala Leu Leu Asp His Phe Lys Gly Lys Val Ala Lys Trp
            450                 455                 460

Trp Val Pro Asp Val Ile Phe Val Asp Ser Leu Pro Gln Gly Pro
465                 470                 475                 480

Thr Gly Lys Ile Leu Lys Thr Glu Leu Arg Gln Arg Phe Ser Arg Arg
                485                 490                 495

Pro

<210> SEQ ID NO 68
<211> LENGTH: 649
<212> TYPE: PRT
<213> ORGANISM: Nannochloropsis gaditana

<400> SEQUENCE: 68

Met Pro Lys Tyr Thr Thr Thr Val Ala Ser Gly Glu Val Asp Leu Arg
1               5                   10                  15

Ile Glu Lys Glu Gly Pro Gly Ser Trp Ala Pro Lys Thr Val Phe Gln
                20                  25                  30

Val Phe Glu Glu Thr Val Lys Lys Tyr Gly Asp Ser Pro Ala Leu His
            35                  40                  45

Tyr Lys Lys Val Pro His Gly Gly Ser Leu Ala Thr Thr Glu Trp Ser
        50                  55                  60

Ser Tyr Thr Trp Arg Glu Tyr Tyr Asp Leu Thr Leu Glu Phe Cys Lys
65                  70                  75                  80

Ser Leu Leu Ser Leu Gly Phe Pro Ala His Gly Ala Ile Asn Leu Ile
                85                  90                  95

Gly Phe Asn Ser Pro Glu Trp Leu Ile Ala Asn Cys Gly Ala Ile Ala
```

```
                100                 105                 110
Ala Gly Gly Val Gly Val Gly Ile Tyr Thr Ser Asn Gly Val Asp Ala
            115                 120                 125

Cys Lys Tyr Ile Thr Glu His Ser Glu Ala Glu Val Val Val Glu
130                 135                 140

Asn Ala Lys Gln Leu Glu Lys Tyr Leu Lys Ile Ala Lys Glu Leu Pro
145                 150                 155                 160

Arg Leu Lys Ala Leu Val Ile Tyr Ser Gly Thr Ala Glu Gly Tyr Lys
                165                 170                 175

Cys Asp Val Pro Ile Tyr Ser Trp Lys Asp Phe Met Ala Leu Gly Ser
            180                 185                 190

Gly Val Lys Asp Glu Ala Val Arg Ala Arg Ile Glu Ala Gln Arg Pro
            195                 200                 205

Gly His Cys Cys Thr Leu Ile Tyr Thr Ser Gly Thr Thr Gly Pro Pro
        210                 215                 220

Lys Ala Val Met Ile Ser His Asp Asn Leu Thr Trp Thr Val Lys Asn
225                 230                 235                 240

Phe Val Ala Ser Leu Pro Phe Thr Leu Thr Cys Glu Asp Arg Ser Val
                245                 250                 255

Ser Tyr Leu Pro Leu Ser His Val Ala Ala Gln Met Leu Asp Ile His
                260                 265                 270

Cys Pro Ile Ala Thr Gly Ala Lys Ile Tyr Phe Ala Gln Pro Asp Ala
            275                 280                 285

Leu Arg Gly Ser Leu Pro Val Thr Leu Lys Asp Val Cys Pro Thr Tyr
        290                 295                 300

Phe Phe Gly Val Pro Arg Val Trp Glu Lys Ile Tyr Glu Lys Met Gln
305                 310                 315                 320

Glu Val Ala Arg Ser Thr Thr Gly Val Lys Arg Ala Leu Ala Gln Trp
                325                 330                 335

Ala Lys Ala Lys Gly Leu Glu Lys Asn Arg Arg Gln Gln Tyr Gly Cys
            340                 345                 350

Gly Gly Gly Ala Pro Val Gly Phe Gly Cys Ala His Ala Leu Val Leu
        355                 360                 365

Ser Lys Val Lys Ala Ala Leu Gly Leu His Gln Thr Lys Met Cys Ile
        370                 375                 380

Thr Ser Ala Ala Pro Ile Ala Val Glu Ile Leu Glu Tyr Phe Ala Ser
385                 390                 395                 400

Leu Asp Ile Pro Val Leu Glu Leu Phe Gly Gln Ser Glu Cys Thr Gly
                405                 410                 415

Pro His Thr Ser Asn Phe Ser Tyr Ala Trp Lys Ile Gly Ser Ile Gly
                420                 425                 430

Arg Asp Ile Pro Gly Val Lys Thr Lys Gln His Ala Asn Met Ser Glu
            435                 440                 445

Phe Cys Met Tyr Gly Arg His Ile Met Met Gly Tyr Met Lys Met Glu
        450                 455                 460

Asp Lys Thr Gln Glu Ala Val Asp Asn Glu Gly Trp Leu His Ser Gly
465                 470                 475                 480

Asp Val Ala Gln Val Asp Ala Asp Gly Phe Trp Ser Ile Thr Gly Arg
                485                 490                 495

Ile Lys Glu Leu Ile Ile Thr Ala Gly Gly Glu Asn Ile Pro Pro Val
            500                 505                 510

Leu Ile Glu Asn Glu Ile Met Ser Ala Leu Pro Ala Val Ala Asn Cys
            515                 520                 525
```

```
Met Val Val Gly Asp Lys Lys Phe Leu Thr Val Leu Thr Met
            530                 535                 540

Lys Ala Lys Leu Asp Asp Gln Gly Asn Pro Thr Lys Glu Leu Asn Lys
545                 550                 555                 560

Glu Ala Leu Asp Ile Gly Lys Glu Ile Gly Ser Asn Ala Ser Thr Thr
                565                 570                 575

Glu Gln Val Ala Ser Asp Pro His Trp Lys Lys Tyr Phe Asp Glu Gly
            580                 585                 590

Leu Lys Lys Ala Asn Ser Thr Ala Thr Ser Asn Ala Gln Phe Val Gln
            595                 600                 605

Lys Trp Ser Val Leu Pro Leu Asp Phe Ser Glu Lys Gly Gly Glu Leu
            610                 615                 620

Thr Pro Thr Leu Lys Leu Lys Arg Ser Val Val Ala Glu Lys Tyr Ala
625                 630                 635                 640

Asp Val Ile Ala Asp Met Tyr Lys Ala
                645

<210> SEQ ID NO 69
<211> LENGTH: 649
<212> TYPE: PRT
<213> ORGANISM: Nannochloropsis gaditana

<400> SEQUENCE: 69

Met Pro Lys Tyr Thr Thr Thr Val Ala Ser Gly Glu Val Asp Leu Arg
1               5                   10                  15

Ile Glu Lys Glu Gly Pro Gly Ser Trp Ala Pro Lys Thr Val Phe Gln
            20                  25                  30

Val Phe Glu Glu Thr Val Lys Lys Tyr Gly Asp Ser Pro Ala Leu His
        35                  40                  45

Tyr Lys Lys Val Pro His Gly Gly Ser Leu Ala Thr Thr Glu Trp Ser
    50                  55                  60

Ser Tyr Thr Trp Arg Glu Tyr Tyr Asp Leu Thr Leu Lys Phe Cys Lys
65                  70                  75                  80

Ser Leu Leu Ser Leu Gly Phe Pro Ala His Gly Ala Ile Asn Leu Ile
                85                  90                  95

Gly Phe Asn Ser Pro Glu Trp Leu Ile Ala Asn Cys Gly Ala Ile Ala
            100                 105                 110

Ala Gly Gly Val Gly Val Gly Ile Tyr Thr Ser Asn Gly Val Asp Ala
        115                 120                 125

Cys Lys Tyr Ile Thr Glu His Ser Glu Ala Glu Val Val Val Val Glu
    130                 135                 140

Asn Ala Lys Gln Leu Glu Lys Tyr Leu Lys Ile Ala Lys Glu Leu Pro
145                 150                 155                 160

Arg Leu Lys Ala Leu Val Ile Tyr Ser Gly Thr Ala Glu Gly Tyr Lys
                165                 170                 175

Cys Asp Val Pro Ile Tyr Ser Trp Lys Asp Phe Met Ala Leu Gly Ser
            180                 185                 190

Gly Val Lys Asp Glu Ala Val Arg Ala Arg Ile Glu Ala Gln Arg Pro
        195                 200                 205

Gly His Cys Cys Thr Leu Ile Tyr Thr Ser Gly Thr Thr Gly Pro Pro
    210                 215                 220

Lys Ala Val Met Ile Ser His Asp Asn Leu Thr Trp Thr Val Lys Asn
225                 230                 235                 240

Phe Val Ala Ser Leu Pro Phe Thr Leu Thr Cys Glu Asp Arg Ser Val
```

```
                    245                 250                 255
Ser Tyr Leu Pro Leu Ser His Val Ala Ala Gln Met Leu Asp Ile His
            260                 265                 270

Cys Pro Ile Ala Thr Gly Ala Lys Ile Tyr Phe Ala Gln Pro Asp Ala
            275                 280                 285

Leu Arg Gly Ser Leu Pro Val Thr Leu Lys Asp Val Cys Pro Thr Tyr
            290                 295                 300

Phe Phe Gly Val Pro Arg Val Trp Glu Lys Ile Tyr Glu Lys Met Gln
305                 310                 315                 320

Glu Val Ala Arg Ser Thr Thr Gly Val Lys Arg Ala Leu Ala Gln Trp
                325                 330                 335

Ala Lys Ala Lys Gly Leu Glu Lys Asn Arg Arg Gln Gln Tyr Gly Cys
                340                 345                 350

Gly Gly Gly Ala Pro Val Gly Phe Gly Cys Ala His Ala Leu Val Leu
            355                 360                 365

Ser Lys Val Lys Ala Ala Leu Gly Leu His Gln Thr Lys Met Cys Ile
            370                 375                 380

Thr Ser Ala Ala Pro Ile Ala Val Glu Ile Leu Glu Tyr Phe Ala Ser
385                 390                 395                 400

Leu Asp Ile Pro Val Leu Glu Leu Phe Gly Gln Ser Glu Cys Thr Gly
                405                 410                 415

Pro His Thr Ser Asn Phe Ser Tyr Ala Trp Lys Ile Gly Ser Ile Gly
                420                 425                 430

Arg Asp Ile Pro Gly Val Lys Thr Lys Gln His Ala Asn Met Ser Glu
            435                 440                 445

Phe Cys Met Tyr Gly Arg His Ile Met Met Gly Tyr Met Lys Met Glu
450                 455                 460

Asp Lys Thr Gln Glu Ala Val Asp Asn Glu Gly Trp Leu His Ser Gly
465                 470                 475                 480

Asp Val Ala Gln Val Asp Ala Asp Gly Phe Trp Ser Ile Thr Gly Arg
                485                 490                 495

Ile Lys Glu Leu Ile Ile Thr Ala Gly Gly Glu Asn Ile Pro Pro Val
            500                 505                 510

Leu Ile Glu Asn Glu Ile Met Ser Ala Leu Pro Ala Val Ala Asn Cys
            515                 520                 525

Met Val Val Gly Asp Lys Lys Lys Phe Leu Thr Val Leu Leu Thr Met
530                 535                 540

Lys Ala Lys Leu Asp Asp Gln Gly Asn Pro Thr Lys Glu Leu Asn Lys
545                 550                 555                 560

Glu Ala Leu Asp Ile Gly Lys Glu Ile Gly Ser Asn Ala Ser Thr Thr
                565                 570                 575

Glu Gln Val Ala Ser Asp Pro His Trp Lys Lys Tyr Phe Asp Glu Gly
            580                 585                 590

Leu Lys Lys Ala Asn Ser Thr Ala Thr Ser Asn Ala Gln Phe Val Gln
            595                 600                 605

Lys Trp Ser Val Leu Pro Leu Asp Phe Ser Glu Lys Gly Gly Glu Leu
            610                 615                 620

Thr Pro Thr Leu Lys Leu Lys Arg Ser Val Val Ala Glu Lys Tyr Ala
625                 630                 635                 640

Asp Val Ile Ala Asp Met Tyr Lys Ala
                645

<210> SEQ ID NO 70
```

```
<211> LENGTH: 340
<212> TYPE: PRT
<213> ORGANISM: Mortierella elongata

<400> SEQUENCE: 70

Met Ser Ala Ser Asn Ala Lys Val Glu Asp Thr Thr Thr Thr Phe Thr
1               5                   10                  15

Gly Trp Ala Ser Thr Gly Ser Leu Pro Leu Lys Lys Phe Ser Tyr His
            20                  25                  30

Pro Arg Pro Leu Gly Pro Lys Asp Ile Glu Ile Glu Ile Thr His Cys
        35                  40                  45

Gly Ile Cys Gly Ser Asp Val Ser Thr Val Thr Gly Gly Phe Gly Pro
    50                  55                  60

Leu Ser Thr Pro Cys Ile Ala Gly His Glu Ile Val Gly Thr Val Val
65                  70                  75                  80

Lys Ala Gly Pro Thr Val Phe Thr Arg Ser Ala Thr Leu Ser Val Leu
                85                  90                  95

Val Ala Leu Leu Ile Pro Ala Val Thr Gly Gly Phe Ala Asp Arg Leu
            100                 105                 110

Arg Val Ser Ser Glu Tyr Ala Tyr Lys Ile Pro Ser Glu Ile Pro Pro
        115                 120                 125

Ala Glu Ala Ala Pro Pro Leu Cys Ala Gly Ile Thr Thr Tyr Thr Pro
    130                 135                 140

Leu Lys His Phe Gly Ala Gly Pro Gly Lys Arg Val Gly Val Met Gly
145                 150                 155                 160

Ile Gly Gly Leu Gly His Leu Ala Ile Gln Trp Ala Ala Ala Leu Lys
                165                 170                 175

Ala Asp Glu Val Val Ala Ile Ser Thr Ser Asp Asn Lys Arg Glu Glu
            180                 185                 190

Ala Lys Lys Leu Gly Ala Thr Lys Phe Val Asn Ser Arg Asn Glu Glu
        195                 200                 205

Glu Arg Lys Ala Ala Arg His Ser Met Asp Ile Leu Leu Leu Thr Ser
    210                 215                 220

Asn Asp Lys Asn Thr Asp Trp Gly Glu Leu Ile Asp Tyr Val Ala Ser
225                 230                 235                 240

His Gly Thr Leu Val Leu Leu Ala Leu Pro Glu Ile Pro Thr Ile Ala
                245                 250                 255

Val Pro Pro Ser Ser Leu Leu Met Arg His Val Ser Ile Ala Gly Ser
            260                 265                 270

Leu Thr Gly Gly Arg Glu Ile Thr Gln Glu Met Leu Glu Phe Ala Ala
        275                 280                 285

Lys His Asn Val His Pro Trp Ile Thr Thr Met Pro Met Ser Asp Ala
    290                 295                 300

Asn Thr Ala Val Lys Leu Trp Leu Glu Thr Ile Trp Cys Asp Val Ala
305                 310                 315                 320

Glu Ser Val Val Ala Ile Val Ala Val Ala Gly Glu Pro Val Met
                325                 330                 335

Pro Ala Arg Lys
        340

<210> SEQ ID NO 71
<211> LENGTH: 367
<212> TYPE: PRT
<213> ORGANISM: Mortierella elongata

<400> SEQUENCE: 71
```

Met Thr Gly Gly Arg Thr Ile Lys Ala Ala Leu Tyr Glu Gly Val Asn
1               5                   10                  15

Pro Ser Ala Pro Leu Leu Lys Val Ile Asp Leu Pro Ala Pro Val Ala
            20                  25                  30

Asn Asn Gly Asp Ala Val Val Lys Ile Leu Ala Thr Arg Val Val Ser
            35                  40                  45

Tyr Ala Lys Glu Val Leu Asp Gly Thr Arg Pro Tyr Pro Asn Leu Leu
    50                  55                  60

Pro Met Val Pro Gly Pro Gly Val Gly Ile Ile Gln Ser Val Ala
65              70                  75                  80

Pro Gly Ala Ile His Ile Lys Pro Gly Gln Met Val Phe Ile Asp Pro
                85                  90                  95

Thr Val Arg Ser Arg Asp His Pro Val Ser Pro Glu Ala Met Leu Gln
                100                 105                 110

Gly Leu Val Ala Phe Gly Ser Gly Gln Glu Leu Gln Lys Val Trp Asn
            115                 120                 125

Asn Gly Ser Trp Ala Glu Glu Met Leu Val Pro Leu Glu Asn Leu Thr
    130                 135                 140

Val Ile Pro Glu Ser Ile Gln Ala Lys Phe Asn Pro Ala Glu Leu Thr
145                 150                 155                 160

Ser Ile Ser Asn Tyr Ala Val Pro Leu Gly Gly Leu Tyr Pro Asn Leu
                165                 170                 175

Arg Pro Gly Gln Thr Val Val Ile Thr Gly Ser Thr Gly Met Phe Gly
                180                 185                 190

Ser Ser Ala Val Ala Val Ala Leu Ala Leu Gly Ala Arg Arg Val Ile
            195                 200                 205

Ala Ser Gly Arg Asn Lys Lys Gln Leu Asp Glu Phe Val Arg Leu Tyr
            210                 215                 220

Gly Pro Arg Val Val Pro Val Val Thr Gly Asp Val Ala Gln Asp
225                 230                 235                 240

Thr Gln Ala Phe Leu Lys Ala Ala Gly Glu Gly Phe Asp Ile Asp Val
                245                 250                 255

Thr Phe Asp Ile Leu Pro Pro Gln Ala Thr Phe Gly Ala Val Gln Ser
                260                 265                 270

Ser Ile Leu Ala Leu Arg Asn Gly Gly Thr Ala Val Leu Met Gly Gly
            275                 280                 285

Leu Asn Ser Ser Ala Glu Ile Pro Tyr Pro Ala Ile Met Asn Lys Gly
            290                 295                 300

Leu Thr Ile Lys Gly His Phe Met Tyr Asp Arg Ser Gly Pro Thr Thr
305                 310                 315                 320

Ile Ile Gly Leu Ala Asp Ala Gly Leu Leu Asp Leu His His Arg Gln
                325                 330                 335

Glu Pro Lys Phe Phe Lys Leu Ser Glu Ile Asn Asp Ala Val Glu Trp
            340                 345                 350

Ser Ala Ala His Pro Gly Ala Phe Asp Ala Thr Leu Val Leu Pro
            355                 360                 365

<210> SEQ ID NO 72
<211> LENGTH: 354
<212> TYPE: PRT
<213> ORGANISM: Mortierella elongata

<400> SEQUENCE: 72

Met Lys Ala Ala Leu Tyr Glu Gly Val Asn His Ser Ala Pro Leu Leu

```
                1               5                   10                  15
            Lys Val Thr Asp Leu Pro Val Pro Ile Ala Thr Asn Gly Asp Ala Val
                            20                  25                  30

Val Lys Ile Leu Ala Ser Arg Val Ser Tyr Ala Lys Asp Val Leu
                            35                  40                  45

Asp Gly Thr Arg Pro Phe Pro Asn Leu Leu Pro Met Val Pro Gly Thr
                50                          55                  60

Gly Gly Val Gly Ile Ile Gln Ser Val Ala Pro Gly Ala Ile His Ile
            65                          70                  75                  80

Lys Pro Gly Gln Met Val Phe Ile Asn Ser Ala Val Arg Ser Arg Asp
                            85                  90                  95

His Pro Val Thr Pro Glu Gly Met Val Gln Gly Leu Leu Ala Phe Gly
                            100                 105                 110

Arg Ser Lys Glu Leu Gln Arg Ala Glu Glu Met Leu Val Pro Leu Glu
                            115                 120                 125

Asn Leu Thr Val Ile Pro Glu Ser Val Gln Ala Lys Phe Asp Pro Ala
                            130                 135                 140

Glu Leu Thr Ser Ile Ser Asn Tyr Ala Val Ser Phe Gly Gly Leu Tyr
            145                         150                 155                 160

Pro Asn Leu Arg Pro Gly Gln Thr Val Ile Thr Gly Ser Thr Gly
                            165                 170                 175

Val Phe Gly Ser Ser Ala Val Ala Val Ala Leu Ala Leu Gly Ala Arg
                            180                 185                 190

Cys Val Ile Ala Ser Gly Arg Asn Lys Lys Gln Leu Asp Glu Phe Ala
                            195                 200                 205

Thr Leu Tyr Gly Pro Arg Val Val Pro Val Val Thr Thr Gly Asp Val
                            210                 215                 220

Ala Lys Asp Thr Ala Ala Phe Val Lys Ala Gly Glu Gly Phe Asp
            225                         230                 235                 240

Ile Asp Val Ser Phe Asp Ile Leu Pro Pro Gln Ala Gly Phe Gly Ala
                            245                 250                 255

Val Lys Ser Ser Ile Leu Ala Leu Arg Ala Gly Gly Thr Ala Leu Leu
                            260                 265                 270

Met Gly Gly Val Asn Ser Ser Val Glu Ile Pro Tyr Ser Val Ile Met
                            275                 280                 285

Asn Lys Gly Leu Thr Ile Lys Gly Val Phe Met Ser Asp Arg Ala Gly
                            290                 295                 300

Pro Thr Thr Ile Ile Gly Leu Ala Glu Ala Gly Leu Leu Asp Leu His
            305                         310                 315                 320

His Arg Gln Glu Pro Lys Ile Phe Lys Leu Asp Glu Ile Asn Asp Ala
                            325                 330                 335

Val Glu Trp Ser Ser Asn His Ser Ser Ala Phe Asp Ala Thr Ile Val
                            340                 345                 350

Ile Pro

<210> SEQ ID NO 73
            <211> LENGTH: 313
            <212> TYPE: PRT
            <213> ORGANISM: Nannochloropsis gaditana

<400> SEQUENCE: 73

Met Pro Val Ile Gly Leu Gly Thr Trp Lys Ala Pro Lys Gly Glu Val
            1                       5                   10                  15

Lys Lys Ala Val Leu Ala Ala Leu Lys Gln Gly Tyr Arg His Leu Asp
```

```
            20                  25                  30
Cys Ala Cys Asp Tyr Gly Asn Glu Glu Val Gly Ala Ala Ile Lys
            35                  40                  45

Glu Ala Met Glu Ala Gly Val Val Thr Arg Lys Asp Leu Phe Val Thr
50                  55                  60

Ser Lys Leu Trp Asn Thr Phe His Ala Arg Glu His Val Glu Val Ala
65                  70                  75                  80

Ile Gln Lys Ser Leu Lys Asp Leu Gly Leu Asp Tyr Leu Asp Leu Tyr
                85                  90                  95

Leu Ile His Phe Pro Ile Ser Met Lys Tyr Val Pro Ile Glu Glu Leu
                100                 105                 110

Tyr Pro Pro Glu Trp Leu Asn Pro Thr Ser Lys Lys Ile Glu Phe Val
                115                 120                 125

Asp Val Pro Val Ser Glu Thr Trp Ala Gly Met Glu Gly Val Cys Arg
130                 135                 140

Lys Gly Leu Ala Arg Asn Ile Gly Val Ser Asn Phe Cys Ala Gln Thr
145                 150                 155                 160

Leu Met Asp Leu Leu Lys Tyr Ala Glu Ile Lys Pro Ala Val Asn Gln
                165                 170                 175

Ile Glu Leu His Pro Tyr Leu Thr Gln Asp Ser Leu Val Ala Phe Cys
                180                 185                 190

Gln Glu Lys Gly Ile Val Leu Thr Ala Phe Ser Pro Leu Gly Ala Ser
                195                 200                 205

Ser Tyr Ile Glu Leu Gly Met Asp Arg Gly Glu Gly Val Gly Val Leu
                210                 215                 220

Asn Asn Pro Val Val Gln Ala Ile Ala Arg Glu His Ser Arg Thr Pro
225                 230                 235                 240

Ala Gln Val Cys Leu Arg Trp Ala Val Gln Arg Gly Tyr Thr Ala Ile
                245                 250                 255

Pro Lys Ser Thr His Glu Ser Arg Leu Gln Glu Asn Leu His Val Phe
                260                 265                 270

Asp Phe Thr Leu Ser Ala Glu Asp Met Val Lys Ile Ser Arg Leu Asn
                275                 280                 285

Arg His Leu Arg Tyr Asn Asp Pro Gly Glu Phe Cys Lys Gly Met Gly
                290                 295                 300

Leu Pro Asn Gly Tyr Pro Ile Tyr Ala
305                 310

<210> SEQ ID NO 74
<211> LENGTH: 361
<212> TYPE: PRT
<213> ORGANISM: Nannochloropsis gaditana

<400> SEQUENCE: 74

Met Thr Asp Pro Ser Ala Ser Thr Thr Ala Ala Ala Gln Leu Pro Gly
1               5                   10                  15

Arg Met Leu Ala Gly Val Ala Asp His His Gly Asp Arg Phe Asp Met
                20                  25                  30

Arg Glu Ile Pro Val Thr Pro Pro Gly Val Gly Gln Ala Leu Val Lys
                35                  40                  45

Val Val Thr Ser Gly Val Cys His Thr Asp Val His Ala Val Asp Gly
                50                  55                  60

Asp Trp Pro Ala Pro Thr Lys Leu Pro Leu Val Pro Gly His Glu Gly
65                  70                  75                  80
```

```
Ala Gly Val Val Ala Val Gly Pro Gly Val Ser Ser Thr Val Val
            85                  90                  95

Ser Leu Gly Asp Arg Val Gly Ile Pro Trp Leu His Ser Cys Gly
            100                 105                 110

Ser Cys Glu Phe Cys Leu Ser Gly Arg Glu Asn Leu Cys Pro Leu Gln
            115                 120                 125

Asp Asn Thr Gly Tyr Ser Val Asp Gly Cys Phe Ala Gln Tyr Val Leu
            130                 135                 140

Ala Pro Ala Ala His Leu Ala Lys Ile Pro Asp Glu Val Ser Phe Glu
145                 150                 155                 160

Gln Ala Ala Pro Ile Leu Cys Ala Gly Val Thr Thr Tyr Ser Ala Ile
            165                 170                 175

Lys Ala Thr Glu Ala Arg Pro Gly Gln Phe Leu Thr Val Ile Gly Ala
            180                 185                 190

Ala Gly Gly Leu Gly His Leu Ala Val Gln Phe Gly Val Ala Leu Gly
            195                 200                 205

Leu Arg Val Met Ala Leu Asp Arg Gly Ala Asp Lys Leu Lys Phe Cys
            210                 215                 220

Thr Asp Thr Leu Gly Ala Glu Ala Ala Phe Glu Ala Met Asp Pro Gly
225                 230                 235                 240

Val Val Asp Gln Val Ile Ala Thr Thr Lys Gly Gly Ser His Gly Val
            245                 250                 255

Leu Cys Leu Ala Pro Ser Ile Gly Ala Phe Lys Ser Ala Val Ser Leu
            260                 265                 270

Cys Arg Arg Gly Gly Thr Ile Val Met Val Gly Leu Pro Lys Gly Asp
            275                 280                 285

Leu Pro Leu Asn Ile Phe Asp Ile Val Ile Arg Gly Ile Thr Val Arg
            290                 295                 300

Gly Ser Ile Val Gly Thr Arg Lys Asp Leu Asp Glu Ala Leu Asp Phe
305                 310                 315                 320

Ala Ala Arg Gly Lys Val Lys Cys His Thr Glu Met His Gly Phe Gly
            325                 330                 335

Glu Leu Asn Gln Val Phe Asp Gln Leu Arg Ser Gly Lys Val Met Gly
            340                 345                 350

Arg Leu Val Leu Ser Val Asp Gly Met
            355                 360

<210> SEQ ID NO 75
<211> LENGTH: 732
<212> TYPE: PRT
<213> ORGANISM: Nannochloropsis gaditana

<400> SEQUENCE: 75

Met Gly Lys Arg Gln Val Ser Tyr Phe Ala Phe Ser Thr Ser Pro Val
1               5                   10                  15

Ser Gly Lys Pro Ala Ala Ile Pro Pro Ser Leu Ile Gly Ile Ser Thr
            20                  25                  30

Leu Asn Ala Leu Arg Asp Ala Glu Lys Val Ala Asp Ala Val Lys His
            35                  40                  45

Ala Val Ser Ser Val Val Lys Tyr Val Asp Cys Ser Ser Asp Ser Gln
50                  55                  60

Asn Glu Lys Gln Ile Gly Asn Ala Leu Ser Ala Phe Asp Arg Ser Ser
65                  70                  75                  80

Phe Tyr Val Gly Ser Lys Leu Ser Cys Cys Asp Ala Ala Pro Glu Asp
            85                  90                  95
```

```
Val Thr Glu Ala Cys Lys Arg Ser Ile Thr Glu Leu Gly Val Ser Tyr
            100                 105                 110

Leu Asp Asn Tyr Met Met His Trp Pro Val Gln Leu Lys Ser Asp Ser
            115                 120                 125

Lys Pro Val Ser Leu Asp Asp Gly Asp Thr Tyr Glu Leu Val Gln Asp
130                 135                 140

Gly Asp Met Asp Cys Ile Met Ala Thr Tyr Glu Ala Met Glu Arg Leu
145                 150                 155                 160

Val Asp Gln Gly Leu Val Arg Ser Leu Gly Val Ser Asn Met Gly Ile
            165                 170                 175

Arg Thr Leu Ser Glu Leu Leu Ser Arg Cys Arg Ile Arg Pro Thr Val
            180                 185                 190

Leu Glu Val Glu Met His Leu Tyr Leu Ala Gln Pro Lys Leu Leu Glu
            195                 200                 205

Phe Cys Arg Glu Glu Asn Ile His Val Val Ala Asn Ser Pro Pro Gly
            210                 215                 220

Lys Met Arg Asn Arg His Pro Asn Asp Pro Ser Leu Leu Asp Asp Pro
225                 230                 235                 240

Val Leu Leu Arg Ile Ala Glu Glu Ala Val Arg Ala Ala Gln Val Leu
            245                 250                 255

Leu Arg Arg Gly Ile Gln Arg Gly Arg Ser Ile Thr Arg Lys Thr Pro
            260                 265                 270

Ser Gln Ser Leu Met Asp Glu Asn Lys Asp Leu Leu Asp Trp Cys Leu
            275                 280                 285

Ser Arg Asp His Met Ser Arg Leu Asp Ala Leu Asp Lys Gly Ser Arg
            290                 295                 300

Phe Pro Ser Val Leu Pro Ser Met Cys Asp Leu Asp Arg Asp Ser Glu
305                 310                 315                 320

Asn Tyr Ala Gly Ala Gly His Pro Val Ser Gln Pro His Arg Thr Pro
            325                 330                 335

Cys Thr Met Asp Lys Asn Gly Gly Phe Arg Asn Arg Phe Glu Arg Pro
            340                 345                 350

Gly Lys Tyr Leu Lys Thr Asp Ile Leu Val Gln Arg Gly Ala Leu Ser
            355                 360                 365

Asp Leu Ala Arg Leu Gly Lys Ser Ile Ile Pro Glu Glu Ser His Gly
            370                 375                 380

Ser Ala Asn Tyr Leu Ile Thr Asp Ser Val Val Asp Ala Leu Tyr Gly
385                 390                 395                 400

Asp Thr Val Leu Asn Gly Leu Lys Ser Ala Gly Leu Asp Met Thr Lys
            405                 410                 415

Ile Val Val Pro Ala Val Ser Met Asp Glu Ser Gly Glu Pro Ser Thr
            420                 425                 430

Glu Pro Asn Lys Asn Gly Ala Ile Phe Asn Ala Cys Val Asp Arg Val
            435                 440                 445

Leu Gly Asn Gly Ile Ser Lys His Ser Cys Ile Ile Ser Leu Gly Gly
            450                 455                 460

Gly Val Ile Asn Asn Leu Cys Gly Val Ile Ala Ala Thr Leu Tyr Arg
465                 470                 475                 480

Gly Ile Lys Leu Val His Phe Thr Thr Thr Thr Met Gly Met Leu Asp
            485                 490                 495

Ala Ala Ile Asp Phe Lys Gln Ala Phe Asn His Ser Cys Gly Lys Asn
            500                 505                 510
```

Leu Val Gly Ala Tyr Tyr Pro Ala Asp Leu Ile Val Met Asp Pro Glu
            515                 520                 525

Cys Leu Lys Thr Leu Ser Asn Arg His Met Leu Asn Gly Val Ala Glu
530                 535                 540

Ala Leu Lys His Gly Leu Thr Gln Ser Trp Glu Leu Thr Ser Ala Ile
545                 550                 555                 560

Val Glu Pro Leu Arg Gly Asp Ser Ala Arg Leu Gly Asp Ser Lys Tyr
            565                 570                 575

Leu Glu Thr Leu Cys Lys Glu Thr Ile Glu Ile Lys Val Pro Thr Leu
            580                 585                 590

Thr His Tyr Lys Glu Ser Asp Phe Asn Glu Met Val Pro Gln Tyr Gly
            595                 600                 605

His Ala Val Ala His Ala Val Glu His Leu Ser Trp Glu Glu Gly Gln
            610                 615                 620

Val Pro Leu Leu His Gly Glu Ala Val Ala Ile Gly Met Cys Val Thr
625                 630                 635                 640

Ala Glu Leu Gly His Leu Leu Gly Leu Cys Asp Lys Ser Val Val Asp
            645                 650                 655

His His Tyr Asp Leu Val Gly Thr Thr Gly Leu Pro Cys Asn Val Pro
            660                 665                 670

Asp Thr Met Lys Val Asn Asp Ile Leu His Val Met Thr Tyr Asp Lys
            675                 680                 685

His Phe Met Ser Lys Pro Cys Met Gly Phe Cys Lys Glu Ile Gly Val
            690                 695                 700

Met Ala Lys Asn Lys Asp Gly Ser Tyr Ala Phe Ser Val Glu Met Glu
705                 710                 715                 720

Pro Val Arg Glu Ala Leu Gln Leu Asn Met Ser Lys
            725                 730

<210> SEQ ID NO 76
<211> LENGTH: 522
<212> TYPE: PRT
<213> ORGANISM: Mortierella elongata

<400> SEQUENCE: 76

Met Pro Ser Phe Ile Gly Ala Ile Asp Asn Gly Thr Thr Ser Ser Arg
1               5                   10                  15

Phe Leu Ile Phe Asp Glu Lys Gly Asn Leu Val Ile Gly His Gln Leu
            20                  25                  30

Glu Tyr Arg Gln Ile Phe Pro His Pro Gly Trp Val Glu His Asp Pro
        35                  40                  45

Met Asp Ile Leu Gly Ser Val Thr Ala Cys Ile Glu Gly Ala Leu Arg
50                  55                  60

Lys Phe Glu Leu Gln Gly Asn Asp Val Lys Asn Leu Arg Gly Ile Gly
65                  70                  75                  80

Ile Thr Asn Gln Arg Glu Thr Ala Val Val Trp Asp Arg Thr Thr Gly
                85                  90                  95

Lys Pro Leu His Asn Ala Ile Val Trp Ser Asp Thr Arg Thr Gln Asp
            100                 105                 110

Val Val Thr Lys Leu Cys Glu Ser Ser Asp Lys Gly Thr Asp Ala Leu
        115                 120                 125

Lys Asp Ile Cys Gly Leu Pro Leu Thr Thr Tyr Phe Ser Ala Val Lys
130                 135                 140

Leu Lys Trp Leu Leu Glu Asn Ser Ser Glu Val Lys Glu Ala His Glu
145                 150                 155                 160

```
Asn Gly Asn Leu Met Phe Gly Thr Val Asp Ser Trp Leu Ile Tyr Asn
                165                 170                 175

Leu Thr Gly Gly Lys Glu Gly Val His Val Thr Asp Val Thr Asn
            180                 185                 190

Ala Ser Arg Thr Met Leu Met Asp Ile Lys Thr Leu Gln Trp Ser Glu
        195                 200                 205

Glu Ala Leu Lys Phe Phe Gly Ile Asn Ala Asp Ile Leu Pro Glu Ile
    210                 215                 220

Lys Pro Ser Ser Thr Leu Phe Gly Lys Val Gln His Pro Ala Leu Glu
225                 230                 235                 240

Gln Leu Gln Asp Val Pro Ile Ala Gly Cys Leu Gly Asp Gln His Ala
            245                 250                 255

Ala Leu Val Gly Gln His Cys Phe Gln Val Gly Glu Ala Lys Asn Thr
        260                 265                 270

Tyr Gly Thr Gly Cys Phe Met Leu Phe Asn Thr Gly Ser Lys Ile Thr
    275                 280                 285

Pro Ser Asn Asn Gly Leu Leu Thr Val Gly Tyr Gln Phe Glu Gly
290                 295                 300

Glu Pro Ala Ala Tyr Ala Leu Glu Gly Ser Ile Ala Val Ala Gly Ser
305                 310                 315                 320

Ala Val Lys Trp Leu Arg Asp Asn Met Gly Ile Ile Arg Ser Ala Glu
            325                 330                 335

Glu Ile Asn Asp Leu Ala Ala Gln Val Asp Ser Asn Gly Gly Val Val
        340                 345                 350

Phe Val Thr Ala Phe Ser Gly Leu Phe Ala Pro Tyr Trp Arg Pro Asp
    355                 360                 365

Val Arg Gly Ser Ile Val Gly Ile Ser Gln His Thr Lys His His
370                 375                 380

Leu Ala Arg Ala Thr Leu Glu Ala Thr Cys Phe Gln Thr Arg Ala Ile
385                 390                 395                 400

Leu Asp Ala Met Asn Ala Asp Ser Gly His Pro Leu Ala Thr Leu Arg
            405                 410                 415

Val Asp Gly Gly Leu Ser Asn Ser Asp Leu Cys Met Gln Leu Gln Ser
        420                 425                 430

Asn Ile Leu Gly Leu Glu Val Ala Arg Pro Gln Met Arg Glu Ser Thr
    435                 440                 445

Ala Leu Gly Ala Ala Thr Ala Ala Gly Val His Leu Gly Ile Gly Ile
450                 455                 460

Trp Lys Gly Gly Phe Lys Ala Phe Ala Glu Arg Ala Arg Glu Ser Lys
465                 470                 475                 480

Glu Val Leu Gln Ile Phe Thr Pro Lys Ile Asn Asp Glu Glu Arg Glu
            485                 490                 495

Lys Glu Tyr Ala Leu Trp Gln Lys Ala Ile Asp Thr Thr Ile Gly Val
        500                 505                 510

Lys Ser Lys Thr Thr Gly Lys Arg Glu Pro
    515                 520

<210> SEQ ID NO 77
<211> LENGTH: 222
<212> TYPE: PRT
<213> ORGANISM: Nannochloropsis gaditana

<400> SEQUENCE: 77

Met Thr Ser Ser Tyr Ile Asn Ser Tyr Val Gly Ala Ile Asp Gln Gly
```

```
1               5                    10                   15
Thr Ser Ser Thr Lys Phe Ile Ile Tyr Asn His Ser Gly Gln Gln Val
                20                  25                  30

Gly Leu His Gln Leu Glu His Ala Gln Ile Tyr Pro Gln Pro Gly Trp
                35                  40                  45

Val Glu His Asp Pro Met Glu Ile Trp Ala Asn Thr Val Thr Cys Ile
    50                  55                  60

Arg Arg Ala Met Glu Ser Ala Asn Val Asp Ala Glu Leu Leu Glu Ala
65                  70                  75                  80

Val Gly Ile Thr Asn Gln Arg Glu Ser Thr Leu Ile Trp Asn Lys Lys
                85                  90                  95

Thr Gly Val Pro Tyr Tyr Asn Val Ile Val Trp Asn Asp Ala Arg Thr
                100                 105                 110

Arg Gly Ile Cys Glu Asp Leu Lys Thr Ala Gly Arg Arg Gly Ile Asp
                115                 120                 125

Arg Phe Arg Glu Lys Thr Gly Leu Pro Ile Ala Thr Tyr Phe Ser Ala
130                 135                 140

Ser Lys Ile Leu Trp Leu Leu Asp Asn Val Pro Gly Leu Arg Asp Asp
145                 150                 155                 160

Ala Glu Lys Gly Glu Ala Ile Phe Gly Thr Leu Asp Ser Trp Leu Ile
                165                 170                 175

Tyr Lys Leu Thr Asp Gly Gln Val His Ser Gly Pro Cys Val Ala Tyr
                180                 185                 190

Pro Gly Gly Leu Ser Pro Ser Ser Leu Ser Ser Ala Leu Arg Pro Pro
                195                 200                 205

Ala Ser Pro Pro Ser Gln Ala Pro Ser Leu Ser Pro Asp Pro
210                 215                 220
```

<210> SEQ ID NO 78
<211> LENGTH: 866
<212> TYPE: PRT
<213> ORGANISM: Nannochloropsis gaditana

<400> SEQUENCE: 78

```
Met Asp Glu Glu Leu Asn Val Leu Ser Pro Phe Leu Val Lys Ala Glu
1               5                   10                  15

Val Leu Leu Val Leu Val Val Leu Val Ala Ser Val Val Trp Leu
                20                  25                  30

Phe Trp Glu Ile Val Ser Phe Met Met Asp Arg Gly Lys Glu Thr
                35                  40                  45

Asn Pro Asp Trp Trp Glu Val Leu Arg Asn Cys Gln His Arg Arg Leu
    50                  55                  60

Ile Ile Pro Pro Tyr Cys Val Gln Glu Val Pro Glu Leu Gly Thr Phe
65                  70                  75                  80

Ser Arg Leu Thr Thr Ala Thr Thr Asn Ala Met Lys Asn Met Ser Gly
                85                  90                  95

Val Ile Gln Arg Thr Ser His Leu Ile Ser Gly Ser Gly Lys Ser
                100                 105                 110

Ala Ala Ala Ile Lys Lys Gly Ala Arg Gln Asp Leu Pro Ser Thr Gln
                115                 120                 125

Gln Glu Gly Asp Glu Asn Met Lys Gly Tyr Thr Val Asp Gly Asn Ala
                130                 135                 140

Arg Gly Val Lys Leu Arg Arg Arg Gly Ser Lys Gln Ser Ile Val Gly
145                 150                 155                 160
```

```
Leu Ser Asn His Gly Thr Ser Ala Gly Gly Lys Pro Ala Leu Gln Pro
            165                 170                 175

Thr Ala Asn Pro Thr Pro Leu Thr Leu Ser Glu Asn Gly Ala Asn Pro
        180                 185                 190

Asp Ala Ser Ala Ala Ser Asp Ala Arg Pro Lys Pro His Arg Leu Asp
            195                 200                 205

Leu Asn Gly Glu Glu Gly Asn Met Val Pro Cys Asn Gly Ser Leu Ser
        210                 215                 220

Ser Arg Ala Gly Asp Gly Lys Arg Val Val Gly Met Ser Gly Leu Ala
225                 230                 235                 240

Ser Thr Ser Ala Ala Gly Ser Asp Ala Ser Ser Ala Asn Val Lys
            245                 250                 255

Ser Met Glu Ile Ser Pro Ala Asp Thr Pro Cys Arg Gly Arg Ile Arg
            260                 265                 270

Phe Leu Pro His Gln Arg Glu Arg Gln Gln Ile Glu Asn His Glu Lys
            275                 280                 285

Ser His Glu Gly Lys Pro Thr Arg Ser Gly Leu Pro Leu Arg Ala Leu
            290                 295                 300

Asp Ser Gln Pro Pro Leu Thr Pro Tyr Ala Leu Pro Asp Ala Glu Gly
305                 310                 315                 320

Val Leu Ala Ser Ser Ala Gln Ser Ser Arg His Ala Pro Asp Ala Ile
                325                 330                 335

Ala Ala Thr Pro Arg Leu Ser Ser His Ala Ala Asn Gly Glu Pro
            340                 345                 350

Ile Thr Thr Pro Ala Gln Pro Val Arg Leu Pro Ser Met Glu His Ala
        355                 360                 365

His Ser Gly Thr Gly Val Ala Leu Ser Gly Gly Ser Ser Gly Val Ala
        370                 375                 380

Gly Arg Gly Phe Ile Phe Ser Pro Leu Pro Glu Asp Cys Thr Pro Leu
385                 390                 395                 400

Leu Ala Phe Val Asn Ser Arg Ser Gly Val Ser Gln Gly Ala Tyr Leu
                405                 410                 415

Ile His Gln Leu Arg Arg Leu Leu Asn Pro Ile Gln Val Ile Asp Leu
            420                 425                 430

Ala Asn Glu Asp Pro Ala Arg Ala Leu Arg Leu Tyr Leu Glu Leu Pro
        435                 440                 445

Arg Leu Arg Val Leu Val Cys Gly Gly Asp Gly Thr Ala Lys Trp Ile
    450                 455                 460

Met Asn Val Leu Glu Asp Leu Asn Pro Glu Cys Trp Pro Pro Ile Ala
465                 470                 475                 480

Ile Leu Pro Leu Gly Thr Gly Asn Asp Met Ala Arg Val Leu Gly Trp
                485                 490                 495

Gly Gly Gly Tyr Asn Asn Gln Ser Ile Val Glu Phe Leu Ala Gln Val
            500                 505                 510

Gln Arg Ala His Val Val Val Asp Arg Trp Glu Met Lys Leu Thr
        515                 520                 525

Pro Ala Gly Lys Gly Ser Ser Arg Ala Lys Thr Val Thr Phe Asn Asn
530                 535                 540

Tyr Phe Gly Ile Gly Val Asp Ala Gln Ala Leu Lys Phe His His
545                 550                 555                 560

Leu Arg Glu Gln Lys Pro Gln Leu Phe Phe Ser Arg Leu Val Asn Lys
            565                 570                 575

Leu Trp Tyr Gly Met Leu Gly Ala Gln Asp Leu Phe Arg Arg Thr Cys
```

```
            580                 585                 590
Val Ser Leu Pro Glu Arg Leu Lys Ile Val Ala Asp Gly Lys Glu Leu
            595                 600                 605

Thr Leu Pro Ala His Val Gln Gly Val Ile Phe Leu Asn Ile Glu Ser
            610                 615                 620

Tyr Gly Gly Gly Val Lys Leu Trp Asn Val Glu Asp Glu Ser
625                 630                 635                 640

Ala Gly Asn Gly Leu Phe Asp Ala Ser Ser Ser Cys Ser Ser Glu
                645                 650                 655

Glu Gly Asp Arg Ser Glu Asp Glu Ser Arg Arg Gln Arg Arg Arg
                660                 665                 670

Arg Arg Arg Glu Arg Gln Arg Gln Gln Ser Gln Ala Glu Glu Glu
            675                 680                 685

Ala His Arg Gln Arg Glu Gln Gln Glu Lys Pro Ser Ser Met Ala Leu
            690                 695                 700

Thr Ser Ser Met Gln Asp Gly Leu Met Glu Val Ala Ile Asn
705                 710                 715                 720

Gly Val Val His Leu Gly Gln Leu Gln Val Gly Leu Ser Lys Ala Val
                725                 730                 735

Lys Ile Cys Gln Cys Arg Glu Ala Val Ile Thr Thr Arg Asp Leu
                740                 745                 750

Pro Met Gln Val Asp Gly Glu Pro Trp Pro Gln Ala Lys Ser Thr Ile
            755                 760                 765

Lys Ile Thr Arg Lys Lys Asp Pro Ala Tyr Leu Leu Arg Arg Thr Met
770                 775                 780

Asp Ser Gly Gly Ala Val Val Gly Glu Val Val Glu Leu Leu Glu Ser
785                 790                 795                 800

Ala Val Lys Asp Gly Val Ile Ser Leu Pro Gln Lys Lys Ser Leu Leu
                805                 810                 815

Thr Glu Leu Ser Arg Arg Val Glu Met Lys Arg Lys Val Phe Glu Gln
            820                 825                 830

Glu Leu Ser Gln Asn Asp Gly Val Pro Ser Phe Ser Lys Gly Phe Asp
            835                 840                 845

Val Ser Arg Leu Arg Leu Ala Ala Asp Ser Asn Ser Lys Asp Cys Val
            850                 855                 860

Leu Met
865

<210> SEQ ID NO 79
<211> LENGTH: 833
<212> TYPE: PRT
<213> ORGANISM: Mortierella elongata

<400> SEQUENCE: 79

Met Trp Arg Arg Ile Pro Ala Thr Gly Ala Arg His Ser Thr Ser Phe
1               5                   10                  15

Arg Thr Lys Ala Val Tyr Ala Thr Ala Gly Ala Thr Thr Leu Ala Leu
            20                  25                  30

Ser Gly Tyr Tyr Tyr Asn Leu Lys Gln Gln Gln Arg Ala Leu Asp Asp
        35                  40                  45

Ser Phe Glu Tyr Pro Pro Gln Ser Ser Met Ile Tyr Leu Glu Pro Gln
    50                  55                  60

Gln Ala Ala Arg Asp Pro Thr Arg Pro His Ala Phe Trp Ala Pro Pro
65                  70                  75                  80
```

```
Ser Arg Glu Asp Met Ile Arg Met Leu Gln Gly Pro Gly Ser Ile
            85                  90                  95

Val Lys Glu Lys Thr Ala Ala Ala Ala Ala Ala Ala Ala Ala Ala
            100                 105                 110

Ala Gly Thr Thr Pro Gly Ser Lys Pro Val Val Ala Val Ala Thr
            115                 120                 125

Met Glu Asp Asp Lys Asp Ser Asp Val Phe Asp Leu Leu Ile Ile Gly
    130                 135                 140

Gly Gly Ala Thr Gly Ala Gly Cys Ala Val Asp Ala Ala Thr Arg Gly
145                 150                 155                 160

Leu Lys Val Ala Met Val Glu Arg Asp Asp Phe Ser Ser Gly Thr Ser
                165                 170                 175

Ser Arg Ser Thr Lys Leu Val His Gly Gly Val Arg Tyr Leu Glu Lys
            180                 185                 190

Ala Val Arg Glu Leu Asp Ile Glu Gln Tyr Lys Leu Val Lys Glu Ala
            195                 200                 205

Leu Asn Glu Arg Ala Asn Phe Leu Lys Val Ala Pro Tyr Leu Ser Tyr
    210                 215                 220

Gln Leu Pro Ile Met Leu Pro Ile Tyr Lys Trp Trp Gln Val Pro Tyr
225                 230                 235                 240

Tyr Trp Ala Gly Ser Lys Ala Tyr Asp Leu Leu Ala Gly His Gln Gly
                245                 250                 255

Met Glu Ser Ser Tyr Phe Leu Ser Arg Gly Lys Ala Leu Glu Ala Phe
            260                 265                 270

Pro Met Leu Lys Asn Asp Lys Leu Val Gly Ala Met Val Tyr Tyr Asp
    275                 280                 285

Gly Gln His Asn Asp Ser Arg Met Asn Val Ala Leu Gly Leu Thr Ala
290                 295                 300

Val Gln Tyr Gly Ala Val Ile Ala Asn His Val Glu Val Ile Glu Leu
305                 310                 315                 320

His Lys Asp Glu Asn Arg Arg Leu Cys Gly Ala Arg Val Arg Asp Ala
            325                 330                 335

Met Thr Gly Lys Glu Phe Asn Val Lys Ala Lys Gly Val Ile Asn Ala
            340                 345                 350

Thr Gly Pro Phe Thr Asp Gly Ile Arg Gln Leu Asp Asp Pro Ser Ile
            355                 360                 365

Gln Ser Ile Val Ser Pro Ser Ala Gly Val His Ile Ile Leu Pro Asn
    370                 375                 380

Tyr Tyr Ser Pro Gly Asn Met Gly Leu Leu Asp Pro Ala Thr Ser Asp
385                 390                 395                 400

Gly Arg Val Ile Phe Phe Leu Pro Trp Gln Gly Asn Thr Ile Ala Gly
            405                 410                 415

Thr Thr Asp Ser Ala Thr Lys Val Thr Pro Asn Pro Met Ala Thr Glu
            420                 425                 430

Glu Glu Ile Asn Trp Ile Leu Gly Glu Val Lys Asn Tyr Leu Asn Pro
    435                 440                 445

Asp Val Lys Val Arg Arg Gly Asp Val Leu Ala Ala Trp Ser Gly Ile
    450                 455                 460

Arg Pro Leu Val Arg Asp Pro Ala Ala Lys Ser Thr Glu Gly Leu Val
465                 470                 475                 480

Arg Asn His Met Ile Asn Val Ser Pro Ser Gly Leu Leu Thr Ile Ala
                485                 490                 495

Gly Gly Lys Trp Thr Thr Tyr Arg Ala Met Ala Ala Glu Thr Ile Asp
```

```
                500                 505                 510
Glu Ala Ile Lys Glu Phe Gly Leu Thr Pro Ala Arg Gly Cys Ser Thr
            515                 520                 525

Glu Arg Val Lys Leu Ile Gly Ser His Gly Tyr Ser Asn Thr Met Phe
        530                 535                 540

Ile Arg Leu Ile Gln Gln Phe Gly Leu Glu Thr Glu Ile Ala Gln His
545                 550                 555                 560

Leu Ala Asn Ser Tyr Gly Asp Arg Ala Trp Ala Val Ala Ser Leu Ala
                565                 570                 575

Gln Ser Thr Gly Lys Arg Trp Pro Val Phe Gly Arg Arg Val Ser Asn
            580                 585                 590

Gln Tyr Pro Tyr Ile Glu Ala Glu Val Arg Tyr Ala Val Arg Arg Glu
        595                 600                 605

Tyr Ala Cys Thr Ala Val Asp Val Leu Ala Arg Leu Arg Leu Ala
    610                 615                 620

Phe Leu Asn Val His Ala Ala Leu Asp Ala Leu Pro Arg Val Val Glu
625                 630                 635                 640

Ile Met Ala Glu Glu Leu Lys Trp Asp Ala Ala Arg Gln Ala Lys Glu
                645                 650                 655

Thr Glu Asp Ala Lys Ala Phe Leu Thr Thr Met Gly Leu Pro Val Ser
            660                 665                 670

Pro Ile Ala Tyr Pro Thr Asn Val Pro Glu Ala Val Val Gly His Pro
        675                 680                 685

Val Val Asp Gly Glu Lys Val Gln Pro Thr Ser Phe Trp Gly Arg Met
    690                 695                 700

Ser Gly Lys Ser Ala Ser Gly Ala Ile Val Thr Asp Ser Phe Tyr Ser
705                 710                 715                 720

Arg Ala Gln Phe Asn Pro Glu Glu Leu Ala Glu Phe His Lys Val Phe
                725                 730                 735

Gly Ala Leu Asp His Asp Gly Asp Gly His Ile Asp Gly His Asp Leu
            740                 745                 750

Glu Glu Val Leu Ile His Leu Asp Val Gln Val Glu Pro Gln Val Leu
        755                 760                 765

Lys Ser Ile Ile Glu Glu Val Asp Leu Asp Asn Ser Gly Thr Ile Glu
    770                 775                 780

Phe Asn Glu Phe Leu Glu Val Met Gly Gly Leu Lys Glu His Ala Ser
785                 790                 795                 800

Arg Thr Ala Phe Ser Lys Ile Ile Val Glu Val Glu Ser Lys Arg Asn
                805                 810                 815

Val Asp Tyr Gly Ile Lys Ala Lys Thr Thr Asp Arg Ser Gly Gly Gly
            820                 825                 830

Ala

<210> SEQ ID NO 80
<211> LENGTH: 340
<212> TYPE: PRT
<213> ORGANISM: Mortierella elongata

<400> SEQUENCE: 80

Met Thr Glu Arg Val Ala Leu Ile Gly Ser Gly Asn Trp Gly Ser Ala
1               5                   10                  15

Val Ala Lys Ile Ile Gly Arg Asn Val Arg Lys Phe Asp His Phe Asp
            20                  25                  30

Asn Lys Val Lys Met Trp Val Phe Glu Glu Lys Val Asn Gly Gln Asn
```

```
                35                  40                  45
Leu Thr Glu Ile Ile Asn Thr Lys His Glu Asn Val Lys Tyr Leu Pro
 50                  55                  60

Gly Ile Gln Leu Pro Ser Asn Ile Val Ala Cys Pro Asp Leu Leu Glu
 65                  70                  75                  80

Thr Cys Arg Asp Ala Thr Met Leu Val Phe Val Pro His Gln Phe
                 85                  90                  95

Val Thr Ser Ile Cys Lys Gln Leu Lys Gly Arg Ile Pro Ala Asn Cys
                100                 105                 110

Lys Ala Ile Ser Leu Ile Lys Gly Ile Asp Val Asn Ala Asp Gly Phe
                115                 120                 125

Arg Leu Ile Thr Asp Met Ile Gln Glu Ser Leu Gly Val Pro Thr Cys
130                 135                 140

Val Leu Ser Gly Ala Asn Ile Ala Asn Glu Val Ala Glu Glu Lys Phe
145                 150                 155                 160

Cys Glu Thr Thr Ile Gly Tyr Arg Asn Arg Ala Asp Gly Glu Leu Phe
                165                 170                 175

Arg Asp Ile Phe His Thr Pro Ser Phe Arg Val Asn Ile Val Pro Asp
                180                 185                 190

Val Val Gly Val Glu Leu Cys Gly Ala Leu Lys Asn Ile Val Ala Ile
                195                 200                 205

Gly Gly Gly Leu Val Asp Gly Leu Lys Leu Gly Asp Asn Thr Lys Ala
                210                 215                 220

Ala Ile Ile Arg Ile Gly Leu Tyr Glu Met Arg Lys Phe Ser Lys Met
225                 230                 235                 240

Phe Tyr Ala Asp Val Lys Asp Glu Thr Phe Phe Glu Ser Cys Gly Val
                245                 250                 255

Ala Asp Leu Ile Thr Thr Cys Ala Gly Gly Arg Asn Arg Lys Val Ala
                260                 265                 270

Glu Ala His Val Thr Thr Gly Lys Ser Phe Asp Gln Leu Glu Gln Glu
                275                 280                 285

Met Leu Asn Gly Gln Lys Leu Gln Gly Thr Ser Thr Ala Gln Asp Met
290                 295                 300

Tyr Asn Ile Leu Ser Lys Lys Asn Leu Cys His Glu Phe Pro Leu Met
305                 310                 315                 320

Thr Thr Ile Tyr Lys Ile Cys Tyr Glu Gly Leu Pro Pro Ile Arg Ile
                325                 330                 335

Val Glu Asp Ile
            340

<210> SEQ ID NO 81
<211> LENGTH: 341
<212> TYPE: PRT
<213> ORGANISM: Mortierella elongata

<400> SEQUENCE: 81

Met Leu Ile Thr Glu Cys Ile Ser Leu Phe His Arg Gly Ser Ala Val
  1               5                  10                  15

Ala Lys Ile Val Gly Gly Asn Val Gln Lys Tyr Asp His Ile Gln Asn
                 20                  25                  30

Glu Val Lys Met Trp Val Phe Glu Glu Gln Val Asp Gly Gln Asn Leu
                 35                  40                  45

Thr Glu Ile Ile Asn Ala Lys His Glu Asn Val Lys Tyr Leu Pro Gly
 50                  55                  60
```

```
Ile Lys Leu Pro Glu Asn Ile Val Ala Cys Pro Asp Leu Ile Lys Thr
 65                  70                  75                  80

Cys Glu Asp Ala Thr Met Leu Val Phe Val Pro His Gln Phe Val
                 85                  90                  95

Ala Ser Val Cys Arg Gln Leu Lys Gly Lys Ile Ser Pro Lys Cys Lys
            100                 105                 110

Ala Ile Ser Leu Ile Lys Gly Val Asp Val Glu Glu Asn Asp Asn Gly
            115                 120                 125

Phe Arg Leu Ile Thr Asp Met Ile Gln Asp Ser Leu Gly Ile Arg Ala
        130                 135                 140

Cys Met Leu Ser Gly Ala Asn Ile Ala Thr Glu Val Ala Glu Arg
145                 150                 155                 160

Phe Cys Glu Thr Thr Ile Gly Tyr Arg Asn Lys Ala Asp Gly Glu Leu
            165                 170                 175

Phe Lys Glu Ile Phe Asn Thr Pro Thr Phe Arg Val Asn Ile Val Glu
            180                 185                 190

Asp Val Val Gly Val Glu Leu Cys Gly Ala Leu Lys Asn Ile Ile Ala
        195                 200                 205

Ile Gly Gly Gly Leu Val Asp Gly Leu Lys Leu Gly Asp Asn Thr Lys
        210                 215                 220

Ala Ala Ile Ile Arg Ile Gly Leu Tyr Glu Met Arg Lys Phe Ala Lys
225                 230                 235                 240

Met Phe Tyr Ala Asp Val Lys Asp Glu Thr Phe Phe Glu Ser Cys Gly
            245                 250                 255

Val Ala Asp Leu Val Thr Thr Cys Ala Gly Gly Arg Asn Arg Lys Val
            260                 265                 270

Ala Glu Ala His Val Thr Thr Gly Lys Ser Phe Asp Gln Leu Glu Lys
        275                 280                 285

Glu Met Leu Gly Gly Gln Lys Leu Gln Gly Thr Ser Thr Ala Lys Asp
        290                 295                 300

Met Tyr Gly Ile Leu Ser Lys Lys Gly Leu Cys Lys Glu Phe Pro Leu
305                 310                 315                 320

Met Thr Thr Ile Tyr Arg Ile Cys Tyr Glu Asp Leu Pro Pro Ile Arg
            325                 330                 335

Ile Val Glu Asp Ile
            340

<210> SEQ ID NO 82
<211> LENGTH: 402
<212> TYPE: PRT
<213> ORGANISM: Nannochloropsis gaditana

<400> SEQUENCE: 82

Met Ala Thr Leu His Ile Ser Asn Leu Thr Leu Thr Ile Tyr Asn His
1               5                   10                  15

Gly Ile Phe Val Leu Met Ser Ala Ala Leu Ser Phe Leu Leu Ile Val
             20                  25                  30

Trp Arg Phe Ser Leu Ala Glu Ala Gly Arg Ser His His Phe Glu Gly
         35                  40                  45

Pro Ser Ser Asn Pro Val Lys Pro His Ser Ile Thr Val Gly Ser
     50                  55                  60

Gly Asn Phe Gly Ser Ala Ile Ala Arg Leu Leu Gly Arg Asn Val Leu
65                  70                  75                  80

Arg Ser Pro Lys His Phe Arg Ser Glu Val Arg Met Trp Val Phe Glu
             85                  90                  95
```

Glu Leu Asp Asp Gly Arg Lys Leu Ser Asp Val Ile Asn Ala Asp
            100                 105                 110

His Glu Asn Val Lys Tyr Leu Pro Gly Ile Gln Leu Pro Thr Asn Val
            115                 120                 125

Arg Ala Val Pro Asp Leu Ser Asp Ala Val Arg Asn Ala Ser Ile Val
        130                 135                 140

Val Phe Val Leu Pro His Gln Phe Leu Pro Gly Leu Leu Pro Arg Ile
145                 150                 155                 160

Ser Ser Cys Leu His Arg Gly Ala Met Ala Val Ser Leu Val Lys Gly
                165                 170                 175

Leu Asp Phe Asp Asp Glu Gly Pro Val Leu Ile Thr Asp Met Ile Arg
            180                 185                 190

Glu Gly Leu Gly Glu Asp Val Ser Glu Val Cys Val Leu Met Gly Ala
        195                 200                 205

Asn Val Ala Asp Glu Met Ala Arg Asp Glu Phe Cys Glu Ala Thr Leu
    210                 215                 220

Gly Cys Pro Asp Pro Glu Gly Ala Gly Ala Val Leu Gln Gln Leu Phe
225                 230                 235                 240

Asp Cys Pro Thr Phe Arg Val Glu Val Thr Pro Asp Pro Ile Gly Val
                245                 250                 255

Glu Leu Cys Gly Ala Leu Lys Asn Val Val Ala Leu Ala Ala Gly Phe
            260                 265                 270

Cys Asp Gly Leu Asp Trp Gly Asn Thr Lys Ala Ala Ile Ile Arg
        275                 280                 285

Arg Gly Leu Glu Glu Met Arg Leu Phe Cys Lys Leu Leu His Pro Ser
    290                 295                 300

Val Arg Asp Met Thr Phe Phe Glu Ser Cys Gly Val Ala Asp Leu Ile
305                 310                 315                 320

Thr Thr Cys Tyr Gly Gly Arg Asn Arg Lys Cys Ala Glu Thr Phe Ala
                325                 330                 335

Arg Ala Gly Gly Thr Met Ala Trp Asp Glu Ile Glu Lys Glu Leu
            340                 345                 350

Gly Gly Gln His Leu Gln Gly Pro Gln Thr Thr Ser Lys Leu His Lys
        355                 360                 365

Val Leu Glu Gln Lys Lys Trp Leu Ser Arg Phe Pro Leu Phe Arg Ser
    370                 375                 380

Val Tyr Gln Ile Ala Tyr Gln Gly Arg Pro Pro Ala Thr Leu Val Gln
385                 390                 395                 400

Asp Leu

<210> SEQ ID NO 83
<211> LENGTH: 429
<212> TYPE: PRT
<213> ORGANISM: Nannochloropsis gaditana

<400> SEQUENCE: 83

Met Ser Pro Thr Phe Arg Arg Arg His Ser Asn Ala Pro Phe Lys Leu
1               5                   10                  15

Gln Ile Phe Met Val Lys Phe Leu Ala Val Val Ala Leu Leu Gly Cys
            20                  25                  30

Cys Cys Leu His Gly Val Ala Ser Gly Thr Pro Pro His Ala Ala Phe
        35                  40                  45

Val Pro Arg Ala Ser Thr Lys Ser Leu Gly Asn Arg Leu Ala Lys Ala
    50                  55                  60

Pro Gln Ala Arg Arg Glu Gln Thr Ile Met Gln Leu Ser Ala Arg Arg
65                  70                  75                  80

Ser Arg Ser Met Arg Pro Leu Pro Tyr Pro Val Arg Phe Ala Val Leu
            85                  90                  95

Gly Gly Gly Ser Phe Gly Leu Ala Leu Ala Ser Val Leu Gly Lys Lys
            100                 105                 110

Ser Ile Pro Val Thr Ile Leu Val Arg Lys Glu Glu Val Ala Glu His
            115                 120                 125

Ile Asn Leu His His Arg His Pro Thr Tyr Leu Ser Asp Ile Ala Leu
            130             135                 140

Ala Pro Ser Ile Arg Ala Thr Val Gln Pro Glu Ala Leu Arg Asp
145                 150                 155                 160

Ala Ser Phe Ile Ile His Ala Val Pro Val Gln Tyr Ser Arg Lys Phe
                165                 170                 175

Leu Glu Asp Ile Ala Pro His Val Pro Lys Asn Thr Pro Ile Ile Ser
            180                 185                 190

Thr Ser Lys Gly Ile Glu Thr Gly Thr Leu Cys Met Met Gln Asp Ile
            195                 200                 205

Leu Leu Glu Thr Leu Gly Pro Asn Arg Glu Thr Ala Tyr Leu Ser Gly
210                 215                 220

Pro Ser Phe Ala Arg Glu Ile Ala Leu Gly Leu Val Thr Ala Val Val
225                 230                 235                 240

Ala Ala Ser Glu Ser Glu Ala Leu Ala Asn Glu Ile Cys Asp Ile Met
            245                 250                 255

Gly Cys Asn Tyr Phe Arg Val Phe Thr Ser Thr Asp Val Gly Val
            260                 265                 270

Glu Val Gly Gly Ala Val Lys Asn Val Ile Ala Ile Ala Ala Gly Met
            275                 280                 285

Cys Glu Gly Leu Gly Leu Gly Thr Asn Ala Met Ala Ala Leu Val Thr
290                 295                 300

Arg Gly Cys Asn Glu Met Gln Arg Leu Ala Leu Ser Leu Gly Ala Arg
305                 310                 315                 320

Pro Ser Thr Leu Thr Gly Leu Ser Gly Val Gly Asp Thr Phe Gly Thr
            325                 330                 335

Cys Phe Gly Pro Leu Ser Arg Asn Arg Asn Leu Gly Val Arg Leu Gly
            340                 345                 350

Lys Gly Glu Arg Leu Glu Asn Ile Leu Gly Ser Ser Thr Glu Val Ala
            355                 360                 365

Glu Gly His Ala Thr Ala Phe Ser Leu Val Gln Leu Ile Glu Lys Thr
            370                 375                 380

Asn Arg Ala Tyr Arg Arg Glu Leu Glu Phe Pro Ile Ile Tyr Gly Val
385                 390                 395                 400

Lys Glu Ile Leu Glu Gly Lys Arg Thr Pro Ala Glu Gly Leu Arg Asp
            405                 410                 415

Leu Met Ala Met Pro Val Arg Val Glu Met Trp Asn Leu
            420                 425

<210> SEQ ID NO 84
<211> LENGTH: 654
<212> TYPE: PRT
<213> ORGANISM: Nannochloropsis gaditana

<400> SEQUENCE: 84

Met Ser Leu Gln Pro His Leu Ala Leu Leu Gly Met Ala Gly Ser Leu

```
1               5                   10                  15
Val Val Ala Asp Arg Leu Arg Ser Gly Pro Gly Arg Lys Ser Arg Ala
                20                  25                  30
Lys Asp Ser His Arg His Leu Pro Thr Ser Arg Ser Ala Asn Cys
        35                  40                  45
Glu Ala Ser Gly Gly Lys Arg Glu Leu Ser Pro Val Glu Gln Leu Glu
        50                  55                  60
Asp Met Arg Thr Thr Pro Ile Lys Cys Arg Asp Gly Thr Leu Val Tyr
65                  70                  75                  80
Pro Tyr Ser Leu Pro Thr Arg Asp Ala Gln Leu Asn Arg Leu Lys Lys
                85                  90                  95
Glu Lys Phe Asp Val Leu Val Ile Gly Gly Gly Cys Val Gly Ser Gly
                100                 105                 110
Val Ala Leu Asp Ala Gln Ile Arg Gly Leu Lys Thr Ala Met Val Glu
                115                 120                 125
Ala Asn Asp Phe Ser Ala Gly Thr Ser Gly Arg Ser Thr Lys Leu Ile
            130                 135                 140
His Gly Gly Ile Arg Tyr Leu Glu Thr Ala Phe Trp Lys Leu Asp Tyr
145                 150                 155                 160
Gly Ser Phe Ala Leu Val Gln Glu Ala Leu Glu Arg Ala His Met
                165                 170                 175
Leu Asn Ala Ala Pro Tyr Met Asn Ser Pro Leu Pro Ile Met Ile Pro
            180                 185                 190
Ile Tyr Lys Trp Trp Glu Val Pro Tyr Phe Trp Ala Gly Ala Lys Ala
                195                 200                 205
Tyr Asp Leu Val Ala Ser Arg Gln Lys Ser Val Pro Ser Ser His Tyr
            210                 215                 220
Met Asp Val Asp Glu Ala Leu Phe Gln Phe Pro Met Leu Arg Gly Lys
225                 230                 235                 240
Gly Leu Lys Gly Ala Ile Ile Tyr Tyr Asp Gly Gln Met Asn Asp Thr
                245                 250                 255
Arg Met Gly Leu Thr Ile Ala Leu Thr Ala Ala Gln Glu Gly Ala Ala
                260                 265                 270
Ile Ala Asn Arg Val Glu Val Ser Leu Leu Lys Asp Pro Gly Thr
            275                 280                 285
Gly Gln Val Asn Gly Ala Arg Val Gln Asp Arg Leu Thr Gly Val Glu
                290                 295                 300
Trp Asp Ile Ala Ala Lys Val Val Asn Ala Thr Gly Val Phe Ala
305                 310                 315                 320
Asp Lys Ile Arg Lys Phe Asp Asp Pro Lys Ala Val Glu Leu Ile Glu
                325                 330                 335
Pro Ala Ala Gly Val His Val Met Phe Pro Ala His Phe Ser Pro Ala
                340                 345                 350
Lys Met Gly Leu Ile Val Pro Lys Thr Thr Asp Gly Arg Val Leu Phe
                355                 360                 365
Phe Leu Pro Trp Glu Gly Cys Thr Leu Ala Gly Thr Thr Asp Ser His
    370                 375                 380
Ser Asp Ile Thr Met His Pro Gln Pro Thr Ala Gln Glu Val Asn Phe
385                 390                 395                 400
Ile Met Gln Glu Thr Asn Arg Tyr Leu Thr Thr Asn Val Ala Ala Lys
                405                 410                 415
Asp Leu Ile Ala Ala Trp Ser Gly Leu Arg Pro Leu Val Lys Asp Pro
            420                 425                 430
```

```
Glu Lys Ile Lys Glu Gly Thr Ala Ala Leu Ser Arg Asn His Val Ile
            435                 440                 445

Glu Val Ser Glu Thr Gly Lys Leu Ile Thr Ile Thr Gly Gly Lys Trp
450                 455                 460

Thr Thr Tyr Arg Arg Met Ala Glu Asp Thr Val Asp Arg Ile Leu Gln
465                 470                 475                 480

Glu His Ala Gly Leu Leu Ala Asn Gly Asp Val Ser Pro Gln Ala Ser
            485                 490                 495

Thr Trp Asn Arg Lys Leu Leu Gly Ala Asp Arg Ala Gly Ile Val Cys
            500                 505                 510

Ala Gln Lys Phe Asn Gln Ile Gly Ile Thr Leu Arg Asn Asp Tyr Glu
            515                 520                 525

Leu Pro Glu Asp Val Ser Ala His Leu Val Lys Ser Tyr Gly Thr Arg
530                 535                 540

Ala Leu Gln Val Ala Glu Trp Val Arg Ala Gly Tyr Leu Asp Thr Lys
545                 550                 555                 560

Pro Gly Lys Ala Lys Arg Leu His Ser Arg Tyr Pro Phe Leu Glu Ala
            565                 570                 575

Glu Val Ile Phe Ala Val Asp Gln Glu Tyr Ala Leu Lys Pro Met Asp
            580                 585                 590

Ile Leu Ala Arg Arg Thr Arg Leu Ala Phe Leu Asp Thr Glu Ala Ala
            595                 600                 605

Arg Ala Ala Val Pro Arg Val Val Lys Leu Met Gly Asp Leu Leu Gly
610                 615                 620

Trp Ser Trp Arg Gln Arg Thr Met Glu Lys Ala Glu Ala Leu Ala Phe
625                 630                 635                 640

Leu Glu Thr Met Asn Val Glu Lys Thr Ala Leu Leu Lys Lys
            645                 650

<210> SEQ ID NO 85
<211> LENGTH: 852
<212> TYPE: PRT
<213> ORGANISM: Mortierella elongata

<400> SEQUENCE: 85

Met Ala Ser Lys Asn Ser Lys Thr Gly Pro Asp Asn Ala Gly Ala Ser
1               5                   10                  15

Thr Gly Pro Ala Leu Glu Leu Lys Pro Leu Lys Asn Val Met Pro Ile
            20                  25                  30

Val Pro Ala Gln Gln Val Asp Ser Ser Cys Pro Pro Ser Gly Glu
        35                  40                  45

Thr Ser Pro Leu Leu Glu Asn Ala Pro Asn Gly Lys Leu Ala Thr Gln
50                  55                  60

Ser Gly Gly Pro Asp Asn Asp Glu Ser Gly Val Glu Asn Ile Thr Lys
65                  70                  75                  80

Lys His Ala Gly Arg Ile Arg Glu Asp Pro Val Gly Phe Val Val Gln
            85                  90                  95

Thr Ala Ala Phe Tyr Gln Gly Thr Gly Trp Arg Ser Tyr Ser Asn Tyr
            100                 105                 110

Val Gly Thr Arg Ile Phe Tyr Glu Gly Phe Ser Ala Ser Phe Lys Asp
            115                 120                 125

Arg Ile Leu Ala Ser Gln Lys Val Val Glu Leu Val Lys Ser Met Ala
            130                 135                 140

Asn Lys Gln Leu Glu Val Leu Ile Lys Gln Arg Gln Asp Ala His Glu
```

```
            145                 150                 155                 160
        Ala Glu Lys Val Ala Asn Ala Gly Lys Lys Asn Phe Lys Pro Lys Val
                        165                 170                 175

Trp Pro Met Arg Pro Glu Asp Val Glu Val Arg Arg Lys Thr Leu Glu
                        180                 185                 190

Ala Glu Leu Thr Ala Val Ala Lys Thr Asn Ile Asp Lys Leu Val Cys
                        195                 200                 205

Asp Met Asn Ser Met Lys Phe Ile Arg Phe Ala Phe Leu Ile Asn
                210                 215                 220

Asn Ile Leu Val Arg Met Tyr His Gln Gly Ile His Ile Lys Glu Ser
        225                 230                 235                 240

Glu Phe Leu Glu Leu Arg Arg Val Ala Glu Tyr Cys Ala Glu Lys Lys
                        245                 250                 255

Tyr Ser Met Val Ile Leu Pro Cys His Lys Ser His Ile Asp Tyr Leu
                        260                 265                 270

Val Ile Ser Tyr Ile Phe Phe Arg Met Gly Leu Ala Leu Pro His Ile
                        275                 280                 285

Ala Ala Gly Asp Asn Leu Asp Met Pro Val Val Gly Lys Ala Leu Lys
                        290                 295                 300

Gly Ala Gly Ala Phe Phe Ile Arg Arg Ser Trp Ala Asp Gln Leu
        305                 310                 315                 320

Tyr Thr Ser Ile Val Gln Glu Tyr Val Gln Glu Leu Leu Glu Gly Gly
                        325                 330                 335

Tyr Asn Ile Glu Cys Phe Ile Glu Gly Thr Arg Ser Arg Thr Gly Lys
                        340                 345                 350

Leu Leu Pro Pro Lys Leu Gly Val Leu Lys Ile Ile Met Asp Ala Met
                        355                 360                 365

Leu Ser Asn Arg Val Gln Asp Cys Tyr Ile Val Pro Ile Ser Ile Gly
                        370                 375                 380

Tyr Asp Lys Val Ile Glu Thr Glu Thr Tyr Ile Asn Glu Leu Leu Gly
        385                 390                 395                 400

Ile Pro Lys Glu Lys Glu Ser Leu Trp Gly Val Ile Thr Asn Ser Arg
                        405                 410                 415

Leu Leu Gln Leu Lys Met Gly Arg Ile Asp Val Arg Phe Ala Lys Pro
                        420                 425                 430

Tyr Ser Leu Arg Glu Phe Met Asn His Glu Ile Asp Arg Arg Glu Ile
                        435                 440                 445

Ile Asn Glu Gln Glu Met Thr Ser Asn Ala Ala Lys Ser Gln Leu Leu
                        450                 455                 460

Lys Ala Leu Gly Tyr Lys Val Leu Ala Asp Ile Asn Ser Val Ser Val
        465                 470                 475                 480

Val Met Pro Thr Ala Leu Val Gly Thr Val Ile Leu Thr Leu Arg Gly
                        485                 490                 495

Arg Gly Val Gly Arg Asn Glu Leu Ile Arg Arg Val Asp Trp Leu Lys
                        500                 505                 510

Arg Glu Ile Leu Ser Lys Gly Gly Arg Val Ala Asn Phe Ser Gly Met
                        515                 520                 525

Glu Thr Gly Glu Val Val Asp Arg Ala Leu Gly Val Leu Lys Asp Leu
                        530                 535                 540

Val Ala Leu Gln Lys Asn Leu Leu Glu Pro Val Phe Tyr Ala Val Lys
        545                 550                 555                 560

Arg Phe Glu Leu Ser Phe Tyr Arg Asn Gln Leu Ile His Leu Phe Ile
                        565                 570                 575
```

His Glu Ala Ile Val Ala Val Thr Met Tyr Thr Arg Ile Lys Ile Gly
            580                 585                 590

Gly Ala Lys Ser Thr Gln Gln Ile Ser Gln Thr Glu Leu Leu Asn Glu
            595                 600                 605

Val Thr Phe Leu Ser Arg Leu Leu Lys Thr Asp Phe Ile Tyr Asn Pro
            610                 615                 620

Gly Asp Ile Gln Ser Asn Leu Glu Asn Thr Leu Glu Tyr Leu Lys Lys
625                 630                 635                 640

Ser Asn Val Ile Glu Ile Asn Ser Glu Gly Phe Val Gly Leu Ser Asp
                645                 650                 655

Val Glu Arg Gly Ile Gly Arg Glu Asn Tyr Asp Phe Tyr Cys Phe Leu
            660                 665                 670

Leu Trp Pro Phe Val Glu Thr Tyr Trp Leu Ala Ala Val Ser Leu Tyr
            675                 680                 685

Thr Leu Ile Pro Thr Ala Lys Glu Ile Thr Glu Gln Ala Asn Ala Gly
            690                 695                 700

Gly Asp Gln Leu His Trp Val Glu Glu Arg Val Phe Val Glu Lys Thr
705                 710                 715                 720

Gln Met Phe Gly Lys Thr Leu Tyr Tyr Gln Gly Asp Leu Ser Tyr Phe
                725                 730                 735

Glu Ser Val Asn Met Glu Thr Leu Lys Asn Gly Phe Asn Arg Leu Cys
            740                 745                 750

Asp Tyr Gly Ile Leu Met Ile Lys Lys Pro Thr Gly Pro Lys Glu Arg
            755                 760                 765

Thr Lys Val Ala Leu His Pro Asp Phe Met Pro Ser Arg Gly Ser Asp
770                 775                 780

Gly His Val Ile Ala Ser Gly Ala Leu Trp Asp Met Val Glu His Ile
785                 790                 795                 800

Gly Thr Phe Arg Arg Glu Gly Lys Asn Arg Arg Asp Asn Ala Thr Val
                805                 810                 815

Ser Ser Arg Val Leu Arg Phe Ala Glu Val Val Ala Asn Ser Pro Ala
            820                 825                 830

Pro Val Lys Val Pro Met Pro Ser Pro Ala Pro Lys Gln Gly Asn Gly
            835                 840                 845

Ala Pro Lys Leu
    850

<210> SEQ ID NO 86
<211> LENGTH: 209
<212> TYPE: PRT
<213> ORGANISM: Mortierella elongata

<400> SEQUENCE: 86

Met Thr Tyr Leu Phe Ile Ala Ala Leu Ala Tyr Gly Ile Gly Ser Ile
1               5                   10                  15

Ser Phe Ala Val Val Ser Ala Ala Met Arg Leu Gln Asp Pro Arg
            20                  25                  30

Ser Tyr Gly Ser Lys Asn Pro Gly Ala Thr Asn Val Leu Arg Ser Gly
            35                  40                  45

Asn Thr Leu Ala Ala Val Leu Thr Leu Ile Gly Asp Ala Leu Lys Gly
            50                  55                  60

Trp Leu Ala Val Trp Leu Thr Ala Gln Phe Val His Ser Phe Gly Ser
65                  70                  75                  80

Gln Tyr Glu Val Gly Asn Glu Ala Ile Gly Leu Ala Ala Leu Ala Val

```
                    85                  90                  95
Phe Leu Gly His Leu Trp Pro Ile Phe Phe His Phe Lys Gly Gly Lys
                100                 105                 110
Gly Val Ala Thr Ala Ala Gly Val Leu Phe Ala Ile His Pro Ile Leu
                115                 120                 125
Gly Leu Ala Thr Ala Ala Ser Trp Leu Ile Ile Ala Phe Phe Phe Arg
            130                 135                 140
Tyr Ser Ser Leu Ala Ala Leu Val Ala Ala Ile Phe Ala Pro Leu Tyr
145                 150                 155                 160
Glu Ile Leu Met Phe Gly Phe Asp Ser Asn Ser Ile Ala Val Leu Ala
                165                 170                 175
Met Ser Leu Leu Leu Ile Ser Arg His Arg Ser Asn Ile Gln Asn Leu
                180                 185                 190
Phe Ala Gly Lys Glu Gly Arg Leu Gly Gln Lys Ser Lys Asp Lys Ser
                195                 200                 205
Leu

<210> SEQ ID NO 87
<211> LENGTH: 306
<212> TYPE: PRT
<213> ORGANISM: Mortierella elongata

<400> SEQUENCE: 87

Met Ser Ile Val Thr Tyr Leu Gln Ala Ala Ile Gly Ile Pro Leu Phe
1               5                   10                  15
Tyr Phe Leu Val Leu Pro Lys Ile Leu Ala Val Leu Pro Lys Lys Ala
                20                  25                  30
Gln Phe Leu Ala Lys Cys Ile Ile Val Leu Leu Ala Thr Leu Ile Met
            35                  40                  45
Ser Val Ala Gly Cys Phe Ile Ser Ile Ala Cys Ala Leu Val Asn Lys
50                  55                  60
Arg Tyr Ile Ile Asn Tyr Val Val Ser Arg Phe Phe Gly Ile Leu Ala
65                  70                  75                  80
Ala Gly Pro Cys Gly Val Thr Tyr Lys Val Val Gly Glu Glu Lys Leu
                85                  90                  95
Glu Asn Tyr Pro Ala Ile Val Val Cys Asn His Gln Ser Ser Met Asp
                100                 105                 110
Met Met Val Leu Gly Arg Val Phe Pro Lys His Cys Val Val Met Ala
                115                 120                 125
Lys Lys Glu Leu Leu Tyr Phe Pro Phe Leu Gly Val Phe Met Lys Leu
            130                 135                 140
Ser Asn Ala Ile Phe Ile Asp Arg Lys Asn His Lys Lys Ala Ile Glu
145                 150                 155                 160
Ser Thr Thr Gln Ala Val Ala Asp Met Lys Lys His Asn Ser Gly Ile
                165                 170                 175
Trp Ile Phe Pro Glu Gly Thr Arg Ser Arg Leu Asp Lys Ala Asp Leu
                180                 185                 190
Leu Ala Phe Lys Lys Gly Ala Phe His Leu Ala Ile Gln Ala Gln Leu
            195                 200                 205
Pro Ile Leu Pro Ile Ile Ser Glu Gly Tyr Ser His Ile Tyr Asp Ser
            210                 215                 220
Ser Lys Arg Ser Phe Pro Gly Gly Glu Leu Glu Ile Arg Val Leu Asp
225                 230                 235                 240
Pro Ile Pro Thr Thr Gly Leu Thr Ala Asp Asp Val Asn Asp Leu Met
```

```
                            245                 250                 255
Glu Lys Thr Arg Asp Leu Met Leu Lys His Leu Lys Glu Met Asp Arg
                260                 265                 270
Ser Ser Ser Thr Val Thr Ser Pro Ala Ala Thr Val Gly Lys Thr Thr
            275                 280                 285
Ala Thr Ala Pro Gln Asp Glu Ala Ser Val Lys Lys Arg Arg Thr Leu
290                 295                 300
Lys Asp
305

<210> SEQ ID NO 88
<211> LENGTH: 304
<212> TYPE: PRT
<213> ORGANISM: Mortierella elongata

<400> SEQUENCE: 88

Met Ser Ser Glu Ser Thr Ile Pro Trp Cys Ile Ile Thr Thr Pro Val
1               5                   10                  15
Phe Ile Leu Ala Leu Pro Arg Leu Leu Ala Val Leu Pro Gln Lys Ile
                20                  25                  30
Gln Phe Val Thr Lys Cys Cys Ile Val Leu Ile Ala Thr Phe Ile Met
            35                  40                  45
Ser Ile Val Gly Cys Phe Val Ala Ile Val Phe Ala Leu Leu Arg Arg
50                  55                  60
Arg His Glu Ile Asn Phe Val Ala Arg Ile Phe Ser Phe Ile Ala
65                  70                  75                  80
Ser Tyr Pro Cys Gly Val Thr Phe Lys Val Val Gly Glu Glu His Leu
                85                  90                  95
Glu Lys Tyr Pro Ala Ile Val Val Cys Asn His Gln Ser Ser Met Asp
            100                 105                 110
Met Met Ile Leu Gly Arg Val Phe Pro Lys His Cys Val Val Met Ala
        115                 120                 125
Lys Lys Glu Leu Gln Tyr Phe Pro Phe Leu Gly Ile Phe Met Thr Leu
130                 135                 140
Ser Asn Ala Ile Phe Ile Asp Arg Lys Asn His Lys Lys Ala Ile Glu
145                 150                 155                 160
Ser Thr Thr Gln Ala Val Thr Asp Met Lys Lys His Asn Ser Gly Ile
                165                 170                 175
Trp Ile Phe Pro Glu Gly Thr Arg Ser Arg Leu Glu Thr Ala Asp Leu
            180                 185                 190
Leu Pro Phe Lys Lys Gly Ala Phe His Leu Ala Ile Gln Ser Gln Gln
        195                 200                 205
Pro Val Met Pro Ile Val Ala Ala Gly Tyr Ser Asn Ile Tyr Asp Ser
210                 215                 220
Ala Asn Arg Ser Phe Pro Gly Gly Glu Leu Glu Ile Arg Val Leu Glu
225                 230                 235                 240
Pro Ile Ser Thr Ile Gly Met Thr Ala Asp Asp Val Asn Glu Leu Met
                245                 250                 255
Glu Arg Thr Arg Ala Val Met Leu Lys Asn Leu Lys Glu Met Asp His
            260                 265                 270
Ser Val Lys Ser Ser Asn Ser Asn Gly Ser Ser Thr Ala Val Ala
        275                 280                 285
Glu Gly Lys Thr Asp Gly Leu Thr Gln Arg Arg Pro Val Lys Glu
290                 295                 300
```

<210> SEQ ID NO 89
<211> LENGTH: 101
<212> TYPE: PRT
<213> ORGANISM: Nannochloropsis gaditana

<400> SEQUENCE: 89

```
Met Val Ile Ser Phe Ile Phe Ser Trp Met Leu Gln Ile Leu Ala Cys
1               5                   10                  15

Ile Phe Ile Cys Pro Phe Leu Pro Ser Cys Lys Glu Arg Leu Leu Leu
            20                  25                  30

Leu Gly Trp Ile Phe Arg Ser Val Ser Ser Leu Val Ile Arg Leu Asn
        35                  40                  45

Pro Tyr Trp His Leu Arg Val Leu Gly Pro Arg Pro Thr Arg Pro Pro
    50                  55                  60

Ser Lys Thr Leu Ile Met Cys Asn His Leu Ser Asn Ala Asp Ala Phe
65                  70                  75                  80

Phe Leu Ser Ser Ala Leu Leu Pro Trp Glu Thr Lys Tyr Ile Ala Lys
                85                  90                  95

Ala Ser Leu Phe Gln
            100
```

<210> SEQ ID NO 90
<211> LENGTH: 199
<212> TYPE: PRT
<213> ORGANISM: Nannochloropsis gaditana

<400> SEQUENCE: 90

```
Met Arg Ser Asn Lys Ser Cys Lys Thr Cys Pro Asn Arg Ile His Val
1               5                   10                  15

Gly Ile Ala Ile Leu Phe Pro Leu Leu Leu Ser Ala Phe Cys Phe Cys
            20                  25                  30

His Phe Leu Met Leu Pro Pro Ala Ile Ala Leu Leu Ile Met Pro Tyr
        35                  40                  45

Ala Pro Val Arg Arg Val Leu Arg Leu Trp Glu Ala Thr Ile Ala Ala
    50                  55                  60

Tyr Trp Leu Ser Phe Gly Ala Trp Leu Leu Glu Asn Phe Gly Gly Val
65                  70                  75                  80

Lys Leu Ile Ile Ser Gly Asp Thr Phe Thr Lys Lys Asp Asn Val Leu
                85                  90                  95

Ile Ile Cys Asn His Arg Thr Arg Leu Asp Trp Met Trp Leu Trp Ser
            100                 105                 110

Trp Ala Ala Tyr Phe Asp Val Leu Ser Ser Tyr Arg Val Ile Leu Lys
        115                 120                 125

Asp Ser Leu Arg Cys Phe Pro Trp Trp Gly Trp Gly Met Ser Leu Cys
    130                 135                 140

Leu Phe Pro Phe Ile Arg Arg Gly Gln Lys His Arg Ser Thr Asp Leu
145                 150                 155                 160

Ala His Leu Lys Arg Asn Cys Arg Tyr Leu Ile Gln Leu Lys Val Pro
                165                 170                 175

Asn Ser Leu Ile Ile Phe Pro Glu Gly Thr Asp Leu Ser Pro Ser Asn
            180                 185                 190

Gln Glu Arg Asp Arg Asn Tyr
        195
```

<210> SEQ ID NO 91
<211> LENGTH: 422

-continued

```
<212> TYPE: PRT
<213> ORGANISM: Nannochloropsis gaditana

<400> SEQUENCE: 91

Met Thr Ser Thr Ala Ser Leu Ala Cys Gly Ala Cys Thr Ala Ala Val
1               5                   10                  15

Leu Val Cys Leu Thr Thr Gly Asp Gly Val Ala Thr Arg His Ile Asp
                20                  25                  30

Ala Asn Val Gly Asn Arg Arg Thr Ser Ala Phe Leu Pro Val Met Pro
            35                  40                  45

Pro Met Gly Thr Pro Val Thr Gly Arg Ile Arg Ser His Pro Leu Glu
50                  55                  60

Ala His Lys Met Tyr Tyr Val Cys Gln Gly Gly Thr Arg Leu Ser Gln
65                  70                  75                  80

Arg Arg His Glu Arg Leu Gly Thr Arg Thr Ala Val Met Val Val Lys
                85                  90                  95

Thr Asp Val Glu Ile Ser Asp Lys Arg Asp Val Asp Pro Glu Val Gly
                100                 105                 110

Ser Ser Ser Lys Ser Thr Asp His Thr Gly Val Ser Arg Phe Gly Ser
            115                 120                 125

Ala Met Pro Lys Ser Ala Glu Gly Val Gly Pro Pro Ala Pro Gln
130                 135                 140

Asp Asn Phe Lys His Lys Ser Leu Ala Gly Val Pro Thr Asp Tyr Gly
145                 150                 155                 160

Pro Tyr Leu Thr Ile Lys Gly Phe Lys Ile Asn Ala Phe Gly Phe Phe
                165                 170                 175

Phe Cys Phe Met Ala Ile Leu Trp Ala Ile Pro Trp Ala Val Phe Leu
                180                 185                 190

Val Val Tyr Lys Ala Leu Leu Glu Phe Val Asp Lys Leu Asp Pro Cys
            195                 200                 205

Arg Tyr Asn Val Asp Arg Ser Ser Leu Trp Gly Trp Leu Thr Ser
210                 215                 220

Leu Ser Thr Asp Ser Leu Pro Glu Met Thr Gly Leu Glu Asn Ile Pro
225                 230                 235                 240

Asp Gly Pro Ala Val Phe Val Ala Asn His Ala Ser Trp Met Asp Val
                245                 250                 255

Pro Tyr Ser Ala Gln Leu Pro Val Arg Ala Lys Tyr Leu Ala Lys Ala
                260                 265                 270

Asp Leu Thr Lys Val Pro Ile Leu Gly Asn Ala Met Ser Met Ala Gln
            275                 280                 285

His Val Leu Val Asp Arg Asp Lys Arg Ser Gln Met Glu Ala Leu
290                 295                 300

Arg Ser Ala Leu Leu Ile Leu Lys Thr Gly Thr Pro Leu Phe Val Phe
305                 310                 315                 320

Pro Glu Gly Thr Arg Gly Pro Gly Gly Lys Met Gln Ala Phe Lys Met
                325                 330                 335

Gly Ala Phe Lys Val Ala Thr Lys Ala Gly Val Pro Ile Val Pro Val
                340                 345                 350

Ser Ile Ala Gly Thr His Ile Met Met Pro Lys Glu Val Ile Met Pro
            355                 360                 365

Gln Cys Ala Gly Arg Gly Ile Thr Ala Ile His Val His Pro Ala Ile
370                 375                 380

Pro Ser Thr Asp Arg Thr Asp Gln Glu Leu Ser Asp Leu Ala Phe Lys
385                 390                 395                 400
```

Ile Ile Asn Asp Ala Leu Pro Asn Glu Gln Gln Cys Glu Ser Thr Ser
            405                 410                 415

Lys Glu Thr Gly Gly Ala
            420

<210> SEQ ID NO 92
<211> LENGTH: 391
<212> TYPE: PRT
<213> ORGANISM: Nannochloropsis gaditana

<400> SEQUENCE: 92

Met Ser Ser His Met Pro Val Cys Arg Gly Asp Pro Glu Ala Gly Val
1               5                   10                  15

Val Pro Ala Gly Gly Thr Val Gly Asn Glu Glu Met Ala Gly Arg Glu
            20                  25                  30

Asn Gly Gly Ser Gly Met Tyr Arg Leu Ala Glu Asp Val Asp Gly Asn
        35                  40                  45

Gly Arg Asp Glu Gly Cys Gln Trp Val Pro Pro Ala Leu Arg Thr Ser
    50                  55                  60

Leu Glu Arg Tyr Arg Trp Leu Glu Ile Ile Leu Leu Ser Val Ile Val
65                  70                  75                  80

Ile Leu Ala Lys Glu Gly Phe Gly Ser Gly Val Lys Asn His Arg Gln
                85                  90                  95

Tyr Ile Pro Leu Val Thr Gln Val Leu Pro Gly Gly Ala Val Val Val
            100                 105                 110

Leu Gly Asn Ala Thr Ala Phe Ser Tyr Pro Val Arg Phe Arg Glu Gly
        115                 120                 125

Thr Leu Glu Cys Pro Pro Val Thr Leu Glu Phe Cys Ala Thr Ser Pro
    130                 135                 140

Glu Ser Ala Leu Ala Asp Pro Cys Cys Glu Phe Met Thr Thr Gly Ala
145                 150                 155                 160

Lys Pro Phe Gln Thr Val Ser His Asp Asp Leu Ile Trp Ile Thr Val
                165                 170                 175

Gly Leu Pro Leu Ile Leu Val Leu Arg His Leu Leu Leu Lys Trp
            180                 185                 190

Tyr Leu Cys Ser Val Pro Ala Ser Ser Ala Asp Pro Met Phe Ser Ser
        195                 200                 205

Glu Asp Lys Ser Ala Leu Arg Pro Leu Ser Gly Leu Pro Phe Gly Tyr
    210                 215                 220

Ser Ala Thr Phe Cys Leu Arg Asp Val Leu Ile Gly Leu Phe Ser
225                 230                 235                 240

Leu Ala Leu Thr Arg Ala Thr Thr Asn Ser Leu Lys Met Leu Thr Ser
                245                 250                 255

Gln Pro Arg Pro Asn His Phe Ala Leu Arg Leu Phe Ala Ser Leu Ser
            260                 265                 270

Pro Asp Ser Ser Ala Ala Ile His Tyr Ala Glu Ser Ala Trp Lys Ala
        275                 280                 285

Trp Pro Ser Gly His Ser Ser Met Ser Met Ala Ser Gly Ala Phe Leu
    290                 295                 300

Ser Leu Val Leu Leu Arg Asp Leu Arg Gln Phe Ala Gly Pro Leu Gln
305                 310                 315                 320

Arg Gln Leu Arg Ala Cys Leu Val Ile Leu Ala Leu Gly Pro Val Tyr
                325                 330                 335

Leu Ala Met Phe Val Ala Gly Thr Arg Val His Asp Tyr Phe His Thr

```
                340             345             350
Thr Ala Asp Ala Val Thr Gly Ser Ala Leu Gly Leu Leu Trp Ala Val
                355             360             365

Leu Ala Phe Tyr Gln Val Val Pro Ala Gly Gly Leu Glu Val Arg Ala
                370             375             380

Asn Pro Pro Leu Lys Tyr Leu
385             390

<210> SEQ ID NO 93
<211> LENGTH: 491
<212> TYPE: PRT
<213> ORGANISM: Mortierella elongata

<400> SEQUENCE: 93

Met Ala Ser Phe Pro Phe Val Leu Gln Ala His Gln Gly Asn His Gln
1               5                   10                  15

Val Glu Leu Val Tyr Asn Gly Gln Gln Leu Glu Phe Asp Gly Leu Ser
                20                  25                  30

Leu Asp Glu Pro Lys Gln Ser Ser Cys Leu Pro Cys Gly Pro Ser
            35                  40                  45

Ser Ala Phe Ala Gly Gly His Arg Ile Ile Lys Thr Val Glu Ile Leu
        50                  55                  60

Asn Ile Asp Ile Glu His Glu Asp Ser Leu Val Leu Ser Val Ala Ser
65                  70                  75                  80

Ala Lys Asn Gly Pro Thr Lys Glu Ser Val Leu Glu Arg Leu Val Phe
                85                  90                  95

Gln Val Arg Asp Lys Ala Asn Ala Val Gln Trp Gln Ser Asn Val Leu
                100                 105                 110

Ser His Val Tyr Lys Asp Ile Lys Lys Gly Arg His Phe Lys Val Leu
            115                 120                 125

Val Asn Pro Phe Gly Gly Gln Gly His Ala Lys Lys Leu Trp Glu Thr
130                 135                 140

Ile Ala Glu Pro Ile Phe Lys Ala Ala Gly Cys Thr Tyr Asp Leu Thr
145                 150                 155                 160

Tyr Thr Thr His Arg Tyr His Ala Lys Glu Ile Ala Arg Asp Leu Asn
                165                 170                 175

Ile Arg Leu Phe Asp Ala Val Val Ser Val Ser Gly Asp Gly Val Leu
            180                 185                 190

His Glu Val Ile Asn Gly Leu Met Glu Arg Pro Asp Ala Ile Ala Ala
        195                 200                 205

His Lys Leu Pro Ile Gly Ala Ile Pro Gly Gly Ser Gly Asn Ala Leu
    210                 215                 220

Ser Tyr Ser Leu Leu Gly Glu Asp His Gly Ser His Val Thr Asn Ala
225                 230                 235                 240

Val Leu Gly Ile Ile Lys Gly Arg Ala Met Pro Val Asp Leu Cys Ser
                245                 250                 255

Val Thr Gln Gly Gln Asn Arg Tyr Phe Ser Phe Val Leu Gln Ser Phe
            260                 265                 270

Gly Leu Val Ala Asp Val Asp Leu Gly Thr Glu Asp Met Arg Trp Met
        275                 280                 285

Gly Glu Ala Arg Phe Thr Val Ala Ala Val Gly Lys Leu Leu Ser Gln
    290                 295                 300

Gln Thr Tyr Pro Cys Glu Ile Ser Tyr Ile Pro Val Glu Thr Asn Val
305                 310                 315                 320
```

```
Asp Lys Ile Arg Ala Glu Tyr Asn Tyr Arg Gln Gln Ser Val Val
            325                 330                 335

Trp Ala Asp Gln Thr His Asp Glu Leu Asp Gln Ser His Pro Thr Ile
        340                 345                 350

Val Asp Arg Phe Gly Gly Val Asn Ala Gln Leu Asn Lys Ser Asp Gly
            355                 360                 365

Trp Val Thr Asp Ser Glu Asp Val Ile Thr Ala Val Gly Ala Lys Leu
370                 375                 380

Pro Trp Ile Ser Lys Gly Met Leu Leu Asn Pro Ala Ser Thr Pro Asn
385                 390                 395                 400

Asp Gly Leu Ile Asp Leu Ile Val Phe Pro Lys Gly Thr Gly Arg Met
            405                 410                 415

Asn Gly Ile Gln Ile Met Leu Gly Thr Glu Thr Gly Glu His Ile Tyr
            420                 425                 430

His Asp Lys Val Arg Tyr Met Lys Val Lys Ala Phe Arg Leu Thr Pro
        435                 440                 445

Lys Asn Glu Ser Gly Phe Ile Ser Met Asp Gly Glu His Thr Pro Tyr
    450                 455                 460

Ser Pro Tyr Gln Val Glu Ala His Pro Gly Leu Ile Ser Val Leu Ser
465                 470                 475                 480

Ile Glu Gly Arg Tyr Ala Arg Ser Met Arg Glu
            485                 490

<210> SEQ ID NO 94
<211> LENGTH: 336
<212> TYPE: PRT
<213> ORGANISM: Mortierella elongata

<400> SEQUENCE: 94

Met Asp Glu Lys Lys Ile Gly Phe Ile Val Asn Arg Arg Gly Gly Gly
1               5                   10                  15

Gly Lys Gly Gly Lys Thr Trp Asp Lys Leu Glu Pro Ala Val Thr Thr
            20                  25                  30

Arg Leu Ala Ser Ala Lys Trp Lys Val Glu Tyr Thr Gln His Ser Gly
        35                  40                  45

His Ala Ser Asp Leu Ala Arg Glu Phe Val Asn Glu Gly Tyr Asn Ile
    50                  55                  60

Ile Val Ala Val Gly Gly Asp Gly Thr Ile Ser Gln Val Val Asn Gly
65                  70                  75                  80

Tyr Met Leu Ala Asp Gly Asn Ser Lys Gly Cys Ala Val Gly Ile Ile
                85                  90                  95

Ser Ser Gly Thr Gly Gly Asp Phe Val Arg Thr Thr Lys Thr Pro Lys
            100                 105                 110

Asp Pro Leu Glu Ala Leu Glu Leu Ile Leu Ser Thr Glu Ser Thr Leu
        115                 120                 125

Val Asp Val Gly His Val Ser Ala Thr Lys Pro Asn Ser Pro Ser Val
    130                 135                 140

Thr Asn Glu Gln Tyr Phe Ile Asn Ile Cys Ser Val Gly Ile Ser Gly
145                 150                 155                 160

Ser Ile Ile Lys Arg Val Glu Ser Ser Ile Ala Lys Tyr Ile Ser
                165                 170                 175

Gly Ser Leu Val Tyr Trp Leu Tyr Thr Tyr Leu Thr Gly Leu Val Tyr
            180                 185                 190

Arg Pro Pro Pro Val Lys Tyr Thr Leu Thr Gly Gly Ser Ala Gly Ala
        195                 200                 205
```

```
Asp Asp Gly Lys Glu Lys His Met Gly Leu Tyr Ile Met Ala Val Ala
        210                 215                 220

Asn Gly Arg Tyr Leu Gly Asn Met His Ile Ala Pro Lys Ala Gln
225                 230                 235                 240

Ile Ser Asp Gly Gln Phe Asp Val Val Cys Leu His Asp Leu Thr Leu
                245                 250                 255

Thr Asp Ala Phe Phe Lys Ala Ser Pro Ala Leu Lys Ser Gly Asn Leu
            260                 265                 270

Met Asn Leu Pro Ala His Gln Ala Phe Thr Gln Arg Asn Thr Lys Val
        275                 280                 285

Ser Ile Ser Pro Val Asn Ala Lys Asp His Ile Tyr Val Glu Ala Asp
    290                 295                 300

Gly Glu Val Ala Gly Val Leu Pro Ala Arg Trp Glu Ile Ile Pro Gln
305                 310                 315                 320

Gly Cys Arg Met Ile Leu Pro Leu Val Gln Gly Ser Thr Gln Ser Val
                325                 330                 335

<210> SEQ ID NO 95
<211> LENGTH: 382
<212> TYPE: PRT
<213> ORGANISM: Mortierella elongata

<400> SEQUENCE: 95

Met Gly Ile Ile Pro Thr Ser Asp Lys Phe Pro Val Leu Val Val Leu
1               5                   10                  15

Asn Pro His Ser Gly Arg Lys Gln Gly Leu Glu Ala Trp Glu Asn Thr
            20                  25                  30

Val Lys Pro Ala Leu Asn Ala Ala Asn Lys Pro Phe Arg Leu Ile Glu
        35                  40                  45

Ser Asn Ser Gln Gly His Val Val Ser Tyr Phe Val Asp Asn Ile Lys
    50                  55                  60

Pro Ile Ile Thr Asp Leu Ala Gln Ser Leu Ser Thr Val Thr Gln Gly
65                  70                  75                  80

Ala Gly Asp Asp Glu Thr Ile Val Tyr Pro Thr Ser Ala Lys Leu Gln
                85                  90                  95

Ile Ile Val Leu Gly Gly Asp Gly Thr Val His Glu Ile Val Asn Gly
                100                 105                 110

Ile Leu Lys Gly Val Glu Gly Thr Gly Phe Val Thr Asp Ala Phe Arg
            115                 120                 125

Pro Glu Val Glu Phe Ser Val Ile Pro Thr Gly Thr Gly Asn Ala Ile
        130                 135                 140

Ser Thr Ser Leu Gly Val Thr Ser Val Gln Asn Ala Val Asp Arg Phe
145                 150                 155                 160

Ile Ala Gly Lys Thr Val Pro Leu His Leu Met Ser Val Ala Thr Gln
                165                 170                 175

Thr Ser Gln Leu Tyr Thr Val Val Asn Ser Tyr Gly Leu His Cys
            180                 185                 190

Ala Thr Val Tyr Asp Ser Glu Glu Phe Arg His Leu Gly Asn Asp Arg
        195                 200                 205

Phe Arg Gln Ala Ala Met Lys Asn Val Glu Asn Leu Lys Gln Tyr Glu
    210                 215                 220

Gly Lys Leu Ser Phe Phe Gly Pro Ile Gln Arg Tyr Asn Arg Ile Ser
225                 230                 235                 240

Ala Ser Leu Val Asp Thr Glu Thr Asp Asn Asn Ile Ala Gln Ala Asp
```

```
                  245                 250                 255
Ser Lys Ser Ser Ala Val Ala Thr Leu Thr Leu Pro Gly Pro Phe Thr
            260                 265                 270

Tyr Leu Leu Ile Ser Lys Gln Ala Ser Leu Glu Pro Gly Phe Thr Pro
            275                 280                 285

Thr Pro Phe Ala Lys Thr Ser Asp Asp Trp Met Asp Val Leu Ala Val
            290                 295                 300

Gln Asn Val Gly Gln Ala Glu Ile Met Gln Met Phe Gly Ser Thr Ala
305                 310                 315                 320

Thr Gly Thr His Val Asn Gln Asp His Val Asp Tyr Ile Lys Ala Lys
                325                 330                 335

Thr Ile Glu Leu Glu Thr Pro Thr Gln Gly Arg Leu Cys Ile Asp Gly
            340                 345                 350

Glu Phe Leu Thr Ile Glu Ala Gly Pro Glu Gly Lys Val Arg Phe Glu
            355                 360                 365

Val Asn Ser Asp Pro Asn Ile Gln Ile Phe His Ile Phe Ala
            370                 375                 380

<210> SEQ ID NO 96
<211> LENGTH: 529
<212> TYPE: PRT
<213> ORGANISM: Mortierella elongata

<400> SEQUENCE: 96

Met Ser Pro Asn Gln Phe Gln Ala Lys Ala Ser Phe Ala Gly His Gln
1               5                   10                  15

Arg Val Ser Asp Ala Arg Leu Ser Leu Gly Thr His Glu Leu Thr Ile
            20                  25                  30

His Ala Pro Lys Gly Ser Asp Asn Asn Thr Thr Thr Ile Gln Val Pro
        35                  40                  45

Tyr Ser Cys Ile Tyr Gly Tyr Glu Thr Ser Thr Asp Lys Ala Thr Gly
    50                  55                  60

Glu Asn Tyr Lys Asn Lys Val Ile Val His Tyr Val Ala Phe Ser Gly
65              70                  75                  80

Pro Asp Leu Arg Asn Pro Ser Ala Ala Lys Arg Thr Thr Ala Gln Leu
            85                  90                  95

Leu Phe Glu Arg Thr Glu Asp Ala Asp Arg Phe Ile Gln Thr Ala Arg
            100                 105                 110

Asp Leu Gly Ala Leu Pro Thr Pro Arg Arg Ile Leu Leu Leu Val Asn
        115                 120                 125

Pro Asn Gly Gly Val Gly Lys Ala Lys Arg Ile Ser Asp Thr Val Val
    130                 135                 140

Lys Pro Met Leu Gln His Ser Gly Leu Thr Val Lys Glu Gln Tyr Thr
145             150                 155                 160

Glu Tyr Gly Arg His Ala Val Asp Ile Ala Ser Lys Val Asn Leu Asp
            165                 170                 175

Glu Val Asp Ser Leu Val Val Ser Gly Asp Gly Val Leu His Glu
        180                 185                 190

Val Ile Asn Gly Leu Leu Ser Arg Pro Asp Trp Asp Arg Ala Arg Lys
    195                 200                 205

Thr Ser Ile Gly Ile Val Pro Ala Gly Ser Gly Asn Ala Ile Ala Ala
210                 215                 220

Ser Leu Gly Ile Val Ser Gln Phe Val Ala Thr Leu Thr Val Ile Arg
225                 230                 235                 240
```

Gly Glu Thr Ser Lys Leu Asp Ile Phe Ser Leu Ser Gln Leu Asn Arg
                245                 250                 255

Pro Lys Ile Tyr Ser Met Leu Ser Phe Ser Trp Gly Met Met Ala Asp
            260                 265                 270

Ala Asp Ile Glu Ser Asp Ser Tyr Arg Trp Leu Gly Pro Leu Arg Phe
        275                 280                 285

Asp Val Ala Gly Phe Ile Arg Met Ile Arg Leu Arg Arg Tyr Pro Gly
    290                 295                 300

Lys Val Tyr Val Leu Pro Lys His Gln Asn Pro Ser Thr Thr
305                 310                 315                 320

Glu Gln Gln Leu Thr Pro Pro Gln Ser Pro Ser His Lys Arg Glu Pro
                325                 330                 335

Glu Ser Gln Phe Gln His Leu Leu Asp Ser Asn Ile Lys Glu Pro Pro
            340                 345                 350

Lys Pro Trp Ser Leu Ile Pro Asn Met Pro Phe Tyr Ser Met Leu Leu
        355                 360                 365

Leu Leu Asn Cys Pro Asn Val Gly Glu Thr Ile Phe Phe Thr Asp Thr
    370                 375                 380

Ile Arg Phe Asn Asp Gly Ile Met Arg Leu Trp Tyr Ser Ala Glu Thr
385                 390                 395                 400

Arg Phe Trp Lys Ile Leu Met Pro Phe Ile Phe Asp Gln Gln Asn Gly
                405                 410                 415

Lys Met Val Glu Arg Asp Leu Met Lys Asp Leu Glu Cys Gly Gly Ile
            420                 425                 430

Leu Ile Ile Pro Gly Val Glu Gly Lys Pro Asp Asp Pro Ser Thr His
        435                 440                 445

Lys Val Ile Glu Pro Asp Trp Val Thr Ser Ser Ala Ala Lys Ala Gln
450                 455                 460

Asn Ile Tyr Gln Asn Pro Gly Leu Phe Asp Val Asp Gly Glu Val Met
465                 470                 475                 480

Pro Thr Ala Arg Thr Leu Ile Glu Ile His Pro Ser Leu Met Asn Ile
                485                 490                 495

Leu Val Pro Glu Trp Leu Tyr His Lys Asp Asp Asp Asn Thr Thr Ala
            500                 505                 510

Arg Ala His Glu Val Ala Val Ile Gln Ala Ile Lys Ala Gln Gln Lys
        515                 520                 525

Leu

<210> SEQ ID NO 97
<211> LENGTH: 866
<212> TYPE: PRT
<213> ORGANISM: Nannochloropsis gaditana

<400> SEQUENCE: 97

Met Asp Glu Glu Leu Asn Val Leu Ser Pro Phe Leu Val Lys Ala Glu
1               5                   10                  15

Val Leu Leu Val Leu Val Val Leu Val Ala Ser Val Val Trp Leu
                20                  25                  30

Phe Trp Glu Ile Val Ser Phe Met Met Asp Arg Gly Lys Glu Thr
            35                  40                  45

Asn Pro Asp Trp Trp Glu Val Leu Arg Asn Cys Gln His Arg Arg Leu
        50                  55                  60

Ile Ile Pro Pro Tyr Cys Val Gln Glu Val Pro Glu Leu Gly Thr Phe
65                  70                  75                  80

```
Ser Arg Leu Thr Thr Ala Thr Thr Asn Ala Met Lys Asn Met Ser Gly
                85                  90                  95

Val Ile Gln Arg Thr Ser His Leu Ile Ser Gly Gly Ser Gly Lys Ser
            100                 105                 110

Ala Ala Ala Ile Lys Lys Gly Ala Arg Gln Asp Leu Pro Ser Thr Gln
            115                 120                 125

Gln Glu Gly Asp Glu Asn Met Lys Gly Tyr Thr Val Asp Gly Asn Ala
            130                 135                 140

Arg Gly Val Lys Leu Arg Arg Gly Ser Lys Gln Ser Ile Val Gly
145                 150                 155                 160

Leu Ser Asn His Gly Thr Ser Ala Gly Gly Lys Pro Ala Leu Gln Pro
                165                 170                 175

Thr Ala Asn Pro Thr Pro Leu Thr Leu Ser Glu Asn Gly Ala Asn Pro
                180                 185                 190

Asp Ala Ser Ala Ala Ser Asp Ala Arg Pro Lys Pro His Arg Leu Asp
                195                 200                 205

Leu Asn Gly Glu Glu Gly Asn Met Val Pro Cys Asn Gly Ser Leu Ser
            210                 215                 220

Ser Arg Ala Gly Asp Gly Lys Arg Val Val Gly Met Ser Gly Leu Ala
225                 230                 235                 240

Ser Thr Ser Ala Ala Ala Gly Ser Asp Ala Ser Ser Ala Asn Val Lys
                245                 250                 255

Ser Met Glu Ile Ser Pro Ala Asp Thr Pro Cys Arg Gly Arg Ile Arg
            260                 265                 270

Phe Leu Pro His Gln Arg Glu Arg Gln Gln Ile Glu Asn His Glu Lys
            275                 280                 285

Ser His Glu Gly Lys Pro Thr Arg Ser Gly Leu Pro Leu Arg Ala Leu
            290                 295                 300

Asp Ser Gln Pro Pro Leu Thr Pro Tyr Ala Leu Pro Asp Ala Glu Gly
305                 310                 315                 320

Val Leu Ala Ser Ser Ala Gln Ser Ser Arg His Ala Pro Asp Ala Ile
                325                 330                 335

Ala Ala Thr Pro Arg Leu Ser Ser His Ala Ala Asn Gly Glu Pro
            340                 345                 350

Ile Thr Thr Pro Ala Gln Pro Val Arg Leu Pro Ser Met Glu His Ala
            355                 360                 365

His Ser Gly Thr Gly Val Ala Leu Ser Gly Gly Ser Ser Gly Val Ala
            370                 375                 380

Gly Arg Gly Phe Ile Phe Ser Pro Leu Pro Glu Asp Cys Thr Pro Leu
385                 390                 395                 400

Leu Ala Phe Val Asn Ser Arg Ser Gly Val Ser Gln Gly Ala Tyr Leu
                405                 410                 415

Ile His Gln Leu Arg Arg Leu Leu Asn Pro Ile Gln Val Ile Asp Leu
            420                 425                 430

Ala Asn Glu Asp Pro Ala Arg Ala Leu Arg Leu Tyr Leu Glu Leu Pro
            435                 440                 445

Arg Leu Arg Val Leu Val Cys Gly Gly Asp Gly Thr Ala Lys Trp Ile
450                 455                 460

Met Asn Val Leu Glu Asp Leu Asn Pro Glu Cys Trp Pro Pro Ile Ala
465                 470                 475                 480

Ile Leu Pro Leu Gly Thr Gly Asn Asp Met Ala Arg Val Leu Gly Trp
                485                 490                 495

Gly Gly Gly Tyr Asn Asn Gln Ser Ile Val Glu Phe Leu Ala Gln Val
```

```
                500             505             510
        Gln Arg Ala His Val Val Val Asp Arg Trp Glu Met Lys Leu Thr
                    515             520             525
        Pro Ala Gly Lys Gly Ser Ser Arg Ala Lys Thr Val Thr Phe Asn Asn
                530             535             540
        Tyr Phe Gly Ile Gly Val Asp Ala Gln Ala Ala Leu Lys Phe His His
        545             550             555             560
        Leu Arg Glu Gln Lys Pro Gln Leu Phe Phe Ser Arg Leu Val Asn Lys
                        565             570             575
        Leu Trp Tyr Gly Met Leu Gly Ala Gln Asp Leu Phe Arg Arg Thr Cys
                    580             585             590
        Val Ser Leu Pro Glu Arg Leu Lys Ile Val Ala Asp Gly Lys Glu Leu
                    595             600             605
        Thr Leu Pro Ala His Val Gln Gly Val Ile Phe Leu Asn Ile Glu Ser
                    610             615             620
        Tyr Gly Gly Gly Val Lys Leu Trp Asn Val Glu Glu Asp Asp Glu Ser
        625             630             635             640
        Ala Gly Asn Gly Leu Phe Asp Ala Ser Ser Ser Cys Ser Ser Glu
                        645             650             655
        Glu Gly Asp Arg Ser Glu Asp Glu Ser Arg Arg Gln Arg Arg Arg
                    660             665             670
        Arg Arg Arg Glu Arg Gln Arg Arg Gln Gln Ser Gln Ala Glu Glu Glu
                    675             680             685
        Ala His Arg Gln Arg Glu Gln Gln Glu Lys Pro Ser Ser Met Ala Leu
                    690             695             700
        Thr Ser Ser Ser Met Gln Asp Gly Leu Met Glu Val Val Ala Ile Asn
        705             710             715             720
        Gly Val Val His Leu Gly Gln Leu Gln Val Gly Leu Ser Lys Ala Val
                    725             730             735
        Lys Ile Cys Gln Cys Arg Glu Ala Val Ile Thr Thr Thr Arg Asp Leu
                    740             745             750
        Pro Met Gln Val Asp Gly Glu Pro Trp Pro Gln Ala Lys Ser Thr Ile
                    755             760             765
        Lys Ile Thr Arg Lys Lys Asp Pro Ala Tyr Leu Leu Arg Arg Thr Met
                    770             775             780
        Asp Ser Gly Gly Ala Val Val Gly Glu Val Val Glu Leu Leu Glu Ser
        785             790             795             800
        Ala Val Lys Asp Gly Val Ile Ser Leu Pro Gln Lys Lys Ser Leu Leu
                        805             810             815
        Thr Glu Leu Ser Arg Arg Val Glu Met Lys Arg Lys Val Phe Glu Gln
                    820             825             830
        Glu Leu Ser Gln Asn Asp Gly Val Pro Ser Phe Ser Lys Gly Phe Asp
                    835             840             845
        Val Ser Arg Leu Arg Leu Ala Ala Asp Ser Asn Ser Lys Asp Cys Val
                    850             855             860
        Leu Met
        865

<210> SEQ ID NO 98
<211> LENGTH: 486
<212> TYPE: PRT
<213> ORGANISM: Nannochloropsis gaditana

<400> SEQUENCE: 98
```

```
Met Lys Leu Ile Gln Tyr Phe Gly Thr Ala Leu Cys Val Val Ile Leu
1               5                   10                  15
Ser Cys Val Thr Asn Ile Ile Pro Gly Gly Arg Ile Ala Leu Gly Arg
            20                  25                  30
Pro Phe Ser Arg Leu Phe Gly Gly Ser Ser Arg Asn Leu Arg Ala Glu
        35                  40                  45
Val Glu Ala Ala Val Pro His Phe Ile Val Pro Glu Asp Arg Val Glu
50                  55                  60
Tyr Pro Thr Pro Lys Leu Ala Ala Leu Lys Ser Lys Leu Lys Glu Ile
65                  70                  75                  80
Gly His His Lys Ala Met Gly His Pro His Gln His Gln Gly Leu Asp
                85                  90                  95
Gly Arg Arg Arg Val Ser Leu His Pro Ser His Arg Pro Ala Pro Ser
            100                 105                 110
Ser Leu Gly Ala Ala Glu Asp Lys Glu Gln Glu Glu Glu Gly Gly Glu
        115                 120                 125
Glu Glu Glu Glu Gly Gln Glu Gly Val Ile Ala Pro Pro Ala Trp Lys
130                 135                 140
Pro Gly His Met Asn Pro Arg Asp Ser Ser Asp Met Gly Lys Ala
145                 150                 155                 160
Thr Lys Gly Lys Pro Gly Thr Pro Ser Ala Phe Leu Pro Leu Gly Val
                165                 170                 175
Pro Pro Pro Ser Leu Phe Pro Pro Ser Ala Arg Pro Ile Arg Arg Ser
            180                 185                 190
Pro Trp Ser Leu Leu Phe Arg Arg Gly Leu Pro Arg Pro Arg Arg Lys
        195                 200                 205
Arg Pro Ile Gly Ile Asn Arg Ile Lys Thr Leu Pro Pro Ser Val Thr
210                 215                 220
Pro Leu Ile Ala Ile Val Asn Ser Lys Ser Gly Gly Arg Gln Gly Lys
225                 230                 235                 240
Asn Leu Phe Lys Arg Leu Arg Ala Ala Leu Ser Arg Ala Gln Val Phe
                245                 250                 255
Asp Ile Gln Lys Val Asp Leu Lys Glu Ala Leu Ser Leu Tyr Cys His
            260                 265                 270
Leu Pro Asn Ser Cys Thr Leu Leu Val Cys Gly Gly Asp Gly Thr Ala
        275                 280                 285
Ser Arg Val Phe Glu Val Val Asp Gly Met Glu Trp Lys His Gly Pro
290                 295                 300
Pro Lys Ile Ala Ile Val Pro Leu Gly Thr Gly Asn Asp Ile Ala Arg
305                 310                 315                 320
Val Leu Asp Trp Asn Leu Gly His Asp Trp Ser Gly Gly Tyr Phe Pro
                325                 330                 335
Trp Ser Asn Asp Ala Ala Asp Ala Asn Leu Leu Ser Val Phe Ser Asp
            340                 345                 350
Leu Thr Arg Ala Met Glu Arg Lys Met Asp Arg Trp Glu Leu Arg Met
        355                 360                 365
Thr Glu Ala Val Pro Ser Ser Asp Arg His Arg Gln Pro Val Lys Tyr
370                 375                 380
Met Leu Gly Tyr Leu Gly Ile Gly Val Asp Gly Lys Val Ala Leu Asp
385                 390                 395                 400
Phe His Lys Leu Arg Asp Arg Ala Pro Tyr Leu Phe Leu Ser Pro Thr
                405                 410                 415
Leu Asn Lys Phe Tyr Tyr Ala Leu Met Gly Leu Arg Asp Phe Phe Val
```

```
                420             425             430
Arg Ser Cys Lys Asn Leu Pro Asp Lys Val Glu Leu Trp Cys Asp Gly
        435                 440                 445
Lys Pro Ile Val Leu Pro Pro Gln Thr Glu Ser Phe Ile Val Leu Asn
    450                 455                 460
Ile Asn Ser His Ala Gly Val Glu Leu Trp Pro Glu Tyr Leu Met
465                 470                 475                 480
Gly Gly Gly Met Glu Gly
                485

<210> SEQ ID NO 99
<211> LENGTH: 603
<212> TYPE: PRT
<213> ORGANISM: Nannochloropsis gaditana

<400> SEQUENCE: 99

Met Lys Leu Ile Gln Tyr Phe Gly Thr Ala Leu Cys Val Val Ile Leu
1               5                   10                  15
Ser Cys Val Thr Asn Ile Ile Pro Gly Gly Arg Ile Ala Leu Gly Arg
                20                  25                  30
Pro Phe Ser Arg Leu Phe Gly Gly Ser Ser Arg Asn Leu Arg Ala Glu
            35                  40                  45
Val Glu Ala Ala Val Pro His Phe Ile Val Pro Glu Asp Arg Val Glu
        50                  55                  60
Tyr Pro Thr Pro Lys Leu Ala Ala Leu Lys Ser Lys Leu Lys Glu Ile
65                  70                  75                  80
Gly His His Lys Ala Met Gly His Pro His Gln His Gln Gly Leu Asp
                85                  90                  95
Gly Arg Arg Arg Val Ser Leu His Pro Ser His Arg Pro Ala Pro Ser
            100                 105                 110
Ser Leu Gly Ala Ala Glu Asp Lys Glu Gln Glu Glu Glu Gly Gly Glu
        115                 120                 125
Glu Glu Glu Glu Gly Gln Glu Gly Val Ile Ala Pro Pro Ala Trp Lys
    130                 135                 140
Pro Gly His Met Asn Pro Arg Asp Ser Ser Asp Met Gly Lys Ala
145                 150                 155                 160
Thr Lys Gly Lys Pro Gly Thr Pro Ser Ala Phe Leu Pro Leu Gly Val
                165                 170                 175
Pro Pro Pro Ser Leu Phe Pro Pro Ser Ala Arg Pro Ile Arg Arg Ser
            180                 185                 190
Pro Trp Ser Leu Leu Phe Arg Arg Gly Leu Pro Arg Pro Arg Arg Lys
        195                 200                 205
Arg Pro Ile Gly Ile Asn Arg Ile Lys Thr Leu Pro Pro Ser Val Thr
    210                 215                 220
Pro Leu Ile Ala Ile Val Asn Ser Lys Ser Gly Gly Arg Gln Gly Lys
225                 230                 235                 240
Asn Leu Phe Lys Arg Leu Arg Ala Ala Leu Ser Arg Ala Gln Val Phe
                245                 250                 255
Asp Ile Gln Lys Val Asp Leu Lys Glu Ala Leu Ser Leu Tyr Cys His
            260                 265                 270
Leu Pro Asn Ser Cys Thr Leu Leu Val Cys Gly Gly Asp Gly Thr Ala
        275                 280                 285
Ser Arg Val Phe Glu Val Val Asp Gly Met Glu Trp Lys His Gly Pro
    290                 295                 300
```

```
Pro Lys Ile Ala Ile Val Pro Leu Gly Thr Gly Asn Asp Ile Ala Arg
305                 310                 315                 320

Val Leu Asp Trp Asn Leu Gly His Asp Trp Ser Gly Gly Tyr Phe Pro
            325                 330                 335

Trp Ser Asn Asp Ala Ala Asp Ala Asn Leu Leu Ser Val Phe Ser Asp
        340                 345                 350

Leu Thr Arg Ala Met Glu Arg Lys Met Asp Arg Trp Glu Leu Arg Met
    355                 360                 365

Thr Glu Ala Val Pro Ser Ser Asp Arg His Arg Gln Pro Val Lys Tyr
370                 375                 380

Met Leu Gly Tyr Leu Gly Ile Gly Val Asp Gly Lys Val Ala Leu Asp
385                 390                 395                 400

Phe His Lys Leu Arg Asp Arg Ala Pro Tyr Leu Phe Leu Ser Pro Thr
            405                 410                 415

Leu Asn Lys Phe Tyr Tyr Ala Leu Met Gly Leu Arg Asp Phe Phe Val
        420                 425                 430

Arg Ser Cys Lys Asn Leu Pro Asp Lys Val Glu Leu Trp Cys Asp Gly
    435                 440                 445

Lys Pro Ile Val Leu Pro Pro Gln Thr Glu Ser Phe Ile Val Leu Asn
450                 455                 460

Ile Asn Ser His Ala Gly Gly Val Glu Leu Trp Pro Glu Tyr Leu Met
465                 470                 475                 480

Gly Gly Gly Met Glu Gly Ala Phe Lys Pro Ser Arg Phe Asp Asp Gly
            485                 490                 495

Tyr Leu Glu Val Val Ala Ile Ser Gly Val Leu His Leu Gly Arg Ile
        500                 505                 510

Arg Val Gly Leu Asp Arg Pro Leu Arg Leu Ala Gln Ala Lys Glu Val
    515                 520                 525

Arg Ile Arg Thr Lys Ser Phe Leu Pro Gly Gln Val Asp Gly Glu Pro
530                 535                 540

Trp Arg Leu Pro Arg Cys Glu Leu Thr Leu Arg His Asn Gly Gln Ala
545                 550                 555                 560

Pro Val Leu Gln His Val Ser Lys Glu Leu Leu Gln Tyr Asn Glu Trp
            565                 570                 575

Leu Val Gly Gln Gly Lys Leu Asp Ala Ala Gly Lys Asp Gln Leu Leu
        580                 585                 590

Gln Ala Phe Lys Arg Arg Leu Gln Val Ser Gln
    595                 600

<210> SEQ ID NO 100
<211> LENGTH: 355
<212> TYPE: PRT
<213> ORGANISM: Mortierella ramanniana

<400> SEQUENCE: 100

Met Ala Ser Lys Asp Gln His Leu Gln Gln Lys Val Lys His Thr Leu
1               5                   10                  15

Glu Ala Ile Pro Ser Pro Arg Tyr Ala Pro Leu Arg Val Pro Leu Arg
            20                  25                  30

Arg Arg Leu Gln Thr Leu Ala Val Leu Leu Trp Cys Ser Met Met Ser
        35                  40                  45

Ile Cys Met Phe Ile Phe Phe Leu Cys Ser Ile Pro Val Leu Leu
    50                  55                  60

Trp Phe Pro Ile Ile Leu Tyr Leu Thr Trp Ile Leu Val Trp Asp Lys
65                  70                  75                  80
```

```
Ala Pro Glu Asn Gly Gly Arg Pro Ile Arg Trp Leu Arg Asn Ala Ala
                85                  90                  95

Trp Trp Lys Leu Phe Ala Gly Tyr Phe Pro Ala His Val Ile Lys Glu
            100                 105                 110

Ala Asp Leu Asp Pro Ser Lys Asn Tyr Ile Phe Gly Tyr His Pro His
        115                 120                 125

Gly Ile Ile Ser Met Gly Ser Phe Cys Thr Phe Ser Thr Asn Ala Thr
    130                 135                 140

Gly Phe Asp Asp Leu Phe Pro Gly Ile Arg Pro Ser Leu Leu Thr Leu
145                 150                 155                 160

Thr Ser Asn Phe Asn Ile Pro Leu Tyr Arg Asp Tyr Leu Met Ala Cys
                165                 170                 175

Gly Leu Cys Ser Val Ser Lys Thr Ser Cys Gln Asn Ile Leu Thr Lys
            180                 185                 190

Gly Gly Pro Gly Arg Ser Ile Ala Ile Val Val Gly Gly Ala Ser Glu
        195                 200                 205

Ser Leu Asn Ala Arg Pro Gly Val Met Asp Leu Val Leu Lys Arg Arg
    210                 215                 220

Phe Gly Phe Ile Lys Ile Ala Val Gln Thr Gly Ala Ser Leu Val Pro
225                 230                 235                 240

Thr Ile Ser Phe Gly Glu Asn Glu Leu Tyr Glu Gln Ile Glu Ser Asn
                245                 250                 255

Glu Asn Ser Lys Leu His Arg Trp Gln Lys Ile Gln His Ala Leu
            260                 265                 270

Gly Phe Thr Met Pro Leu Phe His Gly Arg Gly Val Phe Asn Tyr Asp
        275                 280                 285

Phe Gly Leu Leu Pro His Arg His Pro Ile Tyr Thr Ile Val Gly Lys
    290                 295                 300

Pro Ile Pro Val Pro Ser Ile Lys Tyr Gly Gln Thr Lys Asp Glu Ile
305                 310                 315                 320

Ile Arg Glu Leu His Asp Ser Tyr Met His Ala Val Gln Asp Leu Tyr
                325                 330                 335

Asp Arg Tyr Lys Asp Ile Tyr Ala Lys Asp Arg Val Lys Glu Leu Glu
            340                 345                 350

Phe Val Glu
        355

<210> SEQ ID NO 101
<211> LENGTH: 349
<212> TYPE: PRT
<213> ORGANISM: Mortierella ramanniana

<400> SEQUENCE: 101

Met Glu Gln Val Gln Val Thr Ala Leu Leu Asp His Ile Pro Lys Val
1               5                   10                  15

His Trp Ala Pro Leu Arg Gly Ile Pro Leu Lys Arg Arg Leu Gln Thr
            20                  25                  30

Ser Ala Ile Val Thr Trp Leu Ala Leu Leu Pro Ile Cys Leu Ile Ile
        35                  40                  45

Tyr Leu Tyr Leu Phe Thr Ile Pro Leu Leu Trp Pro Ile Leu Ile Met
    50                  55                  60

Tyr Thr Ile Trp Leu Phe Phe Asp Lys Ala Pro Glu Asn Gly Gly Arg
65                  70                  75                  80

Arg Ile Ser Leu Val Arg Lys Leu Pro Leu Trp Lys His Phe Ala Asn
```

```
                        85                  90                  95

Tyr Phe Pro Val Thr Leu Ile Lys Glu Gly Asp Leu Asp Pro Lys Gly
                100                 105                 110

Asn Tyr Ile Met Ser Tyr His Pro His Gly Ile Ile Ser Met Ala Ala
            115                 120                 125

Phe Ala Asn Phe Ala Thr Glu Ala Thr Gly Phe Ser Glu Gln Tyr Pro
130                 135                 140

Gly Ile Val Pro Ser Leu Leu Thr Leu Ala Ser Asn Phe Arg Leu Pro
145                 150                 155                 160

Leu Tyr Arg Asp Phe Met Met Ser Leu Gly Met Cys Ser Val Ser Arg
                165                 170                 175

His Ser Cys Glu Ala Ile Leu Arg Ser Gly Pro Gly Arg Ser Ile Val
            180                 185                 190

Ile Val Thr Gly Gly Ala Ser Glu Ser Leu Ser Ala Arg Pro Gly Thr
        195                 200                 205

Asn Asp Leu Thr Leu Lys Lys Arg Leu Gly Phe Ile Arg Leu Ala Ile
210                 215                 220

Arg Asn Gly Ala Ser Leu Val Pro Ile Phe Ser Phe Gly Glu Asn Asp
225                 230                 235                 240

Ile Tyr Glu Gln Tyr Asp Asn Lys Lys Gly Ser Leu Ile Trp Arg Tyr
                245                 250                 255

Gln Lys Trp Phe Gln Lys Ile Thr Gly Phe Thr Val Pro Leu Ala His
                260                 265                 270

Ala Arg Gly Ile Phe Asn Tyr Asn Ala Gly Phe Ile Pro Phe Arg His
            275                 280                 285

Pro Ile Val Thr Val Val Gly Lys Pro Ile Ala Val Pro Leu Leu Ala
290                 295                 300

Glu Gly Glu Thr Glu Pro Ser Glu Glu Gln Met His Gln Val Gln Ala
305                 310                 315                 320

Gln Tyr Ile Glu Ser Leu Gln Ala Ile Tyr Asp Lys Tyr Lys Asp Ile
                325                 330                 335

Tyr Ala Lys Asp Arg Ile Lys Asp Met Thr Met Ile Ala
            340                 345
```

<210> SEQ ID NO 102
<211> LENGTH: 566
<212> TYPE: PRT
<213> ORGANISM: Mortierella elongata

<400> SEQUENCE: 102

```
Met Ser Gln Gly Asp Ala Ile Thr Thr Ser His Ser Asp Gly Thr Glu
1               5                   10                  15

Lys Arg His Asp Ser Thr Thr Asn Ile Leu Ser Asp Val Pro Pro Gln
                20                  25                  30

Thr Glu Asp Val Lys Ser Ser Ser Lys Lys Lys Arg Ser Thr Tyr
            35                  40                  45

Arg His Thr Phe Pro Val His Thr Lys Thr Leu Pro Ser Pro Leu Ser
        50                  55                  60

Lys Glu Ala Pro Pro Glu Ser Tyr Arg Gly Phe Val Asn Leu Gly Met
65                  70                  75                  80

Leu Leu Leu Phe Gly Asn Asn Ile Arg Leu Ile Ile Glu Asn Tyr Gln
                85                  90                  95

Lys Tyr Gly Phe Leu Leu Ser Ile Pro Gly Ser Asn Val Ser Lys Gln
                100                 105                 110
```

Asp Trp Ile Leu Ala Gly Leu Thr His Ala Ile Leu Pro Leu His Val
            115                 120                 125
Ile Val Ala Tyr Gln Leu Glu Gln Trp Ala Ser Arg Lys Ala Lys Gly
130                 135                 140
Phe Arg Lys Arg Leu Ala Asp Gln Lys Glu Asn Pro Thr Thr Lys Asp
145                 150                 155                 160
Asp Glu Asp Lys Lys Ala Val Pro Ala Gly Asp Lys Val Arg Gly Gly
            165                 170                 175
Lys Lys Asp Lys Lys Asn Leu Thr Leu Glu Glu Gln Ile Lys Glu Asn
            180                 185                 190
Arg Lys Thr Val Gly Trp Leu His Phe Ala Asn Val Ser Leu Ile Leu
            195                 200                 205
Gly Trp Pro Ser Phe Met Ser Tyr Phe Val Ile Phe His Pro Phe Leu
210                 215                 220
Ala Met Gly Cys Leu Met Thr Ser Leu Ile Leu Phe Leu Lys Met Val
225                 230                 235                 240
Ser Phe Ala Leu Val Asn Gln Asp Leu Arg Tyr Ala Tyr Ile Gln Asp
            245                 250                 255
Thr Pro Ala Thr Glu Gln Ser Ser Pro His Leu Thr Lys Val His Asn
            260                 265                 270
Asp Thr Ile Thr Thr Thr Asn Thr Thr Ser Asp Gly Ala Thr Thr Thr
            275                 280                 285
Thr Thr Leu Thr Thr Thr Thr Val Val Lys Thr Ile Thr Val Lys
            290                 295                 300
Lys Asp Ala Glu Lys His Gly Gly Ala Tyr Gln Tyr Glu Val His Tyr
305                 310                 315                 320
Pro Gln Asn Ile Thr Pro Gly Asn Ile Gly Tyr Phe Tyr Leu Ala Pro
            325                 330                 335
Thr Leu Cys Tyr Gln Pro Ser Tyr Pro Arg Ser Thr Val Phe Arg Pro
            340                 345                 350
Ser Phe Phe Phe Lys Arg Val Leu Glu Ile Val Thr Cys Leu Gly Met
            355                 360                 365
Met Tyr Phe Leu Ile Glu Gln Tyr Ala Thr Pro Thr Leu Gln Asn Ser
370                 375                 380
Val Arg Ala Phe Asp Glu Leu Ala Phe Gly Arg Leu Leu Glu Arg Val
385                 390                 395                 400
Leu Lys Leu Ser Thr Thr Ser Val Ile Ile Trp Leu Leu Met Phe Tyr
            405                 410                 415
Thr Phe Phe His Ala Phe Phe Asn Ala Leu Ala Glu Val Leu Tyr Phe
            420                 425                 430
Gly Asp Arg Arg Phe Tyr Leu Ser Trp Trp Asn Ala Thr Ser Val Gly
            435                 440                 445
Met Tyr Trp Lys Thr Trp Asn Ser Pro Val Tyr Thr Phe Phe Lys Arg
450                 455                 460
His Val Tyr Leu Pro Met Ile Thr Ser Gly His Ser Ala Leu Thr Ala
465                 470                 475                 480
Ser Val Val Ile Phe Thr Ile Ser Ala Leu Leu His Glu Val Leu Ile
            485                 490                 495
Gly Ile Pro Thr Lys Met Ile Tyr Gly Tyr Ala Phe Ala Gly Met Phe
            500                 505                 510
Phe Gln Ile Pro Leu Ile Ala Leu Thr Ala Pro Leu Glu Lys Trp Arg
            515                 520                 525
Gly Thr Gly Ser Gly Leu Gly Asn Met Ile Phe Trp Val Ser Phe Thr

```
              530                 535                 540
Ile Leu Gly Gln Pro Ala Cys Ala Leu Leu Tyr Tyr Tyr His Trp Thr
545                 550                 555                 560

Lys Arg Ser Met Asn Ala
                565

<210> SEQ ID NO 103
<211> LENGTH: 331
<212> TYPE: PRT
<213> ORGANISM: Mortierella alpina

<400> SEQUENCE: 103

Met Pro Leu Phe Ala Pro Leu Arg Met Pro Ile Gln Arg Arg Met Gln
1               5                   10                  15

Thr Gly Ala Val Leu Leu Trp Ile Ser Gly Ile Ile Tyr Thr Leu Gly
            20                  25                  30

Ile Phe Val Phe Leu Cys Thr Phe Lys Val Leu Arg Pro Leu Ile Ile
        35                  40                  45

Ile Tyr Leu Leu Trp Ala Phe Met Leu Asp Arg Gly Pro Gln Arg Gly
    50                  55                  60

Ala Arg Ala Val Gln Trp Tyr Arg Asn Trp Val Gly Trp Lys His Phe
65                  70                  75                  80

Ala Gln Tyr Phe Pro Met Thr Leu Val Lys Glu Gly Glu Leu Asp Pro
                85                  90                  95

Ser Lys Asn Tyr Ile Phe Gly Tyr His Pro His Gly Ile Ile Ser Leu
            100                 105                 110

Gly Ala Phe Cys Thr Phe Gly Thr Glu Gly Leu His Phe Ser Lys Arg
        115                 120                 125

Phe Pro Gly Ile Lys Pro Gln Leu Leu Thr Leu His Ala Asn Phe Gln
130                 135                 140

Ile Pro Leu Tyr Arg Glu Met Val Met Ala His Gly Cys Ala Ser Val
145                 150                 155                 160

Ser Arg Ala Ser Cys Glu His Ile Leu Arg Ser Gly Glu Gly Cys Ser
                165                 170                 175

Val Val Ile Val Val Gly Gly Ala Gln Glu Ser Leu Ser Thr Gln Pro
            180                 185                 190

Gly Thr Leu Asn Leu Thr Leu Lys Lys Arg Leu Gly Phe Cys Lys Leu
        195                 200                 205

Ala Leu Val Asn Gly Ala Ser Leu Val Pro Thr Leu Ala Phe Gly Glu
210                 215                 220

Asn Glu Leu Tyr Glu Val Tyr Thr Ala Lys Pro Lys Ser Leu Met Tyr
225                 230                 235                 240

Lys Ile Gln Gln Phe Ala Lys Arg Thr Met Gly Phe Thr Met Pro Val
                245                 250                 255

Phe Asn Gly Arg Gly Val Phe Asn Tyr Glu Phe Gly Leu Leu Pro Arg
            260                 265                 270

Arg Lys Pro Val Tyr Ile Val Val Gly Lys Pro Ile His Val Asp Lys
        275                 280                 285

Val Glu Asn Pro Thr Val Glu Gln Met Gln Lys Leu Gln Ser Ile Tyr
290                 295                 300

Ile Asp Glu Val Leu Asn Ile Trp Glu Arg Tyr Lys Asp Lys Tyr Ala
305                 310                 315                 320

Ala Gly Arg Thr Gln Glu Leu Cys Ile Ile Glu
                325                 330
```

```
<210> SEQ ID NO 104
<211> LENGTH: 393
<212> TYPE: PRT
<213> ORGANISM: Nannochloropsis oceanica

<400> SEQUENCE: 104

Met Tyr Pro Ile Lys Leu Cys Phe Leu Phe Ile Leu Thr Ile Pro Pro
1               5                   10                  15

Tyr Ala His Val Arg Thr Arg Thr Pro His Arg Arg Gly Thr Thr Ser
            20                  25                  30

Lys Met Ala Lys Ala Asn Phe Pro Pro Ser Ala Arg Tyr Val Asn Met
        35                  40                  45

Thr Gln Val Tyr Ala Thr Gly Ala His Asn Met Pro Asp Glu Asp Arg
    50                  55                  60

Leu Lys Val Met Asn Gly Leu Ser Lys Pro Leu Thr Glu Ala Lys Pro
65                  70                  75                  80

Gly Asp Leu Gly Phe Gly Asp Val Glu Ser Met Thr Phe Cys Glu Glu
                85                  90                  95

Phe Val Ala Ile Met Phe Leu Leu Ile Ile Val Gly Ser Met Leu Trp
            100                 105                 110

Ile Pro Ile Ala Val Leu Gly Phe Ala Leu Tyr Val Arg Ser Ala Met
        115                 120                 125

Ala Trp Val Val Met Leu Ile Val Phe Phe Thr Leu Ser Leu His Pro
    130                 135                 140

Val Pro Arg Ile His Asp Met Val His Ser Pro Leu Asn His Phe Ile
145                 150                 155                 160

Phe Lys Tyr Phe Ser Leu Lys Met Ala Ser Asp Ala Pro Leu Asp Ser
                165                 170                 175

Ala Gly Arg Tyr Ile Phe Val Ala Pro Pro His Gly Val Leu Pro Met
            180                 185                 190

Gly Asn Leu Met Thr Val His Ala Met Lys Ala Cys Gly Gly Leu Glu
        195                 200                 205

Phe Arg Gly Leu Thr Thr Asp Val Ala Leu Arg Leu Pro Leu Phe Arg
    210                 215                 220

His Tyr Leu Gly Ala Ile Gly Thr Ile Ala Ala Thr Arg His Val Ala
225                 230                 235                 240

Lys Gln Tyr Leu Asp Lys Gly Trp Ser Ile Gly Ile Ser Ser Gly Gly
                245                 250                 255

Val Ala Glu Ile Phe Glu Val Asn Asn Lys Asp Glu Val Val Leu Met
            260                 265                 270

Lys Glu Arg Lys Gly Phe Val Lys Leu Ala Leu Arg Thr Gly Thr Pro
        275                 280                 285

Leu Val Ala Cys Tyr Ile Phe Gly Asn Thr Lys Leu Leu Ser Ala Trp
    290                 295                 300

Tyr Asp Asp Gly Gly Val Leu Glu Gly Leu Ser Arg Tyr Leu Lys Cys
305                 310                 315                 320

Gly Val Leu Pro Leu Trp Gly Arg Phe Gly Leu Pro Leu Met His Arg
                325                 330                 335

His Pro Val Leu Gly Ala Met Ala Lys Pro Ile Val Pro Lys Val
            340                 345                 350

Glu Gly Glu Pro Thr Gln Glu Met Ile Asp Glu Tyr His Ser Leu Phe
        355                 360                 365

Cys Gln Thr Leu Val Asp Leu Phe Asp Arg Tyr Lys Thr Leu Tyr Gly
    370                 375                 380
```

Trp Pro Asp Lys Lys Leu Leu Ile Lys
385                 390

<210> SEQ ID NO 105
<211> LENGTH: 179
<212> TYPE: PRT
<213> ORGANISM: Nannochloropsis gaditana

<400> SEQUENCE: 105

Met Gly His Val Gly Lys Leu Asp Leu Leu Lys Ala Leu Gly Glu Leu
1               5                   10                  15

Leu Arg Leu Ala Ile Pro Ser Thr Phe Val Trp Leu Ile Thr Phe Tyr
            20                  25                  30

Val Tyr Phe His Cys Thr Leu Asn Leu Phe Ala Glu Ile Thr Arg Phe
        35                  40                  45

Gly Asp Arg Leu Phe Phe Lys Asp Trp Trp Asn Cys Thr Ser Phe Ser
    50                  55                  60

Arg Tyr Trp Arg Thr Trp Asn Leu Pro Val His Gln Phe Leu Val Arg
65                  70                  75                  80

His Val Tyr Phe Pro Leu Leu Arg Ala Gly Ala Ser Lys Met Thr Ala
                85                  90                  95

Asn Val Thr Val Phe Ala Val Ser Ala Phe Phe His Glu Leu Leu Ile
            100                 105                 110

Ser Ile Pro Cys His Val Val Arg Leu Trp Ala Phe Leu Ala Met Met
        115                 120                 125

Gly Gln Ile Pro Leu Ile Tyr Ile Thr Asp His Leu Asp Lys Thr Leu
    130                 135                 140

Phe Lys Glu Thr Gln Ala Gly Asn Tyr Met Phe Trp Leu Ile Phe Cys
145                 150                 155                 160

Ile Phe Gly Gln Pro Met Ala Val Leu Leu Tyr Tyr Ala Asp Phe Ser
                165                 170                 175

Ala Arg Ser

<210> SEQ ID NO 106
<211> LENGTH: 279
<212> TYPE: PRT
<213> ORGANISM: Nannochloropsis gaditana

<400> SEQUENCE: 106

Met Val Cys Pro Leu Arg Ser Leu Val Arg Asp Tyr Arg Lys Thr Gln
1               5                   10                  15

Gly Leu Val Thr Ser Pro His Arg Ser His Gly Pro Asp Met Ser Phe
            20                  25                  30

Lys Cys Lys Pro Ser Gln Lys Pro Asn Lys Gln Phe Trp Arg Tyr Ala
        35                  40                  45

Ser Phe Leu Ala Phe Ile Ala Thr Phe Leu Leu Val Pro Ser Thr Thr
    50                  55                  60

Ser Trp Ala Ser Ala Leu His Arg Ala Cys Phe Met Ala Tyr Val Met
65                  70                  75                  80

Thr Tyr Leu Asp Thr Ser Tyr Arg Asp Gly Ser Arg Ala Trp Pro Trp
                85                  90                  95

Phe Gln Arg Leu Pro Val Trp Arg Leu Tyr Cys Arg Tyr Ile Lys Gly
            100                 105                 110

Gln Val Ile Thr Thr Val Pro Leu Asp Pro His Arg Gln Tyr Ile Phe
        115                 120                 125

Ala Ala His Pro His Gly Ile Ala Thr Trp Asn His Phe Leu Thr Met
130                 135                 140

Thr Asp Gly Cys Arg Phe Leu Ser Arg Ile Tyr Pro Arg Pro Arg Leu
145                 150                 155                 160

Asp Leu Gly Ala Thr Val Leu Phe Phe Ile Pro Leu Val Lys Glu Val
                165                 170                 175

Leu Leu Trp Val Gly Cys Val Asp Ala Gly Ala Thr Ala Asn Ala
                180                 185                 190

Ile Leu Glu Arg Gly Phe Ser Ser Leu Ile Tyr Val Gly Gly Glu Lys
                195                 200                 205

Glu Gln Ile Leu Thr Glu Arg Gly Arg Asp Leu Val Val Val Leu Pro
210                 215                 220

Arg Lys Gly Phe Cys Lys Leu Ala Leu Arg Tyr Asp Cys Pro Ile Val
225                 230                 235                 240

Pro Ala Tyr Ala Phe Gly Glu Asn Asp Leu Tyr Arg Thr Phe Asn Tyr
                245                 250                 255

Phe Lys Gly Leu Gln Leu Trp Val Glu Arg His Ala Gly Arg Val Val
                260                 265                 270

Pro Arg Asn Arg Ser Glu His
                275

<210> SEQ ID NO 107
<211> LENGTH: 363
<212> TYPE: PRT
<213> ORGANISM: Nannochloropsis oceanica

<400> SEQUENCE: 107

Met Thr Pro Gln Ala Asp Ile Thr Ser Lys Thr Thr Pro Asn Leu Lys
1               5                   10                  15

Thr Ala Ala Ser Ser Pro Ser Lys Thr Ser Pro Ala Pro Ser Val Gln
                20                  25                  30

Tyr Lys Ala Ala Asn Gly Lys Val Ile Thr Val Ala Met Ala Glu Gln
                35                  40                  45

Asp Asp Gly Asn Met Gly Ile Phe Arg Glu Cys Phe Ala Met Val Thr
            50                  55                  60

Met Gly Ile Ile Met Ser Trp Tyr Tyr Ile Val Val Ile Leu Ser Leu
65                  70                  75                  80

Leu Cys Leu Val Gly Ile Cys Ile Phe Pro Ala Trp Arg Ala Val Ala
                85                  90                  95

Ala Thr Val Phe Val Leu Met Trp Ser Ala Ala Leu Leu Pro Leu Asp
                100                 105                 110

Tyr Gln Gly Trp Asp Ala Phe Cys Asn Ser Phe Ile Phe Arg Leu Trp
                115                 120                 125

Arg Asp Tyr Phe His Tyr Glu Tyr Val Leu Glu Glu Met Ile Asp Pro
            130                 135                 140

Asn Lys Arg Tyr Leu Phe Ala Glu Met Pro His Gly Ile Phe Pro Trp
145                 150                 155                 160

Gly Glu Val Ile Ser Ile Ser Ile Thr Lys Gln Leu Phe Pro Gly Ser
                165                 170                 175

Arg Val Gly Ser Ile Gly Ala Ser Val Ile Phe Leu Leu Pro Gly Leu
                180                 185                 190

Arg His Phe Phe Ala Trp Ile Gly Cys Arg Pro Ala Ser Pro Glu Asn
                195                 200                 205

Ile Lys Lys Ile Phe Glu Asp Gly Gln Asp Cys Ala Val Thr Val Gly
                210                 215                 220

Gly Val Ala Glu Met Phe Leu Val Gly Gly Asp Lys Glu Arg Leu Tyr
225                 230                 235                 240

Leu Lys Lys His Lys Gly Phe Val Arg Glu Ala Met Lys Asn Gly Ala
            245                 250                 255

Asp Leu Val Pro Val Phe Cys Phe Gly Asn Ser Lys Leu Phe Asn Val
            260                 265                 270

Val Gly Glu Ser Ser Arg Val Ser Met Gly Leu Met Lys Arg Leu Ser
        275                 280                 285

Arg Arg Ile Lys Ala Ser Val Leu Ile Phe Tyr Gly Arg Leu Phe Leu
    290                 295                 300

Pro Ile Pro Ile Arg His Pro Leu Leu Phe Val Val Gly Lys Pro Leu
305                 310                 315                 320

Pro Val Val His Lys Ala Glu Pro Thr Lys Glu Glu Ile Ala Ala Thr
                325                 330                 335

His Ala Leu Phe Cys Glu Lys Val Glu Glu Leu Tyr Tyr Lys Tyr Arg
            340                 345                 350

Pro Glu Trp Glu Thr Arg Pro Leu Ser Ile Glu
            355                 360

<210> SEQ ID NO 108
<211> LENGTH: 540
<212> TYPE: PRT
<213> ORGANISM: Mortierella elongata

<400> SEQUENCE: 108

Met Asp Lys Gln Gln Pro Asp Ile Val Thr Met Ile Pro Gly Ile Val
1               5                   10                  15

Ser Thr Gly Leu Glu Ser Trp Ser Thr Thr Asn Asn Ser Cys Ser Gln
            20                  25                  30

Lys Tyr Phe Arg Lys Arg Met Trp Gly Thr Thr Met Phe Lys Ala
        35                  40                  45

Val Leu Leu Asp Lys Asp Cys Trp Ile Thr Asn Leu Arg Leu Asp Pro
    50                  55                  60

Glu Thr Gly Val Asp Pro Glu Gly Val Arg Leu Arg Ala Ala Gln Gly
65                  70                  75                  80

Leu Glu Ala Ala Asp Tyr Phe Val Gln Gly Tyr Trp Val Trp Ala Pro
                85                  90                  95

Ile Ile Lys Asn Leu Ala Ala Ile Gly Tyr Asp Asn Asn Met Tyr
            100                 105                 110

Leu Ala Ser Tyr Asp Trp Arg Leu Ser Phe Ala Asn Leu Glu Asn Arg
        115                 120                 125

Asp Asn Tyr Phe Ser Arg Leu Lys Ser Asn Leu Glu Leu Ser Leu Lys
    130                 135                 140

Met Thr Gly Glu Lys Ser Val Leu Val Ala His Ser Met Gly Ser Asn
145                 150                 155                 160

Val Met Phe Tyr Phe Lys Trp Val Glu Ser Asp Lys Gly Gly Lys
                165                 170                 175

Gly Gly Pro Asn Trp Val Asn Asp His Val His Thr Phe Val Asn Ile
            180                 185                 190

Ala Gly Pro Met Leu Gly Val Pro Lys Thr Leu Ala Ala Val Leu Ser
        195                 200                 205

Gly Glu Val Arg Asp Thr Ala Gln Leu Gly Val Val Ser Ala Tyr Val
    210                 215                 220

Leu Glu Lys Phe Phe Ser Arg Arg Glu Arg Ala Asp Leu Phe Arg Ser

```
                  225                 230                 235                 240
Trp Gly Gly Leu Ser Ser Met Ile Pro Lys Gly Gly Asn Arg Ile Trp
                245                 250                 255

Gly Thr Ile His Gly Ala Pro Asp Asp Gly Thr His Asp Glu Glu Glu
            260                 265                 270

Thr Val Arg Asn Glu Lys Ile Ala Lys Ser Glu Thr Pro Gly Ala
        275                 280                 285

Thr Thr Lys Arg Lys His Gly Glu Gln Ser Pro Thr Phe Gly Ala Met
    290                 295                 300

Leu Ala Phe Ala Glu Gly Ser Asn Met Glu Asn His Gly Met Asp Glu
305                 310                 315                 320

Ser Met Gly Leu Leu Ser Lys Met Ala Gly Asn Ala Tyr Asn Thr Met
                325                 330                 335

Leu Ala Lys Asn Tyr Thr Val Gly Ala Ser Val Thr Gln Lys Gln Met
            340                 345                 350

Asp Lys Thr Thr Lys Asp Pro Ala Ser Trp Thr Asn Pro Leu Glu Ala
        355                 360                 365

Thr Leu Pro Tyr Ala Pro Lys Met Lys Ile Tyr Cys Leu Tyr Gly Val
    370                 375                 380

Gly Lys Ser Thr Glu Arg Ser Tyr Thr Tyr Asn Arg Val Ser Asp Leu
385                 390                 395                 400

Ala Pro Gln Ile Phe Asp Gln Arg Pro Gly Asn Val Ser Asp Glu Thr
                405                 410                 415

Gly Gln Val Pro Asn Ile Tyr Ile Asp Thr Thr Val His Asp Asp Lys
            420                 425                 430

Leu Gly Ile Ser Tyr Gly Val His Gln Gly Asp Gly Asp Gly Thr Val
        435                 440                 445

Pro Leu Met Ser Thr Gly Tyr Met Cys Val Asp Gly Trp Ser Lys Lys
    450                 455                 460

Leu Tyr Asn Pro Ala Gly Leu Lys Val Ile Thr Arg Glu Phe Thr His
465                 470                 475                 480

Gln Ser Ser Leu Ser Pro Val Asp Ile Arg Gly Gly Lys Arg Thr Ala
                485                 490                 495

Asp His Val Asp Ile Leu Gly Asn Tyr Gln Val Thr Lys Asp Leu Leu
            500                 505                 510

Ala Ile Val Ala Gly Arg Asp Gly Asp Gly Leu Glu Glu Gln Ile Tyr
        515                 520                 525

Ser Lys Ile Lys Glu Tyr Ser Ala Lys Val Asp Leu
    530                 535                 540

<210> SEQ ID NO 109
<211> LENGTH: 373
<212> TYPE: PRT
<213> ORGANISM: Nannochloropsis oceanica

<400> SEQUENCE: 109

Met Ala His Leu Phe Arg Arg Arg Ser Lys Gly Glu Gly Asn Ser Thr
1               5                   10                  15

Ser Ser Arg Cys Leu Ser Leu Ser Glu Gly Asn Lys Ala Met Leu Ile
            20                  25                  30

Leu Ser Ser Glu Ile Glu Pro Pro Ala Ser Ala Thr Ser Lys Ala Ala
        35                  40                  45

Thr Ser Gly Ile Lys Glu Ile Gly Asp Pro Ser Leu Pro Thr Val Ala
    50                  55                  60
```

Leu Leu Ser Leu Pro Ser Ile Ser Lys Ala Asp Thr Asn Ser Ala Thr
65                  70                  75                  80

Ala Ala Val Ala Ala Gly Thr Leu Glu Asp Ala Ala Gly Ala Leu
            85                  90                  95

Thr Ala Pro Phe Ala Asp Arg Ser Val Lys Lys Gln Tyr Gly Gln Asp
            100                 105                 110

Gly Asp Gly Ala Gln Cys Lys Glu Ala Glu Gly Gly Arg Lys Arg Ser
            115                 120                 125

Gly Ser Val Gly Asn Leu Leu Ser Ser Met Thr Ser Phe Ser Lys
130                 135                 140

Gly Thr Ser Leu Ser Phe Leu Thr Gly Glu Asp Lys Thr Pro Ser Pro
145                 150                 155                 160

Pro Glu Thr Gly Pro Ala Gly Ile Asp Phe Ser Thr Pro Ala His Pro
            165                 170                 175

Thr Met Gln Phe Val Asp Phe Ile Ile Thr Phe Leu Leu Val His Tyr
            180                 185                 190

Ile Gln Val Phe Tyr Ser Leu Val Phe Leu Phe Ile Tyr Leu Val Lys
            195                 200                 205

His Gly His Arg Trp Pro Tyr Phe Leu Ala Ala Ile Tyr Ala Pro Ser
210                 215                 220

Tyr Phe Ile Pro Leu Gln Arg Leu Gly Gly Trp Pro Phe Lys Gly Phe
225                 230                 235                 240

Met Arg Arg Pro Phe Trp Arg Cys Val Gln Arg Thr Leu Ala Leu Gln
            245                 250                 255

Val Glu Arg Glu Val Glu Leu Ser Pro Asp Glu Gln Tyr Ile Phe Gly
            260                 265                 270

Trp His Pro Glu Val Ser Ile Leu Leu Gly Gly Ser Lys Glu Ile
            275                 280                 285

Tyr Thr Thr Asp Pro Tyr Thr Pro Glu Thr Thr Leu Val Leu Lys Ile
            290                 295                 300

Arg Lys Gly Phe Ile Arg Met Ala Leu Arg Tyr Gly Cys Ala Leu Val
305                 310                 315                 320

Pro Val Tyr Thr Phe Gly Glu Lys Tyr Ala Tyr His Arg Leu Gly Gln
            325                 330                 335

Ala Thr Gly Phe Ala Arg Trp Leu Leu Ala Val Leu Lys Val Pro Phe
            340                 345                 350

Leu Ile Phe Trp Gly Arg His Lys His Lys Tyr Ala Lys Pro Glu Glu
            355                 360                 365

Phe Val Ala Ile Ser
            370

<210> SEQ ID NO 110
<211> LENGTH: 352
<212> TYPE: PRT
<213> ORGANISM: Nannochloropsis gaditana

<400> SEQUENCE: 110

Met Met Ser Lys Ser Leu Ile Met Leu Gly Leu Leu Ser Pro Thr Ala
1               5                   10                  15

Phe Ala Phe Val Pro Lys Leu Ser Thr Asn Val Leu Ser Arg Ala Ile
            20                  25                  30

Ser Ser His Ala Arg Lys Asn Leu Val Lys Ala Ser Ala Val Asp Tyr
            35                  40                  45

Lys Thr Ala Phe Met Phe Pro Gly Gln Gly Ala Gln Tyr Val Gly Met
50                  55                  60

```
Gly Ala Gln Val Ser Glu Val Pro Ala Ala Lys Ala Leu Phe Glu
 65                  70                  75                  80

Lys Ala Ser Glu Ile Leu Gly Tyr Asp Leu Leu Asp Arg Ala Met Asn
                 85                  90                  95

Gly Pro Lys Asp Leu Leu Asp Ser Thr Ala Val Ser Gln Pro Ala Ile
            100                 105                 110

Phe Val Ala Ser Ala Ala Ala Val Glu Lys Leu Arg Ala Thr Glu Gly
            115                 120                 125

Glu Asp Ala Ala Asn Ala Ala Thr Val Ala Met Gly Leu Ser Leu Gly
130                 135                 140

Glu Tyr Ser Ala Leu Cys Tyr Ala Gly Ala Phe Ser Phe Glu Asp Gly
145                 150                 155                 160

Val Arg Leu Thr Lys Ala Arg Gly Glu Ala Met Gln Ala Ala Ala Asp
                165                 170                 175

Leu Val Asp Thr Thr Met Val Ser Val Ile Gly Leu Glu Ala Asp Lys
                180                 185                 190

Val Asn Glu Leu Cys Ala Ala Ala Ser Ser Lys Ser Gly Glu Lys Ile
            195                 200                 205

Gln Ile Ala Asn Tyr Leu Cys Pro Gly Asn Tyr Ala Val Ser Gly Ser
210                 215                 220

Leu Lys Ala Ala Gln Val Leu Glu Glu Ile Ala Lys Pro Glu Phe Gly
225                 230                 235                 240

Ala Arg Met Thr Val Arg Leu Ala Val Ala Gly Ala Phe His Thr Glu
                245                 250                 255

Tyr Met Ala Pro Ala Leu Glu Lys Lys Glu Val Leu Ala Lys Thr
                260                 265                 270

Glu Phe Lys Thr Pro Arg Ile Pro Val Ile Ser Asn Val Asp Gly Lys
            275                 280                 285

Pro His Ser Asp Pro Glu Glu Ile Lys Ala Ile Leu Ala Lys Gln Val
290                 295                 300

Thr Ser Pro Val Gln Trp Glu Thr Thr Met Asn Asp Leu Val Lys Gly
305                 310                 315                 320

Gly Leu Glu Thr Gly Tyr Glu Leu Gly Pro Gly Lys Val Cys Ala Gly
                325                 330                 335

Ile Leu Lys Arg Ile Asp Arg Lys Ala Lys Met Val Asn Ile Glu Ala
            340                 345                 350

<210> SEQ ID NO 111
<211> LENGTH: 634
<212> TYPE: PRT
<213> ORGANISM: Pseudomonas aeruginosa

<400> SEQUENCE: 111

Met Ser Arg Leu Pro Val Ile Val Gly Phe Gly Gly Tyr Asn Ala Ala
1                   5                  10                  15

Gly Arg Ser Ser Phe His His Gly Phe Arg Arg Met Val Ile Glu Ser
                20                  25                  30

Met Asp Pro Gln Ala Arg Gln Glu Thr Leu Ala Gly Leu Ala Val Met
            35                  40                  45

Met Lys Leu Val Lys Ala Glu Gly Gly Arg Tyr Leu Ala Glu Asp Gly
        50                  55                  60

Thr Pro Leu Ser Pro Glu Asp Ile Glu Arg Arg Tyr Ala Glu Arg Ile
65                  70                  75                  80

Phe Ala Ser Thr Leu Val Arg Arg Ile Glu Pro Gln Tyr Leu Asp Pro
```

```
                       85                  90                  95
Asp Ala Val His Trp His Lys Val Leu Glu Leu Ser Pro Ala Glu Gly
                100                 105                 110

Gln Ala Leu Thr Phe Lys Ala Ser Pro Lys Gln Leu Pro Glu Pro Leu
            115                 120                 125

Pro Ala Asn Trp Ser Ile Ala Pro Ala Glu Asp Gly Glu Val Leu Val
        130                 135                 140

Ser Ile His Glu Arg Cys Glu Phe Lys Val Asp Ser Tyr Arg Ala Leu
145                 150                 155                 160

Thr Val Lys Ser Ala Gly Gln Leu Pro Thr Gly Phe Glu Pro Gly Glu
                165                 170                 175

Leu Tyr Asn Ser Arg Phe His Pro Arg Gly Leu Gln Met Ser Val Val
                180                 185                 190

Ala Ala Thr Asp Ala Ile Arg Ser Thr Gly Ile Asp Trp Lys Thr Ile
            195                 200                 205

Val Asp Asn Val Gln Pro Asp Glu Ile Ala Val Phe Ser Gly Ser Ile
        210                 215                 220

Met Ser Gln Leu Asp Asp Asn Gly Phe Gly Gly Leu Met Gln Ser Arg
225                 230                 235                 240

Leu Lys Gly His Arg Val Ser Ala Lys Gln Leu Pro Leu Gly Phe Asn
                245                 250                 255

Ser Met Pro Thr Asp Phe Ile Asn Ala Tyr Val Leu Gly Ser Val Gly
                260                 265                 270

Met Thr Gly Ser Ile Thr Gly Ala Cys Ala Thr Phe Leu Tyr Asn Leu
            275                 280                 285

Gln Lys Gly Ile Asp Val Ile Thr Ser Gly Gln Ala Arg Val Val Ile
        290                 295                 300

Val Gly Asn Ser Glu Ala Pro Ile Leu Pro Glu Cys Ile Glu Gly Tyr
305                 310                 315                 320

Ser Ala Met Gly Ala Leu Ala Thr Glu Glu Gly Leu Arg Leu Ile Glu
                325                 330                 335

Gly Arg Asp Asp Val Asp Phe Arg Arg Ala Ser Arg Pro Phe Gly Glu
                340                 345                 350

Asn Cys Gly Phe Thr Leu Ala Glu Ser Ser Gln Tyr Val Val Leu Met
            355                 360                 365

Asp Asp Glu Leu Ala Leu Arg Leu Gly Ala Asp Ile His Gly Ala Val
        370                 375                 380

Thr Asp Val Phe Ile Asn Ala Asp Gly Phe Lys Lys Ser Ile Ser Ala
385                 390                 395                 400

Pro Gly Pro Gly Asn Tyr Leu Thr Val Ala Lys Ala Val Ala Ser Ala
                405                 410                 415

Val Gln Ile Val Gly Leu Asp Thr Val Arg His Ala Ser Phe Val His
                420                 425                 430

Ala His Gly Ser Ser Thr Pro Ala Asn Arg Val Thr Glu Ser Glu Ile
            435                 440                 445

Leu Asp Arg Val Ala Ser Ala Phe Gly Ile Asp Gly Trp Pro Val Thr
        450                 455                 460

Ala Val Lys Ala Tyr Val Gly His Ser Leu Ala Thr Ala Ser Ala Asp
465                 470                 475                 480

Gln Leu Ile Ser Ala Leu Gly Thr Phe Lys Tyr Gly Ile Leu Pro Gly
                485                 490                 495

Ile Lys Thr Ile Asp Lys Val Ala Asp Val His Gln Gln Arg Leu
                500                 505                 510
```

```
Ser Ile Ser Asn Arg Asp Met Arg Gln Asp Lys Pro Leu Glu Val Cys
        515                 520                 525

Phe Ile Asn Ser Lys Gly Phe Gly Gly Asn Asn Ala Ser Gly Val Val
530                 535                 540

Leu Ser Pro Arg Ile Ala Glu Lys Met Leu Arg Lys Arg His Gly Gln
545                 550                 555                 560

Ala Ala Phe Ala Ala Tyr Val Glu Lys Arg Glu Gln Thr Arg Ala Ala
                565                 570                 575

Ala Arg Ala Tyr Asp Gln Arg Ala Leu Gln Gly Asp Leu Glu Ile Ile
            580                 585                 590

Tyr Asn Phe Gly Gln Asp Leu Ile Asp Glu His Ala Ile Glu Val Ser
        595                 600                 605

Ala Glu Gln Val Thr Val Pro Gly Phe Ser Gln Pro Leu Val Tyr Lys
    610                 615                 620

Lys Asp Ala Arg Phe Ser Asp Met Leu Asp
625                 630

<210> SEQ ID NO 112
<211> LENGTH: 487
<212> TYPE: PRT
<213> ORGANISM: Nannochloropsis oceanica

<400> SEQUENCE: 112

Met Ala His Leu Phe Arg Arg Ser Lys Gly Glu Gly Asn Ser Thr
1               5                   10                  15

Ser Ser Arg Cys Leu Ser Leu Ser Glu Gly Asn Lys Ala Met Leu Ile
            20                  25                  30

Leu Ser Ser Glu Ile Glu Pro Pro Ala Ser Ala Thr Ser Lys Ala Ala
        35                  40                  45

Thr Ser Gly Ile Lys Glu Ile Gly Asp Pro Ser Leu Pro Thr Val Ala
    50                  55                  60

Leu Leu Ser Leu Pro Ser Ile Ser Lys Ala Asp Lys Asn Ser Ala Thr
65                  70                  75                  80

Ala Ala Val Ala Ala Gly Thr Leu Glu Asp Ala Ala Ala Gly Ala Leu
                85                  90                  95

Thr Ala Pro Phe Ala Asp Arg Ser Val Lys Lys Gln Tyr Gly Gln Asp
            100                 105                 110

Gly Asp Gly Ala Gln Cys Lys Glu Ala Glu Gly Gly Arg Lys Arg Ser
        115                 120                 125

Gly Ser Val Gly Asn Leu Leu Leu Ser Ser Met Thr Ser Phe Ser Lys
    130                 135                 140

Gly Thr Ser Leu Ser Phe Leu Thr Gly Glu Asp Lys Thr Pro Ser Pro
145                 150                 155                 160

Pro Glu Thr Gly Pro Ala Gly Ile Asp Phe Ser Thr Pro Ala His Pro
                165                 170                 175

Thr Met Gln Phe Val Asp Phe Ile Ile Thr Phe Leu Leu Val His Tyr
            180                 185                 190

Ile Gln Val Phe Tyr Ser Leu Val Phe Leu Phe Ile Tyr Leu Val Lys
        195                 200                 205

His Gly His Arg Trp Pro Tyr Phe Leu Ala Ala Ile Tyr Ala Pro Ser
    210                 215                 220

Tyr Phe Ile Pro Leu Gln Arg Leu Gly Gly Trp Pro Phe Lys Gly Phe
225                 230                 235                 240

Met Arg Arg Pro Phe Trp Arg Cys Val Gln Arg Thr Leu Ala Leu Gln
```

-continued

```
                245                 250                 255
Val Glu Arg Glu Val Glu Leu Ser Pro Asp Glu Gln Tyr Ile Phe Gly
            260                 265                 270

Trp His Pro His Gly Ile Leu Leu Leu Ser Arg Phe Ala Ile Tyr Gly
        275                 280                 285

Gly Leu Trp Glu Lys Leu Phe Pro Gly Ile His Phe Lys Thr Leu Ala
    290                 295                 300

Ala Ser Pro Leu Phe Trp Ile Pro Pro Ile Arg Glu Val Ser Ile Leu
305                 310                 315                 320

Leu Gly Gly Val Asp Ala Gly Arg Ala Ser Ala Ala Arg Ala Leu Thr
                325                 330                 335

Asp Gly Tyr Ser Val Ser Leu Tyr Pro Gly Gly Ser Lys Glu Ile Tyr
            340                 345                 350

Thr Thr Asp Pro Tyr Thr Pro Glu Thr Thr Leu Val Leu Lys Ile Arg
        355                 360                 365

Lys Gly Phe Ile Arg Met Ala Leu Arg Tyr Gly Cys Ala Leu Val Pro
    370                 375                 380

Val Tyr Thr Phe Gly Glu Lys Tyr Ala Tyr His Arg Leu Gly Gln Ala
385                 390                 395                 400

Thr Gly Phe Ala Arg Trp Leu Leu Ala Val Leu Lys Val Pro Phe Leu
                405                 410                 415

Ile Phe Trp Gly Arg Trp Gly Thr Phe Met Pro Leu Lys Glu Thr Gln
            420                 425                 430

Val Ser Val Val Val Gly Thr Pro Leu Arg Val Pro Lys Ile Glu Gly
        435                 440                 445

Glu Pro Ser Pro Glu Val Val Glu Glu Trp Leu His Lys Tyr Cys Asp
    450                 455                 460

Glu Val Gln Ala Leu Phe Arg Arg His Lys His Lys Tyr Ala Lys Pro
465                 470                 475                 480

Glu Glu Phe Val Ala Ile Ser
                485
```

LIPID BIOSYNTHESIS AND ABIOTIC STRESS RESILIENCE IN PHOTOSYNTHETIC ORGANISMS

This application is a continuation-in-part of U.S. Ser. No. 15/894,457 filed Feb. 12, 2018, which claims benefit of priority to the filing date of U.S. Provisional Application Ser. No. 62/458,236, filed Feb. 13, 2017, the contents of which applications are specifically incorporated herein by reference in their entireties.

GOVERNMENT FUNDING

This invention was made with government support under DE-FG02-91ER20021, DE-FC02-07ER64494, and DE-SC0018409 awarded by U.S. Department of Energy, and with government support under 1737898 and 1358474 awarded by the National Science Foundation. The government has certain rights in the invention.

BACKGROUND OF THE INVENTION

Microbes have been used for many manufacturing purposes, including for energy production and the production of useful materials. For example, market prices for energy and fuels have been comparatively low but easily accessible petroleum and natural gas deposits have been depleted. In addition, emerging economies are growing, and environmental concerns are also growing. Significant restructuring or replacement of a portion of fossil fuels may be needed, for example, by renewable energy technologies such as biofuels. Currently, the largest volume of biofuels today is in the form of bioethanol for spark-ignition engines, with a smaller amount in the form of biodiesel for compression-ignition engines. Both bioethanol and biodiesel are produced primarily from terrestrial plant material. However, it is not optimal in the long term to produce fuels using food crops since food crops require premium land, abundant water, and large inputs of energy in the form of agricultural machinery and fertilizer. Thus, it would be advantageous to produce biofuels from alternative sources.

Plant and algal oils are some of the most energy-dense naturally occurring compounds that can be used as feedstocks for biofuel products. Microalgae are promising sustainable feedstocks for supplanting fossil fuels because they provide high oil yield, have short generation times, have low agricultural land requirements, have low fresh water needs, and exhibit reduced greenhouse gas emissions during algal cultivation.

In spite of these apparent advantages, the high cost of microalgal-based fuel production prevents its application in the market. The major barriers for the cost-effective production of microalgal biofuels include: (1) high cost for harvesting microalgae; (2) low oil content and suboptimal composition; (3) high cost of lipid extraction; and (4) impasses in sustainable nutrient supply. Among these barriers harvesting microalgae is particularly challenging because of the small cell size (typically 2-20 µm) and low density (0.3-5 g/L) of microalgae, which can account for up to 50% of the total cost of biofuel products. Traditional harvesting methods include chemical flocculation using multivalent cations such as metal salts and cationic polymers to neutralize the negative charge on the surface of microalgal cell walls, filtration for relatively large algae (>70 µm), sedimentation/floatation for species that either fall out of suspension or float without sufficient mixing, thermal drying, and centrifugation, which has a high cost and energy consumption.

SUMMARY

To overcome the major challenges in algal biofuel production, including the high costs of harvesting, lipid extraction, and the nutrient supply, as well as low oil content in algae, the inventors have developed methods for harvesting oleaginous marine algae such as *Nannochloropsis oceanica* through bio-flocculation with oleaginous fungi such as *Mortierella elongata* AG77. Incorporation of algae into fungi facilitates harvesting of the algae and products produced by the consortia. The algae, the fungi, or both can separately be modified to express heterologous lipid synthesizing enzymes. Improved incubation conditions are described herein that provide increased yields of triacylglycerol (TAG) that, for example, are useful for biofuels.

Described herein are methods for bio-flocculation of algae using fungal mycelia. The methods can include making living fungal mycelia that have incorporated the photosynthetically active algal cells within their hyphae. The consortia formed by fungi and algae are robust and can supply each other with nutrients. For example, the photosynthetic apparatus of algae can supply both the algae and the fungus with useful carbon-based nutrients. As illustrated herein, methods of making such fungal/algal consortia are simple and efficient. Hence, the costs of making, growing, and maintaining fungal/algal consortia are low. Such fungal/algal consortia are therefore useful for making a variety of compounds and materials, including oils, biofuels, and biomass.

One aspect of the invention is a consortium that includes at least one viable fungi and at least one viable algae within hyphae of the fungi. Prior to forming the consortia described herein, the fungi were heterologous to the algae, meaning that fungi and the algae had not previously formed consortia.

Another aspect is a method that includes incubating at least one fungus and at least one alga cell until at least one alga cell is incorporated into hyphae of the fungus, to thereby form a consortium of the at least one fungus and the at least one alga cell.

DESCRIPTION OF THE FIGURES

The patent or application file contains at least one drawing executed in color. Copies of this patent or patent application publication with color drawing(s) will be provided by the Office upon request and payment of the necessary fee.

FIGS. 2A-2H illustrate carbon exchange between *N. oceanica* and *M. elongata* AG77. FIG. 2A includes FIGS.

2A-1 and 2A-2, which illustrate carbon (C) transfer from [$^{14}$C]sodium bicarbonate (NaHCO$_3$)-labeled *N. oceanica* (Noc) cells to *M. elongata* AG77 (FIG. 2A-1) or from [$^{14}$C]glucose-labeled AG77 to Noc cells (FIG. 2A-2) after 7-day co-culture in flasks with physical contact between the *N. oceanica* and *M. elongata* AG77. Radioactivity of $^{14}$C was measured with a scintillation counter (dpm, radioactive disintegrations per minute) and then normalized to the dry weight of samples (dpm/mg biomass). Free Noc refers to unbound Noc cells in supernatant. Attached refers to Noc cells separated from AG77-Noc aggregates. FAAs refers to free amino acids. The "soluble compounds" refers to compounds in the supernatant after acetone precipitation of proteins extracted by SDS buffer. Data are presented in the average of three biological repeats with standard deviation (Means±SD, n=3). FIG. 2B includes FIGS. 2B-1 and 2B-2, which illustrate radioactive $^{14}$C transfer between Noc and AG77 without physical contact. Algae and fungi were incubated in cell-culture plates with filter-bottom inserts (pore size of 0.4 μm) which separate Noc cells and AG77 mycelia from each other but allow metabolic exchange during co-culture. Error bars indicate SD (n=3). Radioactive carbon (C) transfer was measured from [$^{14}$C]sodium bicarbonate (NaHCO$_3$)-labeled *N. oceanica* (Noc) cells to *M. elongata* AG77 (FIG. 2B-1) or from [$^{14}$C]glucose-labeled AG77 to Noc cells (FIG. 2B-2). FIG. 2C illustrates the relative abundance of $^{14}$C radioactivity in AG77 recipient cells compared to $^{14}$C-labeled Noc donor cells after 7-day co-culture (total AG77 dpm/total $^{14}$C-Noc dpm). FIG. 2D illustrates the relative abundance of $^{14}$C radioactivity in Noc recipient cells compared to $^{14}$C-labeled AG77 donor cells after 7-day co-culture (total Noc dpm/total $^{14}$C-AG77 dpm). Physical contact refers to living $^{14}$C-labeled cells added to unlabeled cells for co-cultivation in flasks. No contact refers to samples grown separately in plates with inserts. Heat-killed $^{14}$C-cells, heat-killed $^{14}$C-labeled Noc or heat-killed AG77 were killed by heat treatment at 65° C. for 15 min before the addition to unlabeled cells in flasks. Free refers to unbound Noc cells in supernatant. Att refers to Noc cells attached to AG77. Total refers to Noc cells grown separately with AG77 in plates and inserts. Error bars indicate SD (n=3). FIGS. 2E-2H further illustrate $^{14}$C exchange between *N. oceanica* and *M. elongata* AG77 without physical contact. FIG. 2E illustrates co-culture of *N. oceanica* (Noc) and *M. elongata* AG77 in 6-well plates with filter-bottom inserts (i.e., without physical contact). FIG. 2F illustrates co-culture of *N. oceanica* (Noc) and *M. elongata* AG77 in 6-well plates with filter-bottom inserts (i.e., without physical contact), and after 7-day co-culture, the inserts were moved to the adjacent empty wells (bottom) for harvesting samples. There is no cross contamination observed between Noc and AG77 samples as suggested by the images. FIG. 2G shows a side-view schematic diagram of alga-fungus co-culture (e.g., as illustrated in FIG. 2E) and sample harvesting (e.g., as illustrated in FIG. 2F) with an insert and plate. The hydrophilic polytetrafluoroethylene filter (pore size of 0.4 μm) at the bottom of the inserts separates Noc and AG77 during co-culture but allows metabolic exchange between the plate well and insert. [$^{14}$C]sodium bicarbonate (NaHCO$_3$)-labeled Noc cells were grown in the plate well or insert while recipient AG77 was grown in the insert or plate well, respectively. Similar incubation conditions were used for [$^{14}$C]glucose- or [$^{14}$C]sodium acetate-labeled AG77 and recipient Noc. FIG. 2H graphically illustrates $^{14}$C transfer from [$^{14}$C]sodium acetate-labeled AG77 to recipient Noc. $^{14}$C radioactivity (dpm, radioactive disintegrations per minute) was normalized to the dry weight (dpm/mg). FAAs, free amino acids; soluble compounds, supernatant after acetone precipitation of SDS-protein extraction. Error bars indicate SD (n=3).

FIG. 3A illustrates nitrogen (N) exchange between *N. oceanica* (Noc) and *M. elongata* AG77 as examined by $^{15}$N-labeling experiments. [$^{15}$N] potassium nitrate-labeled Noc cells or [$^{15}$N]ammonium chloride-labeled AG77 were added to unlabeled AG77 or Noc cells, respectively, for 7-days co-culture in flasks (physical contact) or for 7-days cell culture in plates with inserts (no physical contact). Algae and fungi were separated and weighed (dry biomass) after the co-culture, and their isotopic composition (δ$^{15}$N, ratio of stable isotopes $^{15}$N/$^{14}$N) and N content (% N) were determined using an elemental analyzer interfaced to an Elementar Isoprime mass spectrometer following standard protocols. The N uptake rate of $^{15}$N-Noc-derived N ($^{15}$N) by AG77 from and that of $^{15}$N-AG77-derived N by Noc cells ($^{15}$N) were calculated based on the Atom % $^{15}$N [$^{15}$N/($^{15}$N+$^{14}$N)100%], % N and biomass. C, chloroplast; N, nucleus; Nu, nucleolus; M, mitochondrion; V, vacuole; L, lipid droplet. Values are the average of three biological repeats. FIGS. 3B-3D illustrate viabilities of the *N. oceanica* (Noc) and *M. elongata* AG77 under various culture conditions. FIG. 3B shows images illustrating viability assays of Noc cells under nitrogen deprivation (—N). FIG. 3C shows images illustrating viability assays of Noc co-cultured with AG77 under nitrogen deprivation (—N). For FIGS. 3A and 3B, dead Noc cells were indicated by SYTOX Green staining (green fluorescence), while red colors indicate Noc chlorophyll fluorescence. FIG. 3D graphically illustrates that the viability of nutrient-deprived Noc cells increased when co-cultured with *M. elongata* AG77 or *M. elongata* NVP64. The abbreviation —C indicates carbon deprivation. Results were calculated from 1,000 to 5,000 cells of five biological repeats with ImageJ software. Asterisks indicate significant differences compared to the Noc control by Student's t test (*P≤0.05, **P≤0.01; Means±SD, n=5). FIG. 3E illustrates the total organic carbon (C) measured in the buffer of 18-day fungal cultures of *M. elongata* AG77 and NVP64 compared to the f/2 medium control (f/2 con). FIG. 3F graphically illustrates the dissolved nitrogen (N) measured in the buffer of 18-day fungal cultures of *M. elongata* AG77 and NVP64 compared to the f/2 medium control (f/2 con). Fungal cells were removed by 0.22 micron filters. Means±SD, n=4, *P≤0.05, **P≤0.01. FIG. 3G-3H further illustrate nitrogen (N) exchange between *N. oceanica* and *M. elongata* AG77 as examined by $^{15}$N-labeling experiments. FIG. 3G graphically illustrates nitrogen uptake by *M. elongata* AG77 cells after [$^{15}$N]potassium nitrate-labeled Noc cells were added to unlabeled AG77 cells. FIG. 3H graphically illustrates nitrogen uptake by *N. oceanica* cells after [$^{15}$N]ammonium chloride-labeled AG77 (2.7%, Atom % $^{15}$N) were added to unlabeled Noc cells. The results in FIG. 2G were generated by addition of [$^{15}$N]potassium nitrate-labeled Noc cells [7.1%, Atom % $^{15}$N, $^{15}$N/($^{15}$N+$^{14}$N)100%] to unlabeled AG77 for 7-day co-culture in flasks (physical contact, top) or cell-culture plates with inserts (no physical contact, bottom). Similarly, the results in FIG. 3H were generated by addition of [$^{15}$N]ammonium chloride-labeled AG77 (0.2.7%, Atom % $^{15}$N) to unlabeled Noc cells for 7-day co-culture in flasks (physical contact, top) or cell-culture plates with inserts (no physical contact, bottom). Algae and fungi were separated and weighed (dry biomass) after the co-culture, and their isotopic composition (δ$^{15}$N, ratio of stable isotopes $^{15}$N/$^{14}$N) and N content (% N) were determined using an elemental analyzer interfaced to an Elementar Isoprime mass spectrometer following standard protocols. For FIG. 3G, the nitrogen uptake rates (μmol N/mg biomass/d) of Noc from the media (medium-N, isotope dilution) and that of AG77 from $^{15}$N-Noc-derived N ($^{15}$N) were calculated based on the Atom % $^{15}$N, % N and biomass. Error bars indicate SD (n=3). Similar analyses were carried out to obtain the results in FIG. 3H where [$^{15}$N]ammonium chloride-labeled AG77 (2.7%, Atom % $^{15}$N) and unlabeled Noc cells were incubated to calculate the uptake rate of medium-N by AG77 and that of $^{15}$N-AG77-derived N ($^{15}$N) by Noc cells. Error bars indicate SD (n=3). FIGS. 3I-3J illustrate that various fungi from diverse clades exhibit intensive interaction with *N. oceanica*. FIG. 3I schematically illustrates the phylogeny of plant root-associated fungal isolates that were used for co-culture bioassay experiments. A phylogenetically diverse panel of basidiomycete, ascomycete and zygomycete fungi were tested. FIG. 3J illustrates co-culture of *N. oceanica* cells with different fungi and *Saccharomyces cerevisiae* in flasks containing f/2 media for 6 days. *N. oceanica*, algal culture control; the others. *N. oceanica* incubated with respective fungi or *S. cerevisiae*.

FIGS. 4A-4I (where FIG. 4I includes FIG. 4I-1 to 4I-4) illustrate intracellular localization of long-term co-cultured *N. oceanica* within *M. elongata* AG77 hyphae. FIGS. 4A-4C are transmission electron microscope (TEM) images of increasing magnification showing a cross section of AG77 mycelium containing a cluster of dividing Noc cells. AG77 and Noc were co-cultured for ~ one month. Red arrow heads indicate same position. M, mycelium; Mw, *Mortierella* cell wall; Nw, Noc cell wall; C, chloroplast; Cy, cytoplasm; V, vacuole. FIG. 4A shows an image of *N. oceanica* within *M. elongata* AG77 hyphae. FIG. 4B shows an enlarged imaged of the boxed area shown in FIG. 4A. FIG. 4C shows a further enlargement of a portion of the image shown in FIG. 4B. FIGS. 4D-4H shows differential interference contrast (DIC) images of AG77 "green hyphae" with *N. oceanica* (Noc) cells inside. Red arrow heads indicate putative dividing Noc cells. FIG. 4D shows *N. oceanica* (Noc) cells inside *M. elongata* AG77 hyphae after co-culture for about one month. FIG. 4E also shows Noc cells inside *M. elongata* AG77 hyphae after co-culture for about one month. FIG. 4F shows Noc cells inside *M. elongata* AG77 hyphae after co-culture for about two months. FIG. 4G also shows Noc cells inside *M. elongata* AG77 hyphae after co-culture for about two months. FIG. 4H also shows Noc cells inside *M. elongata* AG77 hyphae after co-culture for about two months. FIG. 4I-1 to 4I-4 illustrate the origin of endosymbiosis of *N. oceanica* within *M. elongata* AG77. FIG. 4I-1 shows a differential interference contrast (DIC) micrograph of co-cultured *N. oceanica* (Noc) and *M. elongata* AG77 using a Leica DMi8 DIC microscope. After 35-day co-culture in flasks, AG77-Noc aggregates were transferred to 35 mm-microwell dish (glass top and bottom, MatTek) containing soft solid media (f/2 media supplemented with 0.25% low gelling temperature agarose and 10% PDB) to investigate the establishment of the Noc endosymbiosis in AG77. The red arrow head indicates a hypha coated by Noc cells around the hyphal tip. FIG. 4I-2 to 4I-4 show a differential interference contrast (DIC) micrograph of co-cultured Noc and *M. elongata* AG77 after three days of incubation in soft solid media, the same group of Noc and AG77 cells formed a "green hypha" (with Noc cells inside) as indicated by the red arrow head. Noc cells surrounding the hypha kept growing and dividing and formed a lollipop-like structure because of the solid media, which is not observed in liquid alga-fungus co-culture. In the enlargement of the lollipop region, the cyan arrow head points to Noc cells inside the fungal hypha. FIG. 4I-2 shows a field of *N. oceanica* (Noc) and *M. elongata* AG77. FIG. 4I-3 shows an enlargement of a portion of the image shown in FIG. 4I-4. FIG. 4I-4 shows an enlargement of a portion of the image shown in FIG. 4I-2.

FIG. 5A-5H illustrates physical interaction between algal *N. oceanica* and fungal *M. elongata* cells led to the degradation of the outer layer of *N. oceanica* algal cell wall. FIG. 5A shows lower magnification images of *N. oceanica* (Noc) cells incubated alone in f/2 medium (bar=1 micron). FIG. 5B shows somewhat higher magnification images of Noc cells incubated alone in f/2 medium (bar=1 micron). FIG. 5C shows even higher magnification images of Noc cells incubated alone in f/2 medium (bar=1 micron). FIG. 5D shows an image of an Noc cell wall after incubation of the Noc cell alone in f/2 medium (bar=100 nm). As illustrated, the Noc cells shown in FIG. 5A-5D have a smooth surface. FIG. 5E shows an image of Noc cells attached to *M. elongata* AG77 (AG77) hyphae in a co-culture (bar=10 microns), illustrating that the outer layer of the Noc algal cell walls is not as intact as that of the Noc controls shown in FIG. 5A-5D. FIG. 5F shows an expanded image of Noc cells attached to *M. elongata* AG77 (AG77) hyphae in a co-culture (bar=1 micron), illustrating that the outer layer of the Noc algal cell walls is not as intact as that of the Noc controls shown in FIG. 5A-5D. FIG. 5G further illustrates the structure of *N. oceanica* (Noc) cells without physical interaction with *M. elongata* AG77 (AG77) (bar=1 micron) when using a 6-well culture plate and membrane insert (pore size of 0.4 μm) that separates the Noc and AG77 cells but allows metabolic exchange between the partners. FIG. 5H shows an expanded view of one *N. oceanica* (Noc) (bar=1 micron) cell incubated without physical interaction with *M. elongata* AG77 (AG77) by using a 6-well culture plate and membrane insert (pore size of 0.4 μm) that separates the Noc and AG77 cells but allows metabolic exchange between the partners. As shown in FIG. 5G-5H, the Noc algal cells have intact cell walls, for example in their outer layer, where in contrast, the outer layer is defective when the Noc-algal cells form a consortium with the *M. elongata* AG77 (AG77) hyphae (compare FIGS. 5E-5F with FIGS. 5G-5H).

FIG. 6A shows *N. oceanica* cells when inoculated in f/2 medium containing $NH_4Cl$. FIG. 6B shows *N. oceanica* cells that were incubated in the ePBR to stationary phase (day 1, referred to as S1). FIG. 6C shows *N. oceanica* cells that were incubated in the ePBR after growth for 8 days (referred to as S8). Cultures were incubated under fluctuating light at 23° C. and were sparged with air enriched to 5% $CO_2$ at 0.37 L min$^{-1}$ for 2 min per hour. FIG. 6D graphically illustrates light conditions for the cultures in the ePBR: fluctuating lights (0 to 2,000 μmol photons m$^{-2}$ s$^{-1}$) under diurnal 14/10 h light/dark cycle.

FIG. 7A shows and image of a co-culture of *N. oceanica* (Noc) with *M. elongata* AG77. The red arrow indicates green aggregates formed by AG77 mycelium and attached Noc cells. FIG. 7B shows an image of co-culture of *N. oceanica* (Noc) with *Morchella americana* 3668S. For FIGS. 7A-7B, fungal mycelium was added to the Noc culture and the mixture was incubated for 6 days. FIG. 7C shows an image of Noc cells attached to AG77 mycelium as visualized by differential interference contrast (DIC) microscopy. FIG. 7D shows that there was no obvious attachment of Noc cells on the *Morchella americana* 3668S mycelium. FIG. 7E graphically illustrates bio-flocculation efficiency for harvesting Noc cells by cocultivation with *Mortierella elongata* AG77, *Mortierella elongata* NVP64, and *Mortierella gamsii* GBAus22. The bioflocculation efficiency was determined by the cell density of uncaptured cells compared to that of a no-fungus Noc culture control. A *Morchella* 3668S culture was used as a negative control. The results are the average of five biological replicates and error bars indicate standard deviation. Asterisks indicate significant differences relative to the 2 h co-cultures by paired-sample Student's t-test (*$P \leq 0.05$; **$P \leq 0.01$). F, Measurement of Noc cell size (diameter) in the Noc culture and alga-fungus co-culture.

FIG. 8A shows scanning electron microscopy images illustrating the interaction between *N. oceanica* (Noc) cells and *M. elongata* AG77. FIG. 8B shows scanning electron microscopy images illustrating the interaction between *N. oceanica* (Noc) cells and *M. elongata* NVP64. Noc cells are attached to the fungal mycelium as shown in the top panels of FIGS. 8A-8B. Higher magnification micrographs shown in the lower panels illustrate that Noc cells have a highly structured cell wall with protrusions, with which they attach to the rough surface of the fungal cell wall. The red arrowheads in the lower panels of FIGS. 8A-8B indicate that tube-like structures connect the algal and fungal cell walls. FIG. 8C shows images of *Morchella americana* 3668S mycelium collected from Noc-3668S culture after 6-day co-cultivation, where the *Morchella americana* 3668S mycelium does not aggregate with *N. oceanica* cells.

FIG. 9A shows confocal micrographs of *N. oceanica-M. elongata* AG77 after six days of co-culture in PDB medium, illustrating the lipid droplets within the fungal mycelium. Green fluorescence indicates lipid droplets stained with BODIPY. FIG. 9B shows confocal micrographs of *N. oceanica-M. elongata* NVP64 after six days of co-culture in PDB medium, illustrating the lipid droplets within the fungal mycelium. Green fluorescence indicates lipid droplets stained with BODIPY. FIG. 9C shows confocal micrographs of *N. oceanica-Mortierella* gamsii GBAus22 after six days of co-culture in PDB medium, illustrating the lipid droplets within the fungal mycelium. Green fluorescence indicates lipid droplets stained with BODIPY. FIG. 9C shows confocal micrographs of *N. oceanica-Morchella americana* 3668S after six days of co-culture in PDB medium, illustrating the lipid droplets within the fungal mycelium. Green fluorescence indicates lipid droplets stained with BODIPY. FIG. 9E shows images of lipid droplets in *N. oceanica* (Noc) cells. The red color is from autofluorescence of Noc chloroplast. FIG. 9F shows lipid droplets in the *N. oceanica-M. elongata* AG77 cells after six days of co-cultivation of the algal and fungal cells in f/2 medium. FIG. 9G shows lipid droplets in the *N. oceanica-M. elongata* NVP64 cells after six days of co-cultivation of the algal and fungal cells in f/2 medium. FIG. 9H shows lipid droplets in the *N. oceanica-Mortierella* gamsii GBAus22 cells after six days of co-cultivation of the algal and fungal cells in f/2 medium. FIG. 9I shows lipid droplets in the *N. oceanica-Morchella americana* 3668S cells after six days of co-cultivation of the algal and fungal cells in f/2 medium.

FIG. 10A graphically illustrates the amounts of various fatty acids in triacylglycerol and total lipid detected in assays of *N. oceanica* grown in shaker flasks containing f/2 medium. Fatty acids are indicated with number of carbons:number of double bonds. Results are the average of five biological replicates with error bars indicating standard deviations (n=5). FIG. 10B graphically illustrates the amounts of various fatty acids in triacylglycerol and total lipid detected in assays of *M. elongata* AG77 incubated in f/2 medium. n=5. FIG. 10C graphically illustrates the amounts of various fatty acids in triacylglycerol and total lipid detected in assays of the algae-fungi aggregates after 6-d co-cultivation. n=5.

FIG. 11A graphically illustrates the mole ratio of triacylglycerol (TAG) compared to total lipid. Cells were grown in shaker flasks. N0-120. Nitrogen deprivation (f/2 medium lacking nitrogen for 0-120 hours; R24-72, nitrogen resupply (f/2) medium for 24-72 hours. The average of three biological replicates and standard deviation are shown (n=3). FIG. 11B graphically illustrates the TAG and total lipid content per gram of whole cell dry weight. n=3.

FIG. 12A graphically illustrates cell counts of *N. oceanica* (Noc) cells were inoculated to ~$1 \times 10^6$ mL$^{-1}$ and incubated in the environmental photobioreactor containing modified f/2 media with $NH_4Cl$, $KNO_3$, or urea as nitrogen source. The average of three biological replicates and standard deviation are shown (n=3). FIG. 12B graphically illustrates the dry weight per liter of cells grown in different f/2 media. n=3. FIG. 12C graphically illustrates the cell growth during S1-8 in f/2-$NH_4Cl$. n=3. FIG. 12D graphically illustrates the cell dry weight during S1-8 in f/2-$NH_4Cl$. n=3. L1-6, days 1-6 of log phase; S1 and 2, day 1 and 2 of stationary phase.

FIG. 13A illustrates analysis of triacylglycerol (TAG) by thin layer chromatography (TLC). Red arrowheads indicate the TAG bands. S1 to S8, day 1 to 8 after the cells reached stationary phase; control, TAG standard. FIG. 13B graphically illustrates a correlation between chlorophyll content and TAG-to-total-lipid ratio following prolonged incubation in the environmental photobioreactor (ePBR) containing f/2-$NH_4Cl$ medium. TAG and total lipid were subjected to transesterification reaction and the resulting fatty acid methyl esters were quantified by gas chromatography and flame ionization detection (GC-FID). $r_2$, correlation coefficient; n=4.

FIG. 14A-14B illustrate triacylglycerol accumulation during prolonged incubation in f/2-$NH_4Cl$ medium supplemented with or without sodium bicarbonate. *N. oceanica* cells were inoculated and incubated in f/2-$NH_4Cl$ medium (with or without $NaHCO_3$) in ePBRs and sparged with air enriched to 5% $CO_2$ at 0.37 L min$_{-1}$ for 2 min per h. S1 to 8, day 1 to 8 after the cultures reached stationary phase. FIG. 14A illustrates the pH of the culture from S5 to S8. FIG. 14B graphically illustrates TAG content during prolonged incubation. The results are the average of three biological replicates and error bars indicate standard deviation. Asterisks indicate significant difference between $CO_2$ and $CO_2$ & $NaHCO_3$. **, $P<0.01$; *, $P<0.05$; n=3.

FIG. 15A-15C illustrate increasing triacylglycerol (TAG) content in *N. oceanica* using limited ammonium as nitrogen source. FIG. 15A shows images of *N. oceanica* (Noc) cells, illustrating production of large lipid droplets in *N. oceanica* (Noc) cells during prolonged incubation in the environmental photobioreactor (ePBR) containing f/2-$NH_4Cl$ medium. Noc cells grow fast in f/2-$NH_4Cl$ medium and suffer from nutrient limitation after being for 8 days in the stationary phase, when the confocal micrographs were taken. Green fluorescence indicates lipid droplets stained with BODIPY, while red fluorescence represents autofluorescence of Noc chloroplasts. FIG. 15B shows lipid droplet staining of *M. elongata* AG77 and Noc cells after 6-days co-cultivation. FIG. 15C graphically illustrates fatty acid (FA) analyses of triacylglycerol and total lipid in the alga-fungus aggregate as shown in (FIG. 15B), where the inset shows biomass ratio of TAG, while the larger graph shows total FA relative to the total cell dry weight (DW). n=5.

FIG. 16A-16D shows a schematic diagram illustrating predicted fatty acid/lipid pathways in *M. elongata* AG77. Proteins likely involved in the synthesis of fatty acids (FA), polyunsaturated fatty acids (PUFA), and triacylglycerol (TAG) are identified in the sequenced genome of *M. elongata* AG77 at the JGI fungal genome portal MycoCosm (Table 3). FIG. 16A illustrates the fatty acid (FA) synthetic pathway. ACP, acyl carrier protein; AT, acetyltransferase; MPT, malonyl/palmitoyl transferase; ACSL, acyl-CoA synthetase; KS, β-ketoacyl synthase; ER, β-enoyl reductase; DH, dehydratase; KR, β-ketoacyl reductase. FIG. 16B shows the linear domain organization of fatty acid synthase (FASN) of *M. elongata* AG77. PPT, phosphopantetheine transferase. FIG. 16C illustrates PUFA synthetic pathways. ELOVL, fatty acid elongase; FAD, fatty acid desaturase. Fatty acids are designated by the number of total carbon:the number of double bonds. The position of specific double bonds is indicated either from the carboxyl end (Δ) or from the methyl end (ω). FIG. 16D illustrates TAG synthetic pathways. ALDH, aldehyde dehydrogenase; ADH, alcohol dehydrogenase; GK, glycerol kinase; GPDH, glycerol-3-phosphate dehydrogenase; GPAT, glycero-3-phosphate acyltransferase; PlsC, 1-acyl-sn-glycerol-3-phosphate acyltransferase; LPIN, phosphatidate phosphatase LPIN; PAP, phosphatidate phosphatase 2; Dgk, diacylglycerol kinase; DGAT, diacylglycerol acyltransferase; PDAT, phospholipid diacylglycerol acyltransferase.

FIG. 17A shows a schematic map of a control vector that does not include the DGTT5 nucleic acid segment, and that is referred to as a pnoc ox cerulean hyg vector control. FIG. 17B shows a schematic map of an expression vector for generating *N. oceanica* DGTT5-overexpressing strains where the vector is referred to as a pnoc ox DGTT5 cerulean hyg vector.

DETAILED DESCRIPTION

Figure 1:
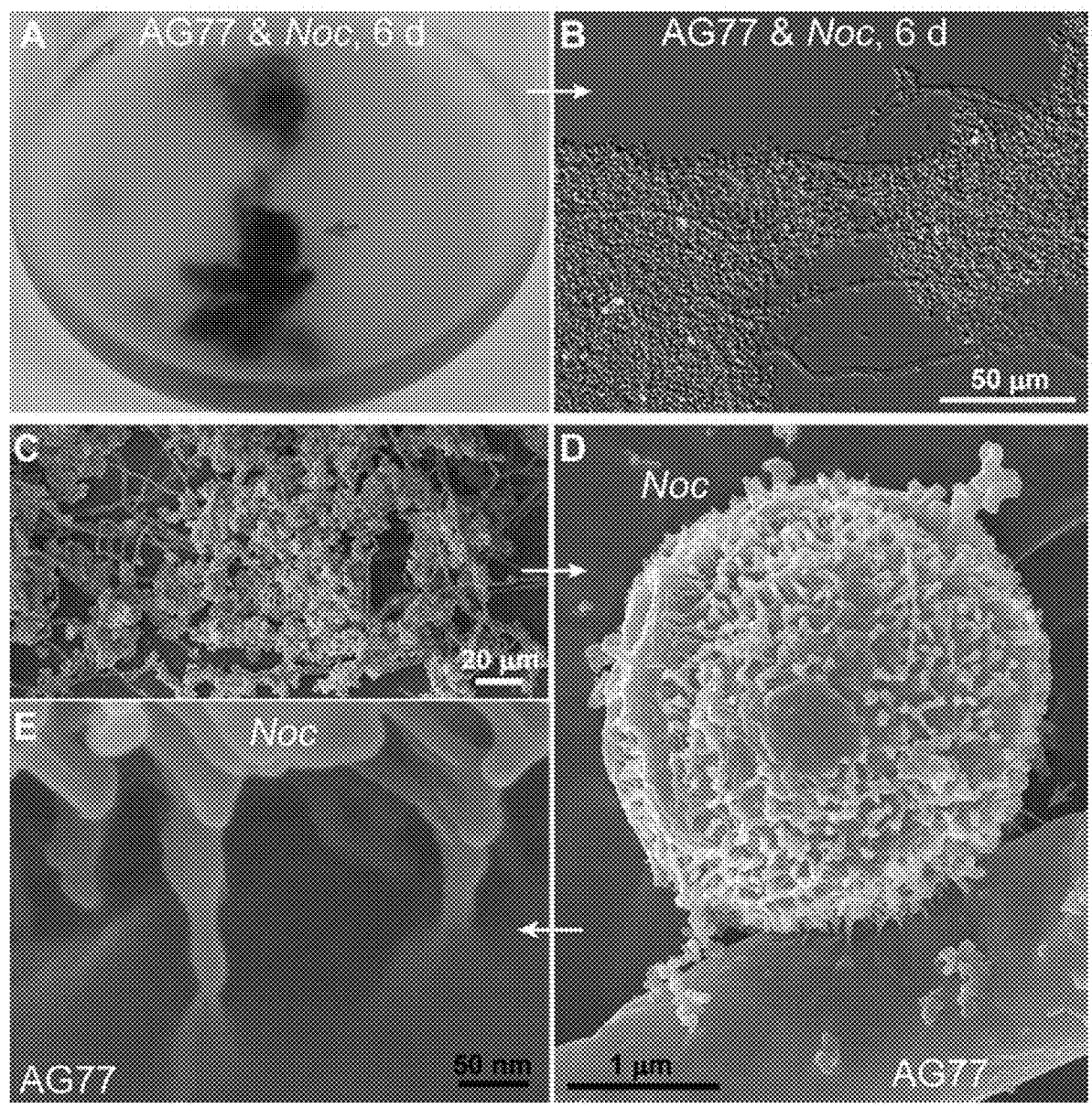
FIG. 1 illustrates interaction between the soil fungus *Mortierella elongata* and the marine alga *Nannochloropsis oceanica*. Panel A shows co-cultivation of *M. elongata* AG77 and *N. oceanica* (Noc) in flasks for 6 days. Green tissues indicated by the red arrow head are aggregates formed by AG77 mycelia and attached Noc cells. Panel B shows differential interference contrast micrographs of the green tissues shown in panel A. A large number of Noc cells were captured by AG77 mycelia. Panels C to E show images of alga-fungus aggregates by scanning electron microscopy. Panel C illustrates that Noc cells stick to the fungal mycelia after 6-d co-culture. Panel D shows a Noc cell adhering tightly to a hypha by the outer extensions of cell wall as indicated with red arrows. Panel E illustrates irregular tube-like extensions of Noc cell wall attached to the surface of fungal cell wall.

As described herein, oleaginous fungi can flocculate algae such as *N. oceanica* CCMP1779, a marine alga with the ability to produce high levels of TAG. Results provided herein also illustrate that the fungus *Mortierella elongata* AG77 can be used to efficiently harvest *N. oceanica* cells. Methods are provided herein for increasing TAG content in *N. oceanica* by optimizing growth conditions and by using genetic engineering approaches in combination with bioflocculation to harvest algal cells.

Described herein are viable fungi having viable algae within their fungi hyphae. In other words, the fungi with internalized algae form can form a consortium where, for example, the internalized algae may depend on the host fungus for nitrogen and other nutrients, while the algae can provide carbon-based nutrients and other metabolites that can be generated by algal photosynthesis. Compositions of such consortia of fungi with viable algae within the fungi hyphae, as well as methods of making and using such consortia and compositions are also described herein.

The algae employed can include a wide variety of algae. Examples include diatoms (bacillariophytes), green algae (chlorophytes), blue-green algae (cyanophytes), and goldenbrown algae (chrysophytes). In addition, a fifth group known as haptophytes may be used. Specific non-limiting examples of bacillariophytes capable of lipid production include the genera *Amphipleura, Amphora, Chaetoceros, Cyclotella, Cymbella, Fragilaria, Hantzschia, Navicula, Nitzschia, Phaeodactylum*, and *Thalassiosira*. Specific non-limiting examples of chlorophytes capable of lipid production include *Ankistrodesmus, Botryococcus, Chlorella, Chlorococcum, Dunaliella, Monoraphidium, Oocystis, Scenedesmnus*, and *Tetraselmis*. In one aspect, the chlorophytes can be *Chlorella* or *Dunaliella*. Specific non-limiting examples of cyanophytes capable of lipid production include *Oscillatoria* and *Synechococcus*. A specific example of chrysophytes capable of lipid production includes *Boekelovia*. Specific non-limiting examples of haptophytes include *Isochrysis* and *Pleurochrysis*. In some cases, an alkenone-producing alga, for example, a species of the *Isochrysis* family which includes, but not limited to, *Isochrysis galbana, Isochrysis* sp. T-Iso, and *Isochrysis* sp. C-Iso can be employed. Other examples of alkenone-producing algae include *Emiliania huxleyi* and *Gephyrocapsa oceanica*. In some cases, the algae is not a cyanobacterium. For example, the algae may not, in some cases, be *Nostoc punctiforme*.

Examples of algae can be species of *Amphipleura, Amphora, Aquamortierella, Chaetoceros, Charophyceae, Chlorodendrophyceae, Chlorokybophyceae, Chlorophyceae, Coleochaetophyceae, Cyclotella, Cymbella, Dissophora, Embryophytes, Endogaceae, Fragilaria, Gamsiella, Hantzschia, Klebsormidiophyceae, Lobosporangium, Mamiellophyceae, Mesostigmatophyceae, Modicella, Mortierella, Mucor, Navicula, Nephroselmidophyceae, Nitzschia, Palmophyllales, Prasinococcales, Prasinophytes, Pedinophyceae, Phaeodactylum, Pyramimonadales, Pycnoccaceae, Pythium, Phytophthora, Phytopythium, Rhizopus, Thalassiosira, Trebouxiophyceae, Ulvophyceae, Zygnematophyceae*, or a combination thereof.

In some cases, the algae is a photosynthetic algae. For example, the alga type employed can be a strain of *Nannochloropsis oceanica*, for example *Nannochloropsis oceanica* CCMP1779.

A variety of fungi can be employed in the formation of consortia with algae. In some cases, the fungus can be a basidiomyccte, ascomycete, or zygomycete. For example, one or more fungi can be a member of a genus such as: *Aspergillus, Blakeslea, Botrytis, Candida, Cercospora, Cryptococcus, Cunninghamella, Fusarium* (*Gibberella*), *Kluyveromyces, Lipomyces, Morchella, Mortierella, Mucor, Neurospora, Penicillium, Phycomyces, Pichia* (*Hansenula*), *Puccinia, Pythium, Rhodosporidium, Rhodotorula, Saccharomyces, Sclerotium, Trichoderma, Trichosporon, Xanthophyllomyces* (*Phqffia*), or *Yarrowia*. For example, the fungus can be a species such as: *Aspergillus terreus, Aspergillus nidulans, Aspergillus niger, Atractiella* PMI152, *Blakeslea trispora, Botrytis cinerea, Candida japonica, Candida pulcherrima, Candida revkaufi, Candida tropicalis, Candida utilis, Cercospora nicotianae, Clavulina* PMI390, *Cryptococcus curvatus, Cunninghamella echinulata, Cunninghamella elegans, Flagelloscypha* PMI526, *Fusarium fujikuroi* (*Gibberella zeae*), *Grifola frondosa* GMNB41, *Kluyveronmyces lactis, Lecythophora* PMI546, *Leptodontidium* PMI413, *Lachnum* PMI789, *Lipomyces starkeyi, Lipomyces lipoferus, Mortierella alpina, Mortierella elongata* AG77,

*Mortierella gamsii* GBAus22, *Mortierella ramanniana*, *Mortierella isabellina*, *Mortierella vinacea*, *Mucor circinelloides*, *Neurospora crassa*, *Phycomyces blakesleanus*, *Pichia pastoris*, *Puccinia distincta*, *Pythium irregulare*, *Rhodosporidium toruloides*, *Rhodotorula glutinis*, *Rhodotorula graminis*, *Rhodolorula mucilaginosa*, *Rhodolorula pinicola*, *Rhodotorula gracilis*, *Saccharomyces cerevisiae*, *Sclerotium rolfsii*, *Trichodenna reesei*, *Trichosporon cutaneum*, *Trichosporon pullans*, *Umbelopsis* PMI120, *Xanthophyllomyces dendrorhous* (*Phqffia rhodozyma*), *Yarrowia lipolytica*, or a combination thereof. In some cases, the fungus is not *Geosiphon pyriformis*.

In some cases, the fungus employed is a multi-celled fungi. For example, the fungus employed can have tissues and/or structures such as hyphae. Many fungi is made up of fine, branching, usually colorless threads called hyphae. Each fungus can have vast numbers of these hyphae, all intertwining to make up a tangled web called the mycelium. The mycelium is generally too fine to be seen by the naked eye, except where the hyphae are very closely packed together.

As illustrated herein, algae can reside and grow within fungal hyphae. The algae can also undergo photosynthesis within the fungi hyphae. In some cases the location of the algae is not within a fungal "bladder" and does not form a multinucleate bladder within the fungi, or a multinucleate bladder within fungal hyphae.

However, in some cases the fungus need not be a multi-celled fungus. For example, the fungus can be a one-celled organism such as a yeast.

In some cases, the fungus can be one or more of *Mortierella elongata*, *Mortierella elongata* AG77, *Mortierella gamsii*, *Mortierella gamsii* GBAus22, *Umbelopsis* sp., *Umbelopsis* PMI120, *Lecythophora* sp., *Lecythophora* PMI546, *Leptodontidium* sp., *Leptodontidium* PMI413, *Lachnum* sp., *Lachnum* PMI789, *Morchella* sp., *Saccharomyces cerevisiae*, *Atractiella* sp., *Atractiella* PMI152, *Clavulina*, *Clavulina* PMI390, *Grifola frondosa*, *Grifola frondosa* GMNB41, *Flagelloscypha* sp., *Flagelloscypha* PMI526, and combinations thereof.

Culture Media

Media for forming fungal/algal consortia can be a simple medium, especially when photosynthetic algae are employed because the algae can supply the fungi as well as the algae cells with carbon-based nutrients. Complex carbon nutrients may therefore not be needed, especially when the fungal/algal consortia are formed and the consortia are exposed to light. However, when initially preparing a consortium between one or more fungal species and one or more algae species, the fungi and algae can be cultured in a culture medium that contains some carbohydrate, such as some sugar. The sugar can be any convenient sugar or a combination of sugars. Examples include dextrose, sucrose, glucose, fructose or a combination thereof. The amount of sugar can be included in amounts of about 1 g/liter to about 20 g/liter, or of about 3 g/liter to about 18 g/liter, or of about 5 g/liter to about 15 g/liter.

Fungi can be grown in PDB media (12 g/L potato dextrose broth, 5 g/L yeast extract, pH 5.3). In some cases the fungi and algae can initially be cultured together to form fungal/algae consortia in the presence of a simple medium that can contain small amounts of PDB media. For example, to form fungal/algae consortia a simple medium such as f/2 medium can be used that is supplemented with small amounts of PDB media.

| f/2 Medium | |
|---|---|
| NaNO$_3$ (75.0 g/L dH$_2$O) | 1.0 mL |
| Na$_2$SiO$_3$·9H$_2$O (30.0 g/L dH$_2$O) | 1.0 mL |
| f/2 Trace Metal Solution | 1.0 mL |
| f/2 Vitamin Solution | 0.5 mL |
| Filtered seawater to | 1.0 L |

Further information on the f/2 medium is available at a website describing the composition of f/2 media (algaeresearchsupply.com/pages/f-2-media).

In some cases, the fungal/algae consortia can be grown and maintained in a media that does not supply a nitrogen source (e.g., without nitrate or ammonium salts, or without other nitrogen-containing salts). For example, the fungus that is part of the fungal/algae consortia can supply a nitrogen source to the algae as well as providing for its own nitrogen needs.

Algae cells and fungal/algae consortia can, for example, be grown or maintained in minimal media such as f/2 media, or even in water (e.g., sea water) with little or no added nutrients, especially when the algae cells and fungal/algae consortia are exposed to light. For example, algae and fungal/algae consortia can be grown or maintained in continuous light (for example, at about 20 µmol photons/m$^2$/s to about 120 µmol photons/m$^2$/s, or at about 40 µmol photons/m$^2$/s to about 100 µmol photons/m$^2$/s, or at about 80 µmol photons/m$^2$/s).

Algae, fungi, and consortia of algae and fungi can be grown or maintained at a convenient moderate temperature. For example, algae, fungi, and consortia of algae and fungi can be grown or maintained at about 15° C. to 37° C. or about 18° C. to 32° C., or at about 20° C. to 30° C., or at about room temperature.

Growing rather than non-growing cells and/or tissues can be used to generate consortia of algae and fungi. For example, log-phase cultures of algae can be used. Fungal tissues employed can include fungal mycelia and/or fungal mycelium. Fungal tissues can be chopped or cut up. For example, fungal tissues can be briefly blended or chopped into small pieces (0.1 to 4 cm, or 0.3 to 3 cm, or 0.5 to 2 cm) before combining the fungal tissues with algae.

As described herein, culturing consortia in media with limited nitrogen can induce production of increased triacylglycerol (TAG). A limited nitrogen supply culturing method was developed as described herein for large-volume cultures to induce TAG accumulation largely without compromising growth and biomass yields. To mimic natural cultivation conditions for *N. oceanica*, such as an open-pond system, environmental photobioreactors (ePBRs) were used to grow the alga under varying light (0 to 2,000 µmol photons m$^{-2}$ s$^{-1}$) under long-day (14/10 h light/dark) cycles, and 5% CO$_2$ was sparged at 0.37 L min$^{-1}$ for 2 minutes per hour at 23° C. (similar to FIG. 6). Illumination in the ePBR was provided by a high power white LED light on top of a conical culture vessel (total height of 27 cm) containing 330 mL of algal culture (20 cm in depth), which was designed to simulate pond depths from 5 to 25 cm (Lucker et al. *Algal research* 2014, 6:242-249 (2014)). Several nitrogen sources were tested in f/2 medium for the incubation of *N. oceanica* including set amounts of ammonium, nitrate, or urea.

Figure 12A:
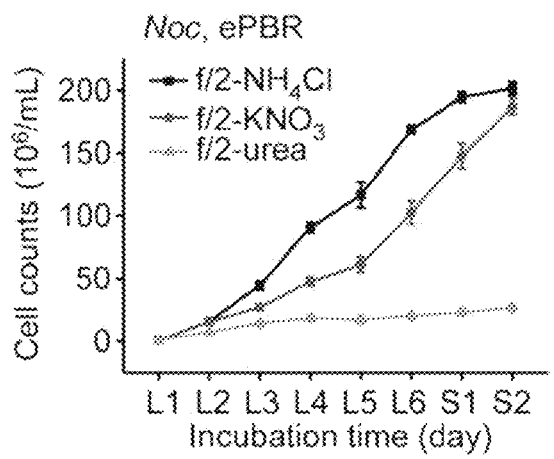
FIG. 12A-12D illustrate cell growth and biomass in the environmental photobioreactor (ePBR).
Figure 12B:
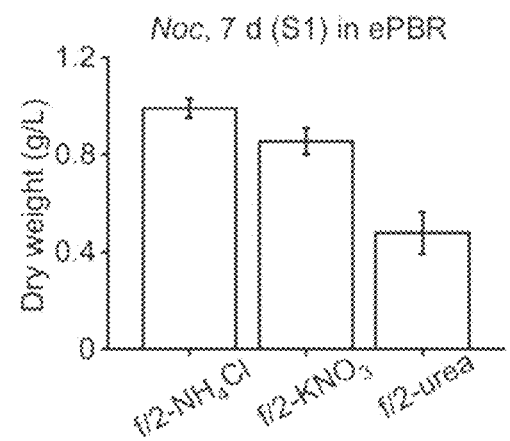

Compared to nitrate and urea, *N. oceanica* grew faster in the f/2-NH$_4$Cl medium (FIG. 12A). The dry weight (DW) of *N. oceanica* cells per liter was also higher in the f/2-NH$_4$Cl culture after 7-day incubation in the ePBR (FIG. 12B).

Hence, use of ammonium salts rather than nitrates or urea can improve TAG production by *N. oceanica* and consortia containing *N. oceanica*.

Figure 12C:
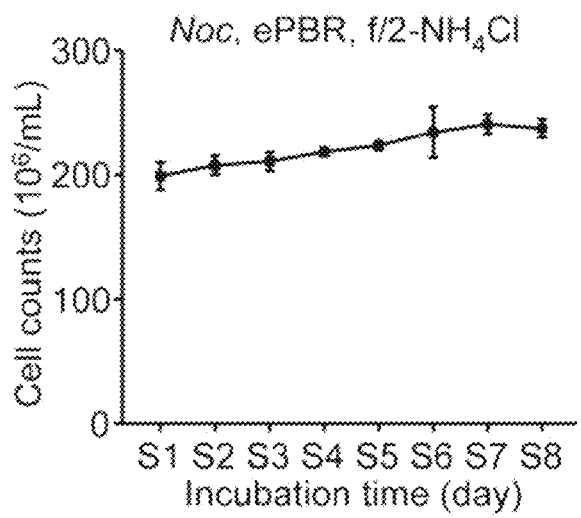
Figure 12D:
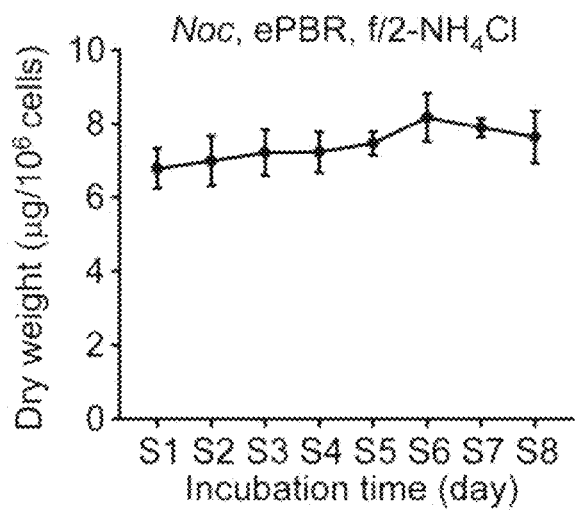
Figure 13A:
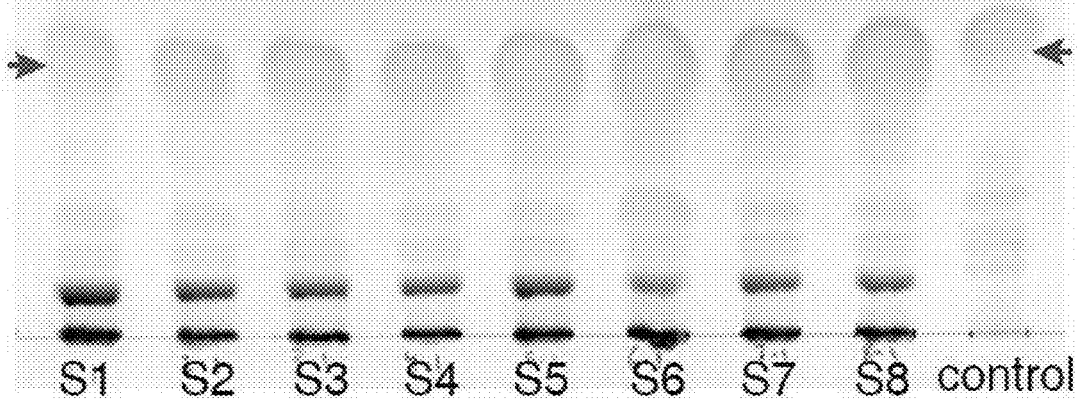
FIG. 13A-13B illustrates that chlorophyll as proxy of triacylglycerol accumulation.
Figure 13B:
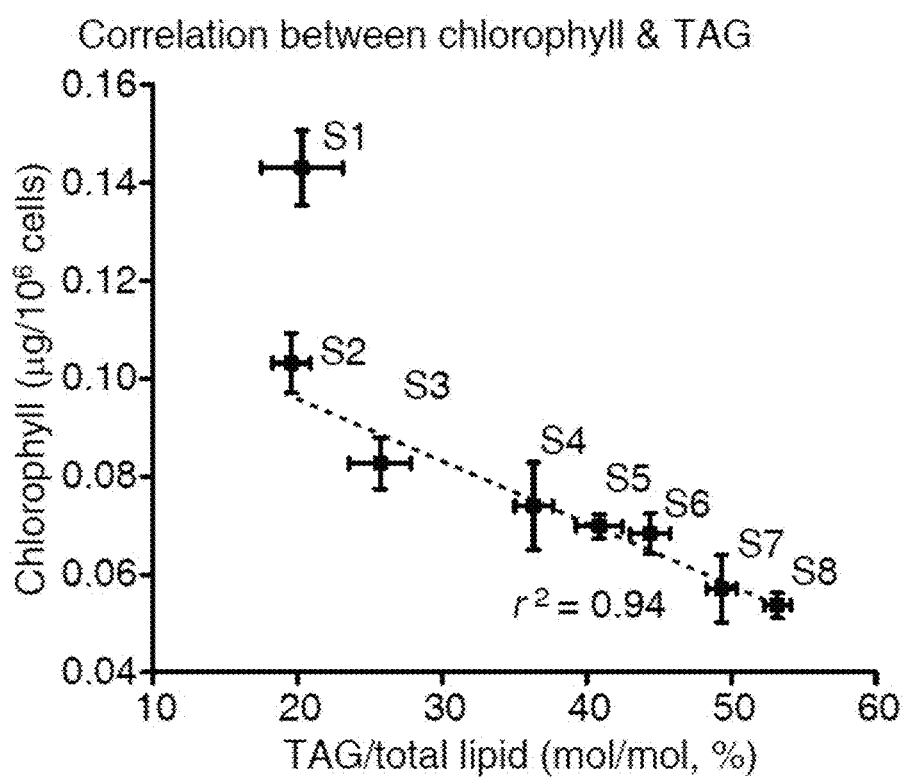
Figure 15B:
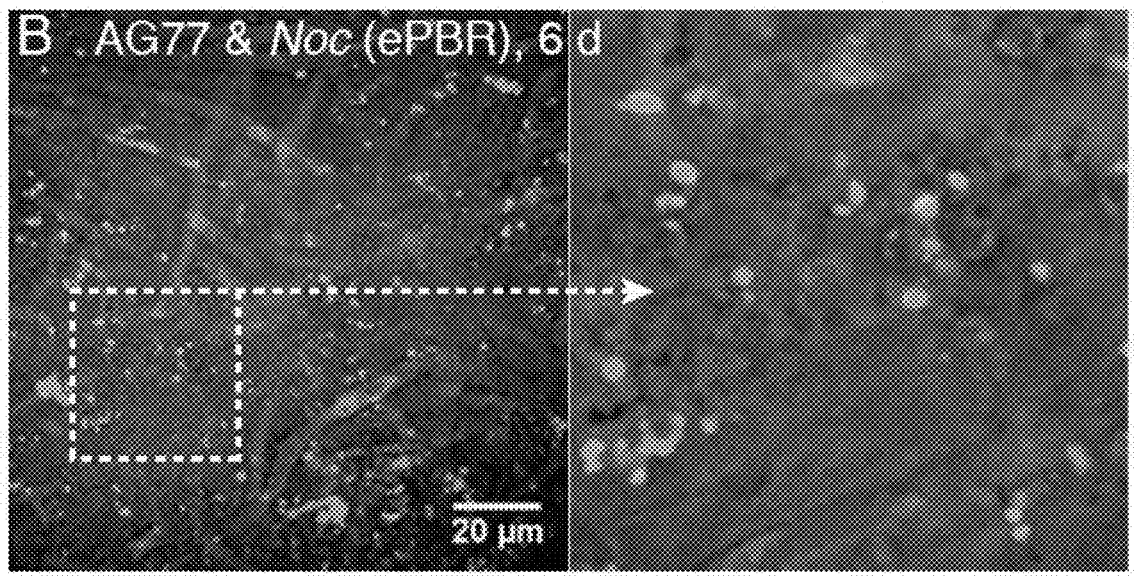
Figure 15C:
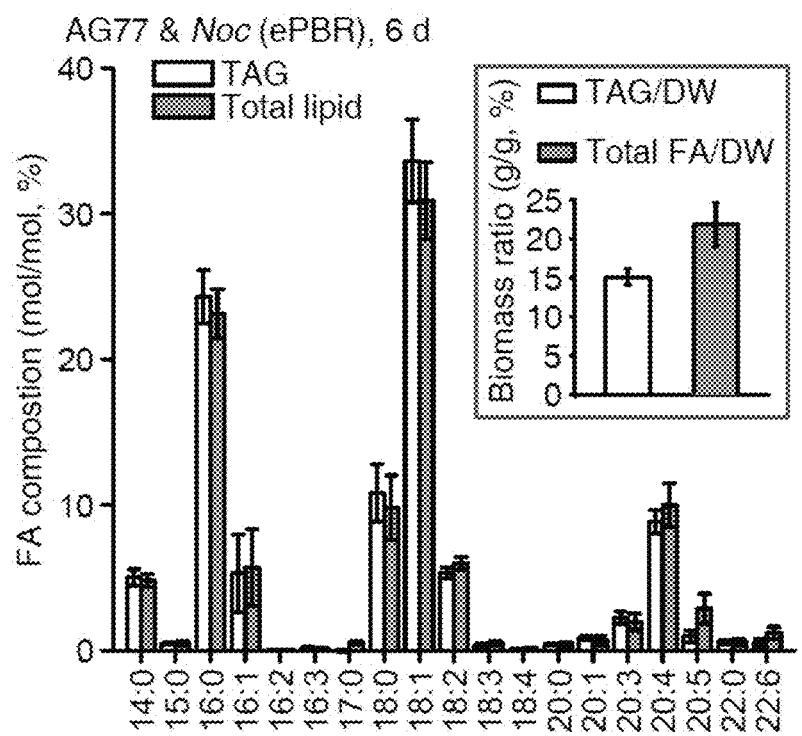

Lipid analysis by TLC (FIG. 13A) and GC-FID (FIG. 13B) demonstrated that TAGs had accumulated during days 2 to 8 after the culture reached stationary phase (incubation time S2 to S8), which is correlated with chlorophyll degradation, while cell density and dry weight remained at similar levels during this period (FIG. 12C-12D). Previously, to prevent carbon limitation, NaHCO$_3$ was added *N. oceanica* cultures in shaker flasks (Vieler et al., *Plant Physiology* 158(4): 1562-1569 (2012)). Addition of NaHCO$_3$ prevented acidification in cultures, which were sparged with 5% CO$_2$ (FIG. 14A). However. *N. oceanica* cells accumulated more TAG upon acidification in the culture medium without NaHCO$_3$ supply, especially from S6 to S8, compared to the NaHCO$_3$ culture (FIG. 12C-12D).

Generating Fungal/Algal Consortia

To form consortia, the algal cells and fungal cells (or fungal tissues) can be mixed together in a selected culture media and incubated together for one or more days, one or more weeks, one or months, one or more years, or indefinitely. The culture media or growth conditions can be changed or modulated as desired to form and maintain the fungal/algal consortia.

To form the fungal/algal consortia, the fungal tissues/cells and the algal cells can be incubated in sufficient cell/tissue density so that the fungal tissues/cells and the algal cells come into contact. For example, algae can be added to fungal cells/tissues at a density of about $1\times10^4$ algae cells/mL to $1\times10^9$ algae cells/mL, or at a density of about $1\times10^5$ algae cells/mL to $1\times10^8$ algae cells/mL, or at a density of about $1\times10^6$ algae cells/mL to $1\times10^8$ algae, or at a density of about $1-3\times10^7$ cells/mL. The ratio of fungal tissues to algae cells can vary. In some cases, it may be useful to use more fungal tissue (by mass) than algal cell mass. For example, the ratio can vary from about 10:1 by mass fungal tissue to algal cells, to about 1:1 by mass fungal tissue to algal cells. In some cases, the ratio can vary from about 5:1 by mass fungal tissue to algal cells, to about 1:1 by mass fungal tissue to algal cells. For example, the ratio can be about 3:1 by mass fungal tissue to algal cells.

In some cases it may be useful to use more algae cell mass than fungal tissue mass. For example, the ratio can vary from about 10:1 by mass algal cells to fungal tissue mass, to about 1:1 by mass algal cells to fungal tissue mass. In some cases, the ratio can vary from about 5:1 by mass algal cells to fungal tissue mass to about 1:1 by mass algal cells to fungal tissue mass.

As indicated in the foregoing section, when initially preparing a consortium between one or more fungal species and one or more algae species, the fungi and algae can be cultured in a culture medium that contains some carbohydrate, such as some sugar. The sugar can be any convenient sugar or a combination of sugars. Examples include dextrose, sucrose, glucose, fructose or a combination thereof. The amount of sugar can be included in amounts of about 1 g/liter to about 20 g/liter, or of about 3 g/liter to about 18 g/liter, or of about 5 g/liter to about 15 g/liter.

The consortium between one or more fungal species and one or more algae species can be formed in a liquid media, in a semi-solid media, or on a solid media.

Consortia of algal cells within fungal tissues can include fungal hyphae with different numbers of algae cells within them. For example, fungal tissues can include 1 to 2000 algae cells per fungal hyphae, or 2 to 1700 algae cells per fungal hyphae, or 5 to 1500 algae cells per fungal hyphae, or 10 to 1000 algae cells per fungal hyphae, or 15 to 500 algae cells per fungal hyphae, or 5 to 100 algae cells per fungal hyphae. Fungal hyphae can typically have any number of algae cells within them, up to about 5000 algae cells.

Consortia Benefits

The fungal/algae consortia are easier to harvest than algae cells.

The fungal/algae consortia described herein can be more robust than separate cultures of algae or separate fungi. For example, the algae can provide it fungal partner with useful carbon-based nutrients while the fungus can provide its algae partner with useful nitrogen-based nutrients, or vice versa. Hence, the fungal/algae consortia described herein can be more tolerant of environmental stresses such as nutrient-poor conditions.

In addition, a fungal partner can protect its algae cells from environmental stresses such as salt imbalances (too much salt or too little) that would otherwise adversely affect the growth or health of the algae.

Algae are useful for production of useful compounds and materials such as oils, biofuels, nutrients (sugars, vitamins, proteins, etc.), and biomass. The protection and support provided by a fungal partner can help foster the growth and production of algae. Similarly, the algae can support and foster the growth of its fungal partner. Hence, the fungal/algae consortia described herein can be used to produce useful products under low cost conditions that do not require expensive monitoring and maintenance.

For example, fungal/algae consortia described herein can be used to produce various types of oils or biofuels. In certain aspects, the fungal-algae consortium can have lipid content greater than about 20%, and preferably greater than about 30% by weight of the consortium weight. Currently known algae species may contain a practical maximum lipid content of about 40% by weight, although levels as high as 60% have been reported. Such species can be algae partners for formation of fungal/algae consortia. In some embodiments, the lipid-producing consortium can comprise lipid content greater than 40%, 50%, 60%, 70%, 80%, or 90% by weight of the consortium. In a specific embodiment, the subject methods involve selection of consortium which produce high levels of simple and/or complex lipids.

For example, the content of lipids provided by cultures and methods described herein can be at least 20%, 30%, 40%, 50%, 60%, 70%, 80%, or 90% by weight of the consortium.

Transgenic Algae and/or Fungi

A method is described herein that includes manufacturing a fungus or algae cell by introducing into the cell at least one exogenous nucleic acid encoding a lipid synthetic enzyme. The lipid synthetic enzyme can be a fatty acid, TAG or other lipid synthetic enzyme. Also described herein are modified fungi, algae, and fungal/algae consortia that have at least one exogenous nucleic acid encoding a lipid synthetic enzyme. The modified fungi, algae, and fungal/algae consortia can express at least one exogenous lipid synthetic enzyme. Such modified fungi, algae, and fungal/algae consortia can produce increased amounts of lipid compared to unmodified fungi, algae, and fungal/algae of the same species.

In order to engineer fungi and/or algae to have increased oil content, one of skill in the art can introduce exogenous nucleic acids (expression cassettes or expression vectors) that increase the expression and/or translation of lipid synthetic enzyme to promote the production of oils. The lipid synthetic enzymes can include one or more acetyl-CoA carboxylase, malonyl-CoA decarboxylase, acyl carrier protein, fatty acid synthase, malonyl-CoA:ACP malonyltransferase, 3-oxoacyl-ACP synthase, KASI/II, 3-hydroxydecanoyl-ACP dehydratase, 3-hydroxydecanoyl-ACP dehydratase, 3-ketoacyl-ACP reductase, acyl-CoA elongase, fatty acid desaturase, acyl-CoA thioesterase, acyl-CoA synthetase, aldehyde dehydrogenase, alcohol dehydrogenase, glycerol kinase, glycerol-3-phosphate dehydrogenase, glycero-3-phosphate acyltransferase, 1-sn-acyl-glycero-3-phosphate acyltransferase, phosphatidic acid phosphatase, lipin-like phosphatidate phosphatase, diacylglycerol kinase, diacylglycerol acyltransferase, phospholipid diacylglycerol acyltransferase, or any combination thereof. Examples of such enzymes and enzyme sequences are provided in Examples 9 and 10.

One of skill in the art can generate genetically-modified algae and/or fungi that contain one or more nucleic acids encoding lipid synthetic enzyme(s). Such genetic modification can be accomplished by a variety of procedures. For example, one of skill in the art can prepare an expression cassette or expression vector that can express one or more lipid synthetic enzyme. Algae and/or fungi cells can be transformed by the expression cassette or expression vector, the cells that were successfully transformed with the lipid synthetic enzyme nucleic can be expanded. Selected algae and fungi can be combined to provide the consortia described herein. Some procedures for making such genetically modified algae and/or fungi are described below.

Promoters:

The lipid synthetic enzyme nucleic acids can be operably linked to a promoter, which provides for expression of RNA encoding the lipid synthetic enzyme(s). The promoter is typically a promoter functional in algae and/or fungi, and can be a promoter functional growth and development of a fungal/algae consortium. The promoter can be a heterologous promoter. As used herein, "heterologous" when used in reference to a gene or nucleic acid refers to a gene or nucleic acid that has been manipulated in some way. For example, a heterologous promoter is a promoter that contains sequences that are not naturally linked to an associated coding region.

A lipid synthetic enzyme nucleic acid is operably linked to the promoter when it is located downstream from the promoter, to thereby form an expression cassette. One lipid synthetic enzyme encoding nucleic acid can be separately regulated from another lipid synthetic enzyme encoding nucleic acid by use of separate promoters and/or separate expression cassettes.

Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired. In some embodiments, the promoter is an inducible promoter and/or a tissue-specific promoter.

Examples of promoters that can be used include, but are not limited to, the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)), the CCR (cinnamoyl CoA:NADP oxidoreductase. EC 1.2.1.44) promoter sequence isolated from *Lollium perenne*, (or a perennial ryegrass) and/or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA.* 83:3320-3324 (1985). Other promoters useful in the practice of the invention are available to those of skill in the art.

Alternatively, novel promoter sequences may be employed in the practice of the present invention. cDNA clones from a particular species are isolated and those clones which are expressed well in algae and/or fungi are identified, for example, using Northern blotting. Preferably, the gene isolated is not present in a high copy number, but is relatively abundant in the cells. The promoter and control elements of corresponding genomic clones can then be localized using techniques available to those of skill in the art.

For example, the promoter can be an inducible promoter. Such inducible promoters can be activated by agents such as chemicals, hormones, sugars, metabolites, or by the age or developmental stage of the algae or fungus. For example, the promoter can be an ethanol-inducible promoter, a sugar-inducible promoter, a senescence-induced promoter or any promoter activated in algae or fungi. One example of a sugar-inducible promoter is a patatin B33 promoter.

A nucleic acid encoding a lipid synthetic enzyme can be combined with the promoter by a variety methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The nucleic acids encoding lipid synthetic enzymes can be subcloned downstream from the promoter using restriction enzymes and positioned to ensure that the DNA is inserted in proper orientation with respect to the promoter so that the DNA can be expressed as sense RNA. Once the lipid synthetic enzyme encoding nucleic acid is operably linked to a promoter, the expression cassette so formed can be subcloned into a plasmid or other vector (e.g., an expression vector). Using restriction endonucleases, the lipid synthetic enzyme nucleic acid is subcloned downstream of the promoter in a 5' to 3' sense orientation.

In some embodiments, a cDNA or other nucleic acid encoding a selected lipid synthetic enzyme is obtained or isolated from a selected species or is prepared by available methods or as described herein. For example, the nucleic acid encoding a lipid synthetic enzyme can be any nucleic acid that encodes any of SEQ ID NO:7-112.

The lipid synthesizing enzymes encoded by the nucleic acids can have sequences that have less than 100% sequence identity to any of SEQ ID NO:7-112. Typically the lipid synthesizing enzymes have about at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity with any of SEQ ID NO:7-112.

In some embodiments, a selectively hybridizing sequence can be employed where the selectively hybridizing sequence encodes a lipid synthesizing enzyme that has at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity to SEQ ID NO:7-112.

The nucleic acids employed in the expression vectors, transgenes, algae, fungi, and methods described herein can also encode a lipid synthesizing enzyme that has less than 100%, or less than 99.5%, or less than 99% sequence identity (or complementarity) with any of SEQ ID NO:7-112. In other words, the lipid synthesizing enzymes and the nucleic acids encoding them that are employed in the expression vectors, transgenes, algae, fungi, consortia, and methods described herein can also not include a wild type sequence.

In some embodiments, the nucleic acids used in the methods, algae, fungi, and consortia provided herein can encode lipid synthesizing enzymes that are less than full length. For example, the enzymes can include those that have at least one amino acid difference, or at least two amino acid differences, or at least three amino acid differences, or at least four amino acid differences, or at least five amino acid differences, or at least six amino acid differences, or at least seven amino acid differences, or at least eight amino acid differences, or at least nine amino acid differences, or at least ten amino acid differences in any of the SEQ ID NO:7-112 sequences. The identical amino acids can be distributed throughout the polypeptide, and need not be contiguous.

A nucleic acid encoding a lipid synthesizing enzyme can have nucleotide sequence variation. For example, the nucleic acid sequences encoding a lipid synthesizing enzyme can be optimized for expression in a particular algal or fungal species by altering selected codons to encode the same amino acid but use nucleotide codons that are more easily 'read' by the transcription/translation machinery of a selected species.

Targeting Sequences:

Additionally, expression cassettes can be constructed and employed to target the lipid synthetic enzyme nucleic acids to an intracellular compartment within the algae or fungal cells or to direct an encoded protein to particular intracellular environment. This can generally be achieved by joining a DNA sequence encoding a transit or signal peptide sequence to the coding sequence of the nucleic acid that encodes the lipid synthetic enzyme. The resultant transit, or signal, peptide will transport the protein to a particular intracellular, or extracellular destination, and can then be posttranslational removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences:

When the expression cassette is to be introduced into an algal or fungal cell, the expression cassette can also optionally include 3' nontranslated regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the nucleic acids encoding the lipid synthetic enzyme by standard methods.

Selectable and Screenable Marker Sequences:

In order to improve identification of transformants, a selectable or screenable marker gene can be employed with the nucleic acids that encode the lipid synthetic enzyme(s). "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are available and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall where the polypeptide includes a unique epitope may be advantageous. Such a secreted antigen marker can employ an epitope sequence that would provide low background in the interior of the cell, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Possible selectable markers for use include, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154, 204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death.

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in cells (Dellaporta et al., In: *Chromosome Structure and Function: Impact of New Concepts.*, 18$^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995).

A further screenable marker contemplated for use is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Numerous other possible selectable and/or screenable marker genes will be apparent to those of skill in the art in addition to the one set forth herein below. Therefore, it will be understood that the discussion provided herein is exemplary rather than exhaustive. In light of the techniques disclosed herein and the general recombinant techniques that are known in the art, the present invention readily allows the introduction of any gene, including marker genes, into a recipient cell to generate a transformed algae or fungal cell.

Other Optional Sequences:

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, such as antibiotic or herbicide resistance, unique multiple cloning sites providing for multiple sites to insert DNA sequences, and/or sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)). This binary Ti vector can be replicated in prokaryotic bacteria such as *E. coli* and *Agrobacterium*. The *Agrobacterium* plasmid vectors can be used to transfer the expression cassette to algae or fungal cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells.

In Vitro Screening of Expression Cassettes:

Once the expression cassette is constructed and subcloned into a suitable plasmid, it can be screened for the ability to express the encoded lipid synthetic enzyme. For example, for expression of one or more lipid synthetic enzymes, the encoding nucleic acid can be subcloned into a selected expression cassette or vector (e.g., a SP6/T7 containing plasmid, which is supplied by ProMega Corp.). The expression of the lipid synthetic enzyme RNA can be detected by Northern analysis, PCR analysis, or other hybridization methods. The lipid synthetic enzyme protein can be detected by antibody staining methods. As a control, a nonsense nucleic acid is expressed from an expression cassette that is introduced into algae or fungal cells. The phenotypes of the control and test cells (e.g., lipid content) can also be assessed.

DNA Delivery of the DNA Molecules into Host Cells:

The present invention generally includes steps directed to introducing at least one nucleic acid encoding a lipid synthetic enzyme into a recipient cell to create a transformed cell. The frequency of occurrence of cells taking up exogenous (foreign) DNA may be low. Moreover, it is most likely that not all recipient cells receiving DNA segments or sequences will result in a transformed cell wherein the DNA is stably integrated into the algae and/or fungal genome and/or expressed. Some may show only initial and transient gene expression. However, certain cells from virtually any species may be stably transformed, and these cells regenerated into transgenic algae, fungi, or algae/fungal consirtia, through the application of the techniques disclosed herein.

Another aspect of the invention is an algae or fungal species, or a fungal/algae consortium with increased oil content, wherein the algae cells, fungal cells, or a fungal/algae consortia has the introduced nucleic acid that encodes the lipid synthetic enzyme(s). The algae or fungal species can, for example, be any species described herein. The cell(s) may be in a suspension cell culture or may be in a consortium.

Transformation of the cells can be conducted by any one of a number of methods known to those of skill in the art. Examples are: Transformation by direct DNA transfer into cells by electroporation (U.S. Pat. Nos. 5,384,253 and 5,472,869, Dekeyser et al., *The Plant Cell.* 2:591-602 (1990)); direct DNA transfer to plant cells by PEG precipitation (Hayashimoto et al., *Plant Physiol.* 93:857-863 (1990)); direct DNA transfer by microprojectile bombardment (McCabe et al., *Bio/Technology.* 6:923-926 (1988); Gordon-Kamm et al., *The Plant Cell.* 2:603-618 (1990); U.S. Pat. Nos. 5,489,520; 5,538,877; and 5,538,880) and DNA transfer to cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

The transformation is carried out under conditions acceptable to the algae and/or fungal cells. The cells are exposed to the DNA or RNA carrying the nucleic acid(s) encoding the lipid synthetic enzyme(s) for an effective period of time. This may range from a less than one second pulse of electricity for electroporation to a 2-3 day co-cultivation in the presence of plasmid-bearing cells. Buffers and media used will also vary with the algae/fungal cells and transformation protocol employed.

Electroporation:

Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, can be employed to render the target recipient cells more susceptible to transformation by electroporation than untreated cells. Alternatively, recipient cells can be made more susceptible to transformation, by mechanical wounding.

To effect transformation by electroporation, one may employ a suspension cell cultures, or friable fungal tissues, or other organized tissues directly. The cell walls of the preselected cells or organs can be partially degraded by exposing them to degrading enzymes (pectinases, pectolyases, polygalacturonases, pectinmethyl esterases, hemicellulose degrading enzymes such as endoxylanases and xyloglucan endoglucanases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment:

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. A low level of transient expression of the nucleic acid encoding the lipid synthetic enzyme(s) may be observed 24-48 hours following DNA delivery. In addition, stable transformants containing the lipid synthetic enzyme nucleic acids can be recovered following bombardment. It is contemplated that particles may contain DNA rather than be coated with DNA. Hence particles may increase the level of DNA delivery but are not, in and of themselves, necessary to introduce DNA into algae or fungal cells.

An advantage of microprojectile bombardment is that the isolation of protoplasts (Christou et al., *PNAS.* 84:3962-3966 (1987)), and the formation of partially degraded cells, or the susceptibility to *Agrobacterium* infection is not required.

For bombardment, cells in suspension can be concentrated on filters or solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

Selection:

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

For example, to use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate may be useful. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

The enzyme luciferase, or fluorescent proteins (e.g., green fluorescent protein, GFP) are also useful as screenable markers. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

Determination of Stably Transformed Algae or Fungi:

To confirm the presence of the nucleic acid encoding the lipid synthesizing enzymes in the algae and/or fungi, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; and also, by analyzing the phenotype of the algae, fungi, or consortia. In some embodiments, the amount of oil in algae, fungi, or consortia is quantified. Such a quantified oil content can be compared to a control, for example, a control algae, fungi, or consortia of the same species that has not be modified to express the nucleic acid(s) that encode the lipid synthesizing enzymes.

Whereas DNA analysis techniques may be conducted using DNA isolated from any part of a plant. RNA may only be expressed in particular cells or tissue types and so RNA for analysis can be obtained from those tissues. PCR techniques may also be used for detection and quantification of RNA produced from the introduced lipid synthesizing enzyme nucleic acid(s). RT-PCR also be used to reverse transcribe expressed RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

Southern blotting, northern blotting and PCR may be used to detect the inhibitory nucleic acid(s) encoding the lipid synthesizing enzymes in question. Expression may also be evaluated by specifically identifying the presence or absence of protein products of the introduced lipid synthesizing enzyme nucleic acids, by assessing the level of enzyme expressed, or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to confirm the identity of the lipid synthesizing enzyme(s) expressed such as evaluation by nucleic acid or amino acid sequencing following purification. Other procedures may be additionally used.

The expression of a nucleic acid or gene product can also be determined by evaluating the phenotypic results of its expression. These assays also may take many forms including but not limited to analyzing changes in the chemical composition, morphology, or physiological properties of the algae, fungus or consortium. For example, the lipid composition of algae, fungus or consortium can be evaluated and/or quantified.

The following non-limiting Examples illustrate how aspects of the invention have been developed and can be made and used.

Example 1: Materials and Methods

This Example describes some of the materials and methods that were used in the development of the invention.

Strains and Growth Conditions

Marine alga *Nannochloropsis oceanica* CCMP1779 was obtained from Provasoli-Guillard National Center for Culture of Marine Phytoplankton and incubated as described by Vieler et al. (PLoS Genet. 8, e1003064 (2012)). In brief, *N. oceanica* cells were grown in flasks containing f/2 media under continuous light (~80 µmol/m$^2$/s) at 22° C. with agitation (100 rpm). Log-phase algal culture (1~3×10$^7$ cells/mL) was used for co-culture with fungi. Cell size and density of algal culture were determined using a Z2 Coulter Counter (Beckman). *Mortierella elongata* AG77 and NVP64 were isolated from soil samples collected at North Carolina. USA (AG77) and Michigan, USA (NVP64). *M. elongata* AG77 and NVP64 hosting bacterial endosymbiont had been cured of their endobacteria by a series of antibiotic treatments as described by Partida-Martinez et al. (Chembiochem. 8, 41-45 (2007)), and the resultant clean strains were used in this study. Other fungal isolates obtained from healthy surface sterilized *Populus* roots were obtained from the Plant-Microbial Interfaces (PMI) project (Bonito et al., Fungal Ecol. 22, 35-42 (2016)) (new strains). Fungi were incubated in flasks containing PDB media (12 g/L potato dextrose broth, 5 g/L yeast extract, pH 5.3) at room temperature (RT, ~22° C.).

For the co-culture of algae and fungi, fungal mycelia were briefly blended into small pieces (0.5 to 2 cm) using a sterilized blender (speed, 30 s). After 24-h recover in PDB medium, fungal tissues were collected by centrifugation (3.000 g for 3 min), washed twice with f/2 medium and resuspended in ~15 mL f/2 medium. A portion of fungal tissues (3-4 mL) were used for the calculation of dry biomass: 1 mL of fungal tissues were transferred with cut-off pipette tip and filtrated through pre-dried and pre-weighed Whatman GF/C filters and dried overnight at 80° C. Similar method was used for the measurement of alga biomass. Fungal tissues about 3 times of alga biomass were added into *N. oceanica* culture for co-cultivation on a shaker (~60 rpm) under continuous light (~80 µmol/m$^2$/s) at RT. After 18-days of co-culture, the shaker was turned off for free settling of algae and fungi overnight. Supernatant was removed with Pasteur pipettes and the same volume of fresh f/2 medium containing 10% PDB was added to the culture. After that, the alga-fungus co-culture was biweekly refreshed with f/2 medium supplemented with 10% PDB.

Nutrient deprivation of the co-culture was performed according to a published protocol for *N. oceanica* (Vieler et al., PLoS Genet. 8, e1003064 (2012)). Mid-log-phase *N. oceanica* cells (~1×10$^7$ cells/mL) grown in f/2 media (25 mL) were harvested by centrifugation and washed twice with nutrient-deficient f/2 media [without carbon (—C), nitrogen (—N) or phosphorus (—P)] and resuspended in 25 mL nutrient-deficient f/2 media, respectively. AG77 mycelia grown in PDB medium were washed twice with the nutrient-deficient f/2 and added into respective *N. oceanica* cultures for co-cultivation. To block carbon dioxide from air, the flasks of —C cultures were carefully sealed with Parafilm M over aluminum foil wrap. Cell viabilities were analyzed by confocal microscopy after 10-d co-culture of —N and 20 d of —C and —P.

Light Microscopy

Interaction and symbiosis between algae and fungi were examined with an inverted microscope with differential interference contrast (DIC) and time-lapse modules (DMi8. Leica). DIC images were taken from the alga-fungus aggregates after short-term (6 days) and long-term (over one month) co-cultivation. To characterize the algal endosymbiosis in fungi, differential interference contrast (DIC) and time-lapse photography were performed using different period of long-term co-culture of algae and fungi (from 1 to 6 months). Alga-fungus aggregates grown in flasks were transferred to 35 mm-microwell dish (glass top and bottom, MatTek) and embedded in a thin layer of soft-solid f/2 medium supplemented with 10% PDB and 0.25% low gelling temperature agarose (Sigma-Aldrich) that immobilized cells for microscopy. Morphology of different age green hyphae (AG77 hyphae containing intracellular *N. oceanica* cells) was recorded in DIC micrographs (FIG. 4A to 4E), as well as real-time videos that showed four groups of green hyphae with manually adjusted focus. Videos were put side by side in a movie (data not shown) using video-editing software VideoStudio X9 (Corel). To investigate the establishment of algal endosymbiosis in fungi, randomly selected alga-fungus aggregates from 35-d co-culture were incubated and observed in 35 mm-microwell dish containing soft-solid f/2 medium with 10% PDB and 0.25% agarose up to two weeks. Time-lapse photographs were combined together to create another movie (data not shown) with VideoStudio.

Scanning Electron Microscopy

SEM was performed to investigate the physical interaction between *N. oceanica* and *M. elongata* at the Center for Advanced Microscopy of Michigan State University (CAM, MSU). Alga-fungus aggregates from 6-d co-culture of *N. oceanica* and *M. elongata* (AG77 or NVP64) were fixed in 4% (v/v) glutaraldehyde solution and dried in critical point dryer (Model 010, Balzers Union). After drying, the samples were mounted on aluminum stub using high vacuum carbon tabs (SPI Supplies) and coated with osmium using a NEOC-AT osmium coater (Meiwafosis). Processed exocarp tissues were examined using a JSM-7500F scanning electron microscope (Japan Electron Optics Laboratories).

Confocal Microscopy

Figure 3A:
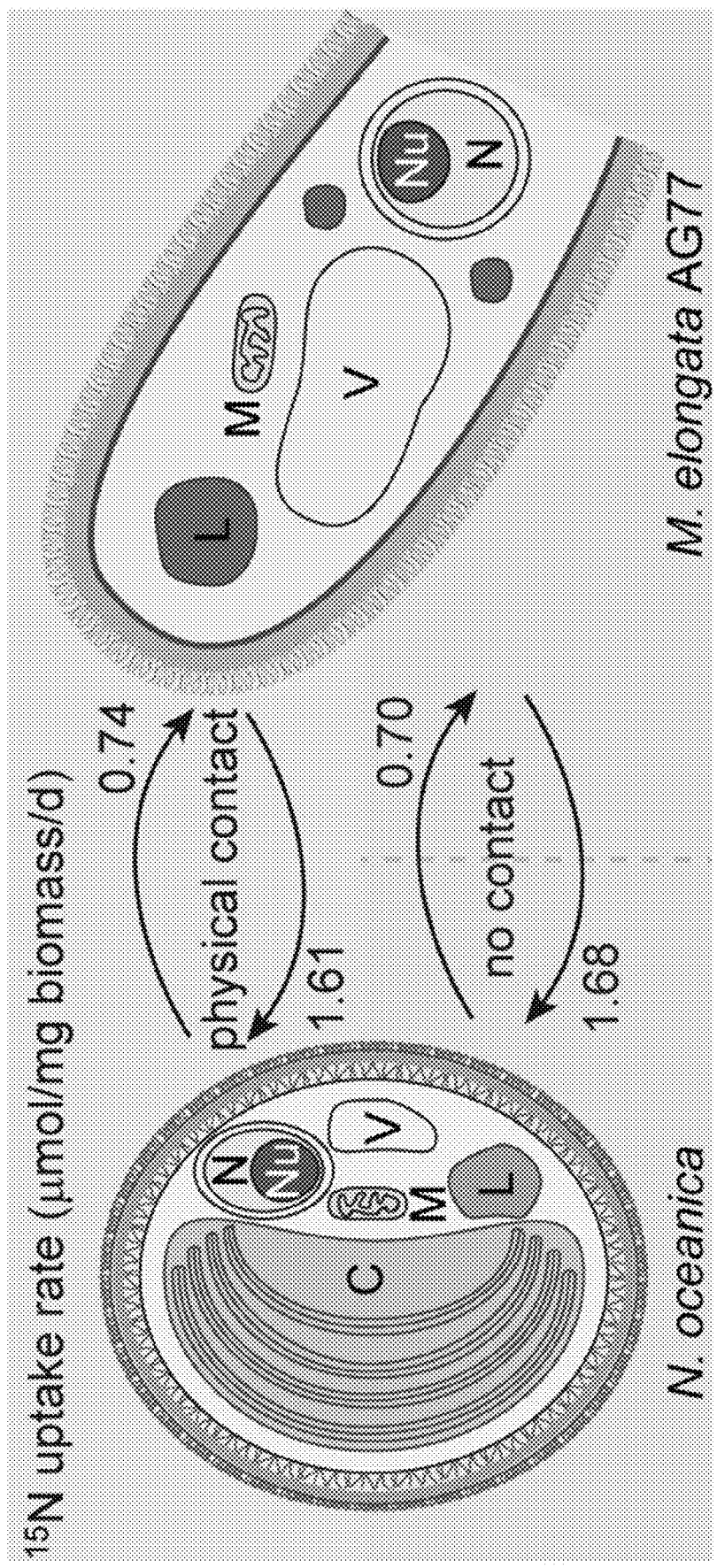
FIGS. 3A-3J illustrate that *N. oceanica* benefits from co-culture with *M. elongata*.
Figure 3B:
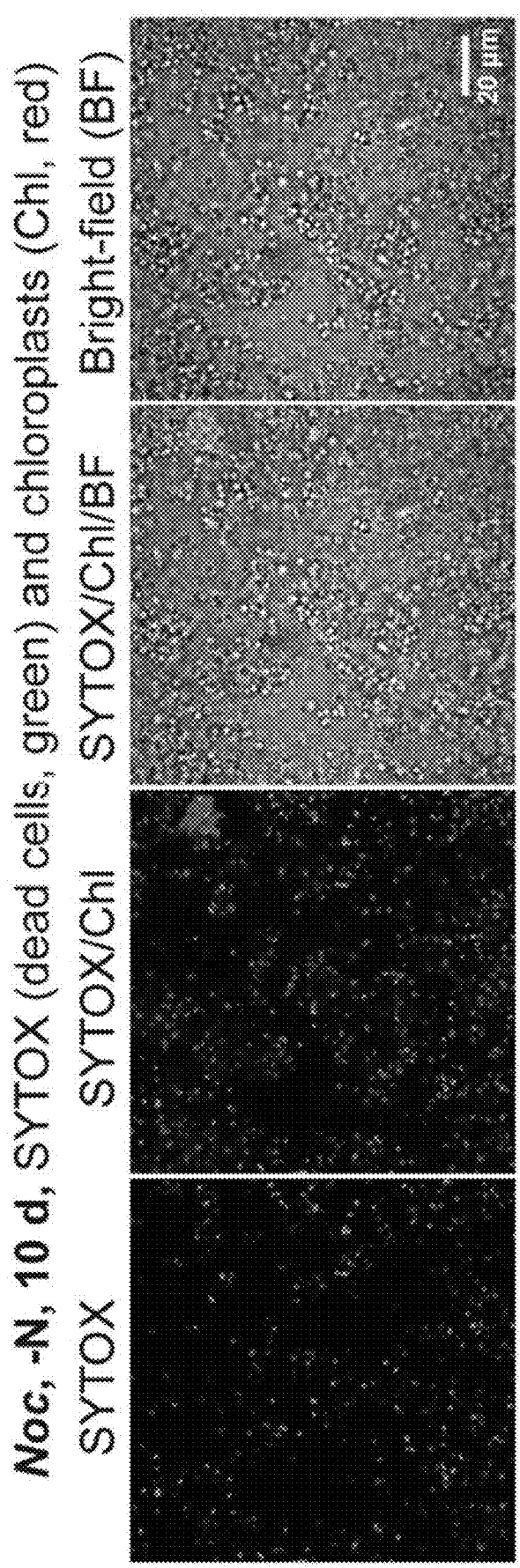
Figure 3C:
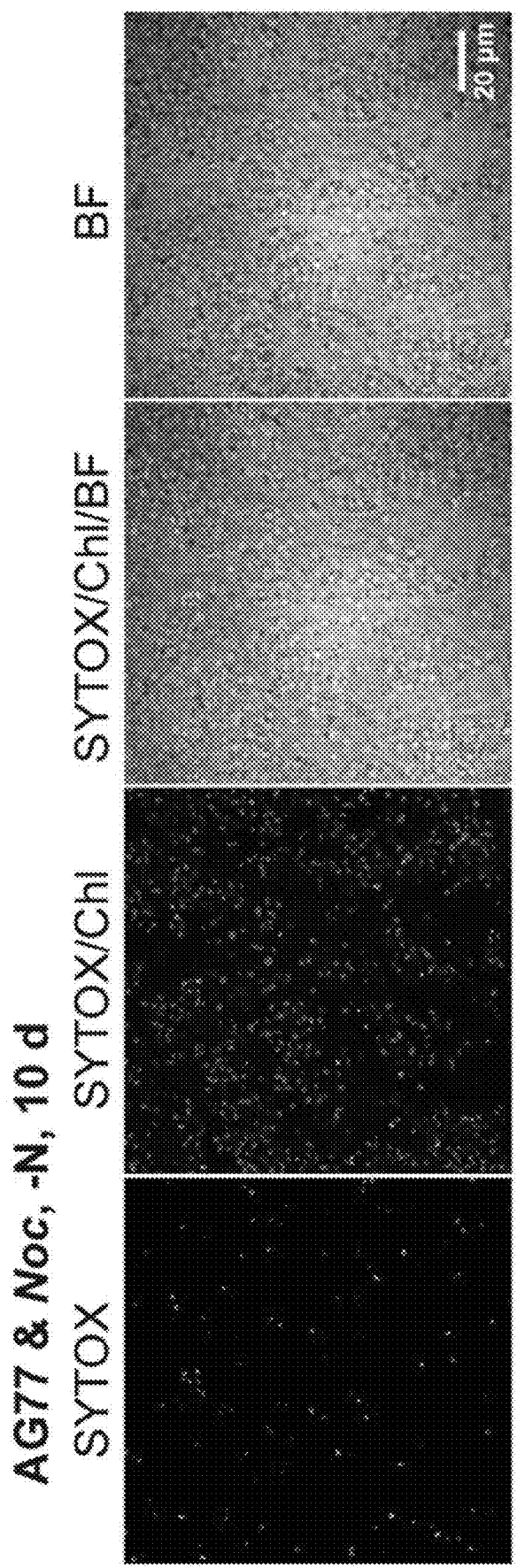
Figures 3D, 3E:
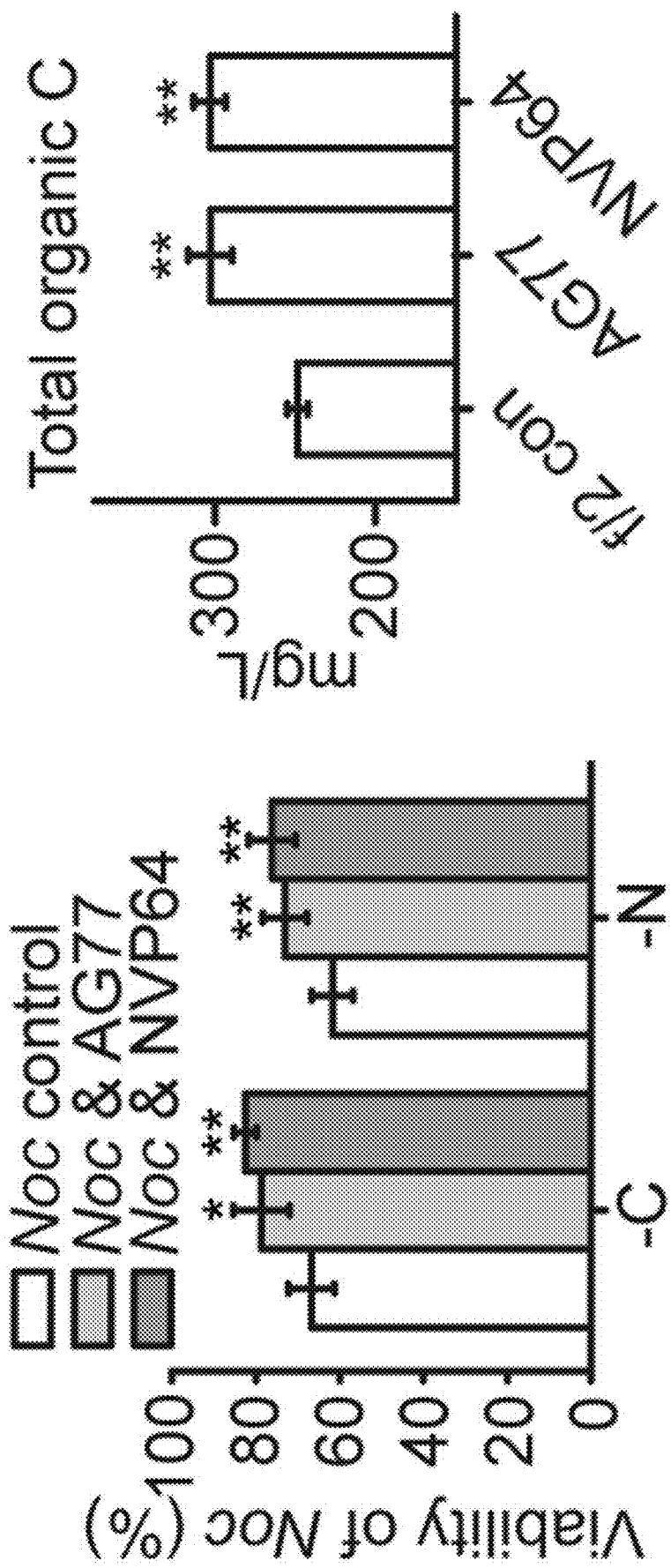

Viability of *N. oceanica* and *M. elongata* cells (e.g., during their co-culture) was determined by confocal microscopy using a confocal laser scanning microscope FluoView 1000 (Olympus) at CAM, MSU. SYTOX® Green nucleic acid stain (Molecular Probes. Life Technologies), a green-fluorescent nuclear and chromosome counterstain impermeant to live cells, was used to indicate dead cells of algae and fungi following a protocol described by Tsai et al. (Proc. Natl. Acad. Sci. U.S.A. 111, 15833-15838 (2014)). Briefly, 1 µL of 5 mM SYTOX Green was added to 1 mL of cell culture and incubated for 5 min in the dark at room temperature. Samples were washed twice with f/2 medium before observation (SYTOX Green, 488 nm excitation, 510 to 530 nm emission; chlorophyll, 559 nm excitation, 655 to 755 nm emission). Viability of *N. oceanica* cells was analyzed using ImageJ software. Cell viability was analyzed during alga-fungus co-culture in flasks containing f/2 medium (1, 4 and 7 days) to investigate whether the cells were living or dead during the 7-day co-culture of $^{14}$C- and $^{15}$N-chasing experiments. Viability of *N. oceanica* cells co-cultivated with *M. elongata* AG77 and NVP64 under nutrient deprivations (without a nitrogen source (—N), without a carbon source (—C), and/or without a phosphate source (—P)) was tested to evaluate whether *N. oceanica* benefits from the co-culture with *Mortierella* fungi (FIG. 3B-3D). Viability of *M. elongata* AG77 was analyzed during its 30-day incubation in f/2 medium to check whether the cells were living or dead when the culture media were collected for nutrient analyses (total organic C and dissolved N, FIG. 3F-3G).

Localization of *N. oceanica* cells in alga-fungus aggregates was investigated by cell-wall staining using Wheat Germ Agglutinin Conjugate Alexa Fluor® 488 (WGA, Molecular Probes) following the manufacturer's instruction. In brief, alga-fungus aggregates were collected by centrifugation and washed once with PBS buffer (pH7.2), followed by addition of 5 µg/mL WGA and incubation at 37° C. for 10 min. Samples were washed twice with f/2 medium and observed under the FluoView 1000 microscope (WGA, 488 nm excitation, 510 to 530 nm emission; chlorophyll, 559 nm excitation, 655 to 755 nm emission).

Transmission Electron Microscopy

Figures 4A, 4B, 4C:
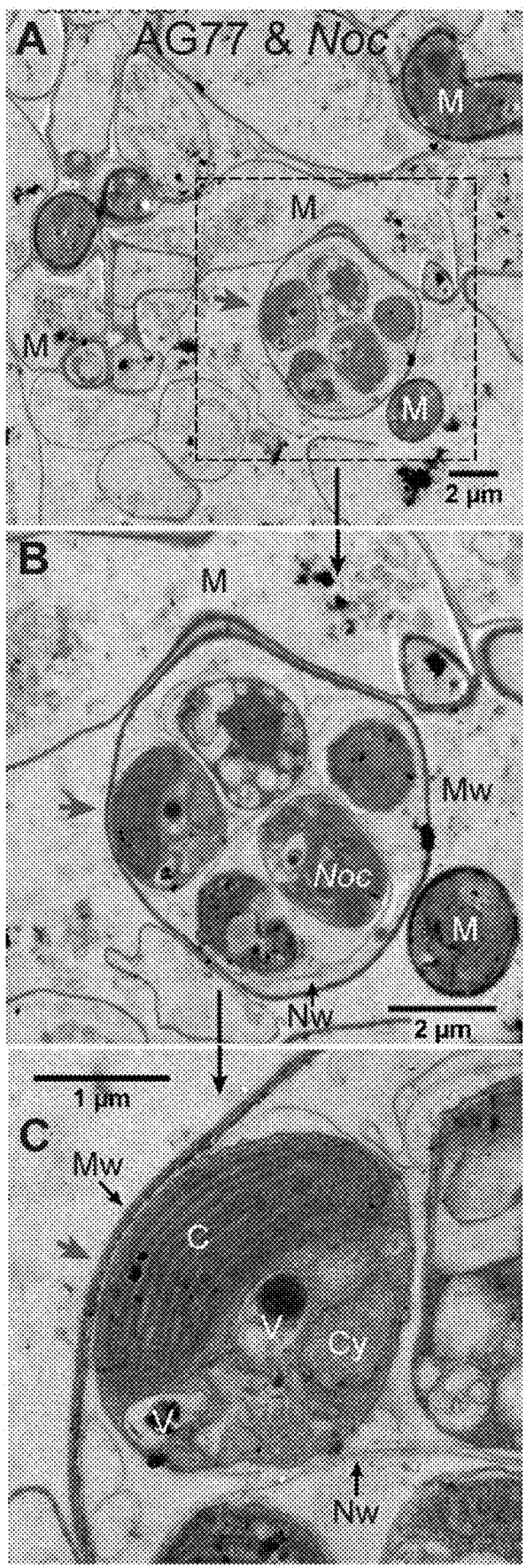
Figures 4D, 4E, 4F:
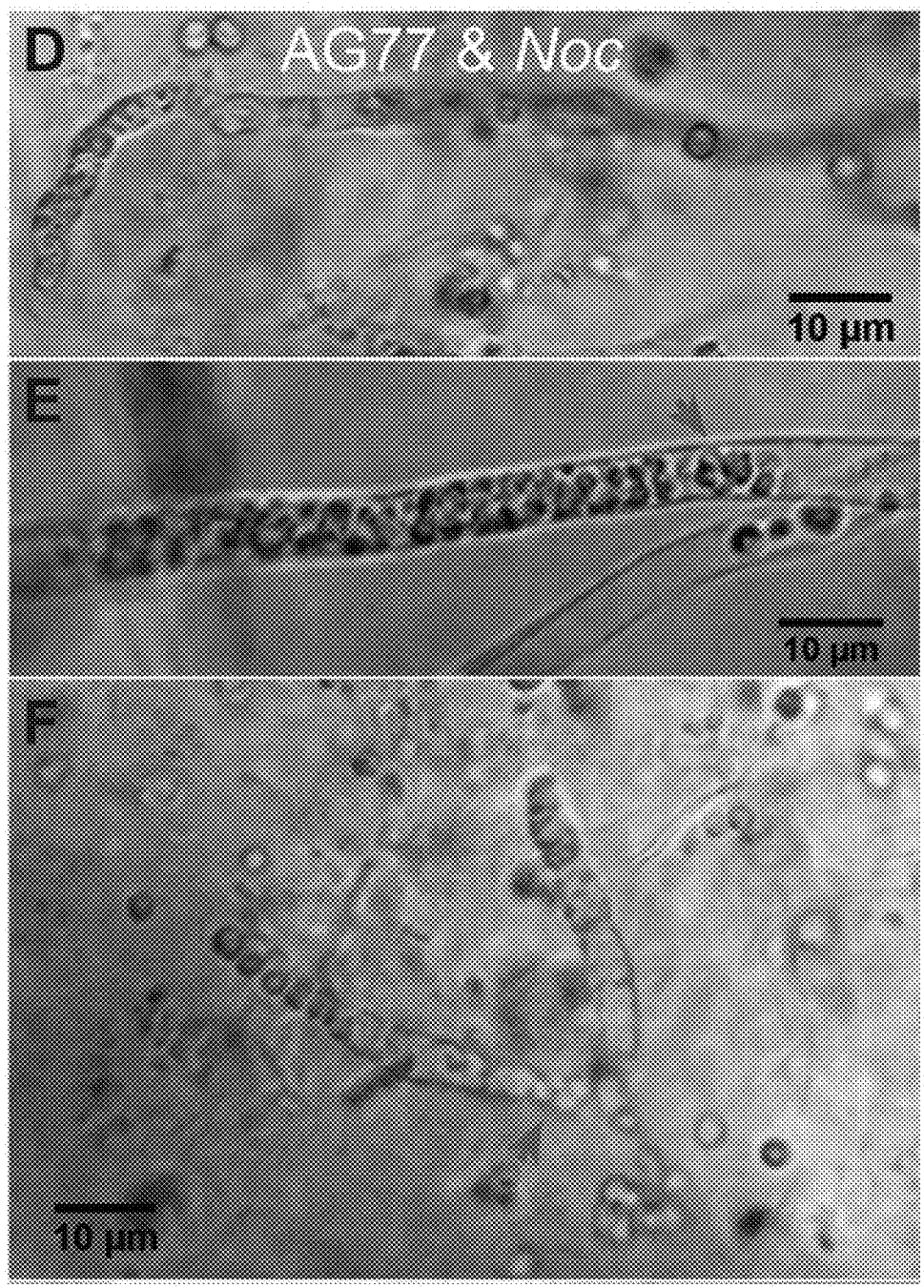
Figure 4G:
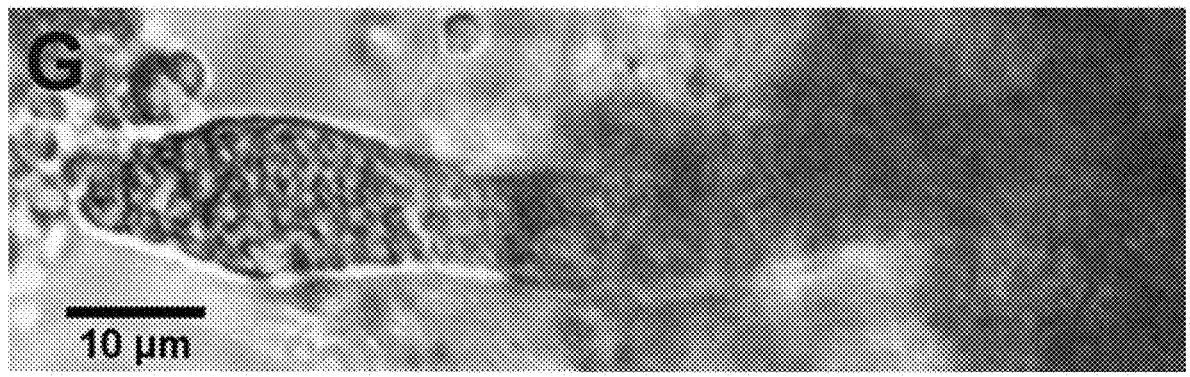
Figure 4H:
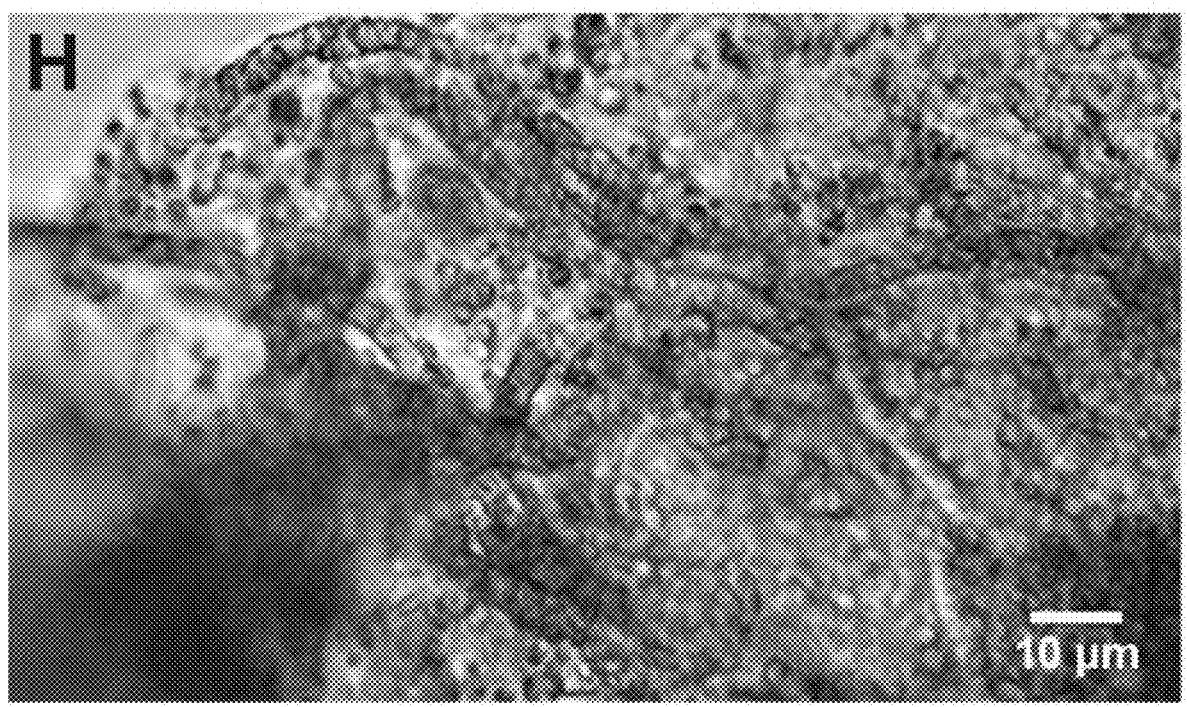
Figure 5E:
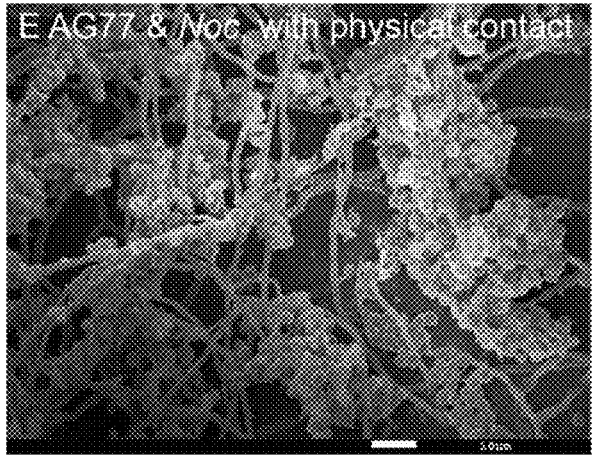
Figure 5F:
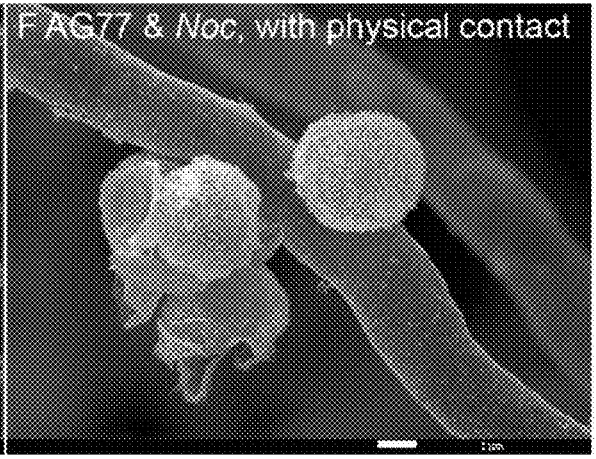
Figure 5G:
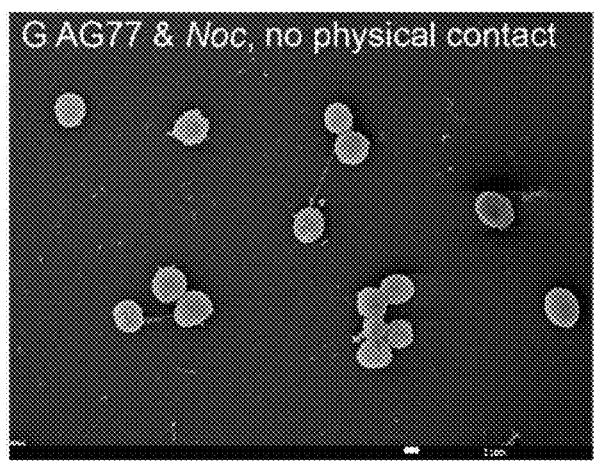
Figure 5H:
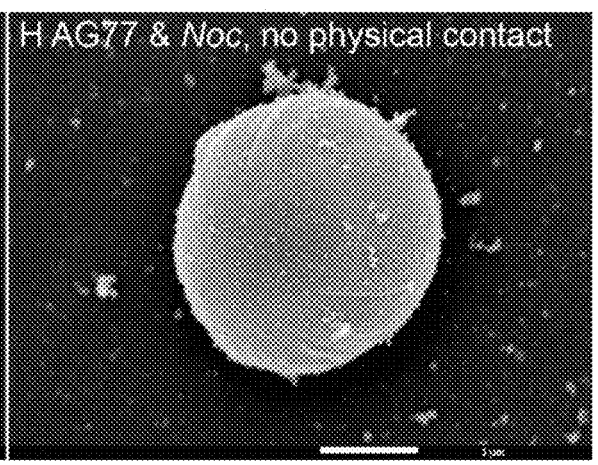

TEM was performed on *Nannochloropsis oceanica* and *Mortierella* aggregates co-cultured for about one month. Randomly collected alga-fungus aggregates were fixed overnight at 4° C. in sodium cacodylate buffer (50 mM, pH 7.2) supplemented with 2.5% (v/v) glutaraldehyde. The fixed samples were washed three times with sodium cacodylate buffer, post-fixed in 1% $OsO_4$ (v/v) for 2 hours at room temperature and then washed three times with sodium cacodylate buffer. After dehydration through a graded series of ethanol and acetone, samples were infiltrated with a series of acetone/resin Epon/Araldite mixtures and finally embedded in resin Epon/Araldite mixture (Electron Microscopy Sciences). Ultrathin sections (70 nm) were cut with an ultramicrotome (RMC Boeckeler) and mounted onto 150 mesh formvar-coated copper grids, followed by staining with uranyl acetate for 30 min at room temperature. The sections were then washed with ultrapure water and stained 10 min with lead citrate and used for observation. Images were taken with a JEOL100 CXII instrument (Japan Electron Optics Laboratories) equipped with SC1000 camera (Model 832, Gatan) and processed with ImageJ (FIG. 4F-4H).

Example 2: Methods for Evaluating Nutrient Exchange Between Fungi and Algae

Light microscopy and SEM showed tight physical interaction between soil fungus *Mortierella elongata* and the marine algae *Nannochloropsis oceanica*. This Example describes experiment procedures for evaluating whether metabolic exchanges occur between *N. oceanica* and *M. elongata*.

Isotope labeling and chasing experiments were performed using labeled carbon and nitrogen ($^{14}C$ and $^{15}N$) nutrients for *N. oceanica* and *M. elongata*. For $^{14}C$ assays, 20 µL of [$^{14}C$]sodium bicarbonate (1 mCi/mL, 56 mCi/mmol, American Radiolabeled Chemicals) was added to 20 mL of early log-phase culture of *N. oceanica* (~2×10$^6$ cells/mL) and incubated for 5 days when the $^{14}C$ incorporation reached ~40%. The $^{14}C$-labeled *N. oceanica* cells were harvested by centrifugation (4.000 g for 10 min) and washed three times with 172 medium. The supernatant of the last wash was analyzed in Bio-Safe II counting cocktail (Research Products International) using a scintillation counter (PerkinElmer 1450 Microbeta Trilux LSC), to confirm that $^{14}C$-labeling medium was washed off. The pellet of $^{14}C$-labeled *N. oceanica* was resuspended in 20 mL f/2 medium. Subsequently, non-labeled *M. elongata* AG77 mycelia (~3 times of algae biomass, intact cells without blending) grown in PDB medium were washed twice with f/2 medium and added to the 20 mL $^{14}C$-labeled algal culture for 7-d co-cultivation. Alga-fungus aggregates were then harvested by PW200-48 mesh (Accu-Mesh) and algal cells in the flow through were collected by centrifugation (4,000 g for 10 min) and kept as the first part of $^{14}C$-labeled alga control. Alga-fungus aggregates were intensively washed in 50 mL conical centrifuge tube containing 40 mL of f/2 medium using a bench vortex mixer (~1500 rpm, 15 min). Fungal mycelia were collected by NITEX 03-25/14 mesh (mesh opening 25 µm, SEFAR), and algal cells in the flow through were harvested by centrifugation and stored as the second fraction of $^{14}C$-labeled alga control. Mesh-harvested fungal mycelia (with obviously reduced amount of algae attached) were added to 1.5 mL microcentrifuge tube containing 300 µL of PBS buffer (pH 5.0) supplemented with 4% hemicellulase (Sigma-Aldrich) and 2% driselase (Sigma-Aldrich) and incubated overnight at 37° C. This step was performed to digest the algal cell walls (Chen et al. J. Phycol. 44, 768-776 (2008)). After cell-wall digestion, 700 µL of f/2 medium was added and algae were separated from fungi by intensive vortex for 15 min. Fungal mycelia were collected by NITEX 03-25/14 mesh while the flow-through was kept as the last fraction of alga control. Three fractions of $^{14}C$-labeled alga controls were combined together while fungi were washed three times with f/2 medium. Half of the samples were dried and weighed for biomass and the others were used for $^{14}C$ measurements. To examine cross contamination after alga-fungus isolation, non-radioactive samples were processed the same way and analyzed by light microscopy and PCR. PCR primers were used that were specific for the *N. oceanica* gene encoding Aureochrome 4 (AUREO4), a blue light-responsive transcription factor that only conserved in photosynthetic stramenopiles such as *N. oceanica*: Aureo4pro F+ (5'-AGAGGAGC-CATGGTAGGAC-3'; SEQ ID NO:1) and Aureo4 DNAD R– (5'-TCGTTCCACGCGCTGGG-3'; SEQ ID NO:2). Primers specific for *M. elongata* were also used, including genes encoding translation elongation factor EF1α and RNA polymerase RPB1: EF1αF (5'-CTTGCCACCCTTGC-CATCG-3'; SEQ ID NO:3) & EF1αR (5'-AACGTCGTCGTTATCGGACAC-3'; SEQ ID NO:4), RPB1F (5'-TCACGWCCTCCCATGGCGT-3'; SEQ ID NO:5) and RPB1R (5'-AAGGAGGGTCGTCTTCGTGG-3'; SEQ ID NO:6).

Isolated algae and fungi were frozen by liquid nitrogen and ground into fine powders by steel beads and TissueLyser II (QIAGEN), followed by lipid extraction in 1.2 mL chloroform:methanol (2:1, v/v) with vortex for 20 min. Double-distilled water (ddH$_2$O, 100 µL) was added to the samples, briefly mixed by vortex and then centrifuged at 15,000 g for 10 min. Organic phase was collected as total lipids. One mL of 80% methanol (v/v) was added to the water phase and cell lysis to extract free amino acids (FAAs). After centrifugation at 20,000 g for 5 min. supernatant was kept as total FAAs and the pellet was air-dried and used to extract protein with 200 µL of SDS protein extraction buffer at 42° C. for 15 min. After centrifugation at 10.000 g for 10 min, supernatant (~200 µL) was collected for further protein precipitation (−20° C., 1 h) with the addition of 800 µL pre-cold acetone, while the pellet was kept for carbohydrate analyses. Total proteins (pellet) and soluble compounds (supernatant) were separated by centrifugation at 20,000 g for 15 min after protein precipitation.

The pellet of total proteins was resuspended in 200 μL of SDS protein extraction buffer for scintillation counting. The pellet of carbohydrates was air-dried, resuspended in 200 μL ethanol, transferred to glass tube with Teflon-liner screw cap, and then dissolved by 2 to 4 mL of 60% sulfuric acid (v/v) according to described protocols (Velichkov, World J. Microbiol. Biotechnol. 8: 527-528 (1992), Scholz et al., Eukaryot. Cell. 13, 1450-1464 (2014)). Vortex and incubation at 50° C. were performed for the hard ones. Total lipids and soluble compounds were counted in 3 mL of xylene-based 4a20 counting cocktail (Research Products International), whereas total FAAs, proteins and carbohydrates were counted in 3 mL of Bio-Safe II counting cocktail. $^{14}C$ radioactivity of the samples (dpm, radioactive disintegrations per minute) was normalized to their dry weight (dpm/mg).

To examine carbon transfer from fungi to algae, 200 μL of 0.1 mCi/mL [$^{14}C$]D-glucose (268 mCi/mmol, Moravek Biochemicals) or 100 μL of 1 mCi/mL [$^{14}C$]sodium acetate (55 mCi/mmol. American Radiolabeled Chemicals) were added to 20 mL of $M.$ $elongata$ AG77 grown in modified Melin-Norkrans medium [MMN, 2.5 g/L D-glucose, 0.25 g/L $(NH_4)_2HPO_4$, 0.5 g/L $KH_2PO_4$, 0.15 g/L $MgSO_4$, 0.05 g/L $CaCl_2$)]. After 5-d $^{14}C$-labeling, fungal mycelia were harvested and washed three times with f/2 medium. Supernatant of the last wash was confirmed clean of $^{14}C$ with scintillation counting. $^{14}C$-labeled fungi were added to 20 mL of $N.$ $oceanica$ culture for a 7-day co-culture. Alga-fungus aggregates were harvested using PW200-48 (first filtration) and NITEX 03-25/14 (second filtration) meshes. Algae in the flow-through were harvested and washed twice with f/2 medium by centrifugation and kept as free $N.$ $oceanica$ (unbound algal cells). The rest steps of sample preparation and $^{14}C$ measurement was performed in the same way as described above.

To test whether physical contact is necessary for the carbon exchange between $N.$ $oceanica$ and $M.$ $elongata.$ $^{14}C$-labeling and chasing experiments were carried out using standard 6-well cell culture plates coupled with cell culture inserts that have a bottom made by hydrophilic polytetrafluoroethylene membrane filters (pore size of 0.4 μm. Millipore) to grow algae and fungi together with metabolic exchange but without physical contact. $^{14}C$-labeling was performed in the same way as described above. For alga-fungus co-culture, $^{14}C$-labeled algae (or fungi) were added in either plate wells or cell culture inserts while respective fungi (or algae) were grown separately in the inserts or plate wells to examine cross contamination. After 7-day co-culture, algae and fungi grown in the insert-plate system were easily separated by moving the insert to adjacent clean well. Samples were then processed following the protocol described above (without the steps of mesh filtration and cell-wall digestion).

Considering that $Mortierella$ fungi are saprotrophic. Experiments were performed that involved $^{14}C$-labeling and chasing experiments using heat-killed $^{14}C$-cells to test whether algae and fungi utilize $^{14}C$ from dead cells. Briefly, $^{14}C$-labeled algae or fungi were washed three times with f/2 medium and incubated in a water bath at 65° C. for 15 min, which killed the cells without causing serious cell lyses and addition of chemicals. Heat-killed $^{14}C$-algae (or fungi) were co-cultivated with unlabeled fungi (or algae) for 7 days in flasks. Subsequently, algae and fungi were separated by cell-wall digestion and mesh filtration, and $^{14}C$ radioactivity of the samples was measured by scintillation counting as described above.

Nitrogen is another major nutrient for $N.$ $oceanica$ and $Mortierella.$ Nitrogen exchange between $N.$ $oceanica$ and $M.$ $elongata$ was tested by $^{15}N$-labeling and chasing experiments using isotope ratio mass spectrometry. For $^{15}N$ labeling of algae and fungi, $N.$ $oceanica$ cells were inoculated and grown in 200 mL of $^{15}N$-f/2 medium containing ~5% of [$^{15}N$]potassium nitrate [$^{15}N/(^{15}N+^{14}N)$, mol/mol], while $M.$ $elongata$ mycelia were inoculated and incubated in 2 L of $^{15}N$-MMN medium containing ~5% of [$^{15}N$]ammonium chloride for two weeks. Algal culture was diluted by the addition of fresh $^{15}N$-f/2 medium to maintain cell density at log phase. $^{15}N$-labeled $N.$ $oceanica$ cells from a 4 liter culture and $^{15}N$-labeled $M.$ $elongata$ mycelia from a 2 liter culture were harvested and a portion of the samples was kept as $^{15}N$-labeled controls. The rest of the sample was added to unlabeled cells in flasks (with physical contact) or to unlabeled cells in 6-well-culture plates with inserts (no physical contact) for a 7-day co-cultivation. Algae and fungi were separated after the co-culture as described above. Samples were then washed three times with $ddH_2O$. Fungal mycelia were homogenized in TissueLyser II (QIAGEN) using steel beads. Algae and fungi were then acidified with 1.5 to 3 mL of 1 N HCl, dried in beakers at 37° C. and weighed for biomass. Isotopic composition of algae or fungi ($\delta^{15}N$, ratio of stable isotopes $^{15}N/^{14}N$) and nitrogen (N) content (% N) were determined using a Eurovector (EuroEA3000) elemental analyzer interfaced to an Elementar Isoprime mass spectrometer following standard protocols (Fry et al., Rapid Commun. Mass Spectrom. (2007)). The N uptake rates (μmol N/mg biomass/day) of $^{15}N$-labeled $N.$ $oceanica$ cells from the media (medium-N, isotope dilution) and that of AG77 from $^{15}N$-labeled $N.$ $oceanica$-derived N ($^{15}N$) were calculated based on the Atom % $^{15}N$ [$^{15}N/(^{15}N+^{14}N)100\%$]. % N and biomass following a protocol by Ostrom et al. (2016). The N uptake rates of $^{15}N$-AG77 from the media and that of recipient $N.$ $oceanica$ from $^{15}N$-AG77-derived N ($^{15}N$) were calculated in the same way.

Carbon and Nitrogen Measurements

Figure 3F:
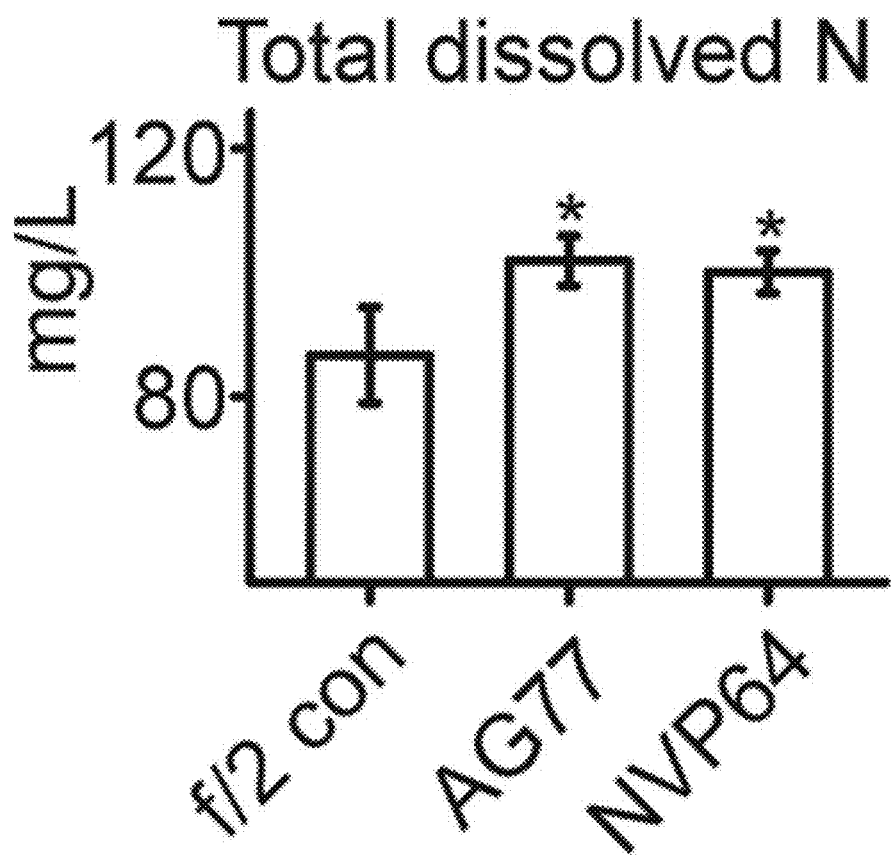
Figure 3G:
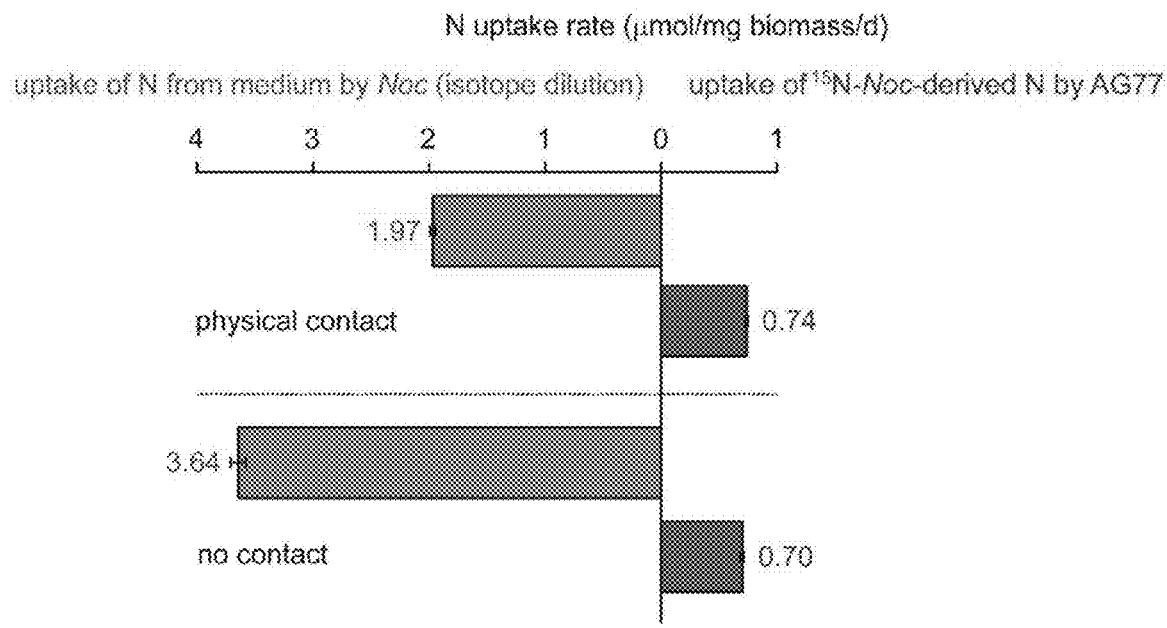

Total organic carbon (TOC) and total dissolved nitrogen (TDN) in the media of $Mortierella$ cultures were measured with a TOC-Vcph carbon analyzer with total nitrogen module (TNM-1) and ASI-V autosampler (Shimadzu) (FIG. 3F-3G). $M.$ $elongata$ AG77 and NVP64 were incubated for 18 days in flasks containing 25 mL of f/2 medium. Fungal tissues were removed by filtration with 0.22 micron filters (Millipore) and the flow-through was subject to TOC and TDN analyses.

Example 3: Carbon Nutrient Exchange Between Fungi and Algae

To test whether carbon or nitrogen exchange underlies the interaction between the soil fungus $Mortierella$ $elongata$ AG77 and the marine algae $Nannochloropsis$ oceanica, a series of experiments were conducted using reciprocally $^{14}C$- and $^{15}N$-labeled algal and fungal partners. For carbon exchange assays algal cells were labeled with [$^{14}C$]-sodium bicarbonate and co-cultivated with non-labeled hyphae in flasks for one week. Conversely, fungal hyphae were grown in either [$^{14}C$]-glucose- or [$^{14}C$]-acetate-containing medium, then were co-incubated with non-labeled algal cells in flasks that allowed the two organisms to interact physically. Co-cultured algal and fungal cells were separated from each other by mesh filtration and were then analyzed for $^{14}C$ exchange.

Figures 1, 2, 2A:
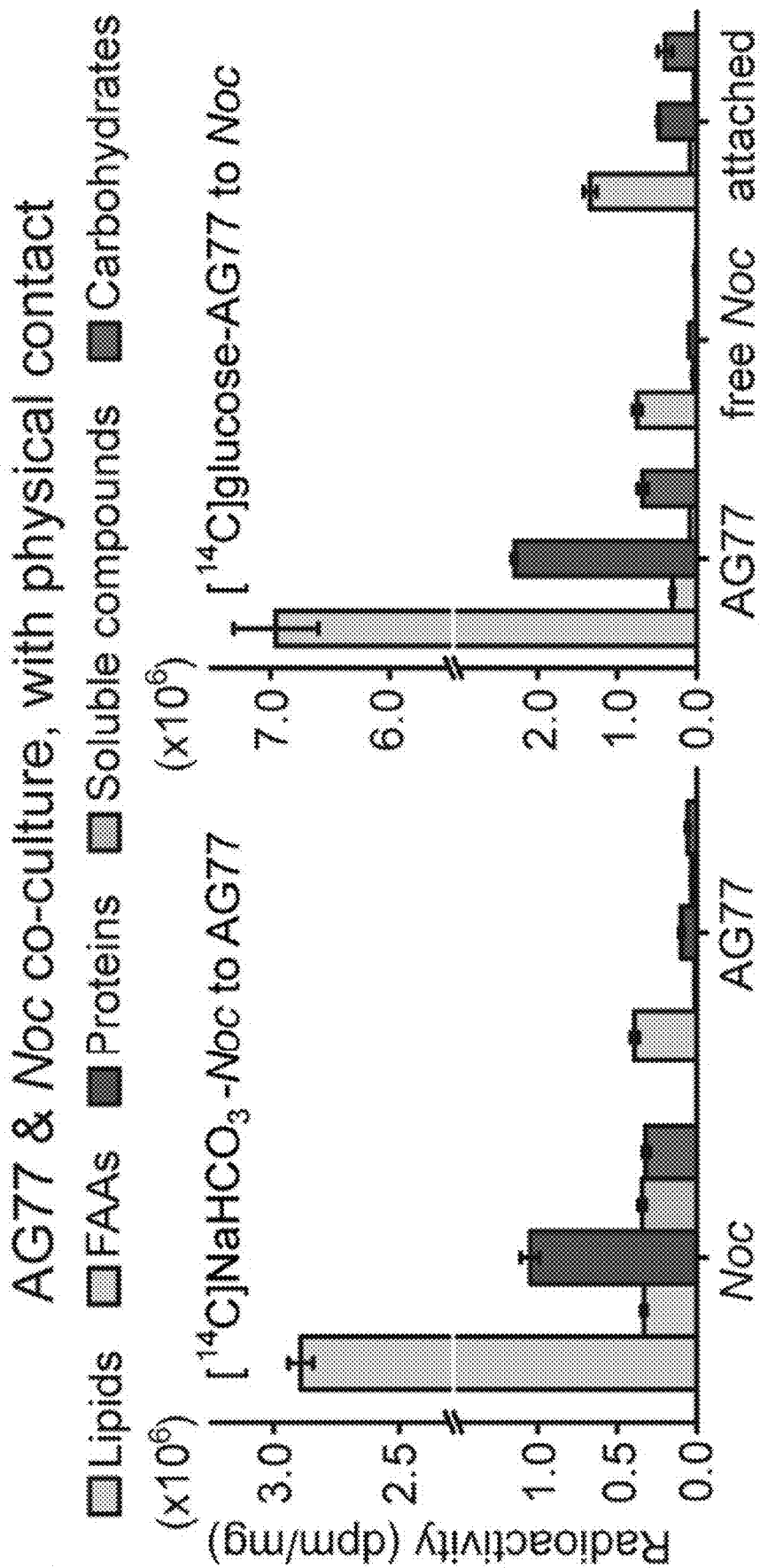

FIG. 2A-1 shows that $^{14}C$-carbon is transferred from the alga ($Nannochloropsis$ $oceanica;$ Noc) to the fungus ($Mor$- tierella elongata AG77). Nearly 70% of the transferred $^{11}$C-carbon was incorporated into the fungal lipid pool. Similarly, $^{14}$C-carbon transfer was observed from the labeled fungus (*Mortierella elongata* AG77) to its algal recipient (*Nannochloropsis oceanica*; Noc) (FIG. 2A-2). Intriguingly, algal cells attached to the fungal hyphae acquired more $^{14}$C than unattached cells grown in the same flask (FIG. 2A).

Figures 1, 2, 2B:
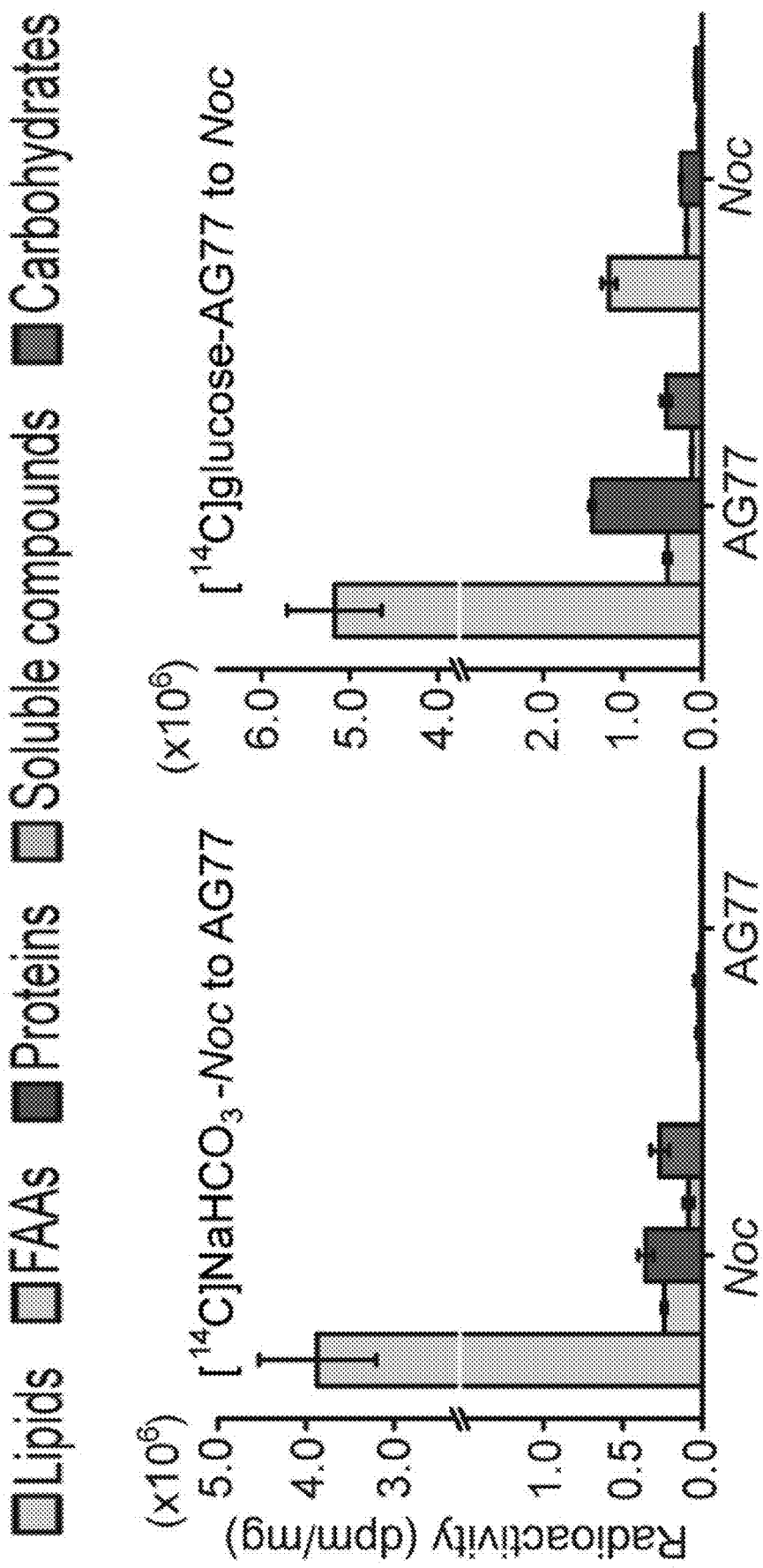
Figure 2C:
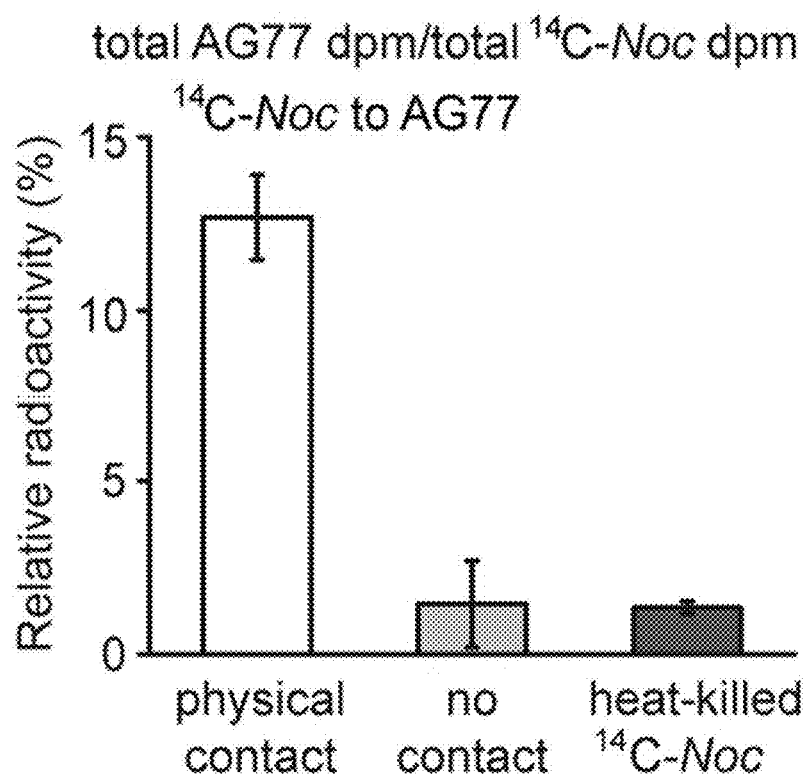
Figure 2D:
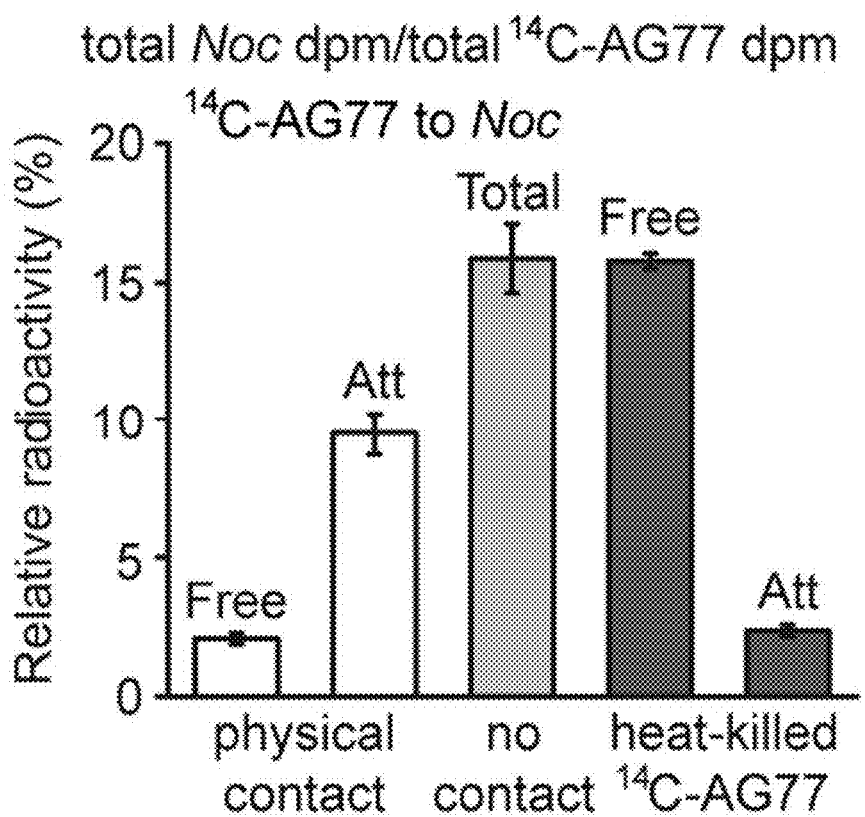
Figure 2H:
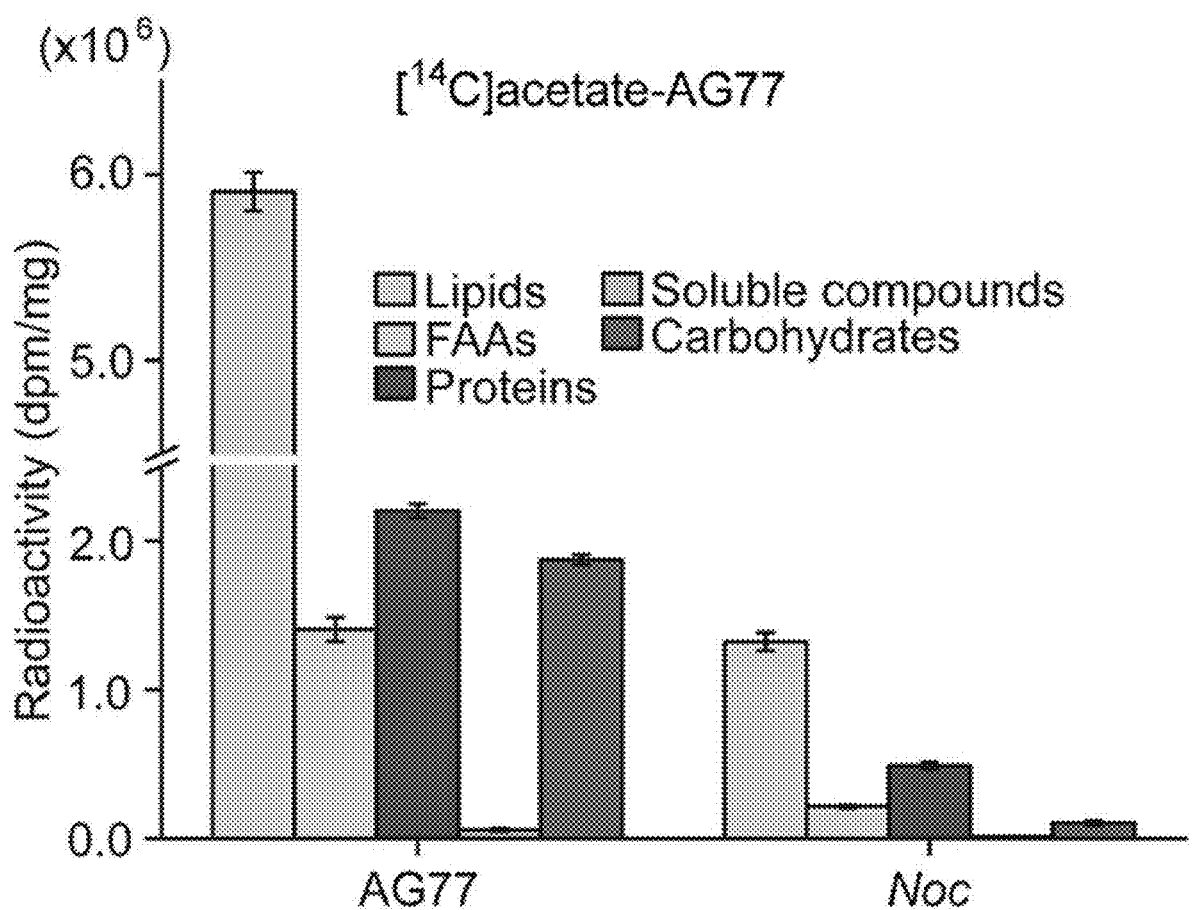

To further assess whether a physical interaction is required for carbon exchange between the photosynthetic alga and the putative fungal saprotroph, membrane inserts were used to physically separate reciprocally $^{14}$C-labeled algal and fungal partners (FIG. 2E-2H). These experiments showed that the physical contact between the algae and fungus is essential for $^{14}$C-carbon transfer to the fungus (FIG. 2B-2C), but is not necessary for $^{14}$C-carbon transfer to the algal cells (FIG. 2B, 2D and FIG. 2H).

*Mortierella* is regarded as a saprotroph that acquires carbon from dead organic matter. Experiments were performed, first, to test whether alga-derived carbon obtained by *Mortierella elongata* was due to the consumption of algal detritus. The $^{14}$C-labeling experiment described above was repeated using a 65° C. water bath to kill $^{14}$C-labeled cells prior to algal-fungal reciprocal pairings. *Mortierella elongata* incorporates a small amount (1.3%) of $^{14}$C-carbon from dead algal cells, compared to $^{14}$C-carbon acquired from living algal cells (12.7%) (FIG. 2C). In contrast, the algal cells attached to fungal hyphae (att) and those free in the medium (free) acquired more $^{14}$C-carbon (att, 2.4%; free, 15.8%) from dead fungal cells (FIG. 2D). The total abundance of $^{14}$C-carbon was higher in the free algal cells, because most of the *Nannochloropsis* oceanica cells were free in the medium.

Second, confocal microscopy and Sytox Green staining was used to assess whether fungal and algal cells remained alive during co-culture. These results confirmed that most algal and fungal cells remain alive throughout the co-cultivation of $^{14}$C-labeling experiment and also demonstrate that the heat treatment was effective in killing algal and fungal cells (data not shown). Together these data indicate that carbon-transfer from the algae to the fungus is dependent upon an intimate physical interaction between living partners. In contrast, algae are able to utilize carbon from the fungus grown in the same culture regardless of whether the hyphae are alive or physically connected.

Example 4: Nitrogen Exchange Between Fungi and Algae

Figure 3H:
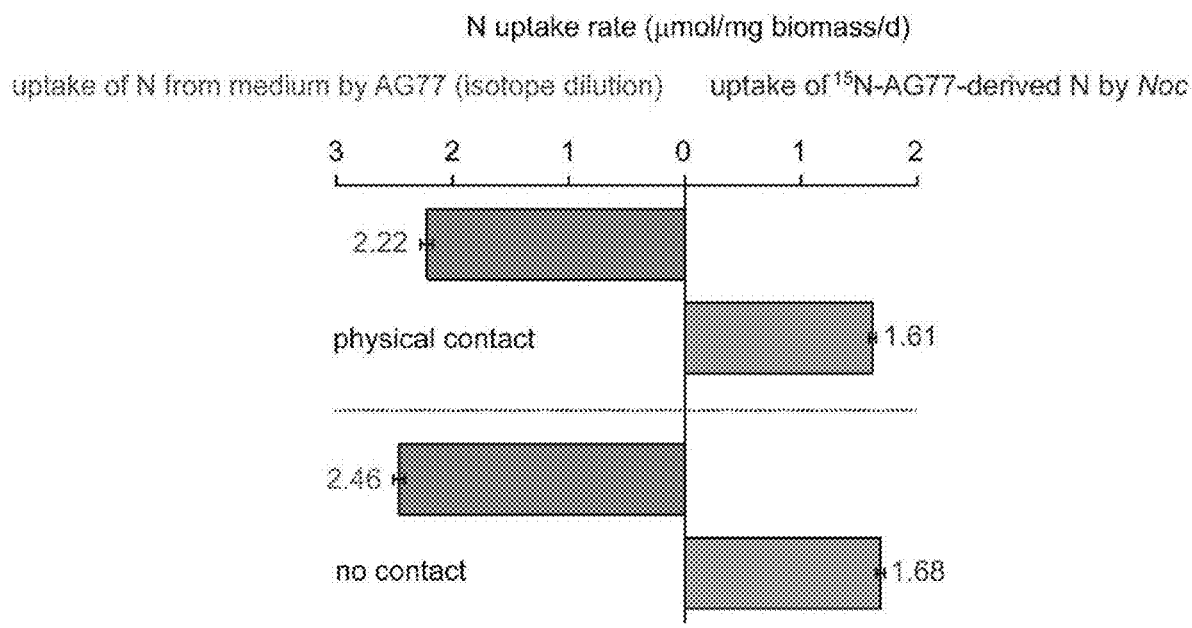

Nitrogen is a major macronutrient that can limit net primary productivity in terrestrial and aquatic ecosystems, including for microalgae such as *N. oceanica*. To determine whether nitrogen-exchange occurs between fungi (*M. elongata*) and algae (*N. oceanica*), the algae were labeled with [$^{15}$N]potassium nitrate and the fungus were labeled with [$^{15}$N]ammonium chloride. The labeled fungal and algal cells were separately co-cultivated with unlabeled partners for one week and then the different cultures were then analyzed for $^{15}$N. Nitrogen ($^{15}$N) transfer occurred between algal and fungal partners, irrespective of whether they were in physical contact or not (FIG. 3A, 3G-3H). Further, over twice as much $^{15}$N (~1.6 μmol/mg biomass/d) was transferred from the $^{15}$N-fungus to the algal recipient, than from the $^{15}$N-algae to the fungus (~0.7 μmol/mg biomass/d—see FIG. 3A, 3G-3H), showing a net nitrogen benefit for the algae when in symbiosis with the fungus.

A nutrient-deficiency test was also performed to assess algae benefits from the nutrient transfer by it fungal partner. Results showed that *N. oceanica* had significantly increased viability when co-cultivated with *M. elongata* under nitrogen or carbon deprivation but not under phosphorus deficient conditions (FIG. 3B-3D). These results indicate that a functional *Mortierella-Nannochloropsis* interaction is established that may be based upon the carbon and nitrogen acquisition and transfer and that is adaptive under nutrient-limited conditions.

Further analysis of the culture supernatant showed an increase in total organic carbon and dissolved nitrogen when the living *Mortierella* fungi were incubated alone in f/2 medium (FIG. 3E-3F) indicative of extracellular release of nutrients by the fungus, and perhaps explaining why physical contact is not required for the $^{14}$C transfer from the fungus to the algae. It appears that algae benefit from this interaction with *Mortierella* by acquiring both nitrogen and carbon from its fungal symbiont. On the other hand, through an intimate interaction with living photosynthetic algae. *Mortierella* is able to grow in nutrient-limited conditions (PBS buffer) by incorporating algal-derived carbon and nitrogen.

Figure 3I:
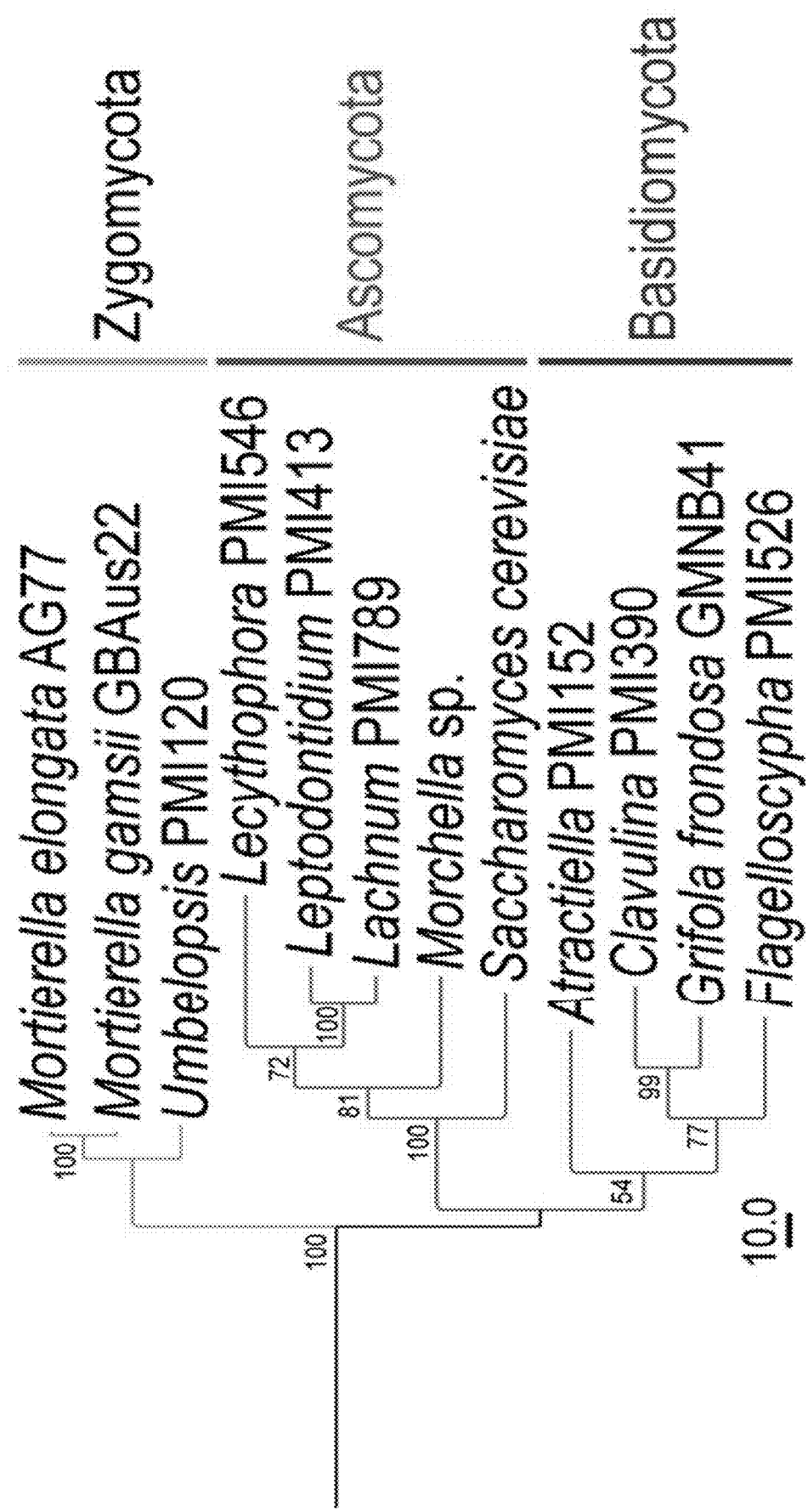
Figure 3J:
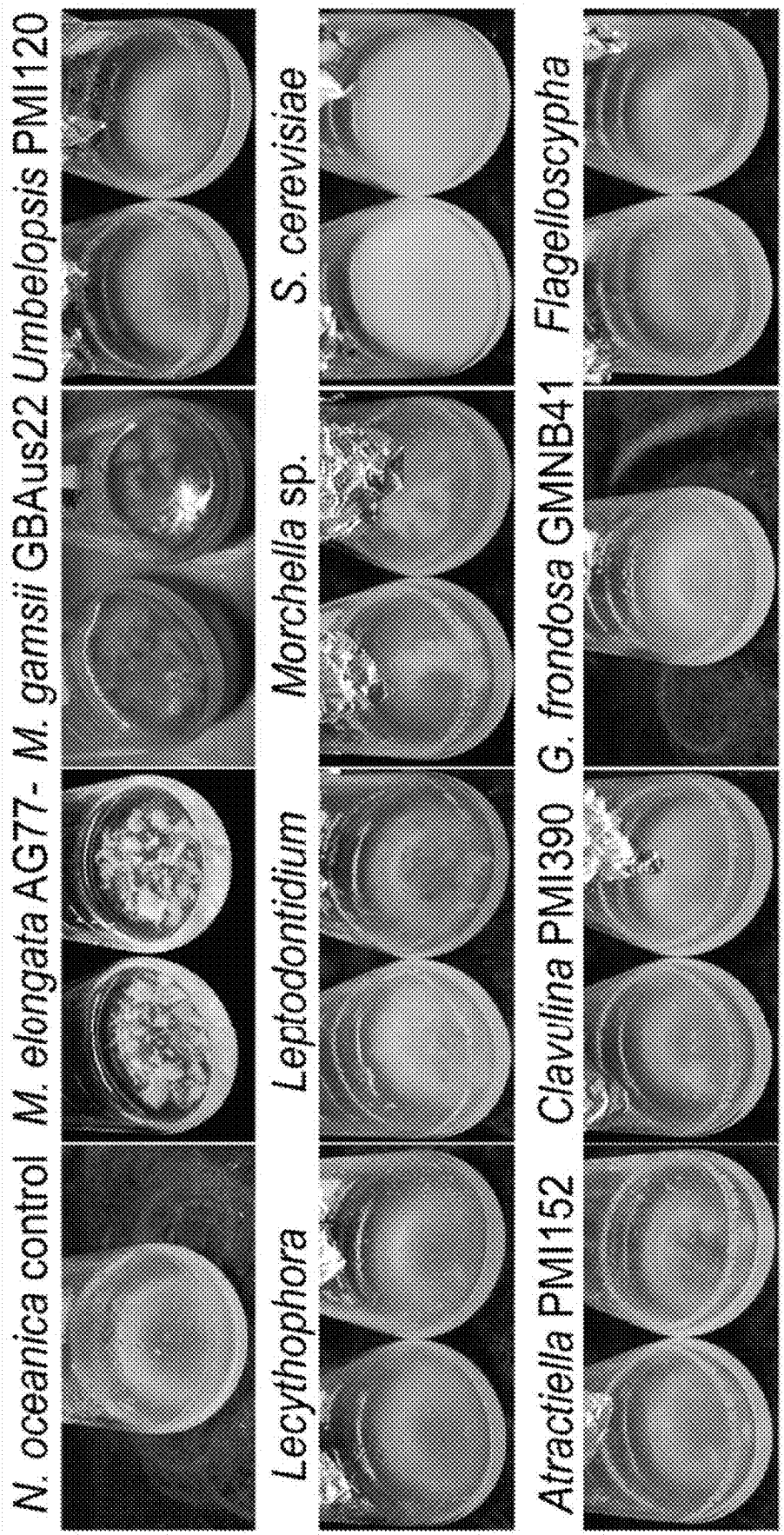

Numerous lineages of fungi have evolved to interact with plants and algae, and the question arises whether the observed interaction is unique to *Mortierella* or alternatively, if it is conserved across diverse lineages of fungi. This was addressed through a series of interaction experiments where *N. oceanica* was paired with a series of fungi sampled across the fungal phylogeny (FIG. 3I-3J). This diverse panel of 21 isolates included the yeast *Saccharomyces cerevisiae*, and filamentous ascomycetes, basidiomycetes, and mucoromycetes isolates representing 3 phyla, 9 orders and 13 families of Fungi. Aside from some *Mortierella* species tested, interactions between these fungi and algae were negative or neutral. *Mortierella elongata* showed the most obvious phenotype and physical attraction to algae, with the algae clustered tightly around the fungal mycelium (FIG. 3J).

Microbial consortia may persist in a stable state, improving the resilience of each to fluctuating environments and stress (Brenner et al., Trends Biotechnol. 26, 483-489 (2008)). To determine whether the observed interactions between *N. oceanica* and *M. elongata* are stable or transient we carried out a series of long-term incubations (from 1 to 6 months) in which the partners were grown together with nutrients refreshed biweekly. After about one month, co-culture confocal microscopy was used to visualize cells inside the thick aggregates that formed between algae and fungus, using the Wheat Germ Agglutinin Conjugate cell wall probe which binds to N-acetylglucosamine, a component in fungal and algal cell walls. From these images some algal cells were within fungal hyphae. Subsequent light and transmission electron microscopies (TEM) were used to provide more details of this interaction and provide evidence for the endosymbiosis of the algae by the fungus. In the algal-fungal aggregates the algae are trapped by the fungus, and some algal cells are indeed intracellular within the hyphae, as shown in TEM micrographs (FIG. 4A-4C). Additional imaging with differential interference contrast (DIC) micrographs and videos demonstrated morphology of the "green hyphae" after different periods of long-term co-culture, further confirming algal endosymbiosis by the fungus and incorporation of intact and functional algal cells intracellularly within the fungal hyphae (FIG. 4D-4H). Both algal and fungal cells remained viable after months of co-culture. This fungal-algae symbiosis may conjure the idea of a lichen, but it differs by the lack of distinct tissue and hyphal structures (i.e. thallus, haustoria) and by the fact that *Mortierella* fungi actually incorporate algal cells intracellularly while lichens do not. The result of this remarkable incorporation of intact and functional algal cells within living fungal mycelia has the hallmarks of a secondary endosymbiosis event.

While observations on endosymbiosis of living eukaryotic cells by fungi have not been reported previously, the rare fungus *Geosiphon pyriformis* (a relative of arbuscular mycorrhizae and of *Mortierella*) is reported to form a unique intracellular association with the cyanobacterium *Nostoc punctiforme* (Mollenhauer et al., Protoplasma. 193, 3-9 (1996)). In this system, the fungus envelops *Nostoc* within a specialized swollen multinucleate fungal "bladder" that is morphologically distinct from the rest of the hyphae. Within this bladder, the cyanobacteria are surrounded by a host-derived symbiosome membrane (Brenner et al., Trends Biotechnol. 26, 483-489 (2008)).

Biogenesis of endosymbiosis of *N. oceanica* by *M. elongata* was evaluated through DIC and time-lapse microscopy. Endosymbiosis was preceded by dense aggregates of algal cells around the fungal hyphal tip (FIG. 4I-1 to FIG. 4I-4). Further, aggregates of algal cells were observed surrounding fungal hyphal tips early in the endosymbiosis process, for example, by 1-2 months. Dense clusters of algal cells formed at the tip of a hypha were consistently observed when the endosymbiosis of algal cells within fungal hyphae happened in plates. Also, hyphae downstream from these tips are often green, and the amount of algae within the cells increased over time (e.g., over 1-2 months). Given these observations we hypothesize that the hyphal tip is the initial point of entry for the algal cells into the fungal protoplasm, as this also where the fungal cell wall is least developed. Not only do algae enter the fungal mycelium, but once inside the mycelium they remain active, appear healthy and are able to multiple. We suspect that the coenocytic nature of *Mortierella*, which has few septa within its mycelium, is one attribute of this fungus that facilities its ability to pack cells with photosynthetic algae. TEM and DIC images show that the fungal host's cell membrane remains intact around the internalized algae (FIG. 4A-4I). Removed from their natural environment, internalized algae would become more completely dependent on the host for nitrogen and other nutrients, which could be exchanged for carbon photosynthate and possibly other metabolites.

Example 5: *N. oceanica* Cell Wall Degradation Upon Interaction with *M. elongata*

*N. oceanica* and *M. elongata* cells were incubated together as described in the previous Examples. Micrographs were taken using scanning electron microscopy (SEM) to view *N. oceanica* cell walls, particularly at the outer layer of the *N. oceanica* cells, after the co-cultivation of *N. oceanica* and *M. elongata* fungi AG77.

A previous study on cell wall structure of *Nannochloropsis gaditana* (Scholz et al., Eukaryot Cell 13(11): 1450-64 (2014)) indicates that *Nannochloropsis gaditana* cells have a layer of extensions in their cell wall when observed using high-resolution quick-freeze deep-etch electron microscopy (QFDE-EM). Those studies suggest that there may be a very thin layer of cell wall outside and connected to an extension layer. The thin outer cell wall observed by Scholz et al. (2014) may be fragile because some cells partially lost the thin outer layer during the QFDE-EM.

As illustrated in FIG. 5A-5H, physical interaction between *N. oceanica* and *M. elongata* fungus AG77 led to degradation of the thin outer layer of the *N. oceanica* cell wall, which exposed an extension layer attached to the rugged surface of fungal hypha. This algal extension layer formed irregular-tube-like structures. Such degradation of the *N. oceanica* cell wall was not observed in *N. oceanica* algal cells co-cultivated with *M. elongata* AG77 but separated from the *M. elongata* AG77 fungi by a membrane insert that physically separates the algal and fungal cells but allows metabolic exchange between the two organisms.

These data indicate that physical or intimate interaction is required for the algal cell wall degradation.

Example 5: Additional Materials and Methods

This Example describes some alternative materials and methods for generating fugal-algal aggregates.

Materials and Growth Condition

Figures 6A, 6B, 6C:
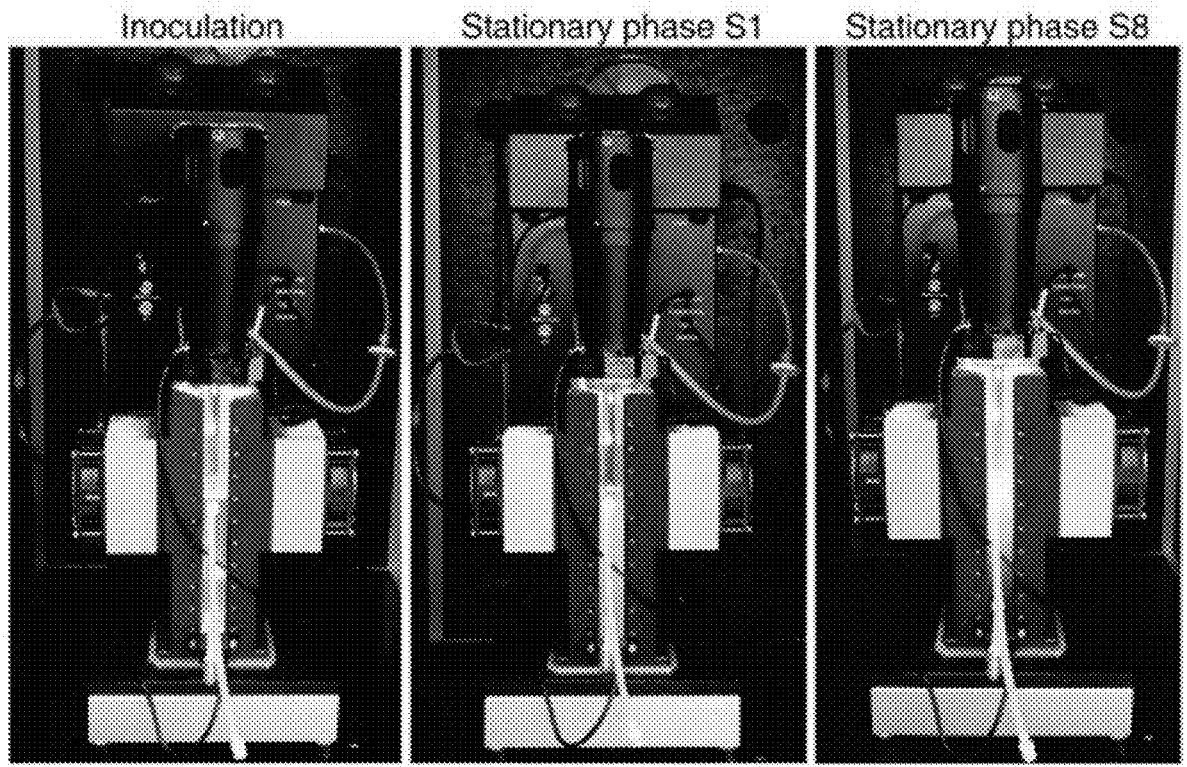
FIG. 6A-6D illustrate incubation of *N. oceanica* cells in the environmental photobioreactor (ePBR).
Figure 6D:
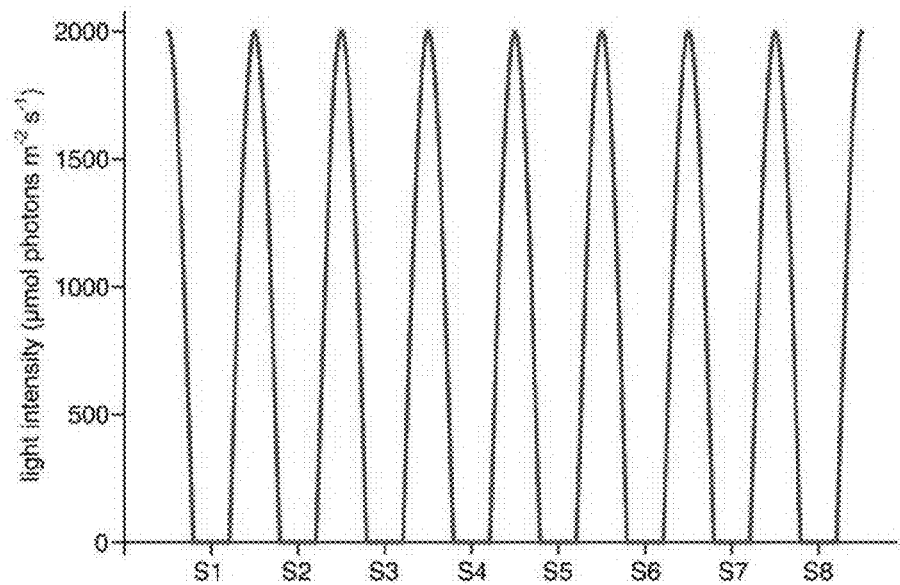
Figure 17A:
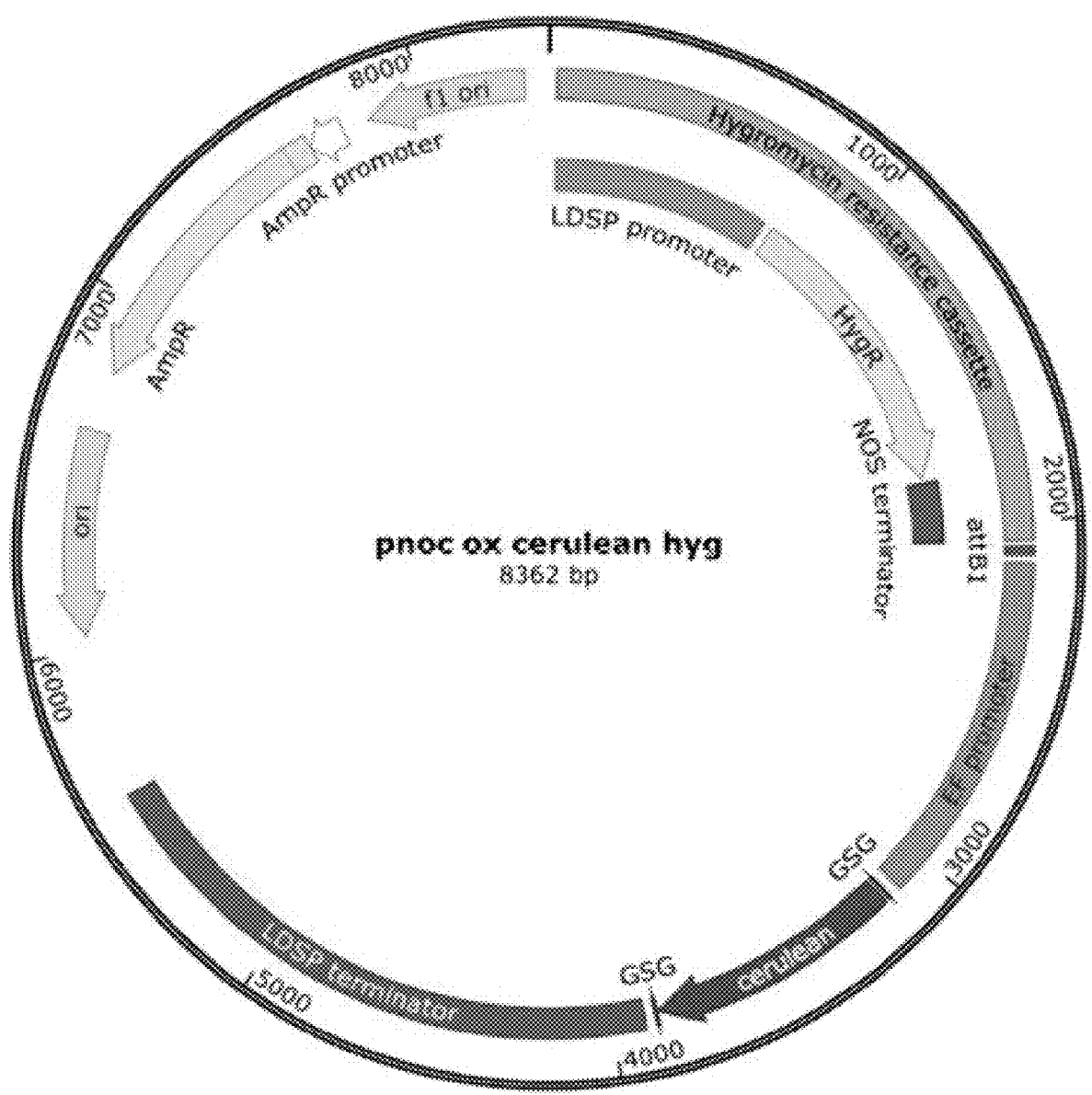
FIG. 17A-17B illustrate expression vectors for lipid synthesizing enzymes.
Figure 17B:
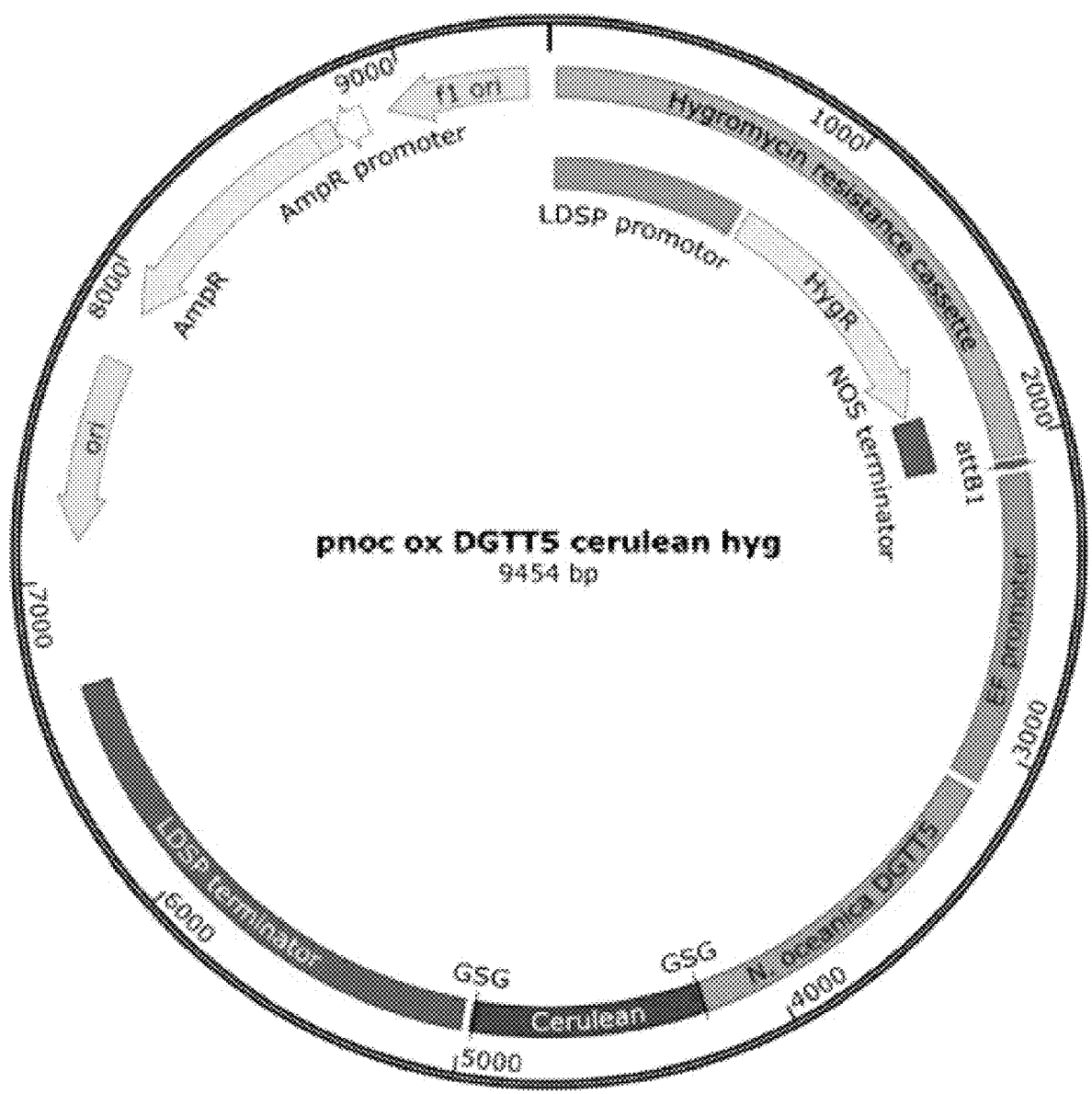

The marine alga *Nannochloropsis oceanica* CCMP1779 was obtained from the Provasoli-Guillard National Center for Culture of Marine Phytoplankton. *N. oceanica* DGTT5-overexpressing strains DGTT5ox3 and DGTT5ox6 were generated using the expression vector shown in FIG. 17A-17B. The *N. oceanica* DGTT5-overexpressing DGTT5ox3 and DGTT5ox6 lines were examined using quantitative RT-PCR methods described by Zienkiewicz et al. (*Biotechnology for biofuels* 10:8 (2017)). f/2 medium was used to grow the alga that contains f/2 nutrients (Andersen et al., Appendix A. Algal Culturing Techniques. San Diego: Elsevier Academic Press (2005)) and 20 mM sodium bicarbonate and 15 mM Tris buffer (pH 7.6) to prevent carbon limitation (Vieler et al. Plant physiology 158(4):1562-1569 (2012)). The cells were grown in batch cultures in two systems: shaker flask with f/2 medium (under ~80 μmole photons $m^{-2}$ $s^{-1}$ at 23° C.) or in environmental photobioreactors (ePBRs) (Lucker et al., 2014) with f/2-$NH_4Cl$ (2.5 mM $NH_4Cl$ replacing 2.5 mM $NaNO_3$) or f/2-urea (2.5 mM urea replacing 2.5 mM $NaNO_3$) media with varying light as indicated in FIG. 6A-6D (e.g., as shown in FIG. 6, the S2 cells were exposed to 0 to 2,000 μmol photons $m^{-2}$ $s^{-1}$ under diurnal 14/10 h light/dark cycle) at 23° C. and sparged with air enriched to 5% $CO_2$ at 0.37 L $min^{-1}$ for 2 min per hour. For prolonged-incubation in the ePBR, *N. oceanica* cells were inoculated to ~1×$10^6$ $mL^{-1}$ in f/2-$NH_4Cl$ medium and grown to stationary phase. The cultures were further incubated for 8 days to increase TAG content.

*Mortierella* fungi *M. elongata* AG77, *M. elongata* NVP64, and *M. gamsii* GBAus22 isolates were isolated from soil samples collected in North Carolina (AG77). Michigan (NVP64), USA, and Australia (GBAus22). *Morchella americana* 3668S was obtained from the USDA NRRL Agriculture Research Station.

Fungal samples were incubated in PDB medium (12 g/L potato dextrose broth and 1 g/L yeast extract, pH5.3) at 23° C. For the algal-fungal cocultivation, fungal mycelia were briefly blended into small pieces (~1 cm) with a sterilized blender and were collected by centrifugation (3,000 g for 3 min) after 24-h recovery in PDB medium. The samples were washed twice with f/2 or f/2-$NH_4Cl$ medium and resuspended in 5-10 mL of the respective medium. One third of the samples were used for determining dry biomass: 1 mL culture was transferred and filtered with pre-dried and -weighed Whatman GF/C filters and dried overnight at 80° C. The remaining fungal mycelia were added to the *N. oceanica* culture (~3 times to algal biomass) for 6-day co-cultivation on a shaker (~60 rpm) under continuous light (~80 µmol photons m$^{-2}$ s$^{-1}$) at 23° C.

Cell size and concentration of *N. oceanica* cultures were calculated with a Z2 Coulter Counter (Beckman). The bio-flocculation efficiency of *N. oceanica* cells using fungal mycelium was determined by the cell density of uncaptured algal cells compared to that of an algal culture control, to which no fungus was added.

Light Microscopy

Interactions between the algal and fungal cells were examined by light microscopy using an inverted microscope with DIC function (DMi8. Leica). DIC images were taken of the algae-fungi aggregates after 6 day co-cultivation.

Scanning Electron Microscopy

SEM was performed to investigate the physical interaction between *N. oceanica* and fungi at the Center for Advanced Microscopy of Michigan State University (CAM, MSU). Algae-fungi aggregates were collected after 6-day co-culture of the alga *N. oceanica* with *M. elongata* (AG77 and NVP64) or *M. americana* 3668S and were fixed in 4% (v/v) glutaraldehyde solution, followed by drying in a critical point dryer (Model 010, Balzers Union). The samples were then mounted on aluminum stubs with high vacuum carbon tabs (SPI Supplies), and were coated with osmium using a NEOC-AT osmium coater (Meiwafosis). The samples were observed with a JSM-7500F scanning electron microscope (Japan Electron Optics Laboratories).

Confocal Microscopy

Confocal microscopy was carried out to visualize and briefly quantify lipid droplets in the alga and fungi. The samples were stained with 10 µg mL$^{-1}$ BODIPY 493/503 (ThermoFisher Scientific) in PBS buffer for ~30 min at 23° C. After two washes with PBS buffer, the samples were observed using an Olympus Spectral FV1000 microscope at CAM, MSU. An argon (488 nm) laser and a solid-state laser (556 nm) were used for BODIPY (emission, 510 to 530 nm) and chloroplast (emission, 655 to 755 nm) fluorescence. *N. oceanica* DGTT5 fused to the cerulean fluorescent protein was overproduced using the EF promotor (Zienkiewicz et al., *Biotechnology for biofuels* 10:8 (2017)). The presence of the fluorescent protein in the DGTT5ox strains was detected by confocal microscopy (emission 420-440 nm) using a LSM 510 Meta Confocal Laser Scanning Microscope (Zeiss).

Lipid Extraction and Analysis

For lipid extraction, log phase *N. oceanica* cells grown in f/2 medium were collected by centrifugation (4.000 g for 5 min). To test lipid content in different media. *Mortierella* fungi grown in PDB medium were washed twice with different media: PDB medium. pH7.6; f/2 medium with 1% glucose; f/2 medium. The cells were incubated in the respective medium for 48 h and were subsequently collected for lipid extraction by centrifugation (3.000 g for 3 min). For total lipid extraction, algae-fungi aggregates were collected by mesh filtration and frozen in liquid nitrogen prior to grinding with mortar and pestle. The fine powders were transferred to a pre-weighed and -frozen glass tube and total lipids were extracted with methanol-chloroform-88% formic acid (1:2:0.1 by volume) on a multi-tube vortexer (1,500 g for ~20 min; Benchmark Scientific), followed by addition of 0.5 volume of 1 M KCl and 0.2 M H$_3$PO$_4$. After phase separation by centrifugation (2,000 g for 3 min), total lipids were collected for TAG separation and fatty acid analysis. The solids were dried at 80° C. overnight to provide the non-lipid biomass.

TAG was separated by TLC using G60 silica gel TLC plates (Machery-Nagel) developed with petroleum ether-diethyl ether-acetic acid (80:20:1 by volume). An internal standard of 5 µg of tridecanoic acid (C13:0) or pentadecanoic acid (C15:0) was added to each tube containing TAG or total lipid. FAMEs were then prepared with 1 M methanolic HCl at 80° C. for 25 min, and were phase separated with hexane and 0.9% NaCl and nitrogen-dried and resuspended in ~50 µL of hexane. Gas chromatography and flame ionization detection (Agilent) were used to quantify the FAMEs in TAG and total lipid as described (Liu et al., *Bioresource technology* 146:310-316 (2013)) [64]. Dry weight of algae-fungi biomass was obtained by summing up non-lipid and total lipid mass.

Chlorophyll Measurement

*N. oceanica* cells were collected by centrifugation from 1 mL culture aliquots during prolonged-incubation in the ePBRs. Chlorophyll of the pelleted cells was extracted with 900 µL of acetone:DMSO (3:2, v/v) for 20 min with agitation at 23° C. and measured with an Uvikon 930 spectrophotometer (Kontron) (Du et al., *The Plant cell* 30(2):447-465 (2018)).

Prediction of Fatty Acid and TAG Pathways

The sequenced genome of *M. elongata* AG77 (Uehling et al. *Environmental microbiology* 19(8):2964-2983 (2017)) was annotated for genes and proteins likely involved in the synthesis of fatty acids, PUFAs, and TAGs using by BLAST searches against KOG and KEGG databases at the JGI fungal genome portal MycoCosm *M. elongata* AG77 v2.0 and by comparison to previously published annotations of lipid pathways of *Mortierella alpina* (Wang et al. *PloS one* 2011, 6(12):e28319.

Abbreviations

ARA: arachidonic acid; DG775: a gene encoding the type II acyl-CoA:diacylglycerol acyltransferase 5; DHA: docosahexaenoic acid; DW: dry weight; EF: elongation factor gene; EPA: eicosapentenoic acid; ePBR: environmental photobioreactor; FAMEs: fatty acid methyl esters; GC-FID: gas chromatography and flame ionization detection; PDAT: phospholipid:diacylglycerol acyltransferase; PDB: potato dextrose broth; PUFAs: polyunsaturated fatty acids; S2 to S8: days 2 to 8 after the culture reached stationary phase; SEM: scanning electron microscopy; TAG: triacylglycerol; TLC: thin layer chromatography.

Example 6: *N. oceanica* Cells are Captured by the *M. elongata* Mycelium

This Example describes experiments illustrating that *N. oceanica* cells are captured by the *M. elongata* mycelium.

Figure 7A:
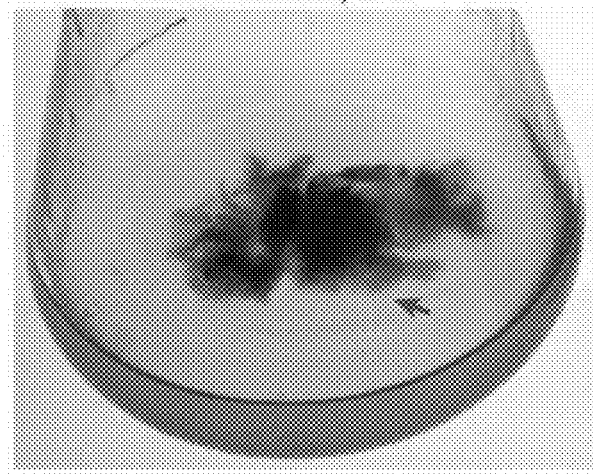
FIG. 7A-7F illustrate harvesting *Nannochloropsis oceanica* by bio-flocculation with *Mortierella* fungi.
Figure 7B:
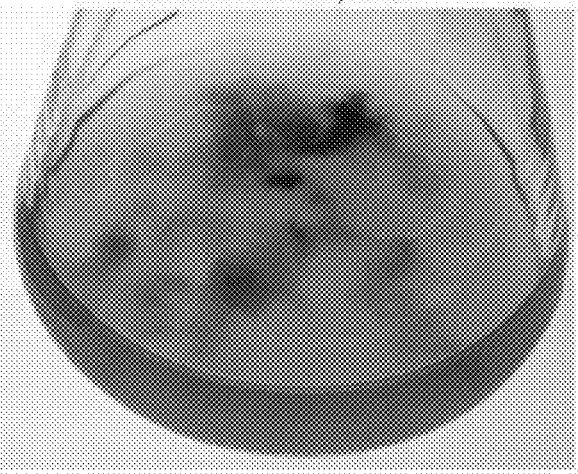
Figure 7C:
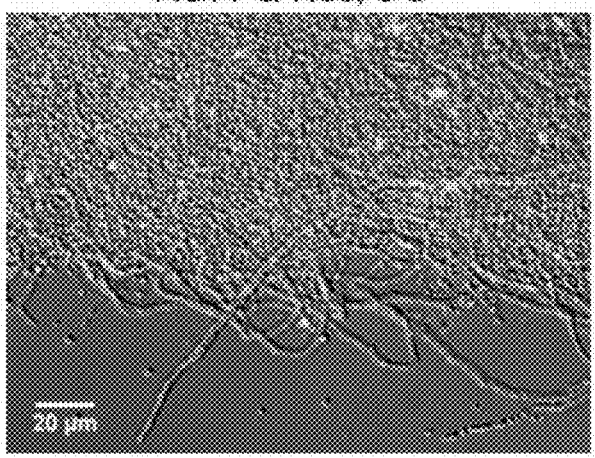
Figure 7D:
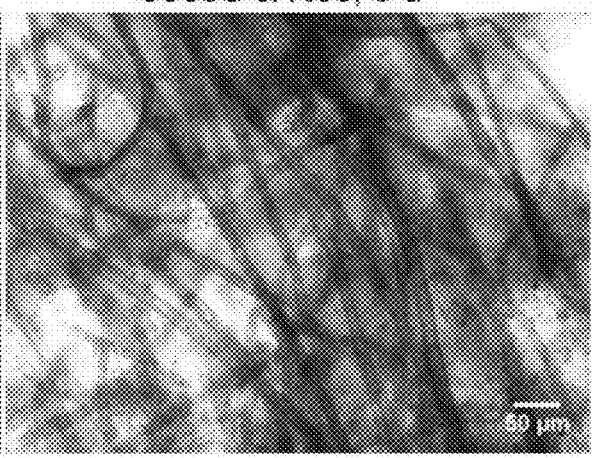
Figure 7E:
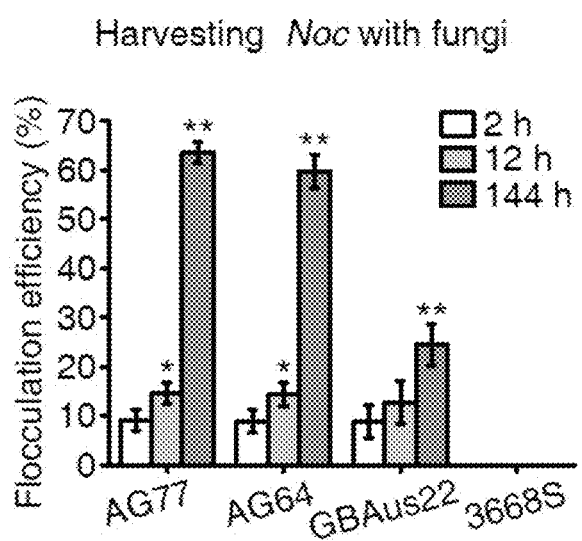
Figure 7F:
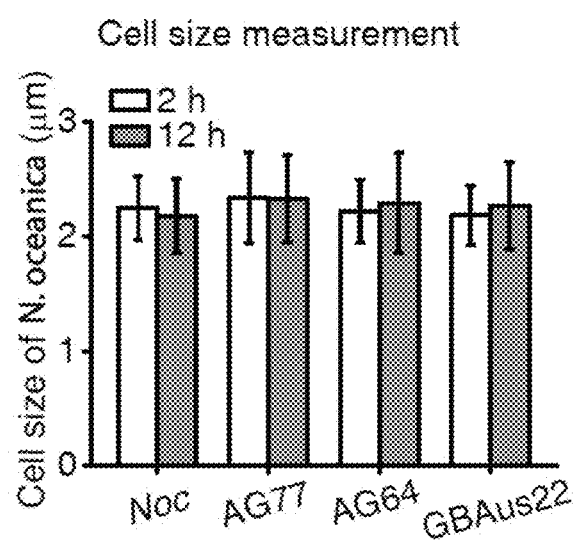

Fungi were incubated in potato dextrose broth (PDB). Fungal mycelium (~3 times of algal biomass) was added to the *N. oceanica* culture containing log-phase cells in f/2 medium. After 6-days co-cultivation with *M. elongata*, *N. oceanica* cells aggregated in dense green clumps along the mycelium of the fungus (FIG. 7A). The interaction of *N. oceanica* with filamentous fungi appeared specific to *M. elongata*, as it was not observed in co-culture with *Morchella americana* 3668S (FIG. 7). Differential interference contrast (DIC) light microscopy showed dense numbers of *N. oceanica* cells attached to the *M. elongata* mycelium (FIG. 7C); in comparison, mycelium of *M. americana* hardly captured any algal cells (FIG. 7D). Three *Mortierella* strains. *M. elongata* AG77, *M. elongata* NVP64, and *M. gamsii* GBAus22 were used to test flocculation efficiency for harvesting of *N. oceanica* with *M. americana* as a negative control. All three *Mortierella* isolates aggregated ~10% of algal cells after 2-hour co-culture and up to ~15% after 12 h (FIG. 7E). After 6-day cocultivation, *M. elongata* AG77 and NVP64 captured ~60% of algal cells *M. gamsii* GBAus 22 captured ~25%. The short period of co-cultivation with fungi did not appear to affect the morphology of the algal cells and did not significantly change their diameter (FIG. 7F).

Example 7: Physical Interaction Between the Cell Walls of *N. oceanica* and *Mortierella* Fungi This Example illustrates physical interaction between *N. oceanica* and *Mortierella elongata*.

Figures 8A, 8B, 8C:
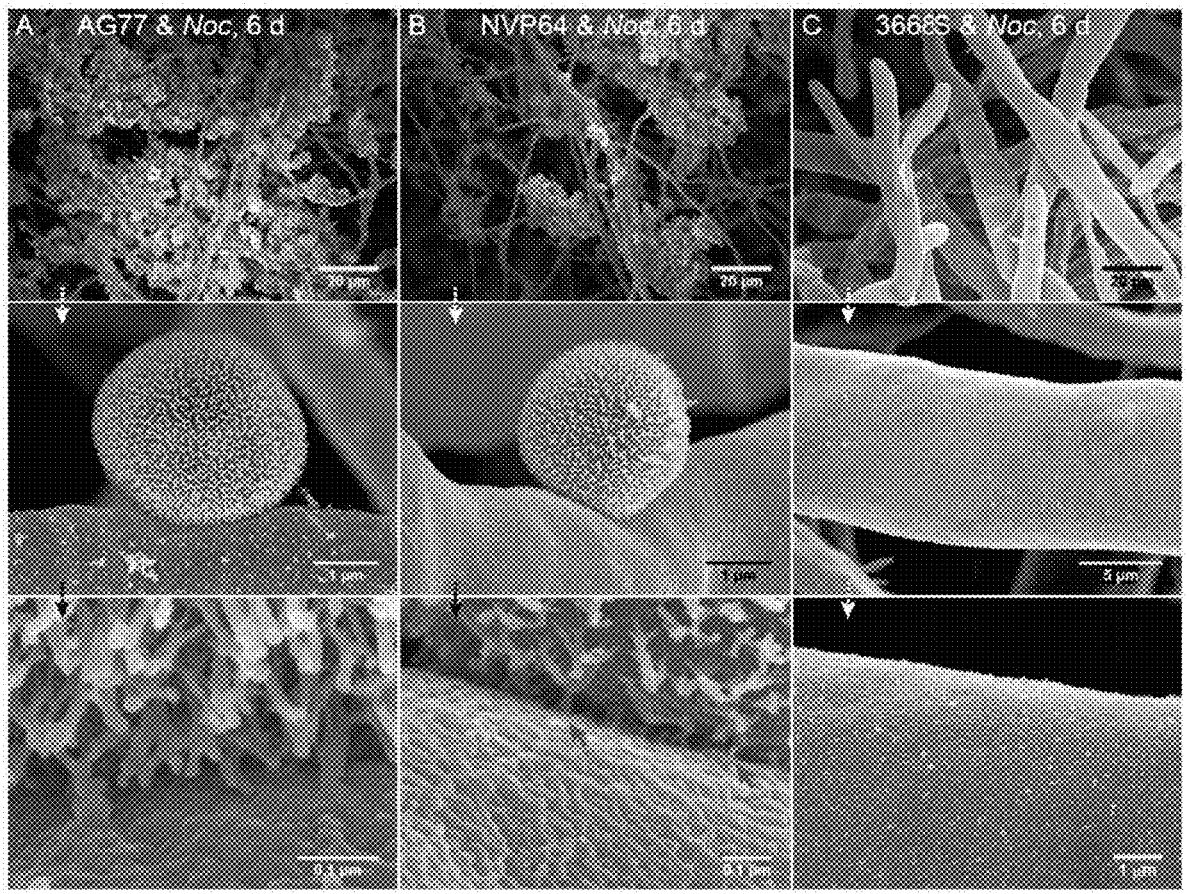
FIG. 8A-8C illustrate interaction between *N. oceanica* and *Mortierella* mycelium.
Figures 9A, 9B, 9C, 9D:
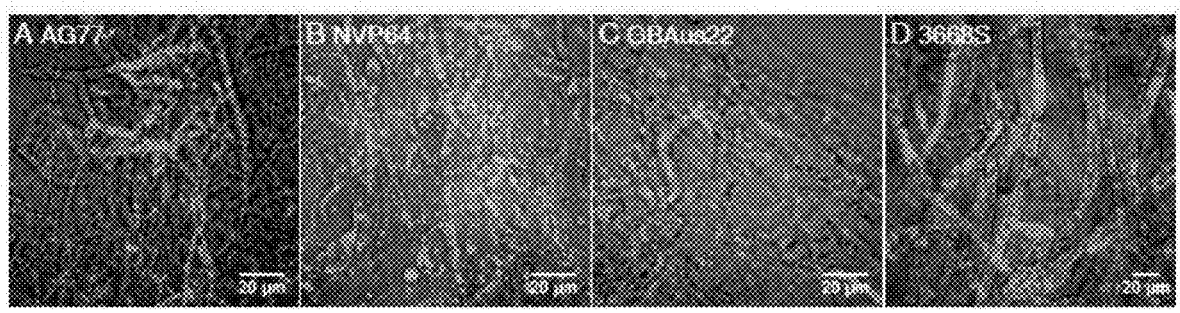
FIG. 9A-9I illustrate that *Mortierella* fungi have more oil droplets than *N. oceanica* in f/2 medium.
Figure 9E:
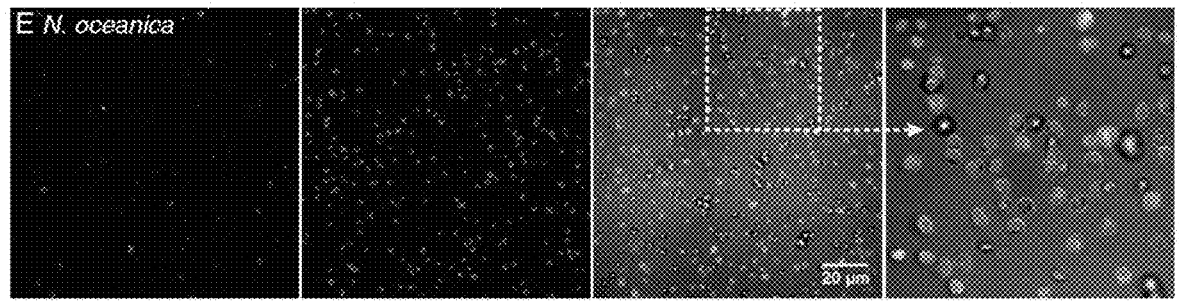
Figure 9F:
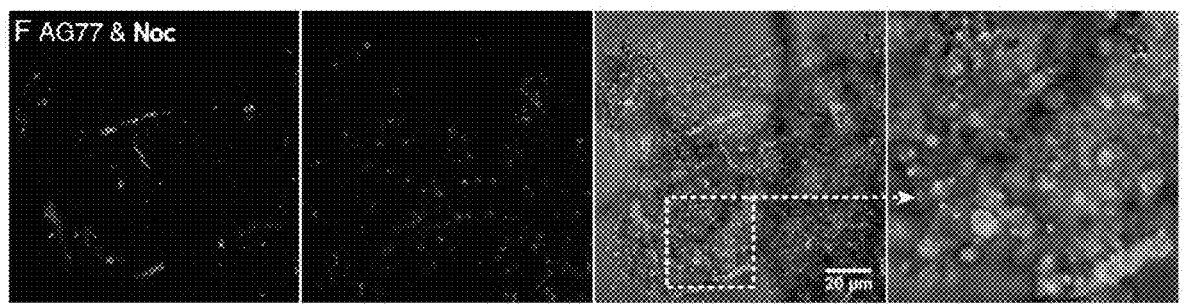
Figure 9G:
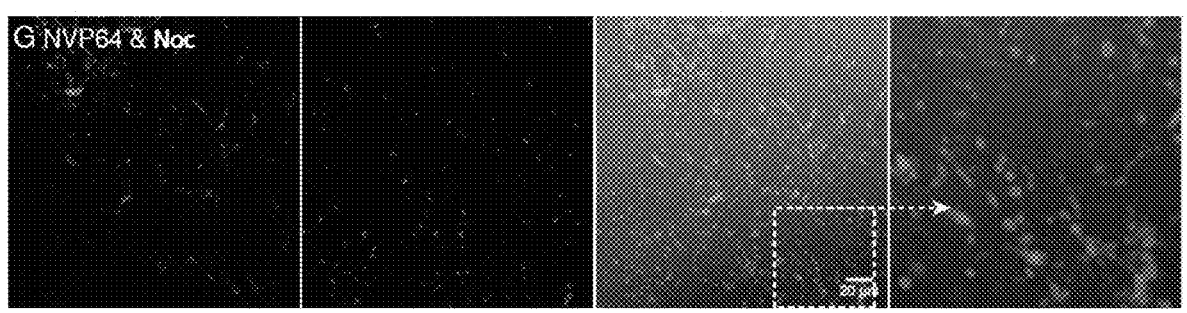
Figure 9H:
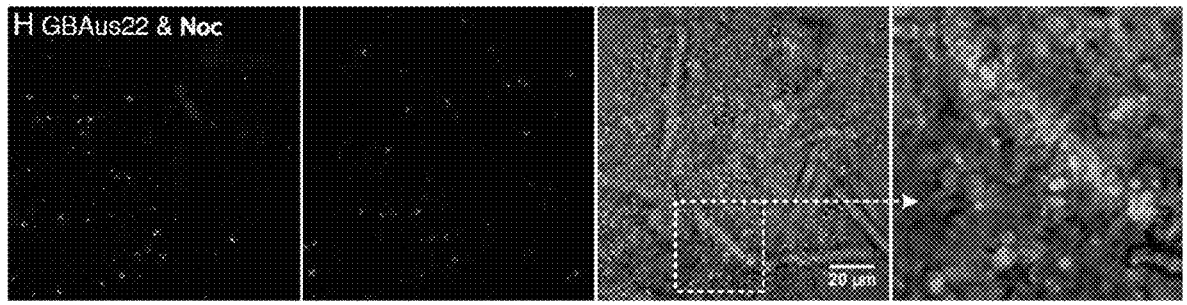
Figure 9I:
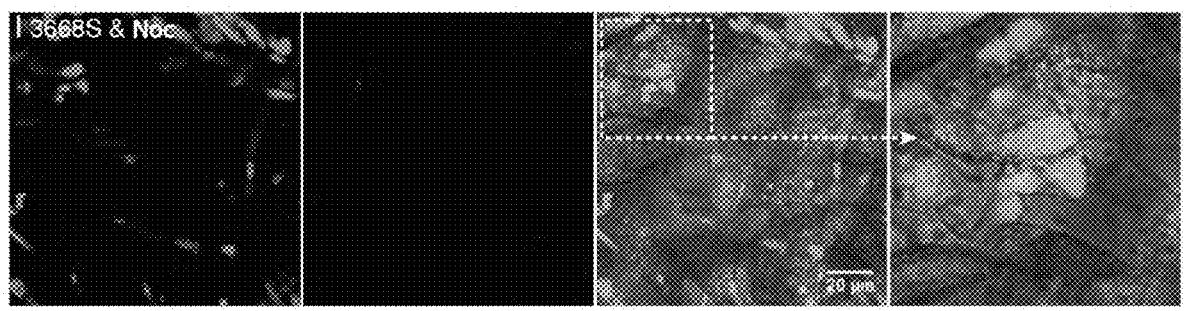

Scanning electron microscopy (SEM) was performed to investigate the physical interaction between *N. oceanica* and *M. elongata* strains AG77 (FIG. 8A) and NVP64 (FIG. 8B). Low magnification images (FIG. 8, top panels) showed an aggregation of algal cells around the fungal mycelium as seen in the light micrographs (FIG. 8C). Higher magnification images displayed details of the physical interaction between the alga and fungi (FIG. 8, middle and bottom panels). Similar to the cell wall structure of *N. gaditana* (Scholz et al. *Eukaryotic cell* 13(11): 1450-1464 (2014)). *N. oceanica* has extensions on the outer layer of the cell wall, which are attached to the rugged surface of the fungal hyphae; irregular tube-like structures are formed between the algal and fungal cell walls, which very likely contribute to anchoring the algal cells to the mycelium. The *M. americana* strain 3668S, which has much thicker hyphae (10-20 μm in diameter) than the *M. elongata* strains AG77 and NVP64 (<2 μm), showed no obvious capture of *N. oceanica* cells (FIG. 8C) or flocculation.

Example 8: Flocculation of *N. oceanica* with *Mortierella* Fungi Increases the Yield of TAG and PUFAs This Example illustrates that increased TAG and PUFA yield is obtained when *N. oceanica* flocculates with *Mortierella* fungi.

*Mortierella* fungi can produce TAG and PUFAs including ARA (Sakuradani et al. *Applied microbiology and biotechnology* 84(1): 1-10 (2009); Ji et al., *Critical reviews in biotechnology* 34(3):197-214 (2014)). Indeed, numerous lipid droplets were observed in both *Mortierella* and *Morchella* fungi tested for alga flocculation (FIG. 9A-9D). In contrast. *N. oceanica* had fewer and smaller lipid droplets when grown in nutrient-sufficient f/2 medium with or without fungi (FIG. 9E-9I).

Figure 10A:
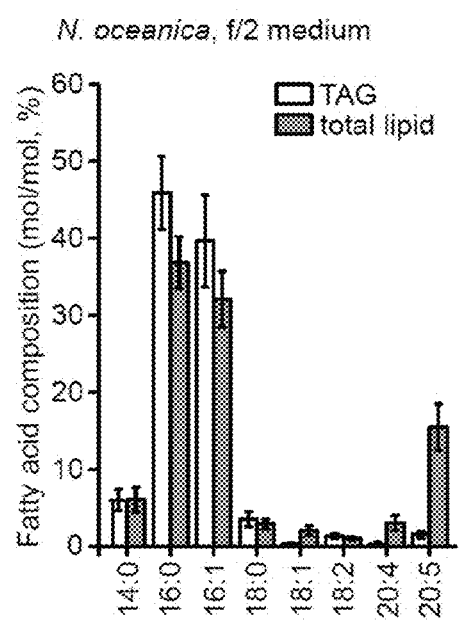
FIG. 10A-10C graphically illustrate fatty acid profiling of triacylglycerol (TAG) and total lipid in *Mortierella* fungi, *N. oceanica*, and algae-fungi aggregates after co-cultivation.
Figure 10B:
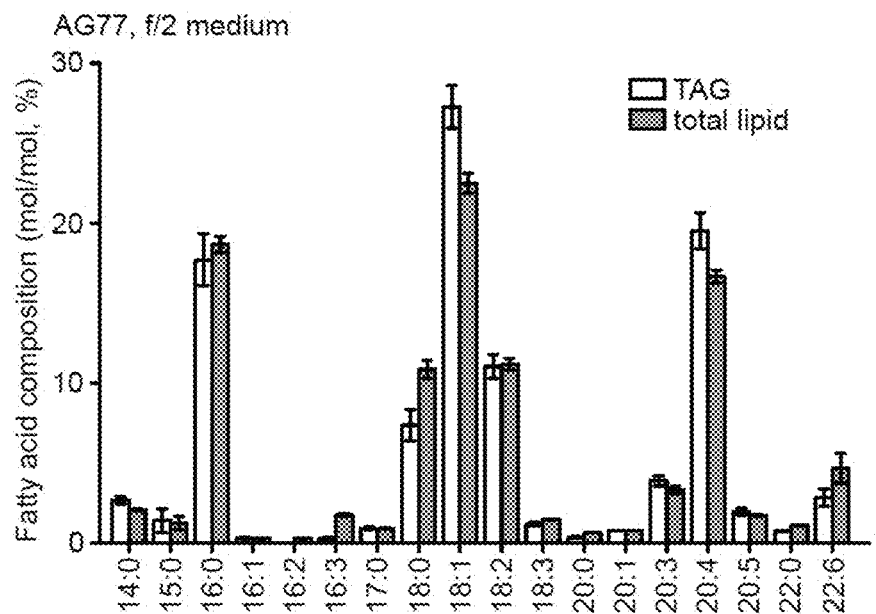
Figure 10C:
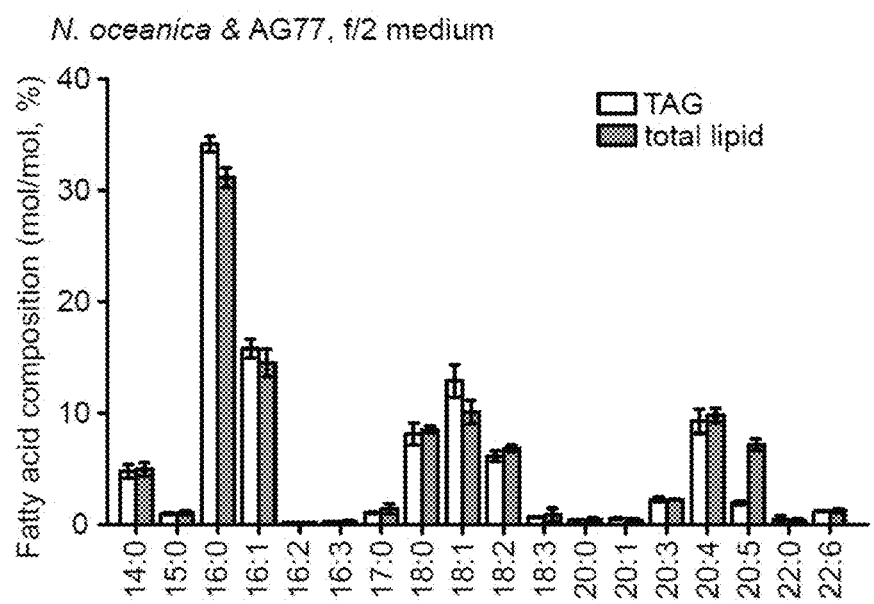

Lipids were extracted and separated by thin-layer chromatography (TLC) and fatty acid methyl esters were quantified by gas chromatography and flame ionization detection (GC-FID) to determine the lipid and fatty acid composition. As shown in Table 1, *M. elongata* AG77 and *M. gamsii* GBAus22 had much higher content of TAG, ARA, total PUFAs and total fatty acids but less EPA compared to *N. oceanica*, which affects the final yield of these compounds in the alga-fungus aggregate. *N. oceanica* TAG is mainly composed of saturated and monounsaturated fatty acids such as C16:0 and C16:1 (FIG. 10A), whereas *Mortierella* fungi have more PUFAs, especially ARA (FIG. 10B). *N. oceanica* has more EPA in total lipid than in TAG (FIG. 10A), and the alga-fungus aggregate contains ~10% ARA and ~7% EPA of total lipid (FIG. 10C).

TABLE 1

| Lipid contents of different strains grown in f/2 medium (mg $g^{-1}$ total dry weight). | | | | | |
|---|---|---|---|---|---|
| Strains | Total fatty acid | TAG | ARA | EPA | Total PUFAs |
| *N. oceanica* | 118.7 ± 18.4 | 15.1 ± 2.3 | 3.1 ± 0.5 | 17.0 ± 2.6 | 21.5 ± 3.3 |
| *M. elongata* AG77 | 238.8 ± 14.5 | 94.6 ± 4.5 | 42.4 ± 2.3 | 4.3 ± 0.5 | 89.1 ± 4.8 |
| *M. gamsii* GBAus 22 | 178.0 ± 23.9 | 54.9 ± 3.9 | 29.3 ± 2.1 | 1.7 ± 0.5 | 66.1 ± 2.2 |
| *M. elongata* AG77 & *N. oceanica* | 168.5 ± 8.9 | 62.1 ± 3.0 | 16.3 ± 1.1 | 12.0 ± 0.9 | 46.5 ± 3.7 |
| *M. gamsii* GBAus22 & *N. oceanica* | 163.3 ± 10.5 | 42.0 ± 9.5 | 17.5 ± 1.7 | 9.0 ± 1.4 | 36.1 ± 6.1 |

Compared to regular PDB medium, f/2 medium has a high salt concentration and an elevated pH (pH=7.6) and lacks sugar (Guillard RRL (ed.): *Culture of phytoplankton for feeding marine invertebrates*. New York, USA.: Plenum Press 1975)).

*M. elongata* AG77 and *M. gamsii* GBAus22 were incubated in different media to test the impact on lipid metabolism of high pH (PDB medium, pH 7.6), high pH and high salinity (f/2+1% sugar), and high pH and high salinity with sugar starvation (f/2 medium). These adverse conditions generally increased the TAG and total lipid content of *M. elongata* AG77 and *M. gamsii* GBAus22, especially under high salinity condition (PDB pH7.6 compared to f/2+1% sugar) (Table 2). Compared to *M. gamsii* GBAus22, *M. elongata* AG77 showed a significant increase in TAG and total lipid under high pH (PDB, from pH 5.3 to 7.6), and a lower increase in total lipid, and slight decrease in TAG, upon sugar starvation (f/2+1% sugar compared to f/2) (Table 2). These adverse conditions reduced the content of ARA and total PUFAs in *M. gamsii* GBAus22, while EPA increased upon high pH but decreased under high salinity and sugar starvation (Table 2). In contrast, *M. elongata* AG77 had increased content of ARA and PUFAs in response to sugar starvation but these fatty acids decreased under high pH and high salinity conditions; EPA of *M. elongata* AG77 was decreased under all stress conditions compared to regular growth condition (Table 2).

TABLE 2

Lipid and fatty acid contents of *Mortierella* fungi incubated in different media in shaker flasks (mg g$^{-1}$ total dry weight).

| Strains | Total lipid | TAG | ARA | EPA | PUFAs |
|---|---|---|---|---|---|
| *M. elongata* AG77, PDB, pH 5.3 | 128.2 ± 11.9 | 15.3 ± 1.0 | 27.9 ± 1.3 | 6.14 ± 0.8 | 78.9 ± 1.3 |
| *M. elongata* AG77, PDB, pH 7.6 | 170.2 ± 17.6 | 31.8 ± 2.0 | 25.2 ± 3.1 | 1.7 ± 1.1 | 48.9 ± 2.9 |
| *M. elongata* AG77, f/2 + 1% sugar | 233.2 ± 21.8 | 106.1 ± 12.3 | 15.5 ± 0.2 | 3.0 ± 0.1 | 41.5 ± 1.1 |
| *M. elongata* AG77, f/2 | 238.8 ± 14.5 | 94.6 ± 4.5 | 42.4 ± 2.3 | 4.3 ± 0.5 | 89.1 ± 4.8 |
| *M. gamsii* GBAus22, PDB, pH 5.3 | 101.2 ± 13.6 | 5.3 ± 1.4 | 33.8 ± 2.4 | 2.09 ± 0.08 | 69.9 ± 0.9 |
| *M. gamsii* GBAus22, PDB, pH 7.6 | 108.9 ± 12.5 | 11.7 ± 1.4 | 31.7 ± 1.4 | 2.9 ± 0.2 | 58.3 ± 1.8 |
| *M. gamsii* GBAus22, f/2 + 1% sugar | 139.4 ± 12.5 | 34.7 ± 4.4 | 16.4 ± 1.6 | 2.1 ± 0.2 | 39.0 ± 3.1 |
| *M. gamsii* GBAus 22, f/2 | 178.0 ± 23.9 | 54.9 ± 3.9 | 29.3 ± 2.1 | 1.7 ± 0.5 | 66.1 ± 2.2 |

TAG, triacylglycerol; ARA, arachidonic acid (20:4); EPA, eicosapentaenoic acid (20:5); PUFAs, polyunsaturated fatty acids; f/2 + 1% sugar, f/2 medium supplemented with 1% glucose, pH 7.6. Results are the average of five biological replicates with error bars indicating standard deviations.

Example 9: Increasing TAG Content in *N. oceanica* Cells Using Ammonium as the Nitrogen Source This Example illustrates that TAG content in *N. oceanica* cells using ammonium as the nitrogen (N) source.

It has been reported that TAG is the major compound for transitory carbon storage in *N. oceanica* cells grown under light/dark cycles (Poliner et al. *The Plant journal: for cell and molecular biology* 83(6): 1097-1113 (2015)). However, the TAG content was relatively low when cells were grown under regular conditions (Vieler et al. *PLoS genetics* 8(11): e1003064 (2012); Jia et al. *Algal Research* 7:66-77 (2015)). Indeed, *N. oceanica* cells produced much less and smaller lipid droplets than the fungi apparent in confocal micrographs (FIG. 10).

Figure 11A:
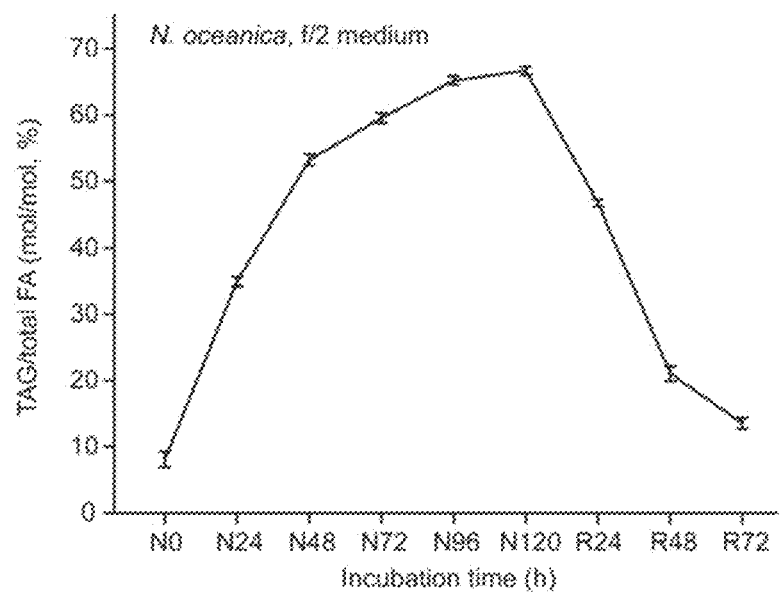
FIG. 11A-11B graphically illustrate the triacylglycerol content in *N. oceanica* cells.
Figure 11B:
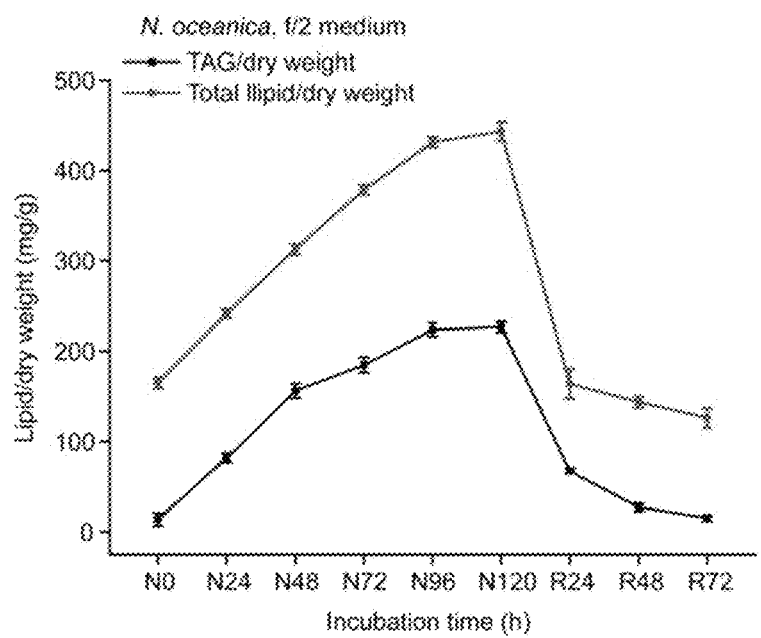

To increase TAG yield in *N. oceanica*, two approaches were employed: nutrient deprivation and genetic engineering. Nitrogen deprivation is one of the most efficient ways to promote TAG synthesis in microalgae. Following 120-hour nitrogen deprivation in shaker flasks. TAG accumulated in *N. oceanica* accounted for up to about 70% of the total lipid fraction (FIG. 11A), which is over 20% of DW (FIG. 11B). The content of TAG quickly increased following nitrogen deprivation and decreased following nitrogen resupply, indicating that *N. oceanica* cells are very sensitive to nitrogen supply (FIG. 11). Under laboratory conditions, nitrogen deprivation of algal cultures can be performed by centrifugation to pellet the algal cells, followed by washes and resuspension in N-deprived medium. However, this approach is not practical during scale up for industrial purposes.

A limited nitrogen supply culturing method was developed for large-volume cultures to induce TAG accumulation largely without compromising growth and biomass yields. To mimic natural cultivation conditions for *N. oceanica*, such as an open-pond system, environmental photobioreactors (ePBRs) were used to grow the alga under varying light (0 to 2.000 μmol photons m$^{-2}$ s$^{-1}$) under long-day (14/10 h light/dark) cycles, and 5% C02 was sparged at 0.37 L min$^{-1}$ for 2 minutes per hour at 23° C. (similar to FIG. 6). Illumination in the ePBR is provided by a high power white LED light on top of a conical culture vessel (total height of 27 cm) containing 330 mL of algal culture (20 cm in depth), which was designed to simulate pond depths from 5 to 25 cm (Lucker et al. *Algal research* 2014, 6:242-249 (2014)).

Several nitrogen sources were tested in f/2 medium for the incubation of *N. oceanica* including set amounts of ammonium, nitrate, or urea.

Compared to nitrate and urea, *N. oceanica* grew faster in the f/2-NH$_4$Cl medium (FIG. 12A). The dry weight (DW) of *N. oceanica* cells per liter was also higher in the f/2-NH$_4$Cl culture after 7-day incubation in the ePBR (FIG. 12B). Intriguingly, the cells grown in f/2-NH$_4$Cl medium turned from vivid green to yellow following 7 days of incubation once they reached stationary phase, indicative of chlorophyll degradation in the algal cells.

Lipid analysis by TLC (FIG. 13A) and GC-FID (FIG. 13B) demonstrated that TAGs had accumulated during days 2 to 8 after the culture reached stationary phase (incubation time S2 to S8), which is correlated with chlorophyll degradation, while cell density and dry weight remained at similar levels during this period (FIG. 12C-12D). Previously, to prevent carbon limitation, NaHCO$_3$ was added *N. oceanica* cultures in shaker flasks (Vieler et al., *Plant Physiology* 158(4): 1562-1569 (2012)). Addition of NaHCO$_3$ prevented acidification in cultures, which were sparged with 5% CO$_2$ (FIG. 14A). *N. oceanica* cells accumulated more TAG upon acidification in the culture medium without NaHCO$_3$ supply, especially from S6 to S8, compared to the NaHCO$_3$ culture (FIG. 12C-12D).

Example 10: Fatty Acid and TAG Synthesis Pathways in *M. elongata* AG77

The genome of *N. oceanica* CCMP1779 has been sequenced and analyzed for the presence of metabolic pathway genes for PUFA and TAG biosynthesis (Vieler et al., *PLoS genetics* 8(11):e1003064 (2012)), information used in the genetic engineering for increased EPA content (Poliner et al., *Plant biotechnology journal* 16(1):298-309 (2018)). For *Mortierella* fungi, nuclear transformation methods were established (Takeno et al. *Journal of bioscience and bioengineering* 2005, 100(6):617-622 (2005); Ando et al., *Current genetics* 55(3):349-356 (2009)), and the *M. elongata* AG77 genome has been sequenced and annotated (Uehling et al., *Environmental microbiology* 19(8):2964-2983 (2017)), but lipid metabolic pathways have not yet been reconstructed.

Thus, the inventors applied the genome browser and BLAST tools from the JGI fungal genome portal MycoCosm to predict fatty acid. PUFA, and TAG synthesis pathways for *M. elongata* AG77. The fatty acid synthesis pathway (FIG. 16A) was predicted according to gene candidates (Table 3).

TABLE 3

Fatty acid and TAG Synthetic Genes and Proteins involved in
fatty acid and glycerolipid synthesis in *M. elongata* AG77.

| | Description | Name | Transcript | Protein ID |
|---|---|---|---|---|
| | Fatty Acid Biosynthesis | | | |
| Acetyl-CoA carboxylase components | acetyl-CoA carboxylase | ACC | 134167 | 133928 |
| | acetyl-CoA carboxylase, subunit beta | ACC | 67410 | 67171 |
| | acetyl-CoA carboxylase, subunit beta | ACC | 75685 | 75446 |
| | acetyl-CoA carboxylase, subunit beta | ACC | 75799 | 75560 |
| | malonyl-CoA decarboxylase | MLYCD | 100665 | 100426 |
| | malonyl-CoA decarboxylase | MLYCD | 81573 | 81334 |
| | acyl carrier protein | ACP | 128202 | 127963 |
| | acyl carrier protein | ACP | 139468 | 139229 |
| Type I fatty acid putative fatty acid synthase components | fatty acid synthase | FAS | 1805138 | 1804883 |
| | malonyl-CoA:ACP | FabD | 144910 | 144671 |
| | malonyl-CoA:ACP | FabD | 522882 | 522643 |
| | 3-oxoacyl-ACP synthase, KASI/II | FabB/F | 115244 | 115005 |
| | 3-oxoacyl-ACP synthase, KASI/II | FabB/F | 1878602 | 1878347 |
| | 3-hydroxydecanoyl-ACP dehydratase | FabA | 131674 | 131435 |
| | putative 3-Ketoacyl-ACP reductase | FabG | 1769266 | 1769011 |
| Elongases | acyl-CoA elongase | ELO | 132697 | 132458 |
| | acyl-CoA elongase | ELO | 134272 | 134033 |
| | acyl-CoA elongase | ELO | 140756 | 140517 |
| | acyl-CoA elongase | ELO | 141020 | 140781 |
| | acyl-CoA elongase | ELO | 14820 | 14581 |
| | acyl-CoA elongase | ELO | 147783 | 147544 |
| | acyl-CoA elongase | ELO | 148635 | 148396 |
| | acyl-CoA elongase | ELO | 165821 | 165582 |
| | acyl-CoA elongase | ELO | 1880273 | 1880018 |
| Desaturases | fatty acid Δ9-desaturase | FADS9 | 107360 | 107121 |
| | fatty acid Δ9-desaturase | FADS9 | 108744 | 108505 |
| | fatty acid Δ9-desaturase | FADS9 | 138135 | 137896 |
| | fatty acid Δ9-desaturase | FADS9 | 1816261 | 1816006 |
| | fatty acid Δ6-desaturase | FADS6 | 134789 | 134550 |
| | fatty acid Δ6-desaturase | FADS6 | 158522 | 158283 |
| | fatty acid desaturase | FAD | 140331 | 140092 |
| | fatty acid desaturase | FAD | 1751385 | 1751130 |
| | fatty acid desaturase | FAD | 15652 | 15413 |
| | fatty acid Δ12-desaturase | FADS12 | 17302 | 17063 |
| | fatty acid Δ5-desaturase | FADS5 | 87849 | 87610 |
| | fatty acid Δ15-desaturase | FADS15 | 152410 | 152171 |
| Acyl-CoA thioesterase and synthetase | acyl-CoA thioesterase | ACOT | 14633 | 14394 |
| | acyl-CoA thioesterase | ACOT | 54405 | 54166 |
| | acyl-CoA thioesterase | ACOT | 561278 | 561039 |
| | acyl-CoA thioesterase | ACOT | 33252 | 33013 |
| | acyl-CoA synthetase | ACSL | 123145 | 122906 |
| | acyl-CoA synthetase | ACSL | 134960 | 134721 |
| | acyl-CoA synthetase | ACSL | 143367 | 143128 |
| | acyl-CoA synthetase | ACSL | 75546 | 75307 |
| | acyl-CoA synthetase | ACSL | 131674 | 131435 |
| | acyl-CoA synthetase | ACSL | 150818 | 150579 |
| | acyl-CoA synthetase | ACSL | 72538 | 72299 |
| | acyl-CoA synthetase | ACSL | 74248 | 74009 |
| | acyl-CoA synthetase | ACSL | 81012 | 80773 |
| | acyl-CoA synthetase | ACSL | 94221 | 93982 |
| | acyl-CoA synthetase | ACSL | 126107 | 125868 |
| | acyl-CoA synthetase | ACSL | 73494 | 73255 |
| | Glycerolipid biosynthesis | | | |
| | aldehyde dehydrogenase | ALDH | 14282 | 14043 |
| | aldehyde dehydrogenase | ALDH | 138532 | 138293 |
| | aldehyde dehydrogenase | ALDH | 138027 | 137788 |
| | aldehyde dehydrogenase | ALDH | 145556 | 145317 |
| | aldehyde dehydrogenase | ALDH | 36004 | 35765 |
| | aldehyde dehydrogenase | ALDH | 34024 | 33785 |
| | alcohol dehydrogenase | ADH | 103662 | 103423 |
| | alcohol dehydrogenase | ADH | 144920 | 144681 |
| | alcohol dehydrogenase | ADH | 157172 | 156933 |
| | alcohol dehydrogenase | ADH | 80690 | 80451 |
| | alcohol dehydrogenase | ADH | 150046 | 149807 |
| | alcohol dehydrogenase | ADH | 36977 | 36738 |
| | alcohol dehydrogenase | ADH | 21055 | 20816 |
| | alcohol dehydrogenase | ADH | 84445 | 84206 |
| | glycerol kinase | GK | 95496 | 95257 |
| | glycerol-3-phosphate dehydrogenase | GPDH | 141744 | 141505 |
| | glycerol-3-phosphate dehydrogenase | GPDH | 133004 | 132765 |
| | glycerol-3-phosphate dehydrogenase | GPDH | 143386 | 143147 |
| | glycero-3-phosphate acyltransferase | GPAT | 132665 | 132426 |

TABLE 3-continued

Fatty acid and TAG Synthetic Genes and Proteins involved in fatty acid and glycerolipid synthesis in *M. elongata* AG77.

| | Description | Name | Transcript | Protein ID |
|---|---|---|---|---|
| | glycero-3-phosphate acyltransferase | GPAT | 71699 | 71460 |
| | glycero-3-phosphate acyltransferase | GPAT | 136092 | 135853 |
| | glycero-3-phosphate acyltransferase | GPAT | 426195 | 425956 |
| | glycero-3-phosphate acyltransferase | GPAT | 114545 | 114306 |
| | glycero-3-phosphate acyltransferase | GPAT | 156906 | 156667 |
| | glycero-3-phosphate acyltransferase | GPAT | 142242 | 142003 |
| | glycero-3-phosphate acyltransferase | GPAT | 138636 | 138397 |
| | 1-sn-acyl-glycero-3-phosphate acyltransferase | PlsC | 133934 | 133695 |
| | 1-sn-acyl-glycero-3-phosphate acyltransferase | PlsC | 15247 | 15008 |
| | phosphatidic acid phosphatase | PAP | 72762 | 72523 |
| | phosphatidic acid phosphatase | PAP | 67757 | 67518 |
| | phosphatidic acid phosphatase | PAP | 118493 | 118254 |
| | phosphatidic acid phosphatase | PAP | 143215 | 142976 |
| | phosphatidic acid phosphatase | PAP | 141373 | 141134 |
| | Lipin like/phosphatidate phosphatase | LPIN | 22296 | 22057 |
| | Lipin like/phosphatidate phosphatase | LPIN | 33916 | 33677 |
| | diacylglycerol kinase | Dgk | 32027 | 31788 |
| | diacylglycerol kinase | Dgk | 143293 | 143054 |
| | diacylglycerol kinase | Dgk | 133967 | 133728 |
| | diacylglycerol kinase | Dgk | 111955 | 111716 |
| | diacylglycerol kinase | Dgk | 133379 | 133140 |
| | diacylglycerol kinase | Dgk | 134894 | 134655 |
| TAG synthesis | diacylglycerol acyltransferase | DGAT | 102618 | 102379 |
| | diacylglycerol acyltransferase | DGAT | 14740 | 14501 |
| | diacylglycerol acyltransferase | DGAT | 135508 | 135269 |
| | phospholipid diacylglycerol acyltransferase | PDAT | 872488 | 872249 |

*M. elongata* AG77 has a type-I fatty acid synthase with a similar domain organization as found in yeast (FIG. 16B). Nine elongases and twelve desaturases were identified within the *M. elongata* AG77 genome for PUFA synthesis, including a A15 fatty acid desaturase (FAD) for EPA synthesis (FIG. 16C. Table 3). Three DGATs and one PDAT (phospholipid:diacylglycerol acyltransferase) were present in the *M. elongata* AG77 genome, which is similar to what was reported for *M. alpina* (Wang et al., PloS one 6(12): e28319 (2011)).

Example 11: Sequences of Some Lipid Synthesizing Enzymes

Amino acid and nucleic acid sequences for lipid synthesizing enzymes are available from various databases including the National Center for Biotechnology Information (see website at ncbi.nlm.nih.gov), and UNIPROT (see website at uniprot.org). Such databases provide both amino acid and nucleic acid sequences for lipid synthesizing enzymes. Some examples of lipid synthesizing enzyme sequences are provided below.

A sequence for *Mortierella elongata* AG-77 acetyl-CoA carboxylase with protein ID 133928 is shown below as SEQ ID NO:7 (Uniprot A0A197K7T6).

```
           10         20         30         40
    MTSNVQSFIG GNALDKAPAG AVHDFVSQHG GHSVITKILI 50         60         70         80
    ANNGIAAVKE IRSVRKWAYE TEGDERAIQF TVMATPEDLK 90        100        110        120
    VNAEYIRMAD QYVEVPGGSN NNNYANVDLI VDIAERTGVH 130        140        150        160
    AVWAGWGHAS ENPKLPESLR DSPQKIIFIG PPGSAMRSLG
```

-continued
```
          170        180        190        200
    DKISSTIVAQ SADVPTMGWS GTGITETEMD PNGFVTVPED 210        220        230        240
    AYQAACVTDA EDGIKKAHAI GFPIMIKASE GGGGKGIRKV 250        260        270        280
    EDPEKFAQAF HQVLGEVPGS PVFIMKLAGN ARHLEVQLLA 290        300        310        320
    DQYGHAISLF GRDCSVQRRH QKIIEEAPVT IAKPDTFEAM 330        340        350        360
    EKAAVRLAKL VGYVSAGTVE YLYSHATDTY FFLELNPRLQ 370        380        390        400
    VEHPTTEIVS GVNLPAAQLQ IAMGLPLNRI KDIRVLYGLQ 410        420        430        440
    PSGTSEIDFE FAQQVSFETQ RKPAPKGHVI AVRITAENPD 450        460        470        480
    AGFKPSSGMM HDLNFRSSTN VWGYFSVSSA GGLHEFADSQ 490        500        510        520
    FGHIFAYGQD RGQSRKNMVV ALKELSIRGD FRTTVEYLIR 530        540        550        560
    LLETQEFEEN TINTGWLDSL ISNNLTAERP ETMLAVMCGA 570        580        590        600
    VNRAHTISEN CLKEYKKSLE KGQIPSKDVL RSVNOLDFIY 610        620        630        640
    DGVRYNFTAT RSGPNSYTMY LNGSMISISV PPLTDGGLLV 650        660        670        680
    LLDGKAETTY SLEEVQATRL MVDGKTCLLE KENDPTQLRS 690        700        710        720
    PSPGKLVRFL VESGDHVKAS QAYAEIEVMK MYMPLIATED 730        740        750        760
    GIVQFIKQPG TTLDAGDIIG ILSLDDPSRV KHAKPFEGQL
```

-continued

```
         770        780        790        800
PPMGQPTIHG AKPHQRYREL RLILDNAMDG YDNQALVQPT 810        820        830        840
LKEIFEVLQT PELPYLEFNE VFAALSGRIP PKLEISLHQE 850        860        870        880
VDQSMKNHEH FPARTLQALI DAHCRANFSK PADVSSFLAS 890        900        910        920
VAPLTTIIQE YQTGLKTHSW TFIAHYLTKY HEVESLFDDS 930        940        950        960
AREEETILAI RDQYKDDVEK VINIAISHSR VTAKNNLVLS 970        980        990       1000
LLDQIKPTSS GGALDKFFSP ILKKLAELNG RLTSKVSLKA 1010       1020       1030       1040
RELLIHVQLP SFEERQAQME KILRSSVTEE IYGGDHEARM 1050       1060       1070       1080
PNYDNLKELV DTTYTVFDVL PNFFYHESAH VRLAAFEVYC 1090       1100       1110       1120
RRAYHAYEIL DINYHMEHNP LLITWKFLLN TPNKSSEGGP 1130       1140       1150       1160
NRVASVSDMS YLINKADPEP VRTGGILAVR DIKELEGRFQ 1170       1180       1190       1200
SVLDFFPTVK SNKHLAHVQA TSVHNNVLNV VLKSESIHPN 1210       1220       1230       1240
DDDYWLNLLS PIVKGQSEHL RSHGIRRMTF LIFRQGNYPS 1250       1260       1270       1280
YFTFRERNNY AEDQTIRHIE PAMAYRLELS RLSNFDIKPC 1290       1300       1310       1320
FIDNRQVHVY YAVGKENVSD CRFFVCALVR PGRLRSSVRT 1330       1340       1350       1360
ADYLISETDR LLNDILDALE IVGATYKQSD CNHLFINFIP 1370       1380       1390       1400
TFQLDATEVE SALKGFIDRH GKRLWRLRVT GAEIRFNVQS 1410       1420       1430       1440
KNDAADPIPL REIISNVSGY VLNVDTYREI QTDKGAIEKS 1450       1460       1470       1480
VGPSGPFHLL PVNQPYPTKE WLQPRRYKAH LMGTTYVYDF 1490       1500       1510       1520
GELFRQAVRA QWNHAVKVNP SLKAPNQVLE MRELVLDEKQ 1530       1540       1550       1560
QLQQVVREAG SNNCGMVAWI FTLRTPEYPE GRQIIVIAND 1570       1580       1590       1600
ITYNIGSFGP EEDLVFYKAS ELARKLGIPR VYLSANSGAR 1610       1620       1630       1640
IGLASEVIGL FNSCWNDASN PSKGFKYIYL TDAGLKQLEA 1650       1660       1670       1680
QEERSGKKSV LTETVVEDGE TRHKITDVIG AVDGLGVENL 1690       1700       1710       1720
RGSGLIAGET SRAYDDIFTI TLVTCRSVGI GAYLVRLGQR 1730       1740       1750       1760
TIQNEGOPII LTGAPALNKL LGRDVYTSNL QLGGTQIMYK 1770       1780       1790       1800
NGVSHLTAQN DYEGIGKIVN WLSYIPERKN APVPITVSND 1810       1820       1830       1840
TWDRDIDYLP PKGAVYDPRW LIGGKDAEEE GAAFQTGFFD 1850       1860       1870       1880
KGSFTETLTG WARTVVVGRA RLGGVPMGVI AVETRSVEHI 1890       1900       1910       1920
IPADPANGDS VEQVLMEAGN VWYPNSAYKT AQAINDFNKG 1930       1940       1950       1960
EQLPLMIFAN WRGFSGGQRD MYNEILKYGS FIVDALSSYK 1970       1980       1990       2000
QPVFVYVVPN GELRGGAWVV VDPTINENMM EMYADKRSRA 2010       2020       2030       2040
GVLEPEGIVE IKFRKAQLLA TMERLDDKYR DLKAQYEKPD 2050       2060       2070       2080
LAGADREAIK TKLTEREQEL LPVYQQLAIQ FADLHDTAGR 2090       2100       2110       2120
MKAKGTIRES LDWTNARRYF YWRVRRRLAE EYIRRRMTIA 2130       2140       2150       2160
SKTQTRDDQT ATLKAWFGRD TVHASEAELT QIWEHEDRVV 2170       2180       2190       2200
LEWFEGQSRK VDALIQELTA AGTAEEVVRM YTSDRAGVVE 2210       2220
GFDRILQSLS DQEKQDILAK FATMTV
```

A sequence for *Nannochloropsis oculate* acetyl-CoA carboxylase is shown below as SEQ ID NO:8 (NCBI AHI17198.1).

```
  1  MATTIPSSNR RAMRAGAALV AVSSILVLLM GPVAEAWRVP

41  GFGQGRSSGV TKPVHAPGFL GRFSTPSSLG PSSASCPTIS

81  AVGPLSAATM APPALSPEAQ KKKDAVAAYV KSRGGNLAIR

121  KVLIANNGMA ATKSILSMRQ WAYMELGDDR AIEFVVMATP

161  EDLNANAEFI RLADRFVEVP GGSNKNNYAN VDLIVQMAQR

201  EGVDAVWPGW GHASENPRLP NTLKQLGIKE IGPTGPVMSV

241  LGDKIAANIL AQTAKVPSIP WSGDGLTAEL TAEGTIPDET

281  FQKAMVRTSE EALAAANRIG YPVMLKASEG GGGKGIRMSN

321  NDKELETNFI QVQNEVPGSP MFMMQLCTQA RHIEVQIVGD

361  EHGNAAALNG RDCSTQRRFQ KIFEEGPPTI VPPEVFKQME

401  LAAQRLTQSI GYIGAGTVEY LFNAATGKYF FLELNPRLQV

441  EHPVTEGLSL VNLPATQLQI AMGIPLNRIP DIRRFYGKDD

481  PYGDSPIDFF NDDYAELPSH VIAARITAEN PDEGFKPTSG

521  RIERVKFQST ANVWGYFSVG ANGGIHEYAD SQFGHLFAKG

561  KSREDARKSL VLALKEIEVR GDIRTTVEYL VQLLETEAFK

601  ENTIDTSWLD GLIREKSVRV ELNPHDVALS AAIARAFARS

641  VDEERKFVEN LSKGQVSIQG IRSINSFPME ITYKDYKYSF

681  HCTRVGPDKL RLAINDQILE TKVRQQPDGS LIAEFGGTTH

721  TIYALEEPLG LRMVLDGVTV LLPTVYDPSE LRTDVTGKIV

761  RYLQEDGTEI QAGQPYVEVE AMKMIMPLKA TESGTVAHRL

801  SPGSIITAGD LLANVQLKDP SKVKKITPFK GALELVGSDD

841  EPGVTGFQAV LKTMNMVLDG YDYEVEFLAQ NLVTSAQDGK
```

-continued

```
 881 ELLDAATALV TKYLAVEEQF AGKVLDEAMV GLVKANKDSL
 921 PTVLALATAH RELPRRNKMV SALIRQLQAL VERSSNDLSL
 961 DTLIALLDRA SRLPGKEYGE VAISSAQALL ALRAPPFSTR
1001 QDELRTTLLN TKDNDALARS ATLTAGVDLL TAMFTDPDAN
1041 VRKNAIEVYI RRIYRAHRIL SLTVEEVDGV MIANWSFKFA
1081 DTPDEESPLR RGFFTVFPSL EAYTAGSEKF SKVLKTALAG
1121 QEAYSQPTNV FHVAVAQLPE SQQPEVIANI EGILAENKDL
1161 LTECRVRMVN VLFVQGAKNP RYFTFTAVKD FKEDPLRRDM
1201 RPTFPQLLEL SRLAANYELQ RLPSIGRNTQ VYLGSERAPV
1241 GTKKRGPGNQ VLFVRGISHS EQTQTPMGAE RVLLMAMDEL
1281 DYALLDERVG GSASSRLFLN LLVPIDSDPK TLAGEWSKIM
1321 DRLLAKYATR LLKLGVDEIE IKVRVAAGSG SAITPVRLMA
1361 SSMTGEFLRT DAFLEYPDPV TGITKQFCSV TSEDQVCLLN
1401 PYPASNSIQT RRASARRIGS TYAYDFLGVM EVSLIQKWDK
1441 HLKELTSVYT SRVDDKMPEQ LFQADELVLE DGVLKPTQRL
1481 VGLNDVGMVA WHATMKTPEY PEGRELVIIA NDVTFQSGSF
1521 GVKEDDFFRA ASEYARVRGL PRIYLSSNSG ARIGLVDDLK
1561 GKFRIAWNDP ANPSLGFKYL YLTPEEYEGL KPGTVNANLV
1601 LSEEGEKRWA LQDIIGQVHG IGVENLRGSG MIAGETSRAY
1641 DETFTLSYVT GRSVGIGAYL VRLGQRTIQM VNGPLILTGY
1681 SALNKLLGRE VYTSQDQLGG PQIMAPNGVS HLVVDNDKEG
1721 ISSIIDWLSF VPKDKFSSVP IIDLPTDSPE RDVEFQPTKT
1761 PYDPRHMLAG TVGPDGAFVP GFFDRGSFIE TLGGWGKSVV
1801 TGRAKLGGIP MGIISVETRL VEQRIPADPA NPESRESLLP
1841 QAGQVWYPDS AFKTAQAIED FNRGENLPLM IFANWRGFSG
1881 GTRDMYGEIL KFGAKIVDAL RTYRHPVFVY IPPNGELRGG
1921 AWVVIDPTIN EEMMEMYADK DSRGGILEPP GICEVKFRAA
1961 DQISAMERLD PVIQALDGEL QNAKTEADAI KLKQQLKERE
2001 EALLPLYMQV AHEFADLHDR AGRMKAKGVI RDVVTWKRSR
2041 SYFYWRARRR VAEDGLVRAM QKADASLSVQ DGREKLEALA
2081 TSGVYGDDKA FVAWVTESGS KIEEQLVSVK HAAVKASLAS
2121 LLEELSPEER KKVLSGL
```

A sequence for *Nannochloropsis gaditana* CCMP526 acetyl-CoA carboxylase is shown below as SEQ ID NO:9 (Uniprot I2CQP5).

```
           10         20         30         40
    MASFPPSNRR ATPARVMVVI FSSVLILLAG PVGDAWRMPS
           50         60         70         80
    IAPGQSTGVA KTSRWAGFLG NFARRSPSIS TSPSLPPSLP
           90        100        110        120
    ASSLGPLSAA TMAPPSTLSP AAQKKKDAVA AYVKSRGGNL
          130        140        150        160
    GIRKVLIANN GMAATKSILS IRQWAYMELG DDKAIEFVVM
          170        180        190        200
    ATPEDLNANA EFIRLADRFV EVPGGSNKMN YANVDLIVQV
          210        220        230        240
    AEREGVDAVW PGQGHASENP RLPNTLKEMG IKFIGPTGPV
          250        260        270        280
    MSVLGDKIAA NILAQTAKVP SIPWSGDGLT AELTAEGTIP
          290        300        310        320
    DETFQKAMVR TAEEALAAAN RIGYPVMLKA SEGGGGKGIR
          330        340        350        360
    MSNNDEFLKN NEVQVSNEVP GSPMFMMQLC TQARHIEVQI
          370        380        390        400
    VGDEHGNAAA LNGRDQSTQR REQKIFEEGP PTIVPPEVEK
          410        420        430        440
    QMELAAQRLT QSIGYIGAGT VEYLFNAATG KYFFLELNRR
          450        460        470        480
    LQVEHRVTEG LSLVNLPATQ LQIAMGIPLN RIPDIRPFYG
          490        500        510        520
    KEDPYGDSPI EFFEDDYADL ASHVIAARIT AENPDEGFKP
          530        540        550        560
    TSGRIERVKF QSTANVWGYF SVGANGGIHE FADSQFGHLF
          570        580        590        600
    AKGKTREDAR KSLVLALKEI EVRGDIRTTV EYLVQLLETD
          610        620        630        640
    AFKENTIDTS WLDGLIREKS VRVELAPHEV ALSAAIARAF
          650        660        670        680
    ARSQFFEKKF VENLGKGQVS IQSIRSINSF PMEITYKDSK
          690        700        710        720
    YSFLCSRIGP DKLRLTINGQ VLETKVRQQR DGSLIAEYGG
          730        740        750        760
    TTHTIYALEF RLGLRMVLDG VIVLLPTVYD PSELRTDVTG
          770        780        790        800
    KVVRYLQDDG AEIQAGQPYV EVEAMKMIMP LKASESGTVT
          810        820        830        840
    HRLSPGSIIT AGDLLANIQL KDPSKVKKII PFKDTLELAG
          850        860        870        880
    SGEEPGTTEI ESVLKTMNLV LDGFDYEVEF LAQNLVTSVR
          890        900        910        920
    DGKELLDAAV ALVSKYLAVE EQFAGKALDE AMVALVKANK
          930        940        950        960
    ESLGTVLQLA TAHRELPRRN KMVSALIRQL QALVERPGTS
          970        980        990       1000
    ELALGPLIDL LERISHLPGK EYGEVAISSA QALLALKAPP
         1010       1020       1030       1040
    FNIRKDELRA TLMQTQDNDA LARSATLTAG VDLLTAMFTD
         1050       1060       1070       1080
    PDVTVRKNAI EVYIRRIYRA HRILSLSVEE VDGVMVARWS
         1090       1100       1110       1120
    FKFADTPDEE SPLRYGFFTV FPSLEAYTEG TEKESKVLKS
         1130       1140       1150       1160
    SLGGKEVYSE PTNVFHAVA QLPESDQPEV IANIEAILAE
         1170       1180       1190       1200
    KKELLTECQV RMVNVLFVKG ASNPRYYTFT AAENFKEDPL
         1210       1220       1230       1240
    RRDMRPTFPQ LLELSRLAAN YELQRLPSIG RNTQVYLGTE
```

-continued

```
         1250        1260        1270        1280
RAAAGVKKRG GSQVLEVRGI SHSEQTQTPL GAERVLLMAM
         1290        1300        1310        1320
DELDYALLDP RVGGSASSRL FLNLLVPITT DPEALAGEWN
         1330        1340        1350        1360
QVMDRLLAKY ATRLLKLGVD EIEIKVRVTA DGNTITPVRL
         1370        1380        1390        1400
MATSMTGEFL RTDAFLEYPD PVNGITKQFC SITREDQICL
         1410        1420        1430        1440
LNPYPASNSI QTRRASARRI GSTYAYDFLG VMEVSLIQKW
         1450        1460        1470        1480
DKHLKELSSV YPSRVDDKMP EQLFTAHELV LEDDELQPTQ
         1490        1500        1510        1520
RLVGLNDIGM IAWHATMKTP EYPEGRELVI IANDVTFQSG
         1530        1540        1550        1560
SFGVKEDEFF RAASEYARVR GLPRIYLSSN SGARIGLVDD
         1570        1580        1590        1600
LKGKFRIAWN DPANPSLGFK YLYLPPEEYE ALKPGIVNAN
         1610        1620        1630        1640
LVETEEGEKR WALQDIVGQV HGIGVENLRG SGMIAGETSR
         1650        1660        1670        1680
AYDETFTLSY VTGRSVGIGA YLVRLGQRTI QMVNGPLILT
         1690        1700        1710        1720
GYSALNKLLG REVYTSQDQL GGPQIMAPNG VSHLVVGNDK
         1730        1740        1750        1760
EGVSSIIDWL SFVPKDKESA PPILDLPIDS PERDVEFLPT
         1770        1780        1790        1800
KTPYDPRHML AGTVGPDGAF VPGFFDRGSF IETLGGWGKS
         1810        1820        1830        1840
VVTGRAKLGG IPMGVISVET RLVEQRVPAD PANPDSRESI
         1850        1860        1870        1880
LPQAGQVWYP DSAFKTAQAM EDFNRGENLP LIIFANWRGF
         1890        1900        1910        1920
SGGTRDMFGE ILKFGAKIVD ALRTYRHPVF VYIPPNGELR
         1930        1940        1950        1960
GGAWVVIDPT INEEMMEMYA DKDSRGGILE PPGICEVKFR
         1970        1980        1990        2000
NADQVSAMHR LDPVIQALDG ELQNAKTEQD AAKLTQQLKE
         2010        2020        2030        2040
REEALLPLYT QVAHEFADLH DRAGRMKAKG VIRDVVIWKR
         2050        2060        2070        2080
SRSYFEWRAR RRIAEDGLIR EMQRVDPILS VQQGREKVSA
         2090        2100        2110        2120
LASPAVYEDD KAFVAWVEEG GEAIAKELEK IKQAAVKASL
         2130
ASLLEGLSAE ERKQVLAGL
```

A sequence for a *Streptococcus salivarius* acetyl-CoA carboxylase beta subunit is shown below as SEQ ID NO:10 (NCBI WP_014633943.1).

```
  1 MGLFDRKEKY IRINPNRSVR NGVDHQVPEV PDELFAKCPG
 41 CKQAIYQKDL GQAKICPNCS YTFRISAKER LDLTVDEGSF
 81 QELFTGIKTE NPLNFPGYME KLAATKEKTG LDEAVVTGFA
121 SIKGQKTALA IMDSNFIMAS MGTVVGEKIT KLFEHAIEEK
161 LPVVIFTASG GAPMQEGIMS LMQMAKISAA VKRHSNAGLL
201 YLTVLTDPTT GGVTASFAME GDIILAEPQT LIGFAGRRVI
241 ENTVRETLPD DFQKAEFLQE HGFVDAIVKR TELADTIATL
281 LSFHGGVQ
```

A sequence for a *Collimonas fungivorans* acetyl-CoA carboxylase beta subunit is shown below as SEQ ID NO:11 (NCBI AMO95008.1).

```
  1 MYRTDLESNI HVCPKCDHEM RIRARERLDA LLDAGGRYEI
 41 GQETLPIDTL KFKDSKKYPD RLKAAMDATG ETDALIVLGG
 81 SIMTLPVVVA AFEFEFMGGS MGSVVGERFV RGAQVALEQK
121 VPFICITATG GARMQEGLLS LMQMAKTTSM LTKLSEKKLP
161 FISVLTDPTM GGVSASFAFM GDVVIAEPKA LIGFAGPRVI
201 ENTVREKLPE GFQRAEFLVT KGAVDMIVDR RKMREEIARL
241 LALLQDQPVE SIA
```

A sequence for a *Marinobacter* sp. acetyl-CoA carboxylase beta subunit is shown below as SEQ ID NO:12 (Uniprot A0A2G1ZII3).

```
            10         20         30         40
   MSNWLDKIMP SKIRSESKQR TGVPEGLWKK CPKCGAFLYK
            50         60         70         80
   PELDKNLDVC PKCQHHLRIT ARRRLDVFLD ADGRQEIAAD
            90        100        110        120
   LEPWDRLKFK DSKRYKDRLS QNQKTTGEKD ALVAMRGACL
           130        140        150        160
   DIPLVAVAFE FNFLGGSMGQ VVGEKFVQAA NVCLEERIPL
           170        180        190        200
   VCFSASGGAR MQEAILSLMQ MSKTAAVLER KKQEGIPYIS
           210        220        230        240
   VMTDPVFGGV SASLAMLGDL NIAEPYALIG FAGPRVIEQT
           250        260        270        280
   VREKLPEGFQ RSEFLLEHGA IDMILRHQM RERIAAVLAK
           290        300
   FTDLDQPATE APIEFEVSER PETDVPAE
```

A sequence for *Helicosporidium* ex *Simulium jonesi* acetyl-CoA carboxylase beta subunit (plastid) is shown below as SEQ ID NO: 13 (NCBI ABD33968.1).

```
  1 MTILAWIKDK KNKAILNTPE YSSQSSLSWC FTHKEAASNK
 41 AVSFINLSKR RALWTRCEKC GMIQFMRFFK ENANLCLSCS
 81 YHHIMTSDER IALLVEKGTW YPLNETISPK DPIKFTDTQS
121 YAQRIQSTQE KLGMQDAVQT GTGLINGIPF AIGIMDFRFM
161 GGSMGSVVGE KLTRLIEYAT KQGLFLLIVS ASGGARMQEG
201 IYSLMQMAKI SAALNVYQNE ANLLYISLCT SPTTGGVTAS
241 FAMLGDIIFS EPEAIIGFAG RRVIQQTLQQ ELPEDFQTSE
```

```
281 SLLHHGLIDA IVPRCFLVNA ISEVASIFAY APSKYKKLGN

321 ISHYHENTLS WATEEILRRN CINNKKVEYR TIEKIYQTTL

361 YKESFFRLNK LLSKLKSEIN FTNKMKKQNN AFNTSSVYAN

401 YYDVMLCNYN IGTHSLNLLF NEESEFCKYF PFNMDHMKKE

441 NRIKYNFITE NSNDFIRKKT INDFSIMLIG D
```

A sequence for *Mortierella elongata* AG-77 malonyl-CoA decarboxylase with protein ID 100426 is shown below as SEQ ID NO:14 (Uniprot A0A197JJC1).

```
             10         20         30         40
      MSRRLIISHL SKPSSRVWSS SSSSSSFYSP AFSTSTTVRS
             50         60         70         80
      PFHIATLQRH RTMASISNGG SNNNNNNSAS SSSNAAGSGT
             90        100        110        120
      LQALRANVVE QYWNDIAAHF REPGFSTFDK ERTRRAADRD
            130        140        150        160
      PEFMRKILLA VITDRPGQGD ILPSVIAKSS CDFFSSLDRN
            170        180        190        200
      GKTEFLRLLA RDFGVLQEDV VKAAEQYQDY AHKEPESKAL
            210        220        230        240
      LRAEQLLRHA IVPGHSKFFD RVSRLPGGLK FLIDMRQDLL
            250        260        270        280
      SIIQANKGDV YLSSLNESLK EKLQAWFVGF LDLERLTWQS
            290        300        310        320
      PAVLLEKITQ YEAVHKEKDV QDLKRRVGPG RRVFALMNKS
            330        340        350        360
      LPAEPLVFVQ VALVERLSDN VQDILNDPSP GHANPAETVK
            370        380        390        400
      CAIFYSITTQ QPYLQWLSGI ELGNFLIKRV VRSLKVEFPQ
            410        420        430        440
      IETFSTLSPI PGFRKWIGQC QNLGQKLLLP QEESIVSQLG
            450        460        470        480
      QETGAASGDV EDQFSAILKH PSTFSDSETM SKLRPILSRL
            490        500        510        520
      CARYILLEKR RHLAIDPVAN FHLRNGACAH RLNWLGDTST
            530        540        550        560
      KGMEESFGLM INYLYSLDHI EMNNQQYLLD GTISVSSKDA
            570        580        590        600
      GFQKVLMDSA VGNSQAAGRG VGEEQGGEEG QVVQVNGSSF
      RLLEIVTA
```

A sequence for *Mortierella elongata* AG-77 malonyl-CoA decarboxylase with protein ID 81334 is shown below as SEQ ID NO:15.

```
             10         20         30         40
      RYILEKKCRH LAMDSVANFH LRNGACAHRL NWLDDTSPKG
             50
      MEEFFGIVTE
      SRRSLAD
```

A sequence for *Mortierella elongata* AG-77 acyl carrier protein with protein ID 127963 is shown below as SEQ ID NO:16.

```
             10         20         30         40
      MFRALVRPAS TIYRQAAIKA TPATVARMPM GLTFARTYAS
             50         60         70         80
      AGLARSDVEK RVLDILAGFN KVDSNKISLN ANFNNDLGLD
             90        100        110        120
      SLDTVEVVMA IEEEFSIEIP DKDADEIKSA AQAVEYITKR
      DDAH
```

Another sequence for *Mortierella elongata* AG-77 acyl carrier protein is shown below as SEQ ID NO:17 (Uniprot A0A197JHD1).

```
       1 MFRAIRPAAL YRSAALYKTA PAVVARNAMA LNFARTYASA

41 GLARSDVEKR VLDILAGFNK IDANKIALKA NFNADLGLDS

81 LDTVEVVMAT EEEFSIEIPD KDADEIKSAE QAVEYISKRE

121 DAH
```

A sequence for *Nannochloropsis gaditana* acyl carrier protein is shown below as SEQ ID NO: 18 (Uniprot W7TK08).

```
             10         20         30         40
      MRVLAFLALL AAPAFAFVPR MPAPVRARAG LTLRFSGEYS
             50         60         70         80
      EKVRAIVLEN MGDDAKVQDY LKANGDDTAE FAAMGFDSLD
             90        100        110        120
      LVEFSMAVQK EFDLPDLNEE DFANLKTIKD VVTMVEANKK
```

A sequence for *Nannochloropsis gaditana* malonyl-ACP transacylaseis shown below as SEQ ID NO:19 (Uniprot S5VRZ9).

```
             10         20         30         40
      MMSKSLIMLG LLSPTAFAFV PKLSTNVLSR AISSHARKNL
             50         60         70         80
      VKASAVDYKT AFMFPGQGAQ YVGMGAQVSE EVPAAKALFE
             90        100        110        120
      KASEILGYDL LDRAMNGPKD LLDSTAVSQP AIFVASAAAV
            130        140        150        160
      EKLRATEGED AANAATVAMG LSLGEYSALC YAGAFSFEDG
            170        180        190        200
      VRLTKARGEA MQAAADLVDT TMVSVIGLEA DKVNELCAAA
            210        220        230        240
      SSKSGEKIQI ANYLQPGNYA VSGSLKAAQV LEEIAKPEFG
            250        260        270        280
      ARMTVRLAVA GAFHTEYMAP ALEKLKEVLA KTEFKTPRIP
            290        300        310        320
      VISNVDGKPH SDPEEIKAIL AKQVTSPVQW ETTMNDLVKG
            330        340        350
      GLETGYELGP GKVCAGILKR IDRKAKMVNI EA
```

A sequence for *Mortierella elongata* AG-77 fatty acid synthase is shown below as SEQ ID NO:20 (Uniprot A0A197K6H).

```
             10         20         30         40
      MESISQFIPN KLPQDLFIDF ATAFGVRAAP YVDPLEDALT
```

```
            50          60          70          80
    AQMEKFFPAL  VHHYRAFLTA  VESPLAAQLP  LMNPFHVVLI 90         100         110         120
    VIAYLVTVFV  GMQIMKNFNR  FEVKTFSLFH  NFCLVSISAY 130         140         150         160
    MCGGILYEAY  QSKYGLFENL  ADHTSTGFPM  AKMIWIFYFS 170         180         190         200
    KIMEFVDTMI  MVLKKNNRQI  SFLHVYHHSS  IFAIWWLVTF 210         220         230         240
    VAPNGEAYFS  AALNSFIHVI  MYGYYFLSAL  GFKQVSFIKF 250         260         270         280
    YITRSQMTQF  CMMSVQSSWD  MFAMKVMGRP  GYPFFITALL 290         300         310
    WFYMWTMLGL  FYNFYRKNAK  LAKQAKADAA  KEKSKKLQ
```

Another sequence for *Mortierella elongata* AG-77 fatty acid synthase is shown below as SEQ ID NO:21 (Uniprot A0A197K854).

```
            10          20          30          40
    MAAAFLDQVN  FSLDQPFGIK  LDNYFAKGYE  LVTGKSIDSF 50          60          70          80
    VFQEGVTPLS  TQYEVAMWTV  TYFIVIFGGR  QIMKSQEAFK 90         100         110         120
    LKPLFILHNF  LLTIASGALL  LLFIENLVPI  LARNGLFYAI 130         140         150         160
    CDQGAWTQRL  ELLYYLNYLV  KYWELADTVF  LVLKKKPLEF 170         180         190         200
    LHYFHHSMTM  ILCFVQLGGY  TSVSWVPITL  NLTVHVLMYY 210         220         230         240
    YYMRSAAGVR  IWWKQYLTTL  QIVQFVLDLG  FIYFCSYTYF 250         260         270         280
    AFTYWPHLPN  VGKCAGTEGA  ALFGCGLLSS  YLLLFINFYR 290         300         310
    LTYNAKAKAA  KERGSNVIRK  TPKADKKKSK  HI
```

Another sequence for *Mortierella elongata* AG-77 fatty acid synthase is shown below as SEQ ID NO:22 (Uniprot A0A197JPT7).

```
            10          20          30          40
    MESAPMPAGV  PFPEYYDFFM  NWKTPLAIAA  TYTVAVTLFN 50          60          70          80
    PKVGKVSRVV  AKSANAKPAE  KTQSGAAMTA  FVFVHNLILC 90         100         110         120
    VYSGITFYNM  FPAMIKNFAT  HSIFDAYCDT  DQSLWNGSLG 130         140         150         160
    YWGYIFYLSK  FYEVIDTIII  ILKGRRSSLL  QTYHHAGAMI 170         180         190         200
    TMWSGINYQA  TPIWIFVVFN  SFIHTIMYAY  YAATSVGLHP 210         220         230         240
    PGKKYLTSMQ  ITQFLVGMSI  AVSYLFIPGC  IRTPGAQMAV 250         260         270
    WINVGYLFPL  TYLFVDFAKR  TYSKRSAAPA  KKTE
```

A sequence for *Nannochloropsis gaditana* fatty acid synthase is shown below as SEQ ID NO:23 (Uniprot W7TQY4).

```
            10          20          30          40
    MGNQNSVYFG  APPVRKKAPQ  HADIQEAWRQ  IASKVARDKG 50          60          70          80
    FEHGRKRKVA  IIGSGVAGLG  AAYHLLTCAA  PGEEVELVVY 90         100         110         120
    EASGTPGGHA  HTELVREEDG  KIIACDTGFM  VFNHQNYPNL 130         140         150         160
    VELFAELGVD  DENTNMSFAV  SMDEGKVEWC  SESVKTLAGP 170         180         190         200
    VYRAMLKDML  RFNRTASNLL  LAEPEDPRRA  WTLAEFLEKE 210         220         230         240
    KYGPEFTNYY  IVPMCAALWS  SSAADVLAAS  AYALLTFMDN 250         260         270         280
    HCMLQLFNRP  QWKTVAQRSQ  TYVQKIVALL  GERLRLNAPV 290         300         310         320
    KKVVVHGKGK  VEVTDASYHA  ETFDEAIFAC  HPDQSLALLE 330         340         350         360
    GEARVRLAPY  LEAFKYAPNA  CYLHSDPRLM  PRKKEAWGSW 370         380         390         400
    NYIGTSAGML  GPGREKPVFV  TYWLNQLQNL  ETETPYFVSL 410         420         430         440
    NPLFPPDRAL  THKILRESHP  QFTPATEAAQ  RRMTEVQGQD 450         460         470         480
    GLWFCGAWMG  HGFHEDGLRS  GLEVATALSG  QKAAWMPPEA 490         500         510         520
    EAPVYPMVKA  HMNARSTWER  CQDLLGQLAC  VPIRNFLASS 530         540         550         560
    IQEGCLVLRL  PGTGDKLWFG  DRTAGRKETV  VLRVQSWWFF 570         580         590         600
    VRVALEYDLG  LARAYMAGEF  EVEGTGWNSD  GLTRLFLLFI 610         620         630         640
    RNRDAPSGGK  RFAVSALLTS  WIGYGLNFLR  YRLSMDNSLA 650         660         670         680
    GSRQNISAHY  DIGNDLYTLM  LDKSLMMYSS  AIYHLELTPS 690         700         710         720
    SLTASAEATS  SDLVPAGNGN  GVVVKSSFPP  SSYSMAFKGS 730         740         750         760
    LEDAQLRKVD  TLIRTCRVER  KHTLLDIGFG  WGGIAIRAAE 770         780         790         800
    TIGCKVVGIT  LSKEQKALAE  EKVRAKGLEH  LIHFELVDYR

VFARR
```

A sequence for a *Mortierella elongata* AG-77 FabD protein is shown below as SEQ ID NO:24 (Uniprot A0A197K6C6).

```
            10          20          30          40
    MGRDLYESYP  IVRQTIDEAD  AILSSMPSSS  SSSSPQEEGY 50          60          70          80
    LKRVMFEGPQ  EELTRTENAQ  PAILTTSIAL  LRVLETEHGL 90         100         110         120
    DLKESCRFAL  GHSLGEYSAL  VATRALSLPD  AVRLVRIRGD 130         140         150         160
    AMAMAVTDKK  GMTAMSALVV  RASKLDELVK  AMHEIQTELS 170         180         190         200
```

```
                    -continued
STVEIAEIAN INSSFQVVIS GTVKGVDHAS KTLQFRKIAA 210        220        230        240
KAVDLPVSAP FHCSLMEPAA RVMKDALADI SFKQPIIPIV 250        260        270        280
SNVQAQPIES SNDIPSLLVQ QVTDTVQWRQ SLVNLHSQQQ 290        300        310        320
QYDISEYICI GPGKVICNLL RKEYPLDTIR SVSTVEDIQQ

WKL
```

A sequence for *Saccharomyces cerevisiae* malonyl CoA-acyl carrier protein transacylase is shown below as SEQ ID NO:25 (Uniprot Q12283).

```
        10         20         30         40
MKLLTFPGQG TSISISILKA IIRNKSREFQ TILSQNGKES 50         60         70         80
NDLLQYIFQN PSSPGSIAVC SNLFYQLYQI LSNPSDPQDQ 90        100        110        120
APKNMTKTDS PDKKDNEQCY LLGHSLGELT CLSVNSLFSL 130        140        150        160
KDLFDIANFR NKLMVTSTEK YLVAHNINRS NKFEMWALSS 170        180        190        200
PRATDLPQEV QKLLNSPNLL SSSQNTISVA NANSVKQCVV 210        220        230        240
TGLVDDLESL RTELNLRFPR LRITELTNPY NIPFHNSTVL 250        260        270        280
RPVQEPLYDY IWDILKKNGT HTLMELNHPI IANLDGNISY 290        300        310        320
YIHHALDRFV KCSSRTVQFT MCYDTINSGT PVEIDKSICF 330        340        350        360
GPGNVIYNLI RRNCPQVDTI EYTSLATIDA YHKAAEENKD
```

A sequence for *Nannochloropsis gaditana* malonyl CoA-acyl carrier protein is shown below as SEQ ID NO:110 (Uniprot S5VRZ9).

```
        10         20         30         40
MMSKSLIMLG LLSPTAFAFV PKLSTNVLSR AISSHARKNL 50         60         70         80
VKASAVDYKT AFMFPGQGAQ YVGMGAQVSE EVPAAKALFE 90        100        110        120
KASEILGYDL LDRAMNGPKD LLDSTAVSQP AIFVASAAAV 130        140        150        160
EKLRATEGED AANAATVAMG LSLGEYSALC YAGAFSFEDG 170        180        190        200
VRLTKARGEA MQAAADLVDT TMVSVIGLEA DKYNELCAAA 210        220        230        240
SSKSGEKIQI ANYLCPGNYA VSGSLKAAQV LEEIAKPEFG 250        260        270        280
ARMTVRLAVA GAFHTEYMAP ALEKLKEVLA KTEFKTPRIP 290        300        310        320
VISNVDGKPH SDPEEIKAIL AKQVTSPVQW ETTMNDLVKG 330        340        350
GLETGYELGP GKVCAGILKR IDRKAKMVNI EA
```

A sequence for a *Pseudomonas aeruginosa* beta-ketoacyl-[acyl-carrier-protein]synthase protein is shown below as SEQ ID NO:111 (NCBI accession no. Q9HU15.1).

```
  1 MSRLPVIVGF GGYNAAGRSS FHHGFRRMVI ESMDPQARQE

41 TLAGLAVMMK LVKAEGGRYL AEDGTPLSPE DIERRYAERI

81 FASTLVRRIE PQYLDPDAVH WHKVLELSPA EGQALTFKAS

121 PKQLPEPLPA NWSIAPAEDG EVLVSIHERC EFKVDSYRAL

161 TVKSAGQLPT GFEPGELYNS RFHPRGLQMS VVAATDAIRS

201 TGIDWKTIVD NVQPDEIAVF SGSIMSQLDD NGFGGLMQSR

241 LKGHRVSAKQ LPLGFNSMPT DFINAYVLGS VGMTGSITGA

281 CATFLYNLQK GIDVITSGQA RVVIVGNSEA PILPECIEGY

321 SAMGALATEE GLRLIEGRDD VDFRRASRPF GENCGFTLAE

361 SSQYVVLMDD ELALRLGADI HGAVTDVFIN ADGFKKSISA

401 PGPGNYLTVA KAVASAVQIV GLDTVRHASF VHAHGSSTPA

441 NRVTESEILD RVASAFGIDG WPVTAVKAYV GHSLATASAD

481 QLISALGTFK YGILPGIKTI DKVADDVHQQ RLSISNRDMR

521 QDKPLEVCFI NSKGFGGNNA SGVVLSPRIA EKMLRKRHGQ

561 AAFAAYVEKR EQTRAAARAY DQRALQGDLE IIYNFGQDLI

601 DEHAIEVSAE QVTVPGFSQP LVYKKDARFS DMLD
```

A sequence for a *Mortierella elongata* AG-77 3-oxoacyl-[acyl-carrier-protein]synthase protein is shown below as SEQ ID NO:26 (Uniprot A0A197JR20).

```
        10         20         30         40
MSLNARRVVV TGLGLVTPLG IGVQQSWSKL IAGECGVVSL 50         60         70         80
KDLPSPTPGL PGFDTLPSQV GAIVKRTGGK ELGGFDSTEW 90        100        110        120
LDRGDEKRMA VFTQYAIAAA RMAIKDANWE TTTEEEKERT 130        140        150        160
GVCLGSGIGS LDDMATTALS FAESGYRKMS PMFVPKILIN 170        180        190        200
MAAGHLTMKY GFKGPNHAVS TACTTGAHSL GDAMRFIQYG 210        220        230        240
DADVMVAGGS EACIHPLAVA GFAKAKSLAT KYNDSPSEAS 250        260        270        280
RPFDKNRDGF VIGEGAGVVV LEEYEHAKKR GAHIYAELRG 290        300        310        320
YGLSGDAHHM TAPPENGTGA AMAMRRALKA ARLTPADIGY 330        340        350        360
VNAHATSTHQ GDIAENRAIK SVFDGHHDTI AVSSTKGAVG 370        380        390        400
HLLGAAGAVE AIFAILAVKN NILPPTLNLH EHDDSGEFTL 410        420        430
NYVPLKAQEK VLKAAITNSF GFGGTNASLC FAKVDTK
```

A sequence for a *Nannochloropsis gaditana* 3-oxoacyl-[acyl-carrier-protein]synthase protein is shown below as SEQ ID NO:27 (Uniprot accession no. W7TRD5).

```
         10         20         30         40
MRLSTLSVLG PALGCAFLLF DSSLAYLPSY MRGSKGQIYM 50         60         70         80
KEKSQRVVVT GLGPISAVGI GKDAFWKALL EGKSGIDRIS 90        100        110        120
GFDPSGLTCQ IGAEVKDFDA KPYFKDRKSA VRNDRVTLMG 130        140        150        160
VAASRIAVDD AKLDLSSVEG ERFGVVVGSA FGGLQTLETQ 170        180        190        200
IQTMNEKGPG SVSPFAVPSL LSNLISGVIA LENGAKGPNY 210        220        230        240
VVNSACAAST HALGLAYAHI AHGEADVCLA GGSEAAVTPF 250        260        270        280
GFAGFCSMKA MATKYNDNPS QGSRPFDKDR CGFVMGEGAG 290        300        310        320
MVVLESLEHA QKRGAHIYAE VAGFGQACDA HHITTPHPEG 330        340        350        360
AGLAQAITLA LEDAGMAKED LTYINAHGTS TAYNDKFETL 370        380        390        400
AVKKALGEEV AKKMYLSSTK GSTGHTLGAA GGLEAIATVL 410        420        430        440
AIETKTLPPT INYETPDPDC DLNVVPNKPI TLNEITGAAS

450
QSAGFGGHDS VVVFKPFK
```

A sequence for a *Nannochloropsis gaditana* (strain CCMP526) 3-oxoacyl-ACP synthase 3 protein is shown below as SEQ ID NO:28 (Uniprot accession no. I2CQW7).

```
         10         20         30         40
MSKRSRASSR GLAYIQRLHL LSLSLCLLLS LQCSIRAAAF 50         60         70         80
LVPSSPLPSL PSSHGPSLPS SRPPSSVPKS QALRMATSLT 90        100        110        120
EGSSVDAPAA VPGRSFLRAK PIGVGSAAPE DVITNTDLES 130        140        150        160
IVETSDEWIF TRTGISQRRI LTSGGQIRAL AATAAARALA 170        180        190        200
SAGLEGKDID LVVLATSSPD DLFGDATSVA AAVGATQAVA 210        220        230        240
FDLTAACSGF LFGYVSASQF LHSGCYRRAL VYGADALSRW 250        260        270        280
VDWEDRNSCI LFGDGAGAVV LEAAEGEEDS GVLGFAMHSD 290        300        310        320
GTGQGDLNLQ FSRDDSQSPP SIREVTPYKG KYNNIAMNGK 330        340        350        360
EVYKFATRKV PTVIEEALAN AGLGVENVDW LLLHQANIRI 370        380        390        400
MDVVADRLGL SKDKILTNLS EYGNTSAGSI PLALDEAVKA 410        420
AKVKKGDIIA CAGFGAGLSW GSAIIRWQG
```

A sequence for a (3R)-hydroxymyristoyl-[ACP] dehydratase from a bacterium endosymbiont of *Mortierella elongata* FMR23-6 is shown below as SEQ ID NO:29 (NCBI GAM51895.1).

```
  1 MLDWRFFTER TCAAVRALGS ERHRHSTRWA LCLSDPFEFA

41 CGLFALLAAG KQIVLPSNHK PAALLPLAGL YDSVLDDLDG

81 LLANGAGGPC AKLRIDPRAP LSLVTSGSSG VPKVIQKTLA

121 QFEAEIHTLA TLWGTVMRGV TVVASVPHHH IYGLLFRLLW

161 PLAAGQPFDR MTCVEPADVR ARLAALQNTV LVSSPAQLTR

201 WPSLINLTQL TPPPGLIFSS GGPLPAETAA IYTQAFGAAP

241 IEVYGSTETG GIAWRCQPQA THQNEVSDAW TPMPAIDVRC

281 DTEGALQLRS PHLPDDQWWR MEDAVQIEAD GRFRLRGRLD

321 RIIKLEEKRV SLPELEHVLM RHPWVKQAAV APLNGARMTL

361 GALLTLTEEG IQAWRSAASR RFITQALRRY LAEYFDGVVL

401 PRHWRFCMQL PFDERGKLSV TQLATRFATH PLQPEVLAEW

441 CDDNTALLEL HVPATLIHFS GHFPGLPILP GVVQIDWVVR

481 YAAHYFARCN GFQTLEQIKF LSMVRPGTTL RLALAHDPER

521 ARITFRYYVG ERDYATGRIV YSKSAVV
```

A sequence for a beta-hydroxyacyl-ACP dehydratase (FabA) from *Nannochloropsis gaditana* is shown below as SEQ ID NO:30 (UniprotW7TUB8).

```
         10         20         30         40
MHLLAALVAL PAMCTAFVVP LPSAPKHAVR MMADGDAAGA 50         60         70         80
EWRGGQAASA VSKDLKTLLT NENVASILPH RYPFLLYDKV 90        100        110        120
IEMEPGKKAV GIKQITANEP QFTGHFPERP IMPGVLMVEA 130        140        150        160
MAQLSGVLCL QPPVSDGKGL FFFAGIDGVK FRKPVVPGDT 170        180        190        200
LVMEVELVKF MESFGIAKLK GKAYVDGDVA VEIKEMTFAL

SK
```

A sequence for a 3-hydroxyacyl-CoA dehydrogenase (FabA) from *Nannochloropsis gaditana* (strain CCMP526) is shown below as SEQ ID NO:31 (Uniprot K8YU30).

```
         10         20         30         40
MADGDAAGAE WRGGQAASAV SKDLKTLLTN ENVASILPHR 50         60         70         80
YPFLLVDKVI EMEPGKKAVG IKQITANEPQ FTGHFPERPI 90        100        110        120
MPGVLMVEAM AQLSGVLCLQ PPVSDGKGLF FFAGIDGVKF 130        140        150        160
RKPVVPGDTL VMEVELVKFM ESFGIAKLKG KAYVDGDVAV

170
EIKEMTFALS K
```

A sequence for a 3-oxoacyl-(Acyl-carrier-protein) reductase from *Nannochloropsis gaditana* is shown below as SEQ ID NO:32 (Uniprot W7U8F0).

```
         10         20         30         40
MASHHLTTQE HARRKVAVVT GAAGTLGESI TGMLLSEGYV
```

```
           50         60         70         80
VAALDIRAEG LSAFKATLDK KSDQYHAFAV DISSASAVEE 90        100        110        120
VCRTILTRLG AVSVLINNAG LLSNHKCVQT SLTEWHRVMH 130        140        150        160
VNVDGAFLLS QQLLPCMRSM HFGRIVNITS MAAKTGGVTA 170        180        190        200
GTAYAVSKGA LASLTFSLAR ETAGDGITVN GVAPAYYKTP 210        220        230        240
MVMQQLREEQ RVQVLNSIPV GRFCEPEEVA HTVRFLISPL

250
AGFITGEITD QNGGYHMD
```

A sequence for a 3-oxoacyl-ACP reductase (FabG) from a bacterium endosymbiont of *Mortierella elongata* FMR23-6 is shown below as SEQ ID NO:33 (NCBI WP_045362092.1).

```
  1 MRRRVLVTGA SRGIGRAIAE QLASDGFALT IHAHSGWTEA

41 QAVVAGIVAQ GGQAQALRFD VRERALCSKI LTEDVAAHGA

81 YYGIVCNAGV VRDAVFPALS GEDWDTVIDT SLDGFYNVVH

121 PLTMPMVRAK AGGRIITISS VSGMIGNRGQ VNYSAAKAGL

161 IGASKALALE LASRAITVNC VAPGIIATEM INTELREQAS

201 KEVPMKRVGT PSEVAALVSF LMSDAAAYIT RQVIGVNGGI

241 V
```

A sequence for an elongation of fatty acids (ELO) protein from *Mortierella elongata* AG-77 is shown below as SEQ ID NO:34 (Uniprot A0A197K6H1).

```
           10         20         30         40
MESISQFIPN KLPQDLFIDF ATAFGVRAAP YVDPLEDALT 50         60         70         80
AQMEKFFPAL VHHYRAFLTA VESPLAAQLP LMNPFHVVLI 90        100        110        120
VIAYLVTVFV GMQIMKNFNR FEVKTFSLFH NFCLVSISAY 130        140        150        160
MCGGILYEAY QSKYGLFENL ADHTSTGFPM AKMIWLFYFS 170        180        190        200
KIMEFVDTMI MVLKKNNRQI SFLHVYHHSS IFAIWWLVTF 210        220        230        240
VAPNGEAYFS AALNSFIHVI MYGYYFLSAL GFKQVSFIKF 250        260        270        280
YITRSQMTQF CMMSVQSSWD MFAMKVMGRP GYPFFITALL 290        300        310
WFYMWTMLGL FYNFYRKNAK LAKQAKADAA KEKSKKLQ
```

Another sequence for an elongation of fatty acids (ELO) protein from *Mortierella elongata* AG-77 is shown below as SEQ ID NO:35 (Uniprot A0A197K854).

```
           10         20         30         40
MAAAFLDQVN FSLDQPFGIK LDNYFAKGYE LVTGKSIDSF 50         60         70         80
VFQEGVTPLS TQYEVAMWTV TYFIVIFGGR QIMKSQEAFK 90        100        110        120
LKPLFILHNF LLTIASGALL LLFIENLVPI LARNGLFYAI 130        140        150        160
CDQGAWTQRL ELLYYLNYLV KYWELADTVF LVLKKKPLEF 170        180        190        200
LHYFHHSMTM ILCFVQLGGY TSVSWVPITL NLTVHVLMYY 210        220        230        240
YYMRSAAGVR IWWKQYLTTL QIVQFVLDLG FIYFCSYTYF 250        260        270        280
AFTYWPHLPN VGKCAGTEGA ALFGCGLLSS YLLLFINFYR 290        300        310
LTYNAKAKAA KERGSNVTPK TPKADKKKSK HI
```

Another sequence for an elongation of fatty acids (ELO) protein from *Mortierella elongata* AG-77 is shown below as SEQ ID NO:36 (Uniprot A0A197JPT7).

```
           10         20         30         40
MESAPMPAGV PFPEYYDFFM NWKTPLAIAA TYTVAVTLFN 50         60         70         80
PKVGKVSRVV AKSANAKPAE KTQSGAAMTA FVFVHNLILC 90        100        110        120
VYSGITFYNM FPAMIKNFAT HSIFDAYCDT DQSLWNGSLG 130        140        150        160
YWGYIFYLSK FYEVIDTIII ILKGRRSSLL QTYHHAGAMI 170        180        190        200
TMWSGINYQA TPIWIFVVFN SFIHTIMYAY YAATSVGLHP 210        220        230        240
PGKKYLTSMQ ITQFLVGMSI AVSYLFIPGC IRTPGAQMAV 250        260        270
WINVGTLFPL TYLFVDFAKR TYSKRSAAPA KKTE
```

Another sequence for an elongation of fatty acids (ELO) protein from *Mortierella elongata* AG-77 is shown below as SEQ ID NO:37 (Uniprot A0A197KI55).

```
           10         20         30         40
MGLSKTVGQA SDKNICMIFC KGQPIGQVQP EGILYPEYFD 50         60         70         80
VLVNWRTPVS VAALYVLMVV LLNPKQGKVS RVVAADSAAK 90        100        110        120
GDNKKQQELS SSSPAMTALV FVHNAILCVY SAWTFYGMFF 130        140        150        160
AWKKAFATHT FMEAVCDSDN TFWDSLGYYS YYFYLSKYYE 170        180        190        200
IVDTIIILLK GRRSSLLQTY HHAGAIFTMY MGFNYRAHPI 210        220        230        240
WIFTTFNSFI HTIMYAYYAA TSVGLKPPGK KYLTSMQITQ 250        260        270        280
FWTGTALAFW YEIGSPKGCF TNPGSRFAIW TVLAYVFPLI 290        300        310
YLFTSFASKM YGNRVKAAAA AKATSQQKKV L
```

A sequence for an elongation of fatty acids (ELO) protein from *Nannochloropsis oculata* is shown below as SEQ ID NO:38 (Uniprot D2DPY9).

```
        10         20         30         40
MPKLPKISNI FKFLKADPSK IVPYKSIPDK VPFTQLFQHY 50         60         70         80
PVLDPLYTQY EKNFYASTYV KFAQDTWPVL PLALCGMYAL 90        100        110        120
MIIVGTKVMV SRPKHEWKTA LACWNLMLSI FSFCGMIRTV 130        140        150        160
PHLLHNVATL PFKDTICRHP AETYGEGACG MWVMLFIFSK 170        180        190        200
VPELVDTVFI VFRKSKLQFL HWYHHITVLL FCWHSYAVTS 210        220        230        240
STGLYFVAMN YSVHAIMYAY YYLTAINAWP KWIPPSIITV 250        260        270        280
AQISQMIVGV GICASSFYFL YTDPEHCQVK RQNVYAGALM 290        300        310        320
YGSYLYLFCD FFVRPFLRGG KPRLGEEKSA VLTMAKKIKA

M
```

Another sequence for an elongation of fatty acids (ELO) protein from *Nannochloropsis oculata* is shown below as SEQ ID NO:39 (Uniprot F7DDK1).

```
        10         20         30         40
MSFLIRTPAD QIKPYFSEAA QTHYTQLFQH FPILERAYFP 50         60         70         80
FEKNFRAEPF VDFAKATWPL LPLALCTAYA LMIVIGTRVM 90        100        110        120
KNREKFDWRG PLAYWNLTLS LFSFCGMLRT VPHLLNNITT 130        140        150        160
LSFRDTVCTS AAKSYGEGVS GLWVMLFIFS KIPELVDTVF

170
IVFRKSKLQF LHW
```

A sequence for a delta-9 fatty acid desaturase protein from *Nannochloropsis oceanica* is shown below as SEQ ID NO:40 (Uniprot A0A1S7C7S1).

```
        10         20         30         40
MVFQLARDSV SALVYHFKEG NLNWPMIIYL VLVHLAGYIG 50         60         70         80
LTTILACKWQ TLLEAFILWP ITGLGITAGV HRLWAHRSYN 90        100        110        120
ATLPYRILLM LFNSIANQGS IYHWSRDHRV HHKYSETDAD 130        140        150        160
PHNATRGFFF AHMGWLIVKK HPKVVEGGKQ LDFSDLAADP 170        180        190        200
VVRFQRDWDP WFAQFMCFVM PALVASRFWG EAFWNAFWVA 210        220        230        240
GALRYMLVLH FTWMVNSAAH LYGDHPYDPT MWPAENPLVS 250        260        270        280
VVAIGEGWHN WHHRYPYDYA ASEFGISQQF NPTKAFIDFF 290        300        310        320
AAIGMVTNRK RATGAWAKLK ESRARDAANG KSMKDFKGRG 330        340        350
SGSDYGTTNT NYAVSNKTVV TDKGAQQPGW EESNHPKYN
```

A sequence for a fatty acid hydroxylase protein from *Nannochloropsis gaditana* is shown below as SEQ ID NO:41 (Uniprot W7UAP1).

```
        10         20         30         40
MAAYFQVFRN SKIGIVLTLS LIFTTAMASP SAYFPEKLSL 50         60         70         80
LLKTLSGSDR LVNPHCIDNP FCAFNDWVNA FLFRDAVKAD 90        100        110        120
VMARLGPAGA HYFLTYVRDL VAGSVLYYLT AGLWHTYIYQ 130        140        150        160
WHGDYFFTQQ GFEKPSAATI KDQIQLAQAS MFLYAALPYL 170        180        190        200
AEWLVESGWT QCYYYVEEIG GWPYYLAFTL LYLAMVEVGV 210        220        230        240
YWMHRTLHEN KVLYKYIHGL HHKYNKPSTL SPWASVAFNP 250        260        270        280
IDGILQASPY VICLFLVPCH YLTHVAMVFF TAVWATNIHD 290        300        310        320
AMDGNTEPVM GSKYHTVHHT HYHYNFGQFF IFADWMFGTL 330        340        350
RIPEPRAAKA VLSPGVVPSS GVRTTGKSGR GKMD
```

A sequence for an omega-6 fatty acid desaturase delta-12 protein from *Nannochloropsis gaditana* (strain CCMP526) is shown below as SEQ ID NO:42 (Uniprot K8YR13).

```
        10         20         30         40
MGRGGEKTVT PPSKTFHAHG HSLTASDLSR ADAASTISSS 50         60         70         80
VRPSKSLEAM PTEELRKKAL QYGHDASADR ASLLQILAPY 90        100        110        120
GDILLRTDAP PSLPLTPPPF TLADIKAAVP RHCFERSLTT 130        140        150        160
SFFHLACDLV LVALLGYLAT LIGHPDVPTM SRYLLWPLYW 170        180        190        200
YAQGSVLTGV WVIAHECGHQ SFSPYERVNN LVGWVLHSAL 210        220        230        240
LVPYHSWRIS HGKHHNNTGS CENDEVFAPP IKEDLMDEIL 250        260        270        280
LHSPLANLAQ IIIMLTVGWM PGYLLMNATG PRKYKGKNNS 290        300        310        320
HFDPNSALFS PKDRLDIIWS DIGFFLALAG VVWACTQYGF 330        340        350        360
STVGKYYLLP YMVVNYHLVL ITYLQHTDVF IPHFRGAEWS 370        380        390        400
WFRGALCTVD RSFGWLLDHT FHHISDTHVC HHIFSKMPFY 410        420        430        440
HAQEASEHIK KALGPYYLKD DTPIWKALWR SYTLCKYVDT

450
DKNAVFYKHR AS
```

A sequence for an omega-6 fatty acid desaturase delta-12 protein from *Nannochloropsis gaditana* (strain CCMP526) is shown below as SEQ ID NO:43 (Uniprot K8Z8R1).

```
          10         20         30         40
MSRYLLWPLY WYAQGSVLTG VWVIAHECGH QSFSPYERVN 50         60         70         80
NLVGWVLHSA LLVPYHSWRI SHGKHHNNTG SCENDEVFAP 90        100        110        120
PIKEDLMDEI LLHSPLANLA QIIIMLTVGW MPGYLLMNAT 130        140        150        160
GPRKYKGKNN SHFDPNSALF SPKDRLDIIW SDIGFFLALA 170        180        190        200
GVVWACTQYG FSTVGKYYLL PYMVVNYHLV LITYLQHTDV 210        220        230        240
FIPHFRGAEW SWFRGALCTV DRSFGWLLDH TFHHISDTHV 250        260        270        280
CHHIFSKMPF YHAQEASEHI KKALGPYYLK DDTPIWKALW 290        300        310        320
RSYTLCKTAE EEEDDEWGVV PKPTEQLYLG NRKARELIGG

330
AYADVNLAVK VAHDDTK
```

A sequence for a delta 5 fatty acid desaturase protein from *Nannochloropsis gaditana* (strain CCMP526) is shown below as SEQ ID NO:44 (Uniprot K8YSX2).

```
          10         20         30         40
MGSTEPVLST AAVPATEPAG KSYTWQEVAE HNTEKSLWVT 50         60         70         80
VRGKVYDISS WVDNHPGGKE ILLLAAGRDI TYAFDSYHPF 90        100        110        120
TEKPTQVLNK FEIGRVTSYE FPQYKADTRG FYKALCTRVN 130        140        150        160
DYFVAHKLNP KDPIPGIWRM CLVALVALAS FVVCNGYVGV 170        180        190        200
EGTWAGTTWA RLVAAVVFGI CQALPLLHVM HDSSHLAFGN 210        220        230        240
TERWWQVGGR LAMDFFAGAN MTSWHNQHVI GHHIYTNVFL 250        260        270        280
ADPDLPDKAA GDPRRLVQKQ AWQAMYKWQH LYLPPLYGIL 290        300        310        320
GIKFRVQDIM ETFGSGTNGP VRVNPLSFFQ WAEMIFTKMF 330        340        350        360
WAGWRIAFPL LSPSFHTGWA AFSALFLVSE FMTGYFLAFN 370        380        390        400
FQVSHVSSEC DYPLGEAPRE GEDGNIVDEW AVSQIKSSVD 410        420        430        440
YAHNNPVTTF LCGALNYQVT HHLFPTVSQY HYPAIAPIIQ 450        460        470        480
DVCREFNVDY KVLPDFYTAF HAHIAHLKTL GERGEAAEVH

MG
```

A sequence for a fatty acid desaturase protein from *Nannochloropsis gaditana* (strain CCMP526) is shown below as SEQ ID NO:45 (Uniprot K8Z7K3).

```
          10         20         30         40
MSGSQGRPER VGEGHPRDAR REEKCGSADN GLRDGRAERA 50         60         70         80
KEEGRGAYPD AMNEVACVFL YPTLPRITSS SPVTVPPGLQ 90        100        110        120
VMAAVVLRHA PFPLLLFLTY TLSGSCNHFL TLIMHEVAHN 130        140        150        160
LAFKRLFANR VFSIIVNLPL GIPAAMWVWE GGPEGGYQAP

TSG
```

A sequence for a delta-9 acyl-CoA desaturase (FADS9) protein from *Mortierella elongata* AG-77 is shown below as SEQ ID NO:46 (Uniprot A0A197K9U9).

```
          10         20         30         40
MATPLPPTFV VPATLTETRR DPLKHQELPP LFPEKVNILN 50         60         70         80
IWKYLDYKHV VGLGVTPLIA LYGLLTTEIQ RKTLIWSIIY 90        100        110        120
YYATGLGITA GYHRLWAHRS YNAGPAMSFV LALLGAGAVE 130        140        150        160
GSIKWWSRGH RAHHRWTDTE KDPYSAHRGL FFSHLGWMLI 170        180        190        200
KRPGWKIGHA DVDDLNKNKL VQWQHKNYLA LIFLMGVVFP 210        220        230        240
TVVAGLGWGD WRGGYFYAAI LRLVFVHHAT FCVNSLAHWL 250        260        270        280
GEGPFDDRHS PRDHFITAFM TLGEGYHNFH HQFPQDYRNA 290        300        310        320
IRFYQYDPTK WVIATCAFLG LASHLKTFPE NEVRKGQLQM 330        340        350        360
IEKRVLEKKT KLQWGTPIAD LPVMSFEDYR HACKNDNKKW 370        380        390        400
ILLEGVVYDV ADFMSEHPGG EKYIKMGIGK DMTAAFNGGL 410        420        430        440
YDHSNAARNL LSLMRVAVVE FGGEVEAQKK NPSAPIYGDD

HAKAA
```

A sequence for an acyl-CoA desaturase (FAD) protein from *Mortierella alpina* is shown below as SEQ ID NO:47 (Uniprot O94747).

```
          10         20         30         40
MATPLPPSFV VPATQTETRR DPLQHEELPP LFPEKITIYN 50         60         70         80
IWRYLDYKHV VGLGLTPLIA LYGLLTTEIQ TKTLIWSIIY 90        100        110        120
YYATGLGITA GYHRLWAHRA YNAGPAMSFV LALLGAGAVE 130        140        150        160
GSIKWWSRGH RAHHRWTDTE KDPYSAHRGL FFSHIGWMLI 170        180        190        200
KRPGWKIGHA DVDDLNKSKL VQWQHKNYLP LVLIMGVVFP 210        220        230        240
TLVAGLCWGD WRGGYFYAAI LRLVFVHHAT FCVNSLAHWL 250        260        270        280
GDGPFDDRHS PRDHFITAFV TLGEGYHNFH HQFPQDYRNA 290        300        310        320
IRFYQYDPTK WVIALCAFFG LASHLKTFPE NEVRKGQLQM
```

```
                330        340        350        360
          IEKRVLEKKT KLQWGTPIAD LPILSFEDYQ HACKNDNKKW 370        380        390        400
          ILLEGVVYDV ADFMSEHPGG EKYIKMGVGK DMTAAFNGGM 410        420        430        440
          YDHSNAARNL LSLMRVAVVE YGGEVEAQKK NPSMPIYGTD

HAKAE
```

A sequence for an acyl-CoA desaturase (FAD) protein from *Mortierella elongata* AG-77 is shown below as SEQ ID NO:48 (Uniprot A0A197JWT1).

```
                10         20         30         40
          MATPLPPTFV VPATQTETRR LPLEHDELPP LFPEKLTITN 50         60         70         80
          IWKYLDYKHV LGLGLTPLIA LYGLLTTEIQ TKTLIWSIVY 90        100        110        120
          YYATGLGITA GYHRLWAHRA YSAGPAMSFA LALLGAGAVE 130        140        150        160
          GSIKWWSRGH RAHHRWTDTE KDPYSAHRGL FFSHIGWMLI 170        180        190        200
          KRPGWKIGHA DVDDLNKNKL VQWQHKHYLP LVLFMGVIFP 210        220        230        240
          TIVAGLGWGD WRGGYFYAAI LRLVFVHHAT FCVNSLAHWL 250        260        270        280
          GEGPFDDRHS PRDHFITAFM TLGEGYHNFH HQFPQDYRNA 290        300        310        320
          IRFYQYDPTK WVIAICAFFG LASHLKTFPE NEVRKGQLQM 330        340        350        360
          IEKKVLEKKT KLQWGTPIAD LPVLSFEDYQ HACKNDGKKW 370        380        390        400
          ILLEGVVYDV AEFMNEHPGG EKYIKMGVGK DMTAAFNGGM 410        420        430        440
          YDHSNAARNL LSLMRVAIVE FGGEVEAQKK NPSVPIYGDD

HHSKSE
```

A sequence for a delta-6 acyl-CoA desaturase (FAD) protein from *Mortierella elongata* AG-77 is shown below as SEQ ID NO:49 (Uniprot A0A197JJR0).

```
                10         20         30         40
          MAATPSVRTF TRSEILNAEA LNEGKKDAEA PFLMIIDNKV 50         60         70         80
          YDVREFVPEH PGGSVILTHV GKDGTDVFDT FHPEAAWETL 90        100        110        120
          ANFYVGDIAE HDRATKGDDF AAEVRKLRSL FQSLGYYDSS 130        140        150        160
          KAYYAFKVSF NLCLWALSTF IVAKWGQTST LATIASASIL 170        180        190        200
          GLFWQQCGWL AHDFLHHQVF QDRFWGDLFG AFLGGVCQGF 210        220        230        240
          SSSWWKDKHN THHAAPNVHG EDPDIDTHPL LTWSEHALEM 250        260        270        280
          FSDVPDEELT RMWSRFMVLN QTWFYFPILS FARLSWCLQS 290        300        310        320
          ILFVLPNGQA HKPSGARVPI SLYEQLSLAM HWTWYFATMF
```

```
                330        340        350        360
          LFIKDPVNMI VYFLVSQAVC GNLLALVFSL NHNGMPVISK 370        380        390        400
          EEAVDMDFFT KQIITGRDVH PGLFANWFTG GLNYQIEHHL 410        420        430        440
          FPSMPRHNFS KIQPAVESLC KKYGVRYHTT GMVDGTAEVF

450
          ARLNEVSRAA SKMGKST
```

A sequence for a delta-5 acyl-CoA desaturase (FAD) protein from *Mortierella elongata* AG-77 is shown below as SEQ ID NO:50 (Uniprot A0A197KDG7).

```
                10         20         30         40
          MGAEKEFTWE ELAKHNIAGD LYVAVRGNVY DVTKFLSRHP 50         60         70         80
          GGVDTLLLGA GRDVTPVFDM YHAFGTGDAI MKKYYVGKLV 90        100        110        120
          SNELPIFPEP SGFHKVVKSR VEGYFKDSGK DPKNRPEIWG 130        140        150        160
          RYFLIFAALF LSYYAQFFVP FVVERTWLQV IFAVIMGFAC 170        180        190        200
          AQIGLNPLHD ASHFSTTHNP TVWKILGATH DFFNGASYLY 210        220        230        240
          WMYQHMLGHH PYTNIAGADP DVSTAERDYR RIKPSQKWFW 250        260        270        280
          NHINQHMFVP FLYGLLAFKV RIQDVNILYF VGTNDAIRVN 290        300        310        320
          PISLWHTVMF WGGKIFFFWY RIYVPLQVLP LKKVLILFTI 330        340        350        360
          ADMISSYWLA LTFQANHVVE EVEWPLPDEN GIIQKDWAAM 370        380        390        400
          QVETTQDYAH ESYIWTSITG SLNYQAVHHL FPNVSQHYYP 410        420        430        440
          EILSIIRDAC TEYKVPYLVK DTFWQAFSSH LEHMRVLGLR

PKEE
```

A sequence for a delta-12 acyl-CoA desaturase (FAD) protein from *Mortierella elongata* AG-77 is shown below as SEQ ID NO:51 (Uniprot A0A197K3I9).

```
                10         20         30         40
          MAPPNTIDAG LTHRHVVNPT AAPVKAAYER NYELPEFTIK 50         60         70         80
          EIRECIPAHC FERSGFRGLC HVAIDLTWAS LLFLAATQID 90        100        110        120
          KFENPLIRYL AWPVYWVMQG IVCIGIWVLA HECGHQSFST 130        140        150        160
          SKTLNNTVGW ILHSFLLVPY HSWRISHSKH HKATGHMTKD 170        180        190        200
          QVFVPKTRIQ VGLPAKKENV VEEDEAVHLD EEAPIVTLFW 210        220        230        240
          MLVQFTFGWP AYLAVNASGQ DYGQWTSHFH TWSPIFEARN 250        260        270        280
          FTDVILSDLG VLVTLGALIY ASLQTSLLAV TKYYIVPYLF
```

```
                290         300         310         320
       VNFWLVLITF  LQHTDPKLPH  YRENVWNFQR  GALCTVDRSF 330         340         350         360
       GKFLDHMFHG  IVHTHVAHHL  FSQMPFYHAE  EATACLKKLL 370         380         390
       GKHYTYDDTP  IVLATWRSFR  ECRFVEDEGD  VVFFKK
```

A sequence for a delta-6 acyl-CoA desaturase (FADS6) protein from *Mortierella alpina* is shown below as SEQ ID NO:52 (Uniprot Q9UVY3).

```
                10          20          30          40
       MAAAPSVRTF  TRAEILNAEA  LNEGKKDAEA  PFLMIIDNKV 50          60          70          80
       YDVREFVPDH  PGGSVILTHV  GKDGTDVFDT  FHPEAAWETL 90         100         110         120
       ANFYVGDIDE  SDRAIKNDDF  AAEVRKLRTL  FQSLGYYDSS 130         140         150         160
       KAYYAFKVSF  NLCIWGLSTF  IVAKWGQIST  LANVLSAALL 170         180         190         200
       GLFWQQCGWL  AEDFLHHQVF  QDRFWGDLFG  AFLGGVCQGF 210         220         230         240
       SSSWWKDKHN  THHAAPNVHG  EDPDIDTHPL  LTWSEHALEM 250         260         270         280
       FSDVPDEELT  RMWSRFMVLN  QTWFYFPILS  FARLSWCLQS 290         300         310         320
       IMFVLPNGQA  HKPSGARVPI  SLVEQLSLAM  HWTWYLATMF 330         340         350         360
       LFIKDPVNMI  VYFLVSQAVC  GNLLAIVFSL  NHNGMPVISK 370         380         390         400
       EEAVDMDFFT  KQIITGRDVH  PGLFANWFTG  GLNYQIEHHL 410         420         430         440
       FPSMPRHNFS  KIQPAVETLC  KKYGVRYHTT  GMIEGTAEVF

450
       SRLNEVSKAA  SKMGKAQ
```

A sequence for a delta-6 acyl-CoA desaturase (FADS6) protein from *Mortierella alpina* is shown below as SEQ ID NO:53 (Uniprot A3RI59).

```
                10          20          30          40
       MAAAPSVRTF  TRAEILNAEA  LNEGKKDAEA  PFLMIIDNKV 50          60          70          80
       YDVREFVPDH  PGGSVILTHV  GKDGTDVFDT  FHPEAAWETL 90         100         110         120
       ANFYVGDIDE  SDRAIKNDDF  AAEVRKLRTL  FQSLGYYDSS 130         140         150         160
       KAYYAFKVSF  NLCIWGLSTF  IVAKWGQTST  LANVLSAALL 170         180         190         200
       GLFWQQCGWL  AHDFLHHQVF  QDRFWGDLFG  AFLGGVCQGF 210         220         230         240
       SSSWWKDKHN  THHAAPNVHG  EDPDIDTHPL  LTWSEHALEM 250         260         270         280
       FSDVPDEELT  RMWSRFMVLN  QTWFYFPILS  FARLSWCLQS 290         300         310         320
       IMFVLPNGQA  HKPSGARVPI  SLVEQLSLAM  HWTWYLATMF 330         340         350         360
       LFIKDPVNMI  VYFLVSQAVC  GNLLAIVFSL  NHNGMPVISK 370         380         390         400
       EEAVDMDFFT  KQIITGRDVH  PGLFADWFTG  GLNYQIEHHL 410         420         430         440
       FPSMPRHNFS  KIQPAVETLC  KKYGVRYHTT  GMIEGTAEVF

450
       SRLNEVSKAA  SKMGKAQ
```

A sequence for acyl-CoA desaturase (FAD) protein from *Mortierella verticillata* is shown below as SEQ ID NO:54 (NCBI KFH69129.1).

```
         1  MVATRTFTRS  EILNAEALNE  GKKNADAPFL  MIIDNKVYDV

41  REFVPDHPGG  SVILTHVGKD  GTDVFDTFHP  EAAWETLANF

81  YVGDIAENDR  AIKNDDFAAE  VRKLRTLFQS  LGYYDSSKAY

121  YAFKVSFNLC  LWALSTFIVA  KWGQTSTLAN  VLSASILGLF

161  WQQCGWLAHD  FLHHQVFQDR  FWGDLFGAFL  GGVCQGFSSS

201  WWKDKHNTHH  AAPNVHGEDP  DIDTHPLLTW  SEHALEMFSD

241  VPDEELTKMW  SRFMVLNQTW  FYFPILSFAR  LSWCLQSIMF

281  VMPNGQAHKP  SGARVPISLV  EQLSLAMHWT  WYFATMFLFI

321  KDPVNIMVYF  LVSQAVCGNL  LALVFSLNHN  GMPVISKEEA

361  VDMDFFTKQI  ITGRDVHPGL  FANWFTGGLN  YQIEHHLFPS

401  MPRHNFSKIQ  PAVASLCKKY  NVRYHTTGMV  DGTAEVFARL

441  NEVSRAASKM  GKSA
```

A sequence for a delta-6 acyl-CoA desaturase (FAD) protein from *Mortierella alpina* is shown below as SEQ ID NO:55 (NCBI ADE06661.1).

```
         1  MAAAPSVRTF  TRAEILNAEA  LNEGKKDAEA  PFLMIIDNKV

41  YDVREFVPDH  PGGSVILTHV  GKDGTDVFDT  FHPEAAWETL

81  ANFYVGDIHE  SDRDIKNDDF  AAEVRKLRTL  FQSLGYYDSS

121  KAYYAFKVSF  NLCIWGLSTF  VVAKWGQTST  LANVVSAALL

161  GLFWQQCGWL  AHDFLHHQVF  QDRFWGDLFG  AFLGGVCQGF

201  SSSWWKDKHN  THHAAPNVHG  EDPDIDTHPL  LTWSEHALEM

241  FSDVPDEELT  RMWSRFMVLN  QTWFYFPILS  FARLSWCLQS

281  ILFVMPNGQA  HKPSGARVPI  SLVEQLSLAM  HWTWYLATMF

321  LFVKDPINMF  VYFLVSQAVC  GNLLALVFSL  NHNGMPVISK

361  EEAVDMDFFT  KQIITGRDVH  PGLFANWFTG  GLNYQIEHHL

401  FPSMPRHNFS  KIQPAVETLC  KKYNVRYHTT  GMIEGTAEVF

441  SRLNEVSRAA  SKMGKAQ
```

A sequence for an acyl-coenzyme A thioesterase protein from *Mortierella elongata* AG-77 is shown below as SEQ ID NO:56 (Uniprot A0A197JUG8).

```
                10          20          30          40
       MSDSHLTVDP  TSTTPHPDAD  GTTNNTIIET  MLDLEEIDKD
```

-continued

```
            50         60         70         80
LYRSKKLWVP MGARGVFGGN VVGQALVAAT NTVSTDYSVH 90        100        110        120
SLHSYFLLPG DHTTPILYHV ERVRDGKSYC TRTVTAKQRG 130        140        150        160
KNIFVCTASY QVPRPGAPSH QYPMPNVPHH STLPSQEELI 170        180        190        200
HAMIDNPKLP ENLKDFLRLR LDEPVALEFK DTKRHTFKEL 210        220        230        240
MNPEVRTDQS FWIRCKGQLG DALALHQCVV AYGSDHNLLN 250        260        270        280
TVPLAHGSSW FSRRSGLSPK ITMMASLDHS MWFHCPFRAD 290        300        310        320
EWLLYVCETP RSGCDRGLTF GRIYKEDGTL AISVAQEGVV

330
RLQPKTPTPA ATVETPKL
```

A sequence for an acyl-coenzyme A thioesterase protein from *Lobosporangium transversale* is shown below as SEQ ID NO:57 (Uniprot A0A1Y2G902).

```
            10         20         30         40
MSSVSEPGST LNLAPTPDGS SNNTIIETML DLEEIDKDLY 50         60         70         80
RSKKLWLPLG ARGVFGGNVV GQALVAATNT VSDLYSVHSL 90        100        110        120
HSTFLLPGDP TIPILYHVDR LRDGHSYCTR TVTATQRGKN 130        140        150        160
IFVCTASFQV PRPNAPSHQY PMPNVPHHST LPSQEDLIRA 170        180        190        200
MIDSPKIPEN LVEFLKQRLD EPVALDFKDT RRHTLKDLMN 210        220        230        240
PPVRTEQTFW IKCKGGLGDA LALHQCVVAY GSDHNLLNTV 250        260        270        280
PLAHGSTWLS RRSSSPSIVM MASLDHSMWF HCPFRADEWM 290        300        310        320
LYVCETPRSG CDRGLTFGRI YKEDGTLAVS VAQEGVVRLR

330
SKAPSSATVD QPKL
```

A sequence for an acyl-coenzyme A thioesterase protein from bacterium endosymbiont of *Mortierella elongata* FMR23-6 is shown below as SEQ ID NO:58 (NCBI WP_045362096.1).

```
  1 MMAKQITQTV LTATVGIEVP FHDIDSMNIC WHGHYVKYFE

41 IARSALLRSF EYDAMRLSNY LWPVVECRLK YLRPARYGQL

81 LDVSAKLVEY ESRLKIGYLI TDRESGAQLT KGYTIQVAVD

121 AQTQALQFVL PRELLDKLEP MLSAVC
```

Another sequence for an acyl-coenzyme A thioesterase protein from bacterium endosymbiont of *Mortierella elongata* FMR23-6 is shown below as SEQ ID NO:59 (NCBI WP_045363294.1).

```
  1 MHSLSHLPHD KTLALRAVPQ PSNANMHGDV FGGWIMAQVD

41 IAGSIPATRP AHGRVVTVAV NSLVFKQPVF VGDLLSFYAD

81 IAKVGNTSVA VSVEVYAQRL NFAEQIFKVA EATLTYVATD

121 NDRRPRALPA EG
```

A sequence for an acyl-coenzyme A thioesterase 13 protein from *Nannochloropsis gaditana* is shown below as SEQ ID NO:60 (Uniprot W7TZE5).

```
            10         20         30         40
MSLKTISPHD YRSKMTRQER TSRQVLELLH AVSKSAFSGV 50         60         70         80
LLRRDIEPNA TELQNVKALK IGPGPQVRLR LRVPSHLCDN 90        100        110        120
YNNNHRLLDA GAVTAWFDEV SSWAFVSADG RHRPGVSVSL 130        140        150        160
NTTVLSWVPV GTEVEIQSHC KKIGETLGFA DMMLLDVATG 170        180        190        200
KELAHGRHVK FLKMGTAWTV AMHAWAFPLT YLMASAVLLP 210        220        230        240
SVRQRTQKSS SFPPEMAPSP DLPRTEPGSA VNINRLLALD 250        260        270        280
NFHVYEPAGA ASPPLAFPAS VPLTMEASAS FRVIPQVCNS 290        300        310        320
FGSLHGGAAA ILAERAALAL YHQAARWAGE RSQHALPRVR 330        340        350        360
SLSIDYMSPC KKNTELLLLV RGMRVERGAG EGDKHSPSRS 370        380        390        400
LFPPLDVAPH PQGNLIPMSY QVLFTRKKDG RYLTQCHVLL 410        420
DSQGDAWHHQ RQSPGEGNRA RL
```

A sequence for a thioesterase superfamily member 2 protein from *Nannochloropsis gaditana* (strain CCMP526) is shown below as SEQ ID NO:61 (Uniprot K8Z9R6).

```
            10         20         30         40
MSLKTISPHG YRSKMTRQEQ TSRQVLELLH AVSKSAFSGV 50         60         70         80
LLRRDIEPNA TELQNVKALK IGPGPRVRLR LRVPSHLCDN 90        100        110        120
YDNNHCLLDA GAVTAWFDEV SSWAFVSADG RHRPGVSVSL 130        140        150        160
NTTVLSWVPV GTEVEIQSHC KKIGETLGFA DMMLLDVATG 170        180        190        200
KELAHGRHVK FLKMGTAWTV AMHAWAFPLT YLMASAVLLP 210        220        230        240
SVRQRTQKSS SFPPEMAPSP DLPRTEPGSA ASVLSMVGPP 250        260        270
QFWLSALLLP CITKPLGGPE RGASTLCRVF VL
```

A sequence for an acyl-CoA synthetase from *Mortierella elongata* FMR23-6 is shown below as SEQ ID NO:62 (NCBI GAM51895.1).

```
  1 MLDWRFFTER TCAAVRALGS ERHRHSTRWA LCLSDPFEFA
 41 CGLFALLAAG KQIVLPSNHK PAALLPLAGL YDSVLDDLDG
 81 LLANGAGGPC AKLRIDPRAP LSLVTSGSSG VPKVIQKTLA
121 QFEAEIHTLA TLWGTVMRGV TVVASVPHHH IYGLLFRLLW
161 PLAAGQPFDR MTCVEPADVR ARLAALQNTV LVSSPAQLTR
201 WPSLINLTQL TPPPGLIFSS GGPLPAETAA IYTQAFGAAP
241 IEVYGSTETG GIAWRCQPQA THQNEVSDAW TPMPAIDVRC
281 DTEGALQLRS PHLPDDQWWR MEDAVQIEAD GRFRLRGRLD
321 RIIKLEEKRV SLPELEHVLM RHPWVKQAAV APLNGARMTL
361 GALLTLTEEG IQAWRSAASR RFITQALRRY LAEYFDGVVL
401 PRHWRFCMQL PFDERGKLSV TQLATRFATH PLQPEVLAEW
441 CDDNTALLEL HVPATLIHFS GHFPGLPILP GVVQIDWVVR
481 YAAHYFARCN GFQTLEQIKF LSMVRRGTTL RLALAHDPER
521 ARITFRYYVG ERDYATGRIV YSKSAVV
```

A sequence for an acyl-CoA synthetase from *Mortierella elongata* AG-77 is shown below as SEQ ID NO:63 (Uniprot A0A197JCK7).

```
           10         20         30         40
    MPDLAWSLPV ARWSAWNAET SAALDMGLKV ANDCAPVGQP
           50         60         70         80
    VRVIFASRHG ESRRTTELLK AQAQDPMQPL SPNAFSLSVL
           90        100        110        120
    NAAAGVFSMM RGDHSNATAL AAGSETLGYA LLEAFAQYAS
          130        140        150        160
    DPQAPVLVIY ADEPPDPIYA SVDDTDAPSG ALALWIADDA
          170        180        190        200
    PGVLECRLLI DALNLEDLTL ADIGDDTPLF DTDGIGLDSI
          210        220        230        240
    DALEIGIALR KKYQLQIETT DSRMREHFRS LLLDALAGVS
          250        260        270        280
    QRPTLFRMTI PLHLLFSNDC VATRPVCIDG DHILDWRFFT
          290        300        310        320
    ERTCAAVRAL GSERHRRSAR WALCLSDPFE FACGLFALLA
          330        340        350        360
    AGKQIVLPSN HKPAALLPLA GLYDSVLDDL DSLFANGAGG
          370        380        390        400
    PCAKLRIDPR APLSLVTSGS SGVPKVIHKT LAQFEAEIHT
          410        420        430        440
    LATLWGTVMR DVTVVASVPH HHIYGLLFRL LWPLAAGQPF
          450        460        470        480
    DRMTCVEPAD VRARLAALQN TVLVSSPAQL TRWPSLINLA
          490        500        510        520
    QLTPPPGLIF SSGGPLPTET AAIYAQAFGA APIEVYGSTE
          530        540        550        560
    TGGIAWRCQP QAMHQNEVSD AWTPMPAIDV RCDTDGALQL
          570        580        590        600
    RSPHLPDDQW WRMEDAVQIK VDGRFRLRGR LDRIIKLEEK
          610        620        630        640
    RVSLPELEHV LMRHPWVKQA AVAPLNGARM TLGALLTLTE
          650        660        670        680
    EGIQAWRSAA SRRFITQALR RYLAEYFDGV VLPRHWRFCM
          690        700        710        720
    QLPFDERGKL SVTQLAARFA THPLQPEVLA EWCDGNTALL
          730        740        750        760
    ELHVPATLSH FSGHFPGLPI LPGVVQIDWV VRYAAHYFAR
          770        780        790        800
    CNGFQTLEQI KFLSMVRPGT TLRLALAHDP ERARITFRYY
          810
    VGERDYATGR IVYSKSAVV
```

A sequence for an acyl-CoA synthetase from a bacterium endosymbiont of *Mortierella elongata* FMR23-6 is shown below as SEQ ID NO:64 (NCBI WP_045365524.1).

```
  1 MTTPLHLLFS HDCVATRPVC IDGDHMLDWR FFTERTCAAV
 41 RALGSERHRH STRWALCLSD PFEFACGLFA LLAAGKQIVL
 81 PSNHKPAALL PLAGLYDSVL DDLDGLLANG AGGPCAKLRI
121 DPRAPLSLVT SGSSGVPKVI QKTLAQFEAE IHTLATLWGT
161 VMRGVTVVAS VPHHHIYGLL FRLLWPLAAG QPFDRMTCVE
201 PADVRARLAA LQNTVLVSSP AQLTRWPSLI NLTQLTPPPG
241 LIFSSGGPLP AETAAIYTQA FGAAPIEVYG STETGGIAWR
281 CQPQATHQNE VSDAWTPMPA IDVRCDTEGA LQLRSPHLPD
321 DQWWRMEDAV QIEADGRFRL RGRLDRIIKL EEKRVSLPEL
361 EHVLMRHPWV KQAAVAPLNG ARMTLGALLT LTEEGIQAWR
401 SAASRRFITQ ALRRYLAEYF DGVVLPRHWR FCMQLPFDER
441 GKLSVTQLAT RFATHPLQPE VLAEWCDDNT ALLELHVPAT
481 LIHFSGHFPG LPILPGVVQI DWVVRYAAHY FARCNGFQTL
521 EQIKFLSMVR PGTTLRLALA HDPERARITF RYYVGERDYA
561 TGRIVYSKSA VV
```

A sequence for an acyl-CoA synthetase from *Neurospora crassa* is shown below as SEQ ID NO:65 (NCBI EAA28332.1).

```
  1 MANTGPGNVP LHFIQKPPFT VEDPNAQPIP GETIPRRHPK
 41 AKNGLATRPA PGVNTTLDLL TRTVELYGDE RAIGSRKLIK
 81 LHKDIKKVPK VVDGETVMVD KEWQCFELTP YSYITYGEYF
121 TIVKQIGAGL RKLGLEPKDK LHIFATTSPQ WLGMSHAASS
161 QSLTIVTAYD TLGESGVQHS LVQSKASAMF TDPHLLKTAT
201 NPLKEATSVK VVIYNNHTTQ PVSQDKIDAF KAEHPDLTVL
241 SFEELRALGE ENPVPLTPPN PDDTYCIMYT SGSTGPPKGV
281 PVSHAGFVAA VAGLYAVMEE SVTHRDRVLA YLPLAHIFEL
321 VLENLGVFVG GTLGYSNART LSDTSMRNCP GDMRAFKPTI
361 MVGVPQVWET VKKGIEGKVN SAGALTKALF WGAYNIKSFL
401 VSNNLPGKTI FDDLVFGQVR TMTGGELRFI VNGASGIAAS
441 TQHFMSMVVA PMLNGYGLTE TCGNGALGSP MQWTSNAIGA
```

```
481 MPAAVEMKLV SLPELNYHTD TVPPQGEILF RGACVIKEYY

521 ENPEETAKAI TPDGWFKSGD IGEIDANGHL RVIDRVKNLV

561 KLQGGEYIAL EKLEAVYRGA VFVHNIMVHG DNSAPRPIAV

601 VVPNEKALAE KAEELGLGAE APGEMHRNRK LRDAVLKELQ

641 SVGRRAGLSG METVAGVVLV DDEWTPANGF VTATQKINRR

681 AVKERYSKEI SDCLDGK
```

A sequence for a long-chain acyl-CoA synthetase from *Nannochloropsis gaditana* (strain CCMP526) is shown below as SEQ ID NO:66 (Uniprot I2CP03).

```
            10         20         30         40
    MDRYKWRTLP DVFETVASLA PEAVAVEDMV HTPTAKMTYG 50         60         70         80
    ELNRQIGALA AFFQHEGLKP GQCVSVFAEN SHRWLIADQA 90        100        110        120
    ILKAGACNAV RGVKAPVDEL QYIYQNSESV ASVVESVEQI 130        140        150        160
    EALMRTNGGL TGRYGPPRFI LVLFPGERSG QEIRELANLP 170        180        190        200
    PPTQVLTFDE ALSASLARPL TFRPVPKDVR SVATLVYTSG 210        220        230        240
    TTNKPKGVVL RHSNLLHQVN YNSFTDSPSK EPAYNPVLGD 250        260        270        280
    VLVSVLPCWH IFERTAEYWM FSKGIHVVYS NVKNFKADLA 290        300        310        320
    KHQPQFIVAV PRLLETIYRG VLQKFATEKG AKKKIIEFFT 330        340        350        360
    RVGSAWVKAW RVARGLVLRS RAPNPIERLL ALVLALVLSP 370        380        390        400
    LAAVGDKLVW SKVRAGLGGR IKVLVAGGSS MPLVLEDFFE 410        420        430        440
    LLRTPVIVGY GMTETSPVIT NRVAEKNLAG SVGRTARDTE 450        460        470        480
    VKIVDPESGA RLPEGQPGLV LMRGPQMMAG YKSNAEASKA 490        500        510        520
    VLDQEGFLDT GDLGRIHPLT KHLIITGRAK DTIVLSNGEN 530        540        550        560
    VEPQPIEDVV CANSALVDQV MCVGQDEKVL GMLVVPNVRA 570        580        590        600
    LARAGLVDRG LAERVAELLG GQVLTNGIAG SRAELEEVEA 610        620        630        640
    SLREKKEVKK ALLADIARAM GKSFRETERV GAVEVVLEPF 650        660        670
    NMANGFLTQT LKVKRNVVSG HYAQEIEQMY R
```

A sequence for an acyl-CoA synthetase from *Nannochloropsis gaditana* (strain CCMP526) is shown below as SEQ ID NO:67 (Uniprot K8YP55).

```
            10         20         30         40
    MHGRSKKLGN ILEELGVKKG DRVATLAMNT YRHMELYFAV 50         60         70         80
    SGAGAVLHTL NPRLFAETLT WIVHHAQDSV LFFDPCFASL 90        100        110        120
    VERLLPHCPS VKHWICLVDE ERMPVLPSLS PSSPFLSLHN 130        140        150        160
    YEALLREGKE DYVWPILEET AASSLCYTSG TTGIPYTAAM 170        180        190        200
    VGCKLVLPGS ALDGASLYEL MKEEGVTLAA GVPTVWLPVL 210        220        230        240
    HHLDQDPGQG LPKLRRLVIG GAACPPSMLR AFKERHGIEG 250        260        270        280
    KHLALPTEDQ HNVLSTQGRT IYGVDLRIVA PSPPPYLPSS 290        300        310        320
    SSSYSPPYPP RWSEVPWDGV SPGELCARGH WVATDYFSPT 330        340        350        360
    QAPEEGERDG GVRAGHQESF YTDDDGERWF LTGDVATICP 370        380        390        400
    DGYIKITDRS KDVIKSGGEW ISSIELENIA TNHPEVALAA 410        420        430        440
    VIAMPHRKWD ERPLLIVVLK DSAALSLHYS TTSSSPSTSS 450        460        470        480
    DTDRAIRLTK EALLDHFKGK VAKWWVPDDV IFVDSLPQGP

490
    TGKILKTELR QRFSRRP
```

A sequence for a long chain acyl-CoA synthetase from *Nannochloropsis gaditana* is shown below as SEQ ID NO:68 (Uniprot W7TGG5).

```
            10         20         30         40
    MPKYTTTVAS GEVDLRIEKE GPGSWAPKTV FQVFEETVKK 50         60         70         80
    YGDSPALHYK KVPHGGSLAT TEWSSYTWRE YYDLTLEFCK 90        100        110        120
    SLLSLGFPAH GAINLIGFNS PEWLIANCGA IAAGGVGVGI 130        140        150        160
    YTSNGVDACK YITEHSEAEV VVVENAKQLE KYLKIAKELP 170        180        190        200
    RLKALVIYSG TAEGYKCDVP IYSWKDFMAL GSGVKDEAVR 210        220        230        240
    ARIEAQRPGH CCTLIYTSGT TGPPKAVMIS HDNLTWTVKN 250        260        270        280
    FVASLPFTLT CEDRSVSYLP LSHVAAQMLD IHCPIATGAK 290        300        310        320
    IYFAQPDALR GSLPVTLKDV CPTYFFGVPR VWEKIYEKMQ 330        340        350        360
    EVARSTTGVK RALAQWAKAK GLEKNRRQQY GCGGGAPVGF 370        380        390        400
    GCAHALVLSK VKAALGLHQT KMCITSAAPI AVEILEYFAS 410        420        430        440
    LDIPVLELFG QSECTGPHTS NFSYAWKIGS IGRDIPGVKT 450        460        470        480
    KQHANMSEFC MYGRHIMMGY MKMEDKTQEA VDNEGWLHSG 490        500        510        520
    DVAQVDADGF WSITGRIKEL IITAGGENIP PVLIENEIMS 530        540        550        560
    ALPAVANCMV VGDKKKFLTV LLTMKAKLDD QGNPTKELNK
```

A sequence for a long chain acyl-CoA synthetase from *Nannochloropsis gaditana* is shown below as SEQ ID NO:69 (Uniprot S5PTC7).

```
         10         20         30         40
 MPKYTTTVAS GEVDLRIEKE GPGSWAPKTV FQVFEETVKK 50         60         70         80
 YGDSPALHYK KVPHGGSLAT TEWSSYTWRE YYDLTLKFCK 90        100        110        120
 SLLSLGFPAH GAINLIGFNS PEWLIANCGA IAAGGVGVGI 130        140        150        160
 YTSNGVDACK YITEHSEAEV VVVENAKQLE KYLKTAKELP 170        180        190        200
 RLKALVIYSG TAEGYKCDVP IYSWKDFMAL GSGVKDEAVR 210        220        230        240
 ARIEAQRPGH CCTLIYTSGT TGPPKAVMIS HDNLTWTVKN 250        260        270        280
 FVASLPFTLT CEDRSVSYLP LSHVAAQMLD IHCPIATGAK 290        300        310        320
 IYFAQPDALR GSLPVTLKDV CPTYFFGVPR VWEKIYEKMQ 330        340        350        360
 EVARSTTGVK RALAQWAKAK GLEKNRRQQY GCGGGAPVGF 370        380        390        400
 GCAHALVLSK VKAALGLHQT KMCITSAAPI AVEILEYFAS 410        420        430        440
 LDIPVLELFG QSECTGPHTS NFSYAWKIGS IGRDIPGVKT 450        460        470        480
 KQHANMSEFC MYGRHIMMGY MKMEDKTQEA VDNEGWLHSG 490        500        510        520
 DVAQVDADGF WSITGRIKEL IITAGGENIP PVLIENEIMS 530        540        550        560
 ALPAVANCMV VGDKKKFLTV LLTMKAKLDD QGNPTKELNK 570        580        590        600
 EALDIGKEIG SNASTTEQVA SDPHWKKYFD EGLKKANSTA 610        620        630        640
 TSNAQFVQKW SVLPLDFSEK GGELTPTLKL KRSVVAEKYA

DVIADMYKA
```

A sequence for an alcohol dehydrogenase from *Mortierella elongata* AG-77 is shown below as SEQ ID NO:70 (Uniprot A0A197K9R3).

```
         10         20         30         40
 MSASNAKVED TTTTFTGWAS TGSLPLKKFS YHPRPLGPKD 50         60         70         80
 IEIEITHCGI CGSDVSTVTG GFGPLSTPCI AGHEIVGTVV 90        100        110        120
 KAGPTVFTRS ATLSVLVALL IPAVTGGFAD RLRVSSEYAY 130        140        150        160
 KIPSEIPPAE AAPPLGAGIT TYTPLKHFGA GPGKRVGVMG 170        180        190        200
 IGGLGHLAIQ WAAALKADEV VAISTSDNKR EEAKKLGATK 210        220        230        240
 FVNSRNEEER KAARHSMDIL LLTSNDKNTD WGELIDYVAS 250        260        270        280
 HGTLVLLALP EIPTIAVPPS SLLMRHVSIA GSLTGGREIT 290        300        310        320
 QEMLEFAAKH NVHPWITTMP MSDANTAVKL WLETIWCDVA 330        340
 ESVVAIVVAV AGEPVMPARK
```

Another sequence for an alcohol dehydrogenase from *Mortierella elongata* AG-77 is shown below as SEQ ID NO:71 (Uniprot A0A197JDD8).

```
         10         20         30         40
 MTGGRTIKAA LYEGVNPSAP LLKVIDLPAP VANNGDAVVK 50         60         70         80
 ILATRVVSYA KEVLDGTRPY PNLLPMVPGP GGVGIIQSVA 90        100        110        120
 PGAIHIKPGQ MVFIDPTVRS RDHPVSPEAM LQGLVAFGSG 130        140        150        160
 QELQKVWNNG SWAEEMLVPL ENLTVIPESI QAKFNPAELT 170        180        190        200
 SISNYAVPLG GLYPNLRPGQ TVVITGSTGM FGSSAVAVAL 210        220        230        240
 ALGARRVIAS GRNKKQLDEF VRLYGPRVVP VVVTGDVAQD 250        260        270        280
 TQAFLKAAGE GFDIDVTFDI LPPQATFGAV QSSILALRNG 290        300        310        320
 GTAVLMGGLN SSAEIPYPAI MNKGLTIKGH FMYDRSGPTT 330        340        350        360
 IIGLADAGLL DLHHRQEPKF FKLSEINDAV EWSAAHPGAF

DATLVLP
```

Another sequence for an alcohol dehydrogenase from *Mortierella elongata* AG-77 is shown below as SEQ ID NO:72 (Uniprot A0A197JLB4).

```
         10         20         30         40
 MKAALYEGVN HSAPLLKVTD LPVPIATNGD AVVKILASRV 50         60         70         80
 VSYAKDVLDG TRPFPNLLPM VPGTGGVGII QSVAPGAIHI 90        100        110        120
 KPGQMVFINS AVRSRDHPVT PEGMVQGLLA FGRSKELQRA 130        140        150        160
 EEMLVPLENL TVIPESVQAK FDPAELTSIS NYAVSFGGLY 170        180        190        200
 PNLRPGQTVV ITGSTGVFGS SAVAVALALG ARCVIASGRN 210        220        230        240
 KKQLDEFATL YGPRVVPVVT TGDVAKDTAA FVKAAGEGFD 250        260        270        280
 IDVSFDILPP QAGFGAVKSS ILALRAGGTA LLMGGVNSSV 290        300        310        320
 EIPYSVIMNK GLTIKGVFMS DRAGPTTIIG LAEAGLLDLH
```

```
                330        340        350
           HRQEPKIFKL DEINDAVEWS SNHSSAFDAT IVIP
```

A sequence for an alcohol dehydrogenase from *Nannochloropsis gaditana* (strain CCMP526) is shown below as SEQ ID NO:73 (Uniprot I2CR67).

```
            10         20         30         40
           MPVIGLGTWK APKGEVKKAV LAALKQGYRH LDCACDYGNE
            50         60         70         80
           EEVGAAIKEA MEAGVVTRKD LFVTSKLWNT FHAREHVEVA
            90        100        110        120
           IQKSLKDLGL DYLDLYLIHF PISMKYVPIE ELYPPEWLNP
           130        140        150        160
           TSKKIEFVDV PVSETWAGME GVCRKGLARN IGVSNFCAQT
           170        180        190        200
           LMDLLKYAEI KPAVNQIELH PYLTQDSLVA FCQEKGIVLT
           210        220        230        240
           AFSPLGASSY IELGMDRGEG VGVLNNPVVQ AIAREHSRTP
           250        260        270        280
           AQVCLRWAVQ RGYTAIPKST HESRLQENLH VFDFTLSAED
           290        300        310
           MVKISRLNRH LRYNDPGEFC KGMGLPNGYP IYA
```

Another sequence for an alcohol dehydrogenase from *Nannochloropsis gaditana* is shown below as SEQ ID NO:74 (Uniprot W7TDK1).

```
            10         20         30         40
           MTDPSASTTA AAQLPGRMLA GVADHHGDRF DMREIPVTPP
            50         60         70         80
           GVGQALVKVV TSGVCHTDVH AVDGDWPAPT KLPLVPGHEG
            90        100        110        120
           AGVVVAVGPG VSSTVVSLGD RVGIPWLHSS CGSCEFCLSG
           130        140        150        160
           RENLCPLQDN TGYSVDGCFA QYVLAPAAHL AKIPDEVSFE
           170        180        190        200
           QAAPILCAGV TTYSAIKATE ARPGQFLTVI GAAGGLGHLA
           210        220        230        240
           VQFGVALGLR VMALDRGADK LKFCTDTLGA EAAFEAMDPG
           250        260        270        280
           VVDQVIATTK GGSHGVLCLA PSIGAFKSAV SLCRRGGTIV
           290        300        310        320
           MVGLPKGDLP LNIFDIVIRG ITVRGSIVGT RKDLDEALDF
           330        340        350        360
           AARGKVKCHT EMHGFGELNQ VFDQLRSGKV MGRLYLSVDG
           M
```

Another sequence for an alcohol dehydrogenase from *Nannochloropsis gaditana* is shown below as SEQ ID NO:75 (Uniprot W7TYB6).

```
            10         20         30         40
           MGKRQVSYFA FSTSPVSGKP AAIPPSLIGI STLNALRDAE
            50         60         70         80
           KVADAVKHAV SSVVKYVDCS SDSQNEKQIG NALSAFDRSS
            90        100        110        120
           FYVGSKLSCC DAAPEDVTEA CKRSITELGV SYLDNYMMHW
           130        140        150        160
           PVQLKSDSKP VSLDDGDTYE LVQDGDMDCI MATYEAMERL
           170        180        190        200
           VDQGLVRSLG VSNMGIRTLS ELLSRCRIRP TVLEVEMHLY
           210        220        230        240
           LAQPKLLEFC REENIHVVAN SPPGKMRNRH PNDPSLLDDP
           250        260        270        280
           VLLRIAEEAV RAAQVLLRRG IQRGRSITRK TPSQSLMDEN
           290        300        310        320
           KDLLDWCLSR DHMSRLDALD KGSRFPSVLP SMCDLDRDSE
           330        340        350        360
           NYAGAGHPVS QPHRTPCTMD KNGGFRNRFE RPGKYLKTDI
           370        380        390        400
           LVQRGALSDL ARLGKSIIPE ESHGSANYLI TDSVVDALYG
           410        420        430        440
           DTVLNGLKSA GLDMTKIVVP AVSMDESGEP STEPNKNGAI
           450        460        470        480
           FNACVDRVLG NGISKHSCII SLGGGYINNL CGVIAATLYR
           490        500        510        520
           GIKLVHFTTT TMGMLDAAID FKQAFNHSCG KNLVGAYYPA
           530        540        550        560
           DLIVMDPECL KTLSNRHMLN GVAEALKHGL TQSWELTSAI
           570        580        590        600
           VEPLRGDSAR LGDSKYLETL CKETIEIKVP TLTHYKESDF
           610        620        630        640
           NEMVPQYGHA VAHAVEHLSW EEGQVPLLHG EAVAIGMCVT
           650        660        670        680
           AELGHLLGLC DKSVVDHHYD LVGTTGLPCN VPDTMKVNDI
           690        700        710        720
           LHVMTYDKHF MSKPCMGFCK EIGVMAKNKD GSYAFSVEME
           730
           PVREALQLNM SK
```

A sequence for a glycerol kinase from *Mortierella elongata* AG-77 is shown below as SEQ ID NO:76 (Uniprot A0A197JVE6).

```
            10         20         30         40
           MPSFIGAIDN GTTSSRFLIF DEKGNLVIGH QLEYRQIFPH
            50         60         70         80
           PGWVEHDPMD ILGSVTACIE GALRKFELQG NDVKNLRGIG
            90        100        110        120
           ITNQRETAVV WDRTTGKPLH NAIVWSDTRT QDVVTKLCES
           130        140        150        160
           SDKGTDALKD ICGLPLTTYF SAVKLKWLLE NSSEVKEAHE
           170        180        190        200
           NGNLMFGTVD SWLIYNLTGG KEGGVHVTDV TNASRTMLMD
           210        220        230        240
           IKTLQWSEEA LKFFGINADI LPEIKPSSTL FGKVQHPALE
           250        260        270        280
           QLQDVPIAGC LGDQHAALVG QHCFQVGEAK NTYGTGCFML
           290        300        310        320
           FNTGSKITPS NNGLLTTVGY QFEGEPAAYA LEGSIAVAGS
```

```
           330        340        350        360
AVKWLRDNMG IIRSAEEIND LAAQVDSNGG VVFVTAFSGL 370        380        390        400
FAPYWRPDVR GSIVGISQHT TKHHLARATL EATCFQTRAI 410        420        430        440
LDAMNADSGH PLATLRVDGG LSNSDLCMQL QSNILGLEVA 450        460        470        480
RPQMRESTAL GAATAAGVHL GIGIWKGGFK AFAERARESK 490        500        510        520
EVLQIFTPKI NDEEREKEYA LWQKAIDTTI GVKSKTTGKR

EP
```

A sequence for a glucose kinase from *Nannochloropsis gaditana* is shown below as SEQ ID NO:77 (Uniprot W7U0M7).

```
            10         20         30         40
MTSSYINSYV GAIDQGTSST KFIIYNHSGQ QVGLHQLEHA 50         60         70         80
QIYPQPGWVE HDPMEIWANT VTCIRRAMES ANVDAELLEA 90        100        110        120
VGITNQREST LIWNKKTGVP YYNVIVWNDA RTRGICEDLK 130        140        150        160
TAGRRGIDRF REKTGLPIAT YFSASKILWL LDNVPGLRDD 170        180        190        200
AEKGEAIFGT LDSWLIYKLT DGQVHSGPCV AYPGGLSPSS 210        220
LSSALRPPAS PPSQAPSLSP DP
```

A sequence for a diacylglycerol kinase from *Nannochloropsis gaditana* is shown below as SEQ ID NO:78 (Uniprot W7UAL1).

```
            10         20         30         40
MDEELNVLSP FLVKAEVLLV LVVVLVASVV WLFWEIVSFM 50         60         70         80
MDRGKEETNP DWWEYLRNCQ HRRLIIPPYC VQEVPELGTF 90        100        110        120
SRLTTATTNA MKNMSGVIQR TSHLISGGSG KSAAAIKKGA 130        140        150        160
RQDLPSTQQE GDENMKGYTV DGNARGVKLR RRGSKQSIVG 170        180        190        200
LSNHGTSAGG KPALQPTANP TPLTLSENGA NPDASAASDA 210        220        230        240
RPKPHRLDLN GEEGNMVPCN GSLSSRAGDG KRVVGMSGLA 250        260        270        280
STSAAAGSDA SSANVKSMEI SPADTPCRGR IRFLPHQRER 290        300        310        320
QQIENHEKSH EGKPTRSGLP LRALDSQPPL TPYALPDAEG 330        340        350        360
VLASSAQSSR HAPDAIAATP RLSSSHAANG EPITTPAQPV 370        380        390        400
RLPSMEHAHS GTGVALSGGS SGVAGRGFIF SPLPEDCTPL 410        420        430        440
LAFVNSRSGV SQGAYLIHQL RRLLNPIQVI DLANEDPARA 450        460        470        480
LRLYLELPRL RVLVCGGDGT AKWIMNVLED LNPECWPPIA 490        500        510        520
ILPLGTGNDM ARVLGWGGGY NNQSIVEFLA QVQRAHVVVV 530        540        550        560
DRWEMKLTPA GKGSSRAKTV TFNNYFGIGV DAQAALKFHH 570        580        590        600
LREQKPQLFF SRLVNKLWYG MLGAQDLFRR TCVSLPERLK 610        620        630        640
IVADGKELTL PAHVQGVIFL NIESYGGGVK LWNVEEDDES 650        660        670        680
AGNGLFDASS SSCSSEEGDR SEDESRRQRR RRRRRERQRR 690        700        710        720
QQSQAEEEAH RQREQQEKPS SMALTSSSMQ DGLMEVVAIN 730        740        750        760
GVVHLGQLQV GLSKAVKICQ CREAVITTTR DLPMQVDGEP 770        780        790        800
WPQAKSTIKI TRKKDPAYLL RRTMDSGGAV VGEVVELLES 810        820        830        840
AVKDGVISLP QKKSLLTELS RRVEMKRKVF EQELSQNDGV 850        860
PSFSKGFDVS RLRLAADSNS KDCVLM
```

A sequence for glycerol-3-phosphate dehydrogenase from *Mortierella elongata* AG-77 is shown below as SEQ ID NO:79 (Uniprot A0A197JEE6).

```
            10         20         30         40
MWRRIPATGA RHSTSFRTKA VYATAGATTL ALSGYYYNLK 50         60         70         80
QQQRALDDSF EYPPQSSMIY LEPQQAARDP TRPHAFWAPP 90        100        110        120
SREDMIRMLQ EGPGSIVKEK TAAAAAAAAA AAAGTTPGSK 130        140        150        160
PVVAVAATME DDKDSDVFDL LIIGGGATGA GCAVDAATRG 170        180        190        200
LKVAMVERDD FSSGTSSRST KLVHGGVRYL EKAVRELDIE 210        220        230        240
QYKLVKEALN ERANFLKVAP YLSYQLPIML PIYKWWQVPY 250        260        270        280
YWAGSKAYDL LAGHQGMESS YFLSRGKALE AFPMLKNDKL 290        300        310        320
VGAMVYYDGQ HNDSRMNVAL GLTAVQYGAV IANHVEVIEL 330        340        350        360
HKDENRRLCG ARVRDAMTGK EFNVKAKGVI NATGPFTDGI 370        380        390        400
RQLDDPSIQS IVSPSAGVHI ILPNYYSPGN MGLLDPATSD 410        420        430        440
GRVIFFLPWQ GNTIAGTTDS ATKVTPNPMA TEEEINWILG 450        460        470        480
EVKNYLNPDV KVRRGDVLAA WSGIRPLVRD PAAKSTEGLV 490        500        510        520
RNHMINVSPS GLLTIAGGKW TTYRAMAAET IDEAIKEFGL 530        540        550        560
TPARGCSTER VKLIGSHGYS NTMFIRLIQQ FGLETEIAQH 570        580        590        600
```

```
LANSYGDRAW AVASLAQSTG KRWPVFGRRV SNQYPYIEAE 610        620        630        640
VRYAVRREYA CTAVDVLARR LRLAFLNVHA ALDALPRVVE 650        660        670        680
IMAEELKWDA ARQAKETEDA KAFLTTMGLP VSPIAYPTNV 690        700        710        720
PEAVVGHPVV DGEKVQPTSF WGRMSGKSAS GAIVTDSFYS 730        740        750        760
RAQFNPEELA EFHKVFGALD HDGDGHIDGH DLEEVLIHLD 770        780        790        800
VQVEPQVLKS IIEEVDLDNS GTIEFNEFLE VMGGLKEHAS 810        820        830
RTAFSKIIVE VESKRNVDYG IKAKTTDRSG GGA
```

Another sequence for glycerol-3-phosphate dehydrogenase from *Mortierella elongata* AG-77 is shown below as SEQ ID NO:80 (Uniprot A0A197JIF5).

```
         10         20         30         40
MTERVALIGS GNWGSAVAKI IGRNVRKFDH FDNKVKMWVF 50         60         70         80
EEKVNGQNLT EIINTKHENV KYLPGIQLPS NIVACPDLLE 90        100        110        120
TCRDATMLVF VVPHQFVTSI CKQLKGRIPA NCKAISLIKG 130        140        150        160
IDVNADGFRL ITDMIQESLG VPTCVLSGAN IANEVAEEKF 170        180        190        200
CETTIGYRNR ADGELFRDIF HTPSFRVNIV PDVVGVELCG 210        220        230        240
ALKNIVAIGG GLVDGLKLGD NTKAAIIRIG LYEMRKFSKM 250        260        270        280
FYADVKDETF FESCGVADLI TTCAGGRNRK VAEAHVTTGK 290        300        310        320
SFDQLEQEML NGQKLQGTST AQDMYNILSK KNLCHEFPLM 330        340
TTIYKICYEG LPPIRIVEDI
```

Another sequence for glycerol-3-phosphate dehydrogenase from *Mortierella elongata* AG-77 is shown below as SEQ ID NO:81 (Uniprot A0A197KEB5).

```
         10         20         30         40
MLITECISLF HRGSAVAKIV GGNVQKYDHI QNEVKMNVFE 50         60         70         80
EQVDGQNLTE IINAKHENVK YLPGIKLPEN IVACPDLIKT 90        100        110        120
CEDATMLVFV VPHQFVASVC RQLKGKISPK CKAISLIKGV 130        140        150        160
DVEENDNGFR LITDMIQDSL GIRACMLSGA NIATEVAEER 170        180        190        200
FCETTIGYRN KADGELFKEI FNTPTFRVNI VEDVVGVELC 210        220        230        240
GALKNIIAIG GGLVDGLKLG DNTKAAIIRI GLYEMRKFAK 250        260        270        280
MFYADVKDET FFESCGVADL VTTCAGGRNR KVAEAHVTTG 290        300        310        320
KSFDQLEKEM LGGQKLQGTS TAKDMYGILS KKGLCKEFPL 330        340
MTTIYRICYE DLPPIRIVED I
```

A sequence for glycerol-3-phosphate dehydrogenase from *Nannochloropsis gaditana* is shown below as SEQ ID NO:82 (Uniprot W7U0Y7).

```
         10         20         30         40
MATLHISNLT LTIYNHGIFV LMSAALSFLL IVWRFSLAEA 50         60         70         80
GRSHHFEGPS SNPVKPHSIT IVGSGNFGSA IARLLGRNVL 90        100        110        120
RSPKHFRSEV RMWVFEEELD DGRKLSDVIN ADHENVKYLP 130        140        150        160
GIQLPTNVRA VPDLSDAVRN ASIVVFVLPH QFLPGLLPRI 170        180        190        200
SSCLHRGAMA VSLVKGLDFD DEGPVLITDM IREGLGEDVS 210        220        230        240
EVCVLMGANV ADEMARDEFC EATLGCPDPE GAGAVLQQLF 250        260        270        280
DCPTFRVEVT PDPIGVELCG ALKNVVALAA GFCDGLDWGG 290        300        310        320
NTKAAIIRRG LEEMRLFCKL LHPSVRDMTF FESCGVADLI 330        340        350        360
TTCYGGRNRK CAETFARAGG TMAWDEIEKE ELGGQHLQGP 370        380        390        400
QTTSKLHKVL EQKKWLSRFP LFRSVYQIAY QGRPPATLVQ

DL
```

Another sequence for glycerol-3-phosphate dehydrogenase from *Nannochloropsis gaditana* is shown below as SEQ ID NO:83 (Uniprot W7TAY6).

```
         10         20         30         40
MSPTFRRRHS NAPFKLQIFM VKFLAVVALL GCCCLHGVAS 50         60         70         80
GTPPHAAFVP RASTKSLGNR LAKAPQARRE QTTMQLSARR 90        100        110        120
SRSMRPLPYP VRFAVLGGGS FGLALASVLG KKSIPVTILV 130        140        150        160
RKEEVAEHIN LHHRHPTYLS DIALAPSIRA TVQPEEALRD 170        180        190        200
ASFIIHAVPV QYSRKFLEDI APHVPKNTPI ISTSKGIETG 210        220        230        240
TLCMMQDILL ETLGPNRETA YLSGPSFARE IALGLVTAVV 250        260        270        280
AASESEALAN EICDIMGCNY FRVFTSTDVV GVEVGGAVKN 290        300        310        320
VIAIAAGMCE GLGLGTNAMA ALVTRGCNEM QRLALSLGAR 330        340        350        360
PSTLTGLSGV GDTFGTCFGP LSRNRNLGVR LGKGERLENI 370        380        390        400
LGSSTEVAEG HATAFSLVQL IEKTNRAYRR ELEFPIIYGV
```

```
                       410        420
            KEILEGKRTP AEGLRDLMAM PVREMWNL
```

Another sequence for glycerol-3-phosphate dehydrogenase from *Nannochloropsis gaditana* is shown below as SEQ ID NO:84 (Uniprot W7TIR6).

```
            10         20         30         40
   MSLQPHLALL GMAGSLVVAD RLRSGPGRKS RAKDSHRHLP 50         60         70         80
   PTSRSANCEA SGGKRELSPV EQLEDMRTTP IKCRDGTLVY 90        100        110        120
   PYSLPTRDAQ LNRLKKEKFD VLVIGGGCVG SGVALDAQIR 130        140        150        160
   GLKTAMVEAN DFSAGTSGRS TKLIHGGIRY LETAFWKLDY 170        180        190        200
   GSFALVQEAL EERAHMLNAA PYMNSPLPIM IPIYKWWEVP 210        220        230        240
   YFWAGAKAYD LVASRQKSVP SSHYMDVDEA LFQFPMLRGK 250        260        270        280
   GLKGAIIYYD GQMNDTRMGL TIALTAAQEG AAIANRVEVV 290        300        310        320
   SLLKDPGTGQ VNGARVQDRL TGVEWDIAAK VVVNATGVFA 330        340        350        360
   DKIRKFDDPK AVELIEPAAG VHVMFPAHFS PAKMGLIVPK 370        380        390        400
   TTDGRVLFFL PWEGCTLAGT TDSHSDITMH PQPTAQEVNF 410        420        430        440
   IMQETNRYLT TNVAAKDLIA AWSGLRPLVK DPEKIKEGTA 450        460        470        480
   ALSRNHVIEV SETGKLITIT GGKWTTYRRM AEDTVDRILQ 490        500        510        520
   EHAGLLANGD VSPQASTWNR KLLGADRAGI VCAQKFNQIG 530        540        550        560
   ITLRNDYELP EDVSAHLVKS YGTRALQVAE WVRAGYLDTK 570        580        590        600
   PGKAKRLHSR YPFLEAEVIF AVDQEYALKP MDILARRTRL 610        620        630        640
   AFLDTEAARA AVPRVVKLMG DLLGWSWRQR TMEKAEALAF

650
   LETMNVEKTA LLKK
```

A sequence for a GPAT acyltransferase from *Mortierella elongata* AG-77 is shown below as SEQ ID NO:85 (Uniprot A0A197K296).

```
            10         20         30         40
   MASKNSKTGP DNAGASTGPA LELKPLKNVM PIVPAQQVDS 50         60         70         80
   SSCPPSGETS PLLENAPNGK LATQSGGPDN DESGVENITK 90        100        110        120
   KHAGRIREDP VGFVVQTAAF YQGTGWRSYS NYVGTRIFYE 130        140        150        160
   GFSASFKDRI LASQKVVELV KSMANKQLEV LIKQRQDAHE 170        180        190        200
   AEKVANAGKK NFKPKVWPMR PEDVEVRRKT LEAELTAVAK 210        220        230        240
   TNIDKLVCDM NSMKFIRFFA FLINNILVRM YHQGIHIKES 250        260        270        280
   EFLELRRVAE YCAEKKYSMV ILPCHKSHID YLVISYIFFR 290        300        310        320
   MGLALPHIAA GDNLDMPVVG KALKGAGAFF IRRSWADDQL 330        340        350        360
   YTSIVQEYVQ ELLEGGYNIE CFIEGTRSRT GKLLPPKLGV 370        380        390        400
   LKIIMDAMLS NRVQDCYIVP ISIGYDKVIE TETYINELLG 410        420        430        440
   IPKEKESLWG VITNSRLLQL KMGRIDVRFA KPYSLREFMN 450        460        470        480
   HEIDRREIIN EQEMTSNAAK SQLLKALGYK VLADINSVSV 490        500        510        520
   VMPTALVGTV ILTLRGRGVG RNELIRRVDW LKREILSKGG 530        540        550        560
   RVANFSGMET GEVVDRALGV LKDLVALQKN LLEPVFYAVK 570        580        590        600
   RFELSFYRNQ LIHLFIHEAI VAVTMYTRIK IGGAKSTQQI 610        620        630        640
   SQTELLNEVT FLSRLLKTDF IYNPGDIQSN LENTLEYLKK 650        660        670        680
   SNVIEINSEG FVGLSDVERG IGRENYDFYC FLLWPFVETY 690        700        710        720
   WLAAVSLYTL IPTAKEITEQ ANAGGDQLHW VEERVFVEKT 730        740        750        760
   QMFGKTLYYQ GDLSYFESVN METLKNGFNR LCDYGILMIK 770        780        790        800
   KPTGPKERTK VALHPDFMPS RGSDGHVIAS GALWDMVEHI 810        820        830        840
   GTFRREGKNR RDNATVSSRV LRFAEVVANS PAPVKVPMPS

850
   PAPKQGNGAP KL
```

A sequence for glycero-3-phosphate acyltransferase from a bacterium endosymbiont of *Mortierella elongata* AG-77 is shown below as SEQ ID NO:86 (NCBI GAM53307.1).

```
     1 MTYLFIAALA YGIGSISFAV VVSAAMRLQD PRSYGSKNPG

41 ATNVLRSGNT LAAVLTLIGD ALKGWLAVWL TAQFVHSFGS

81 QYEVGNEAIG LAALAVFLGH LWPIFFHFKG GKGVATAAGV

121 LFAIHPILGL ATAASWLIIA FFFFRYSSLAA LVAAIFAPLY

161 EILMFGFDSN SIAVLAMSLL LISRHRSNIQ NLFAGKEGRL

201 GQKSKDKSL
```

A sequence for a 1-acyl-sn-glycerol-3-phosphate acyltansferase from *Mortierella elongata* AG-77 is shown below as SEQ ID NO:87 (Uniprot A0A197KCL2).

```
            10         20         30         40
   MSIVTYLQAA IGIPLFYFLV LPKILAVLPK KAQFLAKCII 50         60         70         80
   VLLATLTMSV AGCFISIACA LVNKRYIINY VVSRFFGILA
```

```
         90        100        110        120
AGPCGVTYKV VGEEKLENYP AIVVCNHQSS MDMMVLGRVF 130        140        150        160
PKHCVVMAKK ELLYFPFLGV FMKLSNAIFI DRKNHKKAIE 170        180        190        200
STTQAVADMK KHNSGIWIFP EGTRSRLDKA DLLAFKKGAF 210        220        230        240
HLAIQAQLPI LPIISEGYSH IYDSSKRSFP GGELEIRVLD 250        260        270        280
PIPTTGLTAD DVNDLMEKTR DLMLKHLKEM DRSSSTVTSP 290        300
AATVGKTTAT APQDEASVKK RRTLKD
```

Another sequence for a 1-acyl-sn-glycerol-3-phosphate acyltransferase from *Mortierella elongata* AG-77 is shown below as SEQ ID NO:88 (Uniprot A0A197K8I3).

```
         10         20         30         40
MSSESTIPWC IITTPVFILA LPRLLAVLPQ KIQFVTKCCI 50         60         70         80
VLIATFIMSI VGCFVAIVFA LLRRRHEINF VVARIFSFIA 90        100        110        120
SYPCGVTFKV VGEEHLEKYP AIVVCNHQSS MDMMILGRVF 130        140        150        160
PKHCVVMAKK ELQYFPFLGI FMTLSNAIFI DRKNHKKAIE 170        180        190        200
STTQAVTDMK KHNSGIWIFP EGTRSRLETA DLLPFKKGAF 210        220        230        240
HLAIQSQQPV MPIVAAGYSN IYDSANRSFP GGELEIRVLE 250        260        270        280
PISTIGMTAD DVNELMERTR AVMLKNLKEM DHSVKSSSNS 290        300
NGSSTAVAEG KTDEGLTQRR PVKE
```

A sequence for glycerol-3-phosphate acyltransferase from *Nannochloropsis gaditana* (strain CCMP526) is shown below as SEQ ID NO:89 (Uniprot K8ZBC7).

```
         10         20         30         40
MVISFIFSWM LQILACIFIC PFLPSCKERL LLLGWIFRSV 50         60         70         80
SSLVIRLNPY WHLRVLGPRP TRPPSKTLIM CNHLSNADAF 90        100
FLSSALLPWE TKYIAKASLF Q
```

A sequence for 1-acylglycerol-3-phosphate O-acyltransferase from *Nannochloropsis gaditana* (strain CCMP526) is shown below as SEQ ID NO:90 (Uniprot K8YRH4).

```
         10         20         30         40
MRSNKSCKTC PNRIHVGIAI LFPLLLSAFC FCHFLMLPPA 50         60         70         80
IALLIMPYAP VRRVLRLWEA TIAAYWLSFG AWLLENFGGV 90        100        110        120
KLIISGDTFT KKDNVLIICN HRTRLDWMWL WSWAAYFDVL 130        140        150        160
SSYRVILKDS LRCFPWWGWG MSLCLFPFIR RGQKHRSTDL
```

```
        170        180        190
AHLKRNCRYL IQLKVPNSLI IFPEGTDLSP SNQERDRNY
```

A sequence for 1-acyl-sn-glycerol-3-phosphate acyltransferase from *Nannochloropsis gaditana* is shown below as SEQ ID NO:91 (Uniprot W7U0D6).

```
         10         20         30         40
MTSTASLACG ACTAAVLVCL TTGDGVATRH IDANVGNRRT 50         60         70         80
SAFLPVMPPM GTPVTGRIRS HPLEAHKMYY VCQGGTRLSQ 90        100        110        120
RRHERLGTRT AVMVVKTDVE ISDKRDVDPE VGSSSKSTDH 130        140        150        160
TGVSRFGSAM PKSAEGVGPP PAPQDNFKHK SLAGVPTDYG 170        180        190        200
PYLTIKGFKI NAFGFFFCFM AILWAIPWAV FLVVYKALLE 210        220        230        240
FVDKLDPCRY NVDRSSSLWG WLTSLSTDSL PEMTGLENIP 250        260        270        280
DGPAVFVANH ASWMDVPYSA QLPVRAKYLA KADLTKVPIL 290        300        310        320
GNAMSMAQHV LVDRDDKRSQ MEALRSALLI LKTGTPLFVF 330        340        350        360
PEGTRGPGGK MQAFKMGAFK VATKAGVPIV PVSIAGTHIM 370        380        390        400
MPKEVIMPQC AGRGITAIHV HPAIPSTDRT DQELSDLAFK 410        420
IINDALPNEQ QCESTSKETG GA
```

A sequence for phosphatidic acid phosphatase from *Nannochloropsis gaditana* is shown below as SEQ ID NO:92 (Uniprot W7U3I1).

```
         10         20         30         40
MSSHMPVCRG DPEAGVVPAG GTVGNEEMAG RENGGSGMYR 50         60         70         80
LAEDVDGNGR DEGCQWVPPA LRTSLERYRW LEIILLSVIV 90        100        110        120
ILAKEGFGSG VKNHRQYIPL VTQVLPGGAV VVLGNATAFS 130        140        150        160
YPYRFREGTL ECPPVTLEFC ATSPESALAD PCCEFMTTGA 170        180        190        200
KPFQTVSHDD LIWITVGLPL ILLVLRHLLL KWYLCSVPAS 210        220        230        240
SADPMFSSED KSALRPLSGL PFGYSATFCL RDVLIGLFFS 250        260        270        280
LALTRATTNS LKMLTSQPRP NHFALRLFAS LSPDSSAAIH 290        300        310        320
YAESAWKAWP SGHSSMSMAS GAFLSLVLLR DLRQFAGPLQ 330        340        350        360
RQLRACLVIL ALGPVYLAMF VAGTRVHDYF HTTADAVTGS 370        380        390
ALGLLWAVLA FYQVVPAGGL EVRANPPLKY L
```

A sequence for a diacylglycerol kinase from *Mortierella elongata* AG-77 is shown below as SEQ ID NO:93 (Uniprot A0A197JW38).

```
            10         20         30         40
MASFPFVLQA HQGNHQVELV YNGQQLEFDG LSLDEPKQSS 50         60         70         80
SCLPCGPSSA FAGGHRIIKT VEILNIDIEH EDSLVLSVAS 90        100        110        120
AKNGPTKESV LERLVFQVRD KANAVQWQSN VLSHVYKDIK 130        140        150        160
KGRHFKVLVN PFGGQGHAKK LWETIAEPIF KAAGCTYDLT 170        180        190        200
YTTHRYHAKE IARDLNIRLF DAVVSVSGDG VLHEVINGLM 210        220        230        240
ERPDAIAAHK LPIGAIPGGS GNALSYSLLG EDHGSHVTNA 250        260        270        280
VLGIIKGRAM PVDLCSVTQG QNRYFSFVLQ SFGLVADVDL 290        300        310        320
GTEDMRWMGE ARFTVAAVGK LLSQQTYPCE ISYIPVETNV 330        340        350        360
DKIRAEYNYR RQQSVVWADQ THDELDQSHP TIVDRFGGVN 370        380        390        400
AQLNKSDGWV TDSEDVITAV GAKLPWISKG MLLNPASTPN 410        420        430        440
DGLIDLIVFP KGTGRMNGIQ IMLGTETGEH IYHDKVRYMK 450        460        470        480
VKAFRLTPKN ESGFISMDGE HTPYSPYQVE AHPGLISVLS

490
IEGRYARSMR E
```

Another sequence for a diacylglycerol kinase from *Mortierella elongata* AG-77 is shown below a SEQ ID NO:94 (Uniprot A0A197K901).

```
            10         20         30         40
MDEKKIGFIV NRRGGGGKGG KTWDKLEPAV TTRLASAKWK 50         60         70         80
VEYTQHSGHA SDLAREFVNE GYNIIVAVGG DGTISQVVNG 90        100        110        120
YMLADGNSKG CAVGIISSGT GGDFVRTTKT PKDPLEALEL 130        140        150        160
ILSTESTLVD VGHVSATKPN SPSVTNEQYF INICSVGISG 170        180        190        200
SIIKRVESSS IAKYISGSLV YWLYTYLTGL VYRPPPVKYT 210        220        230        240
LTGGSAGADD GKEKHMGLYI MAVANGRYLG GNMHIAPKAQ 250        260        270        280
ISDGQFDVVC LHDLTLTDAF FKASPALKSG NLMNLPAHQA 290        300        310        320
FTQRNTKVSI SPVNAKDHIY VEADGEVAGV LPARWEIIPQ

330
GCRMILPLVQ GSTQSV
```

Another sequence for a diacylglycerol kinase from *Mortierella elongata* AG-77 is shown below as SEQ ID NO:95 (Uniprot A0A197KB11).

```
            10         20         30         40
MGIIPTSDKF PVLVVLNPHS GRKQGLEAWE NTVKPALNAA 50         60         70         80
NKPFRLIESN SQGHVVSYFV DNIKPIITDL AQSLSTVTQG 90        100        110        120
AGDDETIVYP TSAKLQIIVL GGDGTVHEIV NGILKGVEGT 130        140        150        160
GFVTDAFRPE VEFSVIPTGT GNAISTSLGV TSVQNAVDRF 170        180        190        200
IAGKTVPLHL MSVATQTSQL YTVVVNSYGL HCATVYDSEE 210        220        230        240
FRHLGNDRFR QAAMKNVENL KQYEGKLSFF GPIQRYNRIS 250        260        270        280
ASLVDTETDN NIAQADSKSS AVATLTLPGP FTYLLISKQA 290        300        310        320
SLEPGFTPTP FAKTSDDWMD VLAVQNVGQA EIMQMFGSTA 330        340        350        360
TGTHVNQDHV DYIKAKTIEL ETPTQGRLCI DGEFLTIEAG 370        380
PEGKVRFEVN SDPNIQIFHI FA
```

Another sequence for a diacylglycerol kinase from *Mortierella elongata* AG-77 is shown below as SEQ ID NO:96 (Uniprot A0A197K5S8).

```
            10         20         30         40
MSPNQFQAKA SFAGHQRVSD ARLSLGTHEL TIHAPKGSDN 50         60         70         80
NTTTIQVPYS CIYGYETSTD KATGENYKNK VIVHYVAFSG 90        100        110        120
PDLRNPSAAK RTTAQLLFER TEDADRFIQT ARDLGALPTP 130        140        150        160
RRILLLVNPN GGVGKAKRIS DTVVKPMLQH SGLTVKEQYT 170        180        190        200
EYGRHAVDIA SKVNLDEVDS LVVVSGDGVL HEVINGLLSR 200        210        230        240
PDWDRARKTS IGIYPAGSGN AIAASLGIYS QFVATLTVIR 250        260        270        280
GETSKLDIFS LSQLNRPKIY SMLSFSWGMM ADADIESDSY 290        300        310        320
RWLGPLRFDV AGFIRMIRLR RYPGKVYVLP PKHQQNPSTT 330        340        350        360
EQQLTPPQSP SHKREPESQF QHLLDSNIKE PPKPWSLIPN 370        380        390        400
MPFYSMLLLL NCPNVGETIF FTDTIRFNDG IMRLWYSAET 410        420        430        440
RFWKILMPFI FDQQNGKMVE RDLMKDLECG GILIIPGVEG 450        460        470        480
KPDDPSTHKV IEPDWVTSSA AKAQNIYQNP GLFDVDGEVM 490        500        510        520
PTARTLIEIH PSLMNILVPE WLYHKDDDNT TARAHEVAVI

QAIKAQQKL
```

A sequence for diacylglycerol kinase from *Nannochloropsis gaditana* is shown below as SEQ ID NO:97 (Uniprot W7UAL1).

```
         10         20         30         40
MDEELNVLSP FLVKAEVLLV LVVVLVASVV WLFWEIVSFM 50         60         70         80
MDRGKEETNP DWWEVLRNCQ HRRLIIPPYC VQEVPELGTF 90        100        110        120
SRLTTATTNA MKNMSGVIQR TSHLISGGSG KSAAAIKKGA 130        140        150        160
RQDLPSTQQE GDENMKGYTV DGNARGVKLR RRGSKQSIVG 170        180        190        200
LSNHGTSAGG KPALQPTANP TPLTLSENGA NPDASAASDA 210        220        230        240
RPKPHRLDLN GEEGNMVPCN GSLSSRAGDG KRVVGMSGLA 250        260        270        280
STSAAAGSDA SSANVKSMEI SPADTPCRGR IRFLPHQRER 290        300        310        320
QQIENHEKSH EGKPTRSGLP LRALDSQPPL TPYALPDAEG 330        340        350        360
VLASSAQSSR HAPDAIAATP RLSSSHAANG EPITTPAQPV 370        380        390        400
RLPSMEHAHS GTGVALSGGS SGVAGRGFIF SPLPEDCTPL 410        420        430        440
LAFVNSRSGV SQGAYLIHQL RRLLNPIQVI DLANEDPARA 450        460        470        480
LRLYLELPRL RVLVCGGDGT AKWIMNVLED LNPECWPPIA 490        500        510        520
ILPLGTGNDM ARVLGWGGGY NNQSIVEFLA QVQRAHVVVV 530        540        550        560
DRWEMKLTPA GKGSSRAKTV TFNNYFGIGV DAQAALKFHH 570        580        590        600
LREQKPQLFF SRLVNKLWYG MLGAQDLFRR TCVSLPERLK 610        620        630        640
IVADGKELTL PAHVQGVIFL NIESYGGGVK LWNVEEDDES 650        660        670        680
AGNGLFDASS SSCSSEEGDR SEDESRRQRR RRRRRERQRR 690        700        710        720
QQSQAEEEAH RQREQQEKPS SMALTSSSMQ DGLMEVVAIN 730        740        750        760
GVVHLGQLQV GLSKAVKICQ CREAVITTTR DLPMQVDGEP 770        780        790        800
WPQAKSTIKI TRKKDPAYLL RRTMDSGGAV VGEVVELLES 810        820        830        840
AVKDGVISLP QKKSLLTELS RRVEMKRKVF EQELSQNDGV 850        860
PSFSKGFDVS RLRLAADSNS KDCVLM
```

Another sequence for diacylglycerol kinase from *Nannochloropsis gaditana* is shown below as SEQ ID NO:98 (Uniprot W7TXY0).

```
         10         20         30         40
MKLIQYFGTA LCVVILSCVT NIIPGGRIAL GRPFSRLFGG 50         60         70         80
SSRNLRAEVE AAVPHFIVPE DRVEYPTPKL AALKSKLKEI 90        100        110        120
GHHKAMGHPH QHQGLDGRRR VSLHPSHRPA PSSLGAAEDK 130        140        150        160
EQEEEGGEEE EEGQEGVIAP PAWKPGHMNP RDSSSDMGKA 170        180        190        200
TKGKPGTPSA FLPLGVPPPS LFPPSARPIR RSPWSLLFRR 210        220        230        240
GLPRPRRKRP IGINRIKTLP PSVTPLIAIV NSKSGGRQGK 250        260        270        280
NLFKRLRAAL SRAQVFDIQK VDLKEALSLY CHLPNSCTLL 290        300        310        320
VCGGDGTASR VFEVVDGMEW KHGPPKIAIV PLGTGNDIAR 330        340        350        360
VLDWNLGHDW SGGYFPWSND AADANLLSVF SDLTRAMERK 370        380        390        400
MDRWELRMTE AVPSSDRHRQ PVKYMLGYLG IGVDGKVALD 410        420        430        440
FHKLRDRAPY LFLSPTLNKF YYALMGLRDF FVRSCKNLPD 450        460        470        480
KVELWCDGKP IVLPPQTESF IVLNINSHAG GVELWPEYLM

GGGMEG
```

Another sequence for diacylglycerol kinase from *Nannochloropsis gaditana* is shown below as SEQ ID NO:99 (Uniprot W7TP09).

```
         10         20         30         40
MKLIQYFGTA LCVVILSCVT NIIPGGRIAL GRPFSRLFGG 50         60         70         80
SSRNLRAEVE AAVPHFIVPE DRVEYPTPKL AALKSKLKEI 90        100        110        120
GHHKAMGHPH QHQGLDGRRR VSLHPSHRPA PSSLGAAEDK 130        140        150        160
EQEEEGGEEE EEGQEGVIAP PAWKPGHMNP RDSSSDMGKA 170        180        190        200
TKGKPGTPSA FLPLGVPPPS LFPPSARPIR RSPWSLLFRR 210        220        230        240
GLPRPRRKRP IGINRIKTLP PSVTPLIAIV NSKSGGRQGK 250        260        270        280
NLFKRLRAAL SRAQVFDIQK VDLKEALSLY CHLPNSCTLL 290        300        310        320
VCGGDGTASR VFEVVDGMEW KHGPPKIAIV PLGTGNDIAR 330        340        350        360
VLDWNLGHDW SGGYFPWSND AADANLLSVF SDLTRAMERK 370        380        390        400
MDRWELRMTE AVPSSDRHRQ PVKYMLGYLG IGVDGKVALD 410        420        430        440
FHKLRDRAPY LFLSPTLNKF YYALMGLRDF FVRSCKNLPD 450        460        470        480
KVELWCDGKP IVLPPQTESF IVLNINSHAG GVELWPEYLM 490        500        510        520
GGGMEGAFKP SRFDDGYLEV VAISGVLHLG RIRVGLDRPL 530        540        550        560
RLAQAKEVRI RTKSFLPGQY DGEPWRLPRC ELTLRHNGQA 570        580        590        600
PVLQHVSKEL LQYNEWLVGQ GKLDAAGKDQ LLQAFKRRLQ

VSQ
```

A sequence for a diacylglycerol O-acyltransferase 2A (DGAT2A) from *Mortierella ramanniana* is shown below as SEQ ID NO:100 (Uniprot Q96UY2).

```
            10         20         30         40
     MASKDQHLQQ KVKHTLEAIP SPRYAPLRVP LRRRLQTLAV 50         60         70         80
     LLWCSMMSIC MFIFFFLCSI PVLLWFPIIL YLTWILVWDK 90        100        110        120
     APENGGRPIR WLRNAAWWKL FAGYFPAHVI KEADLDPSKN 130        140        150        160
     YIFGYHPHGI ISMGSFCTFS TNATGFDDLF PGIRPSLLTL 170        180        190        200
     TSNFNIPLYR DYLMACGLCS VSKTSCQNIL TKGGPGRSIA 210        220        230        240
     IVVGGASESL NARPGYMDLY LKRRFGFIKI AVQTGASLVP 250        260        270        280
     TISFGENELY EQIESNENSK LHRWQKKIQH ALGFTMPLFH 290        300        310        320
     GRGVFNYDFG LLPHRHPIYT IVGKPIPVPS IKYCOTKDEI 330        340        350
     IRELHDSYMH AVQDLYDRYK DIYAKDRVKE LEFVE
```

A sequence for a diacylglycerol O-acyltransferase 2B (DGAT2B) from *Mortierella ramanniana* is shown below as SEQ ID NO:101 (Uniprot Q96UY1).

```
            10         20         30         40
     MEQVQVTALL DHIPKVHWAP LRGIPLKRRL QTSAIVTWLA 50         60         70         80
     LLPICLIIYL YLFTIPLLWP ILIMYTIWLF FDKAPENGGR 90        100        110        120
     RISLVRKLPL WKHFANYFPV TLIKEGDLDP KGNYIMSYHP 130        140        150        160
     HGIISMAAFA NFATEATGFS EQYPGIVPSL LTLASNFRLP 170        180        190        200
     LYRDFMMSLG MCSVSRHSCE AILRSGPGRS IVIVTGGASE 210        220        230        240
     SLSARPGTND LTLKKRLGFI RLAIRNGASL VPIFSFGEND 250        260        270        280
     IYEQYDNKKG SLIWRYQKWF QKITGFTVPL AHARGIFNYN 290        300        310        320
     AGFIPFRHPI VTVVGKPIAV PLLAEGETEP SEEQMHQVQA 330        340
     QYIESLQAIY DKYKDIYAKD RIKDMTMIA
```

A sequence for an O-acyltransferase from *Mortierella elongata* AG-77 is shown below as SEQ ID NO:102 (Uniprot A0A197K574)

```
            10         20         30         40
     MSQGDAITTS HSDGTEKRHD STTNILSDVP PQTEDVKSSS 50         60         70         80
     SKKKRSTYRH TFPVHTKTLP SPLSKEAPPE SYRGFVNLGM 90        100        110        120
     LLLFGNNIRL IIENYQKYGF LLSIPGSNVS KQDWILAGLT
```

```
           130        140        150        160
     HAILPLHVIV AYQLEQWASR KAKGFRKRLA DQKENPTTKD 170        180        190        200
     DEDKKAVPAG DKVRGGKKDK KNLTLEEQIK ENRKTVGWLH 210        220        230        240
     FANVSLILGW PSFMSYFVIF HPFLAMGCLM TSLILFLKMV 250        260        270        280
     SFALVNQDLR YAYIQDTPAT EQSSPHLTKV HNDTITTTNT 290        300        310        320
     TSDGATTTTT LTTTTTVVKT ITVKKDAEKH GGAYQYEVHY 330        340        350        360
     PQNITPGNIG YFYLAPTLCY QPSYPRSTYF RPSFFFKRVL 370        380        390        400
     EIVTCLGMMY FLIEQYATPT LQNSVRAFDE LAFGRLLERV 410        420        430        440
     LKLSTTSVII WLLMFYTFFH AFFNALAEVL YFGDRRFYLS 450        460        470        480
     WWNATSVGMY WKTWNSPVYT FFKRHVYLPM ITSGHSALTA 490        500        510        520
     SVVIFTISAL LHEVLIGIPT KMIYGYAFAG MFFQIPLIAL 530        540        550        560
     TAPLEKWRGT GSGLGNMIFW VSFTILGQPA CALLYYYHWT

KRSMNA
```

A sequence for a dacylglycerol acyltransferase from *Mortierella alpina* is shown below as SEQ ID NO:103 (Uniprot A0A1S6XXG5).

```
            10         20         30         40
     MPLFAPLRMP IQRRMQTGAV LLWISGIIYT LGIFVFLCTF 50         60         70         80
     KVLRPLIIIY LLWAFMLDRG PQRGARAVQW YRNWVGWKHF 90        100        110        120
     AQYFPMTLVK EGELDPSKNY IFGYHPHGII SLGAFCTFGT 130        140        150        160
     EGLHFSKRFP GIKPQLLTLH ANFQIPLYRE MVMAHGCASV 170        180        190        200
     SRASCEHILR SGEGCSVVIV VGGAQESLST QPGTLNLTLK 210        220        230        240
     KRLGFCKLAL VNGASLVPTL AFGENELYEV YTAKPKSLMY 250        260        270        280
     KIQQFAKRTM GFTMPVFNGR GVFNYEFGLL PRRKPVYIVV 290        300        310        320
     GKPIHVDKVE NPTVEQMQKL QSIYIDEVLN IWERYKDKYA

330
     AGRTQELCII E
```

A sequence for a type two diacylglycerol acyltransferase from *Nannochloropsis oceanica* is shown below as SEQ ID NO:104 (Uniprot A0A1S6KM83).

```
            10         20         30         40
     MYPIKLCFLF ILTIPPYAHV RTRTPHRRGT TSKMAKANFP 50         60         70         80
     PSARYVNMTQ VYATGAHNMP DEDRLKVMNG LSKPLTEAKP
```

```
        90        100        110        120
GDLGFGDVES MTFCEEFVAI MFLLIIVGSM LWIPIAVLGF 130        140        150        160
ALYVRSAMAW VVMLIVFFTL SLHPVPRIHD MVHSPLNHFI 170        180        190        200
FKYFSLKMAS DAPLDSAGRY IFVAPPHGVL PMGNLMTVHA 210        220        230        240
MKACGGLEFR GLTTDVALRL PLFRHYLGAI GTIAATRHVA 250        260        270        280
KQYLDKGWSI GISSGGVAEI FEVNNKDEVV LMKERKGFVK 290        300        310        320
LALRTGTPLV ACYIFGNTKL LSAWYDDGGV LEGLSRYLKC 330        340        350        360
GVLPLWGRFG LPLMHRHPVL GAMAKPIVVP KVEGEPTQEM 370        380        390
IDEYHSLFCQ TLVDLFDRYK TLYGWPDKKL LIK
```

A sequence for a diacylglycerol acyltransferase from *Nannochloropsis gaditana* (strain CCMP526) is shown below as SEQ ID NO:105 (Uniprot I2CPZ8).

```
        10         20         30         40
MGHVGKLDLL KALGELLRLA IPSTFVWLIT FYVYFHCTLN 50         60         70         80
LFAEITRFGD RLFFKDWWNC TSFSRYWRTW NLPVHQFLVR 90        100        110        120
HVYFPLLRAG ASKMTANVTV FAVSAFFHEL LISIPCHVVR 130        140        150        160
LWAFLAMMGQ IPLIYITDHL DKTLFKETQA GNYMFWLIFC

170
IFGQPMAVLL YYADFSARS
```

A sequence for a diacylglycerol acyltransferase 2 from *Nannochloropsis gaditana* (strain CCMP526) is shown below as SEQ ID NO:106 (Uniprot K8YXL9).

```
        10         20         30         40
MVCPLRSLVR DYRKTQGLVT SPHRSHGPDM SFKCKPSQKP 50         60         70         80
NKQFWRYASF LAFIATFLLV PSTTSWASAL HRACFMAYVM 90        100        110        120
TYLDTSYRDG SRAWPWFQRL PVWRLYCRYI KGQVITTVPL 130        140        150        160
DPHRQYIFAA HPHGIATWNH FLTMTDGCRF LSRIYPRPRL 170        180        190        200
DLGATVLFFI PLVKEVLLWV GCVDAGAATA NAILERGFSS 210        220        230        240
LIYVGGEKEQ ILTERGRDLV VVLPRKGFCK LALRYDCPIV 250        260        270
PAYAFGENDL YRTFNYFKGL QLWVERHAGR YVPRNRSEH
```

A sequence for a type 2 diacylglycerol acyltransferase (DGTT5) from *Nannochloropsis oceanica* is shown below as SEQ ID NO:107 (Uniprot A0A1S6KMA4).

```
        10         20         30         40
MTPQADITSK TTPNLKTAAS SPSKTSPAPS VQYKAANGKV 50         60         70         80
ITVAMAEQDD GNMGIFRECF AMVTMGIIMS WYYIVVILSL 90        100        110        120
LCLVGICIFP AWRAVAATVF VLMWSAALLP LDYQGWDAFC 130        140        150        160
NSFIFRLWRD YFHYEYVLEE MIDPNKRYLF AEMPHGIFPW 170        180        190        200
GEVISISITK QLFPGSRVGS IGASVIFLLP GLRHFFAWIG 210        220        230        240
CRPASPENIK KIFEDGQDCA VTVGGVAEMF LVGGDKERLY 250        260        270        280
LKKHKGFVRE AMKNGADLVP VFCFGNSKLF NVVGESSRVS 290        300        310        320
MGLMKRLSRR IKASVLIFYG RLFLPIPIRH PLLFVYGKPL 330        340        350        360
PVVHKAEPTK EEIAATHALF CEKVEELYYK YRPEWETRPL

SIE
```

A sequence for a lecithin:cholesterol acyltransferase from *Mortierella elongata* AG-77 is shown below as SEQ ID NO: 108 (Uniprot A0A197JIB8).

```
        10         20         30         40
MDKQQPDIVT MIPGIVSTGL ESWSTTNNSC SQKYFRKRMW 50         60         70         80
GTTTMFKAVL LDKDCWITNL RLDPETGVDP EGVRLRAAQG 90        100        110        120
LEAADYFVQG YWVWAPIIKN LAAIGYDNNN MYLASYDWRL 130        140        150        160
SFANLENRDN YFSRLKSNLE LSLKMTGEKS VLVAHSMGSN 170        180        190        200
VMFYFFKWVE SDKGGKGGPN WVNDHVHTFV NIAGPMLGVP 210        220        230        240
KTLAAVLSGE VRDTAQLGVV SAYVLEKFFS RRERADLFRS 250        260        270        280
WGGLSSMIPK GGNRIWGTIH GAPDDGTHDE EETVRNEKIA 290        300        310        320
KSEETPGATT KRKHGEQSPT FGAMLAFAEG SNMENHGMDE 330        340        350        360
SMGLLSKMAG NAYNTMLAKN YTVGASVTQK QMDKTTKDPA 370        380        390        400
SWTNPLEATL PYAPKMKIYC LYGVGKSTER SYTYNRVSDL 410        420        430        440
APQIFDQRPG NVSDETGQVP NIYIDTTVHD DKLGISYGVH 450        460        470        480
QGDGDGTVPL MSTGYMCVDG WSKKLYNPAG LKVITREFTH 490        500        510        520
QSSLSPVDIR GGKRTADHVD ILGNYQYTKD LLAIVAGRDG 530        540
DGLEEQIYSK IKEYSAKVDL
```

A sequence for a diacylglycerol acyltransferase (DGAT23) from *Nannochloropsis oceanica* strain IMET1 is shown below as SEQ ID NO: 112 (Uniprot A0A290G0P3).

```
         10         20         30         40
MAHLFRRRSK GEGNSTSSRC LSLSEGNKAM LILSSEIEPP 50         60         70         80
ASATSKAATS GIKEIGDPSL PTVALLSLPS ISKADKNSAT 90        100        110        120
AAVAAGTLED AAAGALTAPF ADRSVKKQYG ODGDGAQCKE 130        140        150        160
AEGGRKRSGS VGNLLLSSMT SFSKGTSLSF LTGEDKTPSP 170        180        190        200
PETGPAGIDF STPAHPTMQF VDFIITFLLV HYIQVFYSLV 210        220        230        240
FLFIYLVKHG HRWPYFLAAI YAPSYFIPLQ RLGGWPFKGF 250        260        270        280
MRRPFWRCVQ RTLALQVERE VELSPDEQYI FGWHPHGILL 290        300        310        320
LSRFAIYGGL WEKLFPGIHF KTLAASPLFW IPPIREVSIL 330        340        350        360
LGGVDAGRAS AARALTDGYS YSLYPGGSKE IYTTDPYTPE 370        380        390        400
TTLVLKIRKG FIRMALRYGC ALVPVYTFGE KYAYHRLGQA 410        420        430        440
TGFARWLLAV LKVPFLIFWG RWGTFMPLKE TQVSVVVGTP 450        460        470        480
LRVPKIEGEP SPEVVEEWLH KYCDEVQALF RRHKHKYAKP

EEFVAIS
```

A sequence for a type two diacylglycerol acyltransferase (DGTT2) from *Nannochloropsis oceanica* is shown below as SEQ ID NO: 109 (Uniprot A0A1S6KMB4).

```
         10         20         30         40
MAHLFRRRSK GEGNSTSSRC LSLSEGNKAM LILSSEIEPP 50         60         70         80
ASATSKAATS GIKEIGDPSL PTVALLSLPS ISKADTNSAT 90        100        110        120
AAVAAGTLED AAAGALTAPF ADRSVKKQYG QDGDGAQCKE 130        140        150        160
AEGGRKRSGS VGNLLLSSMT SFSKGTSLSF LTGEDKTPSP 170        180        190        200
PETGPAGIDF STPAHPTMQF VDFIITFLLV HYIQVFYSLV 210        220        230        240
FLFIYLVKHG HRWPYFLAAI YAPSYFIPLQ RLGGWPFKGF 250        260        270        280
MRRPFWRCVQ RTLALQVERE VELSPDEQYI FGWHPEVSIL 290        300        310        320
LGGGSKEIYT TDPYTPETTL VLKIRKGFIR MALRYGCALV 330        340        350        360
PVYTFGEKYA YHRLGQATGF ARWLLAVLKV PFLIFWGRHK

370
HKYAKPEEFV AIS
```

REFERENCES

1. R. F. Service, Algae's second try. *Science.* 333, 1238-1239 (2011).
2. N. Okamoto, I. Inouye, A secondary symbiosis in progress? *Science.* 310, 287 (2005).
3. A. F. Little, M. J. H. van Oppen, B. L. Willis, Flexibility in algal endosymbioses shapes growth in reef corals. *Science.* 304, 1492-1494 (2004).
4. E. Tisserant et al., Genome of an arbuscular mycorrhizal fungus provides insight into the oldest plant symbiosis. *Proc. Natl. Acad. Sci. U.S.A.* 110, 20117-20122 (2013).
5. E. F. Y. Hom, A. W. Murray, Plant-fungal ecology. Niche engineering demonstrates a latent capacity for fungal-algal mutualism. *Science.* 345, 94-98 (2014).
6. J. Simon et al., Self-supporting artificial system of the green alga *Chlamydomonas reinhardtii* and the ascomycetous fungus *Alternaria infectoria*. *Symbiosis,* 1-11 (2016).
7. G. Bonito et al., Isolating a functionally relevant guild of fungi from the root microbiome of *Populus. Fungal Ecol.* 22, 35-42 (2016).
8. K. Brenner, L. You, F. H. Arnold, Engineering microbial consortia: a new frontier in synthetic biology. *Trends Biotechnol.* 26, 483-489 (2008).
9. D. Mollenhauer. R. Mollenhauer, M. Kluge, Studies on initiation and development of the partner association in *Geosiphon pyriforme* (Kütz.) v. Wettstein, a unique endocytobiotic system of a fungus (Glomales) and the cyanobacterium *Nostoc punctiorme* (Kütz.) Hariot. *Protoplasma.* 193, 3-9 (1996).
10. P. Bonfante, A. Genre, Mechanisms underlying beneficial plant-fungus interactions in mycorrhizal symbiosis. *Nat. Commun.* 1, 48 (2010).
11. P. M. Delaux et al., Algal ancestor of land plants was preadapted for symbiosis. *Proc. Natl. Acad. Sci. U.S.A.* 112, 13390-13395 (2015).
12. K. J. Field et al., Functional analysis of liverworts in dual symbiosis with Glomeromycota and Mucoromycotina fungi under a simulated Palaeozoic $CO_2$ decline. *ISME J.* 10, 1514-1526 (2015).
13. J. W. Spatafora et al., A phylum-level phylogenetic classification of zygomycete fungi based on genome-scale data. *Mycologia.* Resubmitted. Dataset DOI: 10.5281/zenodo.46700 TreeBase: TB2:S18957
14. D. Redecker, R. Kodner, L. E. Graham, Glomalean fungi from the Ordovician. *Science.* 289, 1920-1921 (2000).
15. S. Wodniok et al., Origin of land plants: do conjugating green algae hold the key? *BMC Evol. Biol.* 11, 104 (2011).
16. K. J. Field, S. Pressel, J. G. Duckett, W. R. Rimington, M. I. Bidartondo, Symbiotic options for the conquest of land. *Trends Ecol. Evol.* 30, 477-486 (2015).
17. P. R. Atsatt, Are vascular plants "inside-out" lichens? *Ecology.* 69, 17-23 (1988).
18. A. Vieler et al., Genome, functional gene annotation, and nuclear transformation of the heterokont oleaginous alga *Nannochloropsis oceanica* CCMP1779. *PLoS Genet.* 8, e1003064 (2012).
19. L. P. Partida-Martinez, C. Hertweck, A gene cluster encoding rhizoxin Biosynthesis in *Burkholderia rhizoxina,* the bacterial endosymbiont of the fungus *Rhizopus microsporus. Chembiochem.* 8, 41-45 (2007).
20. H. L. Chen, S. S. Li, R. Huang, H. J. Tsai, Conditional production of a functional fish growth hormone in the transgenic line of *Nannochloropsis oculata* (Eustigmatophyceae). *J. Phycol.* 44, 768-776 (2008).
21. A. D. Velichkov, A simple procedure for dissolving fungal cell wall preparations for the analysis of neutral sugars. *World J. Microbiol. Biotechnol.* 8, 527-528 (1992).
22. M. J. Scholz et al., Ultrastructure and composition of the *Nannochloropsis gaditana* cell wall. *Eukaryot. Cell.* 13, 1450-1464 (2014).

23. C. H. Tsai et al., The protein compromised hydrolysis of triacylglycerols 7 (CHT7) acts as a repressor of cellular quiescence in *Chlamydomonas*. Proc. Natl. Acad. Sci. U.S.A. 111, 15833-15838 (2014).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to describe and summarize various embodiments of the invention according to the foregoing description in the specification.

Statements:
1. A consortium comprising at least one viable fungus and at least one viable algae linked to or within hyphae of the fungus, wherein the fungus, algae, or both have been modified to express a heterologous (exogenous) lipid synthesizing enzyme.
2. The consortium of statement 1, wherein algae is a diatom (bacillariophyte), green algae (chlorophyte), blue-green algae (cyanophyte), golden-brown algae (chrysophyte), haptophyte, or a combination thereof.
3. The consortium of statement 1 or 2, wherein algae is a species of *Amphipleura, Amphora, Aquamortierella, Chaetoceros, Charophyceae, Chlorodendrophyceae, Chlorokybophyceae, Chlorophyceae, Coleochaetophyceae, Cyclotella, Cymbella, Dissophora, Embryophytes, Endogaceae, Fragilaria, Gamsiella, Hantzschia, Klebsormidiophyceae, Lobosporangium, Mamiellophyceae, Mesostigmatophyceae, Modicella, Mortierella, Mucor, Navicula, Nephroselmidophyceae, Nitzschia, Palmophyllales, Prasinococcales, Prasinophytes, Pedinophyceae, Phaeodactylum, Pyramimonadales, Pycnoccaceae, Pythium, Phytophthora, Phytopythium, Rhizopus, Thalassiosira, Trebouxiophyceae, Ulvophyceae, Zygnematophyceae*, or the algae is a combination of species.
4. The consortium of statement 1, 2, or 3, wherein algae is of genera *Ankistrodesmus, Boekelovia, Botryococcus, Chlorella, Chlorococcum, Dunaliella, Isochrysis, Monoraphidium, Nannochloropsis, Oocystis, Oscillatoria, Pleurochrysis, Scenedesmus, Synechococcus, Tetraselmis*, or a combination thereof.
5. The consortium of statement 1-3, or 4, wherein algae is *Emiliania huxleyi, Gephyrocapsa oceanica, Isochrysis galbana, Isochrysis* sp. T-Iso, *Isochrysis* sp. C-Iso, *Nannochloropsis oceanica*, or a combination thereof.
6. The consortium of statement 1-4, or 5, wherein algae is a photosynthetic algae.
7. The consortium of statement 1-5, or 6, wherein algae may not, in some cases, be *Nostoc punctiforme*.
8. The consortium of statement 1-6, or 7, wherein algae is *Nannochloropsis oceanica* CCMP1779.
9. The consortium of statement 1-7 or 8, wherein the fungus is *Aspergillus, Blakeslea, Botrytis, Candida, Cercospora, Cryptococcus, Cunninghamella, Fusarium (Gibberella), Kluyveronmyces, Lipomyces, Morchella, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Xanthophyllomyces (Phqffia), Yarrowia*, or a combination thereof.
10. The consortium of statement 1-8 or 9, wherein the fungus is *Mortierella elongata, Mortierella elongata* AG77, *Mortierella gamsii, Mortierella gamsii* GBAus22, *Umbelopsis* sp., *Umbelopsis* PMI120, *Lecythophora* sp., *Lecythophora* PMI546, *Leptodontidium* sp., *Leptodontidium* PMI413, *Lachnum* sp., *Lachnum* PMI789, *Morchella* sp., *Saccharomyces cerevisiae, Atractiella* sp., *Atractiella* PMI152. *Clavulina, Clavulina* PMI390, *Grifola frondosa, Grifola frondosa* GMNB41, *Flagelloscypha* sp., *Flagelloscypha* PMI526, or a combination thereof.
11. The consortium of statement 1-9 or 10, wherein the fungus is *Aspergillus terreus, Aspergillus nidulans, Aspergillus niger, Atractiella* PMI152, *Blakeslea trispora, Botrytis cinerea, Candida japonica, Candida pulcherrima, Candida revkaufi, Candida tropicalis, Candida utilis, Cercospora nicotianae, Clavulina* PMI390, *Cryptococcus curvatus, Cunninghamella echinulata, Cunninghamella elegans, Flagelloscypha* PMI526, *Fusarium fujikuroi (Gibberella zeae), Grifola frondosa* GMNB41, *Kluyveromyces lactis, Lecythophora* PMI546, *Leptodontidium* PMI413, *Lachnum* PMI789, *Lipomyces starkeyi, Lipomyces lipoferus, Mortierella alpina, Mortierella elongata* AG77, *Mortierella gamsii* GBAus22, *Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Umbelopsis* PMI120, *Xanthophyllomyces dendrorhous (Phqffia rhodozyma), Yarrowia lipolytica*, or a combination thereof.
12. The consortium of statement 1-10 or 11, wherein the fungus is not *Geosiphon pyriformis*.
13. The consortium of statement 1-11 or 12, wherein the fungus has more than one algae cell within the fungus hyphae.
14. The consortium of statement 1-12 or 13, wherein the fungus has more than two algae cells within the fungus hyphae.
15. The consortium of statement 1-13 or 14, wherein the fungus has more than five, or more than ten, or more than twenty, or more than twenty five, or more than thirty, or more than forty, or more than fifty, or more than one hundred algae cells within the fungus hyphae.
16. The consortium of statement 1-14 or 15, wherein the fungus has less than 10,000 algae cells within the fungus hyphae, or less than 5000 algae cells within the fungus hyphae, or less than 2000 algae cells within the fungus hyphae, or less than 1000 algae cells within the fungus hyphae.
17. The consortium of statement 1-15 or 16, wherein the algae photosynthetically synthesizes sugars.
18. The consortium of statement 1-16 or 17, wherein the algae has a degraded or missing outer cell wall.
19. The consortium of statement 1-17 or 18, wherein the algae has cell wall extensions.
20. The consortium of statement 1-18 or 19, wherein the algae has cell wall is associated with, bound to, or linked to hyphae of the fungus.

21. The consortium of statement 1-19 or 20, wherein the algae or the fungus comprises at least one heterologous expression cassette or expression vector that includes a promoter operably linked to nucleic acid segment encoding a lipid synthetic enzyme.

22. The consortium of statement 21, wherein the lipid synthesizing enzyme is acetyl-CoA carboxylase, malonyl-CoA decarboxylase, acyl carrier protein, fatty acid synthase, malonyl-CoA:ACP malonyltransferase, 3-oxoacyl-ACP synthase, KASI/II, 3-hydroxdecanoyl-ACP dehydratase, 3-hydroxydecanoyl-ACP dehydratase, 3-ketoacyl-ACP reductase, acyl-CoA elongase, fatty acid desaturase, acyl-CoA thioesterase, acyl-CoA synthetase, aldehyde dehydrogenase, alcohol dehydrogenase, glycerol kinase, glycerol-3-phosphate dehydrogenase, glycero-3-phosphate acyltransferase, 1-sn-acyl-glycero-3-phosphate acyltransferase, phosphatidic acid phosphatase, lipin-like phosphatidate phosphatase, diacylglycerol kinase, diacylglycerol acyltransferase, phospholipid diacylglycerol acyltransferase, or any combination thereof.

23. The consortium of statement 21 or 22, wherein the algae or the fungus comprises two or more heterologous expression cassettes or expression vectors, each cassette or vector having a promoter operably linked to nucleic acid segment encoding a lipid synthetic enzyme.

24. A method comprising incubating at least one fungus and at least one algae cell until at least one algae cell is incorporated into hyphae of the fungus, to thereby form a consortium of the at least one fungus and the at least one algae cell, wherein the at least one fungus or at least one algae has been modified to express a heterologous lipid synthesizing enzyme.

25. The method of statement 24, wherein at least one fungus and at least one algae cell are incubated together for one or more days, one or more weeks, one or months, one or more years, or indefinitely.

26. The method of statement 24 or 25 wherein at least one fungus and at least one algae cell are incubated at a fungus tissue and algae cell density sufficient for the fungus and the algae come into contact.

27. The method of statement 24, 25, or 26, wherein algae is added to the fungus at a density of about $1\times10^4$ algae cells/mL to $1\times10^9$ algae cells/mL, or at a density of about $1\times10^5$ algae cells/mL to $1\times10^8$ algae cells/mL, or at a density of about $1\times10^6$ algae cells/mL to $1\times10^8$ algae, or at a density of about $1-3\times10^7$ cells/mL.

28. The method of statement 24-26 or 27, wherein more fungus tissue by mass than algae cells by mass is incubated together.

29. The method of statement 24-27 or 28, wherein the fungus and the algae cells are incubated at a ratio of from about 10:1 by mass fungal tissue to algal cells, to about 1:1 by mass fungal tissue to algal cells; or from about 5:1 by mass of fungal tissue to algal cells to about 1:1 by mass fungal tissue to algal cells; or at a ratio of about 3:1 by mass fungal tissue to algal cells.

30. The method of statement 24-28 or 29, wherein more algae cells by mass than fungal tissue by mass is incubated.

31. The method of statement 24-29 or 30, wherein the fungus and the algae cells are incubated at a ratio of from about 10:1 by mass algal cells to fungal tissue mass to about 1:1 by mass algal cells to fungal tissue mass; or at a ratio of from about 5:1 by mass algal cells to fungal tissue mass to about 1:1 by mass algal cells to fungal tissue mass.

32. The method of statement 24-30 or 31, wherein one or more fungal species and one or more algae species are incubated in a culture medium that contains some carbohydrate or some sugar.

33. The method of statement 32, wherein the some comprises dextrose, sucrose, glucose, fructose or a combination thereof.

34. The method of statement 32 or 33, wherein the carbohydrate or sugar is present in an amount of about 1 g/liter to about 20 g/liter, or of about 3 g/liter to about 18 g/liter, or of about 5 g/liter to about 15 g/liter.

35. The method of statement 24-33 or 34, wherein one or more fungal species and one or more algae species is incubated in a liquid media, in a semi-solid media, or on a solid media.

36. The method of statement 24-34 or 35, wherein the consortium of the at least one fungus and the at least one algae cell is incubated in a minimal medium.

37. The method of statement 24-35 or 36, wherein the consortium comprising the at least one fungus and the at least one algae cell is incubated or maintained in a minimal medium containing no added carbohydrate or sugar.

38. The method of statement 24-36 or 37, wherein the consortium comprising the at least one fungus and the at least one algae cell grows in a minimal medium containing no added carbohydrate or sugar.

39. The method of statement 24-37 or 38, wherein the one or more fungal species and one or more algae species are incubated in a culture medium that contains sodium bicarbonate.

40. The method of statement 24-38 or 39, wherein the one or more fungal species and one or more algae species are incubated in a culture medium that contains ammonium salts.

41. The method of statement 24-39 or 40, wherein the consortium synthesizes one or more lipid, carbohydrate, or protein.

42. The method of statement 24-40 or 41, wherein the consortium comprises a lipid content greater than 40%, 50%, 60%, 70%, 80%, or 90% by weight of the consortium.

43. The method of statement 24-41 or 42, wherein after incubating the algae has a degraded or missing outer cell wall.

44. The method of statement 24-42 or 43, wherein after incubating the algae has cell wall extensions.

45. The method of statement 24-43 or 44, wherein after incubating the algae has a cell wall associated with, bound to, or linked to hyphae of the fungus.

46. The method of statement 24-44 or 45, wherein the algae or the fungus comprises at least one heterologous expression cassette or expression vector that includes a promoter operably linked to nucleic acid segment encoding a lipid synthetic enzyme.

47. The method of statement 26, wherein the lipid synthesizing enzyme is acetyl-CoA carboxylase, malonyl-CoA decarboxylase, acyl carrier protein, fatty acid synthase, malonyl-CoA:ACP malonyltransferase, 3-oxoacyl-ACP synthase, KASI/II, 3-hydroxdecanoyl-ACP dehydratase, 3-hydroxydecanoyl-ACP dehydratase, 3-ketoacyl-ACP reductase, acyl-CoA elongase, fatty acid desaturase, acyl-CoA thioesterase, acyl-CoA synthetase, aldehyde dehydrogenase, alcohol dehydrogenase, glycerol kinase, glycerol-3-phosphate dehydrogenase, glycero-3-phosphate acyltransferase, 1-sn-acyl-glycero-3-phosphate acyltransferase, phosphatidic acid phosphatase, lipin-like phosphatidate phosphatase, diacylglycerol kinase, diacylglycerol acyltransferase, phospholipid diacylglycerol acyltransferase, or any combination thereof.

48. The method of statement 46 or 47, wherein the algae or the fungus comprises two or more heterologous expression cassettes or expression vectors, each cassette or vector having a promoter operably linked to nucleic acid segment encoding a lipid synthetic enzyme.

49. A consortium comprising *Mortierella elongata* AG77 and *Nannochloropsis oceanica* CCMP1779 within hyphae of the *Mortierella elongata* AG77.

50. The consortium of statement 49, wherein the *Mortierella elongata* AG77, the *Nannochloropsis oceanica* CCMP1779, or both are modified to express a heterologous lipid synthesizing enzyme.

51. The consortium of statement 49 or 50, wherein the *Mortierella elongata* AG77, the *Nannochloropsis oceanica* CCMP1779, or both comprises at least one heterologous expression cassette or expression vector that includes a promoter operably linked to nucleic acid segment encoding a lipid synthetic enzyme.

52. The consortium of statement 49, 50 or 51, wherein the lipid synthesizing enzyme is acetyl-CoA carboxylase, malonyl-CoA decarboxylase, acyl carrier protein, fatty acid synthase, malonyl-CoA:ACP malonyltransferase, 3-oxoacyl-ACP synthase, KASI/II, 3-hydroxydecanoyl-ACP dehydratase, 3-hydroxydecanoyl-ACP dehydratase, 3-ketoacyl-ACP reductase, acyl-CoA elongase, fatty acid desaturase, acyl-CoA thioesterase, acyl-CoA synthetase, aldehyde dehydrogenase, alcohol dehydrogenase, glycerol kinase, glycerol-3-phosphate dehydrogenase, glycero-3-phosphate acyltransferase, 1-sn-acyl-glycero-3-phosphate acyltransferase, phosphatidic acid phosphatase, lipin-like phosphatidate phosphatase, diacylglycerol kinase, diacylglycerol acyltransferase, phospholipid diacylglycerol acyltransferase, or any combination thereof.

53. The consortium of statement 51 or 52, wherein the *Mortierella elongata* AG77, the *Nannochloropsis oceanica* CCMP1779, or both comprises two or more heterologous expression cassettes or expression vectors, each cassette or vector having a promoter operably linked to nucleic acid segment encoding a lipid synthetic enzyme.

54. A method of generating a consortium between *Mortierella elongata* AG77 and *Nannochloropsis oceanica* CCMP1779, comprising incubating the *Mortierella elongata* AG77 with *Nannochloropsis oceanica* CCMP1779 until the *Nannochloropsis oceanica* CCMP1779 are incorporated within hyphae of the *Mortierella elongata* AG77.

55. The method of statement 54, wherein the *Mortierella elongata* AG77, the *Nannochloropsis oceanica* CCMP1779, or both are modified to express a heterologous lipid synthesizing enzyme.

56. The method of statement 55, wherein the lipid synthetic enzyme is one or more acetyl-CoA carboxylase, malonyl-CoA decarboxylase, acyl carrier protein, fatty acid synthase, malonyl-CoA:ACP malonyltransferase, 3-oxoacyl-ACP synthase, KASI/II, 3-hydroxydecanoyl-ACP dehydratase, 3-hydroxydecanoyl-ACP dehydratase, 3-ketoacyl-ACP reductase, acyl-CoA elongase, fatty acid desaturase, acyl-CoA thioesterase, acyl-CoA synthetase, aldehyde dehydrogenase, alcohol dehydrogenase, glycerol kinase, glycerol-3-phosphate dehydrogenase, glycero-3-phosphate acyltransferase, 1-sn-acyl-glycero-3-phosphate acyltransferase, phosphatidic acid phosphatase, lipin-like phosphatidate phosphatase, diacylglycerol kinase, diacylglycerol acyltransferase, phospholipid diacylglycerol acyltransferase, or any combination thereof.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "an algae" or "a fungus" or "a cell" includes a plurality of such algae, fungi, or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A consortium comprising at least one viable fungus and at least one viable photosynthetically active alga within hyphae of the fungus, wherein the fungus, alga, or both have been modified to express at least one of the following lipid synthetic enzymes: acetyl-CoA carboxylase, malonyl-CoA decarboxylase, acyl carrier protein, fatty acid synthase, malonyl-CoA:ACP malonyltransferase, 3-oxoacyl-ACP synthase, KASI/II, 3-hydroxydecanoyl-ACP dehydratase, 3-hydroxydecanoyl-ACP dehydratase, 3-ketoacyl-ACP reductase, acyl-CoA elongase, fatty acid desaturase, acyl-CoA thioesterase, acyl-CoA synthetase, aldehyde dehydrogenase, alcohol dehydrogenase, glycerol kinase, glycerol-3-phosphate dehydrogenase, glycero-3-phosphate acyltransferase, 1-sn-acyl-glycero-3-phosphate acyltransferase, phosphatidic acid phosphatase, lipin-like phosphatidate phosphatase, diacylglycerol kinase, diacylglycerol acyltransferase, phospholipid diacylglycerol acyltransferase, or any combination thereof.

2. The consortium of claim 1, wherein alga is a diatom (bacillariophyte), green algae (chlorophyte), blue-green algae (cyanophyte), golden-brown algae (chrysophyte), haptophyte, or a combination thereof.

3. The consortium of claim 1, wherein alga is a species of Amphipleura, Amphora, Ankistrodesmus, Aquamortierella, Boekelovia, Botryococcus, Chaetoceros, Charophyceae, Chlorella, Chlorococcum, Chlorodendrophyceae, Chlorokybophyceae, Chlorophyceae, Coleochaetophyceae, Cyclotella, Cymbella, Dissophora, Dunaliella, Embryophytes, Endogaceae, Fragilaria, Gamsiella, Hantzschia, Isochrysis, Klebsormidiophyceae, Lobosporangium, Mamiellophyceae, Mesostigmatophyceae, Modicella, Monoraphidium, Mortierella, Mucor, Nannochloropsis, Navicula, Nephroselmidophyceae, Nitzschia, Oocystis, Oscillatoria, Palmophyllales, Pleurochrysis, Prasinococcales, Prasinophytes, Pedinophyceae, Phaeodactylum, Pyramimonadales, Pycnoccaceae, Pythium, Phytophthora, Phytopythium, Rhizopus, Scenedesmus, Synechococcus, Tetraselmis, Thalassiosira, Trebouxiophyceae, Ulvophyceae, Zygnematophyceae, or the algae is a combination of species.

4. The consortium of claim 1, wherein alga is *Emiliania huxleyi, Gephyrocapsa oceanica, Isochrysis galbana, Isochrysis* sp. T-Iso, *Isochrysis* sp. C-Iso, *Nannochloropsis oceanica*, or a combination thereof.

5. The consortium of claim 1, wherein algae is *Nannochloropsis oceanica* CCMP1779.

6. The consortium of claim 1, wherein the fungus is a species of *Aspergillus, Atractiella, Blakeslea, Botrytis, Candida, Cercospora, Clavulina, Cryptococcus, Cunninghamella, Flagelloscypha, Fusarium (Gibberella), Grifola,*

*Kluyveromyces, Lachnum, Lecythophora, Leptodontidium, Lipomyces, Morchella, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Umbelopsis, Xanthophyllomyces (Phqffia), Yarrowia*, or a combination thereof.

7. The consortium of claim 1, wherein the fungus is *Atractiella* PMI152, *Clavulina* PMI390, *Flagelloscypha* PMI526, *Grifola frondosa, Grifola frondosa* GMNB41, *Lecythophora* PMI546, *Leptodontidium* PMI413, *Lachnum* PMI789, *Mortierella elongata, Mortierella elongata* AG77, *Mortierella gamsii, Mortierella gamsii* GBAus22, *Saccharomyces cerevisiae, Umbelopsis* PMI120, or a combination thereof.

8. The consortium of claim 1, wherein the fungus has more than one algae cell within the fungus hyphae.

9. The consortium of claim 1, wherein the alga synthesizes sugars.

10. A method of making the consortium of claim 1 comprising incubating at least one fungus and at least one alga cell in a culture medium until at least one alga cell is incorporated into hyphae of the fungus, to thereby form a consortium of the at least one fungus and the at least one alga cell, wherein the fungus, alga, or both have been modified to express at least one of the following lipid synthetic enzymes: acetyl-CoA carboxylase, malonyl-CoA decarboxylase, acyl carrier protein, fatty acid synthase, malonyl-CoA:ACP malonyltransferase, 3-oxoacyl-ACP synthase, KASI/II, 3-hydroxydecanoyl-ACP dehydratase, 3-hydroxydecanoyl-ACP dehydratase, 3-ketoacyl-ACP reductase, acyl-CoA elongase, fatty acid desaturase, acyl-CoA thioesterase, acyl-CoA synthetase, aldehyde dehydrogenase, alcohol dehydrogenase, glycerol kinase, glycerol-3-phosphate dehydrogenase, glycero-3-phosphate acyltransferase, 1-sn-acyl-glycero-3-phosphate acyltransferase, phosphatidic acid phosphatase, lipin-like phosphatidate phosphatase, diacylglycerol kinase, diacylglycerol acyltransferase, phospholipid diacylglycerol acyltransferase, or any combination thereof.

11. The method of claim 10, wherein at least one fungus and at least one alga cell are incubated together for one or more days, one or more weeks, one or months, one or more years, or indefinitely.

12. The method of claim 10, wherein at least one fungus and at least one alga cell are incubated at a fungus cell or fungus tissue, and an algae cell density sufficient for the fungus and the alga come into contact.

13. The method of claim 10, wherein more fungi cells or fungus tissue by mass than algal cells by mass is incubated together.

14. The method of claim 10, wherein more algae cells by number than fungal cells or fungus tissue pieces by number is incubated.

15. The method of claim 10, wherein the fungus and the algae cells are incubated at a ratio of from about 10:1 by mass algal cells to fungal tissue mass to about 1:1 by mass algal cells to fungal tissue mass.

16. The method of claim 10, wherein one or more fungal species and one or more algal species are incubated in a culture medium that contains some carbohydrate or some sugar.

17. The method of claim 16, wherein the carbohydrate or sugar is present in an amount of about 1 g/liter to about 20 g/liter.

18. The method of claim 10, wherein the consortium of the at least one fungus and the at least one alga cell is incubated in a minimal medium.

19. The method of claim 10, comprising incubating a *Mortierella elongata* AG77 fungus with one or more *Nannochloropsis oceanica* CCMP1779 cell until the *Nannochloropsis oceanica* CCMP1779 are incorporated within hyphae of the *Mortierella elongata* AG77.

20. The method of claim 10, wherein prior to or during the incubating, at least one fungus or at least one alga cell, or a combination thereof are incubated in a culture medium that is sparged with carbon dioxide and that does not contain added bicarbonate salts.

21. The method of claim 10, wherein prior to or during the incubating, at least one fungus or at least one alga cell, or a combination thereof are incubated in a culture medium that contains ammonium salts.

22. The method of claim 10, further comprising incubating the consortium for a time and under conditions for the consortium to produce lipid, carbohydrate, protein, or a combination thereof.

23. The method of claim 10, further comprising harvesting the alga by collecting the consortium from the culture medium.

24. The method of claim 10, wherein the consortium comprises a lipid content greater than 40% by weight of the consortium.

* * * * *